United States Patent
Apelian et al.

(10) Patent No.: US 9,290,547 B2
(45) Date of Patent: *Mar. 22, 2016

(54) YEAST-BASED THERAPEUTIC FOR CHRONIC HEPATITIS B INFECTION

(71) Applicant: GlobeImmune, Inc., Louisville, CO (US)

(72) Inventors: David Apelian, Boonton Township, NJ (US); Thomas H. King, Denver, CO (US); Zhimin Guo, Superior, CO (US); Claire Coeshott, Denver, CO (US)

(73) Assignee: GlobeImmune, Inc., Louisville, CO (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/494,235

(22) Filed: Sep. 23, 2014

(65) Prior Publication Data

US 2015/0110828 A1  Apr. 23, 2015

Related U.S. Application Data

(62) Division of application No. 13/984,888, filed as application No. PCT/US2012/024409 on Feb. 9, 2012, now Pat. No. 8,877,205.

(60) Provisional application No. 61/442,204, filed on Feb. 12, 2011, provisional application No. 61/496,945, filed on Jun. 14, 2011, provisional application No. 61/507,361, filed on Jul. 13, 2011.

(51) Int. Cl.

| C12N 7/00 | (2006.01) |
|---|---|
| C07K 14/005 | (2006.01) |
| A61K 39/29 | (2006.01) |
| A61K 36/06 | (2006.01) |
| C07K 14/02 | (2006.01) |
| A61K 47/46 | (2006.01) |
| A61K 36/12 | (2006.01) |
| A61K 31/675 | (2006.01) |
| A61K 39/00 | (2006.01) |

(52) U.S. Cl.
CPC ............ *C07K 14/005* (2013.01); *A61K 31/675* (2013.01); *A61K 36/06* (2013.01); *A61K 36/12* (2013.01); *A61K 39/29* (2013.01); *A61K 47/46* (2013.01); *C07K 14/02* (2013.01); *C12N 7/00* (2013.01); *A61K 2039/51* (2013.01); *A61K 2039/5158* (2013.01); *A61K 2039/521* (2013.01); *A61K 2039/523* (2013.01); *A61K 2039/55* (2013.01); *A61K 2039/55516* (2013.01); *A61K 2039/55588* (2013.01); *A61K 2039/6006* (2013.01); *A61K 2039/70* (2013.01); *C12N 2710/00022* (2013.01); *C12N 2730/10134* (2013.01)

(58) Field of Classification Search
None
See application file for complete search history.

(56) References Cited

U.S. PATENT DOCUMENTS

| 4,775,622 | A | 10/1988 | Hitzeman et al. |
|---|---|---|---|
| 5,164,485 | A | 11/1992 | Yukio et al. |
| 5,234,830 | A | 8/1993 | Oshima et al. |
| 5,310,654 | A | 5/1994 | Isberg et al. |
| 5,413,914 | A | 5/1995 | Franzusoff |
| 5,830,463 | A | 11/1998 | Duke et al. |
| 5,858,378 | A | 1/1999 | Bostwick |
| 5,919,651 | A | 7/1999 | Hitzeman et al. |
| 7,083,787 | B2 | 8/2006 | Duke et al. |
| 7,439,042 | B2 | 10/2008 | Duke et al. |
| 7,465,454 | B2 | 12/2008 | Franzusoff et al. |
| 7,563,447 | B2 | 7/2009 | Franzusoff et al. |
| 7,595,060 | B2 | 9/2009 | Duke et al. |
| 7,625,569 | B2 | 12/2009 | Duke et al. |
| 7,632,511 | B2 | 12/2009 | Duke et al. |
| 7,736,642 | B2 | 6/2010 | Duke et al. |
| 7,744,898 | B2 | 6/2010 | Chisari |
| 7,745,128 | B2 | 6/2010 | Guo et al. |
| 8,007,816 | B2 | 8/2011 | Duke et al. |
| 8,221,763 | B2 | 7/2012 | Duke et al. |
| 8,337,830 | B2 | 12/2012 | Franzusoff et al. |
| 8,388,980 | B2 | 3/2013 | Duke et al. |
| 8,470,313 | B2 | 6/2013 | Guo et al. |
| 8,722,054 | B2 * | 5/2014 | Apelian et al. ............. 424/189.1 |
| 2002/0044948 | A1 | 4/2002 | Khleif et al. |
| 2003/0035810 | A1 | 2/2003 | Caplan et al. |
| 2007/0054262 | A1 | 3/2007 | Baker et al. |
| 2007/0172503 | A1 | 7/2007 | Selitrennikoff et al. |

(Continued)

FOREIGN PATENT DOCUMENTS

| AU | 2004269882 | 3/2005 |
|---|---|---|
| CN | 1171636 | 10/2004 |

(Continued)

OTHER PUBLICATIONS

Baumert et al., "Pathogenesis of hepatitis B virus infection," World Journal of Gastroenterology, 2007, vol. 13, Iss. 1, pp. 82-90.
Bian et al., "Whole recombinant Hansenula polymorpha expressing hepatitis B virus surface antigen (yeast-HBsAg) induces potent HBsAg-specific Th1 and Th2 immune responses," Vaccine, 2010, vol. 28, Iss. 1, pp. 187-194.
Bizzini et al., "Use of live Saccharomyces cerevisiae cells as a biological response modifier in experimental infections," 1990, FEMS Microbiol. Immunol., 64:155-168.
Boni et al., "Restored Function of HBV-Specific T Cells After Long-term Effective Therapy With Nucleos(t)ide Analogues," Gastroenterology, 2012, vol. 143, No. 4, pp. 963-973.
Brake et al., "Alpha-factor-directed synthesis and secretion of mature foreign proteins in Saccharomycet cerevisiae," 1984, Proc. Natl. Acad. Sci. USA, 81:4642-4646.
Chisari, "Cytotoxic T Cells and Viral Hepatitis," The Journal of Clinical Investigation, 1997, vol. 99, No. 7, pp. 1472-1477.

(Continued)

*Primary Examiner* — Agnieszka Boesen
(74) *Attorney, Agent, or Firm* — Sheridan Ross P.C.; Angela Dallas Sebor; Phil Polster

(57) ABSTRACT

Disclosed are yeast-based immunotherapeutic compositions, hepatitis B virus (HBV) antigens, and fusion proteins for the treatment and/or prevention of HBV infection and symptoms thereof, as well as methods of using the yeast-based immunotherapeutic compositions, HBV antigens, and fusion proteins for the prophylactic and/or therapeutic treatment of HBV and/or symptoms thereof.

38 Claims, 29 Drawing Sheets

(56) References Cited

U.S. PATENT DOCUMENTS

| | | |
|---|---|---|
| 2009/0098154 A1 | 4/2009 | Franzusoff et al. |
| 2009/0142366 A1 | 6/2009 | Franzusoff et al. |
| 2010/0034840 A1 | 2/2010 | Apelian et al. |
| 2010/0104604 A1 | 4/2010 | Selitrennikoff et al. |
| 2010/0111912 A1 | 5/2010 | Apelian et al. |
| 2010/0189749 A1 | 7/2010 | Franzusoff et al. |
| 2010/0196411 A1 | 8/2010 | Duke et al. |
| 2011/0150909 A1 | 6/2011 | Franzusoff et al. |
| 2011/0256098 A1 | 10/2011 | Apelian et al. |
| 2012/0107347 A1 | 5/2012 | Hodge et al. |
| 2012/0321664 A1 | 12/2012 | Bellgrau et al. |
| 2014/0065182 A1 | 3/2014 | Apelian et al. |
| 2014/0286984 A1* | 9/2014 | Apelian et al. ............. 424/189.1 |
| 2015/0191509 A1 | 7/2015 | Apelian et al. |

FOREIGN PATENT DOCUMENTS

| | | |
|---|---|---|
| CN | 101036784 | 9/2007 |
| EP | 0414404 | 2/1991 |
| EP | 1054689 | 9/2003 |
| FR | 2486400 | 1/1982 |
| WO | WO 2008/093976 | 8/2008 |
| WO | WO 2010/065626 | 6/2010 |
| WO | WO 2011/115914 | 9/2011 |
| WO | WO 2012/019127 | 2/2012 |
| WO | WO 2012/083302 | 6/2012 |
| WO | WO 2012/109404 | 8/2012 |
| WO | WO 2012/125998 | 9/2012 |
| WO | WO 2012/174220 | 12/2012 |
| WO | WO 2013/025972 | 2/2013 |

OTHER PUBLICATIONS

Eto et al., "Immunization with recombinant *Escherichia coli* expressing retinal S-antigen-induced experimental autoimmune uveitis (EAU) in Lewis rats", Cellular Immunology, vol. 147, No. 1 Mar. 1993, pp. 203-214.

Franzusoff et al. "Biochemical and Genetic Definition of the Cellular Protease Required for HIV-1 gp160 Processing," The Journal of Biological Chemistry, Feb. 1995, vol. 270, No. 7, pp. 3154-3159.

Franzusoff, A. et al. "Yeasts Encoding Tumour Antigens in Cancer Immunotherapy," Expert Opinion on Biological Therapy, Apr. 2005, vol. 5, No. 4, pp. 565-575.

Fujita et al. "Studies in the development of Japanese encephalitis vaccine: expression of virus envelope glycoprotein V3 (E) gene in yeast," Bulletin of the World Health Organization, Feb. 1987, vol. 65, No. 3, pp. 303-308.

Gearhart et al., "The Hepatitis B Virus X Protein Modulates Hepatocyte Proliferation Pathways to Stimulate Viral Replication," Journal of Virology, 2010, vol. 84, No. 6, pp. 2675-2686.

Kim et al., "Culture method to enhance the productivity of hepatitis B surface antigen (pre S2 + S Ag) with recombinant Saccharomyces cerevisiae," Biotechnology Techniques, 1996, vol. 10, Iss. 4, pp. 233-238.

Klepfer et al., "Characterization of rabies glycoprotein expressed in yeast," Archives of Virology, 1993, vol. 128, pp. 269-286.

Li et al., GenBank Accession No. ACN64477, Jan. 2009, 2 pages.

Lin et al., UniProtKB/TrEMBL Accession No. A4UIM2, Dec. 2006, 1 page.

Lu, et al., "Mutation-Selective Tumor Remission with Ras-Targeted, Whole Yeast-Based Immunotherapy, Cancer Research," 2004, vol. 64, pp. 5084-5088.

Luo et al., "Design, synthesis and expression of the multi-epitope gene of hepatitis B virus," Chin. J. Microbiol. Immunol., 2004, vol. 24(6), pp. 426-432 (with English abstract).

Moore et al., "Novel yeast-based vaccine against HIV-SF2 gp 160 promotes a cytotoxic T cell response.", FASEB Journal (online), vol. 10. No. 6. 1996, p. A1473, ZP002186594, Joint.

Nguyen et al., "Hepatitis B Virus-Cell Interactions and Pathogenesis," Journal of Cellular Physiology, 2008, vol. 216, Iss. 2, pp. 289-294.

Sällberg et al., "Immunochemical structure of the carboxy-terminal part of hepatitis B e antigen: identification of internal and surface-exposed sequences," Journal of General Virology, 1993, vol. 74, No. 7, pp. 1335-1340.

Schreuder et al., "Yeast expressing hepatitis B virus surface antigen determinants on its surface: implications for a possible oral vaccine," Vaccine, 1996, vol. 14, Iss. 5, pp. 383-388.

Schödel et al., "Structure of Hepatitis B Virus Core and e-Antigen. A Single Precore Amino Acid Prevents Nucleocapsid Assembly," The Journal of Biological Chemistry, 1993, vol. 268, No. 2, pp. 1332-1337.

Seeger et al., "Hepatitis B Virus Biology," Microbiology and Molecular Biology Reviews, 2000, vol. 64, No. 1, pp. 51-68.

Shiosaki et al., "Production of hepatitis B virion-like particles in yeast," Gene, 1991, vol. 106, Iss. 2, pp. 143-149.

Sinai et al. "Enhancement of Resistance to Infectious Diseases by Oral Administration of Brewer's Yeast," Infection and Immunity, May 1974, vol. 9, No. 5, pp. 781-787.

Stubbs et al. "Whole recombinant yeast vaccine activates dendric cells and elicits protective cell-mediated immunity", Nature Medicine May 2001, vol. 7, pp. 1-5.

Valenzuela et al. "Antigen engineering in yeast: Synthesis and assembly of hybrid hepatitis B surface antigen-Herpes simplex 1 gD particles", Bio/Technology, Apr. 1985, vol. 3, 323-326.

Whitacre et al., "Use of hepadnavirus core proteins as vaccine platforms," Final edited form published in: Expert Review of Vaccines, 2009, vol. 8, No. 11, pp. 1565-1573, (Author Manuscript, 15 pages.).

Wieland et al., "Stealth and Cunning: Hepatitis B and Hepatitis C Viruses," Journal of Virology, 2005, vol. 79, No. 15, pp. 9639-9380.

Wood, "Immunotherapy: Therapeutic potential of genetically modified HBV-specific T cells for chronic HBV infection and HBV-related HCC," Nature Reviews—Gastroenterology & Hepatology, 2011, vol. 8, No. 2, p. 61.

International Search Report and Written Opinion for International (PCT) Patent Application No. PCT/US2012/024409 mailed May 8, 2012, 16 pages.

International Preliminary Report on Patentability for International (PCT) Patent Application No. PCT/US2012/024409 mailed Aug. 22, 2013, 11 pages.

Official Action with English translation and Search Report for Chinese Patent Application No. 201280018222.5, mailed Jun. 20, 2014, 10 pages.

Official Action for New Zealand Patent Application No. 614733 dated Feb. 24, 2014, 2 pages.

Official Action for U.S. Appl. No. 13/798,837 mailed Nov. 12, 2013, 9 pages.

Notice of Allowance for U.S. Appl. No. 13/798,837 mailed Dec. 5, 2013, 12 pages.

Notice of Allowance for U.S. Appl. No. 13/984,888, mailed Jun. 26, 2014, 16 pages.

Notice of Allowance for U.S. Appl. No. 14/184,481 mailed Dec. 23, 2014, 16 pages.

Official Action for Canadian Patent Application No. 2,827,150 dated Jan. 22, 2015, 4 pages.

Feitelson et al., "Putative roles of hepatitis B x antigen in the pathogenesis of chronic liver disease," Cancer Letters, 2009, vol. 286, Iss. 1, pp. 69-79.

Official Action (with English translation) for Chinese Patent Application No. 201280018222.5, dated Feb. 13, 2015, 7 pages.

Official Action (with English translation) for Eurasian Patent Application No. 201391170/82 dated Apr. 8, 2015, 3 pages.

Notice of Allowance (with English translation) for Japanese Patent Application No. 2013-553534 mailed Apr. 7, 2015, 2 pages.

Notice of Acceptance for New Zealand Patent Application No. 614733 dated Mar. 13, 2015, 1 page.

Official Action for New Zealand Patent Application No. 705184 dated Mar. 13, 2015, 2 pages.

"GlobeImmune Announces Top Line Results From GS-4774 Phase 2 Trial in Virally-Suppressed Chronic HBV Patients", Press Release, May 27, 2015, 2 pages.

Haller et al., "Whole recombinant yeast-based immunotherapy induces potent T cell responses targeting HCV NS3 and Core proteins," Vaccine, 2007, vol. 25, Iss. 8, pp. 1452-1463.

(56) References Cited

OTHER PUBLICATIONS

Liang et al., "Low Incidence and High Titers of Antibodies to Hepatitis B Virus X-Protein in Sera of Chinese Patients with Hepatocellular Carcinoma," Journal of Medical Virology, 1988, vol. 25, Iss. 3, pp. 329-337.

Tacket et al., "Safety and Immunogenicity in Humans of an Attenuated Salmonella typhi Vaccine Vector Strain Expressing Plasmid-Encoded Hepatitis B Antigens Stabilized by the Asd-Balanced Lethal Vector System," Infection and Immunity, 1997, vol. 65, No. 8, pp. 3381-3385.

Extended European Search Report for European Patent Application No. 12744328.1 dated Jun. 25, 2015, 9 pages.

Official Action (with English translation of the requirements stated by the Examiner) for Mexican Patent Application No. MX/a/2013/009310, issue date unknown, received Jul. 9, 2015, 1 page.

Decision to Grant (with translated Search Report) for Taiwanese Patent Application No. 101104436 dated Jun. 17, 2015, 5 pages.

Amendment to the Search Report attached to the Decision to Grant (with English translation) for Taiwanese Patent Application No. 101104436 dated Aug. 4, 2015, 2 pages.

Official Action for U.S. Appl. No. 14/591,592 mailed May 21, 2015, 12 pages.

Official Action for U.S. Appl. No. 14/591,592 mailed Nov. 19, 2015, 10 pages.

\* cited by examiner

FIG. 26

SEQUENCE LISTING

```
<160> NUMBER OF SEQ ID NOS: 152

<210> SEQ ID NO 1
<211> LENGTH: 212
<212> TYPE: PRT
<213> ORGANISM: Hepatitis B virus

<400> SEQUENCE: 1

Met Gln Leu Phe His Leu Cys Leu Ile Ile Ser Cys Thr Cys Pro Thr
1               5                   10                  15

Phe Gln Ala Ser Lys Leu Cys Leu Gly Trp Leu Trp Gly Met Asp Ile
            20                  25                  30

Asp Pro Tyr Lys Glu Phe Gly Ala Thr Val Glu Leu Leu Ser Phe Leu
        35                  40                  45

Pro Ser Asp Phe Phe Pro Ser Val Arg Asp Leu Leu Asp Thr Ala Ser
    50                  55                  60

Ala Leu Tyr Arg Glu Ala Leu Glu Ser Pro Glu His Cys Ser Pro His
65                  70                  75                  80

His Thr Ala Leu Arg Gln Ala Ile Leu Cys Trp Gly Glu Leu Met Thr
                85                  90                  95

Leu Ala Thr Trp Val Gly Asn Asn Leu Glu Asp Pro Ala Ser Arg Asp
            100                 105                 110

Leu Val Val Asn Tyr Val Asn Thr Asn Met Gly Leu Lys Ile Arg Gln
        115                 120                 125

Leu Leu Trp Phe His Ile Ser Cys Leu Thr Phe Gly Arg Glu Thr Val
    130                 135                 140

Leu Glu Tyr Leu Val Ser Phe Gly Val Trp Ile Arg Thr Pro Pro Ala
145                 150                 155                 160

Tyr Arg Pro Pro Asn Ala Pro Ile Leu Ser Thr Leu Pro Glu Thr Thr
                165                 170                 175

Val Val Arg Cys Arg Gly Arg Ser Pro Arg Arg Thr Pro Ser Pro
            180                 185                 190
```

```
Arg Arg Arg Arg Ser Gln Ser Pro Arg Arg Arg Ser Lys Ser Arg
        195                 200                 205

Glu Ser Gln Cys
    210

<210> SEQ ID NO 2
<211> LENGTH: 845
<212> TYPE: PRT
<213> ORGANISM: Hepatitis B virus

<400> SEQUENCE: 2

Met Pro Leu Ser Tyr Gln His Phe Arg Lys Leu Leu Leu Asp Asp
1               5                   10                  15

Gly Thr Glu Ala Gly Pro Leu Glu Glu Glu Leu Pro Arg Leu Ala Asp
                20                  25                  30

Ala Asp Leu Asn Arg Arg Val Ala Glu Asp Leu Asn Leu Gly Asn Leu
            35                  40                  45

Asn Val Ser Ile Pro Trp Thr His Lys Val Gly Asn Phe Thr Gly Leu
    50                  55                  60

Tyr Ser Ser Thr Val Pro Ile Phe Asn Pro Glu Trp Gln Thr Pro Ser
65                  70                  75                  80

Phe Pro Lys Ile His Leu Gln Glu Asp Ile Ile Asn Arg Cys Gln Gln
                85                  90                  95

Phe Val Gly Pro Leu Thr Val Asn Glu Lys Arg Arg Leu Lys Leu Ile
                100                 105                 110

Met Pro Ala Arg Phe Tyr Pro Thr His Thr Lys Tyr Leu Pro Leu Asp
                115                 120                 125

Lys Gly Ile Lys Pro Tyr Tyr Pro Asp Gln Val Val Asn His Tyr Phe
        130                 135                 140

Gln Thr Arg His Tyr Leu His Thr Leu Trp Lys Ala Gly Ile Leu Tyr
145                 150                 155                 160

Lys Arg Glu Thr Thr Arg Ser Ala Ser Phe Cys Gly Ser Pro Tyr Ser
                165                 170                 175

Trp Glu Gln Glu Leu Gln His Gly Arg Leu Val Ile Lys Thr Ser Gln
                180                 185                 190

Arg His Gly Asp Glu Ser Phe Cys Ser Gln Pro Ser Gly Ile Leu Ser
        195                 200                 205

Arg Ser Ser Val Gly Pro Cys Ile Arg Ser Gln Leu Lys Gln Ser Arg
    210                 215                 220

Leu Gly Leu Gln Pro His Gln Gly Pro Leu Ala Ser Ser Gln Pro Gly
225                 230                 235                 240

Arg Ser Gly Ser Ile Trp Ala Arg Ala His Pro Ser Thr Arg Arg Tyr
                245                 250                 255

Phe Gly Val Glu Pro Ser Gly Ser Gly His Ile Asp His Ser Val Asn
                260                 265                 270

Asn Ser Ser Ser Cys Leu His Gln Ser Ala Val Arg Lys Ala Ala Tyr
        275                 280                 285

Ser His Leu Ser Thr Ser Lys Arg Gln Ser Ser Gly His Ala Val
    290                 295                 300

Glu Phe His Cys Leu Pro Pro Ser Ser Ala Gly Ser Gln Ser Gln Gly
305                 310                 315                 320

Ser Val Phe Ser Cys Trp Trp Leu Gln Phe Arg Asn Ser Lys Pro Cys
                325                 330                 335

Ser Glu Tyr Cys Leu Ser His Leu Val Asn Leu Arg Glu Asp Trp Gly
```

-continued

```
            340                 345                 350
Pro Cys Asp Glu His Gly Glu His His Ile Arg Ile Pro Arg Thr Pro
            355                 360                 365

Ala Arg Val Thr Gly Gly Val Phe Leu Val Asp Lys Asn Pro His Asn
    370                 375                 380

Thr Ala Glu Ser Arg Leu Val Val Asp Phe Ser Gln Phe Ser Arg Gly
385                 390                 395                 400

Ser Thr Arg Val Ser Trp Pro Lys Phe Ala Val Pro Asn Leu Gln Ser
                405                 410                 415

Leu Thr Asn Leu Leu Ser Ser Asn Leu Ser Trp Leu Ser Leu Asp Val
            420                 425                 430

Ser Ala Ala Phe Tyr His Ile Pro Leu His Pro Ala Ala Met Pro His
            435                 440                 445

Leu Leu Ile Gly Ser Ser Gly Leu Ser Arg Tyr Val Ala Arg Leu Ser
        450                 455                 460

Ser Asn Ser Arg Ile Asn Asn Asn Gln Tyr Gly Thr Met Gln Asn Leu
465                 470                 475                 480

His Asp Ser Cys Ser Arg Gln Leu Tyr Val Ser Leu Met Leu Leu Tyr
                485                 490                 495

Lys Thr Tyr Gly Trp Lys Leu His Leu Tyr Ser His Pro Ile Val Leu
                500                 505                 510

Gly Phe Arg Lys Ile Pro Met Gly Val Gly Leu Ser Pro Phe Leu Leu
            515                 520                 525

Ala Gln Phe Thr Ser Ala Ile Cys Ser Val Val Arg Arg Ala Phe Pro
        530                 535                 540

His Cys Leu Ala Phe Ser Tyr Met Asp Asp Val Val Leu Gly Ala Lys
545                 550                 555                 560

Ser Val Gln His Arg Glu Ser Leu Tyr Thr Ala Val Thr Asn Phe Leu
                565                 570                 575

Leu Ser Leu Gly Ile His Leu Asn Pro Asn Lys Thr Lys Arg Trp Gly
            580                 585                 590

Tyr Ser Leu Asn Phe Met Gly Tyr Ile Ile Gly Ser Trp Gly Thr Leu
        595                 600                 605

Pro Gln Asp His Ile Val Gln Lys Ile Lys His Cys Phe Arg Lys Leu
    610                 615                 620

Pro Val Asn Arg Pro Ile Asp Trp Lys Val Cys Gln Arg Ile Val Gly
625                 630                 635                 640

Leu Leu Gly Phe Ala Ala Pro Phe Thr Gln Cys Gly Tyr Pro Ala Leu
                645                 650                 655

Met Pro Leu Tyr Ala Cys Ile Gln Ala Lys Gln Ala Phe Thr Phe Ser
            660                 665                 670

Pro Thr Tyr Lys Ala Phe Leu Ser Lys Gln Tyr Met Asn Leu Tyr Pro
        675                 680                 685

Val Ala Arg Gln Arg Pro Gly Leu Cys Gln Val Phe Ala Asp Ala Thr
    690                 695                 700

Pro Thr Gly Trp Gly Leu Ala Ile Gly His Gln Arg Met Arg Gly Thr
705                 710                 715                 720

Phe Val Ala Pro Leu Pro Ile His Thr Ala Glu Leu Leu Ala Ala Cys
                725                 730                 735

Phe Ala Arg Ser Arg Ser Gly Ala Lys Leu Ile Gly Thr Asp Asn Ser
            740                 745                 750

Val Val Leu Ser Arg Lys Tyr Thr Ser Phe Pro Trp Leu Leu Gly Cys
        755                 760                 765
```

```
Thr Ala Asn Trp Ile Leu Arg Gly Thr Ser Phe Val Tyr Val Pro Ser
        770                 775                 780

Ala Leu Asn Pro Ala Asp Asp Pro Ser Arg Gly Arg Leu Gly Leu Ser
785                 790                 795                 800

Arg Pro Leu Leu Arg Leu Pro Phe Gln Pro Thr Thr Gly Arg Thr Ser
            805                 810                 815

Leu Tyr Ala Val Ser Pro Ser Val Pro Ser His Leu Pro Val Arg Val
            820                 825                 830

His Phe Ala Ser Pro Leu His Val Ala Trp Arg Pro Pro
            835                 840                 845

<210> SEQ ID NO 3
<211> LENGTH: 400
<212> TYPE: PRT
<213> ORGANISM: Hepatitis B virus

<400> SEQUENCE: 3

Met Gly Gly Trp Ser Ser Lys Pro Arg Lys Gly Met Gly Thr Asn Leu
1               5                   10                  15

Ser Val Pro Asn Pro Leu Gly Phe Phe Pro Asp His Gln Leu Asp Pro
            20                  25                  30

Ala Phe Gly Ala Asn Ser Asn Asn Pro Asp Trp Asp Phe Asn Pro Ile
        35                  40                  45

Lys Asp His Trp Pro Thr Ala Asn Gln Val Gly Val Gly Ala Phe Gly
    50                  55                  60

Pro Gly Leu Thr Pro Pro His Gly Gly Ile Leu Gly Gly Ser Pro Gln
65                  70                  75                  80

Ala Gln Gly Ile Leu Thr Thr Val Ser Thr Ile Pro Pro Pro Ala Ser
                85                  90                  95

Thr Asn Arg Gln Ser Gly Arg Gln Pro Thr Pro Ile Ser Pro Pro Leu
            100                 105                 110

Arg Asp Ser His Pro Gln Ala Met Gln Trp Asn Ser Thr Ala Phe His
        115                 120                 125

Gln Ala Leu Gln Asp Pro Arg Val Arg Gly Leu Tyr Phe Pro Ala Gly
    130                 135                 140

Gly Ser Ser Ser Gly Thr Val Asn Pro Ala Pro Asn Ile Ala Ser His
145                 150                 155                 160

Ile Ser Ser Ile Ser Ala Arg Thr Gly Asp Pro Val Ala Asn Met Glu
                165                 170                 175

Asn Ile Thr Ser Gly Phe Leu Gly Pro Leu Leu Val Leu Gln Ala Gly
            180                 185                 190

Phe Phe Leu Leu Thr Arg Ile Leu Thr Ile Pro Gln Ser Leu Asp Ser
        195                 200                 205

Trp Trp Thr Ser Leu Asn Phe Leu Gly Gly Ser Pro Val Cys Leu Gly
    210                 215                 220

Gln Asn Ser Gln Ser Pro Thr Ser Asn His Ser Pro Thr Ser Cys Pro
225                 230                 235                 240

Pro Ile Cys Pro Gly Tyr Arg Trp Met Cys Leu Arg Arg Phe Ile Ile
                245                 250                 255

Phe Leu Phe Ile Leu Leu Leu Cys Leu Ile Phe Leu Leu Val Leu Leu
            260                 265                 270

Asp Tyr Gln Gly Met Leu Pro Val Cys Pro Leu Ile Pro Gly Ser Thr
        275                 280                 285

Thr Thr Ser Thr Gly Pro Cys Lys Thr Cys Thr Thr Pro Ala Gln Gly
```

```
            290                 295                 300
Asn Ser Met Phe Pro Ser Cys Cys Thr Lys Pro Thr Asp Gly Asn
305                 310                 315                 320

Cys Thr Cys Ile Pro Ile Pro Ser Ser Trp Ala Phe Ala Lys Tyr Leu
                325                 330                 335

Trp Glu Trp Ala Ser Val Arg Phe Ser Trp Leu Ser Leu Leu Val Pro
                340                 345                 350

Phe Val Gln Trp Phe Val Gly Leu Ser Pro Thr Val Trp Leu Ser Ala
                355                 360                 365

Ile Trp Met Met Trp Tyr Trp Gly Pro Ser Leu Tyr Ser Ile Val Ser
                370                 375                 380

Pro Phe Ile Pro Leu Leu Pro Ile Phe Phe Cys Leu Trp Val Tyr Ile
385                 390                 395                 400

<210> SEQ ID NO 4
<211> LENGTH: 154
<212> TYPE: PRT
<213> ORGANISM: Hepatitis B virus

<400> SEQUENCE: 4

Met Ala Ala Arg Leu Tyr Cys Gln Leu Asp Ser Ser Arg Asp Val Leu
1               5                   10                  15

Cys Leu Arg Pro Val Gly Ala Glu Ser Arg Gly Arg Pro Leu Ser Gly
                20                  25                  30

Pro Leu Gly Thr Leu Ser Ser Pro Ser Pro Ser Ala Val Pro Ala Asp
                35                  40                  45

His Gly Ala His Leu Ser Leu Arg Gly Leu Pro Val Cys Ala Phe Ser
        50                  55                  60

Ser Ala Gly Pro Cys Ala Leu Arg Phe Thr Ser Ala Arg Cys Met Glu
65                  70                  75                  80

Thr Thr Val Asn Ala His Gln Ile Leu Pro Lys Val Leu His Lys Arg
                85                  90                  95

Thr Leu Gly Leu Pro Ala Met Ser Thr Thr Asp Leu Glu Ala Tyr Phe
                100                 105                 110

Lys Asp Cys Val Phe Lys Asp Trp Glu Glu Leu Gly Glu Glu Ile Arg
                115                 120                 125

Leu Lys Val Phe Val Leu Gly Gly Cys Arg His Lys Leu Val Cys Ala
        130                 135                 140

Pro Ala Pro Cys Asn Phe Phe Thr Ser Ala
145                 150

<210> SEQ ID NO 5
<211> LENGTH: 212
<212> TYPE: PRT
<213> ORGANISM: Hepatitis B virus

<400> SEQUENCE: 5

Met Gln Leu Phe His Leu Cys Leu Ile Ile Ser Cys Ser Cys Pro Thr
1               5                   10                  15

Val Gln Ala Ser Lys Leu Cys Leu Gly Trp Leu Trp Gly Met Asp Ile
                20                  25                  30

Asp Pro Tyr Lys Glu Phe Gly Ala Thr Val Glu Leu Leu Ser Phe Leu
                35                  40                  45

Pro Ser Asp Phe Phe Pro Ser Val Arg Asp Leu Leu Asp Thr Ala Ala
        50                  55                  60

Ala Leu Tyr Arg Glu Ala Leu Glu Ser Pro Glu His Cys Ser Pro His
```

```
             65                  70                  75                  80
His Thr Ala Leu Arg Gln Ala Ile Leu Cys Trp Gly Glu Leu Met Thr
                    85                  90                  95

Leu Ala Thr Trp Val Gly Asn Asn Leu Glu Asp Pro Ala Ser Arg Asp
                100                 105                 110

Leu Val Val Asn Tyr Val Asn Thr Asn Met Gly Leu Lys Ile Arg Gln
                115                 120                 125

Leu Leu Trp Phe His Ile Ser Cys Leu Thr Phe Gly Arg Glu Thr Val
130                 135                 140

Leu Glu Tyr Leu Val Ser Phe Gly Val Trp Ile Arg Thr Pro Pro Ala
145                 150                 155                 160

Tyr Arg Pro Pro Asn Ala Pro Ile Leu Ser Thr Leu Pro Glu Thr Thr
                165                 170                 175

Val Val Arg Arg Arg Gly Arg Ser Pro Arg Arg Arg Thr Pro Ser Pro
                180                 185                 190

Arg Arg Arg Arg Ser Gln Ser Pro Arg Arg Arg Arg Ser Gln Ser Arg
                195                 200                 205

Glu Ser Gln Cys
        210

<210> SEQ ID NO 6
<211> LENGTH: 843
<212> TYPE: PRT
<213> ORGANISM: Hepatitis B virus

<400> SEQUENCE: 6

Met Pro Leu Ser Tyr Gln His Phe Arg Lys Leu Leu Leu Leu Asp Asp
1               5                   10                  15

Glu Ala Gly Pro Leu Glu Glu Glu Leu Pro Arg Leu Ala Asp Glu Gly
                20                  25                  30

Leu Asn His Arg Val Ala Glu Asp Leu Asn Leu Gly Asn Pro Asn Val
            35                  40                  45

Ser Ile Pro Trp Thr His Lys Val Gly Asn Phe Thr Gly Leu Tyr Ser
        50                  55                  60

Ser Thr Val Pro Val Phe Asn Pro Glu Trp Gln Thr Pro Ser Phe Pro
65                  70                  75                  80

Asp Ile His Leu Gln Glu Asp Ile Val Asp Arg Cys Lys Gln Phe Val
                85                  90                  95

Gly Pro Leu Thr Val Asn Glu Asn Arg Arg Leu Lys Leu Ile Met Pro
                100                 105                 110

Ala Arg Phe Phe Pro Asn Val Thr Lys Tyr Leu Pro Leu Asp Lys Gly
            115                 120                 125

Ile Lys Pro Tyr Tyr Pro Glu His Val Val Asn His Tyr Phe Gln Thr
        130                 135                 140

Arg His Tyr Leu His Thr Leu Trp Lys Ala Gly Ile Leu Tyr Lys Arg
145                 150                 155                 160

Glu Ser Thr His Ser Ala Ser Phe Cys Gly Ser Pro Tyr Ser Trp Glu
                165                 170                 175

Gln Asp Leu Gln His Gly Arg Leu Val Phe Gln Thr Ser Lys Arg His
                180                 185                 190

Gly Asp Lys Ser Phe Cys Pro Gln Ser Pro Gly Ile Leu Pro Arg Ser
            195                 200                 205

Ser Val Gly Pro Cys Ile Gln Ser Gln Leu Arg Lys Ser Arg Leu Gly
        210                 215                 220
```

```
Pro Gln Pro Thr Gln Gly Gln Leu Ala Gly Arg Pro Gln Gly Gly Ser
225                 230                 235                 240

Gly Ser Ile Arg Ala Arg Val His Pro Ser Pro Trp Gly Thr Val Gly
            245                 250                 255

Val Glu Pro Ser Gly Ser Gly His Thr His Ile Cys Ala Ser Ser Ser
        260                 265                 270

Ser Ser Cys Leu His Gln Ser Ala Val Arg Lys Ala Ala Tyr Ser Leu
    275                 280                 285

Ile Ser Thr Ser Lys Gly His Ser Ser Ser Gly His Ala Val Glu Leu
290                 295                 300

His His Phe Pro Pro Asn Ser Ser Arg Ser Gln Ser Gln Gly Ser Val
305                 310                 315                 320

Leu Ser Cys Trp Trp Leu Gln Phe Arg Asn Ser Lys Pro Cys Ser Glu
                325                 330                 335

Tyr Cys Leu Tyr His Ile Val Asn Leu Ile Glu Asp Trp Gly Pro Cys
            340                 345                 350

Ala Glu His Gly Glu His Arg Ile Arg Thr Pro Arg Thr Pro Ala Arg
        355                 360                 365

Val Thr Gly Gly Val Phe Leu Val Asp Lys Asn Pro His Asn Thr Ala
    370                 375                 380

Ala Ser Arg Leu Val Val Asp Phe Ser Gln Phe Ser Arg Gly Asn Thr
385                 390                 395                 400

Arg Val Ser Trp Pro Lys Phe Ala Val Pro Asn Leu Gln Ser Leu Thr
                405                 410                 415

Asn Leu Leu Ser Ser Asn Leu Ser Trp Leu Ser Leu Asp Val Ser Ala
            420                 425                 430

Ala Phe Tyr His Leu Pro Leu His Pro Ala Ala Met Pro His Leu Leu
        435                 440                 445

Val Gly Ser Ser Gly Leu Ser Arg Tyr Val Ala Arg Leu Ser Ser Asn
    450                 455                 460

Ser Arg Ile Ile Asn His Gln His Gly Thr Met Gln Asp Leu His Asn
465                 470                 475                 480

Ser Cys Ser Arg Asn Leu Tyr Val Ser Leu Met Leu Leu Tyr Lys Thr
                485                 490                 495

Tyr Gly Trp Lys Leu His Leu Tyr Ser His Pro Ile Ile Leu Gly Phe
            500                 505                 510

Arg Lys Ile Pro Met Gly Val Gly Leu Ser Pro Phe Leu Leu Ala Gln
        515                 520                 525

Phe Thr Ser Ala Ile Cys Ser Val Val Arg Arg Ala Phe Pro His Cys
    530                 535                 540

Leu Ala Phe Ser Tyr Met Asp Asp Val Val Leu Gly Ala Lys Ser Val
545                 550                 555                 560

Gln His Leu Glu Ser Leu Tyr Ala Ala Val Thr Asn Phe Leu Leu Ser
                565                 570                 575

Leu Gly Ile His Leu Asn Pro His Lys Thr Lys Arg Trp Gly Tyr Ser
            580                 585                 590

Leu Asn Phe Met Gly Tyr Val Ile Gly Ser Trp Gly Thr Leu Pro Gln
        595                 600                 605

Glu His Ile Val Gln Lys Ile Lys Leu Cys Phe Arg Lys Ile Pro Val
    610                 615                 620

Asn Arg Pro Ile Asp Trp Lys Val Cys Gln Arg Ile Val Gly Leu Leu
625                 630                 635                 640

Gly Phe Ala Ala Pro Phe Thr Gln Cys Gly Tyr Pro Ala Leu Met Pro
```

645                 650                 655
Leu Tyr Ala Cys Ile Gln Ala Lys Gln Ala Phe Ser Phe Ser Pro Thr
            660                 665                 670

Tyr Lys Ala Phe Leu Ser Lys Gln Tyr Leu Thr Leu Tyr Pro Val Ala
            675                 680                 685

Arg Gln Arg Pro Gly Leu Cys Gln Val Phe Ala Asp Ala Thr Pro Thr
            690                 695                 700

Gly Trp Gly Leu Ala Ile Gly His Gln Arg Met Arg Gly Thr Phe Val
705                 710                 715                 720

Ser Pro Leu Pro Ile His Thr Ala Glu Leu Leu Ala Ala Cys Phe Ala
                725                 730                 735

Arg Ser Arg Ser Gly Ala Lys Leu Ile Gly Thr Asp Asn Ser Val Val
            740                 745                 750

Leu Ser Arg Lys Tyr Thr Ser Phe Pro Trp Leu Leu Gly Cys Ala Ala
            755                 760                 765

Asn Trp Ile Leu Arg Gly Thr Ser Phe Val Tyr Val Pro Ser Ala Leu
770                 775                 780

Asn Pro Ala Asp Asp Pro Ser Arg Gly Arg Leu Gly Leu Tyr Arg Pro
785                 790                 795                 800

Leu Leu Arg Leu Pro Tyr Arg Pro Thr Thr Gly Arg Thr Ser Leu Tyr
                805                 810                 815

Pro Asp Ser Pro Ser Val Pro Ser His Leu Pro Asp Arg Val His Phe
            820                 825                 830

Ala Ser Pro Leu His Val Ala Trp Lys Pro Pro
            835                 840

<210> SEQ ID NO 7
<211> LENGTH: 400
<212> TYPE: PRT
<213> ORGANISM: Hepatitis B virus

<400> SEQUENCE: 7

Met Gly Gly Trp Ser Ser Lys Pro Arg Lys Gly Met Gly Thr Asn Leu
1               5                   10                  15

Ser Val Pro Asn Pro Leu Gly Phe Phe Pro Asp His Gln Leu Asp Pro
            20                  25                  30

Ala Phe Lys Ala Asn Ser Asp Asn Pro Asp Trp Asp Leu Asn Pro His
        35                  40                  45

Lys Asp Asn Trp Pro Asp Ser Asn Lys Val Gly Val Gly Ala Phe Gly
    50                  55                  60

Pro Gly Phe Thr Pro Pro His Gly Gly Leu Leu Gly Trp Ser Pro Gln
65                  70                  75                  80

Ala Gln Gly Met Ile Thr Thr Val Pro Ala Ala Pro Pro Pro Ala Ser
                85                  90                  95

Thr Asn Arg Gln Leu Gly Arg Gln Pro Thr Pro Leu Ser Pro Pro Leu
            100                 105                 110

Arg Asp Ser His Pro Gln Ala Met Gln Trp Asn Ser Thr Thr Phe His
        115                 120                 125

Lys Thr Leu Gln Asp Pro Arg Val Arg Ala Leu Tyr Phe Pro Ala Gly
    130                 135                 140

Gly Ser Ser Ser Gly Thr Val Asn Pro Val Gln Asn Thr Ala Ser Ser
145                 150                 155                 160

Ile Ser Ser Ile Leu Ser Lys Thr Gly Asp Pro Val Pro Asn Met Glu
                165                 170                 175

```
Asn Ile Ala Ser Gly Leu Leu Gly Pro Leu Val Leu Gln Ala Gly
            180                 185                 190

Phe Phe Leu Leu Thr Lys Ile Leu Thr Ile Pro Gln Ser Leu Asp Ser
        195                 200                 205

Trp Trp Thr Ser Leu Asn Phe Leu Gly Gly Thr Pro Val Cys Leu Gly
        210                 215                 220

Gln Asn Ser Gln Ser Gln Ile Ser Ser His Ser Pro Thr Cys Cys Pro
225                 230                 235                 240

Pro Ile Cys Pro Gly Tyr Arg Trp Met Cys Leu Arg Arg Phe Ile Ile
                245                 250                 255

Phe Leu Cys Ile Leu Leu Leu Cys Leu Ile Phe Leu Leu Val Leu Leu
            260                 265                 270

Asp Tyr Gln Gly Met Leu Pro Val Cys Pro Leu Ile Pro Gly Ser Ser
            275                 280                 285

Thr Thr Ser Thr Gly Pro Cys Arg Thr Cys Thr Thr Pro Ala Gln Gly
        290                 295                 300

Thr Ser Met Phe Pro Ser Cys Cys Cys Thr Lys Pro Thr Asp Gly Asn
305                 310                 315                 320

Cys Thr Cys Ile Pro Ile Pro Ser Ser Trp Ala Phe Ala Lys Tyr Leu
                325                 330                 335

Trp Glu Trp Ala Ser Val Arg Phe Ser Trp Leu Ser Leu Leu Ala Pro
            340                 345                 350

Phe Val Gln Trp Phe Val Gly Leu Ser Pro Thr Val Trp Leu Ser Val
            355                 360                 365

Ile Trp Met Met Trp Phe Trp Gly Pro Ser Leu Tyr Asn Ile Leu Ser
        370                 375                 380

Pro Phe Met Pro Leu Leu Pro Leu Phe Phe Cys Leu Trp Val Tyr Ile
385                 390                 395                 400

<210> SEQ ID NO 8
<211> LENGTH: 155
<212> TYPE: PRT
<213> ORGANISM: Hepatitis B virus

<400> SEQUENCE: 8

Met Ala Ala Arg Leu Cys Cys Gln Leu Asp Pro Ala Arg Asp Val Leu
1               5                   10                  15

Cys Leu Arg Pro Val Gly Ala Glu Ser Arg Gly Arg Pro Leu Pro Gly
            20                  25                  30

Pro Leu Gly Ala Leu Pro Pro Ala Ser Pro Ser Ala Val Pro Thr Asp
        35                  40                  45

His Gly Ala His Leu Ser Leu Pro Gly Leu Pro Val Cys Ala Phe Ser
    50                  55                  60

Ser Ala Gly Pro Cys Ala Leu Arg Phe Thr Ser Ala Arg Arg Met Glu
65                  70                  75                  80

Thr Thr Val Asn Ala His Arg Asn Leu Pro Lys Val Leu His Lys Arg
                85                  90                  95

Thr Leu Gly Leu Ser Ala Met Ser Thr Thr Asp Leu Glu Ala Tyr Phe
            100                 105                 110

Lys Asp Cys Val Phe Asn Glu Trp Glu Glu Leu Gly Glu Glu Ile Arg
        115                 120                 125

Leu Lys Val Leu Phe Val Leu Gly Gly Cys Arg His Lys Leu Val Cys
    130                 135                 140

Ser Pro Ala Pro Cys Asn Phe Phe Thr Ser Ala
145                 150                 155
```

```
<210> SEQ ID NO 9
<211> LENGTH: 212
<212> TYPE: PRT
<213> ORGANISM: Hepatitis B virus

<400> SEQUENCE: 9

Met Gln Leu Phe Pro Leu Cys Leu Ile Ile Ser Cys Ser Cys Pro Thr
1               5                   10                  15

Val Gln Ala Ser Lys Leu Cys Leu Gly Trp Leu Trp Gly Met Asp Ile
            20                  25                  30

Asp Pro Tyr Lys Glu Phe Gly Ala Ser Val Glu Leu Leu Ser Phe Leu
        35                  40                  45

Pro Ser Asp Phe Phe Pro Ser Ile Arg Asp Leu Leu Asp Thr Ala Ser
    50                  55                  60

Ala Leu Tyr Arg Glu Ala Leu Glu Ser Pro Glu His Cys Ser Pro His
65                  70                  75                  80

His Thr Ala Leu Arg Gln Ala Ile Leu Cys Trp Gly Glu Leu Met Asn
                85                  90                  95

Leu Ala Thr Trp Val Gly Ser Asn Leu Glu Asp Pro Ala Ser Arg Glu
            100                 105                 110

Leu Val Val Ser Tyr Val Asn Val Asn Met Gly Leu Lys Ile Arg Gln
        115                 120                 125

Leu Leu Trp Phe His Ile Ser Cys Leu Thr Phe Gly Arg Glu Thr Val
    130                 135                 140

Leu Glu Tyr Leu Val Ser Phe Gly Val Trp Ile Arg Thr Pro Pro Ala
145                 150                 155                 160

Tyr Arg Pro Pro Asn Ala Pro Ile Leu Ser Thr Leu Pro Glu Thr Thr
                165                 170                 175

Val Val Arg Arg Arg Gly Arg Ser Pro Arg Arg Arg Thr Pro Ser Pro
            180                 185                 190

Arg Arg Arg Arg Ser Gln Ser Pro Arg Arg Arg Arg Ser Gln Ser Arg
        195                 200                 205

Glu Ser Gln Cys
    210

<210> SEQ ID NO 10
<211> LENGTH: 843
<212> TYPE: PRT
<213> ORGANISM: Hepatitis B virus

<400> SEQUENCE: 10

Met Pro Leu Ser Tyr Gln His Phe Arg Lys Leu Leu Leu Leu Asp Asp
1               5                   10                  15

Glu Ala Gly Pro Leu Glu Glu Glu Leu Pro Arg Leu Ala Asp Glu Gly
            20                  25                  30

Leu Asn Arg Arg Val Ala Glu Asp Leu Asn Leu Gly Asn Leu Asn Val
        35                  40                  45

Ser Ile Pro Trp Thr His Lys Val Gly Asn Phe Thr Gly Leu Tyr Ser
    50                  55                  60

Ser Thr Val Pro Val Phe Asn Pro Glu Trp Gln Thr Pro Ser Phe Pro
65                  70                  75                  80

His Ile His Leu Gln Glu Asp Ile Ile Asn Arg Cys Gln Gln Tyr Val
                85                  90                  95

Gly Pro Leu Thr Val Asn Glu Lys Arg Arg Leu Lys Leu Ile Met Pro
            100                 105                 110
```

```
Ala Arg Phe Tyr Pro Asn Leu Thr Lys Tyr Leu Pro Leu Asp Lys Gly
            115                 120                 125

Ile Lys Pro Tyr Tyr Pro Glu His Ala Val Asn His Tyr Phe Lys Thr
    130                 135                 140

Arg His Tyr Leu His Thr Leu Trp Lys Ala Gly Ile Leu Tyr Lys Arg
145                 150                 155                 160

Glu Thr Thr Arg Ser Ala Ser Phe Cys Gly Ser Pro Tyr Ser Trp Glu
                165                 170                 175

Gln Glu Leu Gln His Gly Arg Ser Val Phe Gln Thr Ser Lys Arg His
            180                 185                 190

Gly Asp Glu Ser Phe Cys Ser Gln Ser Ser Gly Ile Leu Ser Arg Ser
            195                 200                 205

Pro Val Gly Pro Cys Val Arg Ser Gln Leu Lys Gln Ser Arg Leu Gly
    210                 215                 220

Leu Gln Pro Gln Gln Gly Ser Leu Ala Arg Gly Lys Ser Gly Arg Ser
225                 230                 235                 240

Gly Ser Ile Arg Ala Arg Val His Pro Thr Thr Arg Arg Ser Phe Gly
                245                 250                 255

Val Glu Pro Ser Gly Ser Gly His Ile Asp Asn Ser Ala Ser Ser Thr
            260                 265                 270

Ser Ser Cys Leu His Gln Ser Ala Val Arg Lys Thr Ala Tyr Ser His
            275                 280                 285

Leu Ser Thr Ser Lys Arg Gln Ser Ser Ser Gly His Ala Val Glu Leu
            290                 295                 300

His Asn Ile Pro Pro Ser Ser Thr Arg Ser Gln Ser Glu Gly Pro Ile
305                 310                 315                 320

Phe Ser Cys Trp Trp Leu Gln Phe Arg Asn Ser Lys Pro Cys Ser Asp
                325                 330                 335

Tyr Cys Leu Thr His Ile Val Asn Leu Leu Glu Asp Trp Gly Pro Cys
            340                 345                 350

Thr Glu His Gly Glu His Asn Ile Arg Ile Pro Arg Thr Pro Ala Arg
            355                 360                 365

Val Thr Gly Gly Val Phe Leu Val Asp Lys Asn Pro His Asn Thr Thr
            370                 375                 380

Glu Ser Arg Leu Val Val Asp Phe Ser Gln Phe Ser Arg Gly Ser Thr
385                 390                 395                 400

His Val Ser Trp Pro Lys Phe Ala Val Pro Asn Leu Gln Ser Leu Thr
                405                 410                 415

Asn Leu Leu Ser Ser Asn Leu Ser Trp Leu Ser Leu Asp Val Ser Ala
            420                 425                 430

Ala Phe Tyr His Ile Pro Leu His Pro Ala Ala Met Pro His Leu Leu
            435                 440                 445

Val Gly Ser Ser Gly Leu Pro Arg Tyr Val Ala Arg Leu Ser Ser Thr
    450                 455                 460

Ser Arg Asn Ile Asn Tyr Gln His Gly Thr Met Gln Asp Leu His Asp
465                 470                 475                 480

Ser Cys Ser Arg Asn Leu Tyr Val Ser Leu Leu Leu Leu Tyr Lys Thr
                485                 490                 495

Phe Gly Arg Lys Leu His Leu Tyr Ser His Pro Ile Ile Leu Gly Phe
            500                 505                 510

Arg Lys Ile Pro Met Gly Val Gly Leu Ser Pro Phe Leu Leu Ala Gln
            515                 520                 525
```

```
Phe Thr Ser Ala Ile Cys Ser Val Val Arg Arg Ala Phe Pro His Cys
            530                 535                 540

Leu Ala Phe Ser Tyr Met Asp Asp Val Val Leu Gly Ala Lys Ser Val
545                 550                 555                 560

Gln His Leu Glu Ser Leu Phe Thr Ser Ile Thr Asn Phe Leu Leu Ser
            565                 570                 575

Leu Gly Ile His Leu Asn Pro Asn Lys Thr Lys Arg Trp Gly Tyr Ser
            580                 585                 590

Leu Asn Phe Met Gly Tyr Val Ile Gly Ser Trp Gly Thr Leu Pro Gln
            595                 600                 605

Glu His Ile Val Gln Lys Leu Lys Gln Cys Phe Arg Lys Leu Pro Val
            610                 615                 620

Asn Arg Pro Ile Asp Trp Lys Val Cys Gln Arg Ile Val Gly Leu Leu
625                 630                 635                 640

Gly Phe Ala Ala Pro Phe Thr Gln Cys Gly Tyr Pro Ala Leu Met Pro
            645                 650                 655

Leu Tyr Ala Cys Ile Gln Ala Lys Gln Ala Phe Thr Phe Ser Pro Thr
            660                 665                 670

Tyr Lys Ala Phe Leu Cys Lys Gln Tyr Leu Asn Leu Tyr Pro Val Ala
            675                 680                 685

Arg Gln Arg Ser Gly Leu Cys Gln Val Phe Ala Asp Ala Thr Pro Thr
            690                 695                 700

Gly Trp Gly Leu Ala Ile Gly His Gln Arg Met Arg Gly Thr Phe Val
705                 710                 715                 720

Ala Pro Leu Pro Ile His Thr Ala Glu Leu Leu Ala Ala Cys Phe Ala
            725                 730                 735

Arg Ser Arg Ser Gly Ala Lys Leu Ile Gly Thr Asp Asn Ser Val Val
            740                 745                 750

Leu Ser Arg Lys Tyr Thr Ser Phe Pro Trp Leu Leu Gly Cys Thr Ala
            755                 760                 765

Asn Trp Ile Leu Arg Gly Thr Ser Phe Val Tyr Val Pro Ser Ala Leu
770                 775                 780

Asn Pro Ala Asp Asp Pro Ser Arg Gly Arg Leu Gly Leu Tyr Arg Pro
785                 790                 795                 800

Leu Leu Arg Leu Pro Phe Arg Pro Thr Thr Gly Arg Thr Ser Leu Tyr
            805                 810                 815

Ala Asp Ser Pro Ser Val Pro Ser His Leu Pro Asp Arg Val His Phe
            820                 825                 830

Ala Ser Pro Leu His Val Ala Trp Lys Pro Pro
            835                 840

<210> SEQ ID NO 11
<211> LENGTH: 400
<212> TYPE: PRT
<213> ORGANISM: Hepatitis B virus

<400> SEQUENCE: 11

Met Gly Gly Trp Ser Ser Lys Pro Arg Lys Gly Met Gly Thr Asn Leu
1               5                   10                  15

Ser Val Pro Asn Pro Leu Gly Phe Phe Pro Asp His Gln Leu Asp Pro
            20                  25                  30

Ala Phe Gly Ala Asn Ser Asn Asn Pro Asp Trp Asp Phe Asn Pro Asn
        35                  40                  45

Lys Asp His Trp Pro Glu Ala Asn Gln Val Gly Val Gly Ala Phe Gly
50                  55                  60
```

-continued

Pro Gly Phe Thr Pro Pro His Gly Gly Leu Leu Gly Trp Ser Pro Gln
65                  70                  75                  80

Ala Gln Gly Ile Leu Thr Thr Val Pro Ala Ala Pro Pro Pro Ala Ser
                85                  90                  95

Thr Asn Arg Gln Ser Gly Arg Gln Pro Thr Pro Ile Ser Pro Pro Leu
            100                 105                 110

Arg Asp Ser His Pro Gln Ala Met Gln Trp Asn Ser Thr Thr Phe His
            115                 120                 125

Gln Ala Leu Leu Asp Pro Arg Val Arg Gly Leu Tyr Phe Pro Ala Gly
        130                 135                 140

Gly Ser Ser Ser Gly Thr Val Asn Pro Val Pro Thr Thr Ala Ser Pro
145                 150                 155                 160

Ile Ser Ser Ile Phe Ser Arg Thr Gly Asp Pro Ala Pro Asn Met Glu
                165                 170                 175

Asn Thr Thr Ser Gly Phe Leu Gly Pro Leu Leu Val Leu Gln Ala Gly
            180                 185                 190

Phe Phe Leu Leu Thr Arg Ile Leu Thr Ile Pro Gln Ser Leu Asp Ser
        195                 200                 205

Trp Trp Thr Ser Leu Asn Phe Leu Gly Gly Ala Pro Thr Cys Pro Gly
210                 215                 220

Gln Asn Ser Gln Ser Pro Thr Ser Asn His Ser Pro Thr Ser Cys Pro
225                 230                 235                 240

Pro Ile Cys Pro Gly Tyr Arg Trp Met Cys Leu Arg Arg Phe Ile Ile
                245                 250                 255

Phe Leu Phe Ile Leu Leu Leu Cys Leu Ile Phe Leu Leu Val Leu Leu
            260                 265                 270

Asp Tyr Gln Gly Met Leu Pro Val Cys Pro Leu Leu Pro Gly Thr Ser
        275                 280                 285

Thr Thr Ser Thr Gly Pro Cys Lys Thr Cys Thr Ile Pro Ala Gln Gly
290                 295                 300

Thr Ser Met Phe Pro Ser Cys Cys Cys Thr Lys Pro Ser Asp Gly Asn
305                 310                 315                 320

Cys Thr Cys Ile Pro Ile Pro Ser Ser Trp Ala Phe Ala Arg Phe Leu
                325                 330                 335

Trp Glu Trp Ala Ser Val Arg Phe Ser Trp Leu Ser Leu Leu Val Pro
            340                 345                 350

Phe Val Gln Trp Phe Val Gly Leu Ser Pro Thr Val Trp Leu Ser Val
        355                 360                 365

Ile Trp Met Met Trp Tyr Trp Gly Pro Ser Leu Tyr Asn Ile Leu Asn
370                 375                 380

Pro Phe Leu Pro Leu Leu Pro Ile Phe Phe Cys Leu Trp Val Tyr Ile
385                 390                 395                 400

<210> SEQ ID NO 12
<211> LENGTH: 154
<212> TYPE: PRT
<213> ORGANISM: Hepatitis B virus

<400> SEQUENCE: 12

Met Ala Ala Arg Val Cys Cys Lys Leu Asp Pro Ala Arg Asp Val Leu
1               5                   10                  15

Cys Leu Arg Pro Val Gly Ala Glu Ser Ser Gly Arg Pro Val Ser Gly
            20                  25                  30

Pro Phe Gly Thr Leu Pro Ser Pro Ser Ser Ala Val Pro Ala Asp

```
                  35                  40                  45
His Gly Ala His Leu Ser Leu Arg Gly Leu Pro Val Cys Ala Phe Ser
 50                  55                  60

Ser Ala Gly Pro Cys Ala Leu Arg Phe Thr Ser Ala Arg Arg Met Glu
 65                  70                  75                  80

Thr Thr Val Asn Ala His Gln Val Leu Pro Lys Val Leu His Lys Arg
                 85                  90                  95

Thr Leu Gly Leu Ser Ala Met Ser Thr Thr Asp Leu Glu Ala Tyr Phe
                100                 105                 110

Lys Asp Cys Val Phe Lys Asp Trp Glu Glu Leu Gly Glu Glu Ile Arg
                115                 120                 125

Leu Lys Val Phe Val Leu Gly Gly Cys Arg His Lys Leu Val Cys Ser
                130                 135                 140

Pro Ala Pro Cys Asn Phe Phe Thr Ser Ala
145                 150

<210> SEQ ID NO 13
<211> LENGTH: 212
<212> TYPE: PRT
<213> ORGANISM: Hepatitis B virus

<400> SEQUENCE: 13

Met Gln Leu Phe His Leu Cys Leu Ile Ile Ser Cys Ser Cys Pro Thr
 1               5                  10                  15

Val Gln Ala Ser Lys Leu Cys Leu Gly Trp Leu Trp Asp Met Asp Ile
                20                  25                  30

Asp Pro Tyr Lys Glu Phe Gly Ala Thr Val Glu Leu Leu Ser Phe Leu
                35                  40                  45

Pro Ser Asp Phe Phe Pro Ser Val Arg Asp Leu Leu Asp Thr Ala Ser
 50                  55                  60

Ala Leu Tyr Arg Glu Ala Leu Glu Ser Pro Glu His Cys Ser Pro His
 65                  70                  75                  80

His Thr Ala Leu Arg Gln Ala Ile Leu Cys Trp Gly Glu Leu Met Thr
                 85                  90                  95

Leu Ala Thr Trp Val Gly Val Asn Leu Glu Asp Pro Ala Ser Arg Asp
                100                 105                 110

Leu Val Val Ser Tyr Val Asn Thr Asn Met Gly Leu Lys Phe Arg Gln
                115                 120                 125

Leu Leu Trp Phe His Ile Ser Cys Leu Thr Phe Gly Arg Glu Thr Val
                130                 135                 140

Ile Glu Tyr Leu Val Ser Phe Gly Val Trp Ile Arg Thr Pro Pro Ala
145                 150                 155                 160

Tyr Arg Pro Pro Asn Ala Pro Ile Leu Ser Thr Leu Pro Glu Thr Thr
                165                 170                 175

Val Val Arg Arg Arg Gly Arg Ser Pro Arg Arg Arg Thr Pro Ser Pro
                180                 185                 190

Arg Arg Arg Arg Ser Gln Ser Pro Arg Arg Arg Arg Ser Gln Ser Arg
                195                 200                 205

Glu Ser Gln Cys
    210

<210> SEQ ID NO 14
<211> LENGTH: 832
<212> TYPE: PRT
<213> ORGANISM: Hepatitis B virus
```

```
<400> SEQUENCE: 14

Met Pro Leu Ser Tyr Gln His Phe Arg Arg Leu Leu Leu Asp Pro
1               5                  10                  15

Asp Ala Gly Pro Leu Glu Glu Leu Pro Arg Leu Ala Asp Glu Gly
                20                  25                  30

Leu Asn Arg Arg Val Ala Glu Asp Leu Asn Leu Gly Asn Leu Asn Val
            35                  40                  45

Ser Ile Pro Trp Thr His Lys Val Gly Asn Phe Thr Gly Leu Tyr Ser
    50                  55                  60

Ser Thr Val Pro Val Phe Asn Pro His Trp Lys Thr Pro Ser Phe Pro
65                  70                  75                  80

Asn Ile His Leu His Gln Asp Ile Ile Lys Lys Cys Glu Gln Phe Val
                85                  90                  95

Gly Pro Leu Thr Val Asn Glu Lys Arg Arg Leu Gln Leu Ile Met Pro
                100                 105                 110

Ala Arg Phe Tyr Pro Asn Val Thr Lys Tyr Leu Pro Leu Glu Lys Gly
            115                 120                 125

Ile Lys Pro Tyr Tyr Pro Glu His Leu Val Asn His Tyr Phe Gln Thr
    130                 135                 140

Arg His Tyr Leu His Thr Leu Trp Lys Ala Gly Ile Leu Tyr Lys Arg
145                 150                 155                 160

Glu Thr Thr Arg Ser Ala Ser Phe Cys Gly Ser Pro Tyr Ser Trp Glu
                165                 170                 175

Gln Glu Leu Gln His Gly Ala Glu Ser Phe His Gln Ser Ser Gly
            180                 185                 190

Ile Leu Ser Arg Pro Pro Val Gly Ser Ser Leu Gln Ser Lys His Arg
    195                 200                 205

Lys Ser Arg Leu Gly Leu Gln Ser Gln Gln Gly His Leu Ala Arg Arg
210                 215                 220

Gln Gln Gly Arg Ser Trp Ser Ile Arg Ala Gly Ile His Pro Thr Ala
225                 230                 235                 240

Arg Arg Pro Phe Gly Val Glu Pro Ser Gly Ser Gly His Thr Ala Asn
                245                 250                 255

Leu Ala Asn Lys Ser Ala Ser Cys Leu Tyr Gln Ser Ser Val Arg Lys
            260                 265                 270

Ala Ala Tyr Ser Ser Val Ser Thr Phe Glu Lys His Ser Ser Ser Ser
    275                 280                 285

Asn Ala Val Glu Leu His Asn Leu Pro Pro Asn Pro Ala Arg Ser Gln
290                 295                 300

Ser Glu Arg Pro Val Phe Pro Cys Trp Trp Leu Gln Phe Arg Asn Ser
305                 310                 315                 320

Lys Pro Cys Ser Asp Tyr Cys Leu Ser His Ile Val Asn Leu Leu Glu
                325                 330                 335

Asp Trp Gly Pro Cys Ala Glu His Gly Glu His His Ile Arg Ile Pro
            340                 345                 350

Arg Thr Pro Ala Arg Val Thr Gly Gly Val Phe Leu Val Asp Lys Asn
    355                 360                 365

Pro His Asn Thr Val Glu Ser Arg Leu Val Val Asp Phe Ser Gln Phe
370                 375                 380

Ser Arg Gly Asn His Arg Val Ser Trp Pro Lys Phe Ala Val Pro Asn
385                 390                 395                 400

Leu Gln Ser Leu Thr Asn Leu Leu Ser Ser Asn Leu Ser Trp Leu Ser
                405                 410                 415
```

```
Leu Asp Val Ser Ala Ala Phe Tyr His Leu Pro Leu His Pro Ala Ala
            420                 425                 430

Met Pro His Leu Leu Val Gly Ser Ser Gly Leu Ser Arg Tyr Val Ala
            435                 440                 445

Arg Leu Ser Ser Asn Ser Arg Ile Phe Asn His Gln His Gly Thr Met
            450                 455                 460

Gln Asn Leu His Asp Ser Cys Ser Arg Asn Leu Tyr Val Ser Leu Leu
465                 470                 475                 480

Leu Leu Tyr Gln Thr Phe Gly Arg Lys Leu His Leu Tyr Ser His Pro
                    485                 490                 495

Ile Ile Leu Gly Phe Arg Lys Ile Pro Met Gly Val Gly Leu Ser Pro
            500                 505                 510

Phe Leu Leu Ala Gln Phe Thr Ser Ala Ile Cys Ser Val Val Arg Arg
            515                 520                 525

Ala Phe Pro His Cys Leu Ala Phe Ser Tyr Met Asp Asp Val Val Leu
            530                 535                 540

Gly Ala Lys Ser Val Gln His Leu Glu Ser Leu Phe Thr Ala Val Thr
545                 550                 555                 560

Asn Phe Leu Leu Ser Leu Gly Ile His Leu Asn Pro Asn Lys Thr Lys
                    565                 570                 575

Arg Trp Gly Tyr Ser Leu His Phe Met Gly Tyr Val Ile Gly Ser Tyr
            580                 585                 590

Gly Ser Leu Pro Gln Asp His Ile Arg Gln Lys Ile Lys Glu Cys Phe
            595                 600                 605

Arg Lys Leu Pro Val Asn Arg Pro Ile Asp Trp Lys Val Cys Gln Arg
            610                 615                 620

Ile Val Gly Leu Leu Gly Phe Ala Ala Pro Phe Thr Gln Cys Gly Tyr
625                 630                 635                 640

Pro Ala Leu Lys Pro Leu Tyr Ala Cys Ile Gln Ser Lys Gln Ala Phe
                    645                 650                 655

Thr Phe Ser Pro Thr Tyr Lys Ala Phe Leu Cys Lys Gln Tyr Leu Asn
            660                 665                 670

Leu Tyr Pro Val Ala Arg Gln Arg Pro Gly Leu Cys Gln Val Phe Ala
            675                 680                 685

Asp Ala Thr Pro Thr Gly Trp Gly Leu Val Met Gly His Gln Arg Met
            690                 695                 700

Arg Gly Thr Phe Leu Asp Pro Leu Pro Ile His Thr Ala Glu Leu Leu
705                 710                 715                 720

Ala Ala Cys Phe Ala Arg Ser Arg Ser Gly Ala Asn Ile Leu Gly Thr
                    725                 730                 735

Asp Asn Ser Val Val Leu Ser Arg Lys Tyr Thr Ser Phe Pro Trp Leu
            740                 745                 750

Leu Gly Cys Ala Ala Asn Trp Ile Leu Arg Gly Thr Ser Phe Val Tyr
            755                 760                 765

Val Pro Ser Ala Leu Asn Pro Ala Asp Asp Pro Ser Arg Gly Arg Leu
            770                 775                 780

Gly Leu Ser Arg Pro Leu Leu Arg Leu Pro Phe Arg Pro Thr Thr Gly
785                 790                 795                 800

Arg Thr Ser Leu Tyr Ala Asp Ser Pro Ser Val Pro Ser His Leu Pro
                    805                 810                 815

Asp Arg Val His Phe Ala Ser Pro Leu His Val Ala Trp Arg Pro Pro
            820                 825                 830
```

```
<210> SEQ ID NO 15
<211> LENGTH: 389
<212> TYPE: PRT
<213> ORGANISM: Hepatitis B virus

<400> SEQUENCE: 15

Met Gly Gln Asn Leu Ser Thr Ser Asn Pro Leu Gly Phe Phe Pro Asp
1               5                   10                  15

His Gln Leu Asp Pro Ala Phe Arg Ala Asn Thr Ala Asn Pro Asp Trp
            20                  25                  30

Asp Phe Asn Pro Asn Lys Asp Thr Trp Pro Asp Ala Asn Lys Val Gly
        35                  40                  45

Ala Gly Ala Phe Gly Leu Gly Phe Thr Pro Pro His Gly Gly Leu Leu
    50                  55                  60

Gly Trp Ser Pro Gln Ala Gln Gly Ile Leu Gln Thr Leu Pro Ala Asn
65                  70                  75                  80

Pro Pro Pro Ala Ser Thr Asn Arg Gln Ser Gly Arg Gln Pro Thr Pro
                85                  90                  95

Leu Ser Pro Pro Leu Arg Asn Thr His Pro Gln Ala Met Gln Trp Asn
            100                 105                 110

Ser Thr Thr Phe His Gln Thr Leu Gln Asp Pro Arg Val Arg Gly Leu
        115                 120                 125

Tyr Phe Pro Ala Gly Gly Ser Ser Ser Gly Thr Val Asn Pro Val Pro
    130                 135                 140

Thr Thr Val Ser His Thr Ser Ser Ile Phe Ser Arg Ile Gly Asp Pro
145                 150                 155                 160

Ala Leu Asn Met Glu Asn Ile Thr Ser Gly Leu Leu Gly Pro Leu Leu
                165                 170                 175

Val Leu Gln Ala Gly Phe Phe Leu Leu Thr Arg Ile Leu Thr Ile Pro
            180                 185                 190

Gln Ser Leu Asp Ser Trp Trp Thr Ser Leu Asn Phe Leu Gly Gly Thr
        195                 200                 205

Thr Val Cys Leu Gly Gln Asn Ser Gln Ser Pro Thr Ser Asn His Ser
    210                 215                 220

Pro Thr Ser Cys Pro Pro Thr Cys Pro Gly Tyr Arg Trp Met Cys Leu
225                 230                 235                 240

Arg Arg Phe Ile Ile Phe Leu Phe Ile Leu Leu Leu Cys Leu Ile Phe
                245                 250                 255

Leu Leu Val Leu Leu Asp Tyr Gln Gly Met Leu Pro Val Cys Pro Leu
            260                 265                 270

Ile Pro Gly Ser Ser Thr Thr Ser Thr Gly Pro Cys Arg Thr Cys Thr
        275                 280                 285

Thr Pro Ala Gln Gly Thr Ser Met Tyr Pro Ser Cys Cys Cys Thr Lys
    290                 295                 300

Pro Ser Asp Gly Asn Cys Thr Cys Ile Pro Ile Pro Ser Ser Trp Ala
305                 310                 315                 320

Phe Gly Lys Phe Leu Trp Glu Trp Ala Ser Ala Arg Phe Ser Trp Leu
                325                 330                 335

Ser Leu Leu Val Pro Phe Val Gln Trp Phe Val Gly Leu Ser Pro Thr
            340                 345                 350

Val Trp Leu Ser Val Ile Trp Met Met Trp Tyr Trp Gly Pro Ser Leu
        355                 360                 365

Tyr Asn Ile Leu Ser Pro Phe Leu Pro Leu Leu Pro Ile Phe Phe Cys
    370                 375                 380
```

```
Leu Trp Val Tyr Ile
385

<210> SEQ ID NO 16
<211> LENGTH: 154
<212> TYPE: PRT
<213> ORGANISM: Hepatitis B virus

<400> SEQUENCE: 16

Met Ala Ala Arg Leu Cys Cys Gln Leu Asp Pro Ala Arg Asp Val Leu
1               5                   10                  15

Cys Leu Arg Pro Val Ser Ala Glu Ser Cys Gly Arg Pro Val Ser Gly
            20                  25                  30

Pro Phe Gly Thr Leu Ser Ser Pro Ser Pro Ser Ala Val Ser Thr Asp
        35                  40                  45

His Gly Ala His Leu Ser Leu Arg Gly Leu Pro Val Cys Ala Phe Ser
    50                  55                  60

Ser Ala Gly Pro Cys Ala Leu Arg Phe Thr Ser Ala Arg Arg Met Glu
65                  70                  75                  80

Thr Thr Val Asn Ala His Gln Phe Leu Pro Lys Val Leu His Lys Arg
                85                  90                  95

Thr Leu Gly Leu Ser Val Met Ser Thr Thr Asp Leu Glu Ala Tyr Phe
            100                 105                 110

Lys Asp Cys Leu Phe Lys Asp Trp Glu Glu Leu Gly Glu Glu Thr Arg
        115                 120                 125

Leu Met Ile Phe Val Leu Gly Gly Cys Arg His Lys Leu Val Cys Ala
    130                 135                 140

Pro Ala Pro Cys Asn Phe Phe Thr Ser Ala
145                 150

<210> SEQ ID NO 17
<211> LENGTH: 212
<212> TYPE: PRT
<213> ORGANISM: Hepatitis B virus

<400> SEQUENCE: 17

Met Gln Leu Phe His Leu Cys Leu Ile Ile Ser Cys Ser Cys Pro Thr
1               5                   10                  15

Val Gln Ala Ser Lys Leu Cys Leu Gly Trp Leu Trp Gly Met Asp Ile
            20                  25                  30

Asp Pro Tyr Lys Glu Phe Gly Ala Thr Val Glu Leu Leu Ser Phe Leu
        35                  40                  45

Pro Ser Asp Phe Phe Pro Ser Val Arg Asp Leu Leu Asp Thr Ala Ser
    50                  55                  60

Ala Leu Tyr Arg Asp Ala Leu Glu Ser Pro Glu His Cys Ser Pro His
65                  70                  75                  80

His Thr Ala Leu Arg Gln Ala Ile Leu Cys Trp Gly Glu Leu Met Thr
                85                  90                  95

Leu Ala Thr Trp Val Gly Val Asn Leu Glu Asp Pro Ala Ser Arg Asp
            100                 105                 110

Leu Val Val Ser Tyr Val Asn Thr Asn Met Gly Leu Lys Phe Arg Gln
        115                 120                 125

Leu Leu Trp Phe His Ile Ser Cys Leu Thr Phe Gly Arg Glu Thr Val
    130                 135                 140

Ile Glu Tyr Leu Val Ser Phe Gly Val Trp Ile Arg Thr Pro Pro Ala
145                 150                 155                 160
```

Tyr Arg Pro Pro Asn Ala Pro Ile Leu Ser Thr Leu Pro Glu Asn Thr
                165                 170                 175

Val Val Arg Arg Arg Gly Arg Ser Pro Arg Arg Arg Thr Pro Ser Pro
            180                 185                 190

Cys Arg Arg Arg Ser Gln Ser Pro Arg Arg Arg Ser Gln Ser Pro
            195                 200                 205

Ala Ser Gln Cys
    210

<210> SEQ ID NO 18
<211> LENGTH: 842
<212> TYPE: PRT
<213> ORGANISM: Hepatitis B virus

<400> SEQUENCE: 18

Met Pro Leu Ser Tyr Gln His Phe Arg Arg Ile Leu Leu Leu Asp Glu
1               5                   10                  15

Glu Ala Gly Pro Leu Glu Glu Leu Pro Arg Leu Ala Asp Glu Asp
            20                  25                  30

Leu Asn Arg Arg Val Ala Glu Asp Leu Asn Leu Gln Leu Pro Asn Val
        35                  40                  45

Ser Ile Pro Trp Thr His Lys Val Gly Asn Phe Thr Gly Leu Tyr Ser
    50                  55                  60

Ser Thr Val Pro Val Phe Asn Pro Asn Trp Lys Thr Pro Ser Phe Pro
65                  70                  75                  80

Asp Ile His Leu His Gln Asp Ile Ile Asn Lys Cys Glu Gln Leu Val
                85                  90                  95

Gly Pro Leu Thr Val Asn Glu Lys Arg Arg Leu Asn Leu Val Met Pro
            100                 105                 110

Ala Arg Phe Phe Pro Ile Ser Thr Lys Tyr Leu Pro Leu Asp Lys Gly
        115                 120                 125

Ile Lys Pro Tyr Tyr Pro Asp Asn Val Val Asn His Tyr Phe Gln Thr
    130                 135                 140

Arg His Tyr Leu His Thr Leu Trp Lys Ala Gly Ile Leu Tyr Lys Arg
145                 150                 155                 160

Glu Thr Thr Arg Ser Ala Ser Phe Cys Gly Ser Pro Tyr Ser Trp Glu
                165                 170                 175

Gln Glu Leu His His Gly Ala Phe Leu Asp Gly Pro Ser Arg Met Gly
            180                 185                 190

Glu Glu Ser Phe His His Gln Ser Ser Gly Ile Phe Ser Arg Pro Pro
        195                 200                 205

Val Gly Ser Ser Ile Gln Ser Lys His Gln Lys Ser Arg Leu Gly Pro
    210                 215                 220

Gln Ser Gln Gln Arg Pro Leu Asp Arg Ser Gln Gln Gly Arg Ser Gly
225                 230                 235                 240

Ser Ile Arg Ala Gly Val His Ser Pro Thr Arg Pro Phe Gly Val
                245                 250                 255

Glu Pro Ser Gly Ser Arg His Ala Lys Asn Ile Ala Ser Arg Ser Ala
            260                 265                 270

Ser Cys Leu His Gln Ser Ala Val Arg Lys Ala Ala Tyr Pro Asn His
        275                 280                 285

Ser Thr Phe Glu Arg His Ser Ser Ser Gly His Ala Val Glu Phe His
    290                 295                 300

Asn Ile Pro Pro Ser Ser Ala Gly Ser Gln Ser Lys Arg Pro Val Phe

```
               305                 310                 315                 320
           Ser Cys Trp Trp Leu Gln Phe Arg Asn Ser Glu Pro Cys Ser Asp Tyr
                           325                 330                 335

Cys Leu Thr His Leu Val Asn Leu Leu Gln Asp Trp Gly Pro Cys Thr
                           340                 345                 350

Glu His Gly Lys His His Ile Arg Ile Pro Arg Thr Pro Ala Arg Val
                           355                 360                 365

Thr Gly Gly Val Phe Leu Val Asp Lys Asn Pro His Asn Thr Ala Glu
                           370                 375                 380

Ser Arg Leu Val Val Asp Phe Ser Gln Phe Ser Arg Gly Ser Ser Arg
           385                 390                 395                 400

Val Ser Trp Pro Lys Phe Ala Val Pro Asn Leu Gln Ser Leu Thr Asn
                           405                 410                 415

Leu Leu Ser Ser Asn Leu Ser Trp Leu Ser Leu Asp Val Ser Ala Ala
                           420                 425                 430

Phe Tyr His Leu Pro Leu His Pro Ala Ala Met Pro His Leu Leu Val
                           435                 440                 445

Gly Ser Ser Gly Leu Ser Arg Tyr Val Ala Arg Leu Ser Ser Asn Ser
                           450                 455                 460

Arg Ile Ile Asn His Gln Tyr Gly Thr Leu Pro Asn Leu His Asp Ser
           465                 470                 475                 480

Cys Ser Arg Asn Leu Tyr Ile Ser Leu Met Leu Leu Phe Lys Thr Phe
                           485                 490                 495

Gly Arg Lys Leu His Leu Tyr Ser His Pro Ile Ile Met Gly Phe Arg
                           500                 505                 510

Lys Ile Pro Met Gly Val Gly Leu Ser Pro Phe Leu Leu Ala Gln Phe
                           515                 520                 525

Thr Ser Ala Ile Cys Ser Val Val Arg Arg Ala Phe Pro His Cys Leu
                           530                 535                 540

Ala Phe Ser Tyr Met Asp Asp Val Val Leu Gly Ala Lys Ser Val Gln
           545                 550                 555                 560

His Leu Glu Ser Leu Tyr Thr Ala Val Thr Asn Phe Leu Leu Ser Leu
                           565                 570                 575

Gly Ile His Leu Asn Pro Asn Lys Thr Lys Arg Trp Gly Tyr Ser Leu
                           580                 585                 590

Asn Phe Met Gly Tyr Val Ile Gly Ser Trp Gly Ser Leu Pro Gln Glu
                           595                 600                 605

His Ile Arg Leu Lys Ile Lys Asp Cys Phe Arg Lys Leu Pro Val Asn
                           610                 615                 620

Arg Pro Ile Asp Trp Lys Val Cys Gln Arg Ile Val Gly Leu Leu Gly
           625                 630                 635                 640

Phe Ala Ala Pro Phe Thr Gln Cys Gly Tyr Pro Ala Leu Met Pro Leu
                           645                 650                 655

Tyr Ala Cys Thr Gln Ser Lys Gln Ala Phe Thr Phe Ser Pro Thr Tyr
                           660                 665                 670

Lys Ala Phe Leu Cys Lys Gln Tyr Met Asn Leu Tyr Pro Val Ala Arg
                           675                 680                 685

Gln Arg Pro Gly Leu Cys Gln Val Phe Ala Asp Ala Thr Pro Thr Gly
                           690                 695                 700

Trp Gly Leu Ala Ile Gly His Gln Arg Met Arg Gly Thr Phe Val Ala
           705                 710                 715                 720

Pro Leu Pro Ile His Thr Ala Glu Leu Leu Ala Ala Cys Phe Ala Arg
                           725                 730                 735
```

```
Ser Arg Ser Gly Ala Lys Leu Ile Gly Thr Asp Asn Ser Val Val Leu
        740                 745                 750

Ser Arg Lys Tyr Thr Ser Phe Pro Trp Leu Leu Gly Cys Ala Ala Asn
        755                 760                 765

Trp Ile Leu Arg Gly Thr Ser Phe Val Tyr Val Pro Ser Ala Leu Asn
770                 775                 780

Pro Ala Asp Asp Pro Ser Arg Gly Arg Leu Gly Ile Ser Arg Pro Leu
785                 790                 795                 800

Leu Arg Leu Pro Phe Gln Pro Thr Thr Gly Arg Thr Ser Leu Tyr Ala
                    805                 810                 815

Val Ser Pro Ser Val Pro Ser His Leu Pro Asp Arg Val His Phe Ala
                820                 825                 830

Ser Pro Leu His Val Ala Trp Arg Pro Pro
        835                 840

<210> SEQ ID NO 19
<211> LENGTH: 399
<212> TYPE: PRT
<213> ORGANISM: Hepatitis B virus

<400> SEQUENCE: 19

Met Gly Leu Ser Trp Thr Val Pro Leu Glu Trp Gly Lys Asn His Ser
1               5                   10                  15

Thr Thr Asn Pro Leu Gly Phe Phe Pro Asp His Gln Leu Asp Pro Ala
                20                  25                  30

Phe Arg Ala Asn Thr Arg Asn Pro Asp Trp Asp His Asn Pro Asn Lys
            35                  40                  45

Asp His Trp Thr Glu Ala Asn Lys Val Gly Val Gly Ala Phe Gly Pro
        50                  55                  60

Gly Phe Thr Pro Pro His Gly Gly Leu Leu Gly Trp Ser Pro Gln Ala
65                  70                  75                  80

Gln Gly Met Leu Lys Thr Leu Pro Ala Asn Pro Pro Ala Ser Thr
                85                  90                  95

Asn Arg Gln Ser Gly Arg Gln Pro Thr Pro Ile Thr Pro Pro Leu Arg
                100                 105                 110

Asp Thr His Pro Gln Ala Met Gln Trp Asn Ser Thr Thr Phe His Gln
            115                 120                 125

Ala Leu Gln Asp Pro Arg Val Arg Gly Leu Tyr Leu Pro Ala Gly Gly
        130                 135                 140

Ser Ser Ser Gly Thr Val Asn Pro Val Pro Thr Thr Ala Ser Leu Ile
145                 150                 155                 160

Ser Ser Ile Phe Ser Arg Ile Gly Asp Pro Ala Pro Asn Met Glu Gly
                165                 170                 175

Ile Thr Ser Gly Phe Leu Gly Pro Leu Leu Val Leu Gln Ala Gly Phe
            180                 185                 190

Phe Leu Leu Thr Lys Ile Leu Thr Ile Pro Gln Ser Leu Asp Ser Trp
        195                 200                 205

Trp Thr Ser Leu Asn Phe Leu Gly Gly Ala Pro Val Cys Leu Gly Gln
    210                 215                 220

Asn Ser Gln Ser Pro Ile Ser Asn His Ser Pro Thr Ser Cys Pro Pro
225                 230                 235                 240

Ile Cys Pro Gly Tyr Arg Trp Met Cys Leu Arg Arg Phe Ile Ile Phe
                245                 250                 255

Leu Phe Ile Leu Leu Leu Cys Leu Ile Phe Leu Leu Val Leu Leu Asp
```

```
            260                 265                 270
Tyr Gln Gly Met Leu Pro Val Cys Pro Leu Ile Pro Gly Ser Ser Thr
            275                 280                 285

Thr Ser Thr Gly Pro Cys Arg Thr Cys Thr Thr Leu Ala Gln Gly Thr
        290                 295                 300

Ser Met Phe Pro Ser Cys Cys Cys Leu Lys Pro Ser Asp Gly Asn Cys
305                 310                 315                 320

Thr Cys Ile Pro Ile Pro Ser Ser Trp Ala Phe Gly Lys Phe Leu Trp
                325                 330                 335

Glu Trp Ala Ser Ala Arg Phe Ser Trp Leu Ser Leu Leu Val Pro Phe
            340                 345                 350

Val Gln Trp Phe Ala Gly Leu Ser Pro Thr Val Trp Leu Ser Val Ile
        355                 360                 365

Trp Met Met Trp Tyr Trp Gly Pro Ser Leu Tyr Asn Ile Leu Ser Pro
    370                 375                 380

Phe Ile Pro Leu Leu Pro Ile Phe Phe Cys Leu Trp Val Tyr Ile
385                 390                 395

<210> SEQ ID NO 20
<211> LENGTH: 154
<212> TYPE: PRT
<213> ORGANISM: Hepatitis B virus

<400> SEQUENCE: 20

Met Ala Ala Arg Met Cys Cys Gln Leu Asp Pro Ala Arg Asp Val Leu
1               5                   10                  15

Cys Leu Arg Pro Val Ser Ala Glu Ser Cys Gly Arg Pro Val Ser Gly
            20                  25                  30

Ser Leu Gly Asp Leu Ser Ser Pro Ser Pro Ser Ala Val Pro Ala Asp
        35                  40                  45

His Gly Ala His Leu Ser Leu Arg Gly Leu Pro Val Cys Ala Phe Ser
    50                  55                  60

Ser Ala Gly Pro Cys Ala Leu Arg Phe Thr Ser Ala Arg Arg Met Glu
65                  70                  75                  80

Thr Thr Val Asn Ala His Gln Ile Leu Pro Lys Val Leu His Lys Arg
                85                  90                  95

Thr Leu Gly Leu Ser Ala Met Ser Thr Thr Asp Leu Glu Ala Tyr Phe
            100                 105                 110

Lys Asp Cys Leu Phe Lys Asp Trp Glu Glu Leu Gly Glu Glu Ile Arg
        115                 120                 125

Leu Lys Val Phe Val Leu Gly Gly Cys Arg His Lys Leu Val Cys Ala
    130                 135                 140

Pro Ala Pro Cys Asn Phe Phe Thr Ser Ala
145                 150

<210> SEQ ID NO 21
<211> LENGTH: 212
<212> TYPE: PRT
<213> ORGANISM: Hepatitis B virus

<400> SEQUENCE: 21

Met Gln Leu Phe His Leu Cys Leu Ile Ile Phe Cys Ser Cys Pro Thr
1               5                   10                  15

Val Gln Ala Ser Lys Leu Cys Leu Gly Trp Leu Trp Gly Met Asp Ile
            20                  25                  30

Asp Pro Tyr Lys Glu Phe Gly Ala Ser Val Glu Leu Leu Ser Phe Leu
```

```
                35                  40                  45
Pro Ser Asp Phe Phe Pro Ser Val Arg Asp Leu Leu Asp Thr Ala Ser
 50                  55                  60

Ala Leu Tyr Arg Asp Ala Leu Glu Ser Pro Glu His Cys Thr Pro Asn
 65                  70                  75                  80

His Thr Ala Leu Arg Gln Ala Ile Leu Cys Trp Gly Glu Leu Met Thr
                 85                  90                  95

Leu Ala Ser Trp Val Gly Asn Asn Leu Glu Asp Pro Ala Ala Arg Asp
                100                 105                 110

Leu Val Val Asn Tyr Val Asn Thr Asn Met Gly Leu Lys Ile Arg Gln
                115                 120                 125

Leu Leu Trp Phe His Ile Ser Cys Leu Thr Phe Gly Arg Glu Thr Val
130                 135                 140

Leu Glu Tyr Leu Val Ser Phe Gly Val Trp Ile Arg Thr Pro Pro Ala
145                 150                 155                 160

Tyr Arg Pro Pro Asn Ala Pro Ile Leu Ser Thr Leu Pro Glu Thr Thr
                165                 170                 175

Val Val Arg Arg Arg Gly Arg Ser Pro Arg Arg Arg Thr Pro Ser Pro
                180                 185                 190

Arg Arg Arg Arg Ser Gln Ser Pro Arg Arg Arg Arg Ser Gln Ser Pro
                195                 200                 205

Ala Ser Lys Cys
                210

<210> SEQ ID NO 22
<211> LENGTH: 843
<212> TYPE: PRT
<213> ORGANISM: Hepatitis B virus

<400> SEQUENCE: 22

Met Pro Leu Ser Tyr Pro His Phe Arg Lys Leu Leu Leu Leu Asp Asp
 1               5                  10                  15

Glu Ala Gly Pro Leu Glu Glu Glu Leu Pro Arg Leu Ala Asp Glu Gly
                 20                  25                  30

Leu Asn Arg Arg Val Ala Glu Asp Leu Asn Leu Gln Leu Pro Asn Val
                 35                  40                  45

Ser Ile Pro Trp Thr His Lys Val Gly Asn Phe Thr Gly Leu Tyr Ser
 50                  55                  60

Ser Thr Val Pro Thr Phe Asn Pro Asp Trp Leu Thr Pro Ser Phe Pro
 65                  70                  75                  80

Asp Ile His Leu His Gln Asp Leu Ile His Lys Cys Glu Gln Phe Val
                 85                  90                  95

Gly Pro Leu Thr Lys Asn Glu Leu Arg Arg Leu Lys Leu Val Met Pro
                100                 105                 110

Ser Arg Phe Phe Pro Lys Val Thr Lys Tyr Phe Pro Met Glu Lys Gly
                115                 120                 125

Ile Lys Pro Tyr Tyr Pro Asp Asn Val Val Asn His Tyr Phe Lys Thr
                130                 135                 140

Arg His Tyr Leu His Thr Leu Trp Lys Ala Gly Ile Leu Tyr Lys Arg
145                 150                 155                 160

Glu Ser Thr Arg Ser Ala Ser Phe Cys Gly Ser Pro Tyr Ser Trp Glu
                165                 170                 175

Gln Glu Leu Gln His Gly Ser Thr Ser Ile Asn Asp Ser Lys Gly His
                180                 185                 190
```

-continued

```
Gly Thr Glu Ser Leu Cys Thr Gln Ser Ser Gly Ile Leu Ser Arg Pro
            195                 200                 205

Ser Ala Gly Ser Ser Ile Gln Gly Lys Phe Gln Gln Ser Arg Leu Gly
        210                 215                 220

Leu Gln Gln Lys Gln Gly Gln Leu Ala Asn Gly Lys Gln Gly Arg Ser
225                 230                 235                 240

Gly Arg Ile Arg Ser Trp Val His Thr Pro Thr Arg Trp Pro Val Gly
                245                 250                 255

Val Glu Ser Thr Gly Thr Gly Cys Ala Tyr Asn Ile Ala Ser Arg Ser
            260                 265                 270

Ala Ser Cys Phe His Gln Ser Ala Val Arg Glu Lys Thr Asn Pro Ser
        275                 280                 285

Leu Ser Thr Ser Lys Arg His Ser Ser Thr Gly His Ala Val Glu Leu
    290                 295                 300

His Ser Val Pro Pro Gly Ser Val Arg Ser Glu Gly Lys Gly Ser Val
305                 310                 315                 320

Phe Ser Cys Trp Trp Leu Gln Phe Arg Asp Thr Glu Pro Cys Ser Asp
                325                 330                 335

Tyr Cys Leu Ser His Ile Ile Asn Leu Leu Glu Asp Trp Gly Pro Cys
            340                 345                 350

Tyr Glu His Gly Gln His His Ile Arg Thr Pro Arg Thr Pro Ala Arg
        355                 360                 365

Val Thr Gly Gly Val Phe Leu Val Asp Lys Asn Pro His Asn Thr Thr
    370                 375                 380

Glu Ser Arg Leu Val Val Asp Phe Ser Gln Phe Ser Arg Gly Asn Thr
385                 390                 395                 400

Arg Val Ser Trp Pro Lys Phe Ala Val Pro Asn Leu Gln Ser Leu Thr
                405                 410                 415

Asn Leu Leu Ser Ser Asn Leu Ser Trp Leu Ser Leu Asp Val Ser Ala
            420                 425                 430

Ala Phe Tyr His Leu Pro Leu His Pro Ala Ala Met Pro His Leu Leu
        435                 440                 445

Val Gly Ser Ser Gly Leu Ser Arg Tyr Val Ala Arg Leu Ser Ser Thr
    450                 455                 460

Ser Arg Ile His Asp His Gln His Gly Thr Met Gln Asn Leu His Asn
465                 470                 475                 480

Ser Cys Ser Arg Asn Leu Tyr Val Ser Leu Leu Leu Phe Gln Thr
                485                 490                 495

Phe Gly Arg Lys Leu His Leu Tyr Ser His Pro Ile Ile Leu Gly Phe
            500                 505                 510

Arg Lys Ile Pro Met Gly Val Gly Leu Ser Pro Phe Leu Leu Ala Gln
        515                 520                 525

Phe Thr Ser Ala Ile Cys Ser Val Val Arg Arg Ala Phe Pro His Cys
    530                 535                 540

Leu Ala Phe Ser Tyr Met Asp Asp Leu Val Leu Gly Ala Lys Ser Val
545                 550                 555                 560

Gln His Leu Glu Ser Leu Tyr Thr Ala Val Thr Asn Phe Leu Leu Ser
                565                 570                 575

Val Gly Ile His Leu Asn Thr Ser Lys Thr Lys Arg Trp Gly Tyr Thr
            580                 585                 590

Leu Asn Phe Met Gly Tyr Val Ile Gly Ser Trp Gly Ser Leu Pro Gln
        595                 600                 605

Asp His Ile Val Gln Lys Leu Lys Asp Cys Phe Arg Lys Leu Pro Val
```

-continued

```
            610                 615                 620
Asn Arg Pro Ile Asp Trp Lys Val Cys Gln Arg Ile Val Gly Leu Leu
625                 630                 635                 640

Gly Phe Ala Ala Pro Phe Thr Gln Cys Gly Tyr Pro Ala Leu Met Pro
                    645                 650                 655

Leu Tyr Ala Cys Ile Thr Ala Lys Gln Ala Phe Val Phe Ser Pro Thr
                660                 665                 670

Tyr Lys Ala Phe Leu Cys Gln Gln Tyr Met Asn Leu Tyr Pro Val Ala
            675                 680                 685

Arg Gln Arg Pro Gly Leu Cys Gln Val Phe Ala Asp Ala Thr Pro Thr
        690                 695                 700

Gly Trp Gly Leu Ala Ile Gly His Gln Arg Met Arg Gly Thr Phe Val
705                 710                 715                 720

Ala Pro Leu Pro Ile His Thr Ala Glu Leu Leu Ala Ala Cys Phe Ala
                    725                 730                 735

Arg Ser Arg Ser Gly Ala Lys Leu Ile Gly Thr Asp Asn Ser Val Val
                740                 745                 750

Leu Ser Arg Lys Tyr Thr Ser Phe Pro Trp Leu Leu Gly Cys Ala Ala
            755                 760                 765

Asn Trp Ile Leu Arg Gly Thr Ser Phe Val Tyr Val Pro Ser Ala Leu
        770                 775                 780

Asn Pro Ala Asp Asp Pro Ser Arg Gly Arg Leu Gly Leu Tyr Arg Pro
785                 790                 795                 800

Leu Leu Arg Leu Pro Phe Gln Pro Thr Thr Gly Arg Thr Ser Leu Tyr
                    805                 810                 815

Ala Ala Ser Pro Ser Val Pro Ser His Leu Pro Asp Arg Val His Phe
                820                 825                 830

Ala Ser Pro Leu His Val Ala Trp Arg Pro Pro
            835                 840
```

<210> SEQ ID NO 23
<211> LENGTH: 400
<212> TYPE: PRT
<213> ORGANISM: Hepatitis B virus

<400> SEQUENCE: 23

```
Met Gly Ala Pro Leu Ser Thr Thr Arg Arg Gly Met Gly Gln Asn Leu
1               5                   10                  15

Ser Val Pro Asn Pro Leu Gly Phe Phe Pro Asp His Gln Leu Asp Pro
                20                  25                  30

Leu Phe Lys Ala Asn Ser Ser Ser Pro Asp Trp Asp Phe Asn Lys Asn
            35                  40                  45

Lys Asp Thr Trp Pro Met Ala Asn Lys Val Gly Val Gly Ala Tyr Gly
        50                  55                  60

Pro Gly Phe Thr Pro Pro His Gly Gly Leu Leu Gly Trp Ser Pro Gln
65                  70                  75                  80

Ala Gln Gly Val Leu Thr Thr Leu Pro Ala Asp Pro Pro Pro Ala Ser
                85                  90                  95

Thr Asn Arg Arg Ser Gly Arg Lys Pro Thr Pro Val Ser Pro Pro Leu
            100                 105                 110

Arg Asp Thr His Pro Gln Ala Met Gln Trp Asn Ser Thr Gln Phe His
        115                 120                 125

Gln Ala Leu Leu Asp Pro Arg Val Arg Ala Leu Ser Pro Pro Ala Gly
    130                 135                 140
```

Gly Ser Ser Glu Thr Gln Asn Pro Ala Pro Thr Ile Ala Ser Leu
145                 150                 155                 160

Thr Ser Ser Ile Phe Ser Lys Thr Gly Gly Pro Ala Met Asn Met Asp
                165                 170                 175

Asn Ile Thr Ser Gly Leu Leu Gly Pro Leu Leu Val Leu Gln Ala Val
            180                 185                 190

Cys Phe Leu Leu Thr Lys Ile Leu Thr Ile Pro Gln Ser Leu Asp Ser
        195                 200                 205

Trp Trp Thr Ser Leu Asn Phe Leu Gly Gly Leu Pro Gly Cys Pro Gly
    210                 215                 220

Gln Asn Ser Gln Ser Pro Thr Ser Asn His Leu Pro Thr Ser Cys Pro
225                 230                 235                 240

Pro Thr Cys Pro Gly Tyr Arg Trp Met Cys Leu Arg Arg Phe Ile Ile
                245                 250                 255

Phe Leu Phe Ile Leu Leu Leu Cys Leu Ile Phe Leu Leu Val Leu Leu
            260                 265                 270

Asp Tyr Gln Gly Met Leu Pro Val Cys Pro Leu Ile Pro Gly Ser Thr
        275                 280                 285

Thr Thr Ser Thr Gly Pro Cys Lys Thr Cys Thr Thr Leu Ala Gln Gly
    290                 295                 300

Thr Ser Met Phe Pro Ser Cys Cys Cys Ser Lys Pro Ser Asp Gly Asn
305                 310                 315                 320

Cys Thr Cys Ile Pro Ile Pro Ser Ser Trp Ala Leu Gly Lys Tyr Leu
                325                 330                 335

Trp Glu Trp Ala Ser Ala Arg Phe Ser Trp Leu Ser Leu Leu Val Gln
            340                 345                 350

Phe Val Gln Trp Cys Val Gly Leu Ser Pro Thr Val Trp Leu Leu Ile
        355                 360                 365

Ile Trp Met Ile Trp Tyr Trp Gly Pro Asn Leu Cys Ser Ile Leu Ser
    370                 375                 380

Pro Phe Ile Pro Leu Leu Pro Ile Phe Cys Tyr Leu Trp Val Ser Ile
385                 390                 395                 400

<210> SEQ ID NO 24
<211> LENGTH: 154
<212> TYPE: PRT
<213> ORGANISM: Hepatitis B virus

<400> SEQUENCE: 24

Met Ala Ala Arg Leu Cys Cys Gln Leu Asp Pro Thr Arg Asp Val Leu
1                   5                   10                  15

Cys Leu Arg Pro Val Gly Ala Glu Ser Arg Gly Arg Ser Leu Ser Gly
                20                  25                  30

Ser Leu Gly Ala Val Pro Pro Ser Pro Ser Ala Val Pro Ala Asn
            35                  40                  45

Asp Gly Ser His Leu Ser Leu Arg Gly Leu Pro Val Cys Ser Phe Ser
        50                  55                  60

Ser Ala Gly Pro Cys Ala Leu Arg Phe Thr Ser Ala Arg Arg Met Glu
65                  70                  75                  80

Thr Thr Val Asn Ala Pro Arg Ser Leu Pro Thr Val Leu His Lys Arg
                85                  90                  95

Thr Leu Gly Leu Ser Gly Arg Ser Met Thr Trp Ile Glu Asp Tyr Ile
            100                 105                 110

Lys Asp Cys Val Phe Lys Asp Trp Glu Glu Leu Gly Glu Glu Ile Arg
        115                 120                 125

```
Leu Lys Val Phe Val Leu Gly Gly Cys Arg His Lys Leu Val Cys Ser
    130                 135                 140

Pro Ala Pro Cys Asn Phe Phe Thr Ser Ala
145                 150

<210> SEQ ID NO 25
<211> LENGTH: 194
<212> TYPE: PRT
<213> ORGANISM: Hepatitis B virus

<400> SEQUENCE: 25

Met Asp Arg Thr Thr Leu Pro Tyr Gly Leu Phe Gly Leu Asp Ile Asp
1               5                   10                  15

Pro Tyr Lys Glu Phe Gly Ala Thr Val Glu Leu Leu Ser Phe Leu Pro
                20                  25                  30

Ser Asp Phe Phe Pro Ser Val Arg Asp Leu Leu Asp Thr Ala Ser Ala
            35                  40                  45

Leu Tyr Arg Glu Ser Leu Glu Ser Ser Asp His Cys Ser Pro His His
        50                  55                  60

Thr Ala Leu Arg Gln Ala Ile Leu Cys Trp Gly Glu Leu Met Thr Leu
65                  70                  75                  80

Ala Thr Trp Val Gly Asn Asn Leu Glu Asp Pro Ala Ser Arg Asp Leu
                85                  90                  95

Val Val Asn Tyr Val Asn Thr Asn Met Gly Leu Lys Ile Arg Gln Leu
            100                 105                 110

Leu Trp Phe His Ile Ser Cys Leu Thr Phe Gly Arg Glu Thr Val Leu
        115                 120                 125

Glu Tyr Leu Val Ser Phe Gly Val Trp Ile Arg Thr Pro Pro Ala Tyr
    130                 135                 140

Arg Pro Pro Asn Ala Pro Ile Leu Ser Thr Leu Pro Glu Thr Thr Val
145                 150                 155                 160

Val Arg Arg Arg Gly Arg Ser Pro Arg Arg Arg Thr Pro Ser Pro Arg
                165                 170                 175

Arg Arg Arg Ser Gln Ser Pro Arg Arg Arg Arg Ser Ala Ser Pro Ala
            180                 185                 190

Ser Gln

<210> SEQ ID NO 26
<211> LENGTH: 842
<212> TYPE: PRT
<213> ORGANISM: Hepatitis B virus

<400> SEQUENCE: 26

Met Pro Leu Ser Tyr Gln His Phe Arg Arg Leu Leu Leu Leu Asp Glu
1               5                   10                  15

Glu Ala Gly Pro Leu Glu Glu Glu Leu Pro Arg Leu Ala Asp Glu Asp
                20                  25                  30

Leu Asn Arg Arg Val Ala Glu Asp Leu His Leu Gln Leu Pro Asn Asp
            35                  40                  45

Ser Ile Pro Trp Thr His Lys Val Gly Asn Phe Thr Gly Leu Tyr Ser
        50                  55                  60

Ser Thr Ile Pro Val Phe Asn Pro Asp Trp Gln Thr Pro Ser Phe Pro
65                  70                  75                  80

Asn Ile His Leu His Gln Asp Ile Ile Thr Lys Cys Glu Gln Phe Val
                85                  90                  95
```

-continued

```
Gly Pro Leu Thr Val Asn Glu Lys Arg Leu Lys Leu Val Met Pro
                100                 105                 110

Ala Arg Phe Phe Pro Asn Ser Thr Lys Tyr Leu Pro Leu Asp Lys Gly
115                 120                 125

Ile Lys Pro Tyr Tyr Pro Glu Asn Val Val Asn His Tyr Phe Gln Thr
    130                 135                 140

Arg His Tyr Leu His Thr Leu Trp Lys Thr Gly Ile Leu Tyr Lys Arg
145                 150                 155                 160

Glu Thr Ser Arg Ser Ala Ser Phe Cys Gly Ser Pro Tyr Thr Trp Glu
                165                 170                 175

Gln Asp Leu Gln His Gly Ala Phe Leu Asp Gly Pro Ser Arg Val Gly
                180                 185                 190

Lys Glu Pro Phe His Gln Gln Ser Ser Arg Ile Pro Ser Arg Ser Pro
    195                 200                 205

Val Gly Pro Ser Ile Gln Ser Lys Tyr Gln Gln Ser Arg Leu Gly Leu
    210                 215                 220

Gln Ser Gln Lys Gly Pro Leu Ala Arg Gly Gln Gln Gly Arg Ser Trp
225                 230                 235                 240

Ser Leu Trp Thr Arg Val His Pro Ser Thr Arg Arg Pro Phe Gly Val
                245                 250                 255

Glu Pro Ser Val Ser Gly His Thr Asn Asn Phe Ala Ser Arg Ser Ala
                260                 265                 270

Ser Cys Leu His Gln Ser Ser Val Arg Glu Ala Ala Tyr Ser His Leu
                275                 280                 285

Ser Thr Thr Lys Arg Gln Ser Ser Ser Gly His Ala Val Glu Leu Tyr
290                 295                 300

Ser Ile Pro Pro Ser Ser Thr Lys Ser Gln Ser Gln Gly Pro Val Ser
305                 310                 315                 320

Ser Cys Trp Trp Leu Gln Phe Arg Asp Ser Glu Pro Cys Ser Asp Tyr
                325                 330                 335

Cys Leu Ser His Leu Val Asn Leu Leu Gln Asp Trp Gly Pro Cys Thr
                340                 345                 350

Glu His Gly Glu His His Ile Arg Ile Pro Arg Thr Pro Ala Arg Val
                355                 360                 365

Thr Gly Gly Val Phe Leu Val Asp Lys Asn Pro His Asn Thr Ala Glu
370                 375                 380

Ser Arg Leu Val Val Asp Phe Ser Gln Phe Ser Arg Gly Ser Ala Arg
385                 390                 395                 400

Val Ser Trp Pro Lys Phe Ala Val Pro Asn Leu Gln Ser Leu Thr Asn
                405                 410                 415

Leu Leu Ser Ser Asn Leu Ser Trp Leu Ser Leu Asp Val Ser Ala Ala
                420                 425                 430

Phe Tyr His Ile Pro Leu His Pro Ala Ala Met Pro His Leu Leu Val
                435                 440                 445

Gly Ser Ser Gly Leu Ser Arg Tyr Val Ala Arg Leu Ser Ser Asp Ser
                450                 455                 460

Arg Ile Leu Asp His Gln Tyr Gly Thr Leu Gln Asn Leu His Asp Ser
465                 470                 475                 480

Cys Ser Arg Gln Leu Tyr Val Ser Leu Met Leu Leu Tyr Lys Thr Phe
                485                 490                 495

Gly Arg Lys Leu His Leu Tyr Ser His Pro Ile Ile Leu Gly Phe Arg
                500                 505                 510

Lys Ile Pro Met Gly Leu Gly Leu Ser Pro Phe Leu Met Ala Gln Phe
```

```
                515                 520                 525
Thr Ser Ala Ile Cys Ser Val Val Arg Arg Ala Phe Pro His Cys Leu
530                 535                 540

Ala Phe Ser Tyr Val Asp Asp Val Val Leu Gly Ala Lys Ser Val Gln
545                 550                 555                 560

His Leu Glu Ser Leu Tyr Thr Ala Val Thr Asn Phe Leu Leu Ser Leu
                565                 570                 575

Gly Ile His Leu Asn Pro Asn Lys Thr Lys Arg Trp Gly Tyr Ser Leu
            580                 585                 590

Asn Phe Met Gly Tyr Val Ile Gly Ser Trp Gly Thr Leu Pro Gln Glu
        595                 600                 605

His Ile Thr Gln Lys Ile Lys Gln Cys Phe Arg Lys Leu Pro Val Asn
    610                 615                 620

Arg Pro Ile Asp Trp Lys Val Cys Gln Arg Ile Thr Gly Leu Leu Gly
625                 630                 635                 640

Phe Ala Ala Pro Phe Thr Gln Cys Gly Tyr Pro Ala Leu Met Pro Leu
                645                 650                 655

Tyr Ala Cys Ile Gln Ala Lys Gln Ala Phe Thr Phe Ser Pro Thr Tyr
            660                 665                 670

Lys Ala Phe Leu Cys Lys Gln Tyr Met Asn Leu Tyr Pro Val Ala Arg
        675                 680                 685

Gln Arg Pro Gly Leu Cys Gln Val Phe Ala Asp Ala Thr Pro Thr Gly
    690                 695                 700

Trp Gly Leu Ala Ile Gly His Gln Arg Met Arg Gly Thr Phe Val Ala
705                 710                 715                 720

Pro Leu Pro Ile His Thr Ala Glu Leu Leu Ala Ala Cys Phe Ala Arg
                725                 730                 735

Ser Arg Ser Gly Ala Lys Leu Ile Gly Thr Asp Asn Ser Val Val Leu
            740                 745                 750

Ser Arg Lys Tyr Thr Ser Phe Pro Trp Leu Leu Gly Cys Ala Ala Asn
        755                 760                 765

Trp Ile Leu Arg Gly Thr Ser Phe Val Tyr Val Pro Ser Ala Leu Asn
    770                 775                 780

Pro Ala Asp Asp Pro Ser Arg Gly Arg Leu Gly Leu Tyr Arg Pro Leu
785                 790                 795                 800

Leu Arg Leu Pro Phe Leu Pro Thr Thr Gly Arg Thr Ser Leu Tyr Ala
                805                 810                 815

Val Ser Pro Ser Val Pro Ser His Leu Pro Asp Arg Val His Phe Ala
            820                 825                 830

Ser Pro Leu His Val Thr Trp Lys Pro Pro
        835                 840

<210> SEQ ID NO 27
<211> LENGTH: 399
<212> TYPE: PRT
<213> ORGANISM: Hepatitis B virus

<400> SEQUENCE: 27

Met Gly Leu Ser Trp Thr Val Pro Leu Glu Trp Gly Lys Asn Leu Ser
1               5                   10                  15

Thr Ser Asn Pro Leu Gly Phe Leu Pro Asp His Gln Leu Asp Pro Ala
            20                  25                  30

Phe Arg Ala Asn Thr Asn Asn Pro Asp Trp Asp Phe Asn Pro Lys Lys
        35                  40                  45
```

```
Asp Pro Trp Pro Glu Ala Asn Lys Val Gly Val Gly Ala Tyr Gly Pro
    50                  55                  60

Gly Phe Thr Pro Pro His Gly Gly Leu Leu Gly Trp Ser Pro Pro Ser
65                  70                  75                  80

Gln Gly Thr Leu Thr Thr Leu Pro Ala Asp Pro Pro Ala Ser Thr
                85                  90                  95

Asn Arg Gln Ser Gly Arg Gln Pro Thr Pro Ile Ser Pro Pro Leu Arg
                100                 105                 110

Asp Ser His Pro Gln Ala Met Gln Trp Asn Ser Thr Ala Phe His Gln
            115                 120                 125

Ala Leu Gln Asn Pro Lys Val Arg Gly Leu Tyr Leu Pro Ala Gly Gly
        130                 135                 140

Ser Ser Ser Gly Ile Val Asn Pro Val Pro Thr Ile Ala Ser His Ile
145                 150                 155                 160

Ser Ser Ile Phe Ser Arg Ile Gly Asp Pro Ala Pro Asn Met Glu Asn
                165                 170                 175

Ile Thr Ser Gly Phe Leu Gly Pro Leu Leu Val Leu Gln Ala Gly Phe
            180                 185                 190

Phe Leu Leu Thr Arg Ile Leu Thr Ile Pro Gln Ser Leu Asp Ser Trp
        195                 200                 205

Trp Thr Ser Leu Asn Phe Leu Gly Gly Val Pro Val Cys Pro Gly Leu
210                 215                 220

Asn Ser Gln Ser Pro Thr Ser Asn His Ser Pro Ile Ser Cys Pro Pro
225                 230                 235                 240

Thr Cys Pro Gly Tyr Arg Trp Met Cys Leu Arg Arg Phe Ile Ile Phe
                245                 250                 255

Leu Phe Ile Leu Leu Leu Cys Leu Ile Phe Leu Leu Val Leu Leu Asp
            260                 265                 270

Tyr Gln Gly Met Leu Pro Val Cys Pro Leu Ile Pro Gly Ser Ser Thr
        275                 280                 285

Thr Ser Thr Gly Pro Cys Lys Thr Cys Thr Thr Pro Ala Gln Gly Asn
290                 295                 300

Ser Met Tyr Pro Ser Cys Cys Cys Thr Lys Pro Ser Asp Gly Asn Cys
305                 310                 315                 320

Thr Cys Ile Pro Ile Pro Ser Ser Trp Ala Phe Ala Lys Tyr Leu Trp
                325                 330                 335

Asp Trp Ala Ser Val Arg Phe Ser Trp Leu Ser Leu Leu Val Pro Phe
            340                 345                 350

Val Gln Trp Phe Val Gly Leu Ser Pro Thr Val Trp Leu Ser Ala Met
        355                 360                 365

Trp Met Met Trp Tyr Trp Gly Pro Asn Leu Tyr Asn Ile Leu Ser Pro
370                 375                 380

Phe Ile Pro Leu Leu Pro Ile Phe Phe Cys Leu Trp Val Tyr Ile
385                 390                 395

<210> SEQ ID NO 28
<211> LENGTH: 154
<212> TYPE: PRT
<213> ORGANISM: Hepatitis B virus

<400> SEQUENCE: 28

Met Ala Ala Arg Leu Cys Arg Gln Leu Asp Pro Ser Arg Asp Val Leu
1               5                   10                  15

Cys Leu Arg Pro Val Ser Ala Glu Ser Ser Gly Arg Pro Leu Pro Gly
            20                  25                  30
```

```
Pro Phe Gly Ala Leu Ser Pro Ser Pro Ser Ala Val Pro Ala Asp
            35                  40                  45

His Gly Ala His Leu Ser Leu Arg Gly Leu Pro Val Cys Ser Phe Ser
 50                  55                  60

Ser Ala Gly Pro Cys Ala Leu Arg Phe Thr Ser Ala Arg Tyr Met Glu
 65                  70                  75                  80

Thr Ala Met Asn Thr Ser His His Leu Pro Arg Gln Leu Tyr Lys Arg
                 85                  90                  95

Thr Leu Gly Leu Phe Val Met Ser Thr Thr Gly Val Glu Lys Tyr Phe
                100                 105                 110

Lys Asp Cys Val Phe Ala Glu Trp Glu Leu Gly Asn Glu Ser Arg
                115                 120                 125

Leu Met Thr Phe Val Leu Gly Gly Cys Arg His Lys Leu Val Cys Ala
                130                 135                 140

Pro Ala Pro Cys Asn Phe Phe Thr Ser Ala
145                 150
```

<210> SEQ ID NO 29
<211> LENGTH: 212
<212> TYPE: PRT
<213> ORGANISM: Hepatitis B virus

<400> SEQUENCE: 29

```
Met Ser Leu Phe His Leu Cys Leu Ile Ile Phe Cys Ser Cys Pro Thr
  1               5                  10                  15

Val Gln Ala Ser Lys Leu Cys Leu Gly Trp Leu Trp Gly Met Asp Ile
                 20                  25                  30

Asp Pro Tyr Lys Glu Phe Gly Ala Ser Ala Glu Leu Leu Ser Phe Leu
                 35                  40                  45

Pro Ser Asp Phe Phe Pro Ser Val Arg Asp Leu Leu Asp Thr Ala Ser
 50                  55                  60

Ala Leu Tyr Arg Glu Ala Leu Glu Ser Pro Glu His Cys Thr Pro Asn
 65                  70                  75                  80

His Thr Ala Leu Arg Gln Ala Ile Leu Cys Trp Gly Glu Leu Met Thr
                 85                  90                  95

Leu Ala Ser Trp Val Gly Asn Asn Leu Gln Asp Pro Ala Ala Arg Asp
                100                 105                 110

Leu Val Val Asn Tyr Val Asn Thr Asn Met Gly Leu Lys Ile Arg Gln
                115                 120                 125

Leu Leu Trp Phe His Ile Ser Cys Leu Thr Phe Gly Arg Glu Thr Val
                130                 135                 140

Leu Glu Tyr Leu Val Ser Phe Gly Val Trp Ile Arg Thr Pro Pro Ala
145                 150                 155                 160

Tyr Arg Pro Pro Asn Ala Pro Ile Leu Ser Thr Leu Pro Glu Thr Thr
                165                 170                 175

Val Val Arg Gln Arg Gly Arg Ala Pro Arg Arg Thr Pro Ser Pro
                180                 185                 190

Arg Arg Arg Arg Ser Gln Ser Pro Arg Arg Arg Arg Ser Gln Ser Pro
                195                 200                 205

Ala Ser Gln Cys
            210
```

<210> SEQ ID NO 30
<211> LENGTH: 843
<212> TYPE: PRT

<213> ORGANISM: Hepatitis B virus

<400> SEQUENCE: 30

Met Pro Leu Ser Tyr Gln His Phe Arg Arg Leu Leu Leu Leu Asp Asn
1               5                   10                  15

Glu Ala Gly Pro Leu Glu Glu Glu Leu Pro Arg Leu Ala Asp Glu Asp
            20                  25                  30

Leu Asn Leu Arg Val Ala Glu Asp Leu Asn Leu Gln Leu Pro Asn Val
        35                  40                  45

Ser Ile Pro Trp Thr His Lys Val Gly Asn Phe Thr Gly Leu Tyr Ser
50                  55                  60

Ser Thr Ile Pro Val Phe Asn Pro Asp Trp Leu Thr Pro Ser Phe Pro
65                  70                  75                  80

Asp Ile His Leu His Gln Asp Leu Ile Gln Lys Cys Glu Gln Phe Val
                85                  90                  95

Gly Pro Leu Thr Thr Asn Glu Arg Arg Leu Lys Leu Ile Met Pro
            100                 105                 110

Ala Arg Phe Tyr Pro Lys Val Thr Lys Tyr Phe Pro Leu Asp Lys Gly
            115                 120                 125

Ile Lys Pro Tyr Tyr Pro Glu Asn Val Val Asn His Tyr Phe Lys Thr
        130                 135                 140

Arg His Tyr Leu His Thr Leu Trp Lys Ala Gly Ile Leu Tyr Lys Arg
145                 150                 155                 160

Glu Ser Thr His Ser Ala Ser Phe Cys Gly Ser Pro Tyr Ser Trp Glu
                165                 170                 175

Gln Glu Leu Gln His Gly Ser Thr Ser Leu Asn Gly Glu Lys Gly His
            180                 185                 190

Gly Thr Glu Ser Phe Cys Ala Gln Ser Ser Gly Ile Leu Ser Arg Pro
        195                 200                 205

Pro Val Gly Ser Thr Ile Gln Ser Lys Phe Gln Gln Ser Arg Leu Gly
210                 215                 220

Leu Gln His Lys Gln Gly Gln Leu Ala Asn Gly Lys Gln Gly Arg Ser
225                 230                 235                 240

Gly Arg Leu Arg Ser Arg Val His Thr Pro Thr Arg Trp Pro Ser Gly
                245                 250                 255

Val Glu Pro Ser Gly Thr Gly His Ser Asn Asn Leu Ala Thr Arg Ser
            260                 265                 270

Thr Ser Cys Phe His Gln Ser Glu Val Arg Glu Lys Ala Asn Pro Ser
        275                 280                 285

Leu Ser Thr Ser Lys Gly His Thr Ser Thr Gly His Ala Val Glu Leu
290                 295                 300

Asn Thr Val Pro Pro Ser Thr Val Gly Ser Glu Ser Lys Gly Ala Val
305                 310                 315                 320

Ser Ser Cys Trp Trp Leu Gln Phe Arg Asn Thr Glu Pro Cys Ser Asp
                325                 330                 335

Tyr Cys Leu Ser His Ile Ile Asn Leu Leu Glu Asp Trp Gly Pro Cys
            340                 345                 350

Tyr Glu His Gly Glu His His Ile Arg Thr Pro Arg Thr Pro Ser Arg
        355                 360                 365

Val Thr Gly Gly Val Phe Leu Val Asp Lys Asn Pro His Asn Thr Lys
370                 375                 380

Glu Ser Arg Leu Val Val Asp Phe Ser Gln Phe Ser Arg Gly Thr Thr
385                 390                 395                 400

Arg Val Ser Trp Pro Lys Phe Ala Val Pro Asn Leu Gln Ser Leu Thr
            405                 410                 415
Asn Leu Leu Ser Ser Asn Leu Ser Trp Leu Ser Leu Asp Val Ser Ala
        420                 425                 430
Ala Phe Tyr His Leu Pro Leu His Pro Ala Ala Met Pro His Leu Leu
        435                 440                 445
Val Gly Ser Ser Gly Leu Ser Arg Tyr Val Ala Arg Val Ser Ser Thr
    450                 455                 460
Ser Arg Ile Tyr Asn His Gln His Gly Thr Leu Gln Asn Leu His His
465                 470                 475                 480
Ser Cys Ser Arg Asn Leu Tyr Val Ser Leu Leu Leu Tyr Gln Thr
            485                 490                 495
Phe Gly Arg Lys Leu His Leu Tyr Ser His Pro Ile Ile Leu Gly Phe
            500                 505                 510
Arg Lys Ile Pro Met Gly Val Gly Leu Ser Pro Phe Leu Leu Ala Gln
            515                 520                 525
Phe Thr Ser Ala Ile Cys Ser Val Val Arg Arg Ala Phe Pro His Cys
    530                 535                 540
Leu Ala Phe Ser Tyr Met Asp Asp Leu Val Leu Gly Ala Lys Ser Val
545                 550                 555                 560
Gln His Leu Glu Ser Leu Tyr Thr Ala Val Thr Asn Phe Leu Leu Ser
            565                 570                 575
Val Gly Ile His Leu Asn Thr Ala Lys Thr Lys Trp Trp Gly Tyr Ser
            580                 585                 590
Leu His Phe Met Gly Tyr Val Ile Gly Ser Trp Gly Thr Leu Pro Gln
            595                 600                 605
Glu His Ile Val His Lys Ile Lys Asp Cys Phe Arg Lys Leu Pro Val
    610                 615                 620
Asn Arg Pro Ile Asp Trp Lys Val Cys Gln Arg Ile Val Gly Leu Leu
625                 630                 635                 640
Gly Leu Ala Ala Pro Phe Thr Gln Cys Gly Tyr Pro Ala Leu Met Pro
            645                 650                 655
Leu Tyr Ala Cys Ile Thr Ala Lys Gln Ala Phe Val Phe Ser Pro Thr
            660                 665                 670
Tyr Lys Ala Phe Leu Cys Lys Gln Tyr Met Asn Leu Tyr Pro Val Ala
            675                 680                 685
Arg Gln Arg Pro Gly Leu Cys Gln Val Phe Ala Asp Ala Pro Pro Thr
    690                 695                 700
Gly Trp Gly Leu Ala Ile Gly His Gln Arg Met Arg Gly Thr Phe Val
705                 710                 715                 720
Ala Pro Leu Pro Ile His Thr Ala Glu Leu Leu Ala Ala Cys Phe Ala
            725                 730                 735
Arg Ser Arg Ser Gly Ala Asp Ile Ile Gly Thr Asp Asn Ser Val Val
            740                 745                 750
Leu Ser Arg Lys Tyr Thr Ser Phe Pro Trp Leu Leu Gly Cys Ala Ala
            755                 760                 765
Asn Trp Ile Leu Arg Gly Thr Ser Phe Val Tyr Val Pro Ser Ala Leu
    770                 775                 780
Asn Pro Ala Asp Asp Pro Ser Arg Gly Arg Leu Gly Leu Cys Arg Pro
785                 790                 795                 800
Leu Leu Arg Leu Pro Phe Arg Pro Thr Thr Gly Arg Thr Ser Leu Tyr
            805                 810                 815
Ala Asp Ser Pro Pro Val Pro Ser His Leu Pro Ala Arg Val His Phe

```
                    820                 825                 830

Ala Ser Pro Leu His Val Ala Trp Arg Pro Pro
        835                 840

<210> SEQ ID NO 31
<211> LENGTH: 400
<212> TYPE: PRT
<213> ORGANISM: Hepatitis B virus

<400> SEQUENCE: 31

Met Gly Ala Pro Leu Ser Thr Ala Arg Arg Gly Met Gly Gln Asn Leu
1               5                   10                  15

Ser Val Pro Asn Pro Leu Gly Phe Phe Pro Asp His Gln Leu Asp Pro
            20                  25                  30

Leu Phe Arg Ala Asn Ser Ser Ser Pro Asp Trp Asp Phe Asn Thr Asn
        35                  40                  45

Lys Asp Asn Trp Pro Met Ala Asn Lys Val Gly Val Gly Gly Phe Gly
    50                  55                  60

Pro Gly Phe Thr Pro Pro His Gly Gly Leu Leu Gly Trp Ser Pro Gln
65                  70                  75                  80

Ala Gln Gly Ile Leu Thr Thr Ser Pro Pro Asp Pro Pro Pro Ala Ser
                85                  90                  95

Thr Asn Arg Arg Ser Gly Arg Lys Pro Thr Pro Val Ser Pro Pro Leu
            100                 105                 110

Arg Asp Thr His Pro Gln Ala Met Gln Trp Asn Ser Thr Gln Phe His
        115                 120                 125

Gln Ala Leu Leu Asp Pro Arg Val Arg Gly Leu Tyr Leu Pro Ala Gly
    130                 135                 140

Gly Ser Ser Ser Glu Thr Gln Asn Pro Ala Pro Thr Ile Ala Ser Leu
145                 150                 155                 160

Thr Ser Ser Ile Phe Ser Lys Thr Gly Asp Pro Ala Met Asn Met Glu
                165                 170                 175

Asn Ile Thr Ser Gly Leu Leu Gly Pro Leu Leu Val Leu Gln Ala Val
            180                 185                 190

Cys Phe Leu Leu Thr Lys Ile Leu Thr Ile Pro Lys Ser Leu Asp Ser
        195                 200                 205

Trp Trp Thr Ser Leu Asn Phe Leu Gly Val Pro Pro Gly Cys Pro Gly
    210                 215                 220

Gln Asn Ser Gln Ser Pro Ile Ser Asn His Leu Pro Thr Ser Cys Pro
225                 230                 235                 240

Pro Thr Cys Pro Gly Tyr Arg Trp Met Cys Leu Arg Arg Phe Ile Ile
                245                 250                 255

Phe Leu Phe Ile Leu Leu Leu Cys Leu Ile Phe Leu Leu Val Leu Leu
            260                 265                 270

Asp Tyr Gln Gly Met Leu Pro Val Cys Pro Leu Leu Pro Gly Ser Thr
        275                 280                 285

Thr Thr Ser Thr Gly Pro Cys Lys Thr Cys Thr Thr Leu Ala Gln Gly
    290                 295                 300

Thr Ser Met Phe Pro Ser Cys Cys Cys Thr Lys Pro Ser Asp Gly Asn
305                 310                 315                 320

Cys Thr Cys Ile Pro Ile Pro Ser Ser Trp Ala Phe Gly Lys Tyr Leu
                325                 330                 335

Trp Glu Trp Ala Ser Ala Arg Phe Ser Trp Leu Ser Leu Leu Val Gln
            340                 345                 350
```

```
Phe Val Gln Trp Cys Val Gly Leu Ser Pro Thr Val Trp Leu Leu Val
            355                 360                 365

Ile Trp Met Ile Trp Tyr Trp Gly Pro Asn Leu Cys Ser Ile Leu Ser
    370                 375                 380

Pro Phe Ile Pro Leu Leu Pro Ile Phe Cys Tyr Leu Trp Ala Ser Ile
385                 390                 395                 400

<210> SEQ ID NO 32
<211> LENGTH: 154
<212> TYPE: PRT
<213> ORGANISM: Hepatitis B virus

<400> SEQUENCE: 32

Met Ala Ala Arg Met Cys Cys Gln Leu Asp Pro Ala Arg Asp Val Leu
1               5                   10                  15

Cys Leu Arg Pro Val Gly Ala Glu Ser Cys Gly Arg Pro Leu Ser Trp
            20                  25                  30

Ser Leu Gly Ala Leu Pro Pro Ser Ser Pro Pro Ala Val Pro Ala Asp
        35                  40                  45

Asp Gly Ser His Leu Ser Leu Arg Gly Leu Pro Ala Cys Ala Phe Ser
    50                  55                  60

Ser Ala Gly Pro Cys Ala Leu Arg Phe Thr Ser Ala Arg Arg Met Glu
65                  70                  75                  80

Thr Thr Val Asn Ala Pro Trp Asn Leu Pro Thr Thr Leu His Lys Arg
                85                  90                  95

Thr Leu Gly Leu Ser Pro Arg Ser Thr Thr Trp Ile Glu Glu Tyr Ile
            100                 105                 110

Lys Asp Cys Val Phe Lys Asp Trp Glu Glu Ser Gly Glu Glu Leu Arg
        115                 120                 125

Leu Lys Val Phe Val Leu Gly Gly Cys Arg His Lys Leu Val Cys Ser
    130                 135                 140

Pro Ala Pro Cys Asn Phe Phe Thr Ser Ala
145                 150

<210> SEQ ID NO 33
<211> LENGTH: 1808
<212> TYPE: DNA
<213> ORGANISM: Artificial
<220> FEATURE:
<223> OTHER INFORMATION: synthetic DNA
<220> FEATURE:
<221> NAME/KEY: CDS
<222> LOCATION: (13)..(1800)

<400> SEQUENCE: 33
gaattcgcca cc atg gcc gat gaa gct cca act agt ggt ggg tgg tca tcc        51
              Met Ala Asp Glu Ala Pro Thr Ser Gly Gly Trp Ser Ser
                1               5                   10 aaa cct aga aag gga atg ggt aca aac tta tct gta cca aat cct tta        99
Lys Pro Arg Lys Gly Met Gly Thr Asn Leu Ser Val Pro Asn Pro Leu
        15                  20                  25 ggc ttt ttc cca gac cat cag ttg gac cca gct ttt ggg gcc aac tct       147
Gly Phe Phe Pro Asp His Gln Leu Asp Pro Ala Phe Gly Ala Asn Ser
30                  35                  40                  45 aac aac cca gat tgg gat ttc aat cct aac aaa gac cac tgg cca gaa       195
Asn Asn Pro Asp Trp Asp Phe Asn Pro Asn Lys Asp His Trp Pro Glu
                50                  55                  60 gcc aat caa gta ggt gtt ggc gca ttt ggt cct ggt ttt aca cct cca       243
Ala Asn Gln Val Gly Val Gly Ala Phe Gly Pro Gly Phe Thr Pro Pro
            65                  70                  75
```

| | | |
|---|---|---|
| cat gga ggc ttg tta ggc tgg tca cct caa gca caa ggt att ctg act<br>His Gly Gly Leu Leu Gly Trp Ser Pro Gln Ala Gln Gly Ile Leu Thr<br>        80                      85                      90 | 291 |
| act gtc cca gct gca cca cca cct gcc tca act aat agg caa tct ggt<br>Thr Val Pro Ala Ala Pro Pro Pro Ala Ser Thr Asn Arg Gln Ser Gly<br>95                      100                      105 | 339 |
| aga cag cct acc cct att agt cca cca ttg aga gac tca cat cct caa<br>Arg Gln Pro Thr Pro Ile Ser Pro Pro Leu Arg Asp Ser His Pro Gln<br>110                    115                  120                  125 | 387 |
| gcc atg cag tgg aat agt act act ttc cat caa gcc tta ctg gat cca<br>Ala Met Gln Trp Asn Ser Thr Thr Phe His Gln Ala Leu Leu Asp Pro<br>                  130                    135                  140 | 435 |
| aga gta aga gga cta tac ttc cca gca ggt ggt tca tca tca ggc aca<br>Arg Val Arg Gly Leu Tyr Phe Pro Ala Gly Gly Ser Ser Ser Gly Thr<br>              145                    150                155 | 483 |
| gtg aac cct gtt cca aca aca gca tcc cct ata tct tct atc ttt tct<br>Val Asn Pro Val Pro Thr Thr Ala Ser Pro Ile Ser Ser Ile Phe Ser<br>        160                    165                    170 | 531 |
| aga aca gga gat cca gct cca aac atg gaa aac act aca tct gga ttc<br>Arg Thr Gly Asp Pro Ala Pro Asn Met Glu Asn Thr Thr Ser Gly Phe<br>175                    180                    185 | 579 |
| ctt ggg cct cta tta gta tta caa gct ggg ttt ttc ctg cta acc cgt<br>Leu Gly Pro Leu Leu Val Leu Gln Ala Gly Phe Phe Leu Leu Thr Arg<br>190                    195                  200                  205 | 627 |
| att cta act ata cca caa tca tta gat tcc tgg tgg act tca ttg aat<br>Ile Leu Thr Ile Pro Gln Ser Leu Asp Ser Trp Trp Thr Ser Leu Asn<br>                    210                    215                  220 | 675 |
| ttc cta gga ggt gcc cca aca tgt cca ggt caa aac tcc cag tct cct<br>Phe Leu Gly Gly Ala Pro Thr Cys Pro Gly Gln Asn Ser Gln Ser Pro<br>                225                    230                  235 | 723 |
| aca tct aat cac tct cct acc agt tgc cca cca ata tgt cct ggc tac<br>Thr Ser Asn His Ser Pro Thr Ser Cys Pro Pro Ile Cys Pro Gly Tyr<br>        240                    245                    250 | 771 |
| aga tgg atg tgc tta cgt aga ttc atc atc ttc ctt ttc att ttg ctt<br>Arg Trp Met Cys Leu Arg Arg Phe Ile Ile Phe Leu Phe Ile Leu Leu<br>255                    260                    265 | 819 |
| ttg tgc ctt atc ttt ttg cta gtg cta ctg gac tac caa gga atg ttg<br>Leu Cys Leu Ile Phe Leu Leu Val Leu Leu Asp Tyr Gln Gly Met Leu<br>270                    275                  280                  285 | 867 |
| cca gtt tgt cct tta ctg cct gga aca tca act act tct aca ggc cct<br>Pro Val Cys Pro Leu Leu Pro Gly Thr Ser Thr Thr Ser Thr Gly Pro<br>                290                    295                  300 | 915 |
| tgc aag aca tgt aca atc cca gca caa ggc act tca atg ttt cca tcc<br>Cys Lys Thr Cys Thr Ile Pro Ala Gln Gly Thr Ser Met Phe Pro Ser<br>              305                    310                315 | 963 |
| tgt tgc tgt aca aaa cca agt gat ggt aac tgt aca tgt ata cca atc<br>Cys Cys Cys Thr Lys Pro Ser Asp Gly Asn Cys Thr Cys Ile Pro Ile<br>        320                    325                    330 | 1011 |
| cct tca tct tgg gct ttt gct aga ttc ctt tgg gag tgg gcc tct gtt<br>Pro Ser Ser Trp Ala Phe Ala Arg Phe Leu Trp Glu Trp Ala Ser Val<br>335                    340                    345 | 1059 |
| aga ttc tcc tgg cta tct ctt caa gct cca ttt gtt caa tgg ttt gtc<br>Arg Phe Ser Trp Leu Ser Leu Gln Ala Pro Phe Val Gln Trp Phe Val<br>350                    355                  360                  365 | 1107 |
| gga ttg tca cca act gtt tgg ttg tca gtg atc tgg atg atg tgg tac<br>Gly Leu Ser Pro Thr Val Trp Leu Ser Val Ile Trp Met Met Trp Tyr<br>                370                    375                  380 | 1155 |
| tgg ggt cca tct ttg tac aat atc tta aac cca ttt cta cca ttg ttg<br>Trp Gly Pro Ser Leu Tyr Asn Ile Leu Asn Pro Phe Leu Pro Leu Leu | 1203 |

```
                        385                 390                 395
cca atc ttt ttc tgt ctt tgg gtc tac att gat att gat cca tac aaa      1251
Pro Ile Phe Phe Cys Leu Trp Val Tyr Ile Asp Ile Asp Pro Tyr Lys
            400                 405                 410 gag ttt ggt gca tct gtc gaa tta cta tcc ttt ttg cca tca gac ttt      1299
Glu Phe Gly Ala Ser Val Glu Leu Leu Ser Phe Leu Pro Ser Asp Phe
    415                 420                 425 ttc cct agt ata aga gac tta ttg gat act gct tct gct ttg tat aga      1347
Phe Pro Ser Ile Arg Asp Leu Leu Asp Thr Ala Ser Ala Leu Tyr Arg
430                 435                 440                 445 gaa gca tta gaa tct cca gag cac tgt tct cca cat cat acc gca ttg      1395
Glu Ala Leu Glu Ser Pro Glu His Cys Ser Pro His His Thr Ala Leu
                450                 455                 460 aga caa gca att ctg tgc tgg ggc gag tta atg aac tta gct acc tgg      1443
Arg Gln Ala Ile Leu Cys Trp Gly Glu Leu Met Asn Leu Ala Thr Trp
            465                 470                 475 gtt ggt tct aat ctg gaa gat cct gct tct aga gaa ttg gta gtt tcc      1491
Val Gly Ser Asn Leu Glu Asp Pro Ala Ser Arg Glu Leu Val Val Ser
        480                 485                 490 tac gtg aat gta aac atg ggt ttg aag att agg caa cta ctt tgg ttt      1539
Tyr Val Asn Val Asn Met Gly Leu Lys Ile Arg Gln Leu Leu Trp Phe
    495                 500                 505 cac atc agt tgt ctg act ttc ggg aga gaa aca gtg ttg gaa tat ctt      1587
His Ile Ser Cys Leu Thr Phe Gly Arg Glu Thr Val Leu Glu Tyr Leu
510                 515                 520                 525 gtc tct ttt ggt gtg tgg att aga aca cca cca gct tat aga cct cct      1635
Val Ser Phe Gly Val Trp Ile Arg Thr Pro Pro Ala Tyr Arg Pro Pro
                530                 535                 540 aat gct cca atc ctg agt aca ttg cca gag act acc gtt gtt aga agg      1683
Asn Ala Pro Ile Leu Ser Thr Leu Pro Glu Thr Thr Val Val Arg Arg
            545                 550                 555 aga ggt aga tcc cca aga cgt aga acc cct tct cca agg agg aga aga      1731
Arg Gly Arg Ser Pro Arg Arg Arg Thr Pro Ser Pro Arg Arg Arg Arg
        560                 565                 570 tca caa agt cct cgt cgt aga aga tcc cag agt aga gaa tct caa tgc      1779
Ser Gln Ser Pro Arg Arg Arg Ser Gln Ser Arg Glu Ser Gln Cys
    575                 580                 585 cat cat cat cac cac cat taa gcggccgc                                 1808
His His His His His His
590                 595

<210> SEQ ID NO 34
<211> LENGTH: 595
<212> TYPE: PRT
<213> ORGANISM: Artificial
<220> FEATURE:
<223> OTHER INFORMATION: Synthetic Construct

<400> SEQUENCE: 34

Met Ala Asp Glu Ala Pro Thr Ser Gly Gly Trp Ser Ser Lys Pro Arg
1               5                   10                  15

Lys Gly Met Gly Thr Asn Leu Ser Val Pro Asn Pro Leu Gly Phe Phe
            20                  25                  30

Pro Asp His Gln Leu Asp Pro Ala Phe Gly Ala Asn Ser Asn Asn Pro
        35                  40                  45

Asp Trp Asp Phe Asn Pro Asn Lys Asp His Trp Pro Glu Ala Asn Gln
    50                  55                  60

Val Gly Val Gly Ala Phe Gly Pro Gly Phe Thr Pro Pro His Gly Gly
65                  70                  75                  80
```

-continued

```
Leu Leu Gly Trp Ser Pro Gln Ala Gln Gly Ile Leu Thr Thr Val Pro
             85                  90                  95
Ala Ala Pro Pro Pro Ala Ser Thr Asn Arg Gln Ser Gly Arg Gln Pro
            100                 105                 110
Thr Pro Ile Ser Pro Pro Leu Arg Asp Ser His Pro Gln Ala Met Gln
        115                 120                 125
Trp Asn Ser Thr Thr Phe His Gln Ala Leu Leu Asp Pro Arg Val Arg
    130                 135                 140
Gly Leu Tyr Phe Pro Ala Gly Gly Ser Ser Ser Gly Thr Val Asn Pro
145                 150                 155                 160
Val Pro Thr Thr Ala Ser Pro Ile Ser Ser Ile Phe Ser Arg Thr Gly
                165                 170                 175
Asp Pro Ala Pro Asn Met Glu Asn Thr Thr Ser Gly Phe Leu Gly Pro
            180                 185                 190
Leu Leu Val Leu Gln Ala Gly Phe Phe Leu Leu Thr Arg Ile Leu Thr
        195                 200                 205
Ile Pro Gln Ser Leu Asp Ser Trp Trp Thr Ser Leu Asn Phe Leu Gly
    210                 215                 220
Gly Ala Pro Thr Cys Pro Gly Gln Asn Ser Gln Ser Pro Thr Ser Asn
225                 230                 235                 240
His Ser Pro Thr Ser Cys Pro Pro Ile Cys Pro Gly Tyr Arg Trp Met
                245                 250                 255
Cys Leu Arg Arg Phe Ile Ile Phe Leu Phe Ile Leu Leu Leu Cys Leu
            260                 265                 270
Ile Phe Leu Leu Val Leu Leu Asp Tyr Gln Gly Met Leu Pro Val Cys
        275                 280                 285
Pro Leu Leu Pro Gly Thr Ser Thr Thr Ser Thr Gly Pro Cys Lys Thr
    290                 295                 300
Cys Thr Ile Pro Ala Gln Gly Thr Ser Met Phe Pro Ser Cys Cys Cys
305                 310                 315                 320
Thr Lys Pro Ser Asp Gly Asn Cys Thr Cys Ile Pro Ile Pro Ser Ser
                325                 330                 335
Trp Ala Phe Ala Arg Phe Leu Trp Glu Trp Ala Ser Val Arg Phe Ser
            340                 345                 350
Trp Leu Ser Leu Gln Ala Pro Phe Val Gln Trp Phe Val Gly Leu Ser
        355                 360                 365
Pro Thr Val Trp Leu Ser Val Ile Trp Met Met Trp Tyr Trp Gly Pro
    370                 375                 380
Ser Leu Tyr Asn Ile Leu Asn Pro Phe Leu Pro Leu Leu Pro Ile Phe
385                 390                 395                 400
Phe Cys Leu Trp Val Tyr Ile Asp Ile Asp Pro Tyr Lys Glu Phe Gly
                405                 410                 415
Ala Ser Val Glu Leu Leu Ser Phe Leu Pro Ser Asp Phe Phe Pro Ser
            420                 425                 430
Ile Arg Asp Leu Leu Asp Thr Ala Ser Ala Leu Tyr Arg Glu Ala Leu
        435                 440                 445
Glu Ser Pro Glu His Cys Ser Pro His His Thr Ala Leu Arg Gln Ala
    450                 455                 460
Ile Leu Cys Trp Gly Glu Leu Met Asn Leu Ala Thr Trp Val Gly Ser
465                 470                 475                 480
Asn Leu Glu Asp Pro Ala Ser Arg Glu Leu Val Val Ser Tyr Val Asn
                485                 490                 495
Val Asn Met Gly Leu Lys Ile Arg Gln Leu Leu Trp Phe His Ile Ser
```

|  |  |  | 500 |  |  |  | 505 |  |  |  | 510 |  |
| --- | --- | --- | --- | --- | --- | --- | --- | --- | --- | --- | --- | --- |
| Cys | Leu | Thr | Phe | Gly | Arg | Glu | Thr | Val | Leu | Glu | Tyr | Leu | Val | Ser | Phe |
|  |  |  | 515 |  |  |  | 520 |  |  |  | 525 |  |

Gly Val Trp Ile Arg Thr Pro Pro Ala Tyr Arg Pro Pro Asn Ala Pro
530                     535                     540

Ile Leu Ser Thr Leu Pro Glu Thr Thr Val Val Arg Arg Arg Gly Arg
545                 550                 555                 560

Ser Pro Arg Arg Arg Thr Pro Ser Pro Arg Arg Arg Ser Gln Ser
            565                 570                 575

Pro Arg Arg Arg Arg Ser Gln Ser Arg Glu Ser Gln Cys His His His
            580                 585                 590

His His His
       595

<210> SEQ ID NO 35
<211> LENGTH: 2841
<212> TYPE: DNA
<213> ORGANISM: Artificial
<220> FEATURE:
<223> OTHER INFORMATION: synthetic DNA
<220> FEATURE:
<221> NAME/KEY: CDS
<222> LOCATION: (1)..(2841)

<400> SEQUENCE: 35

| atg | gcc | gat | gaa | gct | cct | tta | ggg | ttt | ttc | cct | gat | cat | caa | tta | gac | 48 |
| Met | Ala | Asp | Glu | Ala | Pro | Leu | Gly | Phe | Phe | Pro | Asp | His | Gln | Leu | Asp |  |
| 1 |  |  |  | 5 |  |  |  |  | 10 |  |  |  |  | 15 |  |  |

| cca | gca | ttc | ggt | gcc | aat | tcc | aac | aat | cct | gat | tgg | gac | ttt | aac | cca | 96 |
| Pro | Ala | Phe | Gly | Ala | Asn | Ser | Asn | Asn | Pro | Asp | Trp | Asp | Phe | Asn | Pro |  |
|  |  |  | 20 |  |  |  |  | 25 |  |  |  |  | 30 |  |  |  |

| gag | aat | aca | aca | tct | ggg | ttc | ctt | ggt | cca | ctt | ttg | gtg | ctg | caa | gct | 144 |
| Glu | Asn | Thr | Thr | Ser | Gly | Phe | Leu | Gly | Pro | Leu | Leu | Val | Leu | Gln | Ala |  |
|  | 35 |  |  |  |  | 40 |  |  |  |  | 45 |  |  |  |  |  |

| ggc | ttt | ttc | ctg | tta | act | aga | atc | cta | aca | att | cca | caa | agt | ttg | gat | 192 |
| Gly | Phe | Phe | Leu | Leu | Thr | Arg | Ile | Leu | Thr | Ile | Pro | Gln | Ser | Leu | Asp |  |
| 50 |  |  |  |  | 55 |  |  |  |  | 60 |  |  |  |  |  |  |

| tca | tgg | tgg | aca | tct | ttg | aac | ttt | ttg | gga | ggt | gct | cca | acc | tgt | cct | 240 |
| Ser | Trp | Trp | Thr | Ser | Leu | Asn | Phe | Leu | Gly | Gly | Ala | Pro | Thr | Cys | Pro |  |
| 65 |  |  |  |  | 70 |  |  |  |  | 75 |  |  |  |  | 80 |  |

| gga | caa | aac | tcc | caa | tcc | cca | act | tct | aat | cat | tca | cct | aca | tcc | tgc | 288 |
| Gly | Gln | Asn | Ser | Gln | Ser | Pro | Thr | Ser | Asn | His | Ser | Pro | Thr | Ser | Cys |  |
|  |  |  |  | 85 |  |  |  |  | 90 |  |  |  |  | 95 |  |  |

| cca | cct | att | tgt | cct | ggt | tat | cgt | tgg | atg | tgt | ctt | aga | cgt | ttc | att | 336 |
| Pro | Pro | Ile | Cys | Pro | Gly | Tyr | Arg | Trp | Met | Cys | Leu | Arg | Arg | Phe | Ile |  |
|  |  |  | 100 |  |  |  |  | 105 |  |  |  |  | 110 |  |  |  |

| atc | ttt | ttg | ttc | ata | cta | ctg | ttg | tgt | ctg | att | ttc | ctg | ttg | gta | ttg | 384 |
| Ile | Phe | Leu | Phe | Ile | Leu | Leu | Leu | Cys | Leu | Ile | Phe | Leu | Leu | Val | Leu |  |
|  | 115 |  |  |  |  | 120 |  |  |  |  | 125 |  |  |  |  |  |

| ttg | gat | tac | caa | ggc | atg | ttg | cca | gtc | tgt | cct | tta | ctt | cca | ggc | act | 432 |
| Leu | Asp | Tyr | Gln | Gly | Met | Leu | Pro | Val | Cys | Pro | Leu | Leu | Pro | Gly | Thr |  |
| 130 |  |  |  |  | 135 |  |  |  |  | 140 |  |  |  |  |  |  |

| tct | act | aca | tca | act | ggc | cct | tgt | aaa | aca | tgt | act | atc | cca | gct | caa | 480 |
| Ser | Thr | Thr | Ser | Thr | Gly | Pro | Cys | Lys | Thr | Cys | Thr | Ile | Pro | Ala | Gln |  |
| 145 |  |  |  |  | 150 |  |  |  |  | 155 |  |  |  |  | 160 |  |

| ggt | act | tca | atg | ttt | cct | agt | tgt | tgt | tgt | acc | aaa | cca | tcc | gat | ggt | 528 |
| Gly | Thr | Ser | Met | Phe | Pro | Ser | Cys | Cys | Cys | Thr | Lys | Pro | Ser | Asp | Gly |  |
|  |  |  |  | 165 |  |  |  |  | 170 |  |  |  |  | 175 |  |  |

| aat | tgt | aca | tgc | ata | cca | ata | cca | tct | tca | tgg | gca | ttt | gca | aga | ttc | 576 |
| Asn | Cys | Thr | Cys | Ile | Pro | Ile | Pro | Ser | Ser | Trp | Ala | Phe | Ala | Arg | Phe |  |

-continued

```
              180                 185                 190
ctt tgg gaa tgg gct tct gtg cgt ttt tcc tgg ctg tct ttg tta gtt      624
Leu Trp Glu Trp Ala Ser Val Arg Phe Ser Trp Leu Ser Leu Leu Val
            195                 200                 205 cct ttt gtc caa tgg ttt gtc ggt tta tct cca aca gta tgg ctg tct      672
Pro Phe Val Gln Trp Phe Val Gly Leu Ser Pro Thr Val Trp Leu Ser
210                 215                 220 gct atc tgg atg atg tgg tat tgg gga cct tcc ttg tac aac att ctg      720
Ala Ile Trp Met Met Trp Tyr Trp Gly Pro Ser Leu Tyr Asn Ile Leu
225                 230                 235                 240 tct cca ttt ctg cct ttg tta cca atc ttt ttc tgt ctt tgg gtg tac      768
Ser Pro Phe Leu Pro Leu Leu Pro Ile Phe Phe Cys Leu Trp Val Tyr
            245                 250                 255 atc ctc gag gaa gat tgg ggt cct tgt act gaa cac ggt gaa cat aac      816
Ile Leu Glu Glu Asp Trp Gly Pro Cys Thr Glu His Gly Glu His Asn
            260                 265                 270 atc aga ata cct aga act cca gct aga gtg aca gga ggt gtt ttc ctg      864
Ile Arg Ile Pro Arg Thr Pro Ala Arg Val Thr Gly Gly Val Phe Leu
            275                 280                 285 gta gac aaa aac cca cac aac aca gca gaa tct aga ctt gtc gtt gac      912
Val Asp Lys Asn Pro His Asn Thr Ala Glu Ser Arg Leu Val Val Asp
290                 295                 300 ttc agt caa ttc tcc aga ggg tct act cat gtt tca tgg cca aag ttt      960
Phe Ser Gln Phe Ser Arg Gly Ser Thr His Val Ser Trp Pro Lys Phe
305                 310                 315                 320 gca gtt cca aac ttg caa tca ttg act aat cta cta tct tca aat ctt     1008
Ala Val Pro Asn Leu Gln Ser Leu Thr Asn Leu Leu Ser Ser Asn Leu
            325                 330                 335 agt tgg ttg tcc ttg gat gtc tct gct gca ttc tat cat ata cca ttg     1056
Ser Trp Leu Ser Leu Asp Val Ser Ala Ala Phe Tyr His Ile Pro Leu
            340                 345                 350 cat cct gca gcc atg cca cat ttg tta gtg ggt agt tct ggt ctg tca     1104
His Pro Ala Ala Met Pro His Leu Leu Val Gly Ser Ser Gly Leu Ser
            355                 360                 365 agg tac gtt gca aga cta tct tct act tct agg aat atc aat tac aaa     1152
Arg Tyr Val Ala Arg Leu Ser Ser Thr Ser Arg Asn Ile Asn Tyr Lys
370                 375                 380 cat ggg aca atg caa gac cta cat gat tca tgt tct aga aac ttg tac     1200
His Gly Thr Met Gln Asp Leu His Asp Ser Cys Ser Arg Asn Leu Tyr
385                 390                 395                 400 gta tcc ctt tta cta ctt tac aaa aca ttt ggt aga aag ttg cac tta     1248
Val Ser Leu Leu Leu Leu Tyr Lys Thr Phe Gly Arg Lys Leu His Leu
            405                 410                 415 tac tca cat cca atc atc tta ggt ttc aga aag ata cct atg ggc gtc     1296
Tyr Ser His Pro Ile Ile Leu Gly Phe Arg Lys Ile Pro Met Gly Val
            420                 425                 430 ggg tta tct cct ttt cta tta gca cag ttt acc tct gcc att tgt tca     1344
Gly Leu Ser Pro Phe Leu Leu Ala Gln Phe Thr Ser Ala Ile Cys Ser
            435                 440                 445 gtg gtt cgt aga gca ttt cct cat tgt cta gca ttt tca tac atg gac     1392
Val Val Arg Arg Ala Phe Pro His Cys Leu Ala Phe Ser Tyr Met Asp
450                 455                 460 gat gtt gtc tta ggc gct aag tct gtt caa cac ctt gaa tca ctg ttt     1440
Asp Val Val Leu Gly Ala Lys Ser Val Gln His Leu Glu Ser Leu Phe
465                 470                 475                 480 acc agt ata acc aat ttc ctt ttg agt cta ggc att cat ctg aat cct     1488
Thr Ser Ile Thr Asn Phe Leu Leu Ser Leu Gly Ile His Leu Asn Pro
            485                 490                 495 aac aaa act aaa aga tgg gga tac tct ctt aac ttt atg ggt tac gtt     1536
```

```
                Asn Lys Thr Lys Arg Trp Gly Tyr Ser Leu Asn Phe Met Gly Tyr Val
                            500                 505                 510 atc gga tca tgg ggc acc ctt cca caa gag cat att gtc ctg aaa atc          1584
Ile Gly Ser Trp Gly Thr Leu Pro Gln Glu His Ile Val Leu Lys Ile
            515                 520                 525 aag cag tgt ttt aga aaa ctg cca gtg aat aga cca att gat tgg aaa          1632
Lys Gln Cys Phe Arg Lys Leu Pro Val Asn Arg Pro Ile Asp Trp Lys
530                 535                 540 gtt tgc cag aga atc gta ggt tta ctt ggt ttt gcc gct cct ttc act          1680
Val Cys Gln Arg Ile Val Gly Leu Leu Gly Phe Ala Ala Pro Phe Thr
545                 550                 555                 560 cag tgc ggc tat cca gct ttg atg cca ttg tac gct tgt atc caa gct          1728
Gln Cys Gly Tyr Pro Ala Leu Met Pro Leu Tyr Ala Cys Ile Gln Ala
            565                 570                 575 aag caa gct ttc aca ttc tct cca acc tat aag gct ttt cta tgc aag          1776
Lys Gln Ala Phe Thr Phe Ser Pro Thr Tyr Lys Ala Phe Leu Cys Lys
            580                 585                 590 cag tac tta aac ctt tat cca gtg gct aga caa aga gat att gac cca          1824
Gln Tyr Leu Asn Leu Tyr Pro Val Ala Arg Gln Arg Asp Ile Asp Pro
            595                 600                 605 tac aaa gag ttt ggg gca tca gtt gaa tta cta tcc ttc cta cca tca          1872
Tyr Lys Glu Phe Gly Ala Ser Val Glu Leu Leu Ser Phe Leu Pro Ser
610                 615                 620 gac ttt ttc cca tca atc aga gat ttg tta gat act gcc tct gca ttg          1920
Asp Phe Phe Pro Ser Ile Arg Asp Leu Leu Asp Thr Ala Ser Ala Leu
625                 630                 635                 640 tac aga gaa gct cta gaa tct cct gaa cat tgc tct cca cac cat act          1968
Tyr Arg Glu Ala Leu Glu Ser Pro Glu His Cys Ser Pro His His Thr
            645                 650                 655 gcc ctt aga caa gca atc ttg tgt tgg ggc gaa ctt atg aat ttg gcc          2016
Ala Leu Arg Gln Ala Ile Leu Cys Trp Gly Glu Leu Met Asn Leu Ala
            660                 665                 670 aca tgg gtt gga agt aat cta gaa gat cca gcc tca aga gag cta gtt          2064
Thr Trp Val Gly Ser Asn Leu Glu Asp Pro Ala Ser Arg Glu Leu Val
            675                 680                 685 gta tct tac gtc aac gtt aac atg ggt cta aag att agg caa tta cta          2112
Val Ser Tyr Val Asn Val Asn Met Gly Leu Lys Ile Arg Gln Leu Leu
690                 695                 700 tgg ttt cac att agt tgc tta act ttc ggt aga gaa aca gtg cta gag          2160
Trp Phe His Ile Ser Cys Leu Thr Phe Gly Arg Glu Thr Val Leu Glu
705                 710                 715                 720 tat ttg gta tca ttt gga gta tgg atc aga act cca cct gca tat aga          2208
Tyr Leu Val Ser Phe Gly Val Trp Ile Arg Thr Pro Pro Ala Tyr Arg
            725                 730                 735 cca cca aat gct cca atc tta tct aca ctg cct gaa aca act gta gtc          2256
Pro Pro Asn Ala Pro Ile Leu Ser Thr Leu Pro Glu Thr Thr Val Val
            740                 745                 750 agg aga aga gga aga tca cca agg agg aga act cca tct cca agg aga          2304
Arg Arg Arg Gly Arg Ser Pro Arg Arg Arg Thr Pro Ser Pro Arg Arg
            755                 760                 765 cgt cgt tct cag tcc cct cgt aga cgt aga tct caa tca aga gaa tct          2352
Arg Arg Ser Gln Ser Pro Arg Arg Arg Ser Gln Ser Arg Glu Ser
            770                 775                 780 caa tgc gca gcc aga gtt tgc tgt aaa ctt gac cca gcc aga gat gta          2400
Gln Cys Ala Ala Arg Val Cys Cys Lys Leu Asp Pro Ala Arg Asp Val
785                 790                 795                 800 cta tgt ctt aga cca gtt ggc gct gaa tca tct ggt aga cca gtc tca          2448
Leu Cys Leu Arg Pro Val Gly Ala Glu Ser Ser Gly Arg Pro Val Ser
            805                 810                 815
```

```
ggc cca ttt ggg aca tta cca tcc cct tca agt agt gcc gta cct gca      2496
Gly Pro Phe Gly Thr Leu Pro Ser Pro Ser Ser Ser Ala Val Pro Ala
            820                 825                 830 gat cac gga gca cat ctg tct cta aga gga ctt cct gtt tgt gct ttt      2544
Asp His Gly Ala His Leu Ser Leu Arg Gly Leu Pro Val Cys Ala Phe
            835                 840                 845 agt tca gca gga cct tgc gcc ttg aga ttc aca tca gct agg aga atg      2592
Ser Ser Ala Gly Pro Cys Ala Leu Arg Phe Thr Ser Ala Arg Arg Met
850                 855                 860 gaa aca aca gtt aat gct cat caa gtt ttg cca aaa gta tta cac aag      2640
Glu Thr Thr Val Asn Ala His Gln Val Leu Pro Lys Val Leu His Lys
865                 870                 875                 880 aga aca ttg ggt ttg tct gcc atg agt acc act gac tta gaa gct tac      2688
Arg Thr Leu Gly Leu Ser Ala Met Ser Thr Thr Asp Leu Glu Ala Tyr
                885                 890                 895 ttt aag gat tgc gtt ttc aaa gat tgg gag gaa tta ggt gag gaa atc      2736
Phe Lys Asp Cys Val Phe Lys Asp Trp Glu Glu Leu Gly Glu Glu Ile
                900                 905                 910 aga cta aaa gtt ttt gtg tta ggt ggt tgc aga cac aaa ttg gtc tgt      2784
Arg Leu Lys Val Phe Val Leu Gly Gly Cys Arg His Lys Leu Val Cys
            915                 920                 925 tcc cct gct cca tgc aac ttt ttc acc tcc gcc cac cat cat cat cac      2832
Ser Pro Ala Pro Cys Asn Phe Phe Thr Ser Ala His His His His His
930                 935                 940 cat tga taa                                                           2841
His
945

<210> SEQ ID NO 36
<211> LENGTH: 945
<212> TYPE: PRT
<213> ORGANISM: Artificial
<220> FEATURE:
<223> OTHER INFORMATION: Synthetic Construct

<400> SEQUENCE: 36

Met Ala Asp Glu Ala Pro Leu Gly Phe Phe Pro Asp His Gln Leu Asp
1               5                   10                  15

Pro Ala Phe Gly Ala Asn Ser Asn Asn Pro Asp Trp Asp Phe Asn Pro
            20                  25                  30

Glu Asn Thr Thr Ser Gly Phe Leu Gly Pro Leu Leu Val Leu Gln Ala
        35                  40                  45

Gly Phe Phe Leu Leu Thr Arg Ile Leu Thr Ile Pro Gln Ser Leu Asp
    50                  55                  60

Ser Trp Trp Thr Ser Leu Asn Phe Leu Gly Ala Pro Thr Cys Pro
65                  70                  75                  80

Gly Gln Asn Ser Gln Ser Pro Thr Ser Asn His Ser Pro Thr Ser Cys
                85                  90                  95

Pro Pro Ile Cys Pro Gly Tyr Arg Trp Met Cys Leu Arg Arg Phe Ile
            100                 105                 110

Ile Phe Leu Phe Ile Leu Leu Leu Cys Leu Ile Phe Leu Leu Val Leu
        115                 120                 125

Leu Asp Tyr Gln Gly Met Leu Pro Val Cys Pro Leu Leu Pro Gly Thr
    130                 135                 140

Ser Thr Thr Ser Thr Gly Pro Cys Lys Thr Cys Thr Ile Pro Ala Gln
145                 150                 155                 160

Gly Thr Ser Met Phe Pro Ser Cys Cys Cys Thr Lys Pro Ser Asp Gly
                165                 170                 175
```

-continued

```
Asn Cys Thr Cys Ile Pro Ile Pro Ser Ser Trp Ala Phe Ala Arg Phe
            180                 185                 190
Leu Trp Glu Trp Ala Ser Val Arg Phe Ser Trp Leu Ser Leu Leu Val
        195                 200                 205
Pro Phe Val Gln Trp Phe Val Gly Leu Ser Pro Thr Val Trp Leu Ser
    210                 215                 220
Ala Ile Trp Met Met Trp Tyr Trp Gly Pro Ser Leu Tyr Asn Ile Leu
225                 230                 235                 240
Ser Pro Phe Leu Pro Leu Leu Pro Ile Phe Phe Cys Leu Trp Val Tyr
                245                 250                 255
Ile Leu Glu Glu Asp Trp Gly Pro Cys Thr Glu His Gly Glu His Asn
            260                 265                 270
Ile Arg Ile Pro Arg Thr Pro Ala Arg Val Thr Gly Gly Val Phe Leu
        275                 280                 285
Val Asp Lys Asn Pro His Asn Thr Ala Glu Ser Arg Leu Val Val Asp
    290                 295                 300
Phe Ser Gln Phe Ser Arg Gly Ser Thr His Val Ser Trp Pro Lys Phe
305                 310                 315                 320
Ala Val Pro Asn Leu Gln Ser Leu Thr Asn Leu Leu Ser Ser Asn Leu
                325                 330                 335
Ser Trp Leu Ser Leu Asp Val Ser Ala Ala Phe Tyr His Ile Pro Leu
            340                 345                 350
His Pro Ala Ala Met Pro His Leu Leu Val Gly Ser Ser Gly Leu Ser
        355                 360                 365
Arg Tyr Val Ala Arg Leu Ser Ser Thr Ser Arg Asn Ile Asn Tyr Lys
    370                 375                 380
His Gly Thr Met Gln Asp Leu His Asp Ser Cys Ser Arg Asn Leu Tyr
385                 390                 395                 400
Val Ser Leu Leu Leu Leu Tyr Lys Thr Phe Gly Arg Lys Leu His Leu
                405                 410                 415
Tyr Ser His Pro Ile Ile Leu Gly Phe Arg Lys Ile Pro Met Gly Val
            420                 425                 430
Gly Leu Ser Pro Phe Leu Leu Ala Gln Phe Thr Ser Ala Ile Cys Ser
        435                 440                 445
Val Val Arg Arg Ala Phe Pro His Cys Leu Ala Phe Ser Tyr Met Asp
    450                 455                 460
Asp Val Val Leu Gly Ala Lys Ser Val Gln His Leu Glu Ser Leu Phe
465                 470                 475                 480
Thr Ser Ile Thr Asn Phe Leu Leu Ser Leu Gly Ile His Leu Asn Pro
                485                 490                 495
Asn Lys Thr Lys Arg Trp Gly Tyr Ser Leu Asn Phe Met Gly Tyr Val
            500                 505                 510
Ile Gly Ser Trp Gly Thr Leu Pro Gln Glu His Ile Val Leu Lys Ile
        515                 520                 525
Lys Gln Cys Phe Arg Lys Leu Pro Val Asn Arg Pro Ile Asp Trp Lys
    530                 535                 540
Val Cys Gln Arg Ile Val Gly Leu Leu Gly Phe Ala Ala Pro Phe Thr
545                 550                 555                 560
Gln Cys Gly Tyr Pro Ala Leu Met Pro Leu Tyr Ala Cys Ile Gln Ala
                565                 570                 575
Lys Gln Ala Phe Thr Phe Ser Pro Thr Tyr Lys Ala Phe Leu Cys Lys
            580                 585                 590
Gln Tyr Leu Asn Leu Tyr Pro Val Ala Arg Gln Arg Asp Ile Asp Pro
```

```
                 595                 600                 605
Tyr Lys Glu Phe Gly Ala Ser Val Glu Leu Leu Ser Phe Leu Pro Ser
    610                 615                 620
Asp Phe Phe Pro Ser Ile Arg Asp Leu Leu Asp Thr Ala Ser Ala Leu
625                 630                 635                 640
Tyr Arg Glu Ala Leu Glu Ser Pro Glu His Cys Ser Pro His His Thr
                645                 650                 655
Ala Leu Arg Gln Ala Ile Leu Cys Trp Gly Glu Leu Met Asn Leu Ala
            660                 665                 670
Thr Trp Val Gly Ser Asn Leu Glu Asp Pro Ala Ser Arg Glu Leu Val
        675                 680                 685
Val Ser Tyr Val Asn Val Asn Met Gly Leu Lys Ile Arg Gln Leu Leu
    690                 695                 700
Trp Phe His Ile Ser Cys Leu Thr Phe Gly Arg Glu Thr Val Leu Glu
705                 710                 715                 720
Tyr Leu Val Ser Phe Gly Val Trp Ile Arg Thr Pro Pro Ala Tyr Arg
                725                 730                 735
Pro Pro Asn Ala Pro Ile Leu Ser Thr Leu Pro Glu Thr Thr Val Val
            740                 745                 750
Arg Arg Arg Gly Arg Ser Pro Arg Arg Thr Pro Ser Pro Arg Arg
        755                 760                 765
Arg Arg Ser Gln Ser Pro Arg Arg Arg Ser Gln Ser Arg Glu Ser
    770                 775                 780
Gln Cys Ala Ala Arg Val Cys Cys Lys Leu Asp Pro Ala Arg Asp Val
785                 790                 795                 800
Leu Cys Leu Arg Pro Val Gly Ala Glu Ser Ser Gly Arg Pro Val Ser
                805                 810                 815
Gly Pro Phe Gly Thr Leu Pro Ser Pro Ser Ser Ala Val Pro Ala
            820                 825                 830
Asp His Gly Ala His Leu Ser Leu Arg Gly Leu Pro Val Cys Ala Phe
        835                 840                 845
Ser Ser Ala Gly Pro Cys Ala Leu Arg Phe Thr Ser Ala Arg Arg Met
    850                 855                 860
Glu Thr Thr Val Asn Ala His Gln Val Leu Pro Lys Val Leu His Lys
865                 870                 875                 880
Arg Thr Leu Gly Leu Ser Ala Met Ser Thr Thr Asp Leu Glu Ala Tyr
                885                 890                 895
Phe Lys Asp Cys Val Phe Lys Asp Trp Glu Glu Leu Gly Glu Glu Ile
            900                 905                 910
Arg Leu Lys Val Phe Val Leu Gly Gly Cys Arg His Lys Leu Val Cys
        915                 920                 925
Ser Pro Ala Pro Cys Asn Phe Phe Thr Ser Ala His His His His
    930                 935                 940
His
945

<210> SEQ ID NO 37
<211> LENGTH: 6
<212> TYPE: PRT
<213> ORGANISM: Artificial
<220> FEATURE:
<223> OTHER INFORMATION: synthetic peptide

<400> SEQUENCE: 37

Met Ala Asp Glu Ala Pro
```

<210> SEQ ID NO 38
<211> LENGTH: 539
<212> TYPE: PRT
<213> ORGANISM: Artificial
<220> FEATURE:
<223> OTHER INFORMATION: Synthetic Construct

<400> SEQUENCE: 38

Met Ala Asp Glu Ala Pro Glu Asp Trp Gly Pro Cys Thr Glu His Gly
1               5                   10                  15

Glu His Asn Ile Arg Ile Pro Arg Thr Pro Ala Arg Val Thr Gly Gly
            20                  25                  30

Val Phe Leu Val Asp Lys Asn Pro His Asn Thr Ala Glu Ser Arg Leu
        35                  40                  45

Val Val Asp Phe Ser Gln Phe Ser Arg Gly Ser Thr His Val Ser Trp
    50                  55                  60

Pro Lys Phe Ala Val Pro Asn Leu Gln Ser Leu Thr Asn Leu Leu Ser
65                  70                  75                  80

Ser Asn Leu Ser Trp Leu Ser Leu Asp Val Ser Ala Ala Phe Tyr His
                85                  90                  95

Ile Pro Leu His Pro Ala Ala Met Pro His Leu Leu Val Gly Ser Ser
            100                 105                 110

Gly Leu Ser Arg Tyr Val Ala Arg Leu Ser Ser Thr Ser Arg Asn Ile
        115                 120                 125

Asn Tyr Lys His Gly Thr Met Gln Asp Leu His Asp Ser Cys Ser Arg
    130                 135                 140

Asn Leu Tyr Val Ser Leu Leu Leu Leu Tyr Lys Thr Phe Gly Arg Lys
145                 150                 155                 160

Leu His Leu Tyr Ser His Pro Ile Ile Leu Gly Phe Arg Lys Ile Pro
                165                 170                 175

Met Gly Val Gly Leu Ser Pro Phe Leu Leu Ala Gln Phe Thr Ser Ala
            180                 185                 190

Ile Cys Ser Val Val Arg Arg Ala Phe Pro His Cys Leu Ala Phe Ser
        195                 200                 205

Tyr Met Asp Asp Val Val Leu Gly Ala Lys Ser Val Gln His Leu Glu
    210                 215                 220

Ser Leu Phe Thr Ser Ile Thr Asn Phe Leu Leu Ser Leu Gly Ile His
225                 230                 235                 240

Leu Asn Pro Asn Lys Thr Lys Arg Trp Gly Tyr Ser Leu Asn Phe Met
                245                 250                 255

Gly Tyr Val Ile Gly Ser Trp Gly Thr Leu Pro Gln Glu His Ile Val
            260                 265                 270

Leu Lys Ile Lys Gln Cys Phe Arg Lys Leu Pro Val Asn Arg Pro Ile
        275                 280                 285

Asp Trp Lys Val Cys Gln Arg Ile Val Gly Leu Leu Gly Phe Ala Ala
    290                 295                 300

Pro Phe Thr Gln Cys Gly Tyr Pro Ala Leu Met Pro Leu Tyr Ala Cys
305                 310                 315                 320

Ile Gln Ala Lys Gln Ala Phe Thr Phe Ser Pro Thr Tyr Lys Ala Phe
                325                 330                 335

Leu Cys Lys Gln Tyr Leu Asn Leu Tyr Pro Val Ala Arg Gln Arg Asp
            340                 345                 350

Ile Asp Pro Tyr Lys Glu Phe Gly Ala Ser Val Glu Leu Leu Ser Phe

```
            355                 360                 365
Leu Pro Ser Asp Phe Phe Pro Ser Ile Arg Asp Leu Leu Asp Thr Ala
    370                 375                 380

Ser Ala Leu Tyr Arg Glu Ala Leu Glu Ser Pro His Cys Ser Pro
385                 390                 395                 400

His His Thr Ala Leu Arg Gln Ala Ile Leu Cys Trp Gly Glu Leu Met
                    405                 410                 415

Asn Leu Ala Thr Trp Val Gly Ser Asn Leu Glu Asp Pro Ala Ser Arg
                420                 425                 430

Glu Leu Val Val Ser Tyr Val Asn Val Asn Met Gly Leu Lys Ile Arg
            435                 440                 445

Gln Leu Leu Trp Phe His Ile Ser Cys Leu Thr Phe Gly Arg Glu Thr
        450                 455                 460

Val Leu Glu Tyr Leu Val Ser Phe Gly Val Trp Ile Arg Thr Pro Pro
465                 470                 475                 480

Ala Tyr Arg Pro Pro Asn Ala Pro Ile Leu Ser Thr Leu Pro Glu Thr
                    485                 490                 495

Thr Val Val Arg Arg Arg Gly Arg Ser Pro Arg Arg Arg Thr Pro Ser
                500                 505                 510

Pro Arg Arg Arg Arg Ser Gln Ser Pro Arg Arg Arg Arg Ser Gln Ser
            515                 520                 525

Arg Glu Ser Gln Cys His His His His His His
    530                 535
```

<210> SEQ ID NO 39
<211> LENGTH: 347
<212> TYPE: PRT
<213> ORGANISM: Artificial
<220> FEATURE:
<223> OTHER INFORMATION: Synthetic Construct

<400> SEQUENCE: 39

```
Met Ala Asp Glu Ala Pro Ala Ala Arg Val Cys Cys Lys Leu Asp Pro
1               5                   10                  15

Ala Arg Asp Val Leu Cys Leu Arg Pro Val Gly Ala Glu Ser Ser Gly
                20                  25                  30

Arg Pro Val Ser Gly Pro Phe Gly Thr Leu Pro Ser Pro Ser Ser Ser
            35                  40                  45

Ala Val Pro Ala Asp His Gly Ala His Leu Ser Leu Arg Gly Leu Pro
        50                  55                  60

Val Cys Ala Phe Ser Ser Ala Gly Pro Cys Ala Leu Arg Phe Thr Ser
65                  70                  75                  80

Ala Arg Arg Met Glu Thr Thr Val Asn Ala His Gln Val Leu Pro Lys
                85                  90                  95

Val Leu His Lys Arg Thr Leu Gly Leu Ser Ala Met Ser Thr Thr Asp
            100                 105                 110

Leu Glu Ala Tyr Phe Lys Asp Cys Val Phe Lys Asp Trp Glu Glu Leu
        115                 120                 125

Gly Glu Glu Ile Arg Leu Lys Val Phe Val Leu Gly Gly Cys Arg His
    130                 135                 140

Lys Leu Val Cys Ser Pro Ala Pro Cys Asn Phe Phe Thr Ser Ala Asp
145                 150                 155                 160

Ile Asp Pro Tyr Lys Glu Phe Gly Ala Ser Val Glu Leu Leu Ser Phe
                165                 170                 175

Leu Pro Ser Asp Phe Phe Pro Ser Ile Arg Asp Leu Leu Asp Thr Ala
```

```
                180                 185                 190
Ser Ala Leu Tyr Arg Glu Ala Leu Glu Ser Pro Glu His Cys Ser Pro
            195                 200                 205

His His Thr Ala Leu Arg Gln Ala Ile Leu Cys Trp Gly Glu Leu Met
210                 215                 220

Asn Leu Ala Thr Trp Val Gly Ser Asn Leu Glu Asp Pro Ala Ser Arg
225                 230                 235                 240

Glu Leu Val Val Ser Tyr Val Asn Val Asn Met Gly Leu Lys Ile Arg
                245                 250                 255

Gln Leu Leu Trp Phe His Ile Ser Cys Leu Thr Phe Gly Arg Glu Thr
            260                 265                 270

Val Leu Glu Tyr Leu Val Ser Phe Gly Val Trp Ile Arg Thr Pro Pro
            275                 280                 285

Ala Tyr Arg Pro Pro Asn Ala Pro Ile Leu Ser Thr Leu Pro Glu Thr
            290                 295                 300

Thr Val Val Arg Arg Arg Gly Arg Ser Pro Arg Arg Arg Thr Pro Ser
305                 310                 315                 320

Pro Arg Arg Arg Ser Gln Ser Pro Arg Arg Arg Arg Ser Gln Ser
                325                 330                 335

Arg Glu Ser Gln Cys His His His His His
            340                 345

<210> SEQ ID NO 40
<211> LENGTH: 357
<212> TYPE: PRT
<213> ORGANISM: Artificial
<220> FEATURE:
<223> OTHER INFORMATION: Synthetic Construct

<400> SEQUENCE: 40

Met Ala Asp Glu Ala Pro Glu Asp Trp Gly Pro Cys Thr Glu His Gly
1               5                   10                  15

Glu His Asn Ile Arg Ile Pro Arg Thr Pro Ala Arg Val Thr Gly Gly
            20                  25                  30

Val Phe Leu Val Asp Lys Asn Pro His Asn Thr Ala Glu Ser Arg Leu
        35                  40                  45

Val Val Asp Phe Ser Gln Phe Ser Arg Gly Ser Thr His Val Ser Trp
    50                  55                  60

Pro Lys Phe Ala Val Pro Asn Leu Gln Ser Leu Thr Asn Leu Leu Ser
65                  70                  75                  80

Ser Asn Leu Ser Trp Leu Ser Leu Asp Val Ser Ala Ala Phe Tyr His
                85                  90                  95

Ile Pro Leu His Pro Ala Ala Met Pro His Leu Leu Val Gly Ser Ser
            100                 105                 110

Gly Leu Ser Arg Tyr Val Ala Arg Leu Ser Ser Thr Ser Arg Asn Ile
        115                 120                 125

Asn Tyr Lys His Gly Thr Met Gln Asp Leu His Asp Ser Cys Ser Arg
    130                 135                 140

Asn Leu Tyr Val Ser Leu Leu Leu Leu Tyr Lys Thr Phe Gly Arg Lys
145                 150                 155                 160

Leu His Leu Tyr Ser His Pro Ile Ile Leu Gly Phe Arg Lys Ile Pro
                165                 170                 175

Met Gly Val Gly Leu Ser Pro Phe Leu Leu Ala Gln Phe Thr Ser Ala
            180                 185                 190

Ile Cys Ser Val Val Arg Arg Ala Phe Pro His Cys Leu Ala Phe Ser
```

```
                195                 200                 205
Tyr Met Asp Asp Val Val Leu Gly Ala Lys Ser Val Gln His Leu Glu
    210                 215                 220

Ser Leu Phe Thr Ser Ile Thr Asn Phe Leu Leu Ser Leu Gly Ile His
225                 230                 235                 240

Leu Asn Pro Asn Lys Thr Lys Arg Trp Gly Tyr Ser Leu Asn Phe Met
                245                 250                 255

Gly Tyr Val Ile Gly Ser Trp Gly Thr Leu Pro Gln Glu His Ile Val
            260                 265                 270

Leu Lys Ile Lys Gln Cys Phe Arg Lys Leu Pro Val Asn Arg Pro Ile
        275                 280                 285

Asp Trp Lys Val Cys Gln Arg Ile Val Gly Leu Leu Gly Phe Ala Ala
    290                 295                 300

Pro Phe Thr Gln Cys Gly Tyr Pro Ala Leu Met Pro Leu Tyr Ala Cys
305                 310                 315                 320

Ile Gln Ala Lys Gln Ala Phe Thr Phe Ser Pro Thr Tyr Lys Ala Phe
                325                 330                 335

Leu Cys Lys Gln Tyr Leu Asn Leu Tyr Pro Val Ala Arg Gln Arg His
            340                 345                 350

His His His His His
            355

<210> SEQ ID NO 41
<211> LENGTH: 792
<212> TYPE: PRT
<213> ORGANISM: Artificial
<220> FEATURE:
<223> OTHER INFORMATION: Synthetic Construct

<400> SEQUENCE: 41

Met Ala Asp Glu Ala Pro Leu Gly Phe Phe Asp His Gln Leu Asp
1               5                   10                  15

Pro Ala Phe Gly Ala Asn Ser Asn Pro Asp Trp Asp Phe Asn Pro
            20                  25                  30

Glu Asn Thr Thr Ser Gly Phe Leu Gly Pro Leu Leu Val Leu Gln Ala
            35                  40                  45

Gly Phe Phe Leu Leu Thr Arg Ile Leu Thr Ile Pro Gln Ser Leu Asp
    50                  55                  60

Ser Trp Trp Thr Ser Leu Asn Phe Leu Gly Gly Ala Pro Thr Cys Pro
65                  70                  75                  80

Gly Gln Asn Ser Gln Ser Pro Thr Ser Asn His Ser Pro Thr Ser Cys
                85                  90                  95

Pro Pro Ile Cys Pro Gly Tyr Arg Trp Met Cys Leu Arg Arg Phe Ile
            100                 105                 110

Ile Phe Leu Phe Ile Leu Leu Leu Cys Leu Ile Phe Leu Leu Val Leu
        115                 120                 125

Leu Asp Tyr Gln Gly Met Leu Pro Val Cys Pro Leu Leu Pro Gly Thr
    130                 135                 140

Ser Thr Thr Ser Thr Gly Pro Cys Lys Thr Cys Thr Ile Pro Ala Gln
145                 150                 155                 160

Gly Thr Ser Met Phe Pro Ser Cys Cys Cys Thr Lys Pro Ser Asp Gly
                165                 170                 175

Asn Cys Thr Cys Ile Pro Ile Pro Ser Ser Trp Ala Phe Ala Arg Phe
            180                 185                 190

Leu Trp Glu Trp Ala Ser Val Arg Phe Ser Trp Leu Ser Leu Leu Val
```

```
            195                 200                 205
Pro Phe Val Gln Trp Phe Val Gly Leu Ser Pro Thr Val Trp Leu Ser
210                 215                 220

Ala Ile Trp Met Met Trp Tyr Trp Gly Pro Ser Leu Tyr Asn Ile Leu
225                 230                 235                 240

Ser Pro Phe Leu Pro Leu Leu Pro Ile Phe Phe Cys Leu Trp Val Tyr
                245                 250                 255

Ile Leu Glu Glu Asp Trp Gly Pro Cys Thr Glu His Gly Glu His Asn
                260                 265                 270

Ile Arg Ile Pro Arg Thr Pro Ala Arg Val Thr Gly Gly Val Phe Leu
            275                 280                 285

Val Asp Lys Asn Pro His Asn Thr Ala Glu Ser Arg Leu Val Val Asp
290                 295                 300

Phe Ser Gln Phe Ser Arg Gly Ser Thr His Val Ser Trp Pro Lys Phe
305                 310                 315                 320

Ala Val Pro Asn Leu Gln Ser Leu Thr Asn Leu Leu Ser Ser Asn Leu
                325                 330                 335

Ser Trp Leu Ser Leu Asp Val Ser Ala Ala Phe Tyr His Ile Pro Leu
                340                 345                 350

His Pro Ala Ala Met Pro His Leu Leu Val Gly Ser Ser Gly Leu Ser
            355                 360                 365

Arg Tyr Val Ala Arg Leu Ser Ser Thr Ser Arg Asn Ile Asn Tyr Lys
370                 375                 380

His Gly Thr Met Gln Asp Leu His Asp Ser Cys Ser Arg Asn Leu Tyr
385                 390                 395                 400

Val Ser Leu Leu Leu Leu Tyr Lys Thr Phe Gly Arg Lys Leu His Leu
                405                 410                 415

Tyr Ser His Pro Ile Ile Leu Gly Phe Arg Lys Ile Pro Met Gly Val
            420                 425                 430

Gly Leu Ser Pro Phe Leu Leu Ala Gln Phe Thr Ser Ala Ile Cys Ser
            435                 440                 445

Val Val Arg Arg Ala Phe Pro His Cys Leu Ala Phe Ser Tyr Met Asp
450                 455                 460

Asp Val Val Leu Gly Ala Lys Ser Val Gln His Leu Glu Ser Leu Phe
465                 470                 475                 480

Thr Ser Ile Thr Asn Phe Leu Leu Ser Leu Gly Ile His Leu Asn Pro
                485                 490                 495

Asn Lys Thr Lys Arg Trp Gly Tyr Ser Leu Asn Phe Met Gly Tyr Val
            500                 505                 510

Ile Gly Ser Trp Gly Thr Leu Pro Gln Glu His Ile Val Leu Lys Ile
            515                 520                 525

Lys Gln Cys Phe Arg Lys Leu Pro Val Asn Arg Pro Ile Asp Trp Lys
530                 535                 540

Val Cys Gln Arg Ile Val Gly Leu Leu Gly Phe Ala Ala Pro Phe Thr
545                 550                 555                 560

Gln Cys Gly Tyr Pro Ala Leu Met Pro Leu Tyr Ala Cys Ile Gln Ala
                565                 570                 575

Lys Gln Ala Phe Thr Phe Ser Pro Thr Tyr Lys Ala Phe Leu Cys Lys
                580                 585                 590

Gln Tyr Leu Asn Leu Tyr Pro Val Ala Arg Gln Arg Asp Ile Asp Pro
            595                 600                 605

Tyr Lys Glu Phe Gly Ala Ser Val Glu Leu Leu Ser Phe Leu Pro Ser
610                 615                 620
```

```
Asp Phe Phe Pro Ser Ile Arg Asp Leu Leu Asp Thr Ala Ser Ala Leu
625                 630                 635                 640

Tyr Arg Glu Ala Leu Glu Ser Pro Glu His Cys Ser Pro His His Thr
                645                 650                 655

Ala Leu Arg Gln Ala Ile Leu Cys Trp Gly Glu Leu Met Asn Leu Ala
            660                 665                 670

Thr Trp Val Gly Ser Asn Leu Glu Asp Pro Ala Ser Arg Glu Leu Val
        675                 680                 685

Val Ser Tyr Val Asn Val Asn Met Gly Leu Lys Ile Arg Gln Leu Leu
    690                 695                 700

Trp Phe His Ile Ser Cys Leu Thr Phe Gly Arg Glu Thr Val Leu Glu
705                 710                 715                 720

Tyr Leu Val Ser Phe Gly Val Trp Ile Arg Thr Pro Pro Ala Tyr Arg
                725                 730                 735

Pro Pro Asn Ala Pro Ile Leu Ser Thr Leu Pro Glu Thr Thr Val Val
            740                 745                 750

Arg Arg Arg Gly Arg Ser Pro Arg Arg Arg Thr Pro Ser Pro Arg Arg
        755                 760                 765

Arg Arg Ser Gln Ser Pro Arg Arg Arg Ser Gln Ser Arg Glu Ser
770                 775                 780

Gln Cys His His His His His His
785                 790

<210> SEQ ID NO 42
<211> LENGTH: 9
<212> TYPE: PRT
<213> ORGANISM: Hepatitis B virus

<400> SEQUENCE: 42

Phe Leu Leu Thr Arg Ile Leu Thr Ile
1               5

<210> SEQ ID NO 43
<211> LENGTH: 10
<212> TYPE: PRT
<213> ORGANISM: Hepatitis B virus

<400> SEQUENCE: 43

Gly Leu Ser Pro Thr Val Trp Leu Ser Val
1               5                   10

<210> SEQ ID NO 44
<211> LENGTH: 10
<212> TYPE: PRT
<213> ORGANISM: Hepatitis B virus

<400> SEQUENCE: 44

Phe Leu Pro Ser Asp Phe Phe Pro Ser Ile
1               5                   10

<210> SEQ ID NO 45
<211> LENGTH: 9
<212> TYPE: PRT
<213> ORGANISM: Hepatitis B virus

<400> SEQUENCE: 45

Phe Leu Leu Ser Leu Gly Ile His Leu
1               5
```

<210> SEQ ID NO 46
<211> LENGTH: 9
<212> TYPE: PRT
<213> ORGANISM: Hepatitis B virus

<400> SEQUENCE: 46

Trp Leu Ser Leu Leu Val Pro Phe Val
1               5

<210> SEQ ID NO 47
<211> LENGTH: 9
<212> TYPE: PRT
<213> ORGANISM: Hepatitis B virus

<400> SEQUENCE: 47

Lys Tyr Thr Ser Phe Pro Trp Leu Leu
1               5

<210> SEQ ID NO 48
<211> LENGTH: 9
<212> TYPE: PRT
<213> ORGANISM: Hepatitis B virus

<400> SEQUENCE: 48

Tyr Val Asn Val Asn Met Gly Leu Lys
1               5

<210> SEQ ID NO 49
<211> LENGTH: 9
<212> TYPE: PRT
<213> ORGANISM: Hepatitis B virus

<400> SEQUENCE: 49

Glu Tyr Leu Val Ser Phe Gly Val Trp
1               5

<210> SEQ ID NO 50
<211> LENGTH: 9
<212> TYPE: PRT
<213> ORGANISM: Hepatitis B virus

<400> SEQUENCE: 50

Gly Leu Ser Arg Tyr Val Ala Arg Leu
1               5

<210> SEQ ID NO 51
<211> LENGTH: 9
<212> TYPE: PRT
<213> ORGANISM: Hepatitis B virus

<400> SEQUENCE: 51

Cys Leu Phe Lys Asp Trp Glu Glu Leu
1               5

<210> SEQ ID NO 52
<211> LENGTH: 8
<212> TYPE: PRT
<213> ORGANISM: Hepatitis B virus

<400> SEQUENCE: 52

Pro Leu Gly Phe Phe Pro Asp His
1               5

<210> SEQ ID NO 53
<211> LENGTH: 9

```
<212> TYPE: PRT
<213> ORGANISM: Hepatitis B virus

<400> SEQUENCE: 53

Ile Pro Ile Pro Ser Ser Trp Ala Phe
1               5

<210> SEQ ID NO 54
<211> LENGTH: 9
<212> TYPE: PRT
<213> ORGANISM: Hepatitis B virus

<400> SEQUENCE: 54

Leu Pro Ser Asp Phe Phe Pro Ser Val
1               5

<210> SEQ ID NO 55
<211> LENGTH: 15
<212> TYPE: PRT
<213> ORGANISM: Hepatitis B virus

<400> SEQUENCE: 55

Met Gln Trp Asn Ser Thr Ala Leu His Gln Ala Leu Gln Asp Pro
1               5                   10                  15

<210> SEQ ID NO 56
<211> LENGTH: 9
<212> TYPE: PRT
<213> ORGANISM: Hepatitis B virus

<400> SEQUENCE: 56

Leu Leu Asp Pro Arg Val Arg Gly Leu
1               5

<210> SEQ ID NO 57
<211> LENGTH: 10
<212> TYPE: PRT
<213> ORGANISM: Hepatitis B virus

<400> SEQUENCE: 57

Ser Ile Leu Ser Lys Thr Gly Asp Pro Val
1               5                   10

<210> SEQ ID NO 58
<211> LENGTH: 9
<212> TYPE: PRT
<213> ORGANISM: Hepatitis B virus

<400> SEQUENCE: 58

Val Leu Gln Ala Gly Phe Phe Leu Leu
1               5

<210> SEQ ID NO 59
<211> LENGTH: 9
<212> TYPE: PRT
<213> ORGANISM: Hepatitis B virus

<400> SEQUENCE: 59

Phe Leu Leu Thr Arg Ile Leu Thr Ile
1               5

<210> SEQ ID NO 60
<211> LENGTH: 9
<212> TYPE: PRT
<213> ORGANISM: Hepatitis B virus
```

<400> SEQUENCE: 60

Phe Leu Gly Gly Thr Pro Val Cys Leu
1               5

<210> SEQ ID NO 61
<211> LENGTH: 9
<212> TYPE: PRT
<213> ORGANISM: Hepatitis B virus

<400> SEQUENCE: 61

Leu Leu Cys Leu Ile Phe Leu Leu Val
1               5

<210> SEQ ID NO 62
<211> LENGTH: 10
<212> TYPE: PRT
<213> ORGANISM: Hepatitis B virus

<400> SEQUENCE: 62

Leu Val Leu Leu Asp Tyr Gln Gly Met Leu
1               5                   10

<210> SEQ ID NO 63
<211> LENGTH: 10
<212> TYPE: PRT
<213> ORGANISM: Hepatitis B virus

<400> SEQUENCE: 63

Leu Leu Asp Tyr Gln Gly Met Leu Pro Val
1               5                   10

<210> SEQ ID NO 64
<211> LENGTH: 10
<212> TYPE: PRT
<213> ORGANISM: Hepatitis B virus

<400> SEQUENCE: 64

Ser Ile Val Ser Pro Phe Ile Pro Leu Leu
1               5                   10

<210> SEQ ID NO 65
<211> LENGTH: 9
<212> TYPE: PRT
<213> ORGANISM: Hepatitis B virus

<400> SEQUENCE: 65

Ile Leu Ser Pro Phe Leu Pro Leu Leu
1               5

<210> SEQ ID NO 66
<211> LENGTH: 10
<212> TYPE: PRT
<213> ORGANISM: Hepatitis B virus

<400> SEQUENCE: 66

Thr Pro Ala Arg Val Thr Gly Gly Val Phe
1               5                   10

<210> SEQ ID NO 67
<211> LENGTH: 10
<212> TYPE: PRT
<213> ORGANISM: Hepatitis B virus

<400> SEQUENCE: 67

Leu Val Val Asp Phe Ser Gln Phe Ser Arg
1               5                   10

<210> SEQ ID NO 68
<211> LENGTH: 9
<212> TYPE: PRT
<213> ORGANISM: Hepatitis B virus

<400> SEQUENCE: 68

Ser Ala Ile Cys Ser Val Val Arg Arg
1               5

<210> SEQ ID NO 69
<211> LENGTH: 9
<212> TYPE: PRT
<213> ORGANISM: Hepatitis B virus

<400> SEQUENCE: 69

Tyr Met Asp Asp Val Val Leu Gly Ala
1               5

<210> SEQ ID NO 70
<211> LENGTH: 9
<212> TYPE: PRT
<213> ORGANISM: Hepatitis B virus

<400> SEQUENCE: 70

Ala Leu Met Pro Leu Tyr Ala Cys Ile
1               5

<210> SEQ ID NO 71
<211> LENGTH: 10
<212> TYPE: PRT
<213> ORGANISM: Hepatitis B virus

<400> SEQUENCE: 71

Gln Ala Phe Thr Phe Ser Pro Thr Tyr Lys
1               5                   10

<210> SEQ ID NO 72
<211> LENGTH: 17
<212> TYPE: PRT
<213> ORGANISM: Hepatitis B virus

<400> SEQUENCE: 72

Ala Thr Val Glu Leu Leu Ser Phe Leu Pro Ser Asp Phe Phe Pro Ser
1               5                   10                  15

Val

<210> SEQ ID NO 73
<211> LENGTH: 9
<212> TYPE: PRT
<213> ORGANISM: Hepatitis B virus

<400> SEQUENCE: 73

Leu Pro Ser Asp Phe Phe Pro Ser Val
1               5

<210> SEQ ID NO 74
<211> LENGTH: 9
<212> TYPE: PRT
<213> ORGANISM: Hepatitis B virus

<400> SEQUENCE: 74

```
Cys Leu Thr Phe Gly Arg Glu Thr Val
1               5

<210> SEQ ID NO 75
<211> LENGTH: 10
<212> TYPE: PRT
<213> ORGANISM: Hepatitis B virus

<400> SEQUENCE: 75

Val Leu Glu Tyr Leu Val Ser Phe Gly Val
1               5                   10

<210> SEQ ID NO 76
<211> LENGTH: 10
<212> TYPE: PRT
<213> ORGANISM: Hepatitis B virus

<400> SEQUENCE: 76

Ile Leu Ser Thr Leu Pro Glu Thr Thr Val
1               5                   10

<210> SEQ ID NO 77
<211> LENGTH: 11
<212> TYPE: PRT
<213> ORGANISM: Hepatitis B virus

<400> SEQUENCE: 77

Ser Thr Leu Pro Glu Thr Thr Val Val Arg Arg
1               5                   10

<210> SEQ ID NO 78
<211> LENGTH: 9
<212> TYPE: PRT
<213> ORGANISM: Hepatitis B virus

<400> SEQUENCE: 78

His Leu Ser Leu Arg Gly Leu Phe Val
1               5

<210> SEQ ID NO 79
<211> LENGTH: 9
<212> TYPE: PRT
<213> ORGANISM: Hepatitis B virus

<400> SEQUENCE: 79

Val Leu His Lys Arg Thr Leu Gly Leu
1               5

<210> SEQ ID NO 80
<211> LENGTH: 10
<212> TYPE: PRT
<213> ORGANISM: Hepatitis B virus

<400> SEQUENCE: 80

Gly Leu Ser Ala Met Ser Thr Thr Asp Leu
1               5                   10

<210> SEQ ID NO 81
<211> LENGTH: 9
<212> TYPE: PRT
<213> ORGANISM: Hepatitis B virus

<400> SEQUENCE: 81

Val Leu Gly Gly Cys Arg His Lys Leu
```

```
<210> SEQ ID NO 82
<211> LENGTH: 8
<212> TYPE: PRT
<213> ORGANISM: Hepatitis B virus

<400> SEQUENCE: 82

Asn Val Ser Ile Trp Thr His Lys
1               5

<210> SEQ ID NO 83
<211> LENGTH: 9
<212> TYPE: PRT
<213> ORGANISM: Hepatitis B virus

<400> SEQUENCE: 83

Lys Val Gly Asn Phe Thr Gly Leu Tyr
1               5

<210> SEQ ID NO 84
<211> LENGTH: 9
<212> TYPE: PRT
<213> ORGANISM: Hepatitis B virus

<400> SEQUENCE: 84

Gly Leu Tyr Ser Ser Thr Val Pro Val
1               5

<210> SEQ ID NO 85
<211> LENGTH: 10
<212> TYPE: PRT
<213> ORGANISM: Hepatitis B virus

<400> SEQUENCE: 85

Thr Leu Trp Lys Ala Gly Ile Leu Tyr Lys
1               5                   10

<210> SEQ ID NO 86
<211> LENGTH: 9
<212> TYPE: PRT
<213> ORGANISM: Hepatitis B virus

<400> SEQUENCE: 86

Lys Tyr Thr Ser Phe Pro Trp Leu Leu
1               5

<210> SEQ ID NO 87
<211> LENGTH: 10
<212> TYPE: PRT
<213> ORGANISM: Hepatitis B virus

<400> SEQUENCE: 87

Ile Leu Arg Gly Thr Ser Phe Val Tyr Val
1               5                   10

<210> SEQ ID NO 88
<211> LENGTH: 9
<212> TYPE: PRT
<213> ORGANISM: Hepatitis B virus

<400> SEQUENCE: 88

Ser Leu Tyr Ala Asp Ser Pro Ser Val
1               5
```

<210> SEQ ID NO 89
<211> LENGTH: 89
<212> TYPE: PRT
<213> ORGANISM: Saccharomyces cerevisiae

<400> SEQUENCE: 89

Met Arg Phe Pro Ser Ile Phe Thr Ala Val Leu Phe Ala Ala Ser Ser
1               5                   10                  15

Ala Ser Ala Ala Pro Val Asn Thr Thr Thr Glu Asp Glu Thr Ala Gln
            20                  25                  30

Ile Pro Ala Glu Ala Val Ile Gly Tyr Leu Asp Leu Glu Gly Asp Phe
        35                  40                  45

Asp Val Ala Val Leu Pro Phe Ser Asn Ser Thr Asn Asn Gly Leu Leu
    50                  55                  60

Phe Ile Asn Thr Thr Ile Ala Ser Ile Ala Ala Lys Glu Glu Gly Val
65                  70                  75                  80

Ser Leu Asp Lys Arg Glu Ala Glu Ala
                85

<210> SEQ ID NO 90
<211> LENGTH: 89
<212> TYPE: PRT
<213> ORGANISM: Saccharomyces cerevisiae

<400> SEQUENCE: 90

Met Arg Phe Pro Ser Ile Phe Thr Ala Val Leu Phe Ala Ala Ser Ser
1               5                   10                  15

Ala Leu Ala Ala Pro Val Asn Thr Thr Thr Glu Asp Glu Thr Ala Gln
            20                  25                  30

Ile Pro Ala Glu Ala Val Ile Gly Tyr Leu Asp Leu Glu Gly Asp Phe
        35                  40                  45

Asp Val Ala Val Leu Pro Phe Ser Asn Ser Thr Asn Asn Gly Leu Leu
    50                  55                  60

Phe Ile Asn Thr Thr Ile Ala Ser Ile Ala Ala Lys Glu Glu Gly Val
65                  70                  75                  80

Ser Leu Asp Lys Arg Glu Ala Glu Ala
                85

<210> SEQ ID NO 91
<211> LENGTH: 3107
<212> TYPE: DNA
<213> ORGANISM: Artificial
<220> FEATURE:
<223> OTHER INFORMATION: Synthetic Construct
<220> FEATURE:
<221> NAME/KEY: CDS
<222> LOCATION: (1)..(3096)

<400> SEQUENCE: 91 atg aga ttt cct tca att ttt act gca gtt tta ttc gca gca tcc tcc      48
Met Arg Phe Pro Ser Ile Phe Thr Ala Val Leu Phe Ala Ala Ser Ser
1               5                   10                  15 gca tca gct gct cca gtc aac act aca aca gaa gat gaa acg gca caa      96
Ala Ser Ala Ala Pro Val Asn Thr Thr Thr Glu Asp Glu Thr Ala Gln
            20                  25                  30 att ccg gct gaa gct gtc atc ggt tac tta gat tta gaa ggg gat ttc     144
Ile Pro Ala Glu Ala Val Ile Gly Tyr Leu Asp Leu Glu Gly Asp Phe
        35                  40                  45 gat gtt gct gtt ttg cca ttt tcc aac agc aca aat aac ggg tta ttg     192
Asp Val Ala Val Leu Pro Phe Ser Asn Ser Thr Asn Asn Gly Leu Leu

```
        50                  55                  60
ttt ata aat act act att gcc agc att gct gct aaa gaa gaa ggg gta    240
Phe Ile Asn Thr Thr Ile Ala Ser Ile Ala Ala Lys Glu Glu Gly Val
 65              70                  75                  80 tct cta gat aaa aga gag gct gaa gct act agt cct tta ggg ttt ttc    288
Ser Leu Asp Lys Arg Glu Ala Glu Ala Thr Ser Pro Leu Gly Phe Phe
                 85                  90                  95 cct gat cat caa tta gac cca gca ttc ggt gcc aat tcc aac aat cct    336
Pro Asp His Gln Leu Asp Pro Ala Phe Gly Ala Asn Ser Asn Asn Pro
            100                 105                 110 gat tgg gac ttt aac cca gag aat aca aca tct ggg ttc ctt ggt cca    384
Asp Trp Asp Phe Asn Pro Glu Asn Thr Thr Ser Gly Phe Leu Gly Pro
        115                 120                 125 ctt ttg gtg ctg caa gct ggc ttt ttc ctg tta act aga atc cta aca    432
Leu Leu Val Leu Gln Ala Gly Phe Phe Leu Leu Thr Arg Ile Leu Thr
    130                 135                 140 att cca caa agt ttg gat tca tgg tgg aca tct ttg aac ttt ttg gga    480
Ile Pro Gln Ser Leu Asp Ser Trp Trp Thr Ser Leu Asn Phe Leu Gly
145                 150                 155                 160 ggt gct cca acc tgt cct gga caa aac tcc caa tcc cca act tct aat    528
Gly Ala Pro Thr Cys Pro Gly Gln Asn Ser Gln Ser Pro Thr Ser Asn
                165                 170                 175 cat tca cct aca tcc tgc cca cct att tgt cct ggt tat cgt tgg atg    576
His Ser Pro Thr Ser Cys Pro Pro Ile Cys Pro Gly Tyr Arg Trp Met
            180                 185                 190 tgt ctt aga cgt ttc att atc ttt ttg ttc ata cta ctg ttg tgt ctg    624
Cys Leu Arg Arg Phe Ile Ile Phe Leu Phe Ile Leu Leu Leu Cys Leu
        195                 200                 205 att ttc ctg ttg gta ttg ttg gat tac caa ggc atg ttg cca gtc tgt    672
Ile Phe Leu Leu Val Leu Leu Asp Tyr Gln Gly Met Leu Pro Val Cys
    210                 215                 220 cct tta ctt cca ggc act tct act aca tca act ggc cct tgt aaa aca    720
Pro Leu Leu Pro Gly Thr Ser Thr Thr Ser Thr Gly Pro Cys Lys Thr
225                 230                 235                 240 tgt act atc cca gct caa ggt act tca atg ttt cct agt tgt tgt tgt    768
Cys Thr Ile Pro Ala Gln Gly Thr Ser Met Phe Pro Ser Cys Cys Cys
                245                 250                 255 acc aaa cca tcc gat ggt aat tgt aca tgc ata cca ata cca tct tca    816
Thr Lys Pro Ser Asp Gly Asn Cys Thr Cys Ile Pro Ile Pro Ser Ser
            260                 265                 270 tgg gca ttt gca aga ttc ctt tgg gaa tgg gct tct gtg cgt ttt tcc    864
Trp Ala Phe Ala Arg Phe Leu Trp Glu Trp Ala Ser Val Arg Phe Ser
        275                 280                 285 tgg ctg tct ttg tta gtt cct ttt gtc caa tgg ttt gtc ggt tta tct    912
Trp Leu Ser Leu Leu Val Pro Phe Val Gln Trp Phe Val Gly Leu Ser
    290                 295                 300 cca aca gta tgg ctg tct gct atc tgg atg atg tgg tat tgg gga cct    960
Pro Thr Val Trp Leu Ser Ala Ile Trp Met Met Trp Tyr Trp Gly Pro
305                 310                 315                 320 tcc ttg tac aac att ctg tct cca ttt ctg cct ttg tta cca atc ttt   1008
Ser Leu Tyr Asn Ile Leu Ser Pro Phe Leu Pro Leu Leu Pro Ile Phe
                325                 330                 335 ttc tgt ctt tgg gtg tac atc ctc gag gaa gat tgg ggt cct tgt act   1056
Phe Cys Leu Trp Val Tyr Ile Leu Glu Glu Asp Trp Gly Pro Cys Thr
            340                 345                 350 gaa cac ggt gaa cat aac atc aga ata cct aga act cca gct aga gtg   1104
Glu His Gly Glu His Asn Ile Arg Ile Pro Arg Thr Pro Ala Arg Val
        355                 360                 365 aca gga ggt gtt ttc ctg gta gac aaa aac cca cac aac aca gca gaa   1152
```

```
                Thr Gly Gly Val Phe Leu Val Asp Lys Asn Pro His Asn Thr Ala Glu
                    370                 375                 380 tct aga ctt gtc gtt gac ttc agt caa ttc tcc aga ggg tct act cat       1200
Ser Arg Leu Val Val Asp Phe Ser Gln Phe Ser Arg Gly Ser Thr His
385                 390                 395                 400 gtt tca tgg cca aag ttt gca gtt cca aac ttg caa tca ttg act aat       1248
Val Ser Trp Pro Lys Phe Ala Val Pro Asn Leu Gln Ser Leu Thr Asn
                405                 410                 415 cta cta tct tca aat ctt agt tgg ttg tcc ttg gat gtc tct gct gca       1296
Leu Leu Ser Ser Asn Leu Ser Trp Leu Ser Leu Asp Val Ser Ala Ala
                420                 425                 430 ttc tat cat ata cca ttg cat cct gca gcc atg cca cat ttg tta gtg       1344
Phe Tyr His Ile Pro Leu His Pro Ala Ala Met Pro His Leu Leu Val
                435                 440                 445 ggt agt tct ggt ctg tca agg tac gtt gca aga cta tct tct act tct       1392
Gly Ser Ser Gly Leu Ser Arg Tyr Val Ala Arg Leu Ser Ser Thr Ser
450                 455                 460 agg aat atc aat tac aaa cat ggg aca atg caa gac cta cat gat tca       1440
Arg Asn Ile Asn Tyr Lys His Gly Thr Met Gln Asp Leu His Asp Ser
465                 470                 475                 480 tgt tct aga aac ttg tac gta tcc ctt tta cta ctt tac aaa aca ttt       1488
Cys Ser Arg Asn Leu Tyr Val Ser Leu Leu Leu Leu Tyr Lys Thr Phe
                485                 490                 495 ggt aga aag ttg cac tta tac tca cat cca atc atc tta ggt ttc aga       1536
Gly Arg Lys Leu His Leu Tyr Ser His Pro Ile Ile Leu Gly Phe Arg
                500                 505                 510 aag ata cct atg ggc gtc ggg tta tct cct ttt cta tta gca cag ttt       1584
Lys Ile Pro Met Gly Val Gly Leu Ser Pro Phe Leu Leu Ala Gln Phe
                515                 520                 525 acc tct gcc att tgt tca gtg gtt cgt aga gca ttt cct cat tgt cta       1632
Thr Ser Ala Ile Cys Ser Val Val Arg Arg Ala Phe Pro His Cys Leu
530                 535                 540 gca ttt tca tac atg gac gat gtt gtc tta ggc gct aag tct gtt caa       1680
Ala Phe Ser Tyr Met Asp Asp Val Val Leu Gly Ala Lys Ser Val Gln
545                 550                 555                 560 cac ctt gaa tca ctg ttt acc agt ata acc aat ttc ctt ttg agt cta       1728
His Leu Glu Ser Leu Phe Thr Ser Ile Thr Asn Phe Leu Leu Ser Leu
                565                 570                 575 ggc att cat ctg aat cct aac aaa act aaa aga tgg gga tac tct ctt       1776
Gly Ile His Leu Asn Pro Asn Lys Thr Lys Arg Trp Gly Tyr Ser Leu
                580                 585                 590 aac ttt atg ggt tac gtt atc gga tca tgg ggc acc ctt cca caa gag       1824
Asn Phe Met Gly Tyr Val Ile Gly Ser Trp Gly Thr Leu Pro Gln Glu
                595                 600                 605 cat att gtc ctg aaa atc aag cag tgt ttt aga aaa ctg cca gtg aat       1872
His Ile Val Leu Lys Ile Lys Gln Cys Phe Arg Lys Leu Pro Val Asn
610                 615                 620 aga cca att gat tgg aaa gtt tgc cag aga atc gta ggt tta ctt ggt       1920
Arg Pro Ile Asp Trp Lys Val Cys Gln Arg Ile Val Gly Leu Leu Gly
625                 630                 635                 640 ttt gcc gct cct ttc act cag tgc ggc tat cca gct ttg atg cca ttg       1968
Phe Ala Ala Pro Phe Thr Gln Cys Gly Tyr Pro Ala Leu Met Pro Leu
                645                 650                 655 tac gct tgt atc caa gct aag caa gct ttc aca ttc tct cca acc tat       2016
Tyr Ala Cys Ile Gln Ala Lys Gln Ala Phe Thr Phe Ser Pro Thr Tyr
                660                 665                 670 aag gct ttt cta tgc aag cag tac tta aac ctt tat cca gtg gct aga       2064
Lys Ala Phe Leu Cys Lys Gln Tyr Leu Asn Leu Tyr Pro Val Ala Arg
                675                 680                 685
```

| | | |
|---|---|---|
| caa aga gat att gac cca tac aaa gag ttt ggg gca tca gtt gaa tta<br>Gln Arg Asp Ile Asp Pro Tyr Lys Glu Phe Gly Ala Ser Val Glu Leu<br>690                       695                     700 | | 2112 |
| cta tcc ttc cta cca tca gac ttt ttc cca tca atc aga gat ttg tta<br>Leu Ser Phe Leu Pro Ser Asp Phe Phe Pro Ser Ile Arg Asp Leu Leu<br>705                     710                     715                 720 | | 2160 |
| gat act gcc tct gca ttg tac aga gaa gct cta gaa tct cct gaa cat<br>Asp Thr Ala Ser Ala Leu Tyr Arg Glu Ala Leu Glu Ser Pro Glu His<br>                   725                     730                     735 | | 2208 |
| tgc tct cca cac cat act gcc ctt aga caa gca atc ttg tgt tgg ggc<br>Cys Ser Pro His His Thr Ala Leu Arg Gln Ala Ile Leu Cys Trp Gly<br>                   740                     745                     750 | | 2256 |
| gaa ctt atg aat ttg gcc aca tgg gtt gga agt aat cta gaa gat cca<br>Glu Leu Met Asn Leu Ala Thr Trp Val Gly Ser Asn Leu Glu Asp Pro<br>755                     760                     765 | | 2304 |
| gcc tca aga gag cta gtt gta tct tac gtc aac gtt aac atg ggt cta<br>Ala Ser Arg Glu Leu Val Val Ser Tyr Val Asn Val Asn Met Gly Leu<br>770                     775                     780 | | 2352 |
| aag att agg caa tta cta tgg ttt cac att agt tgc tta act ttc ggt<br>Lys Ile Arg Gln Leu Leu Trp Phe His Ile Ser Cys Leu Thr Phe Gly<br>785                     790                     795                 800 | | 2400 |
| aga gaa aca gtg cta gag tat ttg gta tca ttt gga gta tgg atc aga<br>Arg Glu Thr Val Leu Glu Tyr Leu Val Ser Phe Gly Val Trp Ile Arg<br>                   805                     810                     815 | | 2448 |
| act cca cct gca tat aga cca cca aat gct cca atc tta tct aca ctg<br>Thr Pro Pro Ala Tyr Arg Pro Pro Asn Ala Pro Ile Leu Ser Thr Leu<br>                   820                     825                     830 | | 2496 |
| cct gaa aca act gta gtc agg aga aga gga aga tca cca agg agg aga<br>Pro Glu Thr Thr Val Val Arg Arg Arg Gly Arg Ser Pro Arg Arg Arg<br>835                     840                     845 | | 2544 |
| act cca tct cca agg aga cgt cgt tct cag tcc cct cgt aga cgt aga<br>Thr Pro Ser Pro Arg Arg Arg Ser Gln Ser Pro Arg Arg Arg<br>850                     855                     860 | | 2592 |
| tct caa tca aga gaa tct caa tgc gca gcc aga gtt tgc tgt aaa ctt<br>Ser Gln Ser Arg Glu Ser Gln Cys Ala Ala Arg Val Cys Cys Lys Leu<br>865                     870                     875                 880 | | 2640 |
| gac cca gcc aga gat gta cta tgt ctt aga cca gtt ggc gct gaa tca<br>Asp Pro Ala Arg Asp Val Leu Cys Leu Arg Pro Val Gly Ala Glu Ser<br>                   885                     890                     895 | | 2688 |
| tct ggt aga cca gtc tca ggc cca ttt ggg aca tta cca tcc cct tca<br>Ser Gly Arg Pro Val Ser Gly Pro Phe Gly Thr Leu Pro Ser Pro Ser<br>                   900                     905                     910 | | 2736 |
| agt agt gcc gta cct gca gat cac gga gca cat ctg tct cta aga gga<br>Ser Ser Ala Val Pro Ala Asp His Gly Ala His Leu Ser Leu Arg Gly<br>                   915                     920                     925 | | 2784 |
| ctt cct gtt tgt gct ttt agt tca gca gga cct tgc gcc ttg aga ttc<br>Leu Pro Val Cys Ala Phe Ser Ser Ala Gly Pro Cys Ala Leu Arg Phe<br>930                     935                     940 | | 2832 |
| aca tca gct agg aga atg gaa aca aca gtt aat gct cat caa gtt ttg<br>Thr Ser Ala Arg Arg Met Glu Thr Thr Val Asn Ala His Gln Val Leu<br>945                     950                     955                 960 | | 2880 |
| cca aaa gta tta cac aag aga aca ttg ggt ttg tct gcc atg agt acc<br>Pro Lys Val Leu His Lys Arg Thr Leu Gly Leu Ser Ala Met Ser Thr<br>                   965                     970                     975 | | 2928 |
| act gac tta gaa gct tac ttt aag gat tgc gtt ttc aaa gat tgg gag<br>Thr Asp Leu Glu Ala Tyr Phe Lys Asp Cys Val Phe Lys Asp Trp Glu<br>980                     985                     990 | | 2976 |
| gaa tta ggt gag gaa atc aga cta   aaa gtt ttt gtg tta   ggt ggt tgc<br>Glu Leu Gly Glu Glu Ile Arg Leu  Lys Val Phe Val Leu  Gly Gly Cys<br>                   995                     1000                  1005 | | 3024 |

```
aga cac aaa ttg gtc tgt tcc cct gct cca tgc aac ttt ttc acc    3069
Arg His Lys Leu Val Cys Ser Pro Ala Pro Cys Asn Phe Phe Thr
    1010            1015                1020 tcc gcc cac cat cat cat cac cat tga taagcggccg c                3107
Ser Ala His His His His His His
    1025            1030

<210> SEQ ID NO 92
<211> LENGTH: 1031
<212> TYPE: PRT
<213> ORGANISM: Artificial
<220> FEATURE:
<223> OTHER INFORMATION: Synthetic Construct

<400> SEQUENCE: 92

Met Arg Phe Pro Ser Ile Phe Thr Ala Val Leu Phe Ala Ala Ser Ser
1               5                   10                  15

Ala Ser Ala Ala Pro Val Asn Thr Thr Thr Glu Asp Glu Thr Ala Gln
            20                  25                  30

Ile Pro Ala Glu Ala Val Ile Gly Tyr Leu Asp Leu Glu Gly Asp Phe
        35                  40                  45

Asp Val Ala Val Leu Pro Phe Ser Asn Ser Thr Asn Asn Gly Leu Leu
    50                  55                  60

Phe Ile Asn Thr Thr Ile Ala Ser Ile Ala Ala Lys Glu Glu Gly Val
65                  70                  75                  80

Ser Leu Asp Lys Arg Glu Ala Glu Ala Thr Ser Pro Leu Gly Phe Phe
                85                  90                  95

Pro Asp His Gln Leu Asp Pro Ala Phe Gly Ala Asn Ser Asn Asn Pro
            100                 105                 110

Asp Trp Asp Phe Asn Pro Glu Asn Thr Thr Ser Gly Phe Leu Gly Pro
        115                 120                 125

Leu Leu Val Leu Gln Ala Gly Phe Phe Leu Leu Thr Arg Ile Leu Thr
    130                 135                 140

Ile Pro Gln Ser Leu Asp Ser Trp Trp Thr Ser Leu Asn Phe Leu Gly
145                 150                 155                 160

Gly Ala Pro Thr Cys Pro Gly Gln Asn Ser Gln Ser Pro Thr Ser Asn
                165                 170                 175

His Ser Pro Thr Ser Cys Pro Pro Ile Cys Pro Gly Tyr Arg Trp Met
            180                 185                 190

Cys Leu Arg Arg Phe Ile Ile Phe Leu Phe Ile Leu Leu Leu Cys Leu
        195                 200                 205

Ile Phe Leu Leu Val Leu Leu Asp Tyr Gln Gly Met Leu Pro Val Cys
    210                 215                 220

Pro Leu Leu Pro Gly Thr Ser Thr Thr Ser Thr Gly Pro Cys Lys Thr
225                 230                 235                 240

Cys Thr Ile Pro Ala Gln Gly Thr Ser Met Phe Pro Ser Cys Cys Cys
                245                 250                 255

Thr Lys Pro Ser Asp Gly Asn Cys Thr Cys Ile Pro Ile Pro Ser Ser
            260                 265                 270

Trp Ala Phe Ala Arg Phe Leu Trp Glu Trp Ala Ser Val Arg Phe Ser
        275                 280                 285

Trp Leu Ser Leu Leu Val Pro Phe Val Gln Trp Phe Val Gly Leu Ser
    290                 295                 300

Pro Thr Val Trp Leu Ser Ala Ile Trp Met Met Trp Tyr Trp Gly Pro
305                 310                 315                 320
```

-continued

```
Ser Leu Tyr Asn Ile Leu Ser Pro Phe Leu Pro Leu Pro Ile Phe
            325                 330                 335

Phe Cys Leu Trp Val Tyr Ile Leu Glu Glu Asp Trp Gly Pro Cys Thr
            340                 345                 350

Glu His Gly Glu His Asn Ile Arg Ile Pro Arg Thr Pro Ala Arg Val
            355                 360                 365

Thr Gly Gly Val Phe Leu Val Asp Lys Asn Pro His Asn Thr Ala Glu
        370                 375                 380

Ser Arg Leu Val Val Asp Phe Ser Gln Phe Ser Arg Gly Ser Thr His
385                 390                 395                 400

Val Ser Trp Pro Lys Phe Ala Val Pro Asn Leu Gln Ser Leu Thr Asn
            405                 410                 415

Leu Leu Ser Ser Asn Leu Ser Trp Leu Ser Leu Asp Val Ser Ala Ala
            420                 425                 430

Phe Tyr His Ile Pro Leu His Pro Ala Ala Met Pro His Leu Leu Val
            435                 440                 445

Gly Ser Ser Gly Leu Ser Arg Tyr Val Ala Arg Leu Ser Ser Thr Ser
        450                 455                 460

Arg Asn Ile Asn Tyr Lys His Gly Thr Met Gln Asp Leu His Asp Ser
465                 470                 475                 480

Cys Ser Arg Asn Leu Tyr Val Ser Leu Leu Leu Leu Tyr Lys Thr Phe
                485                 490                 495

Gly Arg Lys Leu His Leu Tyr Ser His Pro Ile Ile Leu Gly Phe Arg
            500                 505                 510

Lys Ile Pro Met Gly Val Gly Leu Ser Pro Phe Leu Leu Ala Gln Phe
            515                 520                 525

Thr Ser Ala Ile Cys Ser Val Val Arg Arg Ala Phe Pro His Cys Leu
        530                 535                 540

Ala Phe Ser Tyr Met Asp Asp Val Val Leu Gly Ala Lys Ser Val Gln
545                 550                 555                 560

His Leu Glu Ser Leu Phe Thr Ser Ile Thr Asn Phe Leu Leu Ser Leu
            565                 570                 575

Gly Ile His Leu Asn Pro Asn Lys Thr Lys Arg Trp Gly Tyr Ser Leu
            580                 585                 590

Asn Phe Met Gly Tyr Val Ile Gly Ser Trp Gly Thr Leu Pro Gln Glu
        595                 600                 605

His Ile Val Leu Lys Ile Lys Gln Cys Phe Arg Lys Leu Pro Val Asn
            610                 615                 620

Arg Pro Ile Asp Trp Lys Val Cys Gln Arg Ile Val Gly Leu Leu Gly
625                 630                 635                 640

Phe Ala Ala Pro Phe Thr Gln Cys Gly Tyr Pro Ala Leu Met Pro Leu
            645                 650                 655

Tyr Ala Cys Ile Gln Ala Lys Gln Ala Phe Thr Phe Ser Pro Thr Tyr
            660                 665                 670

Lys Ala Phe Leu Cys Lys Gln Tyr Leu Asn Leu Tyr Pro Val Ala Arg
        675                 680                 685

Gln Arg Asp Ile Asp Pro Tyr Lys Glu Phe Gly Ala Ser Val Glu Leu
    690                 695                 700

Leu Ser Phe Leu Pro Ser Asp Phe Phe Pro Ser Ile Arg Asp Leu Leu
705                 710                 715                 720

Asp Thr Ala Ser Ala Leu Tyr Arg Glu Ala Leu Glu Ser Pro Glu His
            725                 730                 735

Cys Ser Pro His His Thr Ala Leu Arg Gln Ala Ile Leu Cys Trp Gly
```

740                 745                 750
Glu Leu Met Asn Leu Ala Thr Trp Val Gly Ser Asn Leu Glu Asp Pro
            755                 760                 765

Ala Ser Arg Glu Leu Val Val Ser Tyr Val Asn Val Asn Met Gly Leu
        770                 775                 780

Lys Ile Arg Gln Leu Leu Trp Phe His Ile Ser Cys Leu Thr Phe Gly
785                 790                 795                 800

Arg Glu Thr Val Leu Glu Tyr Leu Val Ser Phe Gly Val Trp Ile Arg
                805                 810                 815

Thr Pro Pro Ala Tyr Arg Pro Pro Asn Ala Pro Ile Leu Ser Thr Leu
            820                 825                 830

Pro Glu Thr Thr Val Val Arg Arg Gly Arg Ser Pro Arg Arg Arg
        835                 840                 845

Thr Pro Ser Pro Arg Arg Arg Ser Gln Ser Pro Arg Arg Arg Arg
    850                 855                 860

Ser Gln Ser Arg Glu Ser Gln Cys Ala Ala Arg Val Cys Cys Lys Leu
865                 870                 875                 880

Asp Pro Ala Arg Asp Val Leu Cys Leu Arg Pro Val Gly Ala Glu Ser
                885                 890                 895

Ser Gly Arg Pro Val Ser Gly Pro Phe Gly Thr Leu Pro Ser Pro Ser
            900                 905                 910

Ser Ser Ala Val Pro Ala Asp His Gly Ala His Leu Ser Leu Arg Gly
        915                 920                 925

Leu Pro Val Cys Ala Phe Ser Ser Ala Gly Pro Cys Ala Leu Arg Phe
    930                 935                 940

Thr Ser Ala Arg Arg Met Glu Thr Thr Val Asn Ala His Gln Val Leu
945                 950                 955                 960

Pro Lys Val Leu His Lys Arg Thr Leu Gly Leu Ser Ala Met Ser Thr
                965                 970                 975

Thr Asp Leu Glu Ala Tyr Phe Lys Asp Cys Val Phe Lys Asp Trp Glu
            980                 985                 990

Glu Leu Gly Glu Glu Ile Arg Leu Lys Val Phe Val Leu Gly Gly Cys
        995                 1000                1005

Arg His Lys Leu Val Cys Ser Pro Ala Pro Cys Asn Phe Phe Thr
    1010                1015                1020

Ser Ala His His His His His His
    1025                1030

<210> SEQ ID NO 93
<211> LENGTH: 494
<212> TYPE: PRT
<213> ORGANISM: Artificial
<220> FEATURE:
<223> OTHER INFORMATION: Synthetic Construct

<400> SEQUENCE: 93

Met Arg Phe Pro Ser Ile Phe Thr Ala Val Leu Phe Ala Ala Ser Ser
1               5                   10                  15

Ala Ser Ala Ala Pro Val Asn Thr Thr Thr Glu Asp Glu Thr Ala Gln
            20                  25                  30

Ile Pro Ala Glu Ala Val Ile Gly Tyr Leu Asp Leu Glu Gly Asp Phe
        35                  40                  45

Asp Val Ala Val Leu Pro Phe Ser Asn Ser Thr Asn Asn Gly Leu Leu
    50                  55                  60

Phe Ile Asn Thr Thr Ile Ala Ser Ile Ala Ala Lys Glu Glu Gly Val

```
                65                  70                  75                  80
Ser Leu Asp Lys Arg Glu Ala Glu Ala Gly Gly Trp Ser Ser Lys Pro
                    85                  90                  95
Arg Lys Gly Met Gly Thr Asn Leu Ser Val Pro Asn Pro Leu Gly Phe
                100                 105                 110
Phe Pro Asp His Gln Leu Asp Pro Ala Phe Gly Ala Asn Ser Asn Asn
                115                 120                 125
Pro Asp Trp Asp Phe Asn Pro Asn Lys Asp His Trp Pro Glu Ala Asn
130                 135                 140
Gln Val Gly Val Gly Ala Phe Gly Pro Gly Phe Thr Pro Pro His Gly
145                 150                 155                 160
Gly Leu Leu Gly Trp Ser Pro Gln Ala Gln Gly Ile Leu Thr Thr Val
                165                 170                 175
Pro Ala Ala Pro Pro Ala Ser Thr Asn Arg Gln Ser Gly Arg Gln
                180                 185                 190
Pro Thr Pro Ile Ser Pro Pro Leu Arg Asp Ser His Pro Gln Ala Met
            195                 200                 205
Gln Trp Asn Ser Thr Thr Phe His Gln Ala Leu Leu Asp Pro Arg Val
            210                 215                 220
Arg Gly Leu Tyr Phe Pro Ala Gly Gly Ser Ser Ser Gly Thr Val Asn
225                 230                 235                 240
Pro Val Pro Thr Thr Ala Ser Pro Ile Ser Ser Ile Phe Ser Arg Thr
                245                 250                 255
Gly Asp Pro Ala Pro Asn Met Glu Asn Thr Thr Ser Gly Phe Leu Gly
                260                 265                 270
Pro Leu Leu Val Leu Gln Ala Gly Phe Phe Leu Leu Thr Arg Ile Leu
            275                 280                 285
Thr Ile Pro Gln Ser Leu Asp Ser Trp Trp Thr Ser Leu Asn Phe Leu
            290                 295                 300
Gly Gly Ala Pro Thr Cys Pro Gly Gln Asn Ser Gln Ser Pro Thr Ser
305                 310                 315                 320
Asn His Ser Pro Thr Ser Cys Pro Pro Ile Cys Pro Gly Tyr Arg Trp
                325                 330                 335
Met Cys Leu Arg Arg Phe Ile Ile Phe Leu Phe Ile Leu Leu Leu Cys
                340                 345                 350
Leu Ile Phe Leu Leu Val Leu Leu Asp Tyr Gln Gly Met Leu Pro Val
            355                 360                 365
Cys Pro Leu Leu Pro Gly Thr Ser Thr Thr Ser Thr Gly Pro Cys Lys
370                 375                 380
Thr Cys Thr Ile Pro Ala Gln Gly Thr Ser Met Phe Pro Ser Cys Cys
385                 390                 395                 400
Cys Thr Lys Pro Ser Asp Gly Asn Cys Thr Cys Ile Pro Ile Pro Ser
                405                 410                 415
Ser Trp Ala Phe Ala Arg Phe Leu Trp Glu Trp Ala Ser Val Arg Phe
            420                 425                 430
Ser Trp Leu Ser Leu Leu Val Pro Phe Val Gln Trp Phe Val Gly Leu
            435                 440                 445
Ser Pro Thr Val Trp Leu Ser Val Ile Trp Met Met Trp Tyr Trp Gly
450                 455                 460
Pro Ser Leu Tyr Asn Ile Leu Asn Pro Phe Leu Pro Leu Leu Pro Ile
465                 470                 475                 480
Phe Phe Cys Leu Trp Val Tyr Ile His His His His His His
            485                 490
```

<210> SEQ ID NO 94
<211> LENGTH: 440
<212> TYPE: PRT
<213> ORGANISM: Artificial
<220> FEATURE:
<223> OTHER INFORMATION: Synthetic Construct

<400> SEQUENCE: 94

```
Met Arg Phe Pro Ser Ile Phe Thr Ala Val Leu Phe Ala Ala Ser Ser
1               5                   10                  15

Ala Ser Ala Ala Pro Val Asn Thr Thr Thr Glu Asp Glu Thr Ala Gln
            20                  25                  30

Ile Pro Ala Glu Ala Val Ile Gly Tyr Leu Asp Leu Glu Gly Asp Phe
        35                  40                  45

Asp Val Ala Val Leu Pro Phe Ser Asn Ser Thr Asn Asn Gly Leu Leu
    50                  55                  60

Phe Ile Asn Thr Thr Ile Ala Ser Ile Ala Ala Lys Glu Glu Gly Val
65                  70                  75                  80

Ser Leu Asp Lys Arg Glu Ala Glu Ala Glu Asp Trp Gly Pro Cys Thr
                85                  90                  95

Glu His Gly Glu His Asn Ile Arg Ile Pro Arg Thr Pro Ala Arg Val
            100                 105                 110

Thr Gly Gly Val Phe Leu Val Asp Lys Asn Pro His Asn Thr Ala Glu
        115                 120                 125

Ser Arg Leu Val Val Asp Phe Ser Gln Phe Ser Arg Gly Ser Thr His
    130                 135                 140

Val Ser Trp Pro Lys Phe Ala Val Pro Asn Leu Gln Ser Leu Thr Asn
145                 150                 155                 160

Leu Leu Ser Ser Asn Leu Ser Trp Leu Ser Leu Asp Val Ser Ala Ala
                165                 170                 175

Phe Tyr His Ile Pro Leu His Pro Ala Ala Met Pro His Leu Leu Val
            180                 185                 190

Gly Ser Ser Gly Leu Ser Arg Tyr Val Ala Arg Leu Ser Ser Thr Ser
        195                 200                 205

Arg Asn Ile Asn Tyr Lys His Gly Thr Met Gln Asp Leu His Asp Ser
    210                 215                 220

Cys Ser Arg Asn Leu Tyr Val Ser Leu Leu Leu Leu Tyr Lys Thr Phe
225                 230                 235                 240

Gly Arg Lys Leu His Leu Tyr Ser His Pro Ile Ile Leu Gly Phe Arg
                245                 250                 255

Lys Ile Pro Met Gly Val Gly Leu Ser Pro Phe Leu Leu Ala Gln Phe
            260                 265                 270

Thr Ser Ala Ile Cys Ser Val Val Arg Arg Ala Phe Pro His Cys Leu
        275                 280                 285

Ala Phe Ser Tyr Met Asp Asp Val Val Leu Gly Ala Lys Ser Val Gln
    290                 295                 300

His Leu Glu Ser Leu Phe Thr Ser Ile Thr Asn Phe Leu Leu Ser Leu
305                 310                 315                 320

Gly Ile His Leu Asn Pro Asn Lys Thr Lys Arg Trp Gly Tyr Ser Leu
                325                 330                 335

Asn Phe Met Gly Tyr Val Ile Gly Ser Trp Gly Thr Leu Pro Gln Glu
            340                 345                 350

His Ile Val Leu Lys Ile Lys Gln Cys Phe Arg Lys Leu Pro Val Asn
        355                 360                 365
```

Arg Pro Ile Asp Trp Lys Val Cys Gln Arg Ile Val Gly Leu Leu Gly
             370                 375                 380

Phe Ala Ala Pro Phe Thr Gln Cys Gly Tyr Pro Ala Leu Met Pro Leu
385                 390                 395                 400

Tyr Ala Cys Ile Gln Ala Lys Gln Ala Phe Thr Phe Ser Pro Thr Tyr
                405                 410                 415

Lys Ala Phe Leu Cys Lys Gln Tyr Leu Asn Leu Tyr Pro Val Ala Arg
                420                 425                 430

Gln Arg His His His His His His
            435                 440

<210> SEQ ID NO 95
<211> LENGTH: 277
<212> TYPE: PRT
<213> ORGANISM: Artificial
<220> FEATURE:
<223> OTHER INFORMATION: Synthetic Construct

<400> SEQUENCE: 95

Met Arg Phe Pro Ser Ile Phe Thr Ala Val Leu Phe Ala Ala Ser Ser
1               5                   10                  15

Ala Ser Ala Ala Pro Val Asn Thr Thr Thr Glu Asp Glu Thr Ala Gln
                20                  25                  30

Ile Pro Ala Glu Ala Val Ile Gly Tyr Leu Asp Leu Glu Gly Asp Phe
            35                  40                  45

Asp Val Ala Val Leu Pro Phe Ser Asn Ser Thr Asn Asn Gly Leu Leu
        50                  55                  60

Phe Ile Asn Thr Thr Ile Ala Ser Ile Ala Ala Lys Glu Glu Gly Val
65                  70                  75                  80

Ser Leu Asp Lys Arg Glu Ala Glu Ala Asp Ile Asp Pro Tyr Lys Glu
                85                  90                  95

Phe Gly Ala Ser Val Glu Leu Leu Ser Phe Leu Pro Ser Asp Phe Phe
            100                 105                 110

Pro Ser Ile Arg Asp Leu Leu Asp Thr Ala Ser Ala Leu Tyr Arg Glu
        115                 120                 125

Ala Leu Glu Ser Pro Glu His Cys Ser Pro His His Thr Ala Leu Arg
130                 135                 140

Gln Ala Ile Leu Cys Trp Gly Glu Leu Met Asn Leu Ala Thr Trp Val
145                 150                 155                 160

Gly Ser Asn Leu Glu Asp Pro Ala Ser Arg Glu Leu Val Val Ser Tyr
                165                 170                 175

Val Asn Val Asn Met Gly Leu Lys Ile Arg Gln Leu Leu Trp Phe His
            180                 185                 190

Ile Ser Cys Leu Thr Phe Gly Arg Glu Thr Val Leu Glu Tyr Leu Val
        195                 200                 205

Ser Phe Gly Val Trp Ile Arg Thr Pro Pro Ala Tyr Arg Pro Pro Asn
210                 215                 220

Ala Pro Ile Leu Ser Thr Leu Pro Glu Thr Thr Val Val Arg Arg Arg
225                 230                 235                 240

Gly Arg Ser Pro Arg Arg Arg Thr Pro Ser Pro Arg Arg Arg Arg Ser
                245                 250                 255

Gln Ser Pro Arg Arg Arg Arg Ser Gln Ser Arg Glu Ser Gln Cys His
            260                 265                 270

His His His His His
        275

<210> SEQ ID NO 96
<211> LENGTH: 248
<212> TYPE: PRT
<213> ORGANISM: Artificial
<220> FEATURE:
<223> OTHER INFORMATION: Synthetic Construct

<400> SEQUENCE: 96

Met Arg Phe Pro Ser Ile Phe Thr Ala Val Leu Phe Ala Ala Ser Ser
1               5                   10                  15

Ala Ser Ala Ala Pro Val Asn Thr Thr Thr Glu Asp Glu Thr Ala Gln
            20                  25                  30

Ile Pro Ala Glu Ala Val Ile Gly Tyr Leu Asp Leu Glu Gly Asp Phe
        35                  40                  45

Asp Val Ala Val Leu Pro Phe Ser Asn Ser Thr Asn Asn Gly Leu Leu
50                  55                  60

Phe Ile Asn Thr Thr Ile Ala Ser Ile Ala Ala Lys Glu Glu Gly Val
65                  70                  75                  80

Ser Leu Asp Lys Arg Glu Ala Glu Ala Ala Arg Val Cys Cys Lys
                85                  90                  95

Leu Asp Pro Ala Arg Asp Val Leu Cys Leu Arg Pro Val Gly Ala Glu
            100                 105                 110

Ser Ser Gly Arg Pro Val Ser Gly Pro Phe Gly Thr Leu Pro Ser Pro
        115                 120                 125

Ser Ser Ser Ala Val Pro Ala Asp His Gly Ala His Leu Ser Leu Arg
130                 135                 140

Gly Leu Pro Val Cys Ala Phe Ser Ser Ala Gly Pro Cys Ala Leu Arg
145                 150                 155                 160

Phe Thr Ser Ala Arg Arg Met Glu Thr Thr Val Asn Ala His Gln Val
                165                 170                 175

Leu Pro Lys Val Leu His Lys Arg Thr Leu Gly Leu Ser Ala Met Ser
            180                 185                 190

Thr Thr Asp Leu Glu Ala Tyr Phe Lys Asp Cys Val Phe Lys Asp Trp
        195                 200                 205

Glu Glu Leu Gly Glu Glu Ile Arg Leu Lys Val Phe Val Leu Gly Gly
    210                 215                 220

Cys Arg His Lys Leu Val Cys Ser Pro Ala Pro Cys Asn Phe Thr
225                 230                 235                 240

Ser Ala His His His His His His
            245

<210> SEQ ID NO 97
<211> LENGTH: 249
<212> TYPE: PRT
<213> ORGANISM: Artificial
<220> FEATURE:
<223> OTHER INFORMATION: Synthetic Construct

<400> SEQUENCE: 97

Met Gln Trp Asn Ser Thr Ala Leu His Gln Ala Leu Leu Asp Pro Arg
1               5                   10                  15

Val Arg Gly Leu Tyr Phe Pro Ala Gly Gly Ser Ser Ser Gly Thr Val
            20                  25                  30

Asn Pro Val Pro Thr Thr Ala Ser Pro Ile Ser Ile Leu Ser Lys
        35                  40                  45

Thr Gly Asp Pro Val Pro Asn Met Glu Asn Thr Thr Ser Gly Phe Leu

```
            50                  55                  60
Gly Pro Leu Leu Val Leu Gln Ala Gly Phe Phe Leu Leu Thr Arg Ile
 65                  70                  75                  80

Leu Thr Ile Pro Gln Ser Leu Asp Ser Trp Trp Thr Ser Leu Asn Phe
                 85                  90                  95

Leu Gly Gly Thr Pro Val Cys Leu Gly Gln Asn Ser Gln Ser Pro Thr
                100                 105                 110

Ser Asn His Ser Pro Thr Ser Cys Pro Pro Ile Cys Pro Gly Tyr Arg
            115                 120                 125

Trp Met Cys Leu Arg Arg Phe Ile Ile Phe Leu Phe Ile Leu Leu Leu
        130                 135                 140

Cys Leu Ile Phe Leu Leu Val Leu Leu Asp Tyr Gln Gly Met Leu Pro
145                 150                 155                 160

Val Cys Pro Leu Leu Pro Gly Thr Ser Thr Thr Ser Thr Gly Pro Cys
                165                 170                 175

Lys Thr Cys Thr Ile Pro Ala Gln Gly Thr Ser Met Phe Pro Ser Cys
                180                 185                 190

Cys Cys Thr Lys Pro Ser Asp Gly Asn Cys Thr Cys Ile Pro Ile Pro
            195                 200                 205

Ser Ser Trp Ala Phe Ala Arg Phe Leu Trp Glu Trp Ala Ser Val Arg
        210                 215                 220

Phe Ser Trp Leu Ser Leu Leu Val Pro Phe Val Gln Trp Phe Val Gly
225                 230                 235                 240

Leu Ser Pro Thr Val Trp Leu Ser Val
                245

<210> SEQ ID NO 98
<211> LENGTH: 228
<212> TYPE: PRT
<213> ORGANISM: Artificial
<220> FEATURE:
<223> OTHER INFORMATION: Synthetic Construct

<400> SEQUENCE: 98

Gly Leu Ser Arg Tyr Val Ala Arg Leu Ser Ser Thr Ser Arg Asn Ile
 1               5                  10                  15

Asn Tyr Gln His Gly Thr Met Gln Asp Leu His Asp Ser Cys Ser Arg
                20                  25                  30

Asn Leu Tyr Val Ser Leu Leu Leu Tyr Lys Thr Phe Gly Arg Lys
            35                  40                  45

Leu His Leu Tyr Ser His Pro Ile Ile Leu Gly Phe Arg Lys Ile Pro
        50                  55                  60

Met Gly Val Gly Leu Ser Pro Phe Leu Leu Ala Gln Phe Thr Ser Ala
 65                  70                  75                  80

Ile Cys Ser Val Val Arg Arg Ala Phe Pro His Cys Leu Ala Phe Ser
                85                  90                  95

Tyr Met Asp Asp Val Val Leu Gly Ala Lys Ser Val Gln His Leu Glu
                100                 105                 110

Ser Leu Phe Thr Ser Ile Thr Asn Phe Leu Leu Ser Leu Gly Ile His
            115                 120                 125

Leu Asn Pro Asn Lys Thr Lys Arg Trp Gly Tyr Ser Leu Asn Phe Met
        130                 135                 140

Gly Tyr Val Ile Gly Ser Trp Gly Thr Leu Pro Gln Glu His Ile Val
145                 150                 155                 160

Gln Lys Leu Lys Gln Cys Phe Arg Lys Leu Pro Val Asn Arg Pro Ile
```

```
                165                 170                 175
Asp Trp Lys Val Cys Gln Arg Ile Val Gly Leu Leu Gly Phe Ala Ala
            180                 185                 190

Pro Phe Thr Gln Cys Gly Tyr Pro Ala Leu Met Pro Leu Tyr Ala Cys
        195                 200                 205

Ile Gln Ala Lys Gln Ala Phe Thr Phe Ser Pro Thr Tyr Lys Ala Phe
    210                 215                 220

Leu Cys Lys Gln
225

<210> SEQ ID NO 99
<211> LENGTH: 152
<212> TYPE: PRT
<213> ORGANISM: Artificial
<220> FEATURE:
<223> OTHER INFORMATION: Synthetic Construct

<400> SEQUENCE: 99

Glu Phe Gly Ala Ser Val Glu Leu Leu Ser Leu Pro Ser Asp Phe
1               5                   10                  15

Phe Pro Ser Val Arg Asp Leu Leu Asp Thr Ala Ser Ala Leu Tyr Arg
            20                  25                  30

Glu Ala Leu Glu Ser Pro Glu His Cys Ser Pro His His Thr Ala Leu
        35                  40                  45

Arg Gln Ala Ile Leu Cys Trp Gly Glu Leu Met Asn Leu Ala Thr Trp
    50                  55                  60

Val Gly Ser Asn Leu Glu Asp Pro Ala Ser Arg Glu Leu Val Val Ser
65                  70                  75                  80

Tyr Val Asn Val Asn Met Gly Leu Lys Ile Arg Gln Leu Leu Trp Phe
                85                  90                  95

His Ile Ser Cys Leu Thr Phe Gly Arg Glu Thr Val Leu Glu Tyr Leu
            100                 105                 110

Val Ser Phe Gly Val Trp Ile Arg Thr Pro Pro Ala Tyr Arg Pro Pro
        115                 120                 125

Asn Ala Pro Ile Leu Ser Thr Leu Pro Glu Thr Thr Val Val Arg Arg
    130                 135                 140

Arg Gly Arg Ser Pro Arg Arg Arg
145                 150

<210> SEQ ID NO 100
<211> LENGTH: 60
<212> TYPE: PRT
<213> ORGANISM: Artificial
<220> FEATURE:
<223> OTHER INFORMATION: Synthetic Construct

<400> SEQUENCE: 100

His Leu Ser Leu Arg Gly Leu Phe Val Cys Ala Phe Ser Ser Ala Gly
1               5                   10                  15

Pro Asn Ala His Gln Val Leu Pro Lys Val Leu His Lys Arg Thr Leu
            20                  25                  30

Gly Leu Ser Ala Met Ser Thr Thr Asp Leu Glu Ala Tyr Phe Lys Asp
        35                  40                  45

Cys Leu Phe Lys Asp Trp Glu Glu Leu Gly Glu Glu
    50                  55                  60

<210> SEQ ID NO 101
<211> LENGTH: 784
```

```
<212> TYPE: PRT
<213> ORGANISM: Artificial
<220> FEATURE:
<223> OTHER INFORMATION: Synthetic Construct

<400> SEQUENCE: 101

Met Arg Phe Pro Ser Ile Phe Thr Ala Val Leu Phe Ala Ala Ser Ser
1               5                   10                  15

Ala Ser Ala Ala Pro Val Asn Thr Thr Thr Glu Asp Glu Thr Ala Gln
            20                  25                  30

Ile Pro Ala Glu Ala Val Ile Gly Tyr Leu Asp Leu Glu Gly Asp Phe
                35                  40                  45

Asp Val Ala Val Leu Pro Phe Ser Asn Ser Thr Asn Asn Gly Leu Leu
    50                  55                  60

Phe Ile Asn Thr Thr Ile Ala Ser Ile Ala Ala Lys Glu Glu Gly Val
65                  70                  75                  80

Ser Leu Asp Lys Arg Glu Ala Glu Ala Met Gln Trp Asn Ser Thr Ala
                85                  90                  95

Leu His Gln Ala Leu Leu Asp Pro Arg Val Arg Gly Leu Tyr Phe Pro
            100                 105                 110

Ala Gly Gly Ser Ser Ser Gly Thr Val Asn Pro Val Pro Thr Thr Ala
                115                 120                 125

Ser Pro Ile Ser Ser Ile Leu Ser Lys Thr Gly Asp Pro Val Pro Asn
    130                 135                 140

Met Glu Asn Thr Thr Ser Gly Phe Leu Gly Pro Leu Leu Val Leu Gln
145                 150                 155                 160

Ala Gly Phe Phe Leu Leu Thr Arg Ile Leu Thr Ile Pro Gln Ser Leu
                165                 170                 175

Asp Ser Trp Trp Thr Ser Leu Asn Phe Leu Gly Gly Thr Pro Val Cys
            180                 185                 190

Leu Gly Gln Asn Ser Gln Ser Pro Thr Ser Asn His Ser Pro Thr Ser
                195                 200                 205

Cys Pro Pro Ile Cys Pro Gly Tyr Arg Trp Met Cys Leu Arg Arg Phe
    210                 215                 220

Ile Ile Phe Leu Phe Ile Leu Leu Leu Cys Leu Ile Phe Leu Leu Val
225                 230                 235                 240

Leu Leu Asp Tyr Gln Gly Met Leu Pro Val Cys Pro Leu Leu Pro Gly
                245                 250                 255

Thr Ser Thr Thr Ser Thr Gly Pro Cys Lys Thr Cys Thr Ile Pro Ala
            260                 265                 270

Gln Gly Thr Ser Met Phe Pro Ser Cys Cys Thr Lys Pro Ser Asp
                275                 280                 285

Gly Asn Cys Thr Cys Ile Pro Ile Pro Ser Ser Trp Ala Phe Ala Arg
    290                 295                 300

Phe Leu Trp Glu Trp Ala Ser Val Arg Phe Ser Trp Leu Ser Leu Leu
305                 310                 315                 320

Val Pro Phe Val Gln Trp Phe Val Gly Leu Ser Pro Thr Val Trp Leu
                325                 330                 335

Ser Val Gly Leu Ser Arg Tyr Val Ala Arg Leu Ser Ser Thr Ser Arg
            340                 345                 350

Asn Ile Asn Tyr Gln His Gly Thr Met Gln Asp Leu His Asp Ser Cys
                355                 360                 365

Ser Arg Asn Leu Tyr Val Ser Leu Leu Leu Leu Tyr Lys Thr Phe Gly
    370                 375                 380
```

```
Arg Lys Leu His Leu Tyr Ser His Pro Ile Ile Leu Gly Phe Arg Lys
385                 390                 395                 400

Ile Pro Met Gly Val Gly Leu Ser Pro Phe Leu Ala Gln Phe Thr
            405                 410                 415

Ser Ala Ile Cys Ser Val Val Arg Arg Ala Phe Pro His Cys Leu Ala
            420                 425                 430

Phe Ser Tyr Met Asp Asp Val Val Leu Gly Ala Lys Ser Val Gln His
            435                 440                 445

Leu Glu Ser Leu Phe Thr Ser Ile Thr Asn Phe Leu Ser Leu Gly
    450                 455                 460

Ile His Leu Asn Pro Asn Lys Thr Lys Arg Trp Gly Tyr Ser Leu Asn
465                 470                 475                 480

Phe Met Gly Tyr Val Ile Gly Ser Trp Gly Thr Leu Pro Gln Glu His
            485                 490                 495

Ile Val Gln Lys Leu Lys Gln Cys Phe Arg Lys Leu Pro Val Asn Arg
            500                 505                 510

Pro Ile Asp Trp Lys Val Cys Gln Arg Ile Val Gly Leu Leu Gly Phe
            515                 520                 525

Ala Ala Pro Phe Thr Gln Cys Gly Tyr Pro Ala Leu Met Pro Leu Tyr
530                 535                 540

Ala Cys Ile Gln Ala Lys Gln Ala Phe Thr Phe Ser Pro Thr Tyr Lys
545                 550                 555                 560

Ala Phe Leu Cys Lys Gln Glu Phe Gly Ala Ser Val Glu Leu Leu Ser
            565                 570                 575

Phe Leu Pro Ser Asp Phe Phe Pro Ser Val Arg Asp Leu Leu Asp Thr
            580                 585                 590

Ala Ser Ala Leu Tyr Arg Glu Ala Leu Glu Ser Pro Glu His Cys Ser
            595                 600                 605

Pro His His Thr Ala Leu Arg Gln Ala Ile Leu Cys Trp Gly Glu Leu
            610                 615                 620

Met Asn Leu Ala Thr Trp Val Gly Ser Asn Leu Glu Asp Pro Ala Ser
625                 630                 635                 640

Arg Glu Leu Val Val Ser Tyr Val Asn Val Asn Met Gly Leu Lys Ile
            645                 650                 655

Arg Gln Leu Leu Trp Phe His Ile Ser Cys Leu Thr Phe Gly Arg Glu
            660                 665                 670

Thr Val Leu Glu Tyr Leu Val Ser Phe Gly Val Trp Ile Arg Thr Pro
            675                 680                 685

Pro Ala Tyr Arg Pro Pro Asn Ala Pro Ile Leu Ser Thr Leu Pro Glu
            690                 695                 700

Thr Thr Val Val Arg Arg Arg Gly Arg Ser Pro Arg Arg His Leu
705                 710                 715                 720

Ser Leu Arg Gly Leu Phe Val Cys Ala Phe Ser Ser Ala Gly Pro Asn
            725                 730                 735

Ala His Gln Val Leu Pro Lys Val Leu His Arg Thr Leu Gly Leu
            740                 745                 750

Ser Ala Met Ser Thr Thr Asp Leu Glu Ala Tyr Phe Lys Asp Cys Leu
            755                 760                 765

Phe Lys Asp Trp Glu Glu Leu Gly Glu Glu His His His His His
            770                 775                 780

<210> SEQ ID NO 102
<211> LENGTH: 700
<212> TYPE: PRT
```

<213> ORGANISM: Artificial
<220> FEATURE:
<223> OTHER INFORMATION: Synthetic Construct

<400> SEQUENCE: 102

```
Met Ala Asp Glu Ala Pro Gln Trp Asn Ser Thr Ala Leu His Gln Ala
1               5                   10                  15

Leu Leu Asp Pro Arg Val Arg Gly Leu Tyr Phe Pro Ala Gly Gly Ser
            20                  25                  30

Ser Ser Gly Thr Val Asn Pro Val Pro Thr Thr Ala Ser Pro Ile Ser
        35                  40                  45

Ser Ile Leu Ser Lys Thr Gly Asp Pro Val Pro Asn Met Glu Asn Thr
50                  55                  60

Thr Ser Gly Phe Leu Gly Pro Leu Leu Val Leu Gln Ala Gly Phe Phe
65                  70                  75                  80

Leu Leu Thr Arg Ile Leu Thr Ile Pro Gln Ser Leu Asp Ser Trp Trp
                85                  90                  95

Thr Ser Leu Asn Phe Leu Gly Gly Thr Pro Val Cys Leu Gly Gln Asn
            100                 105                 110

Ser Gln Ser Pro Thr Ser Asn His Ser Pro Thr Ser Cys Pro Pro Ile
        115                 120                 125

Cys Pro Gly Tyr Arg Trp Met Cys Leu Arg Arg Phe Ile Ile Phe Leu
130                 135                 140

Phe Ile Leu Leu Leu Cys Leu Ile Phe Leu Leu Val Leu Leu Asp Tyr
145                 150                 155                 160

Gln Gly Met Leu Pro Val Cys Pro Leu Leu Pro Gly Thr Ser Thr Thr
                165                 170                 175

Ser Thr Gly Pro Cys Lys Thr Cys Thr Ile Pro Ala Gln Gly Thr Ser
            180                 185                 190

Met Phe Pro Ser Cys Cys Cys Thr Lys Pro Ser Asp Gly Asn Cys Thr
        195                 200                 205

Cys Ile Pro Ile Pro Ser Ser Trp Ala Phe Ala Arg Phe Leu Trp Glu
210                 215                 220

Trp Ala Ser Val Arg Phe Ser Trp Leu Ser Leu Leu Val Pro Phe Val
225                 230                 235                 240

Gln Trp Phe Val Gly Leu Ser Pro Thr Val Trp Leu Ser Val Gly Leu
                245                 250                 255

Ser Arg Tyr Val Ala Arg Leu Ser Ser Thr Ser Arg Asn Ile Asn Tyr
            260                 265                 270

Gln His Gly Thr Met Gln Asp Leu His Asp Ser Cys Ser Arg Asn Leu
        275                 280                 285

Tyr Val Ser Leu Leu Leu Leu Tyr Lys Thr Phe Gly Arg Lys Leu His
290                 295                 300

Leu Tyr Ser His Pro Ile Ile Leu Gly Phe Arg Lys Ile Pro Met Gly
305                 310                 315                 320

Val Gly Leu Ser Pro Phe Leu Leu Ala Gln Phe Thr Ser Ala Ile Cys
                325                 330                 335

Ser Val Val Arg Arg Ala Phe Pro His Cys Leu Ala Phe Ser Tyr Met
            340                 345                 350

Asp Asp Val Val Leu Gly Ala Lys Ser Val Gln His Leu Glu Ser Leu
        355                 360                 365

Phe Thr Ser Ile Thr Asn Phe Leu Leu Ser Leu Gly Ile His Leu Asn
370                 375                 380

Pro Asn Lys Thr Lys Arg Trp Gly Tyr Ser Leu Asn Phe Met Gly Tyr
```

```
                385                 390                 395                 400
Val Ile Gly Ser Trp Gly Thr Leu Pro Gln Glu His Ile Val Gln Lys
                    405                 410                 415

Leu Lys Gln Cys Phe Arg Lys Leu Pro Val Asn Arg Pro Ile Asp Trp
                420                 425                 430

Lys Val Cys Gln Arg Ile Val Gly Leu Leu Gly Phe Ala Ala Pro Phe
            435                 440                 445

Thr Gln Cys Gly Tyr Pro Ala Leu Met Pro Leu Tyr Ala Cys Ile Gln
        450                 455                 460

Ala Lys Gln Ala Phe Thr Phe Ser Pro Thr Tyr Lys Ala Phe Leu Cys
465                 470                 475                 480

Lys Gln Glu Phe Gly Ala Ser Val Glu Leu Leu Ser Phe Leu Pro Ser
                485                 490                 495

Asp Phe Phe Pro Ser Val Arg Asp Leu Leu Asp Thr Ala Ser Ala Leu
                    500                 505                 510

Tyr Arg Glu Ala Leu Glu Ser Pro Glu His Cys Ser Pro His His Thr
                    515                 520                 525

Ala Leu Arg Gln Ala Ile Leu Cys Trp Gly Glu Leu Met Asn Leu Ala
                530                 535                 540

Thr Trp Val Gly Ser Asn Leu Glu Asp Pro Ala Ser Arg Glu Leu Val
545                 550                 555                 560

Val Ser Tyr Val Asn Val Asn Met Gly Leu Lys Ile Arg Gln Leu Leu
                    565                 570                 575

Trp Phe His Ile Ser Cys Leu Thr Phe Gly Arg Glu Thr Val Leu Glu
                580                 585                 590

Tyr Leu Val Ser Phe Gly Val Trp Ile Arg Thr Pro Pro Ala Tyr Arg
                595                 600                 605

Pro Pro Asn Ala Pro Ile Leu Ser Thr Leu Pro Glu Thr Thr Val Val
            610                 615                 620

Arg Arg Arg Gly Arg Ser Pro Arg Arg His Leu Ser Leu Arg Gly
625                 630                 635                 640

Leu Phe Val Cys Ala Phe Ser Ser Ala Gly Pro Asn Ala His Gln Val
                    645                 650                 655

Leu Pro Lys Val Leu His Lys Arg Thr Leu Gly Leu Ser Ala Met Ser
                660                 665                 670

Thr Thr Asp Leu Glu Ala Tyr Phe Lys Asp Cys Leu Phe Lys Asp Trp
            675                 680                 685

Glu Glu Leu Gly Glu Glu His His His His His
                690                 695                 700

<210> SEQ ID NO 103
<211> LENGTH: 8
<212> TYPE: PRT
<213> ORGANISM: Artificial
<220> FEATURE:
<223> OTHER INFORMATION: Synthetic peptide

<400> SEQUENCE: 103

Gly Tyr His Gly Ser Ser Leu Tyr
1               5

<210> SEQ ID NO 104
<211> LENGTH: 8
<212> TYPE: PRT
<213> ORGANISM: Artificial
<220> FEATURE:
<223> OTHER INFORMATION: Synthetic peptide
```

```
<400> SEQUENCE: 104

Met Gly Leu Lys Phe Arg Gln Leu
1               5

<210> SEQ ID NO 105
<211> LENGTH: 767
<212> TYPE: PRT
<213> ORGANISM: Artificial
<220> FEATURE:
<223> OTHER INFORMATION: Synthetic Construct

<400> SEQUENCE: 105

Met Asp Ile Asp Pro Tyr Lys Glu Phe Gly Ala Thr Val Glu Leu Leu
1               5                   10                  15

Ser Phe Leu Pro Ser Asp Phe Phe Pro Ser Val Arg Asp Leu Leu Asp
                20                  25                  30

Thr Ala Ser Ala Leu Tyr Arg Glu Ala Leu Glu Ser Pro Glu His Cys
            35                  40                  45

Ser Pro His His Thr Ala Leu Arg Gln Ala Ile Leu Cys Trp Gly Glu
        50                  55                  60

Leu Met Thr Leu Ala Thr Trp Val Gly Asn Asn Leu Glu Asp Pro Ala
65                  70                  75                  80

Ser Arg Asp Leu Val Val Asn Tyr Val Asn Val Asn Met Gly Leu Lys
                85                  90                  95

Ile Arg Gln Leu Leu Trp Phe His Ile Ser Cys Leu Thr Phe Gly Arg
            100                 105                 110

Glu Thr Val Leu Glu Tyr Leu Val Ser Phe Gly Val Trp Ile Arg Thr
        115                 120                 125

Pro Pro Ala Tyr Arg Pro Pro Asn Ala Pro Ile Leu Ser Thr Leu Pro
    130                 135                 140

Glu Thr Thr Val Val Arg Arg Arg Gly Arg Ser Pro Arg Arg Arg Thr
145                 150                 155                 160

Pro Ser Pro Arg Arg Arg Arg Ser Gln Ser Pro Arg Arg Arg Arg Ser
                165                 170                 175

Lys Ser Arg Glu Ser Gln Cys Met Gln Leu Phe His Leu Cys Leu Ile
            180                 185                 190

Ile Ser Cys Ser Cys Pro Thr Val Gln Ala Ser Lys Leu Cys Leu Gly
        195                 200                 205

Trp Leu Trp Gly Met Asp Ile Asp Pro Tyr Lys Glu Phe Gly Ala Thr
    210                 215                 220

Val Glu Leu Leu Ser Phe Leu Pro Ser Asp Phe Phe Pro Ser Val Arg
225                 230                 235                 240

Asp Leu Leu Asp Thr Ala Ala Ala Leu Tyr Arg Glu Ala Leu Glu Ser
                245                 250                 255

Pro Glu His Cys Ser Pro His His Thr Ala Leu Arg Gln Ala Ile Leu
            260                 265                 270

Cys Trp Gly Glu Leu Met Thr Leu Ala Thr Trp Val Gly Asn Asn Leu
        275                 280                 285

Glu Asp Pro Ala Ser Arg Asp Leu Val Val Asn Tyr Val Asn Val Asn
    290                 295                 300

Met Gly Leu Lys Ile Arg Gln Leu Leu Trp Phe His Ile Ser Cys Leu
305                 310                 315                 320

Thr Phe Gly Arg Glu Thr Val Leu Glu Tyr Leu Val Ser Phe Gly Val
                325                 330                 335
```

```
Trp Ile Arg Thr Pro Pro Ala Tyr Arg Pro Pro Asn Ala Pro Ile Leu
            340                 345                 350

Ser Thr Leu Pro Glu Thr Thr Val Val Arg Arg Gly Arg Ser Pro
        355                 360                 365

Arg Arg Arg Thr Pro Ser Pro Arg Arg Arg Ser Gln Ser Pro Arg
        370                 375                 380

Arg Arg Arg Ser Gln Ser Arg Glu Ser Gln Cys Met Asp Ile Asp Pro
385                 390                 395                 400

Tyr Lys Glu Phe Gly Ala Thr Val Glu Leu Leu Ser Phe Leu Pro Ser
                405                 410                 415

Asp Phe Phe Pro Ser Val Arg Asp Leu Leu Asp Thr Ala Ser Ala Leu
                420                 425                 430

Tyr Arg Glu Ala Leu Glu Ser Pro Glu His Cys Ser Pro His His Thr
            435                 440                 445

Ala Leu Arg Gln Ala Ile Leu Cys Trp Gly Glu Leu Met Asn Leu Ala
        450                 455                 460

Thr Trp Val Gly Ser Asn Leu Glu Asp Pro Ala Ser Arg Glu Leu Val
465                 470                 475                 480

Val Ser Tyr Val Asn Val Asn Met Gly Leu Lys Ile Arg Gln Leu Leu
                485                 490                 495

Trp Phe His Ile Ser Cys Leu Thr Phe Gly Arg Glu Thr Val Leu Glu
                500                 505                 510

Tyr Leu Val Ser Phe Gly Val Trp Ile Arg Thr Pro Pro Ala Tyr Arg
            515                 520                 525

Pro Pro Asn Ala Pro Ile Leu Ser Thr Leu Pro Glu Thr Thr Val Val
        530                 535                 540

Arg Arg Arg Gly Arg Ser Pro Arg Arg Arg Thr Pro Ser Pro Arg Arg
545                 550                 555                 560

Arg Arg Ser Gln Ser Pro Arg Arg Arg Ser Gln Ser Arg Glu Ser
            565                 570                 575

Gln Cys Met Asp Ile Asp Pro Tyr Lys Glu Phe Gly Ala Thr Val Glu
                580                 585                 590

Leu Leu Ser Phe Leu Pro Ser Asp Phe Phe Pro Ser Val Arg Asp Leu
            595                 600                 605

Leu Asp Thr Ala Ser Ala Leu Tyr Arg Glu Ala Leu Glu Ser Pro Glu
610                 615                 620

His Cys Ser Pro His His Thr Ala Leu Arg Gln Ala Ile Leu Cys Trp
625                 630                 635                 640

Gly Glu Leu Met Thr Leu Ala Thr Trp Val Gly Val Asn Leu Glu Asp
                645                 650                 655

Pro Ala Ser Arg Asp Leu Val Val Ser Tyr Val Asn Val Asn Met Gly
                660                 665                 670

Leu Lys Phe Arg Gln Leu Leu Trp Phe His Ile Ser Cys Leu Thr Phe
            675                 680                 685

Gly Arg Glu Thr Val Leu Glu Tyr Leu Val Ser Phe Gly Val Trp Ile
            690                 695                 700

Arg Thr Pro Pro Ala Tyr Arg Pro Pro Asn Ala Pro Ile Leu Ser Thr
705                 710                 715                 720

Leu Pro Glu Thr Thr Val Val Arg Arg Arg Gly Arg Ser Pro Arg Arg
                725                 730                 735

Arg Thr Pro Ser Pro Arg Arg Arg Arg Ser Gln Ser Pro Arg Arg Lys
            740                 745                 750

Arg Ser Gln Ser Arg Glu Ser Gln Cys His His His His His His
```

```
            755                 760                 765

<210> SEQ ID NO 106
<211> LENGTH: 680
<212> TYPE: PRT
<213> ORGANISM: Artificial
<220> FEATURE:
<223> OTHER INFORMATION: Synthetic Construct

<400> SEQUENCE: 106

Met Asp Ile Asp Pro Tyr Lys Glu Phe Gly Ala Thr Val Glu Leu Leu
1               5                   10                  15

Ser Phe Leu Pro Ser Asp Phe Phe Pro Ser Val Arg Asp Leu Leu Asp
            20                  25                  30

Thr Ala Ser Ala Leu Tyr Arg Glu Ala Leu Glu Ser Pro Glu His Cys
        35                  40                  45

Ser Pro His His Thr Ala Leu Arg Gln Ala Ile Leu Cys Trp Gly Glu
    50                  55                  60

Leu Met Thr Leu Ala Thr Trp Val Gly Asn Asn Leu Glu Asp Pro Ala
65                  70                  75                  80

Ser Arg Asp Leu Val Val Asn Tyr Val Asn Val Asn Met Gly Leu Lys
                85                  90                  95

Ile Arg Gln Leu Leu Trp Phe His Ile Ser Cys Leu Thr Phe Gly Arg
            100                 105                 110

Glu Thr Val Leu Glu Tyr Leu Val Ser Phe Gly Val Trp Ile Arg Thr
        115                 120                 125

Pro Pro Ala Tyr Arg Pro Pro Asn Ala Pro Ile Leu Ser Thr Leu Pro
    130                 135                 140

Glu Thr Thr Val Val Arg Arg Arg Gly Arg Ser Pro Arg Arg Arg Thr
145                 150                 155                 160

Pro Ser Pro Arg Arg Arg Arg Ser Gln Ser Pro Arg Arg Arg Arg Ser
                165                 170                 175

Lys Ser Arg Glu Ser Gln Cys Met Ala Ala Arg Leu Tyr Cys Gln Leu
            180                 185                 190

Asp Ser Ser Arg Asp Val Leu Cys Leu Arg Pro Val Gly Ala Glu Ser
        195                 200                 205

Arg Gly Arg Pro Leu Ser Gly Pro Leu Gly Thr Leu Ser Ser Pro Ser
    210                 215                 220

Pro Ser Ala Val Pro Ala Asp His Gly Ala His Leu Ser Leu Arg Gly
225                 230                 235                 240

Leu Phe Val Cys Ala Phe Ser Ser Ala Gly Pro Cys Ala Leu Arg Phe
                245                 250                 255

Thr Ser Ala Arg Cys Met Glu Thr Thr Val Asn Ala His Gln Ile Leu
            260                 265                 270

Pro Lys Val Leu His Lys Arg Thr Leu Gly Leu Ser Ala Met Ser Thr
        275                 280                 285

Thr Asp Leu Glu Ala Tyr Phe Lys Asp Cys Leu Phe Lys Asp Trp Glu
    290                 295                 300

Glu Leu Gly Glu Glu Ile Arg Leu Lys Val Phe Val Leu Gly Gly Cys
305                 310                 315                 320

Arg His Lys Leu Val Cys Ala Pro Ala Pro Cys Asn Phe Phe Thr Ser
                325                 330                 335

Ala Met Asp Ile Asp Pro Tyr Lys Glu Phe Gly Ala Thr Val Glu Leu
            340                 345                 350

Leu Ser Phe Leu Pro Ser Asp Phe Phe Pro Ser Val Arg Asp Leu Leu
```

```
                355                 360                 365
Asp Thr Ala Ser Ala Leu Tyr Arg Glu Ala Leu Glu Ser Pro Glu His
            370                 375                 380

Cys Ser Pro His His Thr Ala Leu Arg Gln Ala Ile Leu Cys Trp Gly
385                 390                 395                 400

Glu Leu Met Asn Leu Ala Thr Trp Val Gly Ser Asn Leu Glu Asp Pro
                405                 410                 415

Ala Ser Arg Glu Leu Val Val Ser Tyr Val Asn Val Asn Met Gly Leu
            420                 425                 430

Lys Ile Arg Gln Leu Leu Trp Phe His Ile Ser Cys Leu Thr Phe Gly
                435                 440                 445

Arg Glu Thr Val Leu Glu Tyr Leu Val Ser Phe Gly Val Trp Ile Arg
            450                 455                 460

Thr Pro Pro Ala Tyr Arg Pro Pro Asn Ala Pro Ile Leu Ser Thr Leu
465                 470                 475                 480

Pro Glu Thr Thr Val Val Arg Arg Gly Arg Ser Pro Arg Arg Arg
                485                 490                 495

Thr Pro Ser Pro Arg Arg Arg Ser Gln Ser Pro Arg Arg Arg
            500                 505                 510

Ser Gln Ser Arg Glu Ser Gln Cys Met Ala Ala Arg Leu Cys Cys Gln
                515                 520                 525

Leu Asp Pro Ala Arg Asp Val Leu Cys Leu Arg Pro Val Gly Thr Glu
530                 535                 540

Ser Arg Gly Arg Pro Val Ser Arg Pro Phe Gly Thr Leu Ser Ser Pro
545                 550                 555                 560

Ser Ala Ser Ala Val Pro Ala Asp His Gly Ala His Leu Ser Leu Arg
                565                 570                 575

Gly Leu Phe Val Cys Ala Phe Ser Ser Ala Gly Pro Cys Ala Leu Arg
            580                 585                 590

Phe Thr Ser Ala Arg Arg Met Glu Thr Thr Val Asn Ala His Gln Val
                595                 600                 605

Leu Pro Lys Val Leu His Lys Arg Thr Leu Gly Leu Pro Ala Met Ser
610                 615                 620

Thr Thr Asp Leu Glu Ala Tyr Phe Lys Asp Cys Leu Phe Lys Asp Trp
625                 630                 635                 640

Glu Glu Leu Gly Glu Glu Ile Arg Leu Met Ile Phe Val Leu Gly Gly
                645                 650                 655

Cys Arg His Lys Leu Val Cys Ser Pro Ala Pro Cys Asn Phe Phe Thr
            660                 665                 670

Ser Ala His His His His His His
        675                 680

<210> SEQ ID NO 107
<211> LENGTH: 689
<212> TYPE: PRT
<213> ORGANISM: Artificial
<220> FEATURE:
<223> OTHER INFORMATION: Synthetic Construct

<400> SEQUENCE: 107

Met Gln Trp Asn Ser Thr Ala Leu His Gln Ala Leu Leu Asp Pro Arg
1               5                   10                  15

Val Arg Gly Leu Tyr Phe Pro Ala Gly Gly Ser Ser Ser Gly Thr Val
                20                  25                  30

Asn Pro Val Pro Thr Thr Ala Ser Pro Ile Ser Ser Ile Leu Ser Lys
```

```
                    35                  40                  45
Thr Gly Asp Pro Val Pro Asn Met Glu Asn Thr Thr Ser Gly Phe Leu
                50                  55                  60

Gly Pro Leu Leu Val Leu Gln Ala Gly Phe Phe Leu Leu Thr Arg Ile
 65                  70                  75                  80

Leu Thr Ile Pro Gln Ser Leu Asp Ser Trp Trp Thr Ser Leu Asn Phe
                    85                  90                  95

Leu Gly Gly Thr Pro Val Cys Leu Gly Gln Asn Ser Gln Ser Pro Thr
                100                 105                 110

Ser Asn His Ser Pro Thr Ser Cys Pro Pro Ile Cys Pro Gly Tyr Arg
                115                 120                 125

Trp Met Cys Leu Arg Arg Phe Ile Ile Phe Leu Phe Ile Leu Leu Leu
                130                 135                 140

Cys Leu Ile Phe Leu Leu Val Leu Leu Asp Tyr Gln Gly Met Leu Pro
145                 150                 155                 160

Val Cys Pro Leu Leu Pro Gly Thr Ser Thr Thr Ser Thr Gly Pro Cys
                165                 170                 175

Lys Thr Cys Thr Ile Pro Ala Gln Gly Thr Ser Met Phe Pro Ser Cys
                180                 185                 190

Cys Cys Thr Lys Pro Ser Asp Gly Asn Cys Thr Cys Ile Pro Ile Pro
                195                 200                 205

Ser Ser Trp Ala Phe Ala Arg Phe Leu Trp Glu Trp Ala Ser Val Arg
210                 215                 220

Phe Ser Trp Leu Ser Leu Leu Val Pro Phe Val Gln Trp Phe Val Gly
225                 230                 235                 240

Leu Ser Pro Thr Val Trp Leu Ser Val Gly Leu Ser Arg Tyr Val Ala
                245                 250                 255

Arg Leu Ser Ser Asn Ser Arg Ile Asn Asn Asn Gln Tyr Gly Thr Met
                260                 265                 270

Gln Asn Leu His Asp Ser Cys Ser Arg Gln Leu Tyr Val Ser Leu Met
                275                 280                 285

Leu Leu Tyr Lys Thr Tyr Gly Trp Lys Leu His Leu Tyr Ser His Pro
                290                 295                 300

Ile Val Leu Gly Phe Arg Lys Ile Pro Met Gly Val Gly Leu Ser Pro
305                 310                 315                 320

Phe Leu Leu Ala Gln Phe Thr Ser Ala Ile Cys Ser Val Val Arg Arg
                325                 330                 335

Ala Phe Pro His Cys Leu Ala Phe Ser Tyr Met Asp Asp Val Val Leu
                340                 345                 350

Gly Ala Lys Ser Val Gln His Arg Glu Ser Leu Tyr Thr Ala Val Thr
                355                 360                 365

Asn Phe Leu Leu Ser Leu Gly Ile His Leu Asn Pro Asn Lys Thr Lys
                370                 375                 380

Arg Trp Gly Tyr Ser Leu Asn Phe Met Gly Tyr Ile Ile Gly Ser Trp
385                 390                 395                 400

Gly Thr Leu Pro Gln Asp His Ile Val Gln Lys Ile Lys His Cys Phe
                405                 410                 415

Arg Lys Leu Pro Val Asn Arg Pro Ile Asp Trp Lys Val Cys Gln Arg
                420                 425                 430

Ile Val Gly Leu Leu Gly Phe Ala Ala Pro Phe Thr Gln Cys Gly Tyr
                435                 440                 445

Pro Ala Leu Met Pro Leu Tyr Ala Cys Ile Gln Ala Lys Gln Ala Phe
                450                 455                 460
```

```
Thr Phe Ser Pro Thr Tyr Lys Ala Phe Leu Ser Lys Gln Glu Phe Gly
465                 470                 475                 480

Ala Ser Val Glu Leu Leu Ser Phe Leu Pro Ser Asp Phe Phe Pro Ser
                485                 490                 495

Val Arg Asp Leu Leu Asp Thr Ala Ser Ala Leu Tyr Arg Glu Ala Leu
            500                 505                 510

Glu Ser Pro Glu His Cys Ser Pro His His Thr Ala Leu Arg Gln Ala
        515                 520                 525

Ile Leu Cys Trp Gly Glu Leu Met Asn Leu Ala Thr Trp Val Gly Ser
530                 535                 540

Asn Leu Glu Asp Pro Ala Ser Arg Glu Leu Val Val Ser Tyr Val Asn
545                 550                 555                 560

Val Asn Met Gly Leu Lys Ile Arg Gln Leu Leu Trp Phe His Ile Ser
                565                 570                 575

Cys Leu Thr Phe Gly Arg Glu Thr Val Leu Glu Tyr Leu Val Ser Phe
            580                 585                 590

Gly Val Trp Ile Arg Thr Pro Pro Ala Tyr Arg Pro Asn Ala Pro
        595                 600                 605

Ile Leu Ser Thr Leu Pro Glu Thr Thr Val Val Arg Arg Arg Gly Arg
610                 615                 620

Ser Pro Arg Arg Arg His Leu Ser Leu Arg Gly Leu Phe Val Cys Ala
625                 630                 635                 640

Phe Ser Ser Ala Gly Pro Asn Ala His Gln Ile Leu Pro Lys Val Leu
                645                 650                 655

His Lys Arg Thr Leu Gly Leu Ser Ala Met Ser Thr Thr Asp Leu Glu
            660                 665                 670

Ala Tyr Phe Lys Asp Cys Leu Phe Lys Asp Trp Glu Glu Leu Gly Glu
        675                 680                 685

Glu

<210> SEQ ID NO 108
<211> LENGTH: 689
<212> TYPE: PRT
<213> ORGANISM: Artificial
<220> FEATURE:
<223> OTHER INFORMATION: Synthetic Construct

<400> SEQUENCE: 108

Met Gln Trp Asn Ser Thr Ala Leu His Gln Ala Leu Leu Asp Pro Arg
1               5                   10                  15

Val Arg Gly Leu Tyr Phe Pro Ala Gly Gly Ser Ser Ser Gly Thr Val
            20                  25                  30

Asn Pro Val Gln Thr Thr Ala Ser Pro Ile Ser Ser Ile Leu Ser Lys
        35                  40                  45

Thr Gly Asp Pro Val Pro Asn Met Glu Asn Ile Ala Ser Gly Phe Leu
    50                  55                  60

Gly Pro Leu Leu Val Leu Gln Ala Gly Phe Phe Leu Leu Thr Arg Ile
65                  70                  75                  80

Leu Thr Ile Pro Gln Ser Leu Asp Ser Trp Trp Thr Ser Leu Asn Phe
                85                  90                  95

Leu Gly Gly Thr Pro Val Cys Leu Gly Gln Asn Ser Gln Ser Pro Thr
            100                 105                 110

Ser Ser His Ser Pro Thr Ser Cys Pro Pro Ile Cys Pro Gly Tyr Arg
        115                 120                 125
```

```
Trp Met Cys Leu Arg Arg Cys Ile Ile Phe Leu Phe Ile Leu Leu Leu
    130                 135                 140
Cys Leu Ile Phe Leu Leu Val Leu Leu Asp Tyr Gln Gly Met Leu Pro
145                 150                 155                 160
Val Cys Pro Leu Leu Pro Gly Thr Ser Thr Thr Ser Thr Gly Pro Cys
                165                 170                 175
Lys Thr Cys Thr Ile Pro Ala Gln Gly Thr Ser Met Phe Pro Ser Cys
                180                 185                 190
Cys Cys Thr Lys Pro Ser Asp Gly Asn Cys Thr Cys Ile Pro Ile Pro
                195                 200                 205
Ser Ser Trp Ala Phe Ala Arg Phe Leu Trp Glu Trp Ala Ser Val Arg
    210                 215                 220
Phe Ser Trp Leu Ser Leu Leu Val Pro Phe Val Gln Trp Phe Val Gly
225                 230                 235                 240
Leu Ser Pro Thr Val Trp Leu Ser Val Gly Leu Ser Arg Tyr Val Ala
                245                 250                 255
Arg Leu Ser Ser Asn Ser Arg Ile Ile Asn His Gln His Arg Thr Met
                260                 265                 270
Gln Asn Leu His Asn Ser Cys Ser Arg Asn Leu Tyr Val Ser Leu Met
    275                 280                 285
Leu Leu Tyr Lys Thr Tyr Gly Arg Lys Leu His Leu Tyr Ser His Pro
290                 295                 300
Ile Ile Leu Gly Phe Arg Lys Ile Pro Met Gly Val Gly Leu Ser Pro
305                 310                 315                 320
Phe Leu Leu Ala Gln Phe Thr Ser Ala Ile Cys Ser Val Val Arg Arg
                325                 330                 335
Ala Phe Pro His Cys Leu Ala Phe Ser Tyr Met Asp Asp Val Val Leu
                340                 345                 350
Gly Ala Lys Ser Val Gln His Leu Glu Ser Leu Tyr Ala Ala Val Thr
                355                 360                 365
Asn Phe Leu Leu Ser Leu Gly Ile His Leu Asn Pro His Lys Thr Lys
    370                 375                 380
Arg Trp Gly Tyr Ser Leu Asn Phe Met Gly Tyr Val Ile Gly Ser Trp
385                 390                 395                 400
Gly Thr Leu Pro Gln Glu His Ile Val Gln Lys Ile Lys Met Cys Phe
                405                 410                 415
Arg Lys Leu Pro Val Asn Arg Pro Ile Asp Trp Lys Val Cys Gln Arg
                420                 425                 430
Ile Val Gly Leu Leu Gly Phe Ala Ala Pro Phe Thr Gln Cys Gly Tyr
    435                 440                 445
Pro Ala Leu Met Pro Leu Tyr Ala Cys Ile Gln Ala Lys Gln Ala Phe
450                 455                 460
Thr Phe Ser Pro Thr Tyr Lys Ala Phe Leu Ser Lys Gln Glu Phe Gly
465                 470                 475                 480
Ala Ser Val Glu Leu Leu Ser Phe Leu Pro Ser Asp Phe Phe Pro Ser
                485                 490                 495
Val Arg Asp Leu Leu Asp Thr Ala Ser Ala Leu Tyr Arg Glu Ala Leu
                500                 505                 510
Glu Ser Pro Glu His Cys Ser Pro His His Thr Ala Leu Arg Gln Ala
                515                 520                 525
Ile Leu Cys Trp Gly Glu Leu Met Asn Leu Ala Thr Trp Val Gly Ser
    530                 535                 540
Asn Leu Glu Asp Pro Ala Ser Arg Glu Leu Val Val Ser Tyr Val Asn
```

```
545                 550                 555                 560
Val Asn Met Gly Leu Lys Ile Arg Gln Leu Leu Trp Phe His Ile Ser
                565                 570                 575

Cys Leu Thr Phe Gly Arg Glu Thr Val Leu Glu Tyr Leu Val Ser Phe
                580                 585                 590

Gly Val Trp Ile Arg Thr Pro Pro Ala Tyr Arg Pro Asn Ala Pro
                595                 600                 605

Ile Leu Ser Thr Leu Pro Glu Thr Thr Val Val Arg Arg Gly Arg
610                 615                 620

Ser Pro Arg Arg His Leu Ser Leu Arg Gly Leu Phe Val Cys Ala
625                 630                 635                 640

Phe Ser Ser Ala Gly Pro Asn Ala His Arg Asn Leu Pro Lys Val Leu
                645                 650                 655

His Lys Arg Thr Leu Gly Leu Ser Ala Met Ser Thr Thr Asp Leu Glu
                660                 665                 670

Ala Tyr Phe Lys Asp Cys Leu Phe Lys Asp Trp Glu Glu Leu Gly Glu
                675                 680                 685

Glu

<210> SEQ ID NO 109
<211> LENGTH: 689
<212> TYPE: PRT
<213> ORGANISM: Artificial
<220> FEATURE:
<223> OTHER INFORMATION: Synthetic Construct

<400> SEQUENCE: 109

Met Gln Trp Asn Ser Thr Ala Leu His Gln Ala Leu Leu Asp Pro Arg
1               5                   10                  15

Val Arg Gly Leu Tyr Phe Pro Ala Gly Gly Ser Ser Ser Gly Thr Val
                20                  25                  30

Asn Pro Val Pro Thr Thr Ala Ser Pro Ile Ser Ser Ile Leu Ser Lys
                35                  40                  45

Thr Gly Asp Pro Val Pro Asn Met Glu Asn Thr Thr Ser Gly Phe Leu
50                  55                  60

Gly Pro Leu Leu Val Leu Gln Ala Gly Phe Phe Leu Leu Thr Arg Ile
65                  70                  75                  80

Leu Thr Ile Pro Gln Ser Leu Asp Ser Trp Trp Thr Ser Leu Asn Phe
                85                  90                  95

Leu Gly Gly Thr Pro Val Cys Leu Gly Gln Asn Ser Gln Ser Pro Thr
                100                 105                 110

Ser Asn His Ser Pro Thr Ser Cys Pro Pro Ile Cys Pro Gly Tyr Arg
                115                 120                 125

Trp Met Cys Leu Arg Arg Phe Ile Ile Phe Leu Phe Ile Leu Leu Leu
130                 135                 140

Cys Leu Ile Phe Leu Leu Val Leu Leu Asp Tyr Gln Gly Met Leu Pro
145                 150                 155                 160

Val Cys Pro Leu Leu Pro Gly Thr Ser Thr Thr Ser Thr Gly Pro Cys
                165                 170                 175

Lys Thr Cys Thr Ile Pro Ala Gln Gly Thr Ser Met Phe Pro Ser Cys
                180                 185                 190

Cys Cys Thr Lys Pro Ser Asp Gly Asn Cys Thr Cys Ile Pro Ile Pro
                195                 200                 205

Ser Ser Trp Ala Phe Ala Arg Phe Leu Trp Glu Trp Ala Ser Val Arg
                210                 215                 220
```

```
Phe Ser Trp Leu Ser Leu Leu Val Pro Phe Val Gln Trp Phe Val Gly
225                 230                 235                 240

Leu Ser Pro Thr Val Trp Leu Ser Val Gly Leu Ser Arg Tyr Val Ala
            245                 250                 255

Arg Leu Ser Ser Thr Ser Arg Asn Ile Asn Tyr Gln His Gly Thr Met
        260                 265                 270

Gln Asp Leu His Asp Ser Cys Ser Arg Asn Leu Tyr Val Ser Leu Leu
    275                 280                 285

Leu Leu Tyr Lys Thr Phe Gly Arg Lys Leu His Leu Tyr Ser His Pro
290                 295                 300

Ile Ile Leu Gly Phe Arg Lys Ile Pro Met Gly Val Gly Leu Ser Pro
305                 310                 315                 320

Phe Leu Leu Ala Gln Phe Thr Ser Ala Ile Cys Ser Val Val Arg Arg
                325                 330                 335

Ala Phe Pro His Cys Leu Ala Phe Ser Tyr Met Asp Asp Val Val Leu
            340                 345                 350

Gly Ala Lys Ser Val Gln His Leu Glu Ser Leu Phe Thr Ser Ile Thr
        355                 360                 365

Asn Phe Leu Leu Ser Leu Gly Ile His Leu Asn Pro Asn Lys Thr Lys
370                 375                 380

Arg Trp Gly Tyr Ser Leu Asn Phe Met Gly Tyr Val Ile Gly Ser Trp
385                 390                 395                 400

Gly Thr Leu Pro Gln Glu His Ile Val Leu Lys Ile Lys Gln Cys Phe
                405                 410                 415

Arg Lys Leu Pro Val Asn Arg Pro Ile Asp Trp Lys Val Cys Gln Arg
            420                 425                 430

Ile Val Gly Leu Leu Gly Phe Ala Ala Pro Phe Thr Gln Cys Gly Tyr
        435                 440                 445

Pro Ala Leu Met Pro Leu Tyr Ala Cys Ile Gln Ser Lys Gln Ala Phe
    450                 455                 460

Thr Phe Ser Pro Thr Tyr Lys Ala Phe Leu Cys Lys Gln Glu Phe Gly
465                 470                 475                 480

Ala Ser Val Glu Leu Leu Ser Phe Leu Pro Ser Asp Phe Phe Pro Ser
                485                 490                 495

Val Arg Asp Leu Leu Asp Thr Ala Ser Ala Leu Tyr Arg Glu Ala Leu
            500                 505                 510

Glu Ser Pro Glu His Cys Ser Pro His His Thr Ala Leu Arg Gln Ala
        515                 520                 525

Ile Leu Cys Trp Gly Glu Leu Met Asn Leu Ala Thr Trp Val Gly Ser
    530                 535                 540

Asn Leu Glu Asp Pro Ala Ser Arg Glu Leu Val Val Ser Tyr Val Asn
545                 550                 555                 560

Val Asn Met Gly Leu Lys Ile Arg Gln Leu Leu Trp Phe His Ile Ser
                565                 570                 575

Cys Leu Thr Phe Gly Arg Glu Thr Val Leu Glu Tyr Leu Val Ser Phe
            580                 585                 590

Gly Val Trp Ile Arg Thr Pro Pro Ala Tyr Arg Pro Pro Asn Ala Pro
        595                 600                 605

Ile Leu Ser Thr Leu Pro Glu Thr Thr Val Val Arg Arg Arg Gly Arg
    610                 615                 620

Ser Pro Arg Arg Arg His Leu Ser Leu Arg Gly Leu Phe Val Cys Ala
625                 630                 635                 640
```

```
Phe Ser Ser Ala Gly Pro Asn Ala His Gln Val Leu Pro Lys Val Leu
                645                 650                 655

His Lys Arg Thr Leu Gly Leu Ser Ala Met Ser Thr Thr Asp Leu Glu
            660                 665                 670

Ala Tyr Phe Lys Asp Cys Leu Phe Lys Asp Trp Glu Glu Leu Gly Glu
        675                 680                 685

Glu

<210> SEQ ID NO 110
<211> LENGTH: 689
<212> TYPE: PRT
<213> ORGANISM: Artificial
<220> FEATURE:
<223> OTHER INFORMATION: Synthetic Construct

<400> SEQUENCE: 110

Met Gln Trp Asn Ser Thr Ala Leu His Gln Ala Leu Leu Asp Pro Arg
1               5                   10                  15

Val Arg Gly Leu Tyr Phe Pro Ala Gly Gly Ser Ser Ser Gly Thr Val
            20                  25                  30

Asn Pro Val Pro Thr Thr Ala Ser Pro Ile Ser Ser Ile Leu Ser Lys
        35                  40                  45

Thr Gly Asp Pro Val Pro Asn Met Glu Asn Thr Thr Ser Gly Phe Leu
    50                  55                  60

Gly Pro Leu Leu Val Leu Gln Ala Gly Phe Phe Leu Leu Thr Arg Ile
65                  70                  75                  80

Leu Thr Ile Pro Gln Ser Leu Asp Ser Trp Trp Thr Ser Leu Asn Phe
                85                  90                  95

Leu Gly Gly Thr Pro Val Cys Leu Gly Gln Asn Ser Gln Ser Pro Thr
            100                 105                 110

Ser Asn His Ser Pro Thr Ser Cys Pro Pro Ile Cys Pro Gly Tyr Arg
        115                 120                 125

Trp Met Cys Leu Arg Arg Phe Ile Ile Phe Leu Phe Ile Leu Leu Leu
    130                 135                 140

Cys Leu Ile Phe Leu Leu Val Leu Leu Asp Tyr Gln Gly Met Leu Pro
145                 150                 155                 160

Val Cys Pro Leu Leu Pro Gly Thr Ser Thr Thr Ser Thr Gly Pro Cys
                165                 170                 175

Lys Thr Cys Thr Ile Pro Ala Gln Gly Thr Ser Met Phe Pro Ser Cys
            180                 185                 190

Cys Cys Thr Lys Pro Ser Asp Gly Asn Cys Thr Cys Ile Pro Ile Pro
        195                 200                 205

Ser Ser Trp Ala Phe Ala Arg Phe Leu Trp Glu Trp Ala Ser Val Arg
    210                 215                 220

Phe Ser Trp Leu Ser Leu Leu Val Pro Phe Val Gln Trp Phe Val Gly
225                 230                 235                 240

Leu Ser Pro Thr Val Trp Leu Ser Val Gly Leu Ser Arg Tyr Val Ala
                245                 250                 255

Arg Leu Ser Ser Asn Ser Arg Ile Phe Asn His Gln His Gly Thr Met
            260                 265                 270

Gln Asn Leu His Asp Ser Cys Ser Arg Asn Leu Tyr Val Ser Leu Leu
        275                 280                 285

Leu Leu Tyr Gln Thr Phe Gly Arg Lys Leu His Leu Tyr Ser His Pro
    290                 295                 300

Ile Ile Leu Gly Phe Arg Lys Ile Pro Met Gly Val Gly Leu Ser Pro
```

```
            305                 310                 315                 320
        Phe Leu Leu Ala Gln Phe Thr Ser Ala Ile Cys Ser Val Val Arg Arg
                        325                 330                 335

Ala Phe Pro His Cys Leu Ala Phe Ser Tyr Met Asp Asp Val Val Leu
                        340                 345                 350

Gly Ala Lys Ser Val Gln His Leu Glu Ser Leu Phe Thr Ala Val Thr
                        355                 360                 365

Asn Phe Leu Leu Ser Leu Gly Ile His Leu Asn Pro Asn Lys Thr Lys
                        370                 375                 380

Arg Trp Gly Tyr Ser Leu His Phe Met Gly Tyr Val Ile Gly Cys Tyr
        385                 390                 395                 400

Gly Ser Leu Pro Gln Asp His Ile Ile Gln Lys Ile Lys Glu Cys Phe
                        405                 410                 415

Arg Lys Leu Pro Val Asn Arg Pro Ile Asp Trp Lys Val Cys Gln Arg
                        420                 425                 430

Ile Val Gly Leu Leu Gly Phe Ala Ala Pro Phe Thr Gln Cys Gly Tyr
                        435                 440                 445

Pro Ala Leu Met Pro Leu Tyr Ala Cys Ile Gln Ser Lys Gln Ala Phe
                        450                 455                 460

Thr Phe Ser Pro Thr Tyr Lys Ala Phe Leu Cys Lys Gln Glu Phe Gly
        465                 470                 475                 480

Ala Ser Val Glu Leu Leu Ser Phe Leu Pro Ser Asp Phe Phe Pro Ser
                        485                 490                 495

Val Arg Asp Leu Leu Asp Thr Ala Ser Ala Leu Tyr Arg Glu Ala Leu
                        500                 505                 510

Glu Ser Pro Glu His Cys Ser Pro His His Thr Ala Leu Arg Gln Ala
                        515                 520                 525

Ile Leu Cys Trp Gly Glu Leu Met Asn Leu Ala Thr Trp Val Gly Ser
                        530                 535                 540

Asn Leu Glu Asp Pro Ala Ser Arg Glu Leu Val Val Ser Tyr Val Asn
        545                 550                 555                 560

Val Asn Met Gly Leu Lys Ile Arg Gln Leu Leu Trp Phe His Ile Ser
                        565                 570                 575

Cys Leu Thr Phe Gly Arg Glu Thr Val Leu Glu Tyr Leu Val Ser Phe
                        580                 585                 590

Gly Val Trp Ile Arg Thr Pro Pro Ala Tyr Arg Pro Pro Asn Ala Pro
                        595                 600                 605

Ile Leu Ser Thr Leu Pro Glu Thr Thr Val Val Arg Arg Arg Gly Arg
                        610                 615                 620

Ser Pro Arg Arg Arg His Leu Ser Leu Arg Gly Leu Phe Val Cys Ala
        625                 630                 635                 640

Phe Ser Ser Ala Gly Pro Asn Ala His Gln Phe Leu Pro Lys Val Leu
                        645                 650                 655

His Lys Arg Thr Leu Gly Leu Ser Ala Met Ser Thr Thr Asp Leu Glu
                        660                 665                 670

Ala Tyr Phe Lys Asp Cys Leu Phe Lys Asp Trp Glu Glu Leu Gly Glu
                        675                 680                 685

Glu

<210> SEQ ID NO 111
<211> LENGTH: 1808
<212> TYPE: DNA
<213> ORGANISM: Artificial
<220> FEATURE:
```

<223> OTHER INFORMATION: Synthetic Construct
<220> FEATURE:
<221> NAME/KEY: CDS
<222> LOCATION: (37)..(1779)

<400> SEQUENCE: 111

```
gaattcgcca ccatggccga cgaggcacca actagt gga ggt tgg tcc tca aag       54
                                        Gly Gly Trp Ser Ser Lys
                                        1               5 cca agg aaa ggt atg ggt aca aac ttg tct gtt cct aac cca ctt gga      102
Pro Arg Lys Gly Met Gly Thr Asn Leu Ser Val Pro Asn Pro Leu Gly
        10                  15                  20 ttc ttt cca gac cat caa ctt gat cca gca ttt ggt gca aac tct aac      150
Phe Phe Pro Asp His Gln Leu Asp Pro Ala Phe Gly Ala Asn Ser Asn
            25                  30                  35 aat cca gac tgg gat ttc aat cct atc aag gat cac tgg cct gaa gca      198
Asn Pro Asp Trp Asp Phe Asn Pro Ile Lys Asp His Trp Pro Glu Ala
    40                  45                  50 aat caa gtt gga gtg ggg gca ttt ggt cca ggc ttc act cca cca cac      246
Asn Gln Val Gly Val Gly Ala Phe Gly Pro Gly Phe Thr Pro Pro His
55                  60                  65                  70 gga ggg gta ctt gga tgg agt cca cag gct caa ggt att ttg act act      294
Gly Gly Val Leu Gly Trp Ser Pro Gln Ala Gln Gly Ile Leu Thr Thr
                75                  80                  85 gtt cca gct gtc cct cct cct gcg tca acc aat aga caa tct ggt aga      342
Val Pro Ala Val Pro Pro Pro Ala Ser Thr Asn Arg Gln Ser Gly Arg
            90                  95                 100 caa cct aca cca att tca cct cca ctt aga gac tct cat cct cag gca      390
Gln Pro Thr Pro Ile Ser Pro Pro Leu Arg Asp Ser His Pro Gln Ala
        105                 110                 115 atg caa tgg aac tca act acc ttc cat caa gct ctg ttg gat cct aga      438
Met Gln Trp Asn Ser Thr Thr Phe His Gln Ala Leu Leu Asp Pro Arg
    120                 125                 130 gtt aga ggt ctg tat ttt cca gct ggc gga tca tct agt ggt acc gtg      486
Val Arg Gly Leu Tyr Phe Pro Ala Gly Gly Ser Ser Ser Gly Thr Val
135                 140                 145                 150 aat cca gta cct act aca gcc tct cca atc agt tcc atc tca agt aga      534
Asn Pro Val Pro Thr Thr Ala Ser Pro Ile Ser Ser Ile Ser Ser Arg
                155                 160                 165 act ggc gac cct gcc cca aat atg gaa aat atc aca tct gga ttt tta      582
Thr Gly Asp Pro Ala Pro Asn Met Glu Asn Ile Thr Ser Gly Phe Leu
            170                 175                 180 ggg cca ttg cta gtc cta caa gct ggg ttt ttc cta ttg act aga atc      630
Gly Pro Leu Leu Val Leu Gln Ala Gly Phe Phe Leu Leu Thr Arg Ile
        185                 190                 195 ttg acg att cca cag agt tta gac tcc tgg tgg act agc cta aac ttt      678
Leu Thr Ile Pro Gln Ser Leu Asp Ser Trp Trp Thr Ser Leu Asn Phe
    200                 205                 210 ttg ggt ggc tcc cca aca tgt cct ggc caa aac tct cag tct cca aca      726
Leu Gly Gly Ser Pro Thr Cys Pro Gly Gln Asn Ser Gln Ser Pro Thr
215                 220                 225                 230 agt aac cac tct cct act tca tgt cca cca att tgt cct ggt tac aga      774
Ser Asn His Ser Pro Thr Ser Cys Pro Pro Ile Cys Pro Gly Tyr Arg
                235                 240                 245 tgg atg tgc ctc aga agg ttt atc att ttc ctt ttc ata ttg tta ttg      822
Trp Met Cys Leu Arg Arg Phe Ile Ile Phe Leu Phe Ile Leu Leu Leu
            250                 255                 260 tgc ctc ata ttc cta ttg gta tta ttg gat tac caa ggg atg ctt cct      870
Cys Leu Ile Phe Leu Leu Val Leu Leu Asp Tyr Gln Gly Met Leu Pro
        265                 270                 275
```

```
gtc tgt cca ttg ctc cct ggt acg agt aca aca tct act ggc cca tgc        918
Val Cys Pro Leu Leu Pro Gly Thr Ser Thr Thr Ser Thr Gly Pro Cys
280             285                 290 aaa aca tgc acc ata cca gcg caa ggt aca agc atg ttt cca tcc tgt        966
Lys Thr Cys Thr Ile Pro Ala Gln Gly Thr Ser Met Phe Pro Ser Cys
295             300                 305                 310 tgt tgc aca aaa cca tcc gat ggc aat tgc aca tgc att cca ata cca       1014
Cys Cys Thr Lys Pro Ser Asp Gly Asn Cys Thr Cys Ile Pro Ile Pro
                315                 320                 325 tct tca tgg gcc ttc gct cgt ttc cta tgg gaa tgg gcc tca gtt aga       1062
Ser Ser Trp Ala Phe Ala Arg Phe Leu Trp Glu Trp Ala Ser Val Arg
        330                 335                 340 ttt tcc tgg tta tca ttg ttg gtc cca ttt gtg caa tgg ttt gta ggt       1110
Phe Ser Trp Leu Ser Leu Leu Val Pro Phe Val Gln Trp Phe Val Gly
        345                 350                 355 tta tcc cca acc gtc tgg tta tct gta ata tgg atg atg tgg tat tgg       1158
Leu Ser Pro Thr Val Trp Leu Ser Val Ile Trp Met Met Trp Tyr Trp
360             365                 370 ggt cca agt tta tac tca atc gtt tca cct ttt atc cct ttg ctg cca       1206
Gly Pro Ser Leu Tyr Ser Ile Val Ser Pro Phe Ile Pro Leu Leu Pro
375             380                 385                 390 atc ttt ttc tgt ttg tgg gtt tac att gat att gat cct tac aag gag       1254
Ile Phe Phe Cys Leu Trp Val Tyr Ile Asp Ile Asp Pro Tyr Lys Glu
                395                 400                 405 ttt ggt gct act gtt gag tta cta tcc ttt tta cct tct gac ttt ttc       1302
Phe Gly Ala Thr Val Glu Leu Leu Ser Phe Leu Pro Ser Asp Phe Phe
                    410                 415                 420 cct tct gtc aga gat ctt ttg gat act gct tct gct tta tac aga gaa       1350
Pro Ser Val Arg Asp Leu Leu Asp Thr Ala Ser Ala Leu Tyr Arg Glu
            425                 430                 435 gct ttg gaa tca cca gaa cat tgt tca cct cat cat acc gcc tta aga       1398
Ala Leu Glu Ser Pro Glu His Cys Ser Pro His His Thr Ala Leu Arg
        440                 445                 450 caa gca att ctg tgt tgg ggc gaa tta atg aac cta gca aca tgg gtg       1446
Gln Ala Ile Leu Cys Trp Gly Glu Leu Met Asn Leu Ala Thr Trp Val
455                 460                 465                 470 ggt tcc aat ttg gaa gat cca gca tcc aga gag tta gtg gtt agc tac       1494
Gly Ser Asn Leu Glu Asp Pro Ala Ser Arg Glu Leu Val Val Ser Tyr
                475                 480                 485 gtg aat gtc aac atg ggc ttg aaa atc aga cag tta ctt tgg ttc cat       1542
Val Asn Val Asn Met Gly Leu Lys Ile Arg Gln Leu Leu Trp Phe His
                490                 495                 500 atc tct tgt ctg aca ttt ggt aga gaa aca gtt ctg gaa tat ctc gtt       1590
Ile Ser Cys Leu Thr Phe Gly Arg Glu Thr Val Leu Glu Tyr Leu Val
            505                 510                 515 agc ttt gga gta tgg att aga act cca cca gcc tac aga cca cct aat       1638
Ser Phe Gly Val Trp Ile Arg Thr Pro Pro Ala Tyr Arg Pro Pro Asn
520                 525                 530 gca cca ata ttg tca acc ctc cca gag aca aca gtt gtg agg aga aga       1686
Ala Pro Ile Leu Ser Thr Leu Pro Glu Thr Thr Val Val Arg Arg Arg
535             540                 545                 550 gga aga tct cct cgt cgt aga act cca tct cca aga cga agg aga tca       1734
Gly Arg Ser Pro Arg Arg Arg Thr Pro Ser Pro Arg Arg Arg Arg Ser
                555                 560                 565 caa agt cct aga cga cgt aga tct caa tct aga gag tct caa tgt            1779
Gln Ser Pro Arg Arg Arg Arg Ser Gln Ser Arg Glu Ser Gln Cys
            570                 575                 580 caccaccatc accatcatta agcggccgc                                       1808
```

```
<210> SEQ ID NO 112
<211> LENGTH: 581
<212> TYPE: PRT
<213> ORGANISM: Artificial
<220> FEATURE:
<223> OTHER INFORMATION: Synthetic Construct

<400> SEQUENCE: 112

Gly Gly Trp Ser Ser Lys Pro Arg Lys Gly Met Gly Thr Asn Leu Ser
1               5                   10                  15

Val Pro Asn Pro Leu Gly Phe Phe Pro Asp His Gln Leu Asp Pro Ala
            20                  25                  30

Phe Gly Ala Asn Ser Asn Asn Pro Asp Trp Asp Phe Asn Pro Ile Lys
        35                  40                  45

Asp His Trp Pro Glu Ala Asn Gln Val Gly Val Gly Ala Phe Gly Pro
    50                  55                  60

Gly Phe Thr Pro Pro His Gly Gly Val Leu Gly Trp Ser Pro Gln Ala
65                  70                  75                  80

Gln Gly Ile Leu Thr Thr Val Pro Ala Val Pro Pro Pro Ala Ser Thr
                85                  90                  95

Asn Arg Gln Ser Gly Arg Gln Pro Thr Pro Ile Ser Pro Pro Leu Arg
            100                 105                 110

Asp Ser His Pro Gln Ala Met Gln Trp Asn Ser Thr Thr Phe His Gln
        115                 120                 125

Ala Leu Leu Asp Pro Arg Val Arg Gly Leu Tyr Phe Pro Ala Gly Gly
    130                 135                 140

Ser Ser Ser Gly Thr Val Asn Pro Val Pro Thr Thr Ala Ser Pro Ile
145                 150                 155                 160

Ser Ser Ile Ser Ser Arg Thr Gly Asp Pro Ala Pro Asn Met Glu Asn
                165                 170                 175

Ile Thr Ser Gly Phe Leu Gly Pro Leu Leu Val Leu Gln Ala Gly Phe
            180                 185                 190

Phe Leu Leu Thr Arg Ile Leu Thr Ile Pro Gln Ser Leu Asp Ser Trp
        195                 200                 205

Trp Thr Ser Leu Asn Phe Leu Gly Gly Ser Pro Thr Cys Pro Gly Gln
    210                 215                 220

Asn Ser Gln Ser Pro Thr Ser Asn His Ser Pro Thr Ser Cys Pro Pro
225                 230                 235                 240

Ile Cys Pro Gly Tyr Arg Trp Met Cys Leu Arg Arg Phe Ile Ile Phe
                245                 250                 255

Leu Phe Ile Leu Leu Leu Cys Leu Ile Phe Leu Leu Val Leu Leu Asp
            260                 265                 270

Tyr Gln Gly Met Leu Pro Val Cys Pro Leu Leu Pro Gly Thr Ser Thr
        275                 280                 285

Thr Ser Thr Gly Pro Cys Lys Thr Cys Thr Ile Pro Ala Gln Gly Thr
    290                 295                 300

Ser Met Phe Pro Ser Cys Cys Cys Thr Lys Pro Ser Asp Gly Asn Cys
305                 310                 315                 320

Thr Cys Ile Pro Ile Pro Ser Ser Trp Ala Phe Ala Arg Phe Leu Trp
                325                 330                 335

Glu Trp Ala Ser Val Arg Phe Ser Trp Leu Ser Leu Leu Val Pro Phe
            340                 345                 350

Val Gln Trp Phe Val Gly Leu Ser Pro Thr Val Trp Leu Ser Val Ile
        355                 360                 365

Trp Met Met Trp Tyr Trp Gly Pro Ser Leu Tyr Ser Ile Val Ser Pro
```

```
                    370                 375                 380
Phe Ile Pro Leu Leu Pro Ile Phe Phe Cys Leu Trp Val Tyr Ile Asp
385                 390                 395                 400

Ile Asp Pro Tyr Lys Glu Phe Gly Ala Thr Val Glu Leu Leu Ser Phe
                405                 410                 415

Leu Pro Ser Asp Phe Phe Pro Ser Val Arg Asp Leu Leu Asp Thr Ala
            420                 425                 430

Ser Ala Leu Tyr Arg Glu Ala Leu Glu Ser Pro Glu His Cys Ser Pro
        435                 440                 445

His His Thr Ala Leu Arg Gln Ala Ile Leu Cys Trp Gly Glu Leu Met
    450                 455                 460

Asn Leu Ala Thr Trp Val Gly Ser Asn Leu Glu Asp Pro Ala Ser Arg
465                 470                 475                 480

Glu Leu Val Val Ser Tyr Val Asn Val Asn Met Gly Leu Lys Ile Arg
                485                 490                 495

Gln Leu Leu Trp Phe His Ile Ser Cys Leu Thr Phe Gly Arg Glu Thr
            500                 505                 510

Val Leu Glu Tyr Leu Val Ser Phe Gly Val Trp Ile Arg Thr Pro Pro
        515                 520                 525

Ala Tyr Arg Pro Pro Asn Ala Pro Ile Leu Ser Thr Leu Pro Glu Thr
    530                 535                 540

Thr Val Val Arg Arg Gly Arg Ser Pro Arg Arg Arg Thr Pro Ser
545                 550                 555                 560

Pro Arg Arg Arg Ser Gln Ser Pro Arg Arg Arg Ser Gln Ser
                565                 570                 575

Arg Glu Ser Gln Cys
            580

<210> SEQ ID NO 113
<211> LENGTH: 1808
<212> TYPE: DNA
<213> ORGANISM: Artificial
<220> FEATURE:
<223> OTHER INFORMATION: Synthetic Construct
<220> FEATURE:
<221> NAME/KEY: CDS
<222> LOCATION: (37)..(1779)

<400> SEQUENCE: 113
gaattcgcca ccatggccga cgaggcacca actagt gga ggt tgg tca agt aaa        54
                                  Gly Gly Trp Ser Ser Lys
                                   1               5 cct agg aaa ggt atg gga act aac cta tcc gtc cct aac cct ctt ggg       102
Pro Arg Lys Gly Met Gly Thr Asn Leu Ser Val Pro Asn Pro Leu Gly
            10                  15                  20 ttt ttc cct gat cac caa cta gat cca gct ttt aag gcc aat agt gaa       150
Phe Phe Pro Asp His Gln Leu Asp Pro Ala Phe Lys Ala Asn Ser Glu
        25                  30                  35 aat cct gat tgg gac ttg aac cca cac aag gat aat tgg cca gag gcg       198
Asn Pro Asp Trp Asp Leu Asn Pro His Lys Asp Asn Trp Pro Glu Ala
    40                  45                  50 aat cag gta ggc gtt ggg gcc ttt ggc cca ggc ttc acc cca cca cat       246
Asn Gln Val Gly Val Gly Ala Phe Gly Pro Gly Phe Thr Pro Pro His
55                  60                  65                  70 ggc ggc tta ctc ggt tgg tca cca caa gcc caa gga ata ttg acg act       294
Gly Gly Leu Leu Gly Trp Ser Pro Gln Ala Gln Gly Ile Leu Thr Thr
                75                  80                  85 gtg cca gct gct cct cca cca gct agt aca aat aga caa tct ggt aga       342
```

-continued

```
                Val Pro Ala Ala Pro Pro Ala Ser Thr Asn Arg Gln Ser Gly Arg
                             90                  95                 100 caa cct aca cca att tct cca cca ctt aga gat tct cat cct caa gca        390
Gln Pro Thr Pro Ile Ser Pro Pro Leu Arg Asp Ser His Pro Gln Ala
            105                 110                 115 atg cag tgg aac agc act aca ttc cat caa gcc ctg tta gac cca aga        438
Met Gln Trp Asn Ser Thr Thr Phe His Gln Ala Leu Leu Asp Pro Arg
    120                 125                 130 gtt aga ggt ttg tac ttt cct gca ggt ggt tca tct tct gga act gtc        486
Val Arg Gly Leu Tyr Phe Pro Ala Gly Gly Ser Ser Ser Gly Thr Val
135                 140                 145                 150 aat cct gtt cag aca aca gct tca cca atc tct tcc att tta tcc aga        534
Asn Pro Val Gln Thr Thr Ala Ser Pro Ile Ser Ser Ile Leu Ser Arg
                155                 160                 165 act ggt gac cca gca cca aac atg gaa aac atc gca tca ggt ttt cta        582
Thr Gly Asp Pro Ala Pro Asn Met Glu Asn Ile Ala Ser Gly Phe Leu
            170                 175                 180 gga cca tta ttg gta ctt caa gct ggt ttc ttt ttg tta aca cgt atc        630
Gly Pro Leu Leu Val Leu Gln Ala Gly Phe Phe Leu Leu Thr Arg Ile
        185                 190                 195 ttg acc att cca caa agc ttg gat tca tgg tgg act tct ctg aat ttc        678
Leu Thr Ile Pro Gln Ser Leu Asp Ser Trp Trp Thr Ser Leu Asn Phe
    200                 205                 210 ctc ggg gga acc cct aca tgt cct ggt caa aat tct caa tcc cca aca        726
Leu Gly Gly Thr Pro Thr Cys Pro Gly Gln Asn Ser Gln Ser Pro Thr
215                 220                 225                 230 agt tca cat tct cct acg tgc tgt cca cca att tgt cct ggt tac aga        774
Ser Ser His Ser Pro Thr Cys Cys Pro Pro Ile Cys Pro Gly Tyr Arg
                235                 240                 245 tgg atg tgc ctc aga agg ttt atc att ttc ctt ttc ata ttg tta ttg        822
Trp Met Cys Leu Arg Arg Phe Ile Ile Phe Leu Phe Ile Leu Leu Leu
            250                 255                 260 tgc ctc ata ttc cta ttg gta tta ttg gat tac caa ggg atg ctt cct        870
Cys Leu Ile Phe Leu Leu Val Leu Leu Asp Tyr Gln Gly Met Leu Pro
        265                 270                 275 gtc tgt cca ttg ctc cct ggt acg agt aca aca tct act ggc cca tgc        918
Val Cys Pro Leu Leu Pro Gly Thr Ser Thr Thr Ser Thr Gly Pro Cys
    280                 285                 290 aaa aca tgc acc ata cca gcg caa ggt aca agc atg ttt cca tcc tgt        966
Lys Thr Cys Thr Ile Pro Ala Gln Gly Thr Ser Met Phe Pro Ser Cys
295                 300                 305                 310 tgt tgc aca aaa cca tcc gat ggc aat tgc aca tgc att cca ata cca       1014
Cys Cys Thr Lys Pro Ser Asp Gly Asn Cys Thr Cys Ile Pro Ile Pro
                315                 320                 325 tct tca tgg gcc ttc gct cgt ttc cta tgg gaa tgg gcc tca gtt aga       1062
Ser Ser Trp Ala Phe Ala Arg Phe Leu Trp Glu Trp Ala Ser Val Arg
            330                 335                 340 ttt tcc tgg tta tca ttg ttg gtc cca ttt gtg caa tgg ttt gta ggt       1110
Phe Ser Trp Leu Ser Leu Leu Val Pro Phe Val Gln Trp Phe Val Gly
        345                 350                 355 tta tcc cca acc gtc tgg tta tct gta ata tgg atg atg tgg tat tgg       1158
Leu Ser Pro Thr Val Trp Leu Ser Val Ile Trp Met Met Trp Tyr Trp
    360                 365                 370 ggt cca agt tta tac tca atc gtt tca cct ttt atc cct ttg ctg cca       1206
Gly Pro Ser Leu Tyr Ser Ile Val Ser Pro Phe Ile Pro Leu Leu Pro
375                 380                 385                 390 atc ttt ttc tgt ttg tgg gtt tac att gat att gat cct tac aag gag       1254
Ile Phe Phe Cys Leu Trp Val Tyr Ile Asp Ile Asp Pro Tyr Lys Glu
                395                 400                 405
```

```
ttt ggt gct act gtt gag tta cta tcc ttt tta cct tct gac ttt ttc     1302
Phe Gly Ala Thr Val Glu Leu Leu Ser Phe Leu Pro Ser Asp Phe Phe
            410                 415                 420 cct tct gtc aga gat ctt ttg gat act gct tct gct tta tac aga gaa     1350
Pro Ser Val Arg Asp Leu Leu Asp Thr Ala Ser Ala Leu Tyr Arg Glu
        425                 430                 435 gct ttg gaa tca cca gaa cat tgt tca cct cat cat acc gcc tta aga     1398
Ala Leu Glu Ser Pro Glu His Cys Ser Pro His His Thr Ala Leu Arg
440                 445                 450 caa gca att ctg tgt tgg ggc gaa tta atg aac cta gca aca tgg gtg     1446
Gln Ala Ile Leu Cys Trp Gly Glu Leu Met Asn Leu Ala Thr Trp Val
455                 460                 465                 470 ggt tcc aat ttg gaa gat cca gca tcc aga gag tta gtg gtt agc tac     1494
Gly Ser Asn Leu Glu Asp Pro Ala Ser Arg Glu Leu Val Val Ser Tyr
                475                 480                 485 gtg aat gtc aac atg ggc ttg aaa atc aga cag tta ctt tgg ttc cat     1542
Val Asn Val Asn Met Gly Leu Lys Ile Arg Gln Leu Leu Trp Phe His
            490                 495                 500 atc tct tgt ctg aca ttt ggt aga gaa aca gtt ctg gaa tat ctc gtt     1590
Ile Ser Cys Leu Thr Phe Gly Arg Glu Thr Val Leu Glu Tyr Leu Val
        505                 510                 515 agc ttt gga gta tgg att aga act cca cca gcc tac aga cca cct aat     1638
Ser Phe Gly Val Trp Ile Arg Thr Pro Pro Ala Tyr Arg Pro Pro Asn
520                 525                 530 gca cca ata ttg tca acc ctc cca gag aca aca gtt gtg agg aga aga     1686
Ala Pro Ile Leu Ser Thr Leu Pro Glu Thr Thr Val Val Arg Arg Arg
535                 540                 545                 550 gga aga tct cct cgt cgt aga act cca tct cca aga cga agg aga tca     1734
Gly Arg Ser Pro Arg Arg Arg Thr Pro Ser Pro Arg Arg Arg Arg Ser
                555                 560                 565 caa agt cct aga cga cgt aga tct caa tct aga gag tct caa tgt         1779
Gln Ser Pro Arg Arg Arg Arg Ser Gln Ser Arg Glu Ser Gln Cys
                570                 575                 580 caccaccatc accatcatta agcggccgc                                     1808
```

<210> SEQ ID NO 114
<211> LENGTH: 581
<212> TYPE: PRT
<213> ORGANISM: Artificial
<220> FEATURE:
<223> OTHER INFORMATION: Synthetic Construct

<400> SEQUENCE: 114

```
Gly Gly Trp Ser Ser Lys Pro Arg Lys Gly Met Gly Thr Asn Leu Ser
1               5                   10                  15

Val Pro Asn Pro Leu Gly Phe Phe Pro Asp His Gln Leu Asp Pro Ala
            20                  25                  30

Phe Lys Ala Asn Ser Glu Asn Pro Asp Trp Asp Leu Asn Pro His Lys
        35                  40                  45

Asp Asn Trp Pro Glu Ala Asn Gln Val Gly Val Gly Ala Phe Gly Pro
    50                  55                  60

Gly Phe Thr Pro Pro His Gly Gly Leu Leu Gly Trp Ser Pro Gln Ala
65                  70                  75                  80

Gln Gly Ile Leu Thr Thr Val Pro Ala Ala Pro Pro Pro Ala Ser Thr
                85                  90                  95

Asn Arg Gln Ser Gly Arg Gln Pro Thr Pro Ile Ser Pro Pro Leu Arg
            100                 105                 110

Asp Ser His Pro Gln Ala Met Gln Trp Asn Ser Thr Thr Phe His Gln
        115                 120                 125
```

```
Ala Leu Leu Asp Pro Arg Val Arg Gly Leu Tyr Phe Pro Ala Gly Gly
    130                 135                 140

Ser Ser Ser Gly Thr Val Asn Pro Val Gln Thr Thr Ala Ser Pro Ile
145                 150                 155                 160

Ser Ser Ile Leu Ser Arg Thr Gly Asp Pro Ala Pro Asn Met Glu Asn
            165                 170                 175

Ile Ala Ser Gly Phe Leu Gly Pro Leu Leu Val Leu Gln Ala Gly Phe
        180                 185                 190

Phe Leu Leu Thr Arg Ile Leu Thr Ile Pro Gln Ser Leu Asp Ser Trp
    195                 200                 205

Trp Thr Ser Leu Asn Phe Leu Gly Gly Thr Pro Thr Cys Pro Gly Gln
    210                 215                 220

Asn Ser Gln Ser Pro Thr Ser Ser His Ser Pro Thr Cys Cys Pro Pro
225                 230                 235                 240

Ile Cys Pro Gly Tyr Arg Trp Met Cys Leu Arg Arg Phe Ile Ile Phe
            245                 250                 255

Leu Phe Ile Leu Leu Leu Cys Leu Ile Phe Leu Leu Val Leu Leu Asp
        260                 265                 270

Tyr Gln Gly Met Leu Pro Val Cys Pro Leu Leu Pro Gly Thr Ser Thr
    275                 280                 285

Thr Ser Thr Gly Pro Cys Lys Thr Cys Thr Ile Pro Ala Gln Gly Thr
290                 295                 300

Ser Met Phe Pro Ser Cys Cys Cys Thr Lys Pro Ser Asp Gly Asn Cys
305                 310                 315                 320

Thr Cys Ile Pro Ile Pro Ser Ser Trp Ala Phe Ala Arg Phe Leu Trp
            325                 330                 335

Glu Trp Ala Ser Val Arg Phe Ser Trp Leu Ser Leu Leu Val Pro Phe
        340                 345                 350

Val Gln Trp Phe Val Gly Leu Ser Pro Thr Val Trp Leu Ser Val Ile
    355                 360                 365

Trp Met Met Trp Tyr Trp Gly Pro Ser Leu Tyr Ser Ile Val Ser Pro
    370                 375                 380

Phe Ile Pro Leu Leu Pro Ile Phe Phe Cys Leu Trp Val Tyr Ile Asp
385                 390                 395                 400

Ile Asp Pro Tyr Lys Glu Phe Gly Ala Thr Val Glu Leu Leu Ser Phe
            405                 410                 415

Leu Pro Ser Asp Phe Phe Pro Ser Val Arg Asp Leu Leu Asp Thr Ala
        420                 425                 430

Ser Ala Leu Tyr Arg Glu Ala Leu Glu Ser Pro Glu His Cys Ser Pro
    435                 440                 445

His His Thr Ala Leu Arg Gln Ala Ile Leu Cys Trp Gly Glu Leu Met
    450                 455                 460

Asn Leu Ala Thr Trp Val Gly Ser Asn Leu Glu Asp Pro Ala Ser Arg
465                 470                 475                 480

Glu Leu Val Val Ser Tyr Val Asn Val Asn Met Gly Leu Lys Ile Arg
            485                 490                 495

Gln Leu Leu Trp Phe His Ile Ser Cys Leu Thr Phe Gly Arg Glu Thr
        500                 505                 510

Val Leu Glu Tyr Leu Val Ser Phe Gly Val Trp Ile Arg Thr Pro Pro
    515                 520                 525

Ala Tyr Arg Pro Pro Asn Ala Pro Ile Leu Ser Thr Leu Pro Glu Thr
    530                 535                 540
```

```
Thr Val Val Arg Arg Arg Gly Arg Ser Pro Arg Arg Thr Pro Ser
545                 550                 555                 560

Pro Arg Arg Arg Ser Gln Ser Pro Arg Arg Arg Ser Gln Ser
            565                 570                 575

Arg Glu Ser Gln Cys
            580

<210> SEQ ID NO 115
<211> LENGTH: 1808
<212> TYPE: DNA
<213> ORGANISM: Artificial
<220> FEATURE:
<223> OTHER INFORMATION: Synthetic Construct
<220> FEATURE:
<221> NAME/KEY: CDS
<222> LOCATION: (37)..(1779)

<400> SEQUENCE: 115
gaattcgcca ccatggccga cgaggcacca actagt ggt ggc tgg tct agt aaa     54
                                        Gly Gly Trp Ser Ser Lys
                                        1               5 cct aga aag ggt atg gga aca aac tta tca gtt cct aac cca ctg gga   102
Pro Arg Lys Gly Met Gly Thr Asn Leu Ser Val Pro Asn Pro Leu Gly
            10                  15                  20 ttt ttc cca gat cac caa ttg gat cca gct ttt ggt gca aat agt aac   150
Phe Phe Pro Asp His Gln Leu Asp Pro Ala Phe Gly Ala Asn Ser Asn
        25                  30                  35 aat cca gat tgg gac ttt aat cct aac aaa gat cat tgg cca gaa gca   198
Asn Pro Asp Trp Asp Phe Asn Pro Asn Lys Asp His Trp Pro Glu Ala
    40                  45                  50 aat cag gtg gga gtc gga gct ttc ggt cca ggc ttt acc cct cca cat   246
Asn Gln Val Gly Val Gly Ala Phe Gly Pro Gly Phe Thr Pro Pro His
55                  60                  65                  70 ggt ggg ttg tta ggc tgg tcc cca caa gca cag ggg att ttg act act   294
Gly Gly Leu Leu Gly Trp Ser Pro Gln Ala Gln Gly Ile Leu Thr Thr
                75                  80                  85 gtt cct gcc gct cct cct cct gcc tcc aca aat aga caa agt ggt agg   342
Val Pro Ala Ala Pro Pro Pro Ala Ser Thr Asn Arg Gln Ser Gly Arg
            90                  95                  100 caa cca acc cca att tca cct cca ctt aga gat tct cat cca cag gca   390
Gln Pro Thr Pro Ile Ser Pro Pro Leu Arg Asp Ser His Pro Gln Ala
        105                 110                 115 atg caa tgg aac tcc act act ttt cac caa gca tta ctt gat cca aga   438
Met Gln Trp Asn Ser Thr Thr Phe His Gln Ala Leu Leu Asp Pro Arg
    120                 125                 130 gta cgt ggt cta tac ttc cca gct ggg ggt tcc tct tca ggt aca gtt   486
Val Arg Gly Leu Tyr Phe Pro Ala Gly Gly Ser Ser Ser Gly Thr Val
135                 140                 145                 150 aac cca gta cct aca aca gcc tct cca atc tca agc atc ttt tct aga   534
Asn Pro Val Pro Thr Thr Ala Ser Pro Ile Ser Ser Ile Phe Ser Arg
                155                 160                 165 aca ggt gat cca gct cct aat atg gag aat acg act tct ggt ttc ctc   582
Thr Gly Asp Pro Ala Pro Asn Met Glu Asn Thr Thr Ser Gly Phe Leu
            170                 175                 180 ggc cca ctg tta gtc ttg caa gct ggc ttt ttc cta ttg acc aga ata   630
Gly Pro Leu Leu Val Leu Gln Ala Gly Phe Phe Leu Leu Thr Arg Ile
        185                 190                 195 ctt act atc cca caa tca cta gac agc tgg tgg aca tct ctc aac ttt   678
Leu Thr Ile Pro Gln Ser Leu Asp Ser Trp Trp Thr Ser Leu Asn Phe
    200                 205                 210 ttg gga gga gcg cca aca tgt cca ggc caa aat tca caa tct cct aca   726
```

-continued

| | | |
|---|---|---|
| Leu Gly Gly Ala Pro Thr Cys Pro Gly Gln Asn Ser Gln Ser Pro Thr<br>215                    220                    225                    230 | | |
| tca aat cat tct cct aca agt tgt cca cca att tgt cct ggt tac aga<br>Ser Asn His Ser Pro Thr Ser Cys Pro Pro Ile Cys Pro Gly Tyr Arg<br>                    235                    240                    245 | 774 |
| tgg atg tgc ctc aga agg ttt atc att ttc ctt ttc ata ttg tta ttg<br>Trp Met Cys Leu Arg Arg Phe Ile Ile Phe Leu Phe Ile Leu Leu Leu<br>          250                    255                    260 | 822 |
| tgc ctc ata ttc cta ttg gta tta ttg gat tac caa ggg atg ctt cct<br>Cys Leu Ile Phe Leu Leu Val Leu Leu Asp Tyr Gln Gly Met Leu Pro<br>              265                    270                    275 | 870 |
| gtc tgt cca ttg ctc cct ggt acg agt aca aca tct act ggc cca tgc<br>Val Cys Pro Leu Leu Pro Gly Thr Ser Thr Thr Ser Thr Gly Pro Cys<br>280                    285                    290 | 918 |
| aaa aca tgc acc ata cca gcg caa ggt aca agc atg ttt cca tcc tgt<br>Lys Thr Cys Thr Ile Pro Ala Gln Gly Thr Ser Met Phe Pro Ser Cys<br>295                    300                    305                    310 | 966 |
| tgt tgc aca aaa cca tcc gat ggc aat tgc aca tgc att cca ata cca<br>Cys Cys Thr Lys Pro Ser Asp Gly Asn Cys Thr Cys Ile Pro Ile Pro<br>              315                    320                    325 | 1014 |
| tct tca tgg gcc ttc gct cgt ttc cta tgg gaa tgg gcc tca gtt aga<br>Ser Ser Trp Ala Phe Ala Arg Phe Leu Trp Glu Trp Ala Ser Val Arg<br>          330                    335                    340 | 1062 |
| ttt tcc tgg tta tca ttg ttg gtc cca ttt gtg caa tgg ttt gta ggt<br>Phe Ser Trp Leu Ser Leu Leu Val Pro Phe Val Gln Trp Phe Val Gly<br>              345                    350                    355 | 1110 |
| tta tcc cca acc gtc tgg tta tct gta ata tgg atg atg tgg tat tgg<br>Leu Ser Pro Thr Val Trp Leu Ser Val Ile Trp Met Met Trp Tyr Trp<br>360                    365                    370 | 1158 |
| ggt cca agt tta tac tca atc gtt tca cct ttt atc cct ttg ctg cca<br>Gly Pro Ser Leu Tyr Ser Ile Val Ser Pro Phe Ile Pro Leu Leu Pro<br>375                    380                    385                    390 | 1206 |
| atc ttt ttc tgt ttg tgg gtt tac att gat att gat cct tac aag gag<br>Ile Phe Phe Cys Leu Trp Val Tyr Ile Asp Ile Asp Pro Tyr Lys Glu<br>              395                    400                    405 | 1254 |
| ttt ggt gct act gtt gag tta cta tcc ttt tta cct tct gac ttt ttc<br>Phe Gly Ala Thr Val Glu Leu Leu Ser Phe Leu Pro Ser Asp Phe Phe<br>          410                    415                    420 | 1302 |
| cct tct gtc aga gat ctt ttg gat act gct tct gct tta tac aga gaa<br>Pro Ser Val Arg Asp Leu Leu Asp Thr Ala Ser Ala Leu Tyr Arg Glu<br>              425                    430                    435 | 1350 |
| gct ttg gaa tca cca gaa cat tgt tca cct cat cat acc gcc tta aga<br>Ala Leu Glu Ser Pro Glu His Cys Ser Pro His His Thr Ala Leu Arg<br>440                    445                    450 | 1398 |
| caa gca att ctg tgt tgg ggc gaa tta atg aac cta gca aca tgg gtg<br>Gln Ala Ile Leu Cys Trp Gly Glu Leu Met Asn Leu Ala Thr Trp Val<br>455                    460                    465                    470 | 1446 |
| ggt tcc aat ttg gaa gat cca gca tcc aga gag tta gtg gtt agc tac<br>Gly Ser Asn Leu Glu Asp Pro Ala Ser Arg Glu Leu Val Val Ser Tyr<br>              475                    480                    485 | 1494 |
| gtg aat gtc aac atg ggc ttg aaa atc aga cag tta ctt tgg ttc cat<br>Val Asn Val Asn Met Gly Leu Lys Ile Arg Gln Leu Leu Trp Phe His<br>          490                    495                    500 | 1542 |
| atc tct tgt ctg aca ttt ggt aga gaa aca gtt ctg gaa tat ctc gtt<br>Ile Ser Cys Leu Thr Phe Gly Arg Glu Thr Val Leu Glu Tyr Leu Val<br>              505                    510                    515 | 1590 |
| agc ttt gga gta tgg att aga act cca cca gcc tac aga cca cct aat<br>Ser Phe Gly Val Trp Ile Arg Thr Pro Pro Ala Tyr Arg Pro Pro Asn<br>520                    525                    530 | 1638 |

-continued

```
gca cca ata ttg tca acc ctc cca gag aca aca gtt gtg agg aga aga    1686
Ala Pro Ile Leu Ser Thr Leu Pro Glu Thr Thr Val Val Arg Arg Arg
535                 540                 545                 550 gga aga tct cct cgt cgt aga act cca tct cca aga cga agg aga tca    1734
Gly Arg Ser Pro Arg Arg Arg Thr Pro Ser Pro Arg Arg Arg Ser
                555                 560                 565 caa agt cct aga cga cgt aga tct caa tct aga gag tct caa tgt        1779
Gln Ser Pro Arg Arg Arg Arg Ser Gln Ser Arg Glu Ser Gln Cys
                570                 575                 580 caccaccatc accatcatta agcggccgc                                    1808
```

<210> SEQ ID NO 116
<211> LENGTH: 581
<212> TYPE: PRT
<213> ORGANISM: Artificial
<220> FEATURE:
<223> OTHER INFORMATION: Synthetic Construct

<400> SEQUENCE: 116

```
Gly Gly Trp Ser Ser Lys Pro Arg Lys Gly Met Gly Thr Asn Leu Ser
1               5                   10                  15

Val Pro Asn Pro Leu Gly Phe Phe Pro Asp His Gln Leu Asp Pro Ala
                20                  25                  30

Phe Gly Ala Asn Ser Asn Asn Pro Asp Trp Asp Phe Asn Pro Asn Lys
            35                  40                  45

Asp His Trp Pro Glu Ala Asn Gln Val Gly Val Gly Ala Phe Gly Pro
        50                  55                  60

Gly Phe Thr Pro Pro His Gly Gly Leu Leu Gly Trp Ser Pro Gln Ala
65                  70                  75                  80

Gln Gly Ile Leu Thr Thr Val Pro Ala Ala Pro Pro Pro Ala Ser Thr
                85                  90                  95

Asn Arg Gln Ser Gly Arg Gln Pro Thr Pro Ile Ser Pro Pro Leu Arg
                100                 105                 110

Asp Ser His Pro Gln Ala Met Gln Trp Asn Ser Thr Thr Phe His Gln
            115                 120                 125

Ala Leu Leu Asp Pro Arg Val Arg Gly Leu Tyr Phe Pro Ala Gly Gly
        130                 135                 140

Ser Ser Ser Gly Thr Val Asn Pro Val Pro Thr Thr Ala Ser Pro Ile
145                 150                 155                 160

Ser Ser Ile Phe Ser Arg Thr Gly Asp Pro Ala Pro Asn Met Glu Asn
                165                 170                 175

Thr Thr Ser Gly Phe Leu Gly Pro Leu Leu Val Leu Gln Ala Gly Phe
            180                 185                 190

Phe Leu Leu Thr Arg Ile Leu Thr Ile Pro Gln Ser Leu Asp Ser Trp
        195                 200                 205

Trp Thr Ser Leu Asn Phe Leu Gly Gly Ala Pro Thr Cys Pro Gly Gln
    210                 215                 220

Asn Ser Gln Ser Pro Thr Ser Asn His Ser Pro Thr Ser Cys Pro Pro
225                 230                 235                 240

Ile Cys Pro Gly Tyr Arg Trp Met Cys Leu Arg Arg Phe Ile Ile Phe
                245                 250                 255

Leu Phe Ile Leu Leu Leu Cys Leu Ile Phe Leu Leu Val Leu Leu Asp
            260                 265                 270

Tyr Gln Gly Met Leu Pro Val Cys Pro Leu Leu Pro Gly Thr Ser Thr
        275                 280                 285

Thr Ser Thr Gly Pro Cys Lys Thr Cys Thr Ile Pro Ala Gln Gly Thr
```

```
                    290                 295                 300
Ser Met Phe Pro Ser Cys Cys Thr Lys Pro Ser Asp Gly Asn Cys
305                 310                 315                 320

Thr Cys Ile Pro Ile Pro Ser Ser Trp Ala Phe Ala Arg Phe Leu Trp
                325                 330                 335

Glu Trp Ala Ser Val Arg Phe Ser Trp Leu Ser Leu Leu Val Pro Phe
            340                 345                 350

Val Gln Trp Phe Val Gly Leu Ser Pro Thr Val Trp Leu Ser Val Ile
        355                 360                 365

Trp Met Met Trp Tyr Trp Gly Pro Ser Leu Tyr Ser Ile Val Ser Pro
370                 375                 380

Phe Ile Pro Leu Leu Pro Ile Phe Phe Cys Leu Trp Val Tyr Ile Asp
385                 390                 395                 400

Ile Asp Pro Tyr Lys Glu Phe Gly Ala Thr Val Glu Leu Leu Ser Phe
                405                 410                 415

Leu Pro Ser Asp Phe Phe Pro Ser Val Arg Asp Leu Leu Asp Thr Ala
            420                 425                 430

Ser Ala Leu Tyr Arg Glu Ala Leu Glu Ser Pro Glu His Cys Ser Pro
        435                 440                 445

His His Thr Ala Leu Arg Gln Ala Ile Leu Cys Trp Gly Glu Leu Met
450                 455                 460

Asn Leu Ala Thr Trp Val Gly Ser Asn Leu Glu Asp Pro Ala Ser Arg
465                 470                 475                 480

Glu Leu Val Val Ser Tyr Val Asn Val Asn Met Gly Leu Lys Ile Arg
                485                 490                 495

Gln Leu Leu Trp Phe His Ile Ser Cys Leu Thr Phe Gly Arg Glu Thr
            500                 505                 510

Val Leu Glu Tyr Leu Val Ser Phe Gly Val Trp Ile Arg Thr Pro Pro
        515                 520                 525

Ala Tyr Arg Pro Pro Asn Ala Pro Ile Leu Ser Thr Leu Pro Glu Thr
530                 535                 540

Thr Val Val Arg Arg Arg Gly Arg Ser Pro Arg Arg Arg Thr Pro Ser
545                 550                 555                 560

Pro Arg Arg Arg Arg Ser Gln Ser Pro Arg Arg Arg Arg Ser Gln Ser
                565                 570                 575

Arg Glu Ser Gln Cys
            580

<210> SEQ ID NO 117
<211> LENGTH: 1808
<212> TYPE: DNA
<213> ORGANISM: Artificial
<220> FEATURE:
<223> OTHER INFORMATION: Synthetic Construct
<220> FEATURE:
<221> NAME/KEY: CDS
<222> LOCATION: (37)..(1779)

<400> SEQUENCE: 117
gaattcgcca ccatggctga tgaagctcca actagt gga caa tgg tcc tca aag        54
                                       Gly Gln Trp Ser Ser Lys
                                        1               5 cca agg aaa ggt atg ggt aca aac ttg agt gtt tca aac cca ctt ggc       102
Pro Arg Lys Gly Met Gly Thr Asn Leu Ser Val Ser Asn Pro Leu Gly
         10                  15                  20 ttt ttc cca gac cat caa ctt gat cca gca ttc aga gca aac tct gcc      150
Phe Phe Pro Asp His Gln Leu Asp Pro Ala Phe Arg Ala Asn Ser Ala
```

```
                 25                  30                  35
aac cca gac tgg gat ttc aat cca aac aaa gat acc tgg cct gaa gca      198
Asn Pro Asp Trp Asp Phe Asn Pro Asn Lys Asp Thr Trp Pro Glu Ala
 40                  45                  50 aat caa gtt gga gtg ggg gca ttt ggt ttg ggc ttc act cca cca cac      246
Asn Gln Val Gly Val Gly Ala Phe Gly Leu Gly Phe Thr Pro Pro His
 55                  60                  65                  70 gga ggg ttg ctt gga tgg agt cca cag gct caa ggc att ttg caa act      294
Gly Gly Leu Leu Gly Trp Ser Pro Gln Ala Gln Gly Ile Leu Gln Thr
                 75                  80                  85 gtt cca gct aat cct cct cct gct tca acc aat aga caa tct ggt aga      342
Val Pro Ala Asn Pro Pro Pro Ala Ser Thr Asn Arg Gln Ser Gly Arg
         90                  95                 100 caa cct aca cca att tca cct cca ctt aga gac tct cat cct cag gca      390
Gln Pro Thr Pro Ile Ser Pro Pro Leu Arg Asp Ser His Pro Gln Ala
        105                 110                 115 atg caa tgg aac tca act acc ttc cat caa gct ctg ttg gat cct aga      438
Met Gln Trp Asn Ser Thr Thr Phe His Gln Ala Leu Leu Asp Pro Arg
        120                 125                 130 gtt aga ggt ctg tat ttc cca gct ggc gga tca tct agt ggt acc gtg      486
Val Arg Gly Leu Tyr Phe Pro Ala Gly Gly Ser Ser Ser Gly Thr Val
135                 140                 145                 150 aat cca gta cct act aca gcc tct cca atc agt tcc atc ttt agt aga      534
Asn Pro Val Pro Thr Thr Ala Ser Pro Ile Ser Ser Ile Phe Ser Arg
                155                 160                 165 act ggc gac cct gcc ttg aat atg gag aac atc aca tct gga ttc ctg      582
Thr Gly Asp Pro Ala Leu Asn Met Glu Asn Ile Thr Ser Gly Phe Leu
                170                 175                 180 ggg cca ttg cta gtc cta caa gct ggg ttt ttc cta ttg act aga atc      630
Gly Pro Leu Leu Val Leu Gln Ala Gly Phe Phe Leu Leu Thr Arg Ile
        185                 190                 195 ttg aca att cca cag agt tta gac tcc tgg tgg acc agt cta aac ttt      678
Leu Thr Ile Pro Gln Ser Leu Asp Ser Trp Trp Thr Ser Leu Asn Phe
200                 205                 210 ttg ggt ggc aca aca aca tgt cct ggc caa aac tct cag tct cca aca      726
Leu Gly Gly Thr Thr Thr Cys Pro Gly Gln Asn Ser Gln Ser Pro Thr
215                 220                 225                 230 agt aac cac tct cct act tca tgt cca cca att tgt cct ggt tac aga      774
Ser Asn His Ser Pro Thr Ser Cys Pro Pro Ile Cys Pro Gly Tyr Arg
                235                 240                 245 tgg atg tgc ctc aga agg ttt atc att ttc ctt ttc ata ttg tta ttg      822
Trp Met Cys Leu Arg Arg Phe Ile Ile Phe Leu Phe Ile Leu Leu Leu
                250                 255                 260 tgc ctc ata ttc cta ttg gta tta ttg gat tac caa ggg atg ctt cct      870
Cys Leu Ile Phe Leu Leu Val Leu Leu Asp Tyr Gln Gly Met Leu Pro
        265                 270                 275 gtc tgt cca ttg ctc cct ggt acg agt aca aca tct act ggc cca tgc      918
Val Cys Pro Leu Leu Pro Gly Thr Ser Thr Thr Ser Thr Gly Pro Cys
        280                 285                 290 aaa aca tgc acc ata cca gcg caa ggt aca agc atg ttt cca tcc tgt      966
Lys Thr Cys Thr Ile Pro Ala Gln Gly Thr Ser Met Phe Pro Ser Cys
295                 300                 305                 310 tgt tgc aca aaa cca tcc gat ggc aat tgc aca tgc att cca ata cca     1014
Cys Cys Thr Lys Pro Ser Asp Gly Asn Cys Thr Cys Ile Pro Ile Pro
                315                 320                 325 tct tca tgg gcc ttc gct cgt ttc cta tgg gaa tgg gcc tca gtt aga     1062
Ser Ser Trp Ala Phe Ala Arg Phe Leu Trp Glu Trp Ala Ser Val Arg
                330                 335                 340 ttt tcc tgg tta tca ttg ttg gtc cca ttt gtg caa tgg ttt gta ggt     1110
```

```
                Phe Ser Trp Leu Ser Leu Leu Val Pro Phe Val Gln Trp Phe Val Gly
                            345                 350                 355 tta tcc cca acc gtc tgg tta tct gta ata tgg atg atg tgg tat tgg                 1158
Leu Ser Pro Thr Val Trp Leu Ser Val Ile Trp Met Met Trp Tyr Trp
360                 365                 370 ggt cca agt tta tac tca atc gtt tca cct ttt atc cct ttg ctg cca                 1206
Gly Pro Ser Leu Tyr Ser Ile Val Ser Pro Phe Ile Pro Leu Leu Pro
375                 380                 385                 390 atc ttt ttc tgt ttg tgg gtt tac att gat att gat cct tac aag gag                 1254
Ile Phe Phe Cys Leu Trp Val Tyr Ile Asp Ile Asp Pro Tyr Lys Glu
                395                 400                 405 ttt ggt gct act gtt gag tta cta tcc ttt tta cct tct gac ttt ttc                 1302
Phe Gly Ala Thr Val Glu Leu Leu Ser Phe Leu Pro Ser Asp Phe Phe
        410                 415                 420 cct tct gtc aga gat ctt ttg gat act gct tct gct tta tac aga gaa                 1350
Pro Ser Val Arg Asp Leu Leu Asp Thr Ala Ser Ala Leu Tyr Arg Glu
            425                 430                 435 gct ttg gaa tca cca gaa cat tgt tca cct cat cat acc gcc tta aga                 1398
Ala Leu Glu Ser Pro Glu His Cys Ser Pro His His Thr Ala Leu Arg
440                 445                 450 caa gca att ctg tgt tgg ggc gaa tta atg aac cta gca aca tgg gtg                 1446
Gln Ala Ile Leu Cys Trp Gly Glu Leu Met Asn Leu Ala Thr Trp Val
455                 460                 465                 470 ggt tcc aat ttg gaa gat cca gca tcc aga gag tta gtg gtt agc tac                 1494
Gly Ser Asn Leu Glu Asp Pro Ala Ser Arg Glu Leu Val Val Ser Tyr
                475                 480                 485 gtg aat gtc aac atg ggc ttg aaa atc aga cag tta ctt tgg ttc cat                 1542
Val Asn Val Asn Met Gly Leu Lys Ile Arg Gln Leu Leu Trp Phe His
        490                 495                 500 atc tct tgt ctg aca ttt ggt aga gaa aca gtt ctg gaa tat ctc gtt                 1590
Ile Ser Cys Leu Thr Phe Gly Arg Glu Thr Val Leu Glu Tyr Leu Val
            505                 510                 515 agc ttt gga gta tgg att aga act cca cca gcc tac aga cca cct aat                 1638
Ser Phe Gly Val Trp Ile Arg Thr Pro Pro Ala Tyr Arg Pro Pro Asn
520                 525                 530 gca cca ata ttg tca acc ctc cca gag aca aca gtt gtg agg aga aga                 1686
Ala Pro Ile Leu Ser Thr Leu Pro Glu Thr Thr Val Val Arg Arg Arg
535                 540                 545                 550 gga aga tct cct cgt cgt aga act cca tct cca aga cga agg aga tca                 1734
Gly Arg Ser Pro Arg Arg Arg Thr Pro Ser Pro Arg Arg Arg Arg Ser
                555                 560                 565 caa agt cct aga cga cgt aga tct caa tct aga gag tct caa tgt                     1779
Gln Ser Pro Arg Arg Arg Arg Ser Gln Ser Arg Glu Ser Gln Cys
        570                 575                 580 caccaccatc accatcatta agcggccgc                                                 1808

<210> SEQ ID NO 118
<211> LENGTH: 581
<212> TYPE: PRT
<213> ORGANISM: Artificial
<220> FEATURE:
<223> OTHER INFORMATION: Synthetic Construct

<400> SEQUENCE: 118

Gly Gln Trp Ser Ser Lys Pro Arg Lys Gly Met Gly Thr Asn Leu Ser
1               5                   10                  15

Val Ser Asn Pro Leu Gly Phe Phe Pro Asp His Gln Leu Asp Pro Ala
            20                  25                  30

Phe Arg Ala Asn Ser Ala Asn Pro Asp Trp Asp Phe Asn Pro Asn Lys
        35                  40                  45
```

```
Asp Thr Trp Pro Glu Ala Asn Gln Val Gly Val Gly Ala Phe Gly Leu
    50                  55                  60

Gly Phe Thr Pro Pro His Gly Gly Leu Leu Gly Trp Ser Pro Gln Ala
65                  70                  75                  80

Gln Gly Ile Leu Gln Thr Val Pro Ala Asn Pro Pro Ala Ser Thr
                    85                  90                  95

Asn Arg Gln Ser Gly Arg Gln Pro Thr Pro Ile Ser Pro Pro Leu Arg
            100                 105                 110

Asp Ser His Pro Gln Ala Met Gln Trp Asn Ser Thr Thr Phe His Gln
        115                 120                 125

Ala Leu Leu Asp Pro Arg Val Arg Gly Leu Tyr Phe Pro Ala Gly Gly
    130                 135                 140

Ser Ser Ser Gly Thr Val Asn Pro Val Pro Thr Thr Ala Ser Pro Ile
145                 150                 155                 160

Ser Ser Ile Phe Ser Arg Thr Gly Asp Pro Ala Leu Asn Met Glu Asn
                165                 170                 175

Ile Thr Ser Gly Phe Leu Gly Pro Leu Leu Val Leu Gln Ala Gly Phe
                180                 185                 190

Phe Leu Leu Thr Arg Ile Leu Thr Ile Pro Gln Ser Leu Asp Ser Trp
                195                 200                 205

Trp Thr Ser Leu Asn Phe Leu Gly Gly Thr Thr Thr Cys Pro Gly Gln
210                 215                 220

Asn Ser Gln Ser Pro Thr Ser Asn His Ser Pro Thr Ser Cys Pro Pro
225                 230                 235                 240

Ile Cys Pro Gly Tyr Arg Trp Met Cys Leu Arg Arg Phe Ile Ile Phe
                245                 250                 255

Leu Phe Ile Leu Leu Leu Cys Leu Ile Phe Leu Leu Val Leu Leu Asp
                260                 265                 270

Tyr Gln Gly Met Leu Pro Val Cys Pro Leu Leu Pro Gly Thr Ser Thr
                275                 280                 285

Thr Ser Thr Gly Pro Cys Lys Thr Cys Thr Ile Pro Ala Gln Gly Thr
290                 295                 300

Ser Met Phe Pro Ser Cys Cys Cys Thr Lys Pro Ser Asp Gly Asn Cys
305                 310                 315                 320

Thr Cys Ile Pro Ile Pro Ser Ser Trp Ala Phe Ala Arg Phe Leu Trp
                325                 330                 335

Glu Trp Ala Ser Val Arg Phe Ser Trp Leu Ser Leu Leu Val Pro Phe
                340                 345                 350

Val Gln Trp Phe Val Gly Leu Ser Pro Thr Val Trp Leu Ser Val Ile
                355                 360                 365

Trp Met Met Trp Tyr Trp Gly Pro Ser Leu Tyr Ser Ile Val Ser Pro
370                 375                 380

Phe Ile Pro Leu Leu Pro Ile Phe Phe Cys Leu Trp Val Tyr Ile Asp
385                 390                 395                 400

Ile Asp Pro Tyr Lys Glu Phe Gly Ala Thr Val Glu Leu Leu Ser Phe
                405                 410                 415

Leu Pro Ser Asp Phe Phe Pro Ser Val Arg Asp Leu Leu Asp Thr Ala
                420                 425                 430

Ser Ala Leu Tyr Arg Glu Ala Leu Glu Ser Pro Glu His Cys Ser Pro
                435                 440                 445

His His Thr Ala Leu Arg Gln Ala Ile Leu Cys Trp Gly Glu Leu Met
    450                 455                 460
```

```
Asn Leu Ala Thr Trp Val Gly Ser Asn Leu Glu Asp Pro Ala Ser Arg
465                 470                 475                 480

Glu Leu Val Val Ser Tyr Val Asn Val Asn Met Gly Leu Lys Ile Arg
                485                 490                 495

Gln Leu Leu Trp Phe His Ile Ser Cys Leu Thr Phe Gly Arg Glu Thr
            500                 505                 510

Val Leu Glu Tyr Leu Val Ser Phe Gly Val Trp Ile Arg Thr Pro Pro
        515                 520                 525

Ala Tyr Arg Pro Pro Asn Ala Pro Ile Leu Ser Thr Leu Pro Glu Thr
    530                 535                 540

Thr Val Val Arg Arg Gly Arg Ser Pro Arg Arg Thr Pro Ser
545                 550                 555                 560

Pro Arg Arg Arg Ser Gln Ser Pro Arg Arg Arg Ser Gln Ser
                565                 570                 575

Arg Glu Ser Gln Cys
            580

<210> SEQ ID NO 119
<211> LENGTH: 2492
<212> TYPE: DNA
<213> ORGANISM: Artificial
<220> FEATURE:
<223> OTHER INFORMATION: Synthetic Construct
<220> FEATURE:
<221> NAME/KEY: CDS
<222> LOCATION: (37)..(2463)

<400> SEQUENCE: 119
gaattcgcca ccatggctga tgaagctcct actagt ggt cag tgg tcc tcc aaa       54
                                        Gly Gln Trp Ser Ser Lys
                                         1               5 cct aga aag ggt atg ggt act aat ttg tct gta tct aac cct ctc gga     102
Pro Arg Lys Gly Met Gly Thr Asn Leu Ser Val Ser Asn Pro Leu Gly
            10                  15                  20 ttc ttt cca gat cac cag tta gat cca gct ttt cgt gct aac agt gcc     150
Phe Phe Pro Asp His Gln Leu Asp Pro Ala Phe Arg Ala Asn Ser Ala
        25                  30                  35 aac cca gat tgg gat ttc aat cct aat aag gat acc tgg cca gag gct     198
Asn Pro Asp Trp Asp Phe Asn Pro Asn Lys Asp Thr Trp Pro Glu Ala
 40                  45                  50 aac cag gta gga gtt gga gcc ttc ggt cta ggt ttt acc cca cct cac     246
Asn Gln Val Gly Val Gly Ala Phe Gly Leu Gly Phe Thr Pro Pro His
 55                  60                  65                  70 ggt gga cta tta ggc tgg agc cca caa gca caa ggt atc ttg caa acc     294
Gly Gly Leu Leu Gly Trp Ser Pro Gln Ala Gln Gly Ile Leu Gln Thr
                75                  80                  85 gtt cca gct aac cct cca cca gcg tca aca aat aga cag tct ggt aga     342
Val Pro Ala Asn Pro Pro Pro Ala Ser Thr Asn Arg Gln Ser Gly Arg
            90                  95                 100 caa cca acc cct att tct cct cct tta aga gac tct cat cct cag gcg     390
Gln Pro Thr Pro Ile Ser Pro Pro Leu Arg Asp Ser His Pro Gln Ala
        105                 110                 115 atg caa tgg aac tca acg acc ttt cat caa gct ctt ttg gac cct aga     438
Met Gln Trp Asn Ser Thr Thr Phe His Gln Ala Leu Leu Asp Pro Arg
    120                 125                 130 gtc agg ggt tta tac ttc cca gct ggt gga tcc tca tcc ggc act gtt     486
Val Arg Gly Leu Tyr Phe Pro Ala Gly Gly Ser Ser Ser Gly Thr Val
135                 140                 145                 150 aat cct gtc cca act aca gca tca cca att tca tcc ata ttt tct aga     534
Asn Pro Val Pro Thr Thr Ala Ser Pro Ile Ser Ser Ile Phe Ser Arg
```

-continued

|  |  |  | 155 |  |  |  | 160 |  |  |  | 165 |  |  |  |
|---|---|---|---|---|---|---|---|---|---|---|---|---|---|---|
| act | ggg | gat | cct | gct | ctt | aat | atg | gaa | aac | att | aca | agc | ggc | ttc cta | 582 |
| Thr | Gly | Asp | Pro | Ala | Leu | Asn | Met | Glu | Asn | Ile | Thr | Ser | Gly | Phe Leu |  |
|  |  |  | 170 |  |  |  | 175 |  |  |  |  |  | 180 |  |  | gga cca tta tta gtt cta caa gcc gga ttt ttc cta ttg act aga atc    630
Gly Pro Leu Leu Val Leu Gln Ala Gly Phe Phe Leu Leu Thr Arg Ile
        185                     190                     195 cta act att cct caa agt ctt gac tcc tgg tgg aca tcc ttg aat ttc    678
Leu Thr Ile Pro Gln Ser Leu Asp Ser Trp Trp Thr Ser Leu Asn Phe
200                     205                     210 ctt ggc ggt aca aca aca tgt cca ggc caa aac tct caa tca cca act    726
Leu Gly Gly Thr Thr Thr Cys Pro Gly Gln Asn Ser Gln Ser Pro Thr
215                     220                     225                     230 tct aat cac tct cca aca tct tgc cct cca att tgc cca ggt tac aga    774
Ser Asn His Ser Pro Thr Ser Cys Pro Pro Ile Cys Pro Gly Tyr Arg
                235                     240                     245 tgg atg tgc ttg aga agg ttc atc att ttt ctg ttc atc ctc ttg ttg    822
Trp Met Cys Leu Arg Arg Phe Ile Ile Phe Leu Phe Ile Leu Leu Leu
        250                     255                     260 tgt ttg att ttc ctc tta gta ttg ctg gac tac caa ggc atg ctt cca    870
Cys Leu Ile Phe Leu Leu Val Leu Leu Asp Tyr Gln Gly Met Leu Pro
        265                     270                     275 gtc tgc cct cta ttg cca gga act tct aca acc tca aca gga cca tgt    918
Val Cys Pro Leu Leu Pro Gly Thr Ser Thr Thr Ser Thr Gly Pro Cys
280                     285                     290 aaa aca tgt act atc cct gct caa gga aca tca atg ttt cca tct tgt    966
Lys Thr Cys Thr Ile Pro Ala Gln Gly Thr Ser Met Phe Pro Ser Cys
295                     300                     305                     310 tgc tgt aca aaa cca tca gat ggt aat tgt act tgt ata cca ata cca    1014
Cys Cys Thr Lys Pro Ser Asp Gly Asn Cys Thr Cys Ile Pro Ile Pro
                315                     320                     325 agt tca tgg gca ttt gcc cgt ttc ctt tgg gag tgg gct tct gta aga    1062
Ser Ser Trp Ala Phe Ala Arg Phe Leu Trp Glu Trp Ala Ser Val Arg
        330                     335                     340 ttc tct tgg tta agt ttg cta gtc cca ttc gtg cag tgg ttt gtt ggc    1110
Phe Ser Trp Leu Ser Leu Leu Val Pro Phe Val Gln Trp Phe Val Gly
        345                     350                     355 ctg tct cca act gtt tgg tta tct gtt att tgg atg atg tgg tac tgg    1158
Leu Ser Pro Thr Val Trp Leu Ser Val Ile Trp Met Met Trp Tyr Trp
360                     365                     370 ggt cca agc cta tac tca atc gtg tca cct ttt atc cca ttg cta cct    1206
Gly Pro Ser Leu Tyr Ser Ile Val Ser Pro Phe Ile Pro Leu Leu Pro
375                     380                     385                     390 atc ttt ttc tgc ctc tgg gtt tac atc gat att gac cct tac aag gaa    1254
Ile Phe Phe Cys Leu Trp Val Tyr Ile Asp Ile Asp Pro Tyr Lys Glu
                395                     400                     405 ttt ggc gca aca gtt gaa ttg tta tca ttt tta cca tca gat ttc ttt    1302
Phe Gly Ala Thr Val Glu Leu Leu Ser Phe Leu Pro Ser Asp Phe Phe
        410                     415                     420 cca tca gtg cgt gat ttg tta gat acg gca tcc gct ttg tac aga gaa    1350
Pro Ser Val Arg Asp Leu Leu Asp Thr Ala Ser Ala Leu Tyr Arg Glu
        425                     430                     435 gca ctg gaa tca cca gaa cac tgt tct cca cat cac act gct ctc aga    1398
Ala Leu Glu Ser Pro Glu His Cys Ser Pro His His Thr Ala Leu Arg
440                     445                     450 caa gct ata ttg tgt tgg gga gag ttg atg aat cta gcc act tgg gta    1446
Gln Ala Ile Leu Cys Trp Gly Glu Leu Met Asn Leu Ala Thr Trp Val
455                     460                     465                     470 ggg tcc aat ctg gaa gat cct gcc tct aga gaa ctg gtg gta tct tac    1494

-continued

| | |
|---|---|
| Gly Ser Asn Leu Glu Asp Pro Ala Ser Arg Glu Leu Val Val Ser Tyr<br>              475                  480                  485 | |
| gtc aat gtt aac atg ggg ttg aag att aga caa ctt tta tgg ttc cat<br>Val Asn Val Asn Met Gly Leu Lys Ile Arg Gln Leu Leu Trp Phe His<br>              490                  495                  500 | 1542 |
| att tca tgt tta acg ttt ggt aga gaa aca gta ctg gaa tac tta gtt<br>Ile Ser Cys Leu Thr Phe Gly Arg Glu Thr Val Leu Glu Tyr Leu Val<br>         505                  510                  515 | 1590 |
| agt ttc ggt gtc tgg att aga aca cca cca gca tat aga cca cca aat<br>Ser Phe Gly Val Trp Ile Arg Thr Pro Pro Ala Tyr Arg Pro Pro Asn<br>520                  525                  530 | 1638 |
| gcg cct ata ttg agt acg ctc cca gaa acg acg gtc gtt agg aga aga<br>Ala Pro Ile Leu Ser Thr Leu Pro Glu Thr Thr Val Val Arg Arg Arg<br>535                  540                  545                  550 | 1686 |
| ggt aga tca cct agg aga agg aca cct tca cct aga cgt aga cgt tct<br>Gly Arg Ser Pro Arg Arg Arg Thr Pro Ser Pro Arg Arg Arg Arg Ser<br>              555                  560                  565 | 1734 |
| caa tct cca aga cgt aga aga tct caa tct aga gaa tca caa tgc ggt<br>Gln Ser Pro Arg Arg Arg Arg Ser Gln Ser Arg Glu Ser Gln Cys Gly<br>570                  575                  580 | 1782 |
| cta tct aga tat gtc gcc cga cta tca tct aat tct cgt atc ttt aac<br>Leu Ser Arg Tyr Val Ala Arg Leu Ser Ser Asn Ser Arg Ile Phe Asn<br>         585                  590                  595 | 1830 |
| cat caa cac ggc acc atg caa aat ctg cat gac tcc tgt agt aga aat<br>His Gln His Gly Thr Met Gln Asn Leu His Asp Ser Cys Ser Arg Asn<br>600                  605                  610 | 1878 |
| ctt tat gtg agt ctc ttg ctt ttg tac caa act ttc ggc aga aaa ttg<br>Leu Tyr Val Ser Leu Leu Leu Leu Tyr Gln Thr Phe Gly Arg Lys Leu<br>615                  620                  625                  630 | 1926 |
| cac ctt tac tct cat cca att ata cta ggt ttt aga aaa atc cca atg<br>His Leu Tyr Ser His Pro Ile Ile Leu Gly Phe Arg Lys Ile Pro Met<br>              635                  640                  645 | 1974 |
| ggg gtg ggt tta tct cca ttt ttg ctt gcg caa ttc aca agt gca atc<br>Gly Val Gly Leu Ser Pro Phe Leu Leu Ala Gln Phe Thr Ser Ala Ile<br>         650                  655                  660 | 2022 |
| tgt tct gtg gtt agg aga gct ttt cct cat tgc ctc gca ttt tca tac<br>Cys Ser Val Val Arg Arg Ala Phe Pro His Cys Leu Ala Phe Ser Tyr<br>665                  670                  675 | 2070 |
| atg gat gat gtt gtc tta ggt gcc aaa agt gta caa cat ttg gag agt<br>Met Asp Asp Val Val Leu Gly Ala Lys Ser Val Gln His Leu Glu Ser<br>680                  685                  690 | 2118 |
| ttg ttt aca gcc gta act aac ttt ctc ttg tca tta ggg atc cat ttg<br>Leu Phe Thr Ala Val Thr Asn Phe Leu Leu Ser Leu Gly Ile His Leu<br>695                  700                  705                  710 | 2166 |
| aac cct aac aaa aca aaa aga tgg ggg tac tct cta cat ttt atg ggt<br>Asn Pro Asn Lys Thr Lys Arg Trp Gly Tyr Ser Leu His Phe Met Gly<br>              715                  720                  725 | 2214 |
| tat gtt ata ggc tgc tat gga tcc tta cct caa gac cat atc att cag<br>Tyr Val Ile Gly Cys Tyr Gly Ser Leu Pro Gln Asp His Ile Ile Gln<br>         730                  735                  740 | 2262 |
| aaa atc aaa gag tgc ttt aga aag ttg cct gtt aat aga cca atc gac<br>Lys Ile Lys Glu Cys Phe Arg Lys Leu Pro Val Asn Arg Pro Ile Asp<br>745                  750                  755 | 2310 |
| tgg aag gtt tgt caa agg atc gtt ggt tta ctt ggt ttt gca gca cca<br>Trp Lys Val Cys Gln Arg Ile Val Gly Leu Leu Gly Phe Ala Ala Pro<br>760                  765                  770 | 2358 |
| ttc acc caa tgt ggc tac cct gct ctg atg cct tta tat gct tgt ata<br>Phe Thr Gln Cys Gly Tyr Pro Ala Leu Met Pro Leu Tyr Ala Cys Ile<br>775                  780                  785                  790 | 2406 |

-continued

| | | |
|---|---|---|
| caa tct aag caa gct ttt aca ttc tct cca acg tac aag gcc ttt tta<br>Gln Ser Lys Gln Ala Phe Thr Phe Ser Pro Thr Tyr Lys Ala Phe Leu<br>              795                              800                        805 | | 2454 |
| tgc aaa caa catcaccatc accatcacta agcggccgc<br>Cys Lys Gln | | 2492 |

<210> SEQ ID NO 120
<211> LENGTH: 809
<212> TYPE: PRT
<213> ORGANISM: Artificial
<220> FEATURE:
<223> OTHER INFORMATION: Synthetic Construct

<400> SEQUENCE: 120

Gly Gln Trp Ser Ser Lys Pro Arg Lys Gly Met Gly Thr Asn Leu Ser
1               5                   10                  15

Val Ser Asn Pro Leu Gly Phe Phe Pro Asp His Gln Leu Asp Pro Ala
            20                  25                  30

Phe Arg Ala Asn Ser Ala Asn Pro Asp Trp Asp Phe Asn Pro Asn Lys
        35                  40                  45

Asp Thr Trp Pro Glu Ala Asn Gln Val Gly Val Gly Ala Phe Gly Leu
    50                  55                  60

Gly Phe Thr Pro Pro His Gly Gly Leu Leu Gly Trp Ser Pro Gln Ala
65                  70                  75                  80

Gln Gly Ile Leu Gln Thr Val Pro Ala Asn Pro Pro Ala Ser Thr
                85                  90                  95

Asn Arg Gln Ser Gly Arg Gln Pro Thr Pro Ile Ser Pro Pro Leu Arg
            100                 105                 110

Asp Ser His Pro Gln Ala Met Gln Trp Asn Ser Thr Thr Phe His Gln
        115                 120                 125

Ala Leu Leu Asp Pro Arg Val Arg Gly Leu Tyr Phe Pro Ala Gly Gly
    130                 135                 140

Ser Ser Ser Gly Thr Val Asn Pro Val Pro Thr Thr Ala Ser Pro Ile
145                 150                 155                 160

Ser Ser Ile Phe Ser Arg Thr Gly Asp Pro Ala Leu Asn Met Glu Asn
                165                 170                 175

Ile Thr Ser Gly Phe Leu Gly Pro Leu Leu Val Leu Gln Ala Gly Phe
            180                 185                 190

Phe Leu Leu Thr Arg Ile Leu Thr Ile Pro Gln Ser Leu Asp Ser Trp
        195                 200                 205

Trp Thr Ser Leu Asn Phe Leu Gly Gly Thr Thr Thr Cys Pro Gly Gln
    210                 215                 220

Asn Ser Gln Ser Pro Thr Ser Asn His Ser Pro Thr Ser Cys Pro Pro
225                 230                 235                 240

Ile Cys Pro Gly Tyr Arg Trp Met Cys Leu Arg Arg Phe Ile Ile Phe
                245                 250                 255

Leu Phe Ile Leu Leu Leu Cys Leu Ile Phe Leu Leu Val Leu Leu Asp
            260                 265                 270

Tyr Gln Gly Met Leu Pro Val Cys Pro Leu Leu Pro Gly Thr Ser Thr
        275                 280                 285

Thr Ser Thr Gly Pro Cys Lys Thr Cys Thr Ile Pro Ala Gln Gly Thr
    290                 295                 300

Ser Met Phe Pro Ser Cys Cys Cys Thr Lys Pro Ser Asp Gly Asn Cys
305                 310                 315                 320

Thr Cys Ile Pro Ile Pro Ser Ser Trp Ala Phe Ala Arg Phe Leu Trp
                325                 330                 335

```
Glu Trp Ala Ser Val Arg Phe Ser Trp Leu Ser Leu Val Pro Phe
            340                 345                 350

Val Gln Trp Phe Val Gly Leu Ser Pro Thr Val Trp Leu Ser Val Ile
        355                 360                 365

Trp Met Met Trp Tyr Trp Gly Pro Ser Leu Tyr Ser Ile Val Ser Pro
370                 375                 380

Phe Ile Pro Leu Leu Pro Ile Phe Phe Cys Leu Trp Val Tyr Ile Asp
385                 390                 395                 400

Ile Asp Pro Tyr Lys Glu Phe Gly Ala Thr Val Glu Leu Leu Ser Phe
                405                 410                 415

Leu Pro Ser Asp Phe Phe Pro Ser Val Arg Asp Leu Leu Asp Thr Ala
            420                 425                 430

Ser Ala Leu Tyr Arg Glu Ala Leu Glu Ser Pro Glu His Cys Ser Pro
        435                 440                 445

His His Thr Ala Leu Arg Gln Ala Ile Leu Cys Trp Gly Glu Leu Met
    450                 455                 460

Asn Leu Ala Thr Trp Val Gly Ser Asn Leu Glu Asp Pro Ala Ser Arg
465                 470                 475                 480

Glu Leu Val Val Ser Tyr Val Asn Val Asn Met Gly Leu Lys Ile Arg
                485                 490                 495

Gln Leu Leu Trp Phe His Ile Ser Cys Leu Thr Phe Gly Arg Glu Thr
            500                 505                 510

Val Leu Glu Tyr Leu Val Ser Phe Gly Val Trp Ile Arg Thr Pro Pro
        515                 520                 525

Ala Tyr Arg Pro Pro Asn Ala Pro Ile Leu Ser Thr Leu Pro Glu Thr
    530                 535                 540

Thr Val Val Arg Arg Arg Gly Arg Ser Pro Arg Arg Arg Thr Pro Ser
545                 550                 555                 560

Pro Arg Arg Arg Arg Ser Gln Ser Pro Arg Arg Arg Arg Ser Gln Ser
                565                 570                 575

Arg Glu Ser Gln Cys Gly Leu Ser Arg Tyr Val Ala Arg Leu Ser Ser
            580                 585                 590

Asn Ser Arg Ile Phe Asn His Gln His Gly Thr Met Gln Asn Leu His
        595                 600                 605

Asp Ser Cys Ser Arg Asn Leu Tyr Val Ser Leu Leu Leu Leu Tyr Gln
    610                 615                 620

Thr Phe Gly Arg Lys Leu His Leu Tyr Ser His Pro Ile Ile Leu Gly
625                 630                 635                 640

Phe Arg Lys Ile Pro Met Gly Val Gly Leu Ser Pro Phe Leu Leu Ala
                645                 650                 655

Gln Phe Thr Ser Ala Ile Cys Ser Val Val Arg Arg Ala Phe Pro His
            660                 665                 670

Cys Leu Ala Phe Ser Tyr Met Asp Asp Val Val Leu Gly Ala Lys Ser
        675                 680                 685

Val Gln His Leu Glu Ser Leu Phe Thr Ala Val Thr Asn Phe Leu Leu
    690                 695                 700

Ser Leu Gly Ile His Leu Asn Pro Asn Lys Thr Lys Arg Trp Gly Tyr
705                 710                 715                 720

Ser Leu His Phe Met Gly Tyr Val Ile Gly Cys Tyr Gly Ser Leu Pro
                725                 730                 735

Gln Asp His Ile Ile Gln Lys Ile Lys Glu Cys Phe Arg Lys Leu Pro
            740                 745                 750
```

| | |
|---|---|
| Val Asn Arg Pro Ile Asp Trp Lys Val Cys Gln Arg Ile Val Gly Leu<br>755 760 765 | |
| Leu Gly Phe Ala Ala Pro Phe Thr Gln Cys Gly Tyr Pro Ala Leu Met<br>770 775 780 | |
| Pro Leu Tyr Ala Cys Ile Gln Ser Lys Gln Ala Phe Thr Phe Ser Pro<br>785 790 795 800 | |
| Thr Tyr Lys Ala Phe Leu Cys Lys Gln<br>805 | |

<210> SEQ ID NO 121
<211> LENGTH: 1988
<212> TYPE: DNA
<213> ORGANISM: Artificial
<220> FEATURE:
<223> OTHER INFORMATION: Synthetic Construct
<220> FEATURE:
<221> NAME/KEY: CDS
<222> LOCATION: (37)..(1959)

<400> SEQUENCE: 121

| | |
|---|---|
| gaattcgcca ccatggccga tgaggcacct actagt ggt cag tgg tcc tcc aaa<br>Gly Gln Trp Ser Ser Lys<br>1 5 | 54 |
| cct aga aag ggt atg ggt act aat ttg tct gta tct aac cct ctc gga<br>Pro Arg Lys Gly Met Gly Thr Asn Leu Ser Val Ser Asn Pro Leu Gly<br>10 15 20 | 102 |
| ttc ttt cca gat cac cag tta gat cca gct ttt cgt gct aac agt gcc<br>Phe Phe Pro Asp His Gln Leu Asp Pro Ala Phe Arg Ala Asn Ser Ala<br>25 30 35 | 150 |
| aac cca gat tgg gat ttc aat cct aat aag gat acc tgg cca gag gct<br>Asn Pro Asp Trp Asp Phe Asn Pro Asn Lys Asp Thr Trp Pro Glu Ala<br>40 45 50 | 198 |
| aac cag gta gga gtt gga gcc ttc ggt cta ggt ttt acc cca cct cac<br>Asn Gln Val Gly Val Gly Ala Phe Gly Leu Gly Phe Thr Pro Pro His<br>55 60 65 70 | 246 |
| ggt gga cta tta ggc tgg agc cca caa gca caa ggt atc ttg caa acc<br>Gly Gly Leu Leu Gly Trp Ser Pro Gln Ala Gln Gly Ile Leu Gln Thr<br>75 80 85 | 294 |
| gtt cca gct aac cct cca cca gcg tca aca aat aga cag tct ggt aga<br>Val Pro Ala Asn Pro Pro Pro Ala Ser Thr Asn Arg Gln Ser Gly Arg<br>90 95 100 | 342 |
| caa cca acc cct att tct cct cct tta aga gac tct cat cct cag gcg<br>Gln Pro Thr Pro Ile Ser Pro Pro Leu Arg Asp Ser His Pro Gln Ala<br>105 110 115 | 390 |
| atg caa tgg aac tca acg acc ttt cat caa gct ctt ttg gac cct aga<br>Met Gln Trp Asn Ser Thr Thr Phe His Gln Ala Leu Leu Asp Pro Arg<br>120 125 130 | 438 |
| gtc agg ggt tta tac ttc cca gct ggt gga tcc tca tcc ggc act gtt<br>Val Arg Gly Leu Tyr Phe Pro Ala Gly Gly Ser Ser Ser Gly Thr Val<br>135 140 145 150 | 486 |
| aat cct gtc cca act aca gca tca cca att tca tcc ata ttt tct aga<br>Asn Pro Val Pro Thr Thr Ala Ser Pro Ile Ser Ser Ile Phe Ser Arg<br>155 160 165 | 534 |
| act ggg gat cct gct ctt aat atg gaa aac att aca agc ggc ttc cta<br>Thr Gly Asp Pro Ala Leu Asn Met Glu Asn Ile Thr Ser Gly Phe Leu<br>170 175 180 | 582 |
| gga cca tta tta gtt cta caa gcc gga ttt ttc cta ttg act aga atc<br>Gly Pro Leu Leu Val Leu Gln Ala Gly Phe Phe Leu Leu Thr Arg Ile<br>185 190 195 | 630 |
| cta act att cct caa agt ctt gac tcc tgg tgg aca tcc ttg aat ttc<br>Leu Thr Ile Pro Gln Ser Leu Asp Ser Trp Trp Thr Ser Leu Asn Phe | 678 |

```
              200                 205                 210
ctt ggc ggt aca aca aca tgt cca ggc caa aac tct caa tca cca act      726
Leu Gly Gly Thr Thr Thr Cys Pro Gly Gln Asn Ser Gln Ser Pro Thr
215                 220                 225                 230 tct aat cac tct cca aca tct tgc cct cca att tgc cca ggt tac aga      774
Ser Asn His Ser Pro Thr Ser Cys Pro Pro Ile Cys Pro Gly Tyr Arg
                    235                 240                 245 tgg atg tgc ttg aga agg ttc atc att ttt ctg ttc atc ctc ttg ttg      822
Trp Met Cys Leu Arg Arg Phe Ile Ile Phe Leu Phe Ile Leu Leu Leu
            250                 255                 260 tgt ttg att ttc ctc tta gta ttg ctg gac tac caa ggc atg ctt cca      870
Cys Leu Ile Phe Leu Leu Val Leu Leu Asp Tyr Gln Gly Met Leu Pro
        265                 270                 275 gtc tgc cct cta ttg cca gga act tct aca acc tca aca gga cca tgt      918
Val Cys Pro Leu Leu Pro Gly Thr Ser Thr Thr Ser Thr Gly Pro Cys
    280                 285                 290 aaa aca tgt act atc cct gct caa gga aca tca atg ttt cca tct tgt      966
Lys Thr Cys Thr Ile Pro Ala Gln Gly Thr Ser Met Phe Pro Ser Cys
295                 300                 305                 310 tgc tgt aca aaa cca tca gat ggt aat tgt act tgt ata cca ata cca     1014
Cys Cys Thr Lys Pro Ser Asp Gly Asn Cys Thr Cys Ile Pro Ile Pro
                    315                 320                 325 agt tca tgg gca ttt gcc cgt ttc ctt tgg gag tgg gct tct gta aga     1062
Ser Ser Trp Ala Phe Ala Arg Phe Leu Trp Glu Trp Ala Ser Val Arg
            330                 335                 340 ttc tct tgg tta agt ttg cta gtc cca ttc gtg cag tgg ttt gtt ggc     1110
Phe Ser Trp Leu Ser Leu Leu Val Pro Phe Val Gln Trp Phe Val Gly
        345                 350                 355 ctg tct cca act gtt tgg tta tct gtt att tgg atg atg tgg tac tgg     1158
Leu Ser Pro Thr Val Trp Leu Ser Val Ile Trp Met Met Trp Tyr Trp
    360                 365                 370 ggt cca agc cta tac tca atc gtg tca cct ttt atc cca ttg cta cct     1206
Gly Pro Ser Leu Tyr Ser Ile Val Ser Pro Phe Ile Pro Leu Leu Pro
375                 380                 385                 390 atc ttt ttc tgc ctc tgg gtt tac atc gat att gac cct tac aag gaa     1254
Ile Phe Phe Cys Leu Trp Val Tyr Ile Asp Ile Asp Pro Tyr Lys Glu
                    395                 400                 405 ttt ggc gca aca gtt gaa ttg tta tca ttt tta cca tca gat ttc ttt     1302
Phe Gly Ala Thr Val Glu Leu Leu Ser Phe Leu Pro Ser Asp Phe Phe
            410                 415                 420 cca tca gtg cgt gat ttg tta gat acg gca tcc gct ttg tac aga gaa     1350
Pro Ser Val Arg Asp Leu Leu Asp Thr Ala Ser Ala Leu Tyr Arg Glu
        425                 430                 435 gca ctg gaa tca cca gaa cac tgt tct cca cat cac act gct ctc aga     1398
Ala Leu Glu Ser Pro Glu His Cys Ser Pro His His Thr Ala Leu Arg
    440                 445                 450 caa gct ata ttg tgt tgg gga gag ttg atg aat cta gcc act tgg gta     1446
Gln Ala Ile Leu Cys Trp Gly Glu Leu Met Asn Leu Ala Thr Trp Val
455                 460                 465                 470 ggg tcc aat ctg gaa gat cct gcc tct aga gaa ctg gtg gta tct tac     1494
Gly Ser Asn Leu Glu Asp Pro Ala Ser Arg Glu Leu Val Val Ser Tyr
                    475                 480                 485 gtc aat gtt aac atg ggg ttg aag att aga caa ctt tta tgg ttc cat     1542
Val Asn Val Asn Met Gly Leu Lys Ile Arg Gln Leu Leu Trp Phe His
            490                 495                 500 att tca tgt tta acg ttt ggt aga gaa aca gta ctg gaa tac tta gtt     1590
Ile Ser Cys Leu Thr Phe Gly Arg Glu Thr Val Leu Glu Tyr Leu Val
        505                 510                 515 agt ttc ggt gtc tgg att aga aca cca cca gca tat aga cca cca aat     1638
```

```
Ser Phe Gly Val Trp Ile Arg Thr Pro Pro Ala Tyr Arg Pro Pro Asn
      520                 525                 530 gcg cct ata ttg agt acg ctc cca gaa acg acg gtc gtt agg aga aga        1686
Ala Pro Ile Leu Ser Thr Leu Pro Glu Thr Thr Val Val Arg Arg Arg
535                 540                 545                 550 ggt aga tca cct agg aga agg aca cct tca cct aga cgt aga cgt tct        1734
Gly Arg Ser Pro Arg Arg Arg Thr Pro Ser Pro Arg Arg Arg Ser
                555                 560                 565 caa tct cca aga cgt aga aga tct caa tct aga gaa tca caa tgc cac        1782
Gln Ser Pro Arg Arg Arg Ser Gln Ser Arg Glu Ser Gln Cys His
        570                 575                 580 ctc tca tta aga ggc cta ttt gtt tgt gca ttc tcc tct gct ggt cca        1830
Leu Ser Leu Arg Gly Leu Phe Val Cys Ala Phe Ser Ser Ala Gly Pro
            585                 590                 595 aat gct cac caa ttc ctt cct aaa gtc ctg cat aaa cgt acc ctc ggg        1878
Asn Ala His Gln Phe Leu Pro Lys Val Leu His Lys Arg Thr Leu Gly
600                 605                 610 cta agt gca atg tct act act gac ctt gag gca tat ttc aaa gac tgc        1926
Leu Ser Ala Met Ser Thr Thr Asp Leu Glu Ala Tyr Phe Lys Asp Cys
615                 620                 625                 630 ttg ttt aaa gat tgg gaa gag ctt ggc gaa gag catcaccatc accatcacta     1979
Leu Phe Lys Asp Trp Glu Glu Leu Gly Glu Glu
                635                 640 agcggccgc                                                              1988

<210> SEQ ID NO 122
<211> LENGTH: 641
<212> TYPE: PRT
<213> ORGANISM: Artificial
<220> FEATURE:
<223> OTHER INFORMATION: Synthetic Construct

<400> SEQUENCE: 122

Gly Gln Trp Ser Ser Lys Pro Arg Lys Gly Met Gly Thr Asn Leu Ser
1               5                   10                  15

Val Ser Asn Pro Leu Gly Phe Phe Pro Asp His Gln Leu Asp Pro Ala
            20                  25                  30

Phe Arg Ala Asn Ser Ala Asn Pro Asp Trp Asp Phe Asn Pro Asn Lys
        35                  40                  45

Asp Thr Trp Pro Glu Ala Asn Gln Val Gly Val Gly Ala Phe Gly Leu
    50                  55                  60

Gly Phe Thr Pro Pro His Gly Gly Leu Leu Gly Trp Ser Pro Gln Ala
65                  70                  75                  80

Gln Gly Ile Leu Gln Thr Val Pro Ala Asn Pro Pro Ala Ser Thr
            85                  90                  95

Asn Arg Gln Ser Gly Arg Gln Pro Thr Pro Ile Ser Pro Pro Leu Arg
            100                 105                 110

Asp Ser His Pro Gln Ala Met Gln Trp Asn Ser Thr Thr Phe His Gln
        115                 120                 125

Ala Leu Leu Asp Pro Arg Val Arg Gly Leu Tyr Phe Pro Ala Gly Gly
    130                 135                 140

Ser Ser Ser Gly Thr Val Asn Pro Val Pro Thr Thr Ala Ser Pro Ile
145                 150                 155                 160

Ser Ser Ile Phe Ser Arg Thr Gly Asp Pro Ala Leu Asn Met Glu Asn
                165                 170                 175

Ile Thr Ser Gly Phe Leu Gly Pro Leu Leu Val Leu Gln Ala Gly Phe
            180                 185                 190
```

```
Phe Leu Leu Thr Arg Ile Leu Thr Ile Pro Gln Ser Leu Asp Ser Trp
            195                 200                 205

Trp Thr Ser Leu Asn Phe Leu Gly Gly Thr Thr Thr Cys Pro Gly Gln
210                 215                 220

Asn Ser Gln Ser Pro Thr Ser Asn His Ser Pro Thr Ser Cys Pro Pro
225                 230                 235                 240

Ile Cys Pro Gly Tyr Arg Trp Met Cys Leu Arg Arg Phe Ile Ile Phe
                245                 250                 255

Leu Phe Ile Leu Leu Leu Cys Leu Ile Phe Leu Leu Val Leu Leu Asp
            260                 265                 270

Tyr Gln Gly Met Leu Pro Val Cys Pro Leu Leu Pro Gly Thr Ser Thr
        275                 280                 285

Thr Ser Thr Gly Pro Cys Lys Thr Cys Thr Ile Pro Ala Gln Gly Thr
290                 295                 300

Ser Met Phe Pro Ser Cys Cys Cys Thr Lys Pro Ser Asp Gly Asn Cys
305                 310                 315                 320

Thr Cys Ile Pro Ile Pro Ser Ser Trp Ala Phe Ala Arg Phe Leu Trp
                325                 330                 335

Glu Trp Ala Ser Val Arg Phe Ser Trp Leu Ser Leu Leu Val Pro Phe
            340                 345                 350

Val Gln Trp Phe Val Gly Leu Ser Pro Thr Val Trp Leu Ser Val Ile
        355                 360                 365

Trp Met Met Trp Tyr Trp Gly Pro Ser Leu Tyr Ser Ile Val Ser Pro
370                 375                 380

Phe Ile Pro Leu Leu Pro Ile Phe Phe Cys Leu Trp Val Tyr Ile Asp
385                 390                 395                 400

Ile Asp Pro Tyr Lys Glu Phe Gly Ala Thr Val Glu Leu Leu Ser Phe
                405                 410                 415

Leu Pro Ser Asp Phe Phe Pro Ser Val Arg Asp Leu Leu Asp Thr Ala
            420                 425                 430

Ser Ala Leu Tyr Arg Glu Ala Leu Glu Ser Pro Glu His Cys Ser Pro
        435                 440                 445

His His Thr Ala Leu Arg Gln Ala Ile Leu Cys Trp Gly Glu Leu Met
450                 455                 460

Asn Leu Ala Thr Trp Val Gly Ser Asn Leu Glu Asp Pro Ala Ser Arg
465                 470                 475                 480

Glu Leu Val Val Ser Tyr Val Asn Val Asn Met Gly Leu Lys Ile Arg
                485                 490                 495

Gln Leu Leu Trp Phe His Ile Ser Cys Leu Thr Phe Gly Arg Glu Thr
            500                 505                 510

Val Leu Glu Tyr Leu Val Ser Phe Gly Val Trp Ile Arg Thr Pro Pro
        515                 520                 525

Ala Tyr Arg Pro Pro Asn Ala Pro Ile Leu Ser Thr Leu Pro Glu Thr
530                 535                 540

Thr Val Val Arg Arg Gly Arg Ser Pro Arg Arg Thr Pro Ser
545                 550                 555                 560

Pro Arg Arg Arg Arg Ser Gln Ser Pro Arg Arg Arg Ser Gln Ser
                565                 570                 575

Arg Glu Ser Gln Cys His Leu Ser Leu Arg Gly Leu Phe Val Cys Ala
            580                 585                 590

Phe Ser Ser Ala Gly Pro Asn Ala His Gln Phe Leu Pro Lys Val Leu
        595                 600                 605

His Lys Arg Thr Leu Gly Leu Ser Ala Met Ser Thr Thr Asp Leu Glu
```

```
                   610                 615                 620
Ala Tyr Phe Lys Asp Cys Leu Phe Lys Asp Trp Glu Glu Leu Gly Glu
625                 630                 635                 640

Glu

<210> SEQ ID NO 123
<211> LENGTH: 2672
<212> TYPE: DNA
<213> ORGANISM: Artificial
<220> FEATURE:
<223> OTHER INFORMATION: Synthetic Construct
<220> FEATURE:
<221> NAME/KEY: CDS
<222> LOCATION: (37)..(2643)

<400> SEQUENCE: 123
gaattcgcca ccatggctga tgaagctcct actagt ggt cag tgg tcc tcc aaa        54
                                        Gly Gln Trp Ser Ser Lys
                                         1               5 cct aga aag ggt atg ggt act aat ttg tct gta tct aac cct ctc gga       102
Pro Arg Lys Gly Met Gly Thr Asn Leu Ser Val Ser Asn Pro Leu Gly
         10                  15                  20 ttc ttt cca gat cac cag tta gat cca gct ttt cgt gct aac agt gcc       150
Phe Phe Pro Asp His Gln Leu Asp Pro Ala Phe Arg Ala Asn Ser Ala
 25                  30                  35 aac cca gat tgg gat ttc aat cct aat aag gat acc tgg cca gag gct       198
Asn Pro Asp Trp Asp Phe Asn Pro Asn Lys Asp Thr Trp Pro Glu Ala
     40                  45                  50 aac cag gta gga gtt gga gcc ttc ggt cta ggt ttt acc cca cct cac       246
Asn Gln Val Gly Val Gly Ala Phe Gly Leu Gly Phe Thr Pro Pro His
 55                  60                  65                  70 ggt gga cta tta ggc tgg agc cca caa gca caa ggt atc ttg caa acc       294
Gly Gly Leu Leu Gly Trp Ser Pro Gln Ala Gln Gly Ile Leu Gln Thr
                 75                  80                  85 gtt cca gct aac cct cca cca gcg tca aca aat aga cag tct ggt aga       342
Val Pro Ala Asn Pro Pro Pro Ala Ser Thr Asn Arg Gln Ser Gly Arg
         90                  95                 100 caa cca acc cct att tct cct cct tta aga gac tct cat cct cag gcg       390
Gln Pro Thr Pro Ile Ser Pro Pro Leu Arg Asp Ser His Pro Gln Ala
    105                 110                 115 atg caa tgg aac tca acg acc ttt cat caa gct ctt ttg gac cct aga       438
Met Gln Trp Asn Ser Thr Thr Phe His Gln Ala Leu Leu Asp Pro Arg
120                 125                 130 gtc agg ggt tta tac ttc cca gct ggt gga tcc tca tcc ggc act gtt       486
Val Arg Gly Leu Tyr Phe Pro Ala Gly Gly Ser Ser Ser Gly Thr Val
135                 140                 145                 150 aat cct gtc cca act aca gca tca cca att tca tcc ata ttt tct aga       534
Asn Pro Val Pro Thr Thr Ala Ser Pro Ile Ser Ser Ile Phe Ser Arg
                155                 160                 165 act ggg gat cct gct ctt aat atg gaa aac att aca agc ggc ttc cta       582
Thr Gly Asp Pro Ala Leu Asn Met Glu Asn Ile Thr Ser Gly Phe Leu
            170                 175                 180 gga cca tta tta gtt cta caa gcc gga ttt ttc cta ttg act aga atc       630
Gly Pro Leu Leu Val Leu Gln Ala Gly Phe Phe Leu Leu Thr Arg Ile
        185                 190                 195 cta act att cct caa agt ctt gac tcc tgg tgg aca tcc ttg aat ttc       678
Leu Thr Ile Pro Gln Ser Leu Asp Ser Trp Trp Thr Ser Leu Asn Phe
    200                 205                 210 ctt ggc ggt aca aca aca tgt cca ggc caa aac tct caa tca cca act       726
Leu Gly Gly Thr Thr Thr Cys Pro Gly Gln Asn Ser Gln Ser Pro Thr
215                 220                 225                 230
```

-continued

| | | | | | | | | | | | | | | | | |
|---|---|---|---|---|---|---|---|---|---|---|---|---|---|---|---|---|
| tct | aat | cac | tct | cca | aca | tct | tgc | cct | cca | att | tgc | cca | ggt | tac | aga | 774 |
| Ser | Asn | His | Ser | Pro | Thr | Ser | Cys | Pro | Pro | Ile | Cys | Pro | Gly | Tyr | Arg | |
| | | | | 235 | | | | | 240 | | | | | 245 | | |
| tgg | atg | tgc | ttg | aga | agg | ttc | atc | att | ttt | ctg | ttc | atc | ctc | ttg | ttg | 822 |
| Trp | Met | Cys | Leu | Arg | Arg | Phe | Ile | Ile | Phe | Leu | Phe | Ile | Leu | Leu | Leu | |
| | | | 250 | | | | | 255 | | | | | 260 | | | |
| tgt | ttg | att | ttc | ctc | tta | gta | ttg | ctg | gac | tac | caa | ggc | atg | ctt | cca | 870 |
| Cys | Leu | Ile | Phe | Leu | Leu | Val | Leu | Leu | Asp | Tyr | Gln | Gly | Met | Leu | Pro | |
| | | 265 | | | | | 270 | | | | | 275 | | | | |
| gtc | tgc | cct | cta | ttg | cca | gga | act | tct | aca | acc | tca | aca | gga | cca | tgt | 918 |
| Val | Cys | Pro | Leu | Leu | Pro | Gly | Thr | Ser | Thr | Thr | Ser | Thr | Gly | Pro | Cys | |
| | 280 | | | | | 285 | | | | | 290 | | | | | |
| aaa | aca | tgt | act | atc | cct | gct | caa | gga | aca | tca | atg | ttt | cca | tct | tgt | 966 |
| Lys | Thr | Cys | Thr | Ile | Pro | Ala | Gln | Gly | Thr | Ser | Met | Phe | Pro | Ser | Cys | |
| 295 | | | | | 300 | | | | | 305 | | | | | 310 | |
| tgc | tgt | aca | aaa | cca | tca | gat | ggt | aat | tgt | act | tgt | ata | cca | ata | cca | 1014 |
| Cys | Cys | Thr | Lys | Pro | Ser | Asp | Gly | Asn | Cys | Thr | Cys | Ile | Pro | Ile | Pro | |
| | | | | 315 | | | | | 320 | | | | | 325 | | |
| agt | tca | tgg | gca | ttt | gcc | cgt | ttc | ctt | tgg | gag | tgg | gct | tct | gta | aga | 1062 |
| Ser | Ser | Trp | Ala | Phe | Ala | Arg | Phe | Leu | Trp | Glu | Trp | Ala | Ser | Val | Arg | |
| | | | 330 | | | | | 335 | | | | | 340 | | | |
| ttc | tct | tgg | tta | agt | ttg | cta | gtc | cca | ttc | gtg | cag | tgg | ttt | gtt | ggc | 1110 |
| Phe | Ser | Trp | Leu | Ser | Leu | Leu | Val | Pro | Phe | Val | Gln | Trp | Phe | Val | Gly | |
| | | 345 | | | | | 350 | | | | | 355 | | | | |
| ctg | tct | cca | act | gtt | tgg | tta | tct | gtt | att | tgg | atg | atg | tgg | tac | tgg | 1158 |
| Leu | Ser | Pro | Thr | Val | Trp | Leu | Ser | Val | Ile | Trp | Met | Met | Trp | Tyr | Trp | |
| | 360 | | | | | 365 | | | | | 370 | | | | | |
| ggt | cca | agc | cta | tac | tca | atc | gtg | tca | cct | ttt | atc | cca | ttg | cta | cct | 1206 |
| Gly | Pro | Ser | Leu | Tyr | Ser | Ile | Val | Ser | Pro | Phe | Ile | Pro | Leu | Leu | Pro | |
| 375 | | | | | 380 | | | | | 385 | | | | | 390 | |
| atc | ttt | ttc | tgc | ctc | tgg | gtt | tac | atc | gat | att | gac | cct | tac | aag | gaa | 1254 |
| Ile | Phe | Phe | Cys | Leu | Trp | Val | Tyr | Ile | Asp | Ile | Asp | Pro | Tyr | Lys | Glu | |
| | | | | 395 | | | | | 400 | | | | | 405 | | |
| ttt | ggc | gca | aca | gtt | gaa | ttg | tta | tca | ttt | tta | cca | tca | gat | ttc | ttt | 1302 |
| Phe | Gly | Ala | Thr | Val | Glu | Leu | Leu | Ser | Phe | Leu | Pro | Ser | Asp | Phe | Phe | |
| | | | 410 | | | | | 415 | | | | | 420 | | | |
| cca | tca | gtg | cgt | gat | ttg | tta | gat | acg | gca | tcc | gct | ttg | tac | aga | gaa | 1350 |
| Pro | Ser | Val | Arg | Asp | Leu | Leu | Asp | Thr | Ala | Ser | Ala | Leu | Tyr | Arg | Glu | |
| | | 425 | | | | | 430 | | | | | 435 | | | | |
| gca | ctg | gaa | tca | cca | gaa | cac | tgt | tct | cca | cat | cac | act | gct | ctc | aga | 1398 |
| Ala | Leu | Glu | Ser | Pro | Glu | His | Cys | Ser | Pro | His | His | Thr | Ala | Leu | Arg | |
| | 440 | | | | | 445 | | | | | 450 | | | | | |
| caa | gct | ata | ttg | tgt | tgg | gga | gag | ttg | atg | aat | cta | gcc | act | tgg | gta | 1446 |
| Gln | Ala | Ile | Leu | Cys | Trp | Gly | Glu | Leu | Met | Asn | Leu | Ala | Thr | Trp | Val | |
| 455 | | | | | 460 | | | | | 465 | | | | | 470 | |
| ggg | tcc | aat | ctg | gaa | gat | cct | gcc | tct | aga | gaa | ctg | gtg | gta | tct | tac | 1494 |
| Gly | Ser | Asn | Leu | Glu | Asp | Pro | Ala | Ser | Arg | Glu | Leu | Val | Val | Ser | Tyr | |
| | | | | 475 | | | | | 480 | | | | | 485 | | |
| gtc | aat | gtt | aac | atg | ggg | ttg | aag | att | aga | caa | ctt | tta | tgg | ttc | cat | 1542 |
| Val | Asn | Val | Asn | Met | Gly | Leu | Lys | Ile | Arg | Gln | Leu | Leu | Trp | Phe | His | |
| | | | 490 | | | | | 495 | | | | | 500 | | | |
| att | tca | tgt | tta | acg | ttt | ggt | aga | gaa | aca | gta | ctg | gaa | tac | tta | gtt | 1590 |
| Ile | Ser | Cys | Leu | Thr | Phe | Gly | Arg | Glu | Thr | Val | Leu | Glu | Tyr | Leu | Val | |
| | | 505 | | | | | 510 | | | | | 515 | | | | |
| agt | ttc | ggt | gtc | tgg | att | aga | aca | cca | cca | gca | tat | aga | cca | cca | aat | 1638 |
| Ser | Phe | Gly | Val | Trp | Ile | Arg | Thr | Pro | Pro | Ala | Tyr | Arg | Pro | Pro | Asn | |
| | 520 | | | | | 525 | | | | | 530 | | | | | |
| gcg | cct | ata | ttg | agt | acg | ctc | cca | gaa | acg | acg | gtc | gtt | agg | aga | aga | 1686 |
| Ala | Pro | Ile | Leu | Ser | Thr | Leu | Pro | Glu | Thr | Thr | Val | Val | Arg | Arg | Arg | |

-continued

```
          535                 540                 545                 550
ggt aga tca cct agg aga agg aca cct tca cct aga cgt aga cgt tct        1734
Gly Arg Ser Pro Arg Arg Arg Thr Pro Ser Pro Arg Arg Arg Ser
                    555                 560                 565 caa tct cca aga cgt aga aga tct caa tct aga gaa tca caa tgc ggt        1782
Gln Ser Pro Arg Arg Arg Ser Gln Ser Arg Glu Ser Gln Cys Gly
                570                 575                 580 cta tct aga tat gtc gcc cga cta tca tct aat tct cgt atc ttt aac        1830
Leu Ser Arg Tyr Val Ala Arg Leu Ser Ser Asn Ser Arg Ile Phe Asn
            585                 590                 595 cat caa cac ggc acc atg caa aat ctg cat gac tcc tgt agt aga aat        1878
His Gln His Gly Thr Met Gln Asn Leu His Asp Ser Cys Ser Arg Asn
        600                 605                 610 ctt tat gtg agt ctc ttg ctt ttg tac caa act ttc ggc aga aaa ttg        1926
Leu Tyr Val Ser Leu Leu Leu Leu Tyr Gln Thr Phe Gly Arg Lys Leu
615                 620                 625                 630 cac ctt tac tct cat cca att ata cta ggt ttt aga aaa atc cca atg        1974
His Leu Tyr Ser His Pro Ile Ile Leu Gly Phe Arg Lys Ile Pro Met
                    635                 640                 645 ggg gtg ggt tta tct cca ttt ttg ctt gcg caa ttc aca agt gca atc        2022
Gly Val Gly Leu Ser Pro Phe Leu Leu Ala Gln Phe Thr Ser Ala Ile
                650                 655                 660 tgt tct gtg gtt agg aga gct ttt cct cat tgc ctc gca ttt tca tac        2070
Cys Ser Val Val Arg Arg Ala Phe Pro His Cys Leu Ala Phe Ser Tyr
            665                 670                 675 atg gat gat gtt gtc tta ggt gcc aaa agt gta caa cat ttg gag agt        2118
Met Asp Asp Val Val Leu Gly Ala Lys Ser Val Gln His Leu Glu Ser
        680                 685                 690 ttg ttt aca gcc gta act aac ttt ctc ttg tca tta ggg atc cat ttg        2166
Leu Phe Thr Ala Val Thr Asn Phe Leu Leu Ser Leu Gly Ile His Leu
695                 700                 705                 710 aac cct aac aaa aca aaa aga tgg ggg tac tct cta cat ttt atg ggt        2214
Asn Pro Asn Lys Thr Lys Arg Trp Gly Tyr Ser Leu His Phe Met Gly
                    715                 720                 725 tat gtt ata ggc tgc tat gga tcc tta cct caa gac cat atc att cag        2262
Tyr Val Ile Gly Cys Tyr Gly Ser Leu Pro Gln Asp His Ile Ile Gln
                730                 735                 740 aaa atc aaa gag tgc ttt aga aag ttg cct gtt aat aga cca atc gac        2310
Lys Ile Lys Glu Cys Phe Arg Lys Leu Pro Val Asn Arg Pro Ile Asp
            745                 750                 755 tgg aag gtt tgt caa agg atc gtt ggt tta ctt ggt ttt gca gca cca        2358
Trp Lys Val Cys Gln Arg Ile Val Gly Leu Leu Gly Phe Ala Ala Pro
        760                 765                 770 ttc acc caa tgt ggc tac cct gct ctg atg cct tta tat gct tgt ata        2406
Phe Thr Gln Cys Gly Tyr Pro Ala Leu Met Pro Leu Tyr Ala Cys Ile
775                 780                 785                 790 caa tct aag caa gct ttt aca ttc tct cca acg tac aag gcc ttt tta        2454
Gln Ser Lys Gln Ala Phe Thr Phe Ser Pro Thr Tyr Lys Ala Phe Leu
                    795                 800                 805 tgc aaa caa cac tta tca cta aga gga ctt ttt gtg tgt gct ttc tct        2502
Cys Lys Gln His Leu Ser Leu Arg Gly Leu Phe Val Cys Ala Phe Ser
                810                 815                 820 tct gca ggc cca aat gca cac cag ttt ttg cct aaa gtg ttg cat aag        2550
Ser Ala Gly Pro Asn Ala His Gln Phe Leu Pro Lys Val Leu His Lys
            825                 830                 835 aga act cta ggc ttg tcc gca atg tcc aca act gat cta gaa gca tat        2598
Arg Thr Leu Gly Leu Ser Ala Met Ser Thr Thr Asp Leu Glu Ala Tyr
        840                 845                 850 ttc aaa gac tgt ctt ttt aag gat tgg gaa gag ttg ggt gaa gag            2643
Phe Lys Asp Cys Leu Phe Lys Asp Trp Glu Glu Leu Gly Glu Glu
```

```
Phe Lys Asp Cys Leu Phe Lys Asp Trp Glu Leu Gly Glu Glu
855                 860                 865
```

```
catcaccatc atcatcatta agcggccgc                                    2672
```

<210> SEQ ID NO 124
<211> LENGTH: 869
<212> TYPE: PRT
<213> ORGANISM: Artificial
<220> FEATURE:
<223> OTHER INFORMATION: Synthetic Construct
<400> SEQUENCE: 124

```
Gly Gln Trp Ser Ser Lys Pro Arg Lys Gly Met Gly Thr Asn Leu Ser
1               5                   10                  15

Val Ser Asn Pro Leu Gly Phe Phe Pro Asp His Gln Leu Asp Pro Ala
            20                  25                  30

Phe Arg Ala Asn Ser Ala Asn Pro Asp Trp Asp Phe Asn Pro Asn Lys
        35                  40                  45

Asp Thr Trp Pro Glu Ala Asn Gln Val Gly Val Gly Ala Phe Gly Leu
    50                  55                  60

Gly Phe Thr Pro Pro His Gly Gly Leu Leu Gly Trp Ser Pro Gln Ala
65                  70                  75                  80

Gln Gly Ile Leu Gln Thr Val Pro Ala Asn Pro Pro Ala Ser Thr
                85                  90                  95

Asn Arg Gln Ser Gly Arg Gln Pro Thr Pro Ile Ser Pro Pro Leu Arg
            100                 105                 110

Asp Ser His Pro Gln Ala Met Gln Trp Asn Ser Thr Thr Phe His Gln
        115                 120                 125

Ala Leu Leu Asp Pro Arg Val Arg Gly Leu Tyr Phe Pro Ala Gly Gly
    130                 135                 140

Ser Ser Ser Gly Thr Val Asn Pro Val Pro Thr Thr Ala Ser Pro Ile
145                 150                 155                 160

Ser Ser Ile Phe Ser Arg Thr Gly Asp Pro Ala Leu Asn Met Glu Asn
                165                 170                 175

Ile Thr Ser Gly Phe Leu Gly Pro Leu Leu Val Leu Gln Ala Gly Phe
            180                 185                 190

Phe Leu Leu Thr Arg Ile Leu Thr Ile Pro Gln Ser Leu Asp Ser Trp
        195                 200                 205

Trp Thr Ser Leu Asn Phe Leu Gly Gly Thr Thr Cys Pro Gly Gln
    210                 215                 220

Asn Ser Gln Ser Pro Thr Ser Asn His Ser Pro Thr Ser Cys Pro Pro
225                 230                 235                 240

Ile Cys Pro Gly Tyr Arg Trp Met Cys Leu Arg Arg Phe Ile Ile Phe
                245                 250                 255

Leu Phe Ile Leu Leu Leu Cys Leu Ile Phe Leu Leu Val Leu Leu Asp
            260                 265                 270

Tyr Gln Gly Met Leu Pro Val Cys Pro Leu Leu Pro Gly Thr Ser Thr
        275                 280                 285

Thr Ser Thr Gly Pro Cys Lys Thr Cys Thr Ile Pro Ala Gln Gly Thr
    290                 295                 300

Ser Met Phe Pro Ser Cys Cys Cys Thr Lys Pro Ser Asp Gly Asn Cys
305                 310                 315                 320

Thr Cys Ile Pro Ile Pro Ser Ser Trp Ala Phe Ala Arg Phe Leu Trp
                325                 330                 335

Glu Trp Ala Ser Val Arg Phe Ser Trp Leu Ser Leu Leu Val Pro Phe
```

-continued

```
            340                 345                 350
Val Gln Trp Phe Val Gly Leu Ser Pro Thr Val Trp Leu Ser Val Ile
            355                 360                 365

Trp Met Met Trp Tyr Trp Gly Pro Ser Leu Tyr Ser Ile Val Ser Pro
            370                 375                 380

Phe Ile Pro Leu Leu Pro Ile Phe Phe Cys Leu Trp Val Tyr Ile Asp
385                 390                 395                 400

Ile Asp Pro Tyr Lys Glu Phe Gly Ala Thr Val Glu Leu Leu Ser Phe
                405                 410                 415

Leu Pro Ser Asp Phe Phe Pro Ser Val Arg Asp Leu Leu Asp Thr Ala
                420                 425                 430

Ser Ala Leu Tyr Arg Glu Ala Leu Glu Ser Pro Glu His Cys Ser Pro
            435                 440                 445

His His Thr Ala Leu Arg Gln Ala Ile Leu Cys Trp Gly Glu Leu Met
            450                 455                 460

Asn Leu Ala Thr Trp Val Gly Ser Asn Leu Glu Asp Pro Ala Ser Arg
465                 470                 475                 480

Glu Leu Val Val Ser Tyr Val Asn Val Asn Met Gly Leu Lys Ile Arg
                485                 490                 495

Gln Leu Leu Trp Phe His Ile Ser Cys Leu Thr Phe Gly Arg Glu Thr
            500                 505                 510

Val Leu Glu Tyr Leu Val Ser Phe Gly Val Trp Ile Arg Thr Pro Pro
            515                 520                 525

Ala Tyr Arg Pro Pro Asn Ala Pro Ile Leu Ser Thr Leu Pro Glu Thr
            530                 535                 540

Thr Val Val Arg Arg Arg Gly Arg Ser Pro Arg Arg Thr Pro Ser
545                 550                 555                 560

Pro Arg Arg Arg Ser Gln Ser Pro Arg Arg Arg Ser Gln Ser
                565                 570                 575

Arg Glu Ser Gln Cys Gly Leu Ser Arg Tyr Val Ala Arg Leu Ser Ser
                580                 585                 590

Asn Ser Arg Ile Phe Asn His Gln His Gly Thr Met Gln Asn Leu His
            595                 600                 605

Asp Ser Cys Ser Arg Asn Leu Tyr Val Ser Leu Leu Leu Leu Tyr Gln
            610                 615                 620

Thr Phe Gly Arg Lys Leu His Leu Tyr Ser His Pro Ile Ile Leu Gly
625                 630                 635                 640

Phe Arg Lys Ile Pro Met Gly Val Gly Leu Ser Pro Phe Leu Leu Ala
                645                 650                 655

Gln Phe Thr Ser Ala Ile Cys Ser Val Val Arg Arg Ala Phe Pro His
            660                 665                 670

Cys Leu Ala Phe Ser Tyr Met Asp Asp Val Val Leu Gly Ala Lys Ser
            675                 680                 685

Val Gln His Leu Glu Ser Leu Phe Thr Ala Val Thr Asn Phe Leu Leu
            690                 695                 700

Ser Leu Gly Ile His Leu Asn Pro Asn Lys Thr Lys Arg Trp Gly Tyr
705                 710                 715                 720

Ser Leu His Phe Met Gly Tyr Val Ile Gly Cys Tyr Gly Ser Leu Pro
                725                 730                 735

Gln Asp His Ile Ile Gln Lys Ile Lys Glu Cys Phe Arg Lys Leu Pro
            740                 745                 750

Val Asn Arg Pro Ile Asp Trp Lys Val Cys Gln Arg Ile Val Gly Leu
            755                 760                 765
```

```
Leu Gly Phe Ala Ala Pro Phe Thr Gln Cys Gly Tyr Pro Ala Leu Met
    770                 775                 780
Pro Leu Tyr Ala Cys Ile Gln Ser Lys Gln Ala Phe Thr Phe Ser Pro
785                 790                 795                 800
Thr Tyr Lys Ala Phe Leu Cys Lys Gln His Leu Ser Leu Arg Gly Leu
            805                 810                 815
Phe Val Cys Ala Phe Ser Ser Ala Gly Pro Asn Ala His Gln Phe Leu
        820                 825                 830
Pro Lys Val Leu His Lys Arg Thr Leu Gly Leu Ser Ala Met Ser Thr
    835                 840                 845
Thr Asp Leu Glu Ala Tyr Phe Lys Asp Cys Leu Phe Lys Asp Trp Glu
    850                 855                 860
Glu Leu Gly Glu Glu
865

<210> SEQ ID NO 125
<211> LENGTH: 2672
<212> TYPE: DNA
<213> ORGANISM: Artificial
<220> FEATURE:
<223> OTHER INFORMATION: Synthetic Construct
<220> FEATURE:
<221> NAME/KEY: CDS
<222> LOCATION: (37)..(2643)

<400> SEQUENCE: 125
gaattcgcca ccatggccga tgaggcacct actagt ggt cag tgg tcc tcc aaa      54
                                        Gly Gln Trp Ser Ser Lys
                                         1               5 cct aga aag ggt atg ggt act aat ttg tct gta tct aac cct ctc gga    102
Pro Arg Lys Gly Met Gly Thr Asn Leu Ser Val Ser Asn Pro Leu Gly
             10                  15                  20 ttc ttt cca gat cac cag tta gat cca gct ttt cgt gct aac agt gcc    150
Phe Phe Pro Asp His Gln Leu Asp Pro Ala Phe Arg Ala Asn Ser Ala
         25                  30                  35 aac cca gat tgg gat ttc aat cct aat aag gat acc tgg cca gag gct    198
Asn Pro Asp Trp Asp Phe Asn Pro Asn Lys Asp Thr Trp Pro Glu Ala
 40                  45                  50 aac cag gta gga gtt gga gcc ttc ggt cta ggt ttt acc cca cct cac    246
Asn Gln Val Gly Val Gly Ala Phe Gly Leu Gly Phe Thr Pro Pro His
55                  60                  65                  70 ggt gga cta tta ggc tgg agc cca caa gca caa ggt atc ttg caa acc    294
Gly Gly Leu Leu Gly Trp Ser Pro Gln Ala Gln Gly Ile Leu Gln Thr
                 75                  80                  85 gtt cca gct aac cct cca cca gcg tca aca aat aga cag tct ggt aga    342
Val Pro Ala Asn Pro Pro Pro Ala Ser Thr Asn Arg Gln Ser Gly Arg
             90                  95                 100 caa cca acc cct att tct cct cct tta aga gac tct cat cct cag gcg    390
Gln Pro Thr Pro Ile Ser Pro Pro Leu Arg Asp Ser His Pro Gln Ala
        105                 110                 115 atg caa tgg aac tca acg acc ttt cat caa gct ctt ttg gac cct aga    438
Met Gln Trp Asn Ser Thr Thr Phe His Gln Ala Leu Leu Asp Pro Arg
    120                 125                 130 gtc agg ggt tta tac ttc cca gct ggt gga tcc tca tcc ggc act gtt    486
Val Arg Gly Leu Tyr Phe Pro Ala Gly Gly Ser Ser Ser Gly Thr Val
135                 140                 145                 150 aat cct gtc cca act aca gca tca cca att tca tcc ata ttt tct aga    534
Asn Pro Val Pro Thr Thr Ala Ser Pro Ile Ser Ser Ile Phe Ser Arg
                155                 160                 165
```

-continued

| | | |
|---|---|---|
| act ggg gat cct gct ctt aat atg gaa aac att aca agc ggc ttc cta<br>Thr Gly Asp Pro Ala Leu Asn Met Glu Asn Ile Thr Ser Gly Phe Leu<br>                170                        175                        180 | 582 |
| gga cca tta tta gtt cta caa gcc gga ttt ttc cta ttg act aga atc<br>Gly Pro Leu Leu Val Leu Gln Ala Gly Phe Phe Leu Leu Thr Arg Ile<br>        185                        190                        195 | 630 |
| cta act att cct caa agt ctt gac tcc tgg tgg aca tcc ttg aat ttc<br>Leu Thr Ile Pro Gln Ser Leu Asp Ser Trp Trp Thr Ser Leu Asn Phe<br>    200                        205                        210 | 678 |
| ctt ggc ggt aca aca aca tgt cca ggc caa aac tct caa tca cca act<br>Leu Gly Gly Thr Thr Thr Cys Pro Gly Gln Asn Ser Gln Ser Pro Thr<br>215                        220                        225                        230 | 726 |
| tct aat cac tct cca aca tct tgc cct cca att tgc cca ggt tac aga<br>Ser Asn His Ser Pro Thr Ser Cys Pro Pro Ile Cys Pro Gly Tyr Arg<br>                        235                        240                        245 | 774 |
| tgg atg tgc ttg aga agg ttc atc att ttt ctg ttc atc ctc ttg ttg<br>Trp Met Cys Leu Arg Arg Phe Ile Ile Phe Leu Phe Ile Leu Leu Leu<br>                250                        255                        260 | 822 |
| tgt ttg att ttc ctc tta gta ttg ctg gac tac caa ggc atg ctt cca<br>Cys Leu Ile Phe Leu Leu Val Leu Leu Asp Tyr Gln Gly Met Leu Pro<br>              265                        270                        275 | 870 |
| gtc tgc cct cta ttg cca gga act tct aca acc tca aca gga cca tgt<br>Val Cys Pro Leu Leu Pro Gly Thr Ser Thr Thr Ser Thr Gly Pro Cys<br>280                        285                                  290 | 918 |
| aaa aca tgt act atc cct gct caa gga aca tca atg ttt cca tct tgt<br>Lys Thr Cys Thr Ile Pro Ala Gln Gly Thr Ser Met Phe Pro Ser Cys<br>295                        300                        305                        310 | 966 |
| tgc tgt aca aaa cca tca gat ggt aat tgt act tgt ata cca ata cca<br>Cys Cys Thr Lys Pro Ser Asp Gly Asn Cys Thr Cys Ile Pro Ile Pro<br>                        315                        320                        325 | 1014 |
| agt tca tgg gca ttt gcc cgt ttc ctt tgg gag tgg gct tct gta aga<br>Ser Ser Trp Ala Phe Ala Arg Phe Leu Trp Glu Trp Ala Ser Val Arg<br>                330                        335                        340 | 1062 |
| ttc tct tgg tta agt ttg cta gtc cca ttc gtg cag tgg ttt gtt ggc<br>Phe Ser Trp Leu Ser Leu Leu Val Pro Phe Val Gln Trp Phe Val Gly<br>                  345                        350                        355 | 1110 |
| ctg tct cca act gtt tgg tta tct gtt att tgg atg atg tgg tac tgg<br>Leu Ser Pro Thr Val Trp Leu Ser Val Ile Trp Met Met Trp Tyr Trp<br>360                        365                                  370 | 1158 |
| ggt cca agc cta tac tca atc gtg tca cct ttt atc cca ttg cta cct<br>Gly Pro Ser Leu Tyr Ser Ile Val Ser Pro Phe Ile Pro Leu Leu Pro<br>375                        380                        385                        390 | 1206 |
| atc ttt ttc tgc ctc tgg gtt tac atc gat att gac cct tac aag gaa<br>Ile Phe Phe Cys Leu Trp Val Tyr Ile Asp Ile Asp Pro Tyr Lys Glu<br>                        395                        400                        405 | 1254 |
| ttt ggc gca aca gtt gaa ttg tta tca ttt tta cca tca gat ttc ttt<br>Phe Gly Ala Thr Val Glu Leu Leu Ser Phe Leu Pro Ser Asp Phe Phe<br>          410                        415                        420 | 1302 |
| cca tca gtg cgt gat ttg tta gat acg gca tcc gct ttg tac aga gaa<br>Pro Ser Val Arg Asp Leu Leu Asp Thr Ala Ser Ala Leu Tyr Arg Glu<br>                  425                        430                        435 | 1350 |
| gca ctg gaa tca cca gaa cac tgt tct cca cat cac act gct ctc aga<br>Ala Leu Glu Ser Pro Glu His Cys Ser Pro His His Thr Ala Leu Arg<br>440                        445                        450 | 1398 |
| caa gct ata ttg tgt tgg gga gag ttg atg aat cta gcc act tgg gta<br>Gln Ala Ile Leu Cys Trp Gly Glu Leu Met Asn Leu Ala Thr Trp Val<br>455                        460                        465                        470 | 1446 |
| ggg tcc aat ctg gaa gat cct gcc tct aga gaa ctg gtg gta tct tac<br>Gly Ser Asn Leu Glu Asp Pro Ala Ser Arg Glu Leu Val Val Ser Tyr<br>                  475                        480                        485 | 1494 |

```
gtc aat gtt aac atg ggg ttg aag att aga caa ctt tta tgg ttc cat    1542
Val Asn Val Asn Met Gly Leu Lys Ile Arg Gln Leu Leu Trp Phe His
            490                 495                 500 att tca tgt tta acg ttt ggt aga gaa aca gta ctg gaa tac tta gtt    1590
Ile Ser Cys Leu Thr Phe Gly Arg Glu Thr Val Leu Glu Tyr Leu Val
        505                 510                 515 agt ttc ggt gtc tgg att aga aca cca cca gca tat aga cca cca aat    1638
Ser Phe Gly Val Trp Ile Arg Thr Pro Pro Ala Tyr Arg Pro Pro Asn
    520                 525                 530 gcg cct ata ttg agt acg ctc cca gaa acg acg gtc gtt agg aga aga    1686
Ala Pro Ile Leu Ser Thr Leu Pro Glu Thr Thr Val Val Arg Arg Arg
535                 540                 545                 550 ggt aga tca cct agg aga agg aca cct tca cct aga cgt aga cgt tct    1734
Gly Arg Ser Pro Arg Arg Thr Pro Ser Pro Arg Arg Arg Ser
                555                 560                 565 caa tct cca aga cgt aga aga tct caa tct aga gaa tca caa tgc cac    1782
Gln Ser Pro Arg Arg Arg Ser Gln Ser Arg Glu Ser Gln Cys His
                570                 575                 580 ctc tca tta aga ggc cta ttt gtt tgt gca ttc tcc tct gct ggt cca    1830
Leu Ser Leu Arg Gly Leu Phe Val Cys Ala Phe Ser Ser Ala Gly Pro
            585                 590                 595 aat gct cac caa ttc ctt cct aaa gtc ctg cat aaa cgt acc ctc ggg    1878
Asn Ala His Gln Phe Leu Pro Lys Val Leu His Lys Arg Thr Leu Gly
        600                 605                 610 cta agt gca atg tct act act gac ctt gag gca tat ttc aaa gac tgc    1926
Leu Ser Ala Met Ser Thr Thr Asp Leu Glu Ala Tyr Phe Lys Asp Cys
615                 620                 625                 630 ttg ttt aaa gat tgg gaa gag ctt ggc gaa gag ggc ctt agt aga tat    1974
Leu Phe Lys Asp Trp Glu Glu Leu Gly Glu Glu Gly Leu Ser Arg Tyr
                635                 640                 645 gtt gcc cga tta tca tct aac tct aga atc ttt aat cat caa cat ggt    2022
Val Ala Arg Leu Ser Ser Asn Ser Arg Ile Phe Asn His Gln His Gly
            650                 655                 660 aca atg caa aac cta cat gat tca tgc tct aga aac ttg tac gtg tcc    2070
Thr Met Gln Asn Leu His Asp Ser Cys Ser Arg Asn Leu Tyr Val Ser
        665                 670                 675 tta ttg ctt cta tat caa act ttt ggt aga aag ttg cac ctg tac agt    2118
Leu Leu Leu Leu Tyr Gln Thr Phe Gly Arg Lys Leu His Leu Tyr Ser
    680                 685                 690 cac cca atc atc tta ggc ttt aga aag atc cca atg ggt gta ggt tta    2166
His Pro Ile Ile Leu Gly Phe Arg Lys Ile Pro Met Gly Val Gly Leu
695                 700                 705                 710 tcc cca ttt ttg ctg gca caa ttc aca tct gca atc tgt agt gtt gta    2214
Ser Pro Phe Leu Leu Ala Gln Phe Thr Ser Ala Ile Cys Ser Val Val
                715                 720                 725 cga aga gcc ttt cca cat tgt ttg gct ttt agc tat atg gat gac gtt    2262
Arg Arg Ala Phe Pro His Cys Leu Ala Phe Ser Tyr Met Asp Asp Val
            730                 735                 740 gta ttg ggg gct aaa agc gtg caa cat ctc gaa tct ctg ttt aca gcg    2310
Val Leu Gly Ala Lys Ser Val Gln His Leu Glu Ser Leu Phe Thr Ala
        745                 750                 755 gtt act aat ttt ctg ctt tca ttg gga ata cat cta aac cct aat aag    2358
Val Thr Asn Phe Leu Leu Ser Leu Gly Ile His Leu Asn Pro Asn Lys
    760                 765                 770 aca aaa aga tgg ggc tac tct ttg cat ttt atg gga tac gtg ata ggg    2406
Thr Lys Arg Trp Gly Tyr Ser Leu His Phe Met Gly Tyr Val Ile Gly
775                 780                 785                 790 tgt tat ggt agt tta cca caa gac cat atc atc caa aag ata aag gaa    2454
Cys Tyr Gly Ser Leu Pro Gln Asp His Ile Ile Gln Lys Ile Lys Glu
```

-continued

```
                      795                 800                 805
tgt ttt aga aag tta cca gtc aat aga cct att gat tgg aaa gtg tgt    2502
Cys Phe Arg Lys Leu Pro Val Asn Arg Pro Ile Asp Trp Lys Val Cys
        810                 815                 820 cag aga atc gtt ggt ttg tta ggg ttt gct gct cca ttc aca caa tgt    2550
Gln Arg Ile Val Gly Leu Leu Gly Phe Ala Ala Pro Phe Thr Gln Cys
825                 830                 835 ggt tac cct gcc ctt atg cct ttg tat gca tgc att caa tcc aaa cag    2598
Gly Tyr Pro Ala Leu Met Pro Leu Tyr Ala Cys Ile Gln Ser Lys Gln
840                 845                 850 gct ttt aca ttt tct cca act tac aaa gcc ttc ctt tgc aaa caa        2643
Ala Phe Thr Phe Ser Pro Thr Tyr Lys Ala Phe Leu Cys Lys Gln
855                 860                 865 catcatcacc atcatcatta agcggccgc                                    2672
```

<210> SEQ ID NO 126
<211> LENGTH: 869
<212> TYPE: PRT
<213> ORGANISM: Artificial
<220> FEATURE:
<223> OTHER INFORMATION: Synthetic Construct

<400> SEQUENCE: 126

```
Gly Gln Trp Ser Ser Lys Pro Arg Lys Gly Met Gly Thr Asn Leu Ser
1               5                   10                  15

Val Ser Asn Pro Leu Gly Phe Phe Pro Asp His Gln Leu Asp Pro Ala
                20                  25                  30

Phe Arg Ala Asn Ser Ala Asn Pro Asp Trp Asp Phe Asn Pro Asn Lys
            35                  40                  45

Asp Thr Trp Pro Glu Ala Asn Gln Val Gly Val Gly Ala Phe Gly Leu
        50                  55                  60

Gly Phe Thr Pro Pro His Gly Gly Leu Leu Gly Trp Ser Pro Gln Ala
65                  70                  75                  80

Gln Gly Ile Leu Gln Thr Val Pro Ala Asn Pro Pro Ala Ser Thr
                85                  90                  95

Asn Arg Gln Ser Gly Arg Gln Pro Thr Pro Ile Ser Pro Pro Leu Arg
            100                 105                 110

Asp Ser His Pro Gln Ala Met Gln Trp Asn Ser Thr Thr Phe His Gln
        115                 120                 125

Ala Leu Leu Asp Pro Arg Val Arg Gly Leu Tyr Phe Pro Ala Gly Gly
    130                 135                 140

Ser Ser Ser Gly Thr Val Asn Pro Val Pro Thr Thr Ala Ser Pro Ile
145                 150                 155                 160

Ser Ser Ile Phe Ser Arg Thr Gly Asp Pro Ala Leu Asn Met Glu Asn
                165                 170                 175

Ile Thr Ser Gly Phe Leu Gly Pro Leu Leu Val Leu Gln Ala Gly Phe
            180                 185                 190

Phe Leu Leu Thr Arg Ile Leu Thr Ile Pro Gln Ser Leu Asp Ser Trp
        195                 200                 205

Trp Thr Ser Leu Asn Phe Leu Gly Gly Thr Thr Thr Cys Pro Gly Gln
    210                 215                 220

Asn Ser Gln Ser Pro Thr Ser Asn His Ser Pro Thr Ser Cys Pro Pro
225                 230                 235                 240

Ile Cys Pro Gly Tyr Arg Trp Met Cys Leu Arg Arg Phe Ile Ile Phe
                245                 250                 255

Leu Phe Ile Leu Leu Leu Cys Leu Ile Phe Leu Leu Val Leu Leu Asp
```

```
                260                 265                 270
Tyr Gln Gly Met Leu Pro Val Cys Pro Leu Pro Gly Thr Ser Thr
            275                 280                 285
Thr Ser Thr Gly Pro Cys Lys Thr Cys Thr Ile Pro Ala Gln Gly Thr
        290                 295                 300
Ser Met Phe Pro Ser Cys Cys Cys Thr Lys Pro Ser Asp Gly Asn Cys
305                 310                 315                 320
Thr Cys Ile Pro Ile Pro Ser Ser Trp Ala Phe Ala Arg Phe Leu Trp
                325                 330                 335
Glu Trp Ala Ser Val Arg Phe Ser Trp Leu Ser Leu Leu Val Pro Phe
            340                 345                 350
Val Gln Trp Phe Val Gly Leu Ser Pro Thr Val Trp Leu Ser Val Ile
            355                 360                 365
Trp Met Met Trp Tyr Trp Gly Pro Ser Leu Tyr Ser Ile Val Ser Pro
        370                 375                 380
Phe Ile Pro Leu Leu Pro Ile Phe Phe Cys Leu Trp Val Tyr Ile Asp
385                 390                 395                 400
Ile Asp Pro Tyr Lys Glu Phe Gly Ala Thr Val Glu Leu Leu Ser Phe
                405                 410                 415
Leu Pro Ser Asp Phe Phe Pro Ser Val Arg Asp Leu Leu Asp Thr Ala
            420                 425                 430
Ser Ala Leu Tyr Arg Glu Ala Leu Glu Ser Pro Glu His Cys Ser Pro
            435                 440                 445
His His Thr Ala Leu Arg Gln Ala Ile Leu Cys Trp Gly Glu Leu Met
        450                 455                 460
Asn Leu Ala Thr Trp Val Gly Ser Asn Leu Glu Asp Pro Ala Ser Arg
465                 470                 475                 480
Glu Leu Val Val Ser Tyr Val Asn Val Asn Met Gly Leu Lys Ile Arg
                485                 490                 495
Gln Leu Leu Trp Phe His Ile Ser Cys Leu Thr Phe Gly Arg Glu Thr
            500                 505                 510
Val Leu Glu Tyr Leu Val Ser Phe Gly Val Trp Ile Arg Thr Pro Pro
            515                 520                 525
Ala Tyr Arg Pro Pro Asn Ala Pro Ile Leu Ser Thr Leu Pro Glu Thr
        530                 535                 540
Thr Val Val Arg Arg Arg Gly Arg Ser Pro Arg Arg Arg Thr Pro Ser
545                 550                 555                 560
Pro Arg Arg Arg Arg Ser Gln Ser Pro Arg Arg Arg Arg Ser Gln Ser
                565                 570                 575
Arg Glu Ser Gln Cys His Leu Ser Leu Arg Gly Leu Phe Val Cys Ala
            580                 585                 590
Phe Ser Ser Ala Gly Pro Asn His Gln Phe Leu Pro Lys Val Leu
            595                 600                 605
His Lys Arg Thr Leu Gly Leu Ser Ala Met Ser Thr Thr Asp Leu Glu
        610                 615                 620
Ala Tyr Phe Lys Asp Cys Leu Phe Lys Asp Trp Glu Glu Leu Gly Glu
625                 630                 635                 640
Glu Gly Leu Ser Arg Tyr Val Ala Arg Leu Ser Ser Asn Ser Arg Ile
                645                 650                 655
Phe Asn His Gln His Gly Thr Met Gln Asn Leu His Asp Ser Cys Ser
            660                 665                 670
Arg Asn Leu Tyr Val Ser Leu Leu Leu Leu Tyr Gln Thr Phe Gly Arg
            675                 680                 685
```

```
Lys Leu His Leu Tyr Ser His Pro Ile Ile Leu Gly Phe Arg Lys Ile
    690                 695                 700

Pro Met Gly Val Gly Leu Ser Pro Phe Leu Leu Ala Gln Phe Thr Ser
705                 710                 715                 720

Ala Ile Cys Ser Val Val Arg Arg Ala Phe Pro His Cys Leu Ala Phe
                725                 730                 735

Ser Tyr Met Asp Asp Val Val Leu Gly Ala Lys Ser Val Gln His Leu
            740                 745                 750

Glu Ser Leu Phe Thr Ala Val Thr Asn Phe Leu Leu Ser Leu Gly Ile
        755                 760                 765

His Leu Asn Pro Asn Lys Thr Lys Arg Trp Gly Tyr Ser Leu His Phe
    770                 775                 780

Met Gly Tyr Val Ile Gly Cys Tyr Gly Ser Leu Pro Gln Asp His Ile
785                 790                 795                 800

Ile Gln Lys Ile Lys Glu Cys Phe Arg Lys Leu Pro Val Asn Arg Pro
                805                 810                 815

Ile Asp Trp Lys Val Cys Gln Arg Ile Val Gly Leu Leu Gly Phe Ala
            820                 825                 830

Ala Pro Phe Thr Gln Cys Gly Tyr Pro Ala Leu Met Pro Leu Tyr Ala
        835                 840                 845

Cys Ile Gln Ser Lys Gln Ala Phe Thr Phe Ser Pro Thr Tyr Lys Ala
    850                 855                 860

Phe Leu Cys Lys Gln
865

<210> SEQ ID NO 127
<211> LENGTH: 2498
<212> TYPE: DNA
<213> ORGANISM: Artificial
<220> FEATURE:
<223> OTHER INFORMATION: Synthetic Construct
<220> FEATURE:
<221> NAME/KEY: CDS
<222> LOCATION: (37)..(2469)

<400> SEQUENCE: 127
gaattcgcca ccatggccga cgaggcacca actagt gga ttg tct aga tat gtt        54
                                       Gly Leu Ser Arg Tyr Val
                                        1               5 gct aga ctg tca tct aac tct cgt atc ttt aac cac caa cat ggt aca       102
Ala Arg Leu Ser Ser Asn Ser Arg Ile Phe Asn His Gln His Gly Thr
         10                  15                  20 atg caa aat cta cat gac tca tgt tca agg aat ctt tac gtt tca tta       150
Met Gln Asn Leu His Asp Ser Cys Ser Arg Asn Leu Tyr Val Ser Leu
     25                  30                  35 cta ctt ttg tac caa acc ttc ggc aga aaa ctg cac ctt tac tca cat       198
Leu Leu Leu Tyr Gln Thr Phe Gly Arg Lys Leu His Leu Tyr Ser His
 40                  45                  50 cct atc atc tta ggc ttc aga aag atc cca atg ggt gtg ggg tta tct       246
Pro Ile Ile Leu Gly Phe Arg Lys Ile Pro Met Gly Val Gly Leu Ser
55                  60                  65                  70 cca ttt ctg tta gcc cag ttt aca tca gct att tgc agt gtg gtt cgt       294
Pro Phe Leu Leu Ala Gln Phe Thr Ser Ala Ile Cys Ser Val Val Arg
                 75                  80                  85 aga gct ttt cca cat tgt ttg gcc ttt tcc tat atg gat gat gtt gtc       342
Arg Ala Phe Pro His Cys Leu Ala Phe Ser Tyr Met Asp Asp Val Val
             90                  95                 100 tta gga gct aaa agt gtc caa cac tta gaa tct ctt ttc aca gct gtc       390
```

```
                Leu Gly Ala Lys Ser Val Gln His Leu Glu Ser Leu Phe Thr Ala Val
                    105                 110                 115 aca aac ttc cta ctt tca tta ggt att cac tta aac cca aac aaa acc          438
Thr Asn Phe Leu Leu Ser Leu Gly Ile His Leu Asn Pro Asn Lys Thr
120                 125                 130 aag aga tgg ggt tac tca ttg cac ttt atg ggt tac gta atc gga tgt          486
Lys Arg Trp Gly Tyr Ser Leu His Phe Met Gly Tyr Val Ile Gly Cys
135                 140                 145                 150 tat ggc tct tta cct cag gat cac atc atc cag aag ata aag gaa tgt          534
Tyr Gly Ser Leu Pro Gln Asp His Ile Ile Gln Lys Ile Lys Glu Cys
                    155                 160                 165 ttt aga aag cta cct gtc aat aga cct att gat tgg aaa gtt tgt cag          582
Phe Arg Lys Leu Pro Val Asn Arg Pro Ile Asp Trp Lys Val Cys Gln
                170                 175                 180 aga ata gta ggt ttg cta ggg ttt gct gct cca ttc act caa tgc ggg          630
Arg Ile Val Gly Leu Leu Gly Phe Ala Ala Pro Phe Thr Gln Cys Gly
            185                 190                 195 tac cct gca cta atg cct ttg tac gct tgc atc caa tca aaa caa gca          678
Tyr Pro Ala Leu Met Pro Leu Tyr Ala Cys Ile Gln Ser Lys Gln Ala
200                 205                 210 ttc acc ttc tca cca act tac aag gca ttc ctt tgc aaa caa ctc gag          726
Phe Thr Phe Ser Pro Thr Tyr Lys Ala Phe Leu Cys Lys Gln Leu Glu
215                 220                 225                 230 gga caa tgg tcc tca aag cca agg aaa ggt atg ggt aca aac ttg agt          774
Gly Gln Trp Ser Ser Lys Pro Arg Lys Gly Met Gly Thr Asn Leu Ser
                    235                 240                 245 gtt tca aac cca ctt ggc ttt ttc cca gac cat caa ctt gat cca gca          822
Val Ser Asn Pro Leu Gly Phe Phe Pro Asp His Gln Leu Asp Pro Ala
                250                 255                 260 ttc aga gca aac tct gcc aac cca gac tgg gat ttc aat cca aac aaa          870
Phe Arg Ala Asn Ser Ala Asn Pro Asp Trp Asp Phe Asn Pro Asn Lys
            265                 270                 275 gat acc tgg cct gaa gca aat caa gtt gga gtg ggg gca ttt ggt ttg          918
Asp Thr Trp Pro Glu Ala Asn Gln Val Gly Val Gly Ala Phe Gly Leu
280                 285                 290 ggc ttc act cca cca cac gga ggg ttg ctt gga tgg agt cca cag gct          966
Gly Phe Thr Pro Pro His Gly Gly Leu Leu Gly Trp Ser Pro Gln Ala
295                 300                 305                 310 caa ggc att ttg caa act gtt cca gct aat cct cct cct gct tca acc         1014
Gln Gly Ile Leu Gln Thr Val Pro Ala Asn Pro Pro Pro Ala Ser Thr
                    315                 320                 325 aat aga caa tct ggt aga caa cct aca cca att tca cct cca ctt aga         1062
Asn Arg Gln Ser Gly Arg Gln Pro Thr Pro Ile Ser Pro Pro Leu Arg
                330                 335                 340 gac tct cat cct cag gca atg caa tgg aac tca act acc ttc cat caa         1110
Asp Ser His Pro Gln Ala Met Gln Trp Asn Ser Thr Thr Phe His Gln
            345                 350                 355 gct ctg ttg gat cct aga gtt aga ggt ctg tat ttc cca gct ggc gga         1158
Ala Leu Leu Asp Pro Arg Val Arg Gly Leu Tyr Phe Pro Ala Gly Gly
360                 365                 370 tca tct agt ggt acc gtg aat cca gta cct act aca gcc tct cca atc         1206
Ser Ser Ser Gly Thr Val Asn Pro Val Pro Thr Thr Ala Ser Pro Ile
375                 380                 385                 390 agt tcc atc ttt agt aga act ggc gac cct gcc ttg aat atg gag aac         1254
Ser Ser Ile Phe Ser Arg Thr Gly Asp Pro Ala Leu Asn Met Glu Asn
                    395                 400                 405 atc aca tct gga ttc ctg ggg cca ttg cta gtc cta caa gct ggg ttt         1302
Ile Thr Ser Gly Phe Leu Gly Pro Leu Leu Val Leu Gln Ala Gly Phe
                410                 415                 420
```

-continued

| | | |
|---|---|---|
| ttc cta ttg act aga atc ttg aca att cca cag agt tta gac tcc tgg<br>Phe Leu Leu Thr Arg Ile Leu Thr Ile Pro Gln Ser Leu Asp Ser Trp<br>425 430 435 | 1350 | |
| tgg acc agt cta aac ttt ttg ggt ggc aca aca aca tgt cct ggc caa<br>Trp Thr Ser Leu Asn Phe Leu Gly Gly Thr Thr Thr Cys Pro Gly Gln<br>440 445 450 | 1398 | |
| aac tct cag tct cca aca agt aac cac tct cct act tca tgt cca cca<br>Asn Ser Gln Ser Pro Thr Ser Asn His Ser Pro Thr Ser Cys Pro Pro<br>455 460 465 470 | 1446 | |
| att tgt cct ggt tac aga tgg atg tgc ctc aga agg ttt atc att ttc<br>Ile Cys Pro Gly Tyr Arg Trp Met Cys Leu Arg Arg Phe Ile Ile Phe<br>475 480 485 | 1494 | |
| ctt ttc ata ttg tta ttg tgc ctc ata ttc cta ttg gta tta ttg gat<br>Leu Phe Ile Leu Leu Leu Cys Leu Ile Phe Leu Leu Val Leu Leu Asp<br>490 495 500 | 1542 | |
| tac caa ggg atg ctt cct gtc tgt cca ttg ctc cct ggt acg agt aca<br>Tyr Gln Gly Met Leu Pro Val Cys Pro Leu Leu Pro Gly Thr Ser Thr<br>505 510 515 | 1590 | |
| aca tct act ggc cca tgc aaa aca tgc acc ata cca gcg caa ggt aca<br>Thr Ser Thr Gly Pro Cys Lys Thr Cys Thr Ile Pro Ala Gln Gly Thr<br>520 525 530 | 1638 | |
| agc atg ttt cca tcc tgt tgt gca aca aaa cca tcc gat ggc aat tgc<br>Ser Met Phe Pro Ser Cys Cys Cys Thr Lys Pro Ser Asp Gly Asn Cys<br>535 540 545 550 | 1686 | |
| aca tgc att cca ata cca tct tca tgg gcc ttc gct cgt ttc cta tgg<br>Thr Cys Ile Pro Ile Pro Ser Ser Trp Ala Phe Ala Arg Phe Leu Trp<br>555 560 565 | 1734 | |
| gaa tgg gcc tca gtt aga ttt tcc tgg tta tca ttg ttg gtc cca ttt<br>Glu Trp Ala Ser Val Arg Phe Ser Trp Leu Ser Leu Leu Val Pro Phe<br>570 575 580 | 1782 | |
| gtg caa tgg ttt gta ggt tta tcc cca acc gtc tgg tta tct gta ata<br>Val Gln Trp Phe Val Gly Leu Ser Pro Thr Val Trp Leu Ser Val Ile<br>585 590 595 | 1830 | |
| tgg atg atg tgg tat tgg ggt cca agt tta tac tca atc gtt tca cct<br>Trp Met Met Trp Tyr Trp Gly Pro Ser Leu Tyr Ser Ile Val Ser Pro<br>600 605 610 | 1878 | |
| ttt atc cct ttg ctg cca atc ttt ttc tgt ttg tgg gtt tac att gat<br>Phe Ile Pro Leu Leu Pro Ile Phe Phe Cys Leu Trp Val Tyr Ile Asp<br>615 620 625 630 | 1926 | |
| att gat cct tac aag gag ttt ggt gct act gtt gag tta cta tcc ttt<br>Ile Asp Pro Tyr Lys Glu Phe Gly Ala Thr Val Glu Leu Leu Ser Phe<br>635 640 645 | 1974 | |
| tta cct tct gac ttt ttc cct tct gtc aga gat ctt ttg gat act gct<br>Leu Pro Ser Asp Phe Phe Pro Ser Val Arg Asp Leu Leu Asp Thr Ala<br>650 655 660 | 2022 | |
| tct gct tta tac aga gaa gct ttg gaa tca cca gaa cat tgt tca cct<br>Ser Ala Leu Tyr Arg Glu Ala Leu Glu Ser Pro Glu His Cys Ser Pro<br>665 670 675 | 2070 | |
| cat cat acc gcc tta aga caa gca att ctg tgt tgg ggc gaa tta atg<br>His His Thr Ala Leu Arg Gln Ala Ile Leu Cys Trp Gly Glu Leu Met<br>680 685 690 | 2118 | |
| aac cta gca aca tgg gtg ggt tcc aat ttg gaa gat cca gca tcc aga<br>Asn Leu Ala Thr Trp Val Gly Ser Asn Leu Glu Asp Pro Ala Ser Arg<br>695 700 705 710 | 2166 | |
| gag tta gtg gtt agc tac gtg aat gtc aac atg ggc ttg aaa atc aga<br>Glu Leu Val Val Ser Tyr Val Asn Val Asn Met Gly Leu Lys Ile Arg<br>715 720 725 | 2214 | |
| cag tta ctt tgg ttc cat atc tct tgt ctg aca ttt ggt aga gaa aca<br>Gln Leu Leu Trp Phe His Ile Ser Cys Leu Thr Phe Gly Arg Glu Thr<br>730 735 740 | 2262 | |

```
gtt ctg gaa tat ctc gtt agc ttt gga gta tgg att aga act cca cca    2310
Val Leu Glu Tyr Leu Val Ser Phe Gly Val Trp Ile Arg Thr Pro Pro
        745                 750                 755 gcc tac aga cca cct aat gca cca ata ttg tca acc ctc cca gag aca    2358
Ala Tyr Arg Pro Pro Asn Ala Pro Ile Leu Ser Thr Leu Pro Glu Thr
    760                 765                 770 aca gtt gtg agg aga aga gga aga tct cct cgt cgt aga act cca tct    2406
Thr Val Val Arg Arg Arg Gly Arg Ser Pro Arg Arg Thr Pro Ser
775                 780                 785                 790 cca aga cga agg aga tca caa agt cct aga cga cgt aga tct caa tct    2454
Pro Arg Arg Arg Ser Gln Ser Pro Arg Arg Arg Ser Gln Ser
                795                 800                 805 aga gag tct caa tgt caccaccatc accatcatta agcggccgc                 2498
Arg Glu Ser Gln Cys
            810
```

<210> SEQ ID NO 128
<211> LENGTH: 811
<212> TYPE: PRT
<213> ORGANISM: Artificial
<220> FEATURE:
<223> OTHER INFORMATION: Synthetic Construct

<400> SEQUENCE: 128

```
Gly Leu Ser Arg Tyr Val Ala Arg Leu Ser Ser Asn Ser Arg Ile Phe
1               5                   10                  15

Asn His Gln His Gly Thr Met Gln Asn Leu His Asp Ser Cys Ser Arg
            20                  25                  30

Asn Leu Tyr Val Ser Leu Leu Leu Tyr Gln Thr Phe Gly Arg Lys
        35                  40                  45

Leu His Leu Tyr Ser His Pro Ile Ile Leu Gly Phe Arg Lys Ile Pro
    50                  55                  60

Met Gly Val Gly Leu Ser Pro Phe Leu Leu Ala Gln Phe Thr Ser Ala
65                  70                  75                  80

Ile Cys Ser Val Val Arg Arg Ala Phe Pro His Cys Leu Ala Phe Ser
                85                  90                  95

Tyr Met Asp Asp Val Val Leu Gly Ala Lys Ser Val Gln His Leu Glu
            100                 105                 110

Ser Leu Phe Thr Ala Val Thr Asn Phe Leu Leu Ser Leu Gly Ile His
        115                 120                 125

Leu Asn Pro Asn Lys Thr Lys Arg Trp Gly Tyr Ser Leu His Phe Met
    130                 135                 140

Gly Tyr Val Ile Gly Cys Tyr Gly Ser Leu Pro Gln Asp His Ile Ile
145                 150                 155                 160

Gln Lys Ile Lys Glu Cys Phe Arg Lys Leu Pro Val Asn Arg Pro Ile
                165                 170                 175

Asp Trp Lys Val Cys Gln Arg Ile Val Gly Leu Leu Gly Phe Ala Ala
            180                 185                 190

Pro Phe Thr Gln Cys Gly Tyr Pro Ala Leu Met Pro Leu Tyr Ala Cys
        195                 200                 205

Ile Gln Ser Lys Gln Ala Phe Thr Phe Ser Pro Thr Tyr Lys Ala Phe
    210                 215                 220

Leu Cys Lys Gln Leu Glu Gly Gln Trp Ser Ser Lys Pro Arg Lys Gly
225                 230                 235                 240

Met Gly Thr Asn Leu Ser Val Ser Asn Pro Leu Gly Phe Phe Pro Asp
                245                 250                 255
```

```
His Gln Leu Asp Pro Ala Phe Arg Ala Asn Ser Ala Asn Pro Asp Trp
            260                 265                 270

Asp Phe Asn Pro Asn Lys Asp Thr Trp Pro Glu Ala Asn Gln Val Gly
        275                 280                 285

Val Gly Ala Phe Gly Leu Gly Phe Thr Pro Pro His Gly Gly Leu Leu
    290                 295                 300

Gly Trp Ser Pro Gln Ala Gln Gly Ile Leu Gln Thr Val Pro Ala Asn
305                 310                 315                 320

Pro Pro Pro Ala Ser Thr Asn Arg Gln Ser Gly Arg Gln Pro Thr Pro
                325                 330                 335

Ile Ser Pro Pro Leu Arg Asp Ser His Pro Gln Ala Met Gln Trp Asn
            340                 345                 350

Ser Thr Thr Phe His Gln Ala Leu Leu Asp Pro Arg Val Arg Gly Leu
        355                 360                 365

Tyr Phe Pro Ala Gly Gly Ser Ser Gly Thr Val Asn Pro Val Pro
    370                 375                 380

Thr Thr Ala Ser Pro Ile Ser Ser Ile Phe Ser Arg Thr Gly Asp Pro
385                 390                 395                 400

Ala Leu Asn Met Glu Asn Ile Thr Ser Gly Phe Leu Gly Pro Leu Leu
                405                 410                 415

Val Leu Gln Ala Gly Phe Phe Leu Leu Thr Arg Ile Leu Thr Ile Pro
            420                 425                 430

Gln Ser Leu Asp Ser Trp Trp Thr Ser Leu Asn Phe Leu Gly Gly Thr
        435                 440                 445

Thr Thr Cys Pro Gly Gln Asn Ser Gln Ser Pro Thr Ser Asn His Ser
    450                 455                 460

Pro Thr Ser Cys Pro Pro Ile Cys Pro Gly Tyr Arg Trp Met Cys Leu
465                 470                 475                 480

Arg Arg Phe Ile Ile Phe Leu Phe Ile Leu Leu Leu Cys Leu Ile Phe
                485                 490                 495

Leu Leu Val Leu Leu Asp Tyr Gln Gly Met Leu Pro Val Cys Pro Leu
            500                 505                 510

Leu Pro Gly Thr Ser Thr Thr Ser Thr Gly Pro Cys Lys Thr Cys Thr
        515                 520                 525

Ile Pro Ala Gln Gly Thr Ser Met Phe Pro Ser Cys Cys Cys Thr Lys
    530                 535                 540

Pro Ser Asp Gly Asn Cys Thr Cys Ile Pro Ile Pro Ser Ser Trp Ala
545                 550                 555                 560

Phe Ala Arg Phe Leu Trp Glu Trp Ala Ser Val Arg Phe Ser Trp Leu
                565                 570                 575

Ser Leu Leu Val Pro Phe Val Gln Trp Phe Val Gly Leu Ser Pro Thr
            580                 585                 590

Val Trp Leu Ser Val Ile Trp Met Met Trp Tyr Trp Gly Pro Ser Leu
        595                 600                 605

Tyr Ser Ile Val Ser Pro Phe Ile Pro Leu Leu Pro Ile Phe Phe Cys
    610                 615                 620

Leu Trp Val Tyr Ile Asp Ile Asp Pro Tyr Lys Glu Phe Gly Ala Thr
625                 630                 635                 640

Val Glu Leu Leu Ser Phe Leu Pro Ser Asp Phe Phe Pro Ser Val Arg
                645                 650                 655

Asp Leu Leu Asp Thr Ala Ser Ala Leu Tyr Arg Glu Ala Leu Glu Ser
            660                 665                 670

Pro Glu His Cys Ser Pro His His Thr Ala Leu Arg Gln Ala Ile Leu
```

```
                675                 680                 685
    Cys Trp Gly Glu Leu Met Asn Leu Ala Thr Trp Val Gly Ser Asn Leu
        690                 695                 700

Glu Asp Pro Ala Ser Arg Glu Leu Val Val Ser Tyr Val Asn Val Asn
    705                 710                 715                 720

Met Gly Leu Lys Ile Arg Gln Leu Leu Trp Phe His Ile Ser Cys Leu
                725                 730                 735

Thr Phe Gly Arg Glu Thr Val Leu Glu Tyr Leu Val Ser Phe Gly Val
                    740                 745                 750

Trp Ile Arg Thr Pro Pro Ala Tyr Arg Pro Asn Ala Pro Ile Leu
                755                 760                 765

Ser Thr Leu Pro Glu Thr Thr Val Val Arg Arg Gly Arg Ser Pro
        770                 775                 780

Arg Arg Arg Thr Pro Ser Pro Arg Arg Arg Ser Gln Ser Pro Arg
    785                 790                 795                 800

Arg Arg Arg Ser Gln Ser Arg Glu Ser Gln Cys
                    805                 810

<210> SEQ ID NO 129
<211> LENGTH: 1994
<212> TYPE: DNA
<213> ORGANISM: Artificial
<220> FEATURE:
<223> OTHER INFORMATION: Synthetic Construct
<220> FEATURE:
<221> NAME/KEY: CDS
<222> LOCATION: (37)..(1965)

<400> SEQUENCE: 129
gaattcgcca ccatggccga cgaggcacca actagt cat ttg tct cta aga gga        54
                                    His Leu Ser Leu Arg Gly
                                     1               5 ttg ttt gtg tgt gct ttt agt tcc gct gga cca aat gcc cat cag ttc      102
Leu Phe Val Cys Ala Phe Ser Ser Ala Gly Pro Asn Ala His Gln Phe
             10                  15                  20 ctt cca aaa gtt ttg cat aag aga aca ctt ggt ctt tca gca atg agt      150
Leu Pro Lys Val Leu His Lys Arg Thr Leu Gly Leu Ser Ala Met Ser
         25                  30                  35 act aca gat ctt gag gct tac ttt aag gat tgt ttg ttt aag gac tgg      198
Thr Thr Asp Leu Glu Ala Tyr Phe Lys Asp Cys Leu Phe Lys Asp Trp
     40                  45                  50 gag gaa tta ggt gaa gag ctc gag gga caa tgg tcc tca aag cca agg      246
Glu Glu Leu Gly Glu Glu Leu Glu Gly Gln Trp Ser Ser Lys Pro Arg
 55                  60                  65                  70 aaa ggt atg ggt aca aac ttg agt gtt tca aac cca ctt ggc ttt ttc      294
Lys Gly Met Gly Thr Asn Leu Ser Val Ser Asn Pro Leu Gly Phe Phe
                 75                  80                  85 cca gac cat caa ctt gat cca gca ttc aga gca aac tct gcc aac cca      342
Pro Asp His Gln Leu Asp Pro Ala Phe Arg Ala Asn Ser Ala Asn Pro
             90                  95                 100 gac tgg gat ttc aat cca aac aaa gat acc tgg cct gaa gca aat caa      390
Asp Trp Asp Phe Asn Pro Asn Lys Asp Thr Trp Pro Glu Ala Asn Gln
        105                 110                 115 gtt gga gtg ggg gca ttt ggt ttg ggc ttc act cca cca cac gga ggg      438
Val Gly Val Gly Ala Phe Gly Leu Gly Phe Thr Pro Pro His Gly Gly
    120                 125                 130 ttg ctt gga tgg agt cca cag gct caa ggc att ttg caa act gtt cca      486
Leu Leu Gly Trp Ser Pro Gln Ala Gln Gly Ile Leu Gln Thr Val Pro
135                 140                 145                 150
```

-continued

| | | |
|---|---|---|
| gct aat cct cct cct gct tca acc aat aga caa tct ggt aga caa cct<br>Ala Asn Pro Pro Pro Ala Ser Thr Asn Arg Gln Ser Gly Arg Gln Pro<br>                155                      160                165 | | 534 |
| aca cca att tca cct cca ctt aga gac tct cat cct cag gca atg caa<br>Thr Pro Ile Ser Pro Pro Leu Arg Asp Ser His Pro Gln Ala Met Gln<br>        170                      175                    180 | | 582 |
| tgg aac tca act acc ttc cat caa gct ctg ttg gat cct aga gtt aga<br>Trp Asn Ser Thr Thr Phe His Gln Ala Leu Leu Asp Pro Arg Val Arg<br>           185                      190                  195 | | 630 |
| ggt ctg tat ttc cca gct ggc gga tca tct agt ggt acc gtg aat cca<br>Gly Leu Tyr Phe Pro Ala Gly Gly Ser Ser Ser Gly Thr Val Asn Pro<br>200                      205                    210 | | 678 |
| gta cct act aca gcc tct cca atc agt tcc atc ttt agt aga act ggc<br>Val Pro Thr Thr Ala Ser Pro Ile Ser Ser Ile Phe Ser Arg Thr Gly<br>215                      220                    225                  230 | | 726 |
| gac cct gcc ttg aat atg gag aac atc aca tct gga ttc ctg ggg cca<br>Asp Pro Ala Leu Asn Met Glu Asn Ile Thr Ser Gly Phe Leu Gly Pro<br>                  235                      240                  245 | | 774 |
| ttg cta gtc cta caa gct ggg ttt ttc cta ttg act aga atc ttg aca<br>Leu Leu Val Leu Gln Ala Gly Phe Phe Leu Leu Thr Arg Ile Leu Thr<br>           250                      255                  260 | | 822 |
| att cca cag agt tta gac tcc tgg tgg acc agt cta aac ttt ttg ggt<br>Ile Pro Gln Ser Leu Asp Ser Trp Trp Thr Ser Leu Asn Phe Leu Gly<br>        265                      270                    275 | | 870 |
| ggc aca aca aca tgt cct ggc caa aac tct cag tct cca aca agt aac<br>Gly Thr Thr Thr Cys Pro Gly Gln Asn Ser Gln Ser Pro Thr Ser Asn<br>        280                      285                    290 | | 918 |
| cac tct cct act tca tgt cca cca att tgt cct ggt tac aga tgg atg<br>His Ser Pro Thr Ser Cys Pro Pro Ile Cys Pro Gly Tyr Arg Trp Met<br>295                      300                    305                  310 | | 966 |
| tgc ctc aga agg ttt atc att ttc ctt ttc ata ttg tta ttg tgc ctc<br>Cys Leu Arg Arg Phe Ile Ile Phe Leu Phe Ile Leu Leu Leu Cys Leu<br>                  315                      320                  325 | | 1014 |
| ata ttc cta ttg gta tta ttg gat tac caa ggg atg ctt cct gtc tgt<br>Ile Phe Leu Leu Val Leu Leu Asp Tyr Gln Gly Met Leu Pro Val Cys<br>           330                      335                  340 | | 1062 |
| cca ttg ctc cct ggt acg agt aca aca tct act ggc cca tgc aaa aca<br>Pro Leu Leu Pro Gly Thr Ser Thr Thr Ser Thr Gly Pro Cys Lys Thr<br>           345                      350                  355 | | 1110 |
| tgc acc ata cca gcg caa ggt aca agc atg ttt cca tcc tgt tgt tgc<br>Cys Thr Ile Pro Ala Gln Gly Thr Ser Met Phe Pro Ser Cys Cys Cys<br>360                      365                    370 | | 1158 |
| aca aaa cca tcc gat ggc aat tgc aca tgc att cca ata cca tct tca<br>Thr Lys Pro Ser Asp Gly Asn Cys Thr Cys Ile Pro Ile Pro Ser Ser<br>375                      380                    385                  390 | | 1206 |
| tgg gcc ttc gct cgt ttc cta tgg gaa tgg gcc tca gtt aga ttt tcc<br>Trp Ala Phe Ala Arg Phe Leu Trp Glu Trp Ala Ser Val Arg Phe Ser<br>                  395                      400                  405 | | 1254 |
| tgg tta tca ttg ttg gtc cca ttt gtg caa tgg ttt gta ggt tta tcc<br>Trp Leu Ser Leu Leu Val Pro Phe Val Gln Trp Phe Val Gly Leu Ser<br>           410                      415                  420 | | 1302 |
| cca acc gtc tgg tta tct gta ata tgg atg atg tgg tat tgg ggt cca<br>Pro Thr Val Trp Leu Ser Val Ile Trp Met Met Trp Tyr Trp Gly Pro<br>        425                      430                    435 | | 1350 |
| agt tta tac tca atc gtt tca cct ttt atc cct ttg ctg cca atc ttt<br>Ser Leu Tyr Ser Ile Val Ser Pro Phe Ile Pro Leu Leu Pro Ile Phe<br>        440                      445                  450 | | 1398 |
| ttc tgt ttg tgg gtt tac att gat att gat cct tac aag gag ttt ggt<br>Phe Cys Leu Trp Val Tyr Ile Asp Ile Asp Pro Tyr Lys Glu Phe Gly<br>455                      460                    465                  470 | | 1446 |

```
gct act gtt gag tta cta tcc ttt tta cct tct gac ttt ttc cct tct    1494
Ala Thr Val Glu Leu Leu Ser Phe Leu Pro Ser Asp Phe Phe Pro Ser
            475                 480                 485 gtc aga gat ctt ttg gat act gct tct gct tta tac aga gaa gct ttg    1542
Val Arg Asp Leu Leu Asp Thr Ala Ser Ala Leu Tyr Arg Glu Ala Leu
            490                 495                 500 gaa tca cca gaa cat tgt tca cct cat cat acc gcc tta aga caa gca    1590
Glu Ser Pro Glu His Cys Ser Pro His His Thr Ala Leu Arg Gln Ala
            505                 510                 515 att ctg tgt tgg ggc gaa tta atg aac cta gca aca tgg gtg ggt tcc    1638
Ile Leu Cys Trp Gly Glu Leu Met Asn Leu Ala Thr Trp Val Gly Ser
            520                 525                 530 aat ttg gaa gat cca gca tcc aga gag tta gtg gtt agc tac gtg aat    1686
Asn Leu Glu Asp Pro Ala Ser Arg Glu Leu Val Val Ser Tyr Val Asn
535                 540                 545                 550 gtc aac atg ggc ttg aaa atc aga cag tta ctt tgg ttc cat atc tct    1734
Val Asn Met Gly Leu Lys Ile Arg Gln Leu Leu Trp Phe His Ile Ser
                555                 560                 565 tgt ctg aca ttt ggt aga gaa aca gtt ctg gaa tat ctc gtt agc ttt    1782
Cys Leu Thr Phe Gly Arg Glu Thr Val Leu Glu Tyr Leu Val Ser Phe
            570                 575                 580 gga gta tgg att aga act cca cca gcc tac aga cca cct aat gca cca    1830
Gly Val Trp Ile Arg Thr Pro Pro Ala Tyr Arg Pro Pro Asn Ala Pro
            585                 590                 595 ata ttg tca acc ctc cca gag aca aca gtt gtg agg aga aga gga aga    1878
Ile Leu Ser Thr Leu Pro Glu Thr Thr Val Val Arg Arg Arg Gly Arg
            600                 605                 610 tct cct cgt cgt aga act cca tct cca aga cga agg aga tca caa agt    1926
Ser Pro Arg Arg Arg Thr Pro Ser Pro Arg Arg Arg Ser Gln Ser
615                 620                 625                 630 cct aga cga cgt aga tct caa tct aga gag tct caa tgt caccaccatc    1975
Pro Arg Arg Arg Arg Ser Gln Ser Arg Glu Ser Gln Cys
            635                 640 accatcatta agcggccgc                                               1994
```

<210> SEQ ID NO 130
<211> LENGTH: 643
<212> TYPE: PRT
<213> ORGANISM: Artificial
<220> FEATURE:
<223> OTHER INFORMATION: Synthetic Construct

<400> SEQUENCE: 130

```
His Leu Ser Leu Arg Gly Leu Phe Val Cys Ala Phe Ser Ser Ala Gly
1               5                   10                  15

Pro Asn Ala His Gln Phe Leu Pro Lys Val Leu His Lys Arg Thr Leu
            20                  25                  30

Gly Leu Ser Ala Met Ser Thr Thr Asp Leu Glu Ala Tyr Phe Lys Asp
        35                  40                  45

Cys Leu Phe Lys Asp Trp Glu Glu Leu Gly Glu Glu Leu Glu Gly Gln
    50                  55                  60

Trp Ser Ser Lys Pro Arg Lys Gly Met Gly Thr Asn Leu Ser Val Ser
65                  70                  75                  80

Asn Pro Leu Gly Phe Phe Pro Asp His Gln Leu Asp Pro Ala Phe Arg
                85                  90                  95

Ala Asn Ser Ala Asn Pro Asp Trp Asp Phe Asn Pro Asn Lys Asp Thr
            100                 105                 110

Trp Pro Glu Ala Asn Gln Val Gly Val Gly Ala Phe Gly Leu Gly Phe
```

-continued

```
            115                 120                 125
Thr Pro Pro His Gly Leu Leu Gly Trp Ser Pro Gln Ala Gln Gly
    130                 135                 140
Ile Leu Gln Thr Val Pro Ala Asn Pro Pro Ala Ser Thr Asn Arg
145                 150                 155                 160
Gln Ser Gly Arg Gln Pro Thr Pro Ile Ser Pro Leu Arg Asp Ser
                165                 170                 175
His Pro Gln Ala Met Gln Trp Asn Ser Thr Thr Phe His Gln Ala Leu
            180                 185                 190
Leu Asp Pro Arg Val Arg Gly Leu Tyr Phe Pro Ala Gly Gly Ser Ser
            195                 200                 205
Ser Gly Thr Val Asn Pro Val Pro Thr Thr Ala Ser Pro Ile Ser Ser
    210                 215                 220
Ile Phe Ser Arg Thr Gly Asp Pro Ala Leu Asn Met Glu Asn Ile Thr
225                 230                 235                 240
Ser Gly Phe Leu Gly Pro Leu Leu Val Leu Gln Ala Gly Phe Phe Leu
                245                 250                 255
Leu Thr Arg Ile Leu Thr Ile Pro Gln Ser Leu Asp Ser Trp Trp Thr
            260                 265                 270
Ser Leu Asn Phe Leu Gly Gly Thr Thr Thr Cys Pro Gly Gln Asn Ser
    275                 280                 285
Gln Ser Pro Thr Ser Asn His Ser Pro Thr Ser Cys Pro Pro Ile Cys
    290                 295                 300
Pro Gly Tyr Arg Trp Met Cys Leu Arg Arg Phe Ile Ile Phe Leu Phe
305                 310                 315                 320
Ile Leu Leu Leu Cys Leu Ile Phe Leu Leu Val Leu Leu Asp Tyr Gln
                325                 330                 335
Gly Met Leu Pro Val Cys Pro Leu Leu Pro Gly Thr Ser Thr Thr Ser
            340                 345                 350
Thr Gly Pro Cys Lys Thr Cys Thr Ile Pro Ala Gln Gly Thr Ser Met
            355                 360                 365
Phe Pro Ser Cys Cys Cys Thr Lys Pro Ser Asp Gly Asn Cys Thr Cys
    370                 375                 380
Ile Pro Ile Pro Ser Ser Trp Ala Phe Ala Arg Phe Leu Trp Glu Trp
385                 390                 395                 400
Ala Ser Val Arg Phe Ser Trp Leu Ser Leu Leu Val Pro Phe Val Gln
                405                 410                 415
Trp Phe Val Gly Leu Ser Pro Thr Val Trp Leu Ser Val Ile Trp Met
            420                 425                 430
Met Trp Tyr Trp Gly Pro Ser Leu Tyr Ser Ile Val Ser Pro Phe Ile
            435                 440                 445
Pro Leu Leu Pro Ile Phe Phe Cys Leu Trp Val Tyr Ile Asp Ile Asp
    450                 455                 460
Pro Tyr Lys Glu Phe Gly Ala Thr Val Glu Leu Leu Ser Phe Leu Pro
465                 470                 475                 480
Ser Asp Phe Phe Pro Ser Val Arg Asp Leu Leu Asp Thr Ala Ser Ala
                485                 490                 495
Leu Tyr Arg Glu Ala Leu Glu Ser Pro Glu His Cys Ser Pro His His
            500                 505                 510
Thr Ala Leu Arg Gln Ala Ile Leu Cys Trp Gly Glu Leu Met Asn Leu
            515                 520                 525
Ala Thr Trp Val Gly Ser Asn Leu Glu Asp Pro Ala Ser Arg Glu Leu
            530                 535                 540
```

```
Val Val Ser Tyr Val Asn Val Asn Met Gly Leu Lys Ile Arg Gln Leu
545                 550                 555                 560

Leu Trp Phe His Ile Ser Cys Leu Thr Phe Gly Arg Glu Thr Val Leu
                565                 570                 575

Glu Tyr Leu Val Ser Phe Gly Val Trp Ile Arg Thr Pro Pro Ala Tyr
            580                 585                 590

Arg Pro Pro Asn Ala Pro Ile Leu Ser Thr Leu Pro Glu Thr Thr Val
        595                 600                 605

Val Arg Arg Gly Arg Ser Pro Arg Arg Thr Pro Ser Pro Arg
    610                 615                 620

Arg Arg Arg Ser Gln Ser Pro Arg Arg Arg Ser Gln Ser Arg Glu
625                 630                 635                 640

Ser Gln Cys

<210> SEQ ID NO 131
<211> LENGTH: 2672
<212> TYPE: DNA
<213> ORGANISM: Artificial
<220> FEATURE:
<223> OTHER INFORMATION: Synthetic Construct
<220> FEATURE:
<221> NAME/KEY: CDS
<222> LOCATION: (37)..(2643)

<400> SEQUENCE: 131
gaattcgcca ccatggcaga tgaagcacca actagt ggt cta agt cga tat gtt        54
                                  Gly Leu Ser Arg Tyr Val
                                    1               5 gcc aga tta agt tct aat tcc agg atc ttt aac cat caa cat ggc act       102
Ala Arg Leu Ser Ser Asn Ser Arg Ile Phe Asn His Gln His Gly Thr
                10                  15                  20 atg caa aac tta cac gat tca tgt tct aga aac ttg tac gtt agt ttg       150
Met Gln Asn Leu His Asp Ser Cys Ser Arg Asn Leu Tyr Val Ser Leu
            25                  30                  35 tta ctt tta tac caa act ttt ggg aga aaa ctg cat ctc tat tcc cat       198
Leu Leu Leu Tyr Gln Thr Phe Gly Arg Lys Leu His Leu Tyr Ser His
        40                  45                  50 cct att atc cta ggt ttt aga aaa ata cct atg ggg gta ggg ttg tcc       246
Pro Ile Ile Leu Gly Phe Arg Lys Ile Pro Met Gly Val Gly Leu Ser
55                  60                  65                  70 cct ttt ctg ttg gca caa ttc acc tca gcc ata tgt tct gtc gtg aga       294
Pro Phe Leu Leu Ala Gln Phe Thr Ser Ala Ile Cys Ser Val Val Arg
                75                  80                  85 aga gct ttt cca cat tgt ctg gcc ttt tcc tat atg gac gat gtg gtg       342
Arg Ala Phe Pro His Cys Leu Ala Phe Ser Tyr Met Asp Asp Val Val
            90                  95                 100 ttg gga gct aag tct gta caa cat ctt gaa agt ttg ttt aca gcc gtt       390
Leu Gly Ala Lys Ser Val Gln His Leu Glu Ser Leu Phe Thr Ala Val
       105                 110                 115 act aat ttc ctt tta tct ttg ggt ata cat ctt aat cca aat aag act       438
Thr Asn Phe Leu Leu Ser Leu Gly Ile His Leu Asn Pro Asn Lys Thr
   120                 125                 130 aag aga tgg ggc tac tct ttg cac ttt atg ggc tac gtt att ggg tgt       486
Lys Arg Trp Gly Tyr Ser Leu His Phe Met Gly Tyr Val Ile Gly Cys
135                 140                 145                 150 tac ggc agt tta cca caa gat cat atc atc cag aaa atc aaa gag tgt       534
Tyr Gly Ser Leu Pro Gln Asp His Ile Ile Gln Lys Ile Lys Glu Cys
                155                 160                 165 ttt aga aag tta cca gtt aac aga cca atc gac tgg aaa gtg tgc caa       582
```

```
              Phe Arg Lys Leu Pro Val Asn Arg Pro Ile Asp Trp Lys Val Cys Gln
                          170                 175                 180 cgt atc gta ggt ttg ctt ggt ttt gca gca cct ttt aca cag tgt ggt         630
Arg Ile Val Gly Leu Leu Gly Phe Ala Ala Pro Phe Thr Gln Cys Gly
            185                 190                 195 tat cca gct tta atg cca ctt tat gct tgt atc caa tct aaa caa gct         678
Tyr Pro Ala Leu Met Pro Leu Tyr Ala Cys Ile Gln Ser Lys Gln Ala
200                 205                 210 ttt aca ttt tcc cca aca tat aaa gcc ttc ctg tgc aaa caa cat ctc         726
Phe Thr Phe Ser Pro Thr Tyr Lys Ala Phe Leu Cys Lys Gln His Leu
215                 220                 225                 230 tct tta aga ggc cta ttc gtc tgc gct ttt tca tcc gct ggt cct aat         774
Ser Leu Arg Gly Leu Phe Val Cys Ala Phe Ser Ser Ala Gly Pro Asn
            235                 240                 245 gca cac caa ttt ctg cct aaa gtt ctg cat aaa cga aca ttg ggt ttg         822
Ala His Gln Phe Leu Pro Lys Val Leu His Lys Arg Thr Leu Gly Leu
            250                 255                 260 tct gca atg agc act acc gac tta gag gcg tac ttc aag gac tgc ttg         870
Ser Ala Met Ser Thr Thr Asp Leu Glu Ala Tyr Phe Lys Asp Cys Leu
            265                 270                 275 ttt aag gat tgg gaa gag ctt gga gag gaa ggt cag tgg tcc tcc aaa         918
Phe Lys Asp Trp Glu Glu Leu Gly Glu Glu Gly Gln Trp Ser Ser Lys
280                 285                 290 cct aga aag ggt atg ggt act aat ttg tct gta tct aac cct ctc gga         966
Pro Arg Lys Gly Met Gly Thr Asn Leu Ser Val Ser Asn Pro Leu Gly
295                 300                 305                 310 ttc ttt cca gat cac cag tta gat cca gct ttt cgt gct aac agt gcc        1014
Phe Phe Pro Asp His Gln Leu Asp Pro Ala Phe Arg Ala Asn Ser Ala
            315                 320                 325 aac cca gat tgg gat ttc aat cct aat aag gat acc tgg cca gag gct        1062
Asn Pro Asp Trp Asp Phe Asn Pro Asn Lys Asp Thr Trp Pro Glu Ala
            330                 335                 340 aac cag gta gga gtt gga gcc ttc ggt cta ggt ttt acc cca cct cac        1110
Asn Gln Val Gly Val Gly Ala Phe Gly Leu Gly Phe Thr Pro Pro His
            345                 350                 355 ggt gga cta tta ggc tgg agc cca caa gca caa ggt atc ttg caa acc        1158
Gly Gly Leu Leu Gly Trp Ser Pro Gln Ala Gln Gly Ile Leu Gln Thr
360                 365                 370 gtt cca gct aac cct cca cca gcg tca aca aat aga cag tct ggt aga        1206
Val Pro Ala Asn Pro Pro Pro Ala Ser Thr Asn Arg Gln Ser Gly Arg
375                 380                 385                 390 caa cca acc cct att tct cct cct tta aga gac tct cat cct cag gcg        1254
Gln Pro Thr Pro Ile Ser Pro Pro Leu Arg Asp Ser His Pro Gln Ala
            395                 400                 405 atg caa tgg aac tca acg acc ttt cat caa gct ctt ttg gac cct aga        1302
Met Gln Trp Asn Ser Thr Thr Phe His Gln Ala Leu Leu Asp Pro Arg
            410                 415                 420 gtc agg ggt tta tac ttc cca gct ggt gga tcc tca tcc ggc act gtt        1350
Val Arg Gly Leu Tyr Phe Pro Ala Gly Gly Ser Ser Ser Gly Thr Val
            425                 430                 435 aat cct gtc cca act aca gca tca cca att tca tcc ata ttt tct aga        1398
Asn Pro Val Pro Thr Thr Ala Ser Pro Ile Ser Ser Ile Phe Ser Arg
440                 445                 450 act ggg gat cct gct ctt aat atg gaa aac att aca agc ggc ttc cta        1446
Thr Gly Asp Pro Ala Leu Asn Met Glu Asn Ile Thr Ser Gly Phe Leu
455                 460                 465                 470 gga cca tta tta gtt cta caa gcc gga ttt ttc cta ttg act aga atc        1494
Gly Pro Leu Leu Val Leu Gln Ala Gly Phe Phe Leu Leu Thr Arg Ile
            475                 480                 485
```

-continued

| | | |
|---|---|---|
| cta act att cct caa agt ctt gac tcc tgg tgg aca tcc ttg aat ttc<br>Leu Thr Ile Pro Gln Ser Leu Asp Ser Trp Trp Thr Ser Leu Asn Phe<br>490                        495                        500 | | 1542 |
| ctt ggc ggt aca aca aca tgt cca ggc caa aac tct caa tca cca act<br>Leu Gly Gly Thr Thr Thr Cys Pro Gly Gln Asn Ser Gln Ser Pro Thr<br>505                       510                        515 | | 1590 |
| tct aat cac tct cca aca tct tgc cct cca att tgc cca ggt tac aga<br>Ser Asn His Ser Pro Thr Ser Cys Pro Pro Ile Cys Pro Gly Tyr Arg<br>520                       525                       530 | | 1638 |
| tgg atg tgc ttg aga agg ttc atc att ttt ctg ttc atc ctc ttg ttg<br>Trp Met Cys Leu Arg Arg Phe Ile Ile Phe Leu Phe Ile Leu Leu Leu<br>535                   540                       545               550 | | 1686 |
| tgt ttg att ttc ctc tta gta ttg ctg gac tac caa ggc atg ctt cca<br>Cys Leu Ile Phe Leu Leu Val Leu Leu Asp Tyr Gln Gly Met Leu Pro<br>555                       560                       565 | | 1734 |
| gtc tgc cct cta ttg cca gga act tct aca acc tca aca gga cca tgt<br>Val Cys Pro Leu Leu Pro Gly Thr Ser Thr Thr Ser Thr Gly Pro Cys<br>570                       575                       580 | | 1782 |
| aaa aca tgt act atc cct gct caa gga aca tca atg ttt cca tct tgt<br>Lys Thr Cys Thr Ile Pro Ala Gln Gly Thr Ser Met Phe Pro Ser Cys<br>585                       590                       595 | | 1830 |
| tgc tgt aca aaa cca tca gat ggt aat tgt act tgt ata cca ata cca<br>Cys Cys Thr Lys Pro Ser Asp Gly Asn Cys Thr Cys Ile Pro Ile Pro<br>600                       605                       610 | | 1878 |
| agt tca tgg gca ttt gcc cgt ttc ctt tgg gag tgg gct tct gta aga<br>Ser Ser Trp Ala Phe Ala Arg Phe Leu Trp Glu Trp Ala Ser Val Arg<br>615                   620                       625               630 | | 1926 |
| ttc tct tgg tta agt ttg cta gtc cca ttc gtg cag tgg ttt gtt ggc<br>Phe Ser Trp Leu Ser Leu Leu Val Pro Phe Val Gln Trp Phe Val Gly<br>635                   640                       645 | | 1974 |
| ctg tct cca act gtt tgg tta tct gtt att tgg atg atg tgg tac tgg<br>Leu Ser Pro Thr Val Trp Leu Ser Val Ile Trp Met Met Trp Tyr Trp<br>650                       655                       660 | | 2022 |
| ggt cca agc cta tac tca atc gtg tca cct ttt atc cca ttg cta cct<br>Gly Pro Ser Leu Tyr Ser Ile Val Ser Pro Phe Ile Pro Leu Leu Pro<br>665                       670                       675 | | 2070 |
| atc ttt ttc tgc ctc tgg gtt tac atc gat att gac cct tac aag gaa<br>Ile Phe Phe Cys Leu Trp Val Tyr Ile Asp Ile Asp Pro Tyr Lys Glu<br>680                       685                       690 | | 2118 |
| ttt ggc gca aca gtt gaa ttg tta tca ttt tta cca tca gat ttc ttt<br>Phe Gly Ala Thr Val Glu Leu Leu Ser Phe Leu Pro Ser Asp Phe Phe<br>695                   700                       705               710 | | 2166 |
| cca tca gtg cgt gat ttg tta gat acg gca tcc gct ttg tac aga gaa<br>Pro Ser Val Arg Asp Leu Leu Asp Thr Ala Ser Ala Leu Tyr Arg Glu<br>715                       720                       725 | | 2214 |
| gca ctg gaa tca cca gaa cac tgt tct cca cat cac act gct ctc aga<br>Ala Leu Glu Ser Pro Glu His Cys Ser Pro His His Thr Ala Leu Arg<br>730                       735                       740 | | 2262 |
| caa gct ata ttg tgt tgg gga gag ttg atg aat cta gcc act tgg gta<br>Gln Ala Ile Leu Cys Trp Gly Glu Leu Met Asn Leu Ala Thr Trp Val<br>745                       750                       755 | | 2310 |
| ggg tcc aat ctg gaa gat cct gcc tct aga gaa ctg gtg gta tct tac<br>Gly Ser Asn Leu Glu Asp Pro Ala Ser Arg Glu Leu Val Val Ser Tyr<br>760                       765                       770 | | 2358 |
| gtc aat gtt aac atg ggg ttg aag att aga caa ctt tta tgg ttc cat<br>Val Asn Val Asn Met Gly Leu Lys Ile Arg Gln Leu Leu Trp Phe His<br>775                   780                       785               790 | | 2406 |
| att tca tgt tta acg ttt ggt aga gaa aca gta ctg gaa tac tta gtt<br>Ile Ser Cys Leu Thr Phe Gly Arg Glu Thr Val Leu Glu Tyr Leu Val<br>795                       800                       805 | | 2454 |

```
agt ttc ggt gtc tgg att aga aca cca cca gca tat aga cca cca aat    2502
Ser Phe Gly Val Trp Ile Arg Thr Pro Pro Ala Tyr Arg Pro Pro Asn
        810                 815                 820 gcg cct ata ttg agt acg ctc cca gaa acg acg gtc gtt agg aga aga    2550
Ala Pro Ile Leu Ser Thr Leu Pro Glu Thr Thr Val Val Arg Arg Arg
    825                 830                 835 ggt aga tca cct agg aga agg aca cct tca cct aga cgt aga cgt tct    2598
Gly Arg Ser Pro Arg Arg Arg Thr Pro Ser Pro Arg Arg Arg Arg Ser
840                 845                 850 caa tct cca aga cgt aga aga tct caa tct aga gaa tca caa tgc        2643
Gln Ser Pro Arg Arg Arg Arg Ser Gln Ser Arg Glu Ser Gln Cys
855                 860                 865 catcaccacc atcatcatta agcggccgc                                    2672

<210> SEQ ID NO 132
<211> LENGTH: 869
<212> TYPE: PRT
<213> ORGANISM: Artificial
<220> FEATURE:
<223> OTHER INFORMATION: Synthetic Construct

<400> SEQUENCE: 132

Gly Leu Ser Arg Tyr Val Ala Arg Leu Ser Ser Asn Ser Arg Ile Phe
1               5                   10                  15

Asn His Gln His Gly Thr Met Gln Asn Leu His Asp Ser Cys Ser Arg
            20                  25                  30

Asn Leu Tyr Val Ser Leu Leu Leu Tyr Gln Thr Phe Gly Arg Lys
        35                  40                  45

Leu His Leu Tyr Ser His Pro Ile Ile Leu Gly Phe Arg Lys Ile Pro
    50                  55                  60

Met Gly Val Gly Leu Ser Pro Phe Leu Leu Ala Gln Phe Thr Ser Ala
65                  70                  75                  80

Ile Cys Ser Val Val Arg Arg Ala Phe Pro His Cys Leu Ala Phe Ser
                85                  90                  95

Tyr Met Asp Asp Val Val Leu Gly Ala Lys Ser Val Gln His Leu Glu
            100                 105                 110

Ser Leu Phe Thr Ala Val Thr Asn Phe Leu Leu Ser Leu Gly Ile His
        115                 120                 125

Leu Asn Pro Asn Lys Thr Lys Arg Trp Gly Tyr Ser Leu His Phe Met
    130                 135                 140

Gly Tyr Val Ile Gly Cys Tyr Gly Ser Leu Pro Gln Asp His Ile Ile
145                 150                 155                 160

Gln Lys Ile Lys Glu Cys Phe Arg Lys Leu Pro Val Asn Arg Pro Ile
                165                 170                 175

Asp Trp Lys Val Cys Gln Arg Ile Val Gly Leu Leu Gly Phe Ala Ala
            180                 185                 190

Pro Phe Thr Gln Cys Gly Tyr Pro Ala Leu Met Pro Leu Tyr Ala Cys
        195                 200                 205

Ile Gln Ser Lys Gln Ala Phe Thr Phe Ser Pro Thr Tyr Lys Ala Phe
    210                 215                 220

Leu Cys Lys Gln His Leu Ser Leu Arg Gly Leu Phe Val Cys Ala Phe
225                 230                 235                 240

Ser Ser Ala Gly Pro Asn Ala His Gln Phe Leu Pro Lys Val Leu His
                245                 250                 255

Lys Arg Thr Leu Gly Leu Ser Ala Met Ser Thr Thr Asp Leu Glu Ala
            260                 265                 270
```

-continued

```
Tyr Phe Lys Asp Cys Leu Phe Lys Asp Trp Glu Glu Leu Gly Glu Glu
            275                 280                 285

Gly Gln Trp Ser Ser Lys Pro Arg Lys Gly Met Gly Thr Asn Leu Ser
        290                 295                 300

Val Ser Asn Pro Leu Gly Phe Phe Pro Asp His Gln Leu Asp Pro Ala
305                 310                 315                 320

Phe Arg Ala Asn Ser Ala Asn Pro Asp Trp Asp Phe Asn Pro Asn Lys
                325                 330                 335

Asp Thr Trp Pro Glu Ala Asn Gln Val Gly Val Gly Ala Phe Gly Leu
            340                 345                 350

Gly Phe Thr Pro Pro His Gly Gly Leu Leu Gly Trp Ser Pro Gln Ala
        355                 360                 365

Gln Gly Ile Leu Gln Thr Val Pro Ala Asn Pro Pro Pro Ala Ser Thr
    370                 375                 380

Asn Arg Gln Ser Gly Arg Gln Pro Thr Pro Ile Ser Pro Pro Leu Arg
385                 390                 395                 400

Asp Ser His Pro Gln Ala Met Gln Trp Asn Ser Thr Thr Phe His Gln
                405                 410                 415

Ala Leu Leu Asp Pro Arg Val Arg Gly Leu Tyr Phe Pro Ala Gly Gly
            420                 425                 430

Ser Ser Ser Gly Thr Val Asn Pro Val Pro Thr Thr Ala Ser Pro Ile
        435                 440                 445

Ser Ser Ile Phe Ser Arg Thr Gly Asp Pro Ala Leu Asn Met Glu Asn
    450                 455                 460

Ile Thr Ser Gly Phe Leu Gly Pro Leu Leu Val Leu Gln Ala Gly Phe
465                 470                 475                 480

Phe Leu Leu Thr Arg Ile Leu Thr Ile Pro Gln Ser Leu Asp Ser Trp
                485                 490                 495

Trp Thr Ser Leu Asn Phe Leu Gly Gly Thr Thr Thr Cys Pro Gly Gln
            500                 505                 510

Asn Ser Gln Ser Pro Thr Ser Asn His Ser Pro Thr Ser Cys Pro Pro
        515                 520                 525

Ile Cys Pro Gly Tyr Arg Trp Met Cys Leu Arg Arg Phe Ile Ile Phe
    530                 535                 540

Leu Phe Ile Leu Leu Leu Cys Leu Ile Phe Leu Leu Val Leu Leu Asp
545                 550                 555                 560

Tyr Gln Gly Met Leu Pro Val Cys Pro Leu Leu Pro Gly Thr Ser Thr
                565                 570                 575

Thr Ser Thr Gly Pro Cys Lys Thr Cys Thr Ile Pro Ala Gln Gly Thr
            580                 585                 590

Ser Met Phe Pro Ser Cys Cys Cys Thr Lys Pro Ser Asp Gly Asn Cys
        595                 600                 605

Thr Cys Ile Pro Ile Pro Ser Ser Trp Ala Phe Ala Arg Phe Leu Trp
    610                 615                 620

Glu Trp Ala Ser Val Arg Phe Ser Trp Leu Ser Leu Leu Val Pro Phe
625                 630                 635                 640

Val Gln Trp Phe Val Gly Leu Ser Pro Thr Val Trp Leu Ser Val Ile
                645                 650                 655

Trp Met Met Trp Tyr Trp Gly Pro Ser Leu Tyr Ser Ile Val Ser Pro
            660                 665                 670

Phe Ile Pro Leu Leu Pro Ile Phe Phe Cys Leu Trp Val Tyr Ile Asp
        675                 680                 685
```

```
Ile Asp Pro Tyr Lys Glu Phe Gly Ala Thr Val Glu Leu Leu Ser Phe
    690             695                 700
Leu Pro Ser Asp Phe Phe Pro Ser Val Arg Asp Leu Leu Asp Thr Ala
705                 710                 715                 720
Ser Ala Leu Tyr Arg Glu Ala Leu Glu Ser Pro Glu His Cys Ser Pro
                725                 730                 735
His His Thr Ala Leu Arg Gln Ala Ile Leu Cys Trp Gly Glu Leu Met
            740                 745                 750
Asn Leu Ala Thr Trp Val Gly Ser Asn Leu Glu Asp Pro Ala Ser Arg
        755                 760                 765
Glu Leu Val Val Ser Tyr Val Asn Val Asn Met Gly Leu Lys Ile Arg
    770                 775                 780
Gln Leu Leu Trp Phe His Ile Ser Cys Leu Thr Phe Gly Arg Glu Thr
785                 790                 795                 800
Val Leu Glu Tyr Leu Val Ser Phe Gly Val Trp Ile Arg Thr Pro Pro
                805                 810                 815
Ala Tyr Arg Pro Pro Asn Ala Pro Ile Leu Ser Thr Leu Pro Glu Thr
            820                 825                 830
Thr Val Val Arg Arg Arg Gly Arg Ser Pro Arg Arg Arg Thr Pro Ser
        835                 840                 845
Pro Arg Arg Arg Arg Ser Gln Ser Pro Arg Arg Arg Arg Ser Gln Ser
    850                 855                 860
Arg Glu Ser Gln Cys
865

<210> SEQ ID NO 133
<211> LENGTH: 2672
<212> TYPE: DNA
<213> ORGANISM: Artificial
<220> FEATURE:
<223> OTHER INFORMATION: Synthetic Construct
<220> FEATURE:
<221> NAME/KEY: CDS
<222> LOCATION: (37)..(2643)

<400> SEQUENCE: 133
gaattcgcca ccatggccga cgaggcacct actagt cat ctt tca ctt aga ggg        54
                                       His Leu Ser Leu Arg Gly
                                       1               5 ctc ttt gtt tgt gca ttc agt tct gca ggc cca aac gcc cac caa ttt       102
Leu Phe Val Cys Ala Phe Ser Ser Ala Gly Pro Asn Ala His Gln Phe
            10                  15                  20 ttg cct aag gta ttg cat aaa cgt aca cta gga tta agt gca atg tct       150
Leu Pro Lys Val Leu His Lys Arg Thr Leu Gly Leu Ser Ala Met Ser
        25                  30                  35 act act gat ttg gaa gcc tat ttc aaa gat tgt ctg ttt aaa gat tgg       198
Thr Thr Asp Leu Glu Ala Tyr Phe Lys Asp Cys Leu Phe Lys Asp Trp
    40                  45                  50 gag gaa ttg ggc gag gaa gga ttg tcc aga tat gtt gct aga cta tct       246
Glu Glu Leu Gly Glu Glu Gly Leu Ser Arg Tyr Val Ala Arg Leu Ser
55                  60                  65                  70 tct aat agt aga atc ttt aat cat cag cat ggc aca atg cag aat ttg       294
Ser Asn Ser Arg Ile Phe Asn His Gln His Gly Thr Met Gln Asn Leu
                75                  80                  85 cat gat tca tgt tct aga aat ttg tac gtg tca tta ttg ctt ttg tat       342
His Asp Ser Cys Ser Arg Asn Leu Tyr Val Ser Leu Leu Leu Leu Tyr
            90                  95                  100 caa act ttt ggt aga aag tta cat ctc tat tct cat cca ata atc ctc       390
Gln Thr Phe Gly Arg Lys Leu His Leu Tyr Ser His Pro Ile Ile Leu
```

```
                105                 110                 115
ggc ttt cga aaa atc cct atg ggg gtt ggc tta tcc cca ttt ctg ctg      438
Gly Phe Arg Lys Ile Pro Met Gly Val Gly Leu Ser Pro Phe Leu Leu
    120                 125                 130 gcc caa ttc act tct gca att tgt tcc gtg gtt aga aga gct ttt cct      486
Ala Gln Phe Thr Ser Ala Ile Cys Ser Val Val Arg Arg Ala Phe Pro
135                 140                 145                 150 cac tgt tta gct ttt agt tac atg gac gat gtg gtc ctt ggg gca aag      534
His Cys Leu Ala Phe Ser Tyr Met Asp Asp Val Val Leu Gly Ala Lys
                155                 160                 165 tca gtc caa cac tta gaa tca ctt ttt acc gcc gta acc aac ttc ctt      582
Ser Val Gln His Leu Glu Ser Leu Phe Thr Ala Val Thr Asn Phe Leu
            170                 175                 180 cta agt ttg ggt ata cat ctg aac cct aac aaa aca aaa cga tgg ggt      630
Leu Ser Leu Gly Ile His Leu Asn Pro Asn Lys Thr Lys Arg Trp Gly
        185                 190                 195 tac agc tta cat ttt atg ggg tac gtg atc ggt tgc tat ggt tcc ctt      678
Tyr Ser Leu His Phe Met Gly Tyr Val Ile Gly Cys Tyr Gly Ser Leu
    200                 205                 210 cct caa gac cac att atc caa aag ata aaa gag tgc ttt aga aag ctt      726
Pro Gln Asp His Ile Ile Gln Lys Ile Lys Glu Cys Phe Arg Lys Leu
215                 220                 225                 230 cca gtt aat aga cca atc gac tgg aaa gtt tgc caa cga atc gtg ggt      774
Pro Val Asn Arg Pro Ile Asp Trp Lys Val Cys Gln Arg Ile Val Gly
                235                 240                 245 ctg ctg ggt ttt gct gct cca ttc aca caa tgt ggt tac cca gct cta      822
Leu Leu Gly Phe Ala Ala Pro Phe Thr Gln Cys Gly Tyr Pro Ala Leu
            250                 255                 260 atg cca tta tat gca tgc atc caa tcc aaa caa gct ttt aca ttt tca      870
Met Pro Leu Tyr Ala Cys Ile Gln Ser Lys Gln Ala Phe Thr Phe Ser
        265                 270                 275 cct act tac aaa gcg ttt ttg tgt aag caa ggt cag tgg tcc tcc aaa      918
Pro Thr Tyr Lys Ala Phe Leu Cys Lys Gln Gly Gln Trp Ser Ser Lys
    280                 285                 290 cct aga aag ggt atg ggt act aat ttg tct gta tct aac cct ctc gga      966
Pro Arg Lys Gly Met Gly Thr Asn Leu Ser Val Ser Asn Pro Leu Gly
295                 300                 305                 310 ttc ttt cca gat cac cag tta gat cca gct ttt cgt gct aac agt gcc     1014
Phe Phe Pro Asp His Gln Leu Asp Pro Ala Phe Arg Ala Asn Ser Ala
                315                 320                 325 aac cca gat tgg gat ttc aat cct aat aag gat acc tgg cca gag gct     1062
Asn Pro Asp Trp Asp Phe Asn Pro Asn Lys Asp Thr Trp Pro Glu Ala
            330                 335                 340 aac cag gta gga gtt gga gcc ttc ggt cta ggt ttt acc cca cct cac     1110
Asn Gln Val Gly Val Gly Ala Phe Gly Leu Gly Phe Thr Pro Pro His
        345                 350                 355 ggt gga cta tta ggc tgg agc cca caa gca caa ggt atc ttg caa acc     1158
Gly Gly Leu Leu Gly Trp Ser Pro Gln Ala Gln Gly Ile Leu Gln Thr
    360                 365                 370 gtt cca gct aac cct cca cca gcg tca aca aat aga cag tct ggt aga     1206
Val Pro Ala Asn Pro Pro Pro Ala Ser Thr Asn Arg Gln Ser Gly Arg
375                 380                 385                 390 caa cca acc cct att tct cct cct tta aga gac tct cat cct cag gcg     1254
Gln Pro Thr Pro Ile Ser Pro Pro Leu Arg Asp Ser His Pro Gln Ala
                395                 400                 405 atg caa tgg aac tca acg acc ttt cat caa gct ctt ttg gac cct aga     1302
Met Gln Trp Asn Ser Thr Thr Phe His Gln Ala Leu Leu Asp Pro Arg
            410                 415                 420 gtc agg ggt tta tac ttc cca gct ggt gga tcc tca tcc ggc act gtt     1350
```

-continued

```
                Val Arg Gly Leu Tyr Phe Pro Ala Gly Gly Ser Ser Gly Thr Val
                        425                 430                 435 aat cct gtc cca act aca gca tca cca att tca tcc ata ttt tct aga          1398
Asn Pro Val Pro Thr Thr Ala Ser Pro Ile Ser Ser Ile Phe Ser Arg
        440                 445                 450 act ggg gat cct gct ctt aat atg gaa aac att aca agc ggc ttc cta          1446
Thr Gly Asp Pro Ala Leu Asn Met Glu Asn Ile Thr Ser Gly Phe Leu
455                 460                 465                 470 gga cca tta tta gtt cta caa gcc gga ttt ttc cta ttg act aga atc          1494
Gly Pro Leu Leu Val Leu Gln Ala Gly Phe Phe Leu Leu Thr Arg Ile
                    475                 480                 485 cta act att cct caa agt ctt gac tcc tgg tgg aca tcc ttg aat ttc          1542
Leu Thr Ile Pro Gln Ser Leu Asp Ser Trp Trp Thr Ser Leu Asn Phe
                490                 495                 500 ctt ggc ggt aca aca aca tgt cca ggc caa aac tct caa tca cca act          1590
Leu Gly Gly Thr Thr Thr Cys Pro Gly Gln Asn Ser Gln Ser Pro Thr
            505                 510                 515 tct aat cac tct cca aca tct tgc cct cca att tgc cca ggt tac aga          1638
Ser Asn His Ser Pro Thr Ser Cys Pro Pro Ile Cys Pro Gly Tyr Arg
        520                 525                 530 tgg atg tgc ttg aga agg ttc atc att ttt ctg ttc atc ctc ttg ttg          1686
Trp Met Cys Leu Arg Arg Phe Ile Ile Phe Leu Phe Ile Leu Leu Leu
535                 540                 545                 550 tgt ttg att ttc ctc tta gta ttg ctg gac tac caa ggc atg ctt cca          1734
Cys Leu Ile Phe Leu Leu Val Leu Leu Asp Tyr Gln Gly Met Leu Pro
                    555                 560                 565 gtc tgc cct cta ttg cca gga act tct aca acc tca aca gga cca tgt          1782
Val Cys Pro Leu Leu Pro Gly Thr Ser Thr Thr Ser Thr Gly Pro Cys
                570                 575                 580 aaa aca tgt act atc cct gct caa gga aca tca atg ttt cca tct tgt          1830
Lys Thr Cys Thr Ile Pro Ala Gln Gly Thr Ser Met Phe Pro Ser Cys
            585                 590                 595 tgc tgt aca aaa cca tca gat ggt aat tgt act tgt ata cca ata cca          1878
Cys Cys Thr Lys Pro Ser Asp Gly Asn Cys Thr Cys Ile Pro Ile Pro
        600                 605                 610 agt tca tgg gca ttt gcc cgt ttc ctt tgg gag tgg gct tct gta aga          1926
Ser Ser Trp Ala Phe Ala Arg Phe Leu Trp Glu Trp Ala Ser Val Arg
615                 620                 625                 630 ttc tct tgg tta agt ttg cta gtc cca ttc gtg cag tgg ttt gtt ggc          1974
Phe Ser Trp Leu Ser Leu Leu Val Pro Phe Val Gln Trp Phe Val Gly
                    635                 640                 645 ctg tct cca act gtt tgg tta tct gtt att tgg atg atg tgg tac tgg          2022
Leu Ser Pro Thr Val Trp Leu Ser Val Ile Trp Met Met Trp Tyr Trp
                650                 655                 660 ggt cca agc cta tac tca atc gtg tca cct ttt atc cca ttg cta cct          2070
Gly Pro Ser Leu Tyr Ser Ile Val Ser Pro Phe Ile Pro Leu Leu Pro
            665                 670                 675 atc ttt ttc tgc ctc tgg gtt tac atc gat att gac cct tac aag gaa          2118
Ile Phe Phe Cys Leu Trp Val Tyr Ile Asp Ile Asp Pro Tyr Lys Glu
        680                 685                 690 ttt ggc gca aca gtt gaa ttg tta tca ttt tta cca tca gat ttc ttt          2166
Phe Gly Ala Thr Val Glu Leu Leu Ser Phe Leu Pro Ser Asp Phe Phe
695                 700                 705                 710 cca tca gtg cgt gat ttg tta gat acg gca tcc gct ttg tac aga gaa          2214
Pro Ser Val Arg Asp Leu Leu Asp Thr Ala Ser Ala Leu Tyr Arg Glu
                    715                 720                 725 gca ctg gaa tca cca gaa cac tgt tct cca cat cac act gct ctc aga          2262
Ala Leu Glu Ser Pro Glu His Cys Ser Pro His His Thr Ala Leu Arg
                730                 735                 740
```

-continued

| | | |
|---|---|---|
| caa gct ata ttg tgt tgg gga gag ttg atg aat cta gcc act tgg gta<br>Gln Ala Ile Leu Cys Trp Gly Glu Leu Met Asn Leu Ala Thr Trp Val<br>        745                        750                      755 | | 2310 |
| ggg tcc aat ctg gaa gat cct gcc tct aga gaa ctg gtg gta tct tac<br>Gly Ser Asn Leu Glu Asp Pro Ala Ser Arg Glu Leu Val Val Ser Tyr<br>760                          765                        770 | | 2358 |
| gtc aat gtt aac atg ggg ttg aag att aga caa ctt tta tgg ttc cat<br>Val Asn Val Asn Met Gly Leu Lys Ile Arg Gln Leu Leu Trp Phe His<br>775                          780                        785                        790 | | 2406 |
| att tca tgt tta acg ttt ggt aga gaa aca gta ctg gaa tac tta gtt<br>Ile Ser Cys Leu Thr Phe Gly Arg Glu Thr Val Leu Glu Tyr Leu Val<br>        795                        800                        805 | | 2454 |
| agt ttc ggt gtc tgg att aga aca cca cca gca tat aga cca cca aat<br>Ser Phe Gly Val Trp Ile Arg Thr Pro Pro Ala Tyr Arg Pro Pro Asn<br>                  810                        815                        820 | | 2502 |
| gcg cct ata ttg agt acg ctc cca gaa acg acg gtc gtt agg aga aga<br>Ala Pro Ile Leu Ser Thr Leu Pro Glu Thr Thr Val Val Arg Arg Arg<br>                825                        830                        835 | | 2550 |
| ggt aga tca cct agg aga agg aca cct tca cct aga cgt aga cgt tct<br>Gly Arg Ser Pro Arg Arg Arg Thr Pro Ser Pro Arg Arg Arg Arg Ser<br>840                          845                        850 | | 2598 |
| caa tct cca aga cgt aga aga tct caa tct aga gaa tca caa tgc<br>Gln Ser Pro Arg Arg Arg Ser Gln Ser Arg Glu Ser Gln Cys<br>855                          860                        865 | | 2643 |
| catcatcatc accatcatta agcggccgc | | 2672 |

```
<210> SEQ ID NO 134
<211> LENGTH: 869
<212> TYPE: PRT
<213> ORGANISM: Artificial
<220> FEATURE:
<223> OTHER INFORMATION: Synthetic Construct

<400> SEQUENCE: 134
```

His Leu Ser Leu Arg Gly Leu Phe Val Cys Ala Phe Ser Ser Ala Gly
1               5                   10                  15

Pro Asn Ala His Gln Phe Leu Pro Lys Val Leu His Lys Arg Thr Leu
            20                  25                  30

Gly Leu Ser Ala Met Ser Thr Thr Asp Leu Glu Ala Tyr Phe Lys Asp
        35                  40                  45

Cys Leu Phe Lys Asp Trp Glu Glu Leu Gly Glu Gly Leu Ser Arg
    50                  55                  60

Tyr Val Ala Arg Leu Ser Ser Asn Ser Arg Ile Phe Asn His Gln His
65                  70                  75                  80

Gly Thr Met Gln Asn Leu His Asp Ser Cys Ser Arg Asn Leu Tyr Val
                85                  90                  95

Ser Leu Leu Leu Tyr Gln Thr Phe Gly Arg Lys Leu His Leu Tyr
            100                 105                 110

Ser His Pro Ile Ile Leu Gly Phe Arg Lys Ile Pro Met Gly Val Gly
        115                 120                 125

Leu Ser Pro Phe Leu Leu Ala Gln Phe Thr Ser Ala Ile Cys Ser Val
    130                 135                 140

Val Arg Arg Ala Phe Pro His Cys Leu Ala Phe Ser Tyr Met Asp Asp
145                 150                 155                 160

Val Val Leu Gly Ala Lys Ser Val Gln His Leu Glu Ser Leu Phe Thr
                165                 170                 175

Ala Val Thr Asn Phe Leu Leu Ser Leu Gly Ile His Leu Asn Pro Asn
            180                 185                 190

```
Lys Thr Lys Arg Trp Gly Tyr Ser Leu His Phe Met Gly Tyr Val Ile
        195                 200                 205
Gly Cys Tyr Gly Ser Leu Pro Gln Asp His Ile Ile Gln Lys Ile Lys
        210                 215                 220
Glu Cys Phe Arg Lys Leu Pro Val Asn Arg Pro Ile Asp Trp Lys Val
225                 230                 235                 240
Cys Gln Arg Ile Val Gly Leu Leu Gly Phe Ala Ala Pro Phe Thr Gln
                245                 250                 255
Cys Gly Tyr Pro Ala Leu Met Pro Leu Tyr Ala Cys Ile Gln Ser Lys
        260                 265                 270
Gln Ala Phe Thr Phe Ser Pro Thr Tyr Lys Ala Phe Leu Cys Lys Gln
        275                 280                 285
Gly Gln Trp Ser Ser Lys Pro Arg Lys Gly Met Gly Thr Asn Leu Ser
        290                 295                 300
Val Ser Asn Pro Leu Gly Phe Phe Pro Asp His Gln Leu Asp Pro Ala
305                 310                 315                 320
Phe Arg Ala Asn Ser Ala Asn Pro Asp Trp Asp Phe Asn Pro Asn Lys
                325                 330                 335
Asp Thr Trp Pro Glu Ala Asn Gln Val Gly Val Gly Ala Phe Gly Leu
        340                 345                 350
Gly Phe Thr Pro Pro His Gly Gly Leu Leu Gly Trp Ser Pro Gln Ala
        355                 360                 365
Gln Gly Ile Leu Gln Thr Val Pro Ala Asn Pro Pro Ala Ser Thr
        370                 375                 380
Asn Arg Gln Ser Gly Arg Gln Pro Thr Pro Ile Ser Pro Pro Leu Arg
385                 390                 395                 400
Asp Ser His Pro Gln Ala Met Gln Trp Asn Ser Thr Thr Phe His Gln
                405                 410                 415
Ala Leu Leu Asp Pro Arg Val Arg Gly Leu Tyr Phe Pro Ala Gly Gly
        420                 425                 430
Ser Ser Ser Gly Thr Val Asn Pro Val Pro Thr Thr Ala Ser Pro Ile
        435                 440                 445
Ser Ser Ile Phe Ser Arg Thr Gly Asp Pro Ala Leu Asn Met Glu Asn
        450                 455                 460
Ile Thr Ser Gly Phe Leu Gly Pro Leu Leu Val Leu Gln Ala Gly Phe
465                 470                 475                 480
Phe Leu Leu Thr Arg Ile Leu Thr Ile Pro Gln Ser Leu Asp Ser Trp
                485                 490                 495
Trp Thr Ser Leu Asn Phe Leu Gly Gly Thr Thr Thr Cys Pro Gly Gln
        500                 505                 510
Asn Ser Gln Ser Pro Thr Ser Asn His Ser Pro Thr Ser Cys Pro Pro
        515                 520                 525
Ile Cys Pro Gly Tyr Arg Trp Met Cys Leu Arg Arg Phe Ile Ile Phe
        530                 535                 540
Leu Phe Ile Leu Leu Leu Cys Leu Ile Phe Leu Leu Val Leu Leu Asp
545                 550                 555                 560
Tyr Gln Gly Met Leu Pro Val Cys Pro Leu Leu Pro Gly Thr Ser Thr
                565                 570                 575
Thr Ser Thr Gly Pro Cys Lys Thr Cys Thr Ile Pro Ala Gln Gly Thr
        580                 585                 590
Ser Met Phe Pro Ser Cys Cys Cys Thr Lys Pro Ser Asp Gly Asn Cys
        595                 600                 605
```

```
Thr Cys Ile Pro Ile Pro Ser Ser Trp Ala Phe Ala Arg Phe Leu Trp
        610                 615                 620
Glu Trp Ala Ser Val Arg Phe Ser Trp Leu Ser Leu Leu Val Pro Phe
625                 630                 635                 640
Val Gln Trp Phe Val Gly Leu Ser Pro Thr Val Trp Leu Ser Val Ile
                645                 650                 655
Trp Met Met Trp Tyr Trp Gly Pro Ser Leu Tyr Ser Ile Val Ser Pro
            660                 665                 670
Phe Ile Pro Leu Leu Pro Ile Phe Phe Cys Leu Trp Val Tyr Ile Asp
        675                 680                 685
Ile Asp Pro Tyr Lys Glu Phe Gly Ala Thr Val Glu Leu Leu Ser Phe
    690                 695                 700
Leu Pro Ser Asp Phe Phe Pro Ser Val Arg Asp Leu Leu Asp Thr Ala
705                 710                 715                 720
Ser Ala Leu Tyr Arg Glu Ala Leu Glu Ser Pro Glu His Cys Ser Pro
                725                 730                 735
His His Thr Ala Leu Arg Gln Ala Ile Leu Cys Trp Gly Glu Leu Met
            740                 745                 750
Asn Leu Ala Thr Trp Val Gly Ser Asn Leu Glu Asp Pro Ala Ser Arg
        755                 760                 765
Glu Leu Val Val Ser Tyr Val Asn Val Asn Met Gly Leu Lys Ile Arg
    770                 775                 780
Gln Leu Leu Trp Phe His Ile Ser Cys Leu Thr Phe Gly Arg Glu Thr
785                 790                 795                 800
Val Leu Glu Tyr Leu Val Ser Phe Gly Val Trp Ile Arg Thr Pro Pro
                805                 810                 815
Ala Tyr Arg Pro Pro Asn Ala Pro Ile Leu Ser Thr Leu Pro Glu Thr
            820                 825                 830
Thr Val Val Arg Arg Arg Gly Arg Ser Pro Arg Arg Arg Thr Pro Ser
        835                 840                 845
Pro Arg Arg Arg Arg Ser Gln Ser Pro Arg Arg Arg Arg Ser Gln Ser
    850                 855                 860
Arg Glu Ser Gln Cys
865

<210> SEQ ID NO 135
<211> LENGTH: 9
<212> TYPE: PRT
<213> ORGANISM: Hepatitis B virus

<400> SEQUENCE: 135

Lys Leu His Leu Tyr Ser His Pro Ile
1               5

<210> SEQ ID NO 136
<211> LENGTH: 10
<212> TYPE: PRT
<213> ORGANISM: Hepatitis B virus

<400> SEQUENCE: 136

Leu Leu Val Pro Phe Val Gln Trp Phe Val
1               5                   10

<210> SEQ ID NO 137
<211> LENGTH: 9
<212> TYPE: PRT
<213> ORGANISM: Hepatitis B virus
```

```
<400> SEQUENCE: 137

His Leu Tyr Ser His Pro Ile Ile Leu
1               5

<210> SEQ ID NO 138
<211> LENGTH: 9
<212> TYPE: PRT
<213> ORGANISM: Hepatitis B virus

<400> SEQUENCE: 138

Trp Ser Pro Gln Ala Gln Gly Ile Leu
1               5

<210> SEQ ID NO 139
<211> LENGTH: 8
<212> TYPE: PRT
<213> ORGANISM: Hepatitis B virus

<400> SEQUENCE: 139

Val Leu Leu Asp Tyr Gln Gly Met
1               5

<210> SEQ ID NO 140
<211> LENGTH: 8
<212> TYPE: PRT
<213> ORGANISM: Hepatitis B virus

<400> SEQUENCE: 140

Ala Ser Val Arg Phe Ser Trp Leu
1               5

<210> SEQ ID NO 141
<211> LENGTH: 9
<212> TYPE: PRT
<213> ORGANISM: Hepatitis B virus

<400> SEQUENCE: 141

Thr Val Pro Ala Asn Pro Pro Pro Ala
1               5

<210> SEQ ID NO 142
<211> LENGTH: 9
<212> TYPE: PRT
<213> ORGANISM: Hepatitis B virus

<400> SEQUENCE: 142

Gly Met Leu Pro Val Cys Pro Leu Leu
1               5

<210> SEQ ID NO 143
<211> LENGTH: 9
<212> TYPE: PRT
<213> ORGANISM: Hepatitis B virus

<400> SEQUENCE: 143

Met Gly Leu Lys Ile Arg Gln Leu Leu
1               5

<210> SEQ ID NO 144
<211> LENGTH: 8
<212> TYPE: PRT
<213> ORGANISM: Hepatitis B virus

<400> SEQUENCE: 144
```

```
Ile Cys Pro Gly Tyr Arg Trp Met
1               5

<210> SEQ ID NO 145
<211> LENGTH: 8
<212> TYPE: PRT
<213> ORGANISM: Hepatitis B virus

<400> SEQUENCE: 145

Ile Ile Phe Leu Phe Ile Leu Leu
1               5

<210> SEQ ID NO 146
<211> LENGTH: 8
<212> TYPE: PRT
<213> ORGANISM: Hepatitis B virus

<400> SEQUENCE: 146

Phe Val Gln Trp Phe Val Gly Leu
1               5

<210> SEQ ID NO 147
<211> LENGTH: 8
<212> TYPE: PRT
<213> ORGANISM: Hepatitis B virus

<400> SEQUENCE: 147

Leu Leu Pro Ile Phe Phe Cys Leu
1               5

<210> SEQ ID NO 148
<211> LENGTH: 21
<212> TYPE: PRT
<213> ORGANISM: Hepatitis B virus

<400> SEQUENCE: 148

Val Ser Phe Gly Val Trp Ile Arg Thr Pro Pro Ala Tyr Arg Pro Pro
1               5                   10                  15

Asn Ala Pro Ile Leu
            20

<210> SEQ ID NO 149
<211> LENGTH: 8
<212> TYPE: PRT
<213> ORGANISM: Hepatitis B virus

<400> SEQUENCE: 149

Ile Leu Ser Pro Phe Leu Pro Leu
1               5

<210> SEQ ID NO 150
<211> LENGTH: 657
<212> TYPE: PRT
<213> ORGANISM: Artificial
<220> FEATURE:
<223> OTHER INFORMATION: Synthetic Construct

<400> SEQUENCE: 150

Met Ala Asp Glu Ala Pro Thr Ser His Leu Ser Leu Arg Gly Leu Phe
1               5                   10                  15

Val Cys Ala Phe Ser Ser Ala Gly Pro Asn Ala His Gln Phe Leu Pro
                20                  25                  30

Lys Val Leu His Lys Arg Thr Leu Gly Leu Ser Ala Met Ser Thr Thr
            35                  40                  45
```

```
Asp Leu Glu Ala Tyr Phe Lys Asp Cys Leu Phe Lys Asp Trp Glu Glu
 50                  55                  60

Leu Gly Glu Glu Leu Glu Gly Gln Trp Ser Ser Lys Pro Arg Lys Gly
 65                  70                  75                  80

Met Gly Thr Asn Leu Ser Val Ser Asn Pro Leu Gly Phe Phe Pro Asp
                 85                  90                  95

His Gln Leu Asp Pro Ala Phe Arg Ala Asn Ser Ala Asn Pro Asp Trp
            100                 105                 110

Asp Phe Asn Pro Asn Lys Asp Thr Trp Pro Glu Ala Asn Gln Val Gly
        115                 120                 125

Val Gly Ala Phe Gly Leu Gly Phe Thr Pro Pro His Gly Gly Leu Leu
    130                 135                 140

Gly Trp Ser Pro Gln Ala Gln Gly Ile Leu Gln Thr Val Pro Ala Asn
145                 150                 155                 160

Pro Pro Pro Ala Ser Thr Asn Arg Gln Ser Gly Arg Gln Pro Thr Pro
                165                 170                 175

Ile Ser Pro Pro Leu Arg Asp Ser His Pro Gln Ala Met Gln Trp Asn
                180                 185                 190

Ser Thr Thr Phe His Gln Ala Leu Leu Asp Pro Arg Val Arg Gly Leu
            195                 200                 205

Tyr Phe Pro Ala Gly Gly Ser Ser Ser Gly Thr Val Asn Pro Val Pro
        210                 215                 220

Thr Thr Ala Ser Pro Ile Ser Ser Ile Phe Ser Arg Thr Gly Asp Pro
225                 230                 235                 240

Ala Leu Asn Met Glu Asn Ile Thr Ser Gly Phe Leu Gly Pro Leu Leu
                245                 250                 255

Val Leu Gln Ala Gly Phe Phe Leu Leu Thr Arg Ile Leu Thr Ile Pro
            260                 265                 270

Gln Ser Leu Asp Ser Trp Trp Thr Ser Leu Asn Phe Leu Gly Gly Thr
        275                 280                 285

Thr Thr Cys Pro Gly Gln Asn Ser Gln Ser Pro Thr Ser Asn His Ser
    290                 295                 300

Pro Thr Ser Cys Pro Pro Ile Cys Pro Gly Tyr Arg Trp Met Cys Leu
305                 310                 315                 320

Arg Arg Phe Ile Ile Phe Leu Phe Ile Leu Leu Leu Cys Leu Ile Phe
                325                 330                 335

Leu Leu Val Leu Leu Asp Tyr Gln Gly Met Leu Pro Val Cys Pro Leu
            340                 345                 350

Leu Pro Gly Thr Ser Thr Thr Ser Thr Gly Pro Cys Lys Thr Cys Thr
        355                 360                 365

Ile Pro Ala Gln Gly Thr Ser Met Phe Pro Ser Cys Cys Cys Thr Lys
    370                 375                 380

Pro Ser Asp Gly Asn Cys Thr Cys Ile Pro Ile Pro Ser Ser Trp Ala
385                 390                 395                 400

Phe Ala Arg Phe Leu Trp Glu Trp Ala Ser Val Arg Phe Ser Trp Leu
                405                 410                 415

Ser Leu Leu Val Pro Phe Val Gln Trp Phe Val Gly Leu Ser Pro Thr
            420                 425                 430

Val Trp Leu Ser Val Ile Trp Met Met Trp Tyr Trp Gly Pro Ser Leu
        435                 440                 445

Tyr Ser Ile Val Ser Pro Phe Ile Pro Leu Leu Pro Ile Phe Phe Cys
    450                 455                 460
```

```
Leu Trp Val Tyr Ile Asp Ile Asp Pro Tyr Lys Glu Phe Gly Ala Thr
465                 470                 475                 480

Val Glu Leu Leu Ser Phe Leu Pro Ser Asp Phe Phe Pro Ser Val Arg
            485                 490                 495

Asp Leu Leu Asp Thr Ala Ser Ala Leu Tyr Arg Glu Ala Leu Glu Ser
        500                 505                 510

Pro Glu His Cys Ser Pro His His Thr Ala Leu Arg Gln Ala Ile Leu
        515                 520                 525

Cys Trp Gly Glu Leu Met Asn Leu Ala Thr Trp Val Gly Ser Asn Leu
    530                 535                 540

Glu Asp Pro Ala Ser Arg Glu Leu Val Val Ser Tyr Val Asn Val Asn
545                 550                 555                 560

Met Gly Leu Lys Ile Arg Gln Leu Leu Trp Phe His Ile Ser Cys Leu
                565                 570                 575

Thr Phe Gly Arg Glu Thr Val Leu Glu Tyr Leu Val Ser Phe Gly Val
            580                 585                 590

Trp Ile Arg Thr Pro Pro Ala Tyr Arg Pro Pro Asn Ala Pro Ile Leu
            595                 600                 605

Ser Thr Leu Pro Glu Thr Thr Val Val Arg Arg Arg Gly Arg Ser Pro
        610                 615                 620

Arg Arg Arg Thr Pro Ser Pro Arg Arg Arg Ser Gln Ser Pro Arg
625                 630                 635                 640

Arg Arg Arg Ser Gln Ser Arg Glu Ser Gln Cys His His His His
                645                 650                 655

His

<210> SEQ ID NO 151
<211> LENGTH: 595
<212> TYPE: PRT
<213> ORGANISM: Artificial
<220> FEATURE:
<223> OTHER INFORMATION: Synthetic Construct

<400> SEQUENCE: 151

Met Ala Asp Glu Ala Pro Thr Ser Gly Gln Trp Ser Ser Lys Pro Arg
1               5                   10                  15

Lys Gly Met Gly Thr Asn Leu Ser Val Ser Asn Pro Leu Gly Phe Phe
            20                  25                  30

Pro Asp His Gln Leu Asp Pro Ala Phe Arg Ala Asn Ser Ala Asn Pro
        35                  40                  45

Asp Trp Asp Phe Asn Pro Asn Lys Asp Thr Trp Pro Glu Ala Asn Gln
    50                  55                  60

Val Gly Val Gly Ala Phe Gly Leu Gly Phe Thr Pro Pro His Gly Gly
65                  70                  75                  80

Leu Leu Gly Trp Ser Pro Gln Ala Gln Gly Ile Leu Gln Thr Val Pro
                85                  90                  95

Ala Asn Pro Pro Pro Ala Ser Thr Asn Arg Gln Ser Gly Arg Gln Pro
            100                 105                 110

Thr Pro Ile Ser Pro Pro Leu Arg Asp Ser His Pro Gln Ala Met Gln
        115                 120                 125

Trp Asn Ser Thr Thr Phe His Gln Ala Leu Leu Asp Pro Arg Val Arg
    130                 135                 140

Gly Leu Tyr Phe Pro Ala Gly Gly Ser Ser Ser Gly Thr Val Asn Pro
145                 150                 155                 160

Val Pro Thr Thr Ala Ser Pro Ile Ser Ser Ile Phe Ser Arg Thr Gly
```

-continued

```
              165                 170                 175
Asp Pro Ala Leu Asn Met Glu Asn Ile Thr Ser Gly Phe Leu Gly Pro
            180                 185                 190
Leu Leu Val Leu Gln Ala Gly Phe Phe Leu Leu Thr Arg Ile Leu Thr
            195                 200                 205
Ile Pro Gln Ser Leu Asp Ser Trp Trp Thr Ser Leu Asn Phe Leu Gly
210                 215                 220
Gly Thr Thr Thr Cys Pro Gly Gln Asn Ser Gln Ser Pro Thr Ser Asn
225                 230                 235                 240
His Ser Pro Thr Ser Cys Pro Pro Ile Cys Pro Gly Tyr Arg Trp Met
            245                 250                 255
Cys Leu Arg Arg Phe Ile Ile Phe Leu Phe Ile Leu Leu Leu Cys Leu
            260                 265                 270
Ile Phe Leu Leu Val Leu Leu Asp Tyr Gln Gly Met Leu Pro Val Cys
            275                 280                 285
Pro Leu Leu Pro Gly Thr Ser Thr Thr Ser Thr Gly Pro Cys Lys Thr
            290                 295                 300
Cys Thr Ile Pro Ala Gln Gly Thr Ser Met Phe Pro Ser Cys Cys Cys
305                 310                 315                 320
Thr Lys Pro Ser Asp Gly Asn Cys Thr Cys Ile Pro Ile Pro Ser Ser
                325                 330                 335
Trp Ala Phe Ala Arg Phe Leu Trp Glu Trp Ala Ser Val Arg Phe Ser
            340                 345                 350
Trp Leu Ser Leu Leu Val Pro Phe Val Gln Trp Phe Val Gly Leu Ser
            355                 360                 365
Pro Thr Val Trp Leu Ser Val Ile Trp Met Met Trp Tyr Trp Gly Pro
            370                 375                 380
Ser Leu Tyr Ser Ile Val Ser Pro Phe Ile Pro Leu Leu Pro Ile Phe
385                 390                 395                 400
Phe Cys Leu Trp Val Tyr Ile Asp Ile Asp Pro Tyr Lys Glu Phe Gly
                405                 410                 415
Ala Thr Val Glu Leu Leu Ser Phe Leu Pro Ser Asp Phe Phe Pro Ser
            420                 425                 430
Val Arg Asp Leu Leu Asp Thr Ala Ser Ala Leu Tyr Arg Glu Ala Leu
            435                 440                 445
Glu Ser Pro Glu His Cys Ser Pro His His Thr Ala Leu Arg Gln Ala
            450                 455                 460
Ile Leu Cys Trp Gly Glu Leu Met Asn Leu Ala Thr Trp Val Gly Ser
465                 470                 475                 480
Asn Leu Glu Asp Pro Ala Ser Arg Glu Leu Val Val Ser Tyr Val Asn
                485                 490                 495
Val Asn Met Gly Leu Lys Ile Arg Gln Leu Leu Trp Phe His Ile Ser
            500                 505                 510
Cys Leu Thr Phe Gly Arg Glu Thr Val Leu Glu Tyr Leu Val Ser Phe
            515                 520                 525
Gly Val Trp Ile Arg Thr Pro Pro Ala Tyr Arg Pro Pro Asn Ala Pro
            530                 535                 540
Ile Leu Ser Thr Leu Pro Glu Thr Thr Val Val Arg Arg Arg Gly Arg
545                 550                 555                 560
Ser Pro Arg Arg Arg Thr Pro Ser Pro Arg Arg Arg Ser Gln Ser
                565                 570                 575
Pro Arg Arg Arg Arg Ser Gln Ser Arg Glu Ser Gln Cys His His His
            580                 585                 590
```

```
His His His
        595

<210> SEQ ID NO 152
<211> LENGTH: 8
<212> TYPE: PRT
<213> ORGANISM: Hepatitis B virus

<400> SEQUENCE: 152

Val Trp Leu Ser Val Ile Trp Met
1               5
```

YEAST-BASED THERAPEUTIC FOR CHRONIC HEPATITIS B INFECTION

CROSS REFERENCE TO RELATED APPLICATIONS

This application is a divisional application of U.S. application Ser. No. 13/984,888, filed Nov. 18, 2013, now issued U.S. Pat. No. 8,877,205, which is a national stage application under 35 U.S.C. 371 of PCT Application No. PCT/US2012/024409, having an international filing date of Feb. 9, 2012, which designated the United States, which PCT application claims the benefit of priority under 35 U.S.C. §119(e) from each of U.S. Provisional Application No. 61/442,204, filed Feb. 12, 2011, U.S. Provisional Application No. 61/496,945, filed Jun. 14, 2011, and U.S. Provisional Application No. 61/507,361, filed Jul. 13, 2011. The entire disclosure of each of U.S. application Ser. No. 13/984,888, PCT Application No. PCT/US12/24409, U.S. Provisional Application No. 61/442,204, U.S. Provisional Application No. 61/496,945, and U.S. Provisional Application No. 61/507,361 is incorporated herein by reference.

REFERENCE TO A SEQUENCE LISTING

This application contains a Sequence Listing submitted electronically as a text file by EFS-Web. The text file, named "3923-32-PCT_ST25", has a size in bytes of 476 KB, and was recorded on Feb. 7, 2012. The information contained in the text file is incorporated herein by reference in its entirety pursuant to 37 CFR §1.52(e)(5).

FIELD OF THE INVENTION

The present invention generally relates to immunotherapeutic compositions and methods for preventing and/or treating hepatitis B virus (HBV) infection.

BACKGROUND OF THE INVENTION

Hepatitis B virus (HBV) is a member of the hepadnavirus family and is a causative agent of acute and chronic hepatitis worldwide. HBV epidemics have been prevalent in Asia and Africa, and HBV infection is endemic in China (Williams, R. (2006), "Global challenges in liver disease", Hepatology (Baltimore, Md.) 44 (3): 521-526). More than 2 billion people have been infected with the virus, and it is estimated that there are 350 million chronically HBV-infected individuals worldwide ("Hepatitis B", World Health Organization, 2009; "FAQ About Hepatitis B", Stanford School of Medicine. 2008-07-10). Routes of infection are through blood and bodily fluid contact, including blood transfusions and IV drug use, sexual transmission, bites and lesions, and vertical transmission (e.g., childbirth).

HBV is found as one of four major serotypes (adr, adw, ayr, ayw) that are determined based on antigenic epitopes within its envelope proteins. There are eight different genotypes (A-H) based on the nucleotide sequence variations in the genome. Genotype differences impact disease severity, disease course and likelihood of complications, response to treatment and possibly response to vaccination (Kramvis et al., (2005), Vaccine 23 (19): 2409-2423; Magnius and Norder, (1995), Intervirology 38 (1-2): 24-34).

The clinical incubation period for HBV is usually 2-3 months; approximately two thirds of those acutely infected are asymptomatic or have mild, subclinical symptoms. The remaining one third of acutely infected individuals may experience jaundice, inflammation of the liver, vomiting, aches and/or mild fever, but the disease is eventually resolved in most adults and rarely leads to liver failure. Indeed, approximately 95% of adults recover completely from HBV infection and do not become chronically infected. However, approximately 90% of infants and 25%-50% of children aged 1-5 years will remain chronically infected with HBV (Centers for Disease Control and Prevention as of September 2010). Approximately 25% of those who become chronically infected during childhood and 15% of those who become chronically infected after childhood die prematurely from cirrhosis or hepatocellular carcinoma, and the majority of chronically infected individuals remain asymptomatic until onset of cirrhosis or end-stage liver disease (CDC as of September 2010). 1 million deaths per year worldwide (about 2000-4000 deaths per year in the U.S.) result from chronic HBV infection. Chronically infected individuals have elevated serum alanine aminotransferase (ALT) levels (a marker of liver damage), liver inflammation and/or fibrosis upon liver biopsy. For those patients who develop cirrhosis, the 5 year survival rate is about 50%.

HBV infection and its treatment are typically monitored by the detection of viral antigens and/or antibodies against the antigens. Upon infection with HBV, the first detectable antigen is the hepatitis B surface antigen (HBsAg), followed by the hepatitis B "e" antigen (HBeAg). Clearance of the virus is indicated by the appearance of IgG antibodies in the serum against HBsAg and/or against the core antigen (HBcAg), also known as seroconversion. Numerous studies indicate that viral replication, the level of viremia and progression to the chronic state in HBV-infected individuals are influenced directly and indirectly by HBV-specific cellular immunity mediated by $CD4^+$ helper ($T_H$) and $CD8^+$ cytotoxic T lymphocytes (CTLs). Patients progressing to chronic disease tend to have absent, weaker, or narrowly focused HBV-specific T cell responses as compared to patients who clear acute infection. See, e.g., Chisari, 1997, J Clin Invest 99: 1472-1477; Maini et al., 1999, Gastroenterology 117:1386-1396; Rehermann et al., 2005, Nat Rev Immunol 2005; 5:215-229; Thimme et al., 2001, J Virol 75: 3984-3987; Urbani et al., 2002, J Virol 76: 12423-12434; Wieland and Chisari, 2005, J Virol 79: 9369-9380; Webster et al., 2000, Hepatology 32:1117-1124; Penna et al., 1996, J Clin Invest 98: 1185-1194; Sprengers et al., 2006, J Hepatol 2006; 45: 182-189.

Vaccines for the prevention of HBV have been commercially available since the early 1980's. Current commercial vaccines are non-infectious, subunit viral vaccines providing purified recombinant hepatitis B virus surface antigen (HBsAg), and can be administered beginning at birth. The vaccines have been effective at reducing the incidence of infection in countries where the vaccine is routinely administered. While a few immunotherapeutics are in development, including various HBV protein or epitope vaccines and cytokines, there are currently no approved immunotherapeutics for the treatment of active HBV infection in the United States.

Current standard of care (SOC) therapy for HBV infection includes primarily antiviral drugs, such as tenofovir (VIREAD®), lamivudine (EPIVIR®), adefovir (HEPSERA®), telbivudine (TYZEKA®) and entecavir (BARACLUDE®), as well as interferon-α2a and pegylated interferon-α2a (PEGASYS®). These drugs, and particularly the antiviral drugs, are typically administered for long periods of time (e.g., daily or weekly for one to five years or longer), and although they slow or stop viral replication, they typically do not provide a complete "cure" or eradication of the virus. Interferon-based approaches are toxic and have modest remission rates. The antiviral therapies inhibit viral replication and are better tolerated than interferon, but as mentioned above, these drugs typically do not provide a complete viral cure, and in some cases long term remission rates are not achieved. Moreover, in some cases, development of drug resistance ensues. For example, lamivudine is a potent oral antiviral that inhibits HBV reverse transcriptase (Pol). As lamivudine is well tolerated, and because it is now a generic drug, lamivudine is an option for HBV antiviral therapy in developing countries. However, a 20% annual viral resistance rate from point mutations in the Pol sequence limits the utility of lamivudine for HBV. Moreover, response to current antiviral and interferon treatment is differently effective among HBV genotypes (Cao, *World Journal of Gastroenterology* 2009; 15(46):5761-9) and in some patients, because the hepatitis B virus DNA can persist in the body even after infection clears, reactivation of the virus can occur over time.

Accordingly, while standard of care (SOC) therapy provides the best currently approved treatment for patients suffering from chronic HBV, the length of time for therapy and the significant adverse effects of the regimens can lead to noncompliance, dose reduction, and treatment discontinuation, combined with viral escape, reactivation of the virus, and patients who still fail to respond or sustain response to therapy. Therefore, there remains a need in the art for improved therapeutic treatments for HBV infection.

SUMMARY OF THE INVENTION

One embodiment of the invention relates to an immunotherapeutic composition for the treatment and/or prevention of hepatitis B virus (HBV) infection and/or a symptom of HBV infection. The immunotherapeutic composition comprises: (a) a yeast vehicle; and (b) one or more HBV antigens. In one aspect, the HBV antigens are provided as one or more fusion proteins, although single protein HBV antigens may also be provided. The HBV antigens consist of: (i) an HBV surface antigen comprising at least one immunogenic domain of a full-length HBV large (L), medium (M) and/or small (S) surface antigen; (ii) an HBV polymerase antigen comprising at least one immunogenic domain of a full-length HBV polymerase or domain thereof (e.g., a reverse transcriptase (RT) domain); (iii) an HBV core antigen or HBV e-antigen comprising at least one immunogenic domain of a full-length HBV core protein and/or a full-length HBV e-antigen, respectively; and/or (iv) an HBV X antigen comprising at least one immunogenic domain of a full-length HBV X antigen. The composition elicits an HBV-specific immune response against one or more HBV antigens in the composition and/or against one or more antigens in a hepatitis B virus that has infected, or may infect, an individual.

In any of the embodiments of the invention described herein, including any embodiment related to an immunotherapeutic composition, HBV antigen, fusion protein or use of such composition, HBV antigen or fusion protein, in one aspect, the amino acid sequence of the HBV large surface antigen (L) can include, but is not limited to, an amino acid sequence represented by SEQ ID NO:3, SEQ ID NO:7, SEQ ID NO:11, SEQ ID NO:15, SEQ ID NO:19, SEQ ID NO:23, SEQ ID NO:27 or SEQ ID NO:31, or a corresponding sequence from another HBV strain/isolate. The amino acid sequence of HBV polymerase can include, but is not limited to, an amino acid sequence represented by SEQ ID NO:2, SEQ ID NO:6, SEQ ID NO:10, SEQ ID NO:14, SEQ ID NO:18, SEQ ID NO:22, SEQ ID NO:26 or SEQ ID NO:30, a domain of these sequences, such as the reverse transcriptase (RT) domain, or a corresponding sequence from another HBV strain/isolate. The amino acid sequence of HBV precore protein, which includes both HBV core protein sequence and HBV e-antigen sequence, can include, but is not limited to, an amino acid sequence represented by SEQ ID NO:1, SEQ ID NO:5, SEQ ID NO:9, SEQ ID NO:13, SEQ ID NO:17, SEQ ID NO:21, SEQ ID NO:25, or SEQ ID NO:29, or a corresponding sequence from another HBV strain/isolate. The amino acid sequence of an HBV X antigen can include, but is not limited to, an amino acid sequence represented by SEQ ID NO:4, SEQ ID NO:8, SEQ ID NO:12, SEQ ID NO:16, SEQ ID NO:20, SEQ ID NO:24, SEQ ID NO:28, or SEQ ID NO:32, or a corresponding sequence from another HBV strain/isolate.

In any of the embodiments of the invention described herein, including any embodiment related to an immunotherapeutic composition, HBV antigen, fusion protein or use of such composition, HBV antigen or fusion protein, in one aspect, an amino acid of an HBV surface antigen useful as an HBV antigen or in a fusion protein or an immunotherapeutic composition of the invention can include, but is not limited to, SEQ ID NO:3, SEQ ID NO:7, SEQ ID NO:11, positions 21-47 of SEQ ID NO:11, positions 176-400 of SEQ ID NO:11, SEQ ID NO:15, SEQ ID NO:19, SEQ ID NO:23, SEQ ID NO:27, SEQ ID NO:31, positions 9-407 of SEQ ID NO:34, positions 6-257 of SEQ ID NO:36, positions 6-257 of SEQ ID NO:41, positions 92-343 of SEQ ID NO:92, positions 90-488 of SEQ ID NO:93, SEQ ID NO:97, positions 90-338 of SEQ ID NO:101, positions 7-254 of SEQ ID NO:102, positions 1-249 of SEQ ID NO:107, positions 1-249 of SEQ ID NO:108, positions 1-249 of SEQ ID NO:109, positions 1-249 of SEQ ID NO:110, positions 1-399 of SEQ ID NO:112, positions 1-399 of SEQ ID NO:114, or positions 1-399 of SEQ ID NO:116, positions 1-399 of SEQ ID NO:118, positions 1-399 of SEQ ID NO:120, positions 1-399 of SEQ ID NO:122, positions 1-399 of SEQ ID NO:124, positions 1-399 of SEQ ID NO:126, positions 231-629 of SEQ ID NO:128, positions 63-461 of SEQ ID NO:130, positions 289-687 of SEQ ID NO:132, positions 289-687 of SEQ ID NO:134, or a corresponding sequence from a different HBV strain.

In any of the embodiments of the invention described herein, including any embodiment related to an immunotherapeutic composition, HBV antigen, fusion protein or use of such composition, HBV antigen or fusion protein, in one aspect, an amino acid of an HBV polymerase antigen useful as an HBV antigen or in a fusion protein or an immunotherapeutic composition of the invention can include, but is not limited to, positions 383-602 of SEQ ID NO:2, positions 381-600 of SEQ ID NO:6, positions 381-600 of SEQ ID NO:10, positions 453 to 680 of SEQ ID NO:10, positions 370-589 of SEQ ID NO:14, positions 380-599 of SEQ ID NO:18, positions 381-600 of SEQ ID NO:22, positions 380-599 of SEQ ID NO:26, positions 381-600 of SEQ ID NO:30, positions 260 to 604 of SEQ ID NO:36, positions 7-351 of SEQ ID NO:38, positions 7-351 of SEQ ID NO:40, 260 to 604 of SEQ ID NO:41, positions 346 to 690 of SEQ ID NO:92, positions 90-434 of SEQ ID NO:94, SEQ ID NO:98, positions 339 to 566 of SEQ ID NO:101, positions 255 to 482 of SEQ ID NO:102, positions 250-477 of SEQ ID NO:107, positions 250-477 of SEQ ID NO:108, positions 250-477 of SEQ ID NO:109, positions 250-477 of SEQ ID NO:110, positions 582 to 809 of SEQ ID NO:120, positions 582 to 809 of SEQ ID NO:124, positions 642 to 869 of SEQ ID NO:126, positions 1 to 228 of SEQ ID NO:128, positions 1 to 228 of SEQ ID NO:132, positions 61 to 288 of SEQ ID NO:134, or a corresponding sequence from a different HBV strain.

In any of the embodiments of the invention described herein, including any embodiment related to an immunotherapeutic composition, HBV antigen, fusion protein or use of such composition, HBV antigen or fusion protein, in one aspect, an amino acid of an HBV core antigen useful as an HBV antigen or in a fusion protein or an immunotherapeutic composition of the invention can include, but is not limited to, positions 31-212 of SEQ ID NO:1, positions 31-212 of SEQ ID NO:5, positions 31-212 of SEQ ID NO:9, positions 37 to 188 of SEQ ID NO:9, positions 31-212 of SEQ ID NO:13, positions 31-212 of SEQ ID NO:17, positions 31-212 of SEQ ID NO:21, positions 14-194 of SEQ ID NO:25, positions 31-212 of SEQ ID NO:29, positions 408-589 of SEQ ID NO:34, positions 605 to 786 of SEQ ID NO:36, positions 352-533 of SEQ ID NO:38, positions 160-341 of SEQ ID NO:39, positions 605-786 of SEQ ID NO:41, positions 691-872 of SEQ ID NO:92, positions 90-271 of SEQ ID NO:95, SEQ ID NO:99, positions 567 to 718 of SEQ ID NO:101, positions 483 to 634 of SEQ ID NO:102, positions 2-183 of SEQ ID NO:105, positions 184-395 of SEQ ID NO:105, positions 396-578 of SEQ ID NO:105, positions 579-761 of SEQ ID NO:105, positions 2-183 of SEQ ID NO:106, 338-520 of SEQ ID NO:106, positions 478-629 of SEQ ID NO:107, positions 478-629 of SEQ ID NO:108, positions 478-629 of SEQ ID NO:109, positions 478-629 of SEQ ID NO:110, positions 400-581 of SEQ ID NO:112, positions 400-581 of SEQ ID NO:114, positions 400-581 of SEQ ID NO:116, positions 400-581 of SEQ ID NO:118, positions 400 to 581 of SEQ ID NO:120, positions 400 to 581 of SEQ ID NO:122, positions 400 to 581 of SEQ ID NO:124, positions 400 to 581 of SEQ ID NO:126, positions 630 to 811 of SEQ ID NO:128, positions 462 to 643 of SEQ ID NO:130, positions 688 to 869 of SEQ ID NO:132, positions 688 to 869 of SEQ ID NO:134, or a corresponding sequence from a different HBV strain.

In any of the embodiments of the invention described herein, including any embodiment related to an immunotherapeutic composition, HBV antigen, fusion protein or use of such composition, HBV antigen or fusion protein, in one aspect, an amino acid of an HBV X antigen useful as an HBV antigen or in a fusion protein or an immunotherapeutic composition of the invention can include, but is not limited to, SEQ ID NO:4, SEQ ID NO:8, SEQ ID NO:12, positions 2 to 154 of SEQ ID NO:12, SEQ ID NO:16, SEQ ID NO:20, SEQ ID NO:24, SEQ ID NO:28, SEQ ID NO:32, positions 52-68 followed by positions 84-126 of SEQ ID NO:4, positions 52-68 followed by positions 84-126 of SEQ ID NO:8, positions 52-68 followed by positions 84-126 of SEQ ID NO:12, positions 52-68 followed by positions 84-126 of SEQ ID NO:16, positions 52-68 followed by positions 84-126 of SEQ ID NO:20, positions 52-68 followed by positions 84-126 of SEQ ID NO:24, positions 52-68 followed by positions 84-126 of SEQ ID NO:28, positions 52-68 followed by positions 84-126 of SEQ ID NO:32, positions 787 to 939 of SEQ ID NO:36, positions 7-159 of SEQ ID NO:39, positions 873-1025 of SEQ ID NO:92, positions 90-242 of SEQ ID NO:96, SEQ ID NO:100, positions 719-778 of SEQ ID NO:101, positions 635-694 of SEQ ID NO:102, positions 184-337 of SEQ ID NO:106, positions 521-674 of SEQ ID NO:106, positions 630-689 of SEQ ID NO:107, positions 630-689 of SEQ ID NO:108, positions 630-689 of SEQ ID NO:109, positions 630-689 of SEQ ID NO:110, positions 582-641 of SEQ ID NO:122, positions 810-869 of SEQ ID NO:124, positions 582-641 of SEQ ID NO:126, positions 1-60 of SEQ ID NO:130, positions 229 to 288 of SEQ ID NO:132, positions 1 to 60 of SEQ ID NO:134, or a corresponding sequence from a different HBV strain.

In one embodiment, the present invention includes an immunotherapeutic composition comprising: (a) a yeast vehicle; and (b) a fusion protein comprising HBV antigens, wherein the HBV antigens consist of: (i) an HBV X antigen comprising at least one immunogenic domain of a full-length HBV X antigen; (ii) an HBV surface antigen comprising at least one immunogenic domain of a full-length HBV large surface antigen (L), and; (iii) an HBV core antigen comprising at least one immunogenic domain of a full-length HBV core protein. In one aspect of this embodiment, the immunotherapeutic composition comprises: (a) a yeast vehicle; and (b) a fusion protein comprising HBV antigens, wherein the HBV antigens consist of: (i) an HBV X antigen having an amino acid sequence that is at least 80% identical to positions 52 to 126 of a full-length HBV X antigen; (ii) an HBV surface antigen having an amino acid sequence that is at least 95% identical to an amino acid sequence of a full-length HBV large surface antigen (L), and; (iii) an HBV core antigen having an amino acid sequence that is at least 95% identical to an amino acid sequence of a full-length HBV core protein. The composition elicits an HBV-specific immune response.

In one aspect of this embodiment of the invention, the amino acid sequence of HBV X antigen is at least 95% identical, or at least 96% identical, or at least 97% identical, or at least 98% identical, or at least 99% identical, or is identical, to an amino acid sequence selected from: positions 1-60 of SEQ ID NO:130, positions 630-689 of SEQ ID NO:110, positions 582-641 of SEQ ID NO:122, positions 630-689 of SEQ ID NO:107, positions 630-689 of SEQ ID NO:108, positions 630-689 of SEQ ID NO:109, positions 52-68 followed by positions 84-126 of SEQ ID NO:4, positions 52-68 followed by positions 84-126 of SEQ ID NO:8, positions 52-68 followed by positions 84-126 of SEQ ID NO:12, positions 52-68 followed by positions 84-126 of SEQ ID NO:16, positions 52-68 followed by positions 84-126 of SEQ ID NO:20, positions 52-68 followed by positions 84-126 of SEQ ID NO:24, positions 52-68 followed by positions 84-126 of SEQ ID NO:28, positions 52-68 followed by positions 84-126 of SEQ ID NO:32, SEQ ID NO:100, positions 719-778 of SEQ ID NO:101, positions 635-694 of SEQ ID NO:102, positions 810-869 of SEQ ID NO:124, positions 582-641 of SEQ ID NO:126, positions 229 to 288 of SEQ ID NO:132, positions 1 to 60 of SEQ ID NO:134, or a corresponding sequence from a different HBV strain. In one aspect, the amino acid sequence of HBV X antigen is selected from: positions 1-60 of SEQ ID NO:130, positions 630-689 of SEQ ID NO:110, positions 582-641 of SEQ ID NO:122, positions 630-689 of SEQ ID NO:109, positions 630-689 of SEQ ID NO:108, positions 630-689 of SEQ ID NO:107, SEQ ID NO:100, or a corresponding sequence from a different HBV strain.

In one aspect of this embodiment of the invention, the amino acid sequence of the HBV surface antigen is at least 95% identical, or at least 96% identical, or at least 97% identical, or at least 98% identical, or at least 99% identical, or is identical, to an amino acid sequence selected from: positions 63-461 of SEQ ID NO:130, positions 1-399 of SEQ ID NO:118, positions 1-399 of SEQ ID NO:122, positions 9-407 of SEQ ID NO:34, positions 1-399 of SEQ ID NO:112, positions 1-399 of SEQ ID NO:114, positions 1-399 of SEQ ID NO:116, SEQ ID NO:3, SEQ ID NO:7, SEQ ID NO:11, SEQ ID NO:15, SEQ ID NO:19, SEQ ID NO:23, SEQ ID NO:27, SEQ ID NO:31, positions 90-488 of SEQ ID NO:93, positions 1-399 of SEQ ID NO:120, positions 1-399 of SEQ ID NO:124, positions 1-399 of SEQ ID NO:126, positions 231-629 of SEQ ID NO:128, positions 289-687 of SEQ ID NO:132, positions 289-687 of SEQ ID NO:134, or a corresponding sequence from a different HBV strain. In one aspect, the amino acid sequence of the HBV surface antigen is selected from: positions 63-461 of SEQ ID NO:130, positions 1-399 of SEQ ID NO:118, positions 1-399 of SEQ ID NO:122, positions 9-407 of SEQ ID NO:34, positions 1-399 of SEQ ID NO:112, positions 1-399 of SEQ ID NO:114, positions 1-399 of SEQ ID NO:116, or a corresponding sequence from a different HBV strain.

In one aspect of this embodiment of the invention, the amino acid sequence of the HBV core antigen is at least 95% identical, or at least 96% identical, or at least 97% identical, or at least 98% identical, or at least 99% identical, or is identical, to an amino acid sequence selected from: positions 462 to 643 of SEQ ID NO:130, positions 400-581 of SEQ ID NO:118, positions 400 to 581 of SEQ ID NO:122, positions 408-589 of SEQ ID NO:34, positions 400-581 of SEQ ID NO:112, positions 400-581 of SEQ ID NO:114, positions 400-581 of SEQ ID NO:116, positions 31-212 of SEQ ID NO:1, positions 31-212 of SEQ ID NO:5, positions 31-212 of SEQ ID NO:9, positions 31-212 of SEQ ID NO:13, positions 31-212 of SEQ ID NO:17, positions 31-212 of SEQ ID NO:21, positions 14-194 of SEQ ID NO:25, positions 31-212 of SEQ ID NO:29, positions 605 to 786 of SEQ ID NO:36, positions 352-533 of SEQ ID NO:38, positions 160-341 of SEQ ID NO:39, positions 605-786 of SEQ ID NO:41, positions 691-872 of SEQ ID NO:92, positions 90-271 of SEQ ID NO:95, positions 2-183 of SEQ ID NO:105, positions 184-395 of SEQ ID NO:105, positions 396-578 of SEQ ID NO:105, positions 579-761 of SEQ ID NO:105, positions 2-183 of SEQ ID NO:106, 338-520 of SEQ ID NO:106, positions 400 to 581 of SEQ ID NO:120, positions 400 to 581 of SEQ ID NO:124, positions 400 to 581 of SEQ ID NO:126, positions 630 to 811 of SEQ ID NO:128, positions 688 to 869 of SEQ ID NO:132, positions 688 to 869 of SEQ ID NO:134, or a corresponding sequence from a different HBV strain. In one aspect, the amino acid sequence of the HBV core antigen is selected from: positions 462 to 643 of SEQ ID NO:130, positions 400-581 of SEQ ID NO:118, positions 400 to 581 of SEQ ID NO:122, positions 408-589 of SEQ ID NO:34, positions 400-581 of SEQ ID NO:116, positions 400-581 of SEQ ID NO:112, positions 400-581 of SEQ ID NO:114, or a corresponding sequence from a different HBV strain.

In one aspect of this embodiment of the invention, the HBV antigens are arranged in the following order, from N- to C-terminus, in the fusion protein: HBV X antigen, HBV surface antigen, HBV core antigen. In one aspect of this embodiment of the invention, the HBV antigens are arranged in the following order, from N- to C-terminus, in the fusion protein: HBV surface antigen, HBV core antigen, HBV X antigen.

In one aspect of this embodiment of the invention, the fusion protein comprises an amino acid sequence that is at least 95% identical, or at least 96% identical, or at least 97% identical, or at least 98% identical, or at least 99% identical, or is identical, to an amino acid sequence selected from SEQ ID NO:130, SEQ ID NO:122, or SEQ ID NO:150.

Yet another embodiment of the invention relates to an immunotherapeutic composition comprising: (a) a whole, heat-inactivated yeast from *Saccharomyces cerevisiae*; and (b) an HBV fusion protein expressed by the yeast, wherein the fusion protein comprises SEQ ID NO:130.

Another embodiment of the invention relates to an immunotherapeutic composition comprising: (a) a whole, heat-inactivated yeast from *Saccharomyces cerevisiae*; and (b) an HBV fusion protein expressed by the yeast, wherein the fusion protein comprises SEQ ID NO:150.

Yet another embodiment of the invention relates to an immunotherapeutic composition comprising: (a) a whole, heat-inactivated yeast from *Saccharomyces cerevisiae*; and (b) an HBV fusion protein expressed by the yeast, wherein the fusion protein comprises SEQ ID NO:122. In one aspect, the fusion protein is a single polypeptide with the following sequences fused in frame from N- to C-terminus: (1) an amino acid sequence of SEQ ID NO:37; (2) a two amino acid linker peptide of threonine-serine; (3) an amino acid sequence of SEQ ID NO:122; and (4) a hexahistidine peptide.

In another embodiment of the invention, the immunotherapeutic composition includes: (a) a yeast vehicle; and (b) a fusion protein comprising HBV antigens consisting of: (i) at least one immunogenic domain of HBV large surface antigen (L) and (ii) at least one immunogenic domain of HBV core protein or HBV e-antigen. The composition elicits an HBV-specific immune response, such as an immune response against HBV large surface antigen (L) and/or HBV core protein or HBV e-antigen.

In one embodiment, the present invention includes an immunotherapeutic composition comprising: (a) a yeast vehicle; and (b) a fusion protein comprising HBV antigens consisting of: (i) an HBV surface antigen having an amino acid sequence that is at least 95% identical to an amino acid sequence of a full-length HBV large surface antigen (L), and; (ii) an HBV core antigen having an amino acid sequence that is at least 95% identical to an amino acid sequence of a full-length HBV core protein. The composition elicits an HBV-specific immune response. In one aspect of this embodiment, the HBV antigens consist of an amino acid sequence comprising at least 95% of a full-length HBV large surface antigen (L) fused to an amino acid sequence comprising at least 95% of a full-length HBV core protein or HBV e-antigen. In one aspect of this embodiment, the HBV antigens consist of an amino acid sequence comprising at least 95% of a full-length HBV large surface antigen (L) fused to the N-terminus of an amino acid sequence comprising at least 95% of a full-length HBV core protein. In one aspect, the HBV antigens consist of: amino acids 2 to 400 of HBV large surface antigen (L); and amino acids 31 to 212 of the HBV precore protein comprising HBV core protein and a portion of HBV e-antigen.

In one aspect of this embodiment of the invention, the amino acid sequence of the HBV surface antigen is at least 95% identical, or at least 96% identical, or at least 97% identical, or at least 98% identical, or at least 99% identical, or is identical, to an amino acid sequence selected from: positions 1-399 of SEQ ID NO:118, positions 9-407 of SEQ ID NO:34, positions 1-399 of SEQ ID NO:116, positions 1-399 of SEQ ID NO:112, positions 1-399 of SEQ ID NO:114, SEQ ID NO:3 or positions 2-400 of SEQ ID NO:3, SEQ ID NO:7 or positions 2-400 of SEQ ID NO:7, SEQ ID NO:11 or positions 2-400 of SEQ ID NO:11, SEQ ID NO:15 or positions 2-389 of SEQ ID NO:15, SEQ ID NO:19 or positions 2-399 of SEQ ID NO:19, SEQ ID NO:23 or positions 2-400 of SEQ ID NO:23, SEQ ID NO:27 or positions 2-399 of SEQ ID NO:27, SEQ ID NO:31 or positions 2-400 of SEQ ID NO:31, positions 90-488 of SEQ ID NO:93, positions 1-399 of SEQ ID NO:120, positions 1-399 of SEQ ID NO:122, positions 1-399 of SEQ ID NO:124, positions 1-399 of SEQ ID NO:126, positions 231-629 of SEQ ID NO:128, positions 63-461 of SEQ ID NO:130, positions 289-687 of SEQ ID NO:132, positions 289-687 of SEQ ID NO:134, or a corresponding sequence from a different HBV strain. In one aspect, the amino acid sequence of the HBV surface antigen is selected from: positions 1-399 of SEQ ID NO:118, positions 9-407 of SEQ ID NO:34, positions 1-399 of SEQ ID NO:112, positions 1-399 of SEQ ID NO:114, positions 1-399 of SEQ ID NO:116, or a corresponding sequence from a different HBV strain.

In one aspect of this embodiment of the invention, the amino acid sequence of the HBV core antigen is at least 95% identical, or at least 96% identical, or at least 97% identical, or at least 98% identical, or at least 99% identical, or is identical, to an amino acid sequence selected from: positions 400-581 of SEQ ID NO:118, positions 408-589 of SEQ ID NO:34, positions 400-581 of SEQ ID NO:116, positions 400-581 of SEQ ID NO:112, positions 400-581 of SEQ ID NO:114, positions 31-212 of SEQ ID NO:1, positions 31-212 of SEQ ID NO:5, positions 31-212 of SEQ ID NO:9, positions 31-212 of SEQ ID NO:13, positions 31-212 of SEQ ID NO:17, positions 31-212 of SEQ ID NO:21, positions 14-194 of SEQ ID NO:25, positions 31-212 of SEQ ID NO:29, positions 605 to 786 of SEQ ID NO:36, positions 352-533 of SEQ ID NO:38, positions 160-341 of SEQ ID NO:39, positions 605-786 of SEQ ID NO:41, positions 691-872 of SEQ ID NO:92, positions 90-271 of SEQ ID NO:95, positions 2-183 of SEQ ID NO:105, positions 184-395 of SEQ ID NO:105, positions 396-578 of SEQ ID NO:105, positions 579-761 of SEQ ID NO:105, positions 2-183 of SEQ ID NO:106, 338-520 of SEQ ID NO:106, positions 400 to 581 of SEQ ID NO:120, positions 400 to 581 of SEQ ID NO:122, positions 400 to 581 of SEQ ID NO:124, positions 400 to 581 of SEQ ID NO:126, positions 630 to 811 of SEQ ID NO:128, positions 462 to 643 of SEQ ID NO:130, positions 688 to 869 of SEQ ID NO:132, positions 688 to 869 of SEQ ID NO:134, or a corresponding sequence from a different HBV strain. In one aspect, the amino acid sequence of the HBV core antigen is selected from: positions 400-581 of SEQ ID NO:118, positions 408-589 of SEQ ID NO:34, positions 400-581 of SEQ ID NO:116, positions 400-581 of SEQ ID NO:112, positions 400-581 of SEQ ID NO:114, or a corresponding sequence from a different HBV strain.

In one aspect of this embodiment of the invention, the HBV antigens consist of amino acids 9 to 589 of SEQ ID NO:34, or a corresponding sequence from a different HBV strain. In one aspect, the HBV antigens consist of an amino acid sequence that is at least 95% identical, or at least 96% identical, or at least 97% identical, or at least 98% identical, or at least 99% identical, or is identical, to an amino acid sequence selected from: SEQ ID NO:118, SEQ ID NO:116, positions 9-589 of SEQ ID NO:34, SEQ ID NO:112, SEQ ID NO:114, or a corresponding sequence for a different HBV strain. In one aspect, the HBV antigens consist of a full-length or near full-length HBV large surface antigen (L) and a full-length or near full-length HBV core protein.

In one aspect of this embodiment of the invention, any of the fusion proteins can include an N-terminal amino acid sequence (appended to the N-terminus of the fusion protein) of SEQ ID NO:37. In another aspect, any of the fusion proteins can include an N-terminal amino acid sequence selected from SEQ ID NO:89 or SEQ ID NO:90. In one aspect, the fusion protein comprises an amino acid sequence of SEQ ID NO:151.

Yet another embodiment of the invention relates to an immunotherapeutic composition comprising: (a) a whole, heat-inactivated yeast from Saccharomyces cerevisiae; and (b) an HBV fusion protein expressed by the yeast, wherein the fusion protein comprises SEQ ID NO:118.

Another embodiment of the invention relates to an immunotherapeutic composition comprising: (a) a whole, heat-inactivated yeast from Saccharomyces cerevisiae; and (b) an HBV fusion protein expressed by the yeast, wherein the fusion protein comprises SEQ ID NO:151.

Yet another embodiment of the invention relates to an immunotherapeutic composition comprising: (a) a whole, heat-inactivated yeast from Saccharomyces cerevisiae; and (b) an HBV fusion protein expressed by the yeast, wherein the fusion protein comprises the amino acid sequence of SEQ ID NO:34.

In another embodiment, the present invention includes an immunotherapeutic composition comprising: (a) a yeast vehicle; and (b) a fusion protein comprising HBV antigens. The HBV antigens consist of: (i) an HBV surface antigen consisting of at least one immunogenic domain of full-length HBV large (L), medium (M) or small (S) surface antigen; (ii) an HBV polymerase antigen consisting of at least one immunogenic domain of full-length HBV polymerase or of the reverse transcriptase (RT) domain of HBV polymerase; (iii) an HBV core antigen consisting of at least one immunogenic domain of full-length HBV core protein or of full-length HBV e-antigen; and (iv) an HBV X antigen consisting of at least one immunogenic domain of full-length HBV X antigen. The composition elicits an HBV-specific immune response. In one aspect of this embodiment, the HBV surface antigen comprises at least one immunogenic domain of hepatocyte receptor region of Pre-S1 of the HBV large surface antigen (L) and at least one immunogenic domain of HBV small surface antigen (S).

In one aspect of this embodiment, the HBV antigens consist of: at least 95% of the full-length hepatocyte receptor of Pre-S1 of the HBV large surface antigen (L), at least 95% of the full-length HBV small surface antigen (S), at least 95% of the reverse transcriptase domain of HBV polymerase, at least 95% of the full-length HBV core protein or HBV e-antigen, and at least 95% of the full-length X antigen. In one aspect, the HBV antigens consist of: an HBV large surface antigen (L) comprising at least 95% of amino acids 120 to 368 of HBV large surface antigen (L); an RT domain of HBV polymerase comprising at least 95% of amino acids 453 to 680 of the RT domain of HBV polymerase; an HBV core protein comprising at least 95% of amino acids 37 to 188 of HBV core protein; and an HBV X antigen comprising at least 80% of amino acids 52 to 127 of HBV X antigen. In one aspect, the HBV antigens consist of: amino acids 21 to 47 of HBV large surface antigen (L) comprising the hepatocyte receptor domain of Pre-S1; amino acids 176 to 400 of HBV large surface antigen (L) comprising HBV small surface antigen (S); amino acids 247 to 691 of HBV polymerase comprising the reverse transcriptase domain; amino acids 31 to 212 of HBV precore protein comprising HBV core protein and a portion of HBV e-antigen; and amino acids 2 to 154 of HBV X antigen. In one aspect, the HBV antigens consist of: an amino acid sequence at least 95% identical to amino acids 120 to 368 of HBV large surface antigen (L); an amino acid sequence at least 95% identical to amino acids 453 to 680 of the RT domain of HBV polymerase; an amino acid sequence at least 95% identical to amino acids 37 to 188 of HBV core protein; and an amino acid sequence at least 80% identical to amino acids 52 to 127 of HBV X antigen. In one aspect, the HBV antigens have been modified to incorporate one or more T cell epitopes set forth in Table 5 and represented herein by SEQ ID NOs:42 to 88 or SEQ ID NOs:135-140. In one aspect, the HBV large surface antigen (L) comprises an amino acid sequence of SEQ ID NO:97 or a sequence that is 95% identical to SEQ ID NO:97. In one aspect, the RT domain of an HBV polymerase comprises an amino acid sequence of SEQ ID NO:98 or a sequence that is 95% identical to SEQ ID NO:98. In one aspect, the HBV core protein comprises an amino acid sequence of SEQ ID NO:99 or a sequence that is 95% identical to SEQ ID NO:99. In one aspect, the HBV X antigen comprises an amino acid sequence of SEQ ID NO:100 or a sequence that is 95% identical to SEQ ID NO:100.

In one aspect of this embodiment of the invention, the amino acid sequence of the HBV surface antigen is at least 95% identical to an amino acid sequence of a full-length HBV large surface antigen (L). In one aspect, the amino acid sequence of the HBV surface antigen is at least 95% identical, or at least 96% identical, or at least 97% identical, or at least 98% identical, or at least 99% identical, or is identical, to an amino acid sequence selected from: positions 1-399 of SEQ ID NO:124, positions 1-399 of SEQ ID NO:126, positions 289-687 of SEQ ID NO:132, positions 289-687 of SEQ ID NO:134, SEQ ID NO:3, SEQ ID NO:7, SEQ ID NO:11, SEQ ID NO:15, SEQ ID NO:19, SEQ ID NO:23, SEQ ID NO:27, SEQ ID NO:31, positions 9-407 of SEQ ID NO:34, positions 90-488 of SEQ ID NO:93, positions 1-399 of SEQ ID NO:112, positions 1-399 of SEQ ID NO:114, positions 1-399 of SEQ ID NO:116, positions 1-399 of SEQ ID NO:118, positions 1-399 of SEQ ID NO:120, positions 1-399 of SEQ ID NO:122, positions 231-629 of SEQ ID NO:128, positions 63-461 of SEQ ID NO:130, or a corresponding sequence from a different HBV strain.

In one aspect of this embodiment, the amino acid sequence of the HBV surface antigen is at least 95% identical, or at least 96% identical, or at least 97% identical, or at least 98% identical, or at least 99% identical, or is identical, to an amino acid sequence selected from: SEQ ID NO:97, positions 1-249 of SEQ ID NO:107, positions 1-249 of SEQ ID NO:108, positions 1-249 of SEQ ID NO:109, positions 1-249 of SEQ ID NO:110, positions 21-47 of SEQ ID NO:11, positions 176-400 of SEQ ID NO:11, positions 6-257 of SEQ ID NO:36, positions 6-257 of SEQ ID NO:41, positions 92-343 of SEQ ID NO:92, positions 90-338 of SEQ ID NO:101, positions 7-254 of SEQ ID NO:102, or a corresponding sequence from a different HBV strain.

In one aspect of this embodiment, the HBV polymerase antigen consists of at least one immunogenic domain of the RT domain of HBV polymerase. In one aspect, the amino acid sequence of the HBV polymerase antigen is at least 95% identical, or at least 96% identical, or at least 97% identical, or at least 98% identical, or at least 99% identical, or is identical, to an amino acid sequence selected from: SEQ ID NO:98, positions 582 to 809 of SEQ ID NO:124, positions 642 to 869 of SEQ ID NO:126, positions 1 to 228 of SEQ ID NO:132, positions 61 to 288 of SEQ ID NO:134, positions 250-477 of SEQ ID NO:107, positions 250-477 of SEQ ID NO:108, positions 250-477 of SEQ ID NO:109, positions 250-477 of SEQ ID NO:110, positions 383-602 of SEQ ID NO:2, positions 381-600 of SEQ ID NO:6, positions 381-600 of SEQ ID NO:10, positions 453 to 680 of SEQ ID NO:10, positions 370-589 of SEQ ID NO:14, positions 380-599 of SEQ ID NO:18, positions 381-600 of SEQ ID NO:22, positions 380-599 of SEQ ID NO:26, positions 381-600 of SEQ ID NO:30, positions 260 to 604 of SEQ ID NO:36, positions 7-351 of SEQ ID NO:38, positions 7-351 of SEQ ID NO:40, 260 to 604 of SEQ ID NO:41, positions 346 to 690 of SEQ ID NO:92, positions 90-434 of SEQ ID NO:94, positions 339 to 566 of SEQ ID NO:101, positions 255 to 482 of SEQ ID NO:102, positions 582 to 809 of SEQ ID NO:120, positions 1 to 228 of SEQ ID NO:128, or a corresponding sequence from a different HBV strain.

In one aspect of this embodiment, the amino acid sequence of the HBV core antigen is at least 95% identical to an amino acid sequence of a full-length HBV core protein. In one aspect, the amino acid sequence of the HBV core antigen is at least 95% identical, or at least 96% identical, or at least 97% identical, or at least 98% identical, or at least 99% identical, or is identical, to an amino acid sequence selected from: positions 400 to 581 of SEQ ID NO:124, positions 400 to 581 of SEQ ID NO:126, positions 688 to 869 of SEQ ID NO:132, positions 688 to 869 of SEQ ID NO:134, positions 408-589 of SEQ ID NO:34, positions 400-581 of SEQ ID NO:112, positions 400-581 of SEQ ID NO:114, positions 400-581 of SEQ ID NO:116, positions 400-581 of SEQ ID NO:118, positions 31-212 of SEQ ID NO:1, positions 31-212 of SEQ ID NO:5, positions 31-212 of SEQ ID NO:9, positions 31-212 of SEQ ID NO:13, positions 31-212 of SEQ ID NO:17, positions 31-212 of SEQ ID NO:21, positions 14-194 of SEQ ID NO:25, positions 31-212 of SEQ ID NO:29, positions 605 to 786 of SEQ ID NO:36, positions 352-533 of SEQ ID NO:38, positions 160-341 of SEQ ID NO:39, positions 605-786 of SEQ ID NO:41, positions 691-872 of SEQ ID NO:92, positions 90-271 of SEQ ID NO:95, positions 2-183 of SEQ ID NO:105, positions 184-395 of SEQ ID NO:105, positions 396-578 of SEQ ID NO:105, positions 579-761 of SEQ ID NO:105, positions 2-183 of SEQ ID NO:106, 338-520 of SEQ ID NO:106, positions 400 to 581 of SEQ ID NO:120, positions 400 to 581 of SEQ ID NO:122, positions 630 to 811 of SEQ ID NO:128, positions 462 to 643 of SEQ ID NO:130, or a corresponding sequence from a different HBV strain.

In one aspect of this embodiment, the amino acid sequence of the HBV core antigen is at least 95% identical, or at least 96% identical, or at least 97% identical, or at least 98% identical, or at least 99% identical, or is identical, to an amino acid sequence selected from: positions SEQ ID NO:99, 37 to 188 of SEQ ID NO:9, positions 567 to 718 of SEQ ID NO:101, positions 483 to 634 of SEQ ID NO:102, positions 478-629 of SEQ ID NO:107, positions 478-629 of SEQ ID NO:108, positions 478-629 of SEQ ID NO:109, positions 478-629 of SEQ ID NO:110, or a corresponding sequence from a different HBV strain.

In one aspect of this embodiment, the HBV X antigen consists of an amino acid sequence that is at least 95% identical to a full-length HBV X antigen. In one aspect, the HBV X antigen is at least 95% identical, or at least 96% identical, or at least 97% identical, or at least 98% identical, or at least 99% identical, or is identical, to an amino acid sequence selected from: SEQ ID NO:4, SEQ ID NO:8, SEQ ID NO:12, positions 2 to 154 of SEQ ID NO:12, SEQ ID NO:16, SEQ ID NO:20, SEQ ID NO:24, SEQ ID NO:28, SEQ ID NO:32, positions 787 to 939 of SEQ ID NO:36, positions 7-159 of SEQ ID NO:39, positions 873-1025 of SEQ ID NO:92, positions 90-242 of SEQ ID NO:96, positions 184-337 of SEQ ID NO:106, positions 521-674 of SEQ ID NO:106, or a corresponding sequence from a different HBV strain.

In one aspect, the HBV X antigen consists of an amino acid sequence that is at least 80% identical to positions 52 to 126 of a full-length HBV X antigen. In one aspect, the amino acid sequence of HBV X antigen is at least 95% identical, or at least 96% identical, or at least 97% identical, or at least 98% identical, or at least 99% identical, or is identical, to an amino acid sequence selected from: SEQ ID NO:100, positions 810-869 of SEQ ID NO:124, positions 582-641 of SEQ ID NO:126, positions 229 to 288 of SEQ ID NO:132, positions 1 to 60 of SEQ ID NO:134, positions 630-689 of SEQ ID NO:107, positions 630-689 of SEQ ID NO:108, positions 630-689 of SEQ ID NO:109, positions 630-689 of SEQ ID NO:110, positions 52-68 followed by positions 84-126 of SEQ ID NO:4, positions 52-68 followed by positions 84-126 of SEQ ID NO:8, positions 52-68 followed by positions 84-126 of SEQ ID NO:12, positions 52-68 followed by positions 84-126 of SEQ ID NO:16, positions 52-68 followed by positions 84-126 of SEQ ID NO:20, positions 52-68 followed by positions 84-126 of SEQ ID NO:24, positions 52-68 followed by positions 84-126 of SEQ ID NO:28, positions 52-68 followed by positions 84-126 of SEQ ID NO:32, positions 719-778 of SEQ ID NO:101, positions 635-694 of SEQ ID NO:102, positions 582-641 of SEQ ID NO:122, positions 1-60 of SEQ ID NO:130, or a corresponding sequence from a different HBV strain.

In one aspect of this embodiment, the HBV antigens have an amino acid sequence that is at least 95% identical, or at least 96% identical, or at least 97% identical, or at least 98% identical, or at least 99% identical, or is identical, to an amino acid sequence selected from: positions 6 to 939 of SEQ ID NO:36, positions 92 to 1025 of SEQ ID NO:92, positions 90 to 778 of SEQ ID NO:101, positions 7 to 694 of SEQ ID NO:102, or a corresponding sequence from a different HBV strain.

In one aspect of this embodiment, the fusion protein comprises an amino acid sequence that is at least 95% identical, or at least 96% identical, or at least 97% identical, or at least 98% identical, or at least 99% identical, or is identical, to an amino acid sequence selected from: SEQ ID NO:107, SEQ ID NO:108, SEQ ID NO:109, SEQ ID NO:110, SEQ ID NO:124, SEQ ID NO:126, SEQ ID NO:132 or SEQ ID NO: 134.

Any of the fusion proteins may, in one aspect, comprise an N-terminal sequence selected from SEQ ID NO:37, SEQ ID NO:89, or SEQ ID NO:90.

In one aspect of this embodiment, the fusion protein comprises an amino acid sequence that is at least 95% identical, or at least 96% identical, or at least 97% identical, or at least 98% identical, or at least 99% identical, or is identical, to an amino acid sequence selected from: SEQ ID NO:36, SEQ ID NO:92, SEQ ID NO:101, or SEQ ID NO:102.

Another embodiment of the invention relates to an immunotherapeutic composition comprising: (a) a yeast vehicle; and (b) a fusion protein comprising HBV antigens, wherein the HBV antigens consist of: (i) an HBV surface antigen consisting of at least one immunogenic domain of hepatocyte receptor region of Pre-S1 of the HBV large surface antigen (L) and at least one immunogenic domain of HBV small surface antigen (S); (ii) an HBV polymerase antigen consisting of at least one immunogenic domain of reverse transcriptase domain of HBV polymerase; and (iii) an HBV core antigen consisting of at least one immunogenic domain of HBV core protein. The composition elicits an HBV-specific immune response. In one aspect, the HBV antigens consist of at least 95% of full-length hepatocyte receptor of Pre-S1 of HBV large surface antigen (L), at least 95% of full-length HBV small surface antigen, at least 95% of full-length reverse transcriptase domain of HBV polymerase, and at least 95% of full-length HBV core protein. In one aspect, the HBV antigens consist of at least 95% of full-length HBV large surface antigen (L), at least 95% of full-length reverse transcriptase domain of HBV polymerase, and at least 95% of full-length HBV core protein.

In one aspect of this embodiment, the amino acid sequence of the HBV surface antigen is at least 95% identical, or at least 96% identical, or at least 97% identical, or at least 98% identical, or at least 99% identical, or is identical, to an amino acid sequence selected from: positions 1-399 of SEQ ID NO:120, positions 231-629 of SEQ ID NO:128, positions 1-399 of SEQ ID NO:112, positions 1-399 of SEQ ID NO:114, positions 1-399 of SEQ ID NO:116, positions 1-399 of SEQ ID NO:118, positions 6-257 of SEQ ID NO:41, SEQ ID NO:3, SEQ ID NO:7, SEQ ID NO:11, positions 21-47 of SEQ ID NO:11, positions 176-400 of SEQ ID NO:11, SEQ ID NO:15, SEQ ID NO:19, SEQ ID NO:23, SEQ ID NO:27, SEQ ID NO:31, positions 9-407 of SEQ ID NO:34, positions 6-257 of SEQ ID NO:36, positions 92-343 of SEQ ID NO:92, positions 90-488 of SEQ ID NO:93, SEQ ID NO:97, positions 90-338 of SEQ ID NO:101, positions 7-254 of SEQ ID NO:102, positions 1-249 of SEQ ID NO:107, positions 1-249 of SEQ ID NO:108, positions 1-249 of SEQ ID NO:109, positions 1-249 of SEQ ID NO:110, positions 1-399 of SEQ ID NO:122, positions 1-399 of SEQ ID NO:124, positions 1-399 of SEQ ID NO:126, positions 63-461 of SEQ ID NO:130, positions 289-687 of SEQ ID NO:132, positions 289-687 of SEQ ID NO:134, or a corresponding sequence from a different HBV strain.

In one aspect of this embodiment of the invention, the amino acid sequence of the HBV polymerase antigen is at least 95% identical, or at least 96% identical, or at least 97% identical, or at least 98% identical, or at least 99% identical, or is identical, to an amino acid sequence selected from: positions 582 to 809 of SEQ ID NO:120, positions 1 to 228 of SEQ ID NO:128, positions 250-477 of SEQ ID NO:107, positions 250-477 of SEQ ID NO:108, positions 250-477 of SEQ ID NO:109, positions 250-477 of SEQ ID NO:110, 260 to 604 of SEQ ID NO:41, positions 383-602 of SEQ ID NO:2, positions 381-600 of SEQ ID NO:6, positions 381-600 of SEQ ID NO:10, positions 453 to 680 of SEQ ID NO:10, positions 370-589 of SEQ ID NO:14, positions 380-599 of SEQ ID NO:18, positions 381-600 of SEQ ID NO:22, positions 380-599 of SEQ ID NO:26, positions 381-600 of SEQ ID NO:30, positions 260 to 604 of SEQ ID NO:36, positions 7-351 of SEQ ID NO:38, positions 7-351 of SEQ ID NO:40, positions 346 to 690 of SEQ ID NO:92, positions 90-434 of SEQ ID NO:94, SEQ ID NO:98, positions 339 to 566 of SEQ ID NO:101, positions 255 to 482 of SEQ ID NO:102, positions 582 to 809 of SEQ ID NO:124, positions 642 to 869 of SEQ ID NO:126, positions 1 to 228 of SEQ ID NO:132, positions 61 to 288 of SEQ ID NO:134, or a corresponding sequence from a different HBV strain.

In one aspect of this embodiment of the invention, the amino acid sequence of the HBV core antigen is at least 95% identical, or at least 96% identical, or at least 97% identical, or at least 98% identical, or at least 99% identical, or is identical, to an amino acid sequence selected from: positions 400 to 581 of SEQ ID NO:120, positions 630 to 811 of SEQ ID NO:128, positions 400-581 of SEQ ID NO:112, positions 400-581 of SEQ ID NO:114, positions 400-581 of SEQ ID NO:116, positions 400-581 of SEQ ID NO:118, positions 605-786 of SEQ ID NO:41, positions 31-212 of SEQ ID NO:1, positions 31-212 of SEQ ID NO:5, positions 31-212 of SEQ ID NO:9, positions 37 to 188 of SEQ ID NO:9, positions 31-212 of SEQ ID NO:13, positions 31-212 of SEQ ID NO:17, positions 31-212 of SEQ ID NO:21, positions 14-194 of SEQ ID NO:25, positions 31-212 of SEQ ID NO:29, positions 408-589 of SEQ ID NO:34, positions 605 to 786 of SEQ ID NO:36, positions 352-533 of SEQ ID NO:38, positions 160-341 of SEQ ID NO:39, positions 691-872 of SEQ ID NO:92, positions 90-271 of SEQ ID NO:95, SEQ ID NO:99, positions 567 to 718 of SEQ ID NO:101, positions 483 to 634 of SEQ ID NO:102, positions 2-183 of SEQ ID NO:105, positions 184-395 of SEQ ID NO:105, positions 396-578 of SEQ ID NO:105, positions 579-761 of SEQ ID NO:105, positions 2-183 of SEQ ID NO:106, 338-520 of SEQ ID NO:106, positions 478-629 of SEQ ID NO:107, positions 478-629 of SEQ ID NO:108, positions 478-629 of SEQ ID NO:109, positions 478-629 of SEQ ID NO:110, positions 400 to 581 of SEQ ID NO:122, positions 400 to 581 of SEQ ID NO:124, positions 400 to 581 of SEQ ID NO:126, positions 462 to 643 of SEQ ID NO:130, positions 688 to 869 of SEQ ID NO:132, positions 688 to 869 of SEQ ID NO:134, or a corresponding sequence from a different HBV strain.

In one aspect of this embodiment of the invention, the fusion protein has an amino acid sequence that is at least 95% identical, or at least 96% identical, or at least 97% identical, or at least 98% identical, or at least 99% identical, or is identical, to an amino acid sequence selected from: SEQ ID NO:120, SEQ ID NO:128, positions 6-786 of SEQ ID NO:41, or SEQ ID NO:41, or a corresponding sequence from a different HBV strain.

Another embodiment of the invention relates to an immunotherapeutic composition comprising: (a) a yeast vehicle; and (b) a fusion protein comprising HBV antigens, wherein the HBV antigens consist of: (i) an HBV polymerase antigen consisting of at least one immunogenic domain of the reverse transcriptase (RT) domain of HBV polymerase; and (ii) an HBV core antigen consisting of at least one immunogenic domain of HBV core protein. The composition elicits an HBV-specific immune response. In one aspect of this embodiment of the invention, the HBV antigens consist of: an amino acid sequence that is at least 95% identical to full-length RT domain of HBV polymerase and an amino acid sequence that is at least 95% identical to full-length HBV core protein.

In one aspect of this embodiment of the invention, the amino acid sequence of the HBV polymerase antigen is at least 95% identical, or at least 96% identical, or at least 97% identical, or at least 98% identical, or at least 99% identical, or is identical, to an amino acid sequence selected from: positions 7-351 of SEQ ID NO:38, positions 383-602 of SEQ ID NO:2, positions 381-600 of SEQ ID NO:6, positions 381-600 of SEQ ID NO:10, positions 453 to 680 of SEQ ID NO:10, positions 370-589 of SEQ ID NO:14, positions 380-599 of SEQ ID NO:18, positions 381-600 of SEQ ID NO:22, positions 380-599 of SEQ ID NO:26, positions 381-600 of SEQ ID NO:30, positions 260 to 604 of SEQ ID NO:36, positions 7-351 of SEQ ID NO:40, 260 to 604 of SEQ ID NO:41, positions 346 to 690 of SEQ ID NO:92, positions 90-434 of SEQ ID NO:94, SEQ ID NO:98, positions 339 to 566 of SEQ ID NO:101, positions 255 to 482 of SEQ ID NO:102, positions 250-477 of SEQ ID NO:107, positions 250-477 of SEQ ID NO:108, positions 250-477 of SEQ ID NO:109, positions 250-477 of SEQ ID NO:110, positions 582 to 809 of SEQ ID NO:120, positions 582 to 809 of SEQ ID NO:124, positions 642 to 869 of SEQ ID NO:126, positions 1 to 228 of SEQ ID NO:128, positions 1 to 228 of SEQ ID NO:132, positions 61 to 288 of SEQ ID NO:134, or a corresponding sequence from a different HBV strain.

In one aspect of this embodiment of the invention, the amino acid sequence of the HBV core antigen is at least 95% identical, or at least 96% identical, or at least 97% identical, or at least 98% identical, or at least 99% identical, or is identical, to an amino acid sequence selected from: positions 352-533 of SEQ ID NO:38, positions 31-212 of SEQ ID NO:1, positions 31-212 of SEQ ID NO:5, positions 31-212 of SEQ ID NO:9, positions 37 to 188 of SEQ ID NO:9, positions 31-212 of SEQ ID NO:13, positions 31-212 of SEQ ID NO:17, positions 31-212 of SEQ ID NO:21, positions 14-194 of SEQ ID NO:25, positions 31-212 of SEQ ID NO:29, positions 408-589 of SEQ ID NO:34, positions 605 to 786 of SEQ ID NO:36, positions 160-341 of SEQ ID NO:39, positions 605-786 of SEQ ID NO:41, positions 691-872 of SEQ ID NO:92, positions 90-271 of SEQ ID NO:95, SEQ ID NO:99, positions 567 to 718 of SEQ ID NO:101, positions 483 to 634 of SEQ ID NO:102, positions 2-183 of SEQ ID NO:105, positions 184-395 of SEQ ID NO:105, positions 396-578 of SEQ ID NO:105, positions 579-761 of SEQ ID NO:105, positions 2-183 of SEQ ID NO:106, 338-520 of SEQ ID NO:106, positions 478-629 of SEQ ID NO:107, positions 478-629 of SEQ ID NO:108, positions 478-629 of SEQ ID NO:109, positions 478-629 of SEQ ID NO:110, positions 400-581 of SEQ ID NO:112, positions 400-581 of SEQ ID NO:114, positions 400-581 of SEQ ID NO:116, positions 400-581 of SEQ ID NO:118, positions 400 to 581 of SEQ ID NO:120, positions 400 to 581 of SEQ ID NO:122, positions 400 to 581 of SEQ ID NO:124, positions -400 to 581 of SEQ ID NO:126, positions 630 to 811 of SEQ ID NO:128, positions 462 to 643 of SEQ ID NO:130, positions 688 to 869 of SEQ ID NO:132, positions 688 to 869 of SEQ ID NO:134, or a corresponding sequence from a different HBV strain.

In one aspect of this embodiment of the invention, the fusion protein has an amino acid sequence that is at least 95% identical, or at least 96% identical, or at least 97% identical, or at least 98% identical, or at least 99% identical, or is identical, to an amino acid sequence of SEQ ID NO:38, or a corresponding sequence from a different HBV strain.

Yet another embodiment of the invention relates to an immunotherapeutic composition comprising: (a) a yeast vehicle; and (b) a fusion protein comprising HBV antigens, wherein the HBV antigens consist of: (i) an HBV X antigen consisting of at least one immunogenic domain of HBV X antigen; and (ii) an HBV core antigen consisting of at least one immunogenic domain of HBV core protein. The composition elicits an HBV-specific immune response. In one aspect of this embodiment, the HBV antigens consist of: an amino acid sequence that is at least 95% identical to full-length HBV X antigen and an amino acid sequence that is at least 95% identical to full-length HBV core protein.

In one aspect of this embodiment of the invention, the amino acid sequence of the HBV core antigen is at least 95% identical, or at least 96% identical, or at least 97% identical, or at least 98% identical, or at least 99% identical, or is identical, to an amino acid sequence selected from: positions 160-341 of SEQ ID NO:39, positions 31-212 of SEQ ID NO:1, positions 31-212 of SEQ ID NO:5, positions 31-212 of SEQ ID NO:9, positions 37 to 188 of SEQ ID NO:9, positions 31-212 of SEQ ID NO:13, positions 31-212 of SEQ ID NO:17, positions 31-212 of SEQ ID NO:21, positions 14-194 of SEQ ID NO:25, positions 31-212 of SEQ ID NO:29, positions 408-589 of SEQ ID NO:34, positions 605 to 786 of SEQ ID NO:36, positions 352-533 of SEQ ID NO:38, positions 605-786 of SEQ ID NO:41, positions 691-872 of SEQ ID NO:92, positions 90-271 of SEQ ID NO:95, SEQ ID NO:99, positions 567 to 718 of SEQ ID NO:101, positions 483 to 634 of SEQ ID NO:102, positions 2-183 of SEQ ID NO:105, positions 184-395 of SEQ ID NO:105, positions 396-578 of SEQ ID NO:105, positions 579-761 of SEQ ID NO:105, positions 2-183 of SEQ ID NO:106, 338-520 of SEQ ID NO:106, positions 478-629 of SEQ ID NO:107, positions 478-629 of SEQ ID NO:108, positions 478-629 of SEQ ID NO:109, positions 478-629 of SEQ ID NO:110, positions 400-581 of SEQ ID NO:112, positions 400-581 of SEQ ID NO:114, positions 400-581 of SEQ ID NO:116, positions 400-581 of SEQ ID NO:118, positions 400 to 581 of SEQ ID NO:120, positions 400 to 581 of SEQ ID NO:122, positions 400 to 581 of SEQ ID NO:124, positions 400 to 581 of SEQ ID NO:126, positions 630 to 811 of SEQ ID NO:128, positions 462 to 643 of SEQ ID NO:130, positions 688 to 869 of SEQ ID NO:132, positions 688 to 869 of SEQ ID NO:134, or a corresponding sequence from a different HBV strain.

In one aspect of this embodiment of the invention, the amino acid sequence of the HBV X antigen is at least 95% identical, or at least 96% identical, or at least 97% identical, or at least 98% identical, or at least 99% identical, or is identical, to an amino acid sequence selected from: positions 7-159 of SEQ ID NO:39, SEQ ID NO:4, SEQ ID NO:8, SEQ ID NO:12, positions 2 to 154 of SEQ ID NO:12, SEQ ID NO:16, SEQ ID NO:20, SEQ ID NO:24, SEQ ID NO:28, SEQ ID NO:32, positions 52-68 followed by positions 84-126 of SEQ ID NO:4, positions 52-68 followed by positions 84-126 of SEQ ID NO:8, positions 52-68 followed by positions 84-126 of SEQ ID NO:12, positions 52-68 followed by positions 84-126 of SEQ ID NO:16, positions 52-68 followed by positions 84-126 of SEQ ID NO:20, positions 52-68 followed by positions 84-126 of SEQ ID NO:24, positions 52-68 followed by positions 84-126 of SEQ ID NO:28, positions 52-68 followed by positions 84-126 of SEQ ID NO:32, positions 787 to 939 of SEQ ID NO:36, positions 873-1025 of SEQ ID NO:92, positions 90-242 of SEQ ID NO:96, SEQ ID NO:100, positions 719-778 of SEQ ID NO:101, positions 635-694 of SEQ ID NO:102, positions 184-337 of SEQ ID NO:106, positions 521-674 of SEQ ID NO:106, positions 630-689 of SEQ ID NO:107, positions 630-689 of SEQ ID NO:108, positions 630-689 of SEQ ID NO:109, positions 630-689 of SEQ ID NO:110, positions 582-641 of SEQ ID NO:122, positions 810-869 of SEQ ID NO:124, positions 582-641 of SEQ ID NO:126, positions 1-60 of SEQ ID NO:130, positions 229 to 288 of SEQ ID NO:132, positions 1 to 60 of SEQ ID NO:134, or a corresponding sequence from a different HBV strain.

In one aspect of this embodiment of the invention, the fusion protein has the amino acid sequence that is at least 95% identical, or at least 96% identical, or at least 97% identical, or at least 98% identical, or at least 99% identical, or is identical, to an amino acid sequence to SEQ ID NO:39, or a corresponding sequence from a different HBV strain.

Another embodiment of the invention relates to an immunotherapeutic composition comprising: (a) a yeast vehicle; and (b) a fusion protein comprising an HBV surface antigen consisting of at least one immunogenic domain of an HBV large surface antigen (L), wherein the composition elicits an HBV-specific immune response. In one aspect of this embodiment, the HBV surface antigen consists of at least 95% of full-length HBV large surface antigen (L). In one aspect, the amino acid sequence of the HBV surface antigen is at least 95% identical, or at least 96% identical, or at least 97% identical, or at least 98% identical, or at least 99% identical, or is identical, to an amino acid sequence selected from: positions 90-488 of SEQ ID NO:93, SEQ ID NO:3, SEQ ID NO:7, SEQ ID NO:11, positions 21-47 of SEQ ID NO:11, positions 176-400 of SEQ ID NO:11, SEQ ID NO:15, SEQ ID NO:19, SEQ ID NO:23, SEQ ID NO:27, SEQ ID NO:31, positions 9-407 of SEQ ID NO:34, positions 6-257 of SEQ ID NO:36, positions 6-257 of SEQ ID NO:41, positions 92-343 of SEQ ID NO:92, positions 90-488 of SEQ ID NO:93, SEQ ID NO:97, positions 90-338 of SEQ ID NO:101, positions 7-254 of SEQ ID NO:102, positions 1-249 of SEQ ID NO:107, positions 1-249 of SEQ ID NO:108, positions 1-249 of SEQ ID NO:109, positions 1-249 of SEQ ID NO:110, positions 1-399 of SEQ ID NO:112, positions 1-399 of SEQ ID NO:114, positions 1-399 of SEQ ID NO:116, positions 1-399 of SEQ ID NO:118, positions 1-399 of SEQ ID NO:120, positions 1-399 of SEQ ID NO:122, positions 1-399 of SEQ ID NO:124, positions 1-399 of SEQ ID NO:126, positions 231-629 of SEQ ID NO:128, positions 63-461 of SEQ ID NO:130, positions 289-687 of SEQ ID NO:132, positions 289-687 of SEQ ID NO:134, or a corresponding sequence from a different HBV strain. In one aspect, the fusion protein has the amino acid sequence that is at least 95% identical, or at least 96% identical, or at least 97% identical, or at least 98% identical, or at least 99% identical, or is identical, to an amino acid sequence of SEQ ID NO:93, or a corresponding sequence from a different HBV strain.

Yet another embodiment of the invention relates to an immunotherapeutic composition comprising: (a) a yeast vehicle; and (b) a fusion protein comprising an HBV polymerase antigen consisting of at least one immunogenic domain of a reverse transcriptase domain of HBV polymerase, wherein the composition elicits an HBV-specific immune response. In one aspect of this embodiment of the invention, the HBV polymerase antigen consists of at least 95% of full-length reverse transcriptase domain of HBV polymerase. In one aspect, the amino acid sequence of the HBV polymerase antigen is at least 95% identical, or at least 96% identical, or at least 97% identical, or at least 98% identical, or at least 99% identical, or is identical, to an amino acid sequence selected from: positions 7-351 of SEQ ID NO:40, positions 90-434 of SEQ ID NO:94, positions 383-602 of SEQ ID NO:2, positions 381-600 of SEQ ID NO:6, positions 381-600 of SEQ ID NO:10, positions 453 to 680 of SEQ ID NO:10, positions 370-589 of SEQ ID NO:14, positions 380-599 of SEQ ID NO:18, positions 381-600 of SEQ ID NO:22, positions 380-599 of SEQ ID NO:26, positions 381-600 of SEQ ID NO:30, positions 260 to 604 of SEQ ID NO:36, positions 7-351 of SEQ ID NO:38, 260 to 604 of SEQ ID NO:41, positions 346 to 690 of SEQ ID NO:92, SEQ ID NO:98, positions 339 to 566 of SEQ ID NO:101, positions 255 to 482 of SEQ ID NO:102, positions 250-477 of SEQ ID NO:107, positions 250-477 of SEQ ID NO:108, positions 250-477 of SEQ ID NO:109, positions 250-477 of SEQ ID NO:110, positions 582 to 809 of SEQ ID NO:120, positions 582 to 809 of SEQ ID NO:124, positions 642 to 869 of SEQ ID NO:126, positions 1 to 228 of SEQ ID NO:128, positions 1 to 228 of SEQ ID NO:132, positions 61 to 288 of SEQ ID NO:134, or a corresponding sequence from a different HBV strain. In one aspect, the fusion protein has the amino acid sequence that is at least 95% identical, or at least 96% identical, or at least 97% identical, or at least 98% identical, or at least 99% identical, or is identical, to an amino acid sequence of SEQ ID NO:40 or SEQ ID NO:94, or a corresponding sequence from a different HBV strain.

Another embodiment of the invention relates to an immunotherapeutic composition comprising: (a) a yeast vehicle; and (b) a fusion protein comprising an HBV core antigen consisting of at least one immunogenic domain of an HBV core protein, wherein the composition elicits an HBV-specific immune response. In one aspect of this embodiment of the invention, the HBV antigens consist of at least 95% of full-length HBV core protein. In one aspect, the amino acid sequence of the HBV core antigen is at least 95% identical, or at least 96% identical, or at least 97% identical, or at least 98% identical, or at least 99% identical, or is identical, to an amino acid sequence selected from: positions 90-271 of SEQ ID NO:95, positions 31-212 of SEQ ID NO:1, positions 31-212 of SEQ ID NO:5, positions 31-212 of SEQ ID NO:9, positions 37 to 188 of SEQ ID NO:9, positions 31-212 of SEQ ID NO:13, positions 31-212 of SEQ ID NO:17, positions 31-212 of SEQ ID NO:21, positions 14-194 of SEQ ID NO:25, positions 31-212 of SEQ ID NO:29, positions 408-589 of SEQ ID NO:34, positions 605 to 786 of SEQ ID NO:36, positions 352-533 of SEQ ID NO:38, positions 160-341 of SEQ ID NO:39, positions 605-786 of SEQ ID NO:41, positions 691-872 of SEQ ID NO:92, SEQ ID NO:99, positions 567 to 718 of SEQ ID NO:101, positions 483 to 634 of SEQ ID NO:102, positions 2-183 of SEQ ID NO:105, positions 184-395 of SEQ ID NO:105, positions 396-578 of SEQ ID NO:105, positions 579-761 of SEQ ID NO:105, positions 2-183 of SEQ ID NO:106, 338-520 of SEQ ID NO:106, positions 478-629 of SEQ ID NO:107, positions 478-629 of SEQ ID NO:108, positions 478-629 of SEQ ID NO:109, positions 478-629 of SEQ ID NO:110, positions 400-581 of SEQ ID NO:112, positions 400-581 of SEQ ID NO:114, positions 400-581 of SEQ ID NO:116, positions 400-581 of SEQ ID NO:118, positions 400 to 581 of SEQ ID NO:120, positions 400 to 581 of SEQ ID NO:122, positions 400 to 581 of SEQ ID NO:124, positions 400 to 581 of SEQ ID NO:126, positions 630 to 811 of SEQ ID NO:128, positions 462 to 643 of SEQ ID NO:130, positions 688 to 869 of SEQ ID NO:132, positions 688 to 869 of SEQ ID NO:134, or a corresponding sequence from a different HBV strain. In one aspect, the protein has the amino acid sequence that is at least 95% identical, or at least 96% identical, or at least 97% identical, or at least 98% identical, or at least 99% identical, or is identical, to an amino acid sequence of SEQ ID NO:95, or a corresponding sequence from a different HBV strain.

Yet another embodiment of the invention relates to an immunotherapeutic composition comprising: (a) a yeast vehicle; and (b) a fusion protein comprising an HBV X antigen consisting of at least one immunogenic domain of a full-length HBV X antigen, wherein the composition elicits an HBV-specific immune response. In one aspect, the HBV antigen consists of at least 95% of full-length HBV X antigen. In one aspect, the amino acid sequence of the HBV X antigen is at least 95% identical, or at least 96% identical, or at least 97% identical, or at least 98% identical, or at least 99% identical, or is identical, to an amino acid sequence selected from: positions 90-242 of SEQ ID NO:96, SEQ ID NO:4, SEQ ID NO:8, SEQ ID NO:12, positions 2 to 154 of SEQ ID NO:12, SEQ ID NO:16, SEQ ID NO:20, SEQ ID NO:24, SEQ ID NO:28, SEQ ID NO:32, positions 52-68 followed by positions 84-126 of SEQ ID NO:4, positions 52-68 followed by positions 84-126 of SEQ ID NO:8, positions 52-68 followed by positions 84-126 of SEQ ID NO:12, positions 52-68 followed by positions 84-126 of SEQ ID NO:16, positions 52-68 followed by positions 84-126 of SEQ ID NO:20, positions 52-68 followed by positions 84-126 of SEQ ID NO:24, positions 52-68 followed by positions 84-126 of SEQ ID NO:28, positions 52-68 followed by positions 84-126 of SEQ ID NO:32, positions 787 to 939 of SEQ ID NO:36, positions 7-159 of SEQ ID NO:39, positions 873-1025 of SEQ ID NO:92, SEQ ID NO:100, positions 719-778 of SEQ ID NO:101, positions 635-694 of SEQ ID NO:102, positions 184-337 of SEQ ID NO:106, positions 521-674 of SEQ ID NO:106, positions 630-689 of SEQ ID NO:107, positions 630-689 of SEQ ID NO:108, positions 630-689 of SEQ ID NO:109, positions 630-689 of SEQ ID NO:110, positions 582-641 of SEQ ID NO:122, positions 810-869 of SEQ ID NO:124, positions 582-641 of SEQ ID NO:126, positions 1-60 of SEQ ID NO:130, positions 229 to 288 of SEQ ID NO:132, positions 1 to 60 of SEQ ID NO:134, or a corresponding sequence from a different HBV strain. In one aspect, the protein has the amino acid sequence that is at least 95% identical, or at least 96% identical, or at least 97% identical, or at least 98% identical, or at least 99% identical, or is identical, to an amino acid sequence of SEQ ID NO:96, or a corresponding sequence from a different HBV strain.

Another embodiment of the invention relates to an immunotherapeutic composition comprising any two, three or four of the immunotherapeutic compositions described above, or elsewhere herein and in particular, any two, three, or four of the immunotherapeutic compositions described above that relate to single HBV proteins.

Yet another embodiment of the invention relates to an immunotherapeutic composition comprising: (a) a yeast vehicle; and (b) a fusion protein comprising HBV antigens, wherein the HBV antigens consist of at least one immunogenic domain of two, three or four HBV surface antigen proteins, wherein each of the HBV surface antigen proteins is from a different HBV genotype. The composition elicits an HBV-specific immune response.

Yet another embodiment of the invention relates to an immunotherapeutic composition comprising: (a) a yeast vehicle; and (b) a fusion protein comprising HBV antigens, wherein the HBV antigens consist of at least one immunogenic domain of two, three or four HBV polymerase proteins, wherein each of the HBV polymerase proteins is from a different HBV genotype. The composition elicits an HBV-specific immune response.

Yet another embodiment of the invention relates to an immunotherapeutic composition comprising: (a) a yeast vehicle; and (b) a fusion protein comprising HBV antigens, wherein the HBV antigens consist of at least one immunogenic domain of two, three or four HBV X antigens, wherein each of the HBV X antigens is from a different HBV genotype. The composition elicits an HBV-specific immune response.

Yet another embodiment of the invention relates to an immunotherapeutic composition comprising: (a) a yeast vehicle; and (b) a fusion protein comprising HBV antigens, wherein the HBV antigens consist of at least one immunogenic domain of two, three or four HBV core proteins, wherein each of the HBV core proteins is from a different HBV genotype. The composition elicits an HBV-specific immune response. In one aspect, each of the HBV core proteins consists of at least 95% of a full-length HBV core protein. In one aspect, each of the HBV core proteins consists of amino acids 31 to 212 of HBV core protein. In one aspect, the HBV genotypes include genotype C, and in one aspect, the HBV genotypes include genotype D, and in one aspect, the HBV genotypes include genotype A, and in one aspect, the HBV genotypes include genotype B. In one aspect, each of the HBV core proteins consists of amino acids 37 to 188 of HBV core protein. In one aspect, the fusion protein comprises four HBV core proteins from genotype A, genotype B, genotype C and genotype D.

In one aspect of this embodiment of the invention, the amino acid sequence of any one or more of the HBV core antigens is at least 95% identical, or at least 96% identical, or at least 97% identical, or at least 98% identical, or at least 99% identical, or is identical, to an amino acid sequence selected from: positions 90-271 of SEQ ID NO:95, positions 31-212 of SEQ ID NO:1, positions 31-212 of SEQ ID NO:5, positions 31-212 of SEQ ID NO:9, positions 37 to 188 of SEQ ID NO:9, positions 31-212 of SEQ ID NO:13, positions 31-212 of SEQ ID NO:17, positions 31-212 of SEQ ID NO:21, positions 14-194 of SEQ ID NO:25, positions 31-212 of SEQ ID NO:29, positions 408-589 of SEQ ID NO:34, positions 605 to 786 of SEQ ID NO:36, positions 352-533 of SEQ ID NO:38, positions 160-341 of SEQ ID NO:39, positions 605-786 of SEQ ID NO:41, positions 691-872 of SEQ ID NO:92, SEQ ID NO:99, positions 567 to 718 of SEQ ID NO:101, positions 483 to 634 of SEQ ID NO:102, positions 2-183 of SEQ ID NO:105, positions 184-395 of SEQ ID NO:105, positions 396-578 of SEQ ID NO:105, positions 579-761 of SEQ ID NO:105, positions 2-183 of SEQ ID NO:106, 338-520 of SEQ ID NO:106, positions 478-629 of SEQ ID NO:107, positions 478-629 of SEQ ID NO:108, positions 478-629 of SEQ ID NO:109, positions 478-629 of SEQ ID NO:110, positions 400-581 of SEQ ID NO:112, positions 400-581 of SEQ ID NO:114, positions 400-581 of SEQ ID NO:116, positions 400-581 of SEQ ID NO:118, positions 400 to 581 of SEQ ID NO:120, positions 400 to 581 of SEQ ID NO:122, positions 400 to 581 of SEQ ID NO:124, positions 400 to 581 of SEQ ID NO:126, positions 630 to 811 of SEQ ID NO:128, positions 462 to 643 of SEQ ID NO:130, positions 688 to 869 of SEQ ID NO:132, positions 688 to 869 of SEQ ID NO:134, or a corresponding sequence from a different HBV strain. In one aspect, the HBV antigens have an amino acid sequence that is at least 95% identical, or at least 96% identical, or at least 97% identical, or at least 98% identical, or at least 99% identical, or is identical, to an amino acid sequence of SEQ ID NO:105, or a corresponding sequence from a different HBV strain.

Yet another embodiment of the invention relates to an immunotherapeutic composition comprising: (a) a yeast vehicle; and (b) a fusion protein comprising at least two HBV Core proteins and at least two HBV X antigens, where each of the HBV Core proteins is from a different HBV genotype and where each of the HBV X antigens is from a different HBV genotype. The composition elicits an HBV-specific immune response. In one aspect, the HBV genotypes include genotype C; in one aspect, the HBV genotypes include genotype D; in one aspect, the HBV genotypes include genotype A; and in one aspect, the HBV genotypes include genotype B. In one aspect, each of the HBV core proteins consists of at least 95% of a full-length HBV Core protein. In one aspect, each of the HBV core proteins comprises amino acids 31 to 212 of HBV Core protein. In one aspect, each of the HBV core proteins comprises amino acids 37 to 188 of HBV Core protein. In one aspect, each of the HBV X antigens comprises at least 95% of a full-length of HBV X antigen. In one aspect, each of the HBV X antigens comprises amino acids 52 to 127 of HBV X antigen.

In one aspect, the amino acid sequence of the HBV core antigen is at least 95% identical, or at least 96% identical, or at least 97% identical, or at least 98% identical, or at least 99% identical, or is identical, to an amino acid sequence selected from: positions 90-271 of SEQ ID NO:95, positions 31-212 of SEQ ID NO:1, positions 31-212 of SEQ ID NO:5, positions 31-212 of SEQ ID NO:9, positions 37 to 188 of SEQ ID NO:9, positions 31-212 of SEQ ID NO:13, positions 31-212 of SEQ ID NO:17, positions 31-212 of SEQ ID NO:21, positions 14-194 of SEQ ID NO:25, positions 31-212 of SEQ ID NO:29, positions 408-589 of SEQ ID NO:34, positions 605 to 786 of SEQ ID NO:36, positions 352-533 of SEQ ID NO:38, positions 160-341 of SEQ ID NO:39, positions 605-786 of SEQ ID NO:41, positions 691-872 of SEQ ID NO:92, SEQ ID NO:99, positions 567 to 718 of SEQ ID NO:101, positions 483 to 634 of SEQ ID NO:102, positions 2-183 of SEQ ID NO:105, positions 184-395 of SEQ ID NO:105, positions 396-578 of SEQ ID NO:105, positions 579-761 of SEQ ID NO:105, positions 2-183 of SEQ ID NO:106, 338-520 of SEQ ID NO:106, positions 478-629 of SEQ ID NO:107, positions 478-629 of SEQ ID NO:108, positions 478-629 of SEQ ID NO:109, positions 478-629 of SEQ ID NO:110, positions 400-581 of SEQ ID NO:112, positions 400-581 of SEQ ID NO:114, positions 400-581 of SEQ ID NO:116, positions 400-581 of SEQ ID NO:118, positions 400 to 581 of SEQ ID NO:120, positions 400 to 581 of SEQ ID NO:122, positions 400 to 581 of SEQ ID NO:124, positions 400 to 581 of SEQ ID NO:126, positions 630 to 811 of SEQ ID NO:128, positions 462 to 643 of SEQ ID NO:130, positions 688 to 869 of SEQ ID NO:132, positions 688 to 869 of SEQ ID NO:134, or a corresponding sequence from a different HBV strain.

In one aspect, the amino acid sequence of the HBV X antigen is at least 95% identical, or at least 96% identical, or at least 97% identical, or at least 98% identical, or at least 99% identical, or is identical, to an amino acid sequence selected from: positions 90-242 of SEQ ID NO:96, SEQ ID NO:4, SEQ ID NO:8, SEQ ID NO:12, positions 2 to 154 of SEQ ID NO:12, SEQ ID NO:16, SEQ ID NO:20, SEQ ID NO:24, SEQ ID NO:28, SEQ ID NO:32, positions 52-68 followed by positions 84-126 of SEQ ID NO:4, positions 52-68 followed by positions 84-126 of SEQ ID NO:8, positions 52-68 followed by positions 84-126 of SEQ ID NO:12, positions 52-68 followed by positions 84-126 of SEQ ID NO:16, positions 52-68 followed by positions 84-126 of SEQ ID NO:20, positions 52-68 followed by positions 84-126 of SEQ ID NO:24, positions 52-68 followed by positions 84-126 of SEQ ID NO:28, positions 52-68 followed by positions 84-126 of SEQ ID NO:32, positions 787 to 939 of SEQ ID NO:36, positions 7-159 of SEQ ID NO:39, positions 873-1025 of SEQ ID NO:92, SEQ ID NO:100, positions 719-778 of SEQ ID NO:101, positions 635-694 of SEQ ID NO:102, positions 184-337 of SEQ ID NO:106, positions 521-674 of SEQ ID NO:106, positions 630-689 of SEQ ID NO:107, positions 630-689 of SEQ ID NO:108, positions 630-689 of SEQ ID NO:109, positions 630-689 of SEQ ID NO:110, positions 582-641 of SEQ ID NO:122, positions 810-869 of SEQ ID NO:124, positions 582-641 of SEQ ID NO:126, positions 1-60 of SEQ ID NO:130, positions 229 to 288 of SEQ ID NO:132, positions 1 to 60 of SEQ ID NO:134, or a corresponding sequence from a different HBV strain.

In one aspect of this embodiment of the invention, the fusion protein has an amino acid sequence that is at least 95% identical, or at least 96% identical, or at least 97% identical, or at least 98% identical, or at least 99% identical, or is identical, to an amino acid sequence of SEQ ID NO:106, or a corresponding sequence from a different HBV strain.

In any of the embodiments described herein, including above and below, related to a fusion protein, HBV antigens, or immunotherapeutic composition comprising such a fusion protein or HBV antigens, in one further embodiment, the fusion protein can be appended at its N-terminus to add an additional sequence. In one aspect, the N-terminal sequence is selected from an amino acid sequence that is 95% identical to SEQ ID NO:37, an amino acid sequence that is 95% identical to SEQ ID NO:89, or an amino acid sequence that is 95% identical to SEQ ID NO:90. In one aspect, the N-terminal sequence is selected from SEQ ID NO:37, positions 1 to 5 of SEQ ID NO:37, SEQ ID NO:89, or SEQ ID NO:90, or a corresponding sequence from a different HBV strain.

In one aspect of any of the embodiments of the invention described above or elsewhere herein, the fusion protein is expressed by the yeast vehicle. In another aspect of any of the embodiments of the invention described above or elsewhere herein, the yeast vehicle is a whole yeast. The whole yeast, in one aspect is killed. In one aspect, the whole yeast is heat-inactivated.

In one aspect of any of any of the embodiments of the invention described above or elsewhere herein, the yeast vehicle can be from a yeast genus selected from: *Saccharomyces, Candida, Cryptococcus, Hansenula, Kluyveromyces, Pichia, Rhodotorula, Schizosaccharomyces* and *Yarrowia*. In one aspect, the yeast vehicle is from *Saccharomyces*. In one aspect, the yeast vehicle is from *Saccharomyces cerevisiae*.

In one aspect of any of the embodiments of the invention described above or elsewhere herein, the composition is formulated for administration to a subject or patient. In one aspect, the composition is formulated for administration by injection of a subject or patient (e.g., by a parenteral route, such as subcutaneous or intraperitoneal or intramuscular injection). In one aspect, the composition is formulated in a pharmaceutically acceptable excipient that is suitable for administration to a human. In one aspect, the composition contains greater than 90% yeast protein. In one aspect, the composition contains greater than 90% yeast protein and is formulated for administration to a patient.

In one aspect of any of the embodiments of the invention described above or elsewhere herein, the fusion protein is not aggregated in the yeast. In one aspect, the fusion protein does not form inclusion bodies in the yeast. In one aspect, the fusion protein does not form VLPs or other large antigen particles in the yeast. In one aspect, the fusion protein does form VLPs or other large antigen particles in the yeast.

In one aspect of any embodiment of the invention described above or elsewhere herein, in one aspect, the HBV sequences are from HBV genotype A. In another aspect, the HBV sequences are from HBV genotype B. In another aspect, the HBV sequences are from HBV genotype C. In another aspect, the HBV sequences are from HBV genotype D. In another aspect, the HBV sequences are from HBV genotype E. In another aspect, the HBV sequences are from HBV genotype F. In another aspect, the HBV sequences are from HBV genotype G. In another aspect, the HBV sequences are from HBV genotype H. In one aspect, the HBV sequences are from a combination of any of the above-referenced HBV genotypes or of any known HBV genotypes or sub-genotypes.

Another embodiment of the invention relates to any of the fusion proteins described above as part of an immunotherapeutic composition of the invention, or elsewhere herein. In one aspect of this embodiment, a fusion protein comprises HBV antigens, the HBV antigens selected from, but not limited to: (a) HBV antigens consisting of: HBV large surface antigen (L), HBV core protein and HBV X antigen; (b) HBV antigens consisting of: HBV large surface antigen (L) and HBV core protein; (c) HBV antigens consisting of: hepatocyte receptor of Pre-S1 of the HBV large surface antigen (L), HBV small surface antigen (S), the reverse transcriptase domain of HBV polymerase, HBV core protein or HBV e-antigen, and HBV X antigen; (d) HBV antigens consisting of: HBV large surface antigen (L), the reverse transcriptase domain of HBV polymerase, HBV core protein or HBV e-antigen, and HBV X antigen; (e) HBV antigens consisting of: HBV large surface antigen (L), the reverse transcriptase domain of HBV polymerase, and HBV core protein; (f) HBV antigens consisting of: HBV polymerase (RT domain) and HBV core protein; (g) HBV antigens consisting of: HBV X antigen and HBV core protein; (h) HBV antigens consisting of: hepatocyte receptor of Pre-S1 of the HBV large surface antigen (L), HBV small surface antigen (S), the reverse transcriptase domain of HBV polymerase, and HBV core protein or HBV e-antigen; (i) HBV antigens consisting of HBV large surface antigen (L); (j) HBV antigens consisting of HBV core antigen; (k) HBV antigens consisting of: HBV polymerase including the reverse transcriptase domain; (l) HBV antigens consisting of HBV X antigen; (m) HBV antigens consisting of between two and four HBV surface antigens, HBV polymerase antigens, HBV core antigens, or HBV X antigens, where each of the between two and four HBV antigens is from a different HBV genotype; and (n) HBV antigens consisting of two HBV core antigens and two HBV X antigens, wherein each of the two HBV core antigens and each of the two HBV X antigens are from a different HBV genotype. Aspects of the invention related to each of the HBV antigens, including a variety of sequences useful in these antigens, have been described above.

In one aspect of this embodiment, the fusion protein comprises an amino acid sequence that is at least 95% identical, or at least 96% identical, or at least 97% identical, or at least 98% identical, or at least 99% identical, or is identical, to an amino acid sequence selected from: SEQ ID NO:130, SEQ ID NO:150, SEQ ID NO:118, SEQ ID NO:151, SEQ ID NO:34, SEQ ID NO:120, SEQ ID NO:122, SEQ ID NO:124, SEQ ID NO:126, SEQ ID NO:128, SEQ ID NO:132, SEQ ID NO:134, SEQ ID NO:112, SEQ ID NO:114, SEQ ID NO:116, SEQ ID NO:36, SEQ ID NO:38, SEQ ID NO:39, SEQ ID NO:40, SEQ ID NO:41, SEQ ID NO:92, SEQ ID NO:93, SEQ ID NO:94, SEQ ID NO:95, SEQ ID NO:96, SEQ ID NO:97, SEQ ID NO:98, SEQ ID NO:99, SEQ ID NO:100, SEQ ID NO:101, SEQ ID NO:102, SEQ ID NO:105, SEQ ID NO:106, SEQ ID NO:107, SEQ ID NO:108, SEQ ID NO:109, and SEQ ID NO:110.

Another embodiment of the invention relates to a recombinant nucleic acid molecule encoding any of the fusion proteins described herein. In one aspect, the recombinant nucleic acid molecule comprises a nucleic acid sequence selected from, but not limited to: SEQ ID NO:33, SEQ ID NO:35, SEQ ID NO:91, SEQ ID NO:111, SEQ ID NO:113, SEQ ID NO:115, SEQ ID NO:117, SEQ ID NO:119, SEQ ID NO:121, SEQ ID NO:123, SEQ ID NO:125, SEQ ID NO:127, SEQ ID NO:129, SEQ ID NO:131, or SEQ ID NO:133.

Yet another embodiment of the invention relates to an isolated cell transfected with any of the recombinant nucleic acid molecules described herein. In one aspect, the cell is a yeast cell.

Another embodiment of the invention relates to a composition comprising any of the fusion proteins described herein. Yet another embodiment of the invention relates to a composition comprising any of the recombinant nucleic acid molecules described herein. Another embodiment of the invention relates to a composition comprising any of the isolated cells described herein.

Yet another embodiment of the invention relates to a method to treat hepatitis B virus (HBV) infection or at least one symptom resulting from HBV infection in a subject, comprising administering to a subject that is infected with HBV at least one of any of the immunotherapeutic compositions, including any HBV antigen, fusion protein, or yeast-based immunotherapeutic composition, described herein. The administration of the composition to the subject reduces HBV infection or at least one symptom resulting from HBV infection in a subject.

Yet another embodiment of the invention relates to a method to elicit an antigen-specific, cell-mediated immune response against an HBV antigen, comprising administering to a subject any one or more of the compositions, including any HBV antigen, fusion protein, or yeast-based immunotherapeutic composition, described herein.

Yet another embodiment of the invention relates to a method to prevent HBV infection in a subject, comprising administering to a subject that has not been infected with HBV, any one or more of the compositions, including any HBV antigen, fusion protein, or yeast-based immunotherapeutic composition, described herein.

Another embodiment of the invention relates to a method to immunize a population of individuals against HBV, comprising administering to the population of individuals any one or more of the compositions, including any HBV antigen, fusion protein, or yeast-based immunotherapeutic composition, described herein.

Another embodiment of the invention relates to any one or more of the compositions, including any HBV antigen, fusion protein, or yeast-based immunotherapeutic composition, described herein, for use to treat HBV infection or a symptom thereof.

Another embodiment of the invention relates to any one or more of the compositions, including any HBV antigen, fusion protein, or yeast-based immunotherapeutic composition, described herein, for use to prevent HBV infection or a symptom thereof.

Yet another embodiment of the invention relates to the use of any one or more of the compositions, including any HBV antigen, fusion protein, or yeast-based immunotherapeutic composition, described herein in the preparation of a medicament to treat HBV infection or a symptom thereof.

Yet another embodiment of the invention relates to the use of any one or more of the compositions, including any HBV antigen, fusion protein, or yeast-based immunotherapeutic composition, described herein in the preparation of a medicament to prevent HBV infection or a symptom thereof.

In one aspect of any of the embodiments related to methods or uses of the invention described above or elsewhere herein, the method can include administration of at least two, three, four or more of the compositions, including any HBV antigen, fusion protein, or yeast-based immunotherapeutic composition, described herein. In one aspect, additional compositions or compounds useful for the prevention or treatment of HBV infection can be administered (e.g., anti-viral compounds, interferons, other immunotherapeutic compositions, or combinations thereof). In one aspect, the various compositions or compounds are administered concurrently to an individual. In one aspect, the various compositions or compounds are administered sequentially to an individual. In one aspect, each of the various compositions is administered by injection to a different site on the individual. In one aspect, a single dose of a yeast-based HBV immunotherapeutic composition of the invention is between 40 Y.U. total and 80 Y.U. total, administered in equal parts at two, three or four different sites on an individual, per dose.

In one aspect of any of the embodiments related to methods or uses of the invention described above or elsewhere herein, administration of the composition to the subject causes seroconversion in the subject or improves seroconversion rates in a population of subjects. In one aspect, administration of the composition to the subject reduces serum HBsAg or results in loss of serum HBsAg in the subject or improves rates of loss of serum HBsAg in a population of subjects. In one aspect, administration of the composition to the subject reduces serum HBeAg or results in loss of serum HBeAg in the subject or improves rates of loss of serum HBeAg in a population of subjects. In one aspect, administration of the composition to the subject reduces HBV viral load in the subject or improves rates in reduction of HBV viral load in a population of subjects. In one aspect, administration of the composition to the subject results in undetectable HBV DNA in infected cells in the subject or results in higher rates of HBV DNA negativity in a population of subjects. In one aspect, administration of the composition to the subject reduces liver damage or improves liver function in the subject or reduces the rate of liver damage or increases the rate of improved liver function in a population of subjects. In one aspect, administration of the composition to the subject improves ALT normalization in the subject or in a population of subjects.

In any of the embodiments related to an HBV antigen, fusion protein, immunotherapeutic composition, or any method of use of the HBV antigen, fusion protein or immunotherapeutic composition described herein, in one aspect, the composition further comprises, or is used in conjunction with, at least one biological response modifier. In one aspect, the composition further comprises, or is used in conjunction with, one or more additional compounds useful for treating or ameliorating a symptom of HBV infection. In one aspect, the composition further comprises, or is used in conjunction with, at least one anti-viral compound. In one aspect, the anti-viral is a nucleotide analogue reverse transcriptase inhibitor. An anti-viral compound can include, but is not limited to, tenofovir, lamivudine, adefovir, telbivudine, entecavir, and combinations thereof. In one aspect, the anti-viral compound is tenofovir. In one aspect, the anti-viral compound is entecavir. In one aspect, the composition further comprises, or is used in conjunction with, at least one interferon. In one aspect, the interferon is interferon-α. In one aspect, the interferon is pegylated interferon-α2a. In one aspect, the interferon is interferon-λ.

BRIEF DESCRIPTION OF THE DRAWINGS

FIG. 26 is a graph showing the proliferation of splenic CD4$^+$ T cells from mice immunized with a yeast-based immunotherapeutic product expressing an HBV Surface-Pol-Core-X antigen (denoted a-Spex) to an S/Core antigen mix or to a MHC Class II SAg mimetope peptide (error bars are Standard Deviation).

FIGS. 29A and 29B are graphs showing interferon-γ (IFN-γ) production in splenocytes from mice immunized with: (FIG. 29A) a yeast-based immunotherapeutic product expressing an HBV Surface-Core antigen (denoted Sc) or (FIG. 29B) a yeast-based immunotherapeutic product expressing an HBV Surface-Pol-Core-X antigen (denoted Sp) (error bars are Standard Deviation).

DETAILED DESCRIPTION OF THE INVENTION

Figure 1:
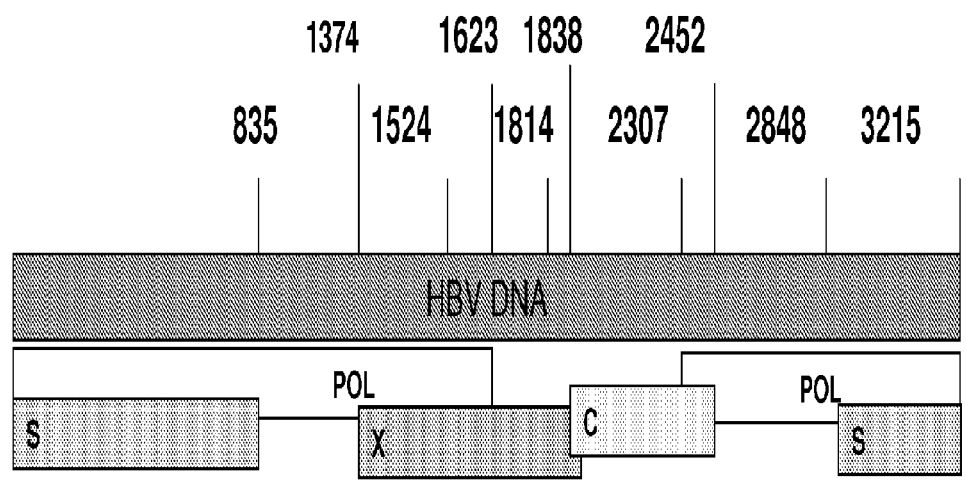
FIG. 1 is a schematic drawing showing the hepatitis B virus genome arrangement.

This invention generally relates to compositions and methods for preventing and/or treating hepatitis B virus (HBV) infection. The invention includes a yeast-based immunotherapeutic composition (also referred to as "yeast-based HBV immunotherapy") comprising a yeast vehicle and HBV antigen(s) that have been designed to elicit a prophylactic and/or therapeutic immune response against HBV infection in an individual, and the use of such compositions to prevent and/or treat HBV infection and related symptoms thereof. The invention also includes the recombinant nucleic acid molecules used in the yeast-based compositions of the invention, as well as the proteins and fusion proteins encoded thereby, for use in any immunotherapeutic composition and/or any therapeutic or prophylactic protocol for HBV infection, including any therapeutic or prophylactic protocol that combines the HBV-specific yeast-based compositions of the invention with any one or more other therapeutic or prophylactic compositions, agents, drugs, compounds, and/or protocols for HBV infection.

The yeast-based, HBV-specific immunotherapeutic compositions are unique among various types of immunotherapy, in that these compositions of the invention induce innate immune responses, as well as adaptive immune responses that specifically target HBV, including CD4-dependent TH17 and TH1 T cell responses and antigen-specific $CD8^+$ T cell responses. The breadth of the immune response elicited by HBV-specific yeast-based immunotherapy is well-suited to target HBV. First, HBV is believed to evade the innate immune response early in infection by "hiding" from the innate response and thereby not inducing it, rather than by directly counteracting innate immunity (Wieland and Chisari, 2005, *J. Virol.* 15:9369-9380; Wieland, et al., 2004, *PNAS USA* 101:6669-6674). Accordingly, it can be expected that HBV will be sensitive to innate immune responses if they are activated by another mechanism, i.e., the yeast-based immunotherapeutic compositions of the invention. Second, HBV produces high-level antigen expression in infected host cells that is expected to be visible to the adaptive immune response (Guidotti, et al., 1999, *Science* 284:825-829; Thimme et al., 2003, *J. Virol.* 77:68-76), and clearance of acute infection has been associated with robust $CD4^+$ and $CD8^+$ T cell responses (Maini et al., 1999, *Gastroenterol.* 117:1386-1396; Rehermann et al., 1995, *J. Exp. Med.* 181:1047-1058; Thimme et al., 2003, *J. Virol.* 77:68-76; Wieland and Chisari, 2005, *J. Virol.* 15:9369-9380). Therefore, yeast-based HBV immunotherapy, by activating the adaptive immune response, is expected to effectively target HBV-infected cells for destruction and/or is expected to effectively enhance viral clearance. Moreover, the immune response generated by yeast-based immunotherapy is believed to be interferon-independent and interferon-dependent (Tamburini et al., 2012, *J. Immunother.* 35(1):14-22); accordingly, the ability, or lack thereof, of an individual to respond to interferon-based therapy, which is one standard of care treatment for HBV, is not believed to directly impact the ability of the subject to respond to yeast-based immunotherapy of the invention. In addition, the yeast-based HBV immunotherapy compositions described herein are designed to target immunogenic and conserved regions of HBV, multiple CTL epitopes, and include regions of HBV that may be targeted for escape (allowing for modifications of the compositions as needed to target such escape mutations), making it a highly adaptable therapy for HBV that optimizes the opportunity for effective immune responses against this virus.

In addition, and without being bound by theory, yeast-based immunotherapy for HBV is believed to induce an immune response that is not only directed specifically against the target antigen carried by the yeast-based immunotherapeutic product, but that also evolves to be directed against other immunological epitopes on the virus (i.e., other than those carried by the yeast-antigen composition). In other words, a primary cellular immune response to the antigen(s) and/or epitope(s) contained in the yeast-based immunotherapeutic can lead to secondary cellular immune responses to antigen(s) and/or epitope(s) that are present in the infected cells in the treated subject but that are not present in the yeast-based immunotherapeutic, thereby leading to the evolution of complex and unpredictable immune response profiles that are unique to each treated subject. These secondary immune responses are specific to the molecular profile of the HBV infection in each subject treated, and the yeast-based immunotherapeutic may drive these downstream effects in a unique manner when compared to other treatment modalities, including other immunotherapy platforms. This phenomenon may also be generally referred to as "epitope spreading" and represents an advantage of using yeast-based HBV immunotherapy, because induction of an immune response against a particular HBV antigen or even against a particular HBV genotype (e.g., by providing that antigen in the context of the yeast immunotherapeutic), is expected to result in the cascading targeting of the immune system against a variety of additional HBV antigens, which may result in effective immune responses against antigens from different HBV genotypes or strains than those represented in the yeast-based immunotherapeutic composition.

As discussed above, patients who become chronically infected with HBV tend to have weaker (or absent) and more narrow HBV-specific, T cell-mediated immunity. Accordingly, the yeast-based HBV immunotherapy compositions of the invention address the need for therapeutic compositions to treat patients who are actively infected with HBV, including chronically infected patients, and further provide an additional vaccine for the prevention of HBV infection that may have advantages with respect to the production of durable memory immune responses. Indeed, the yeast-based HBV immunotherapy compositions of the invention are expected to promote durable memory T cell responses against HBV, which can prevent infection, as well as provide long term benefits that can protect a chronically infected patient from viral reactivation. Yeast-based HBV immunotherapy compositions as monotherapy or in combination with other therapeutic approaches for the treatment of HBV (e.g., in combination with anti-viral compounds) are expected to increase the percentage of chronically infected patients who achieve clearance of HBsAg and HBeAg, who achieve complete seroconversion, and/or who achieve sustained viral clearance for at least 6 months after the completion of therapy.

Accordingly, yeast-based HBV immunotherapy can be combined with anti-viral drugs and/or interferon therapy, and/or with other therapies for HBV, in order to reduce the viral load in an individual to a level that can be more effectively handled by the immune system. HBV viral titers are typically very high (as many as $10^{11}$ hepatocytes may be infected) and thus may overwhelm an individual's ability to mount an effective CTL response; accordingly, reduction of viral load using anti-viral drugs in combination with induction of HBV-specific CTL activity using yeast-based immunotherapy is expected to be beneficial to the infected individual. In addition, reduction of viral load through the use of anti-viral drugs may also reduce negative effects, if any, of immune activation in the context of a high number of infected hepatocytes being targeted for destruction. Yeast-based HBV immunotherapy is also expected to play a role in reducing and/or eliminating compartments of latent viral infection. For example, there are many tissues that have been shown to be HBV-positive by PCR, and that are considered potential sanctuaries for re-activation of HBV. HBV DNA can integrate into the host genome, which provides for a quiescent persistence of HBV, and cccDNA is a supercoiled, dormant form of the HBV genome that also contributes to quiescence. Without being bound by theory, the inventors believe that yeast-based HBV immunotherapy described herein will play a role in eliminating all of these types of HBV "sanctuaries" that likely contribute to the low disease-free cure rate observed with the current anti-viral approaches.

In another scenario, use of a yeast-based HBV immunotherapeutic of the invention, alone or in combination with an anti-viral or other HBV therapeutic, if sufficient to achieve complete clearance of HBsAg, but not sufficient to achieve anti-HB production, may be followed by, or further combined with, existing prophylactic subunit vaccines to achieve complete seroconversion. Alternatively, any of the fusion proteins described herein may also be used as subunit vaccines to achieve complete seroconversion, or to protect a subject from HBV infection, alone or in combination with a yeast-based HBV immunotherapeutic of the invention. Finally, the immunotherapeutic composition of the invention is well-suited for modification and/or combination with additional immunotherapeutic compositions, including any described herein, to treat escape mutations of HBV that are elicited by treatment with anti-viral drugs.

Yeast-based immunotherapeutic compositions are administered as biologics or pharmaceutically acceptable compositions. Accordingly, rather than using yeast as an antigen production system followed by purification of the antigen from the yeast, the entire yeast vehicle as described herein must be suitable for, and formulated for, administration to a patient. In contrast, existing commercial HBV vaccines as well as many in development, comprise recombinant HBV proteins (e.g., HBsAg proteins) that are produced in Saccharomyces cerevisiae, but are subsequently released from the yeast by disruption and purified from the yeast so that the final vaccine, combined with an adjuvant (e.g., aluminum hydroxyphosphate sulfate or aluminum hydroxide), contains no detectable yeast DNA and contains no more than 1-5% yeast protein. The HBV yeast-based immunotherapeutic compositions of the invention, on the other hand, contain readily detectable yeast DNA and contain substantially more than 5% yeast protein; generally, yeast-based immunotherapeutics of the invention contain more than 70%, more than 80%, or generally more than 90% yeast protein.

Yeast-based immunotherapeutic compositions are administered to a patient in order to immunize the patient for therapeutic and/or prophylactic purposes. In one embodiment of the invention, the yeast-based compositions are formulated for administration in a pharmaceutically acceptable excipient or formulation. The composition should be formulated, in one aspect, to be suitable for administration to a human subject (e.g., the manufacturing conditions should be suitable for use in humans, and any excipients or formulations used to finish the composition and/or prepare the dose of the immunotherapeutic for administration should be suitable for use in humans). In one aspect of the invention, yeast-based immunotherapeutic compositions are formulated for administration by injection of the patient or subject, such as by a parenteral route (e.g., by subcutaneous, intraperitoneal, intramuscular or intradermal injection, or another suitable parenteral route).

In one embodiment, the yeast express the antigen (e.g., detectable by a Western blot), and the antigen is not aggregated in the yeast, the antigen does not form inclusion bodies in the yeast, and/or does not form very large particles (VLPs) or other large antigen particles in the yeast. In one embodiment, the antigen is produced as a soluble protein in the yeast, and/or is not secreted from the yeast or is not substantially or primarily secreted from the yeast. In another embodiment, without being bound by theory, the present inventors believe that particular combinations and perhaps, arrangements, of antigens in an HBV fusion protein including surface antigen and core antigen, described in detail herein, may form VLPs or aggregate to some extent within the yeast expressing the antigens. As a result, the antigen expressed by the yeast has immunogenic properties which appear to be related to its overall structure and form, as a separate characteristic from the immunogenic properties of the immune epitopes (e.g., T cell epitopes) carried within the antigen. When the yeast expressing such fusion proteins are provided in a yeast-based HBV immunotherapeutic of the invention, the immunotherapeutic composition derives properties that activate the innate immune system not only from the yeast vehicle as discussed above (as with all yeast-based immunotherapeutics described herein), but also in part from the fusion protein antigen structure (e.g., the surface-core fusion protein as expressed in the yeast also has adjuvant-like properties); in addition, the immunotherapeutic composition derives properties that activate the adaptive immune system in an antigen-specific manner from the fusion protein (via provision of various T cell epitopes), as with all of the yeast-based immunotherapeutics described herein. This specific combination of properties appears to be unique to yeast-based immunotherapeutics expressing particular surface-core fusion proteins from HBV described herein. However, in all of the embodiments of the invention described herein, the yeast-based immunotherapeutics should be readily phagocytosed by dendritic cells of the immune system, and the yeast and antigens readily processed by such dendritic cells, in order to elicit an effective immune response against HBV.

Compositions of the Invention

One embodiment of the present invention relates to a yeast-based immunotherapy composition which can be used to prevent and/or treat HBV infection and/or to alleviate at least one symptom resulting from the HBV infection. The composition comprises: (a) a yeast vehicle; and (b) one or more antigens comprising HBV protein(s) and/or immunogenic domain(s) thereof. In conjunction with the yeast vehicle, the HBV proteins are most typically expressed as recombinant proteins by the yeast vehicle (e.g., by an intact yeast or yeast spheroplast, which can optionally be further processed to a yeast cytoplast, yeast ghost, or yeast membrane extract or fraction thereof), although it is an embodiment of the invention that one or more such HBV proteins are loaded into a yeast vehicle or otherwise complexed with, attached to, mixed with or administered with a yeast vehicle as described herein to form a composition of the present invention. According to the present invention, reference to a "heterologous" protein or "heterologous" antigen, including a heterologous fusion protein, in connection with a yeast vehicle of the invention, means that the protein or antigen is not a protein or antigen that is naturally expressed by the yeast, although a fusion protein that includes heterologous antigen or heterologous protein may also include yeast sequences or proteins or portions thereof that are also naturally expressed by yeast (e.g., an alpha factor prepro sequence as described herein).

One embodiment of the invention relates to various HBV fusion proteins. In one aspect, such HBV fusion proteins are useful in a yeast-based immunotherapeutic composition of the invention. Such fusion proteins, and/or the recombinant nucleic acid molecules encoding such proteins, can also be used in, in combination with, or to produce, a non-yeast-based immunotherapeutic composition, which may include, without limitation, a DNA vaccine, a protein subunit vaccine, a recombinant viral-based immunotherapeutic composition, a killed or inactivated pathogen vaccine, and/or a dendritic cell vaccine. In another embodiment, such fusion proteins can be used in a diagnostic assay for HBV and/or to generate antibodies against HBV. Described herein are exemplary HBV fusion proteins providing selected portions of HBV antigens, including, for example, selected portions of and/or modified polymerase; selected portions of and/or modified surface antigen; selected portions of and/or modified core (including at least portions of or most of e-antigen); selected portions of and/or modified X antigen; as well as selected portions of and/or arrangements of any one, two, three or all four of the antigens (surface antigen, core, X and polymerase), such as, but not limited to, selected portions and/or arrangements of surface antigen and core (including at least portions of or most of e-antigen); selected portions and/or arrangements of surface antigen, core (including at least portions of or most of e-antigen), polymerase and X antigen; selected portions and/or arrangements of surface antigen, core (including at least portions of or most of e-antigen), and polymerase; and selected portions and/or arrangements of surface antigen, core (including at least portions of or most of e-antigen), and X antigen.

In one embodiment, HBV antigens, including immunogenic domains of full-length proteins, as described herein, are fused to host proteins that are overexpressed in HBV infected, but not in non-infected, host cells. In one embodiment, HBV antigens, including immunogenic domains of full-length proteins, as described herein, are fused to protein R2, a host factor required for HBV replication, which in one embodiment, is expressed in hepatocytes. R2 is a protein component of ribonucleotide reductase (RNR), and is critical for the HBV life-cycle (see, e.g., Cohen et al., 2010, *Hepatol.* 51(5): 1538-1546). Other embodiments of the invention will be apparent in view of the disclosure provided herein.

Hepatitis B Virus, Genes, and Proteins.

Hepatitis B virus (HBV) is a member of the Hepadnaviridae (hepadnavirus) family of viruses and causes transient and chronic infections of the liver in humans and the great apes. The hepadnaviruses that infect mammals have similar DNA sequences and genome organization, and are grouped in the genus *Orthohepadnavirus*. The hepatitis B virus particle has an outer envelope containing lipid and surface antigen particles known as HBsAg. A nucleocapsid core containing core protein (HBcAg) surrounds the viral DNA and a DNA polymerase with reverse transcriptase activity. As reviewed in Seeger and Mason, 2000, *Microbiol. Mol. Biol. Rev.* 64(1): 51-68, HBV has a 3.2 kb partially double-stranded relaxed-circular DNA (rcDNA) genome that is converted into a covalently closed circular double-stranded DNA (cccDNA) molecule upon delivery of the viral genome to the nucleus of an infected hepatocyte. The host cell RNA polymerase II transcribes four viral RNAs from the cccDNA template which are transported to the host cell cytoplasm. The viral RNAs include mRNAs that are transcribed to produce the viral core and envelope structural proteins and the precore, polymerase and X nonstructural viral proteins. The RNA that is translated to produce core and polymerase also serves as the pregenomic RNA (pgRNA) which is the template for reverse transcription. pgRNA and the polymerase are encapsulated by the core protein, producing the viral nucleocapsid where the pgRNA is reverse transcribed into rcDNA. These rcDNA-containing nucleocapsids are then enclosed by envelope proteins and secreted from the host cell as mature virions or shuttled to the nucleus to amplify the viral cccDNA.

The structural and non-structural proteins produced by the HBV genome are shown in Table 1. The partially double-stranded HBV genome contains four genes known as C, X, P, and S (see also FIG. 1).

TABLE 1

HBV genes and gene products

| Gene | Protein | Function(s) |
|---|---|---|
| C | core protein (HBcAg) | Forms viral capsid surrounding viral pgRNA and polymerase |
|  | e antigen (HBeAg) | Function unknown; may be HBV-specific immune suppressive factor for adaptive immune response |
| P | polymerase | Polymerase for viral DNA replication<br>Domain 1: terminal protein (TP) domain packages pgRNA and primes minus strand DNA<br>Domain 2: reverse transcriptase (RT) domain, RNase H; degrades pgRNA |
| S | S HBsAg (surface antigen; small) | Envelope protein and forms surface antigen particles; may suppress immune function |
|  | M HBsAg (surface antigen; middle = Pre-S2 + S) | Envelope protein and forms surface antigen particles together with S; may suppress immune function |
|  | L HBsAg (surface antigen; large = Pre-S1 + pre-S2 + S) | Envelope protein and forms surface antigen particles together with S; pre-S1 domain provides ligand for core particles during assembly of viral envelope; hepatocyte receptor; may suppress immune function |
| X | X antigen (HBx) | Transcriptional transactivation; regulation of DNA repair pathways; elevation of cytosolic calcium levels; modulation of protein degradation pathways; modulation of cell cycle progression and cell proliferation pathways in host cell; stimulation of HBV replication |

Gene C encodes two closely related antigens: a 21-kDa protein called "core protein" or "core antigen" (HBcAg) which forms the viral capsid, and a 17-kDa protein called e-antigen (HBeAg) that forms dimers but that does not assemble into capsid. Full-length core protein is an approximately 183 amino acid protein, comprising all but the N-terminal 10 amino acids of e-antigen and comprising approximately 34 additional amino acids at the C-terminus that are proteolytically cleaved in the production of e-antigen. In other words, core protein and e-antigen have 149 amino acid residues in common (this section sometimes being referred to as the hepatitis core antigen), but differ at the N-terminal and C-terminal regions. Precore protein is a precursor protein comprising an amino acid sequence that includes sequence from both core and e-antigen, from which e-antigen is produced via proteolytic processing. Intracellular HBeAg includes precore residues −29 to −1 (the residue numbering in this particular description is provided with the first amino acid residue of core protein within the precore protein being denoted as position "1"), which contains a signal sequence that directs the protein to the endoplasmic reticulum at which point amino acids −29 to −11 are cleaved; another proteolytic cleavage between amino acids 149 and 150 removes the C-terminal portion of precore (which is present in full-length core protein), and the remaining HBeAg (consisting of amino acids −10 to −1 of precore plus amino acids 1-149 of HBcAg or core) is then secreted as e-antigen (Standing et al., 1988, PNAS USA 85: 8405-8409; Ou et al., 1986, PNAS USA 83:1578-1582; Bruss and Gerlich, 1988, Virology 163:268-275; Takahashi et al., 1983, J. Immunol. 130:2903-2907). HBeAg consisting of the entire precore region has also been found in human sera (Takahashi et al., 1992, J. Immunol. 147:3156-3160). As mentioned, HBcAg (core) forms dimers that assemble into the viral capsid and contain the polymerase and viral DNA or pgRNA. The function of HBeAg (e-antigen) is unknown, but it is not required for HBV replication or infection, and it is thought to be an immune suppressive factor that protects HBV against attack by the immune system (Milich et al., 1990, PNAS USA 87:6599-6603; Che et al., 2004, PNAS USA 101:14913-14918; Wieland and Chisari, 2005, J. Virol. 79:9369-9380). For clarity, in the HBV sequences described herein (e.g., see Table 3), the sequence for precore from representative HBV genotypes is provided, and the positions of core protein and e-antigen are denoted within the precore sequence, with the first amino acid of precore designated as position 1.

Gene P encodes the HBV DNA polymerase (Pol), which consists of two major domains linked by a spacer. The N-terminal domain of the polymerase (also referred to as "terminal protein" or TP) is involved in the packaging of pgRNA and in the priming of non-sense strand DNA. The C-terminal domain is a reverse transcriptase (RT) that has RNase H (RH) activity.

Gene S has multiple start codons and encodes three envelope proteins (also referred to herein generally as "surface protein" or "surface antigen") denoted S, M and L, which are all components of the infectious viral particles, also known as Dane particles. S, by itself, and together with M and L, also form surface antigen particles (HBsAg) which can be secreted from infected cells in large quantities (Seeger and Mason, 2000, Microbiol. Mol. Biol. Rev. 64(1):51-68; Beck, (2007), "Hepatitis B virus replication", World Journal of Gastroenterology: WJG 13(1):48-64). The codons for M and L are located approximately 165 (M) and 489 (L) nucleotides, respectively, upstream of the initiation codon for S. S or "small" surface antigen is the smallest and most abundant of the surface antigens. Antibodies produced against this antigen represent seroconversion in infected individuals. M or "middle" surface antigen has an extra protein domain, as compared to S, known as pre-S2, and the protein domain that is unique to L or "large" surface antigen is known as pre-S1 (L therefore also contains pre-S2 and the additional sequence belonging to M and S). Pre-S1 contains the viral hepatocyte receptor domain (hepatocyte receptor binding site), which is located approximately between amino acid positions 21 and 47 of Pre-S1. Epitopes in pre-S1 can elicit virus-neutralizing antibodies. In addition, the pre-S1 domain provides the ligand for core particles during the assembly of the viral envelope. Surface antigen particles (HBsAg) may also suppress immune elimination of infected cells by functioning as a high-dose toleragen (Reignat et al., 2002, J. Exp. Med. 195: 1089-1101; Webster et al., 2004, J. Virol. 78:5707-5719).

Gene X encodes X antigen (HBx) (which may also be referred to as "X protein") which is involved in transcriptional transactivation, regulation of DNA repair pathways, elevation of cytosolic calcium levels, modulation of protein degradation pathways, and modulation of cell cycle progression and cell proliferation pathways in the host cell (Gearhart et al., 2010, J. Virol.), which enhances stimulation of HBV replication. HBx is also associated with the development of liver cancer (Kim et al., Nature 1991, 351:317-320; Terradillos et al., Oncogene 1997, 14:395-404).

HBV is found as one of four major serotypes (adr, adw, ayr, ayw) that are determined based on antigenic epitopes within its envelope proteins. There are eight different HBV genotypes (A-H) based on the nucleotide sequence variations in the genome. The geographical distribution of the genotypes is shown in Table 2 (Kramvis et al., 2005, Vaccine 23(19):2409-2423; Magnius and Norder, 1995, Intervirology 38(1-2):24-34; Sakamoto et al., 2006, J. Gen. Virol. 87:1873-1882; Lim et al., 2006, Int. J. Med. Sci. 3:14-20).

TABLE 2

| HBV genotype | Prevalent Geographical Distribution |
| --- | --- |
| HBV/A | Americas, Europe, Africa, Southeast Asia |
| HBV/B | Asia (China, Japan, Southeast Asia), United States |
| HBV/C | Asia (China, Japan, Southeast Asia), United States |
| HBV/D | United States, Mediterranean, Middle East and India |
| HBV/E | Sub-Saharan and West Africa |
| HBV/F | Central and South America |
| HBV/G | France, Germany, United States |
| HBV/H | Central America, United States (California) |

The nucleic acid and amino acid sequence for HBV genes and the proteins encoded thereby are known in the art for each of the known genotypes. Table 3 provides reference to sequence identifiers for exemplary (representative) amino acid sequences of all of the HBV structural and non-structural proteins in each of the eight known genotypes of HBV, and further indicates the position of certain structural domains. It is noted that small variations may occur in the amino acid sequence between different viral isolates of the same protein or domain from the same HBV genotype. However, as discussed above, strains and serotypes of HBV and genotypes of HBV display high amino acid identity even between serotypes and genotypes (e.g., see Table 4). Therefore, using the guidance provided herein and the reference to the exemplary HBV sequences, one of skill in the art will readily be able to produce a variety of HBV-based proteins, including fusion proteins, from any HBV strain (isolate), serotype, or genotype, for use in the compositions and methods of the present invention, and as such, the invention is not limited to the specific sequences disclosed herein. Reference to an HBV protein or HBV antigen anywhere in this disclosure, or to any functional, structural, or immunogenic domain thereof, can accordingly be made by reference to a particular sequence from one or more of the sequences presented in this disclosure, or by reference to the same, similar or corresponding sequence from a different HBV isolate (strain).

TABLE 3

| Organism, Genotype, Gene | Protein | Sequence Identifier (Database Accession No.) |
|---|---|---|
| HBV, Genotype A, C | Precore | SEQ ID NO: 1 (Accession No. AAX83988.1) |
| | Core (HBcAg) | *Positions 30/31-212 of SEQ ID NO: 1 |
| | e-antigen (HBeAg) | *Positions 20-178 of SEQ ID NO: 1 |
| HBV, Genotype A, P | Polymerase | SEQ ID NO: 2 (Accession No. BAI81985) |
| | reverse transcriptase | *Positions 383-602 of SEQ ID NO: 2 |
| HBV, Genotype A, S | Surface HBsAg (L) | SEQ ID NO: 3 (Accession No. BAD91280.1) |
| | Surface HBsAg (M) | *Positions 120-400 of SEQ ID NO: 3 |
| | Surface HBsAg (S) | *Positions 175-400 of SEQ ID NO: 3 |
| HBV, Genotype A, X | X (HBx) | SEQ ID NO: 4 (Accession No. AAK97189.1) |
| HBV, Genotype B, C | Precore | SEQ ID NO: 5 (Accession No. BAD90067) |
| | Core (HBcAg) | *Positions 30/31-212 of SEQ ID NO: 5 |
| | e-antigen (HBeAg) | *Positions 20-178 of SEQ ID NO: 5 |
| HBV, Genotype B, P | Polymerase | SEQ ID NO: 6 (Accession No. BAD90068.1) |
| | reverse transcriptase | *Positions 381-600 of SEQ ID NO: 6 |
| HBV, Genotype B, S | Surface HBsAg (L) | SEQ ID NO: 7 (Accession No. BAJ06634.1) |
| | Surface HBsAg (M) | *Positions 120-400 of SEQ ID NO: 7 |
| | Surface HBsAg (S) | *Positions 175-400 of SEQ ID NO: 7 |
| HBV, Genotype B, X | X (HBx) | SEQ ID NO: 8 (Accession No. BAD90066.1) |
| HBV, Genotype C, C | Precore | SEQ ID NO: 9 (Accession No. YP_355335) |
| | Core (HBcAg) | *Positions 30/31-212 of SEQ ID NO: 9 |
| | e-antigen (HBeAg) | *Positions 20-178 of SEQ ID NO: 9 |
| HBV, Genotype C, P | Polymerase | SEQ ID NO: 10 (Accession No. ACH57822) |
| | reverse transcriptase | *Positions 381-600 of SEQ ID NO: 10 |
| HBV, Genotype C, S | Surface HBsAg (L) | SEQ ID NO: 11 (Accession No. BAJ06646.1) |
| | Surface HBsAg (M) | *Positions 120-400 of SEQ ID NO: 11 |
| | Surface HBsAg (S) | *Positions 175-400 of SEQ ID NO: 11 |
| HBV, Genotype C, X | X (HBx) | SEQ ID NO: 12 (Accession No. BAJ06639.1) |
| HBV, Genotype D, C | Precore | SEQ ID NO: 13 (Accession No. ADF29260.1) |
| | Core (HBcAg) | *Positions 30/31-212 of SEQ ID NO: 13 |
| | e-antigen (HBeAg) | *Positions 20-178 of SEQ ID NO: 13 |
| HBV, Genotype D, P | Polymerase | SEQ ID NO: 14 (Accession No. ADD12642.1) |
| | reverse transcriptase | *Positions 370-589 of SEQ ID NO: 14 |
| HBV, Genotype D, S | Surface HBsAg (L) | SEQ ID NO: 15 (Accession No. ACP20363.1) |
| | Surface HBsAg (M) | *Positions 109-389 of SEQ ID NO: 15 |
| | Surface HBsAg (S) | *Positions 164-389 of SEQ ID NO: 15 |
| HBV, Genotype D, X | X (HBx) | SEQ ID NO: 16 (Accession No. BAF47226.1) |
| HBV, Genotype E, C | Precore | SEQ ID NO: 17 (Accession No. ACU25047.1) |
| | Core (HBcAg) | *Positions 30/31-212 of SEQ ID NO: 17 |
| | e-antigen (HBeAg) | *Positions 20-178 of SEQ ID NO: 17 |
| HBV, Genotype E, P | Polymerase | SEQ ID NO: 18 (Accession No. ACO89764.1) |
| | reverse transcriptase | *Positions 380-599 of SEQ ID NO: 18 |
| HBV, Genotype E, S | Surface HBsAg (L) | SEQ ID NO: 19 (Accession No. BAD91274.1) |
| | Surface HBsAg (M) | *Positions 119-399 of SEQ ID NO: 19 |
| | Surface HBsAg (S) | *Positions 174-399 of SEQ ID NO: 19 |
| HBV, Genotype E, X | X (HBx) | SEQ ID NO: 20 (Accession No. ACU24870.1) |
| HBV, Genotype F, C | Precore | SEQ ID NO: 21 (Accession No. BAB17946.1) |
| | Core (HBcAg) | *Positions 30/31-212 of SEQ ID NO: 21 |
| | e-antigen (HBeAg) | *Positions 20-178 of SEQ ID NO: 21 |

TABLE 3-continued

| Organism, Genotype, Gene | Protein | Sequence Identifier (Database Accession No.) |
|---|---|---|
| HBV, Genotype F, P | Polymerase | SEQ ID NO: 22 (Accession No. ACD03788.2) |
| | reverse transcriptase | *Positions 381-600 of SEQ ID NO: 22 |
| HBV, Genotype F, S | Surface HBsAg (L) | SEQ ID NO: 23 (Accession No. BAD98933.1) |
| | Surface HBsAg (M) | *Positions 120-400 of SEQ ID NO: 23 |
| | Surface HBsAg (S) | *Positions 175-400 of SEQ ID NO: 23 |
| HBV, Genotype F, X | X (HBx) | SEQ ID NO: 24 (Accession No. AAM09054.1) |
| HBV, Genotype G, C | Precore | SEQ ID NO: 25 (Accession No. ADD62622.1) |
| | Core (HBcAg) | *Positions 14-194 of SEQ ID NO: 25 |
| | e-antigen (HBeAg) | *Positions 4-161 of SEQ ID NO: 25 |
| HBV, Genotype G, P | Polymerase | SEQ ID NO: 26 (Accession No. ADD62619.1) |
| | reverse transcriptase | *Positions 380-599 of SEQ ID NO: 26 |
| HBV, Genotype G, S | Surface (HBsAg) (L) | SEQ ID NO: 27 (Accession No. ADD62620.1) |
| | Surface HBsAg (M) | *Positions 119-399 of SEQ ID NO: 27 |
| | Surface HBsAg (S) | *Positions 174-399 of SEQ ID NO: 27 |
| HBV, Genotype G, X | X (HBx) | SEQ ID NO: 28 (Accession No. BAB82400.1) |
| HBV, Genotype H, C | Precore | SEQ ID NO: 29 (Accession No. BAD91265.1) |
| | Core (HBcAg) | *Positions 30/31-212 of SEQ ID NO: 29 |
| | e-antigen (HBeAg) | *Positions 20-178 of SEQ ID NO: 29 |
| HBV, Genotype H, P | Polymerase | SEQ ID NO: 30 (Accession No. BAF49208.1) |
| | reverse transcriptase | *Positions 381-600 of SEQ ID NO: 30 |
| HBV, Genotype H, S | Surface HBsAg (L) | SEQ ID NO: 31 (Accession No. BAE20065.1) |
| | Surface HBsAg (M) | *Positions 120-400 of SEQ ID NO: 31 |
| | Surface HBsAg (S) | *Positions 175-400 of SEQ ID NO: 31 |
| HBV, Genotype H, X | X (HBx) | SEQ ID NO: 32 (Accession No. BAF49206.1) |

*Position numbering is approximate and may include additional amino acids flanking either side of the indicated position Hepatitis B Virus Antigens and Constructs. One embodiment of the invention relates to novel HBV antigens and fusion proteins and recombinant nucleic acid molecules encoding these antigens and proteins. Described herein are several different novel HBV antigens for use in a yeast-based immunotherapeutic composition or other composition (e.g., other immunotherapeutic or diagnostic composition) that provide one or multiple (two, three, four, five, six, seven, eight, nine or more) antigens and/or immunogenic domains from one or more proteins, all contained within the same fusion protein and encoded by the same recombinant nucleic acid construct (recombinant nucleic acid molecule). The antigens used in the compositions of the invention include at least one HBV protein or immunogenic domain thereof for immunizing an animal (prophylactically or therapeutically). The composition can include one, two, three, four, a few, several or a plurality of HBV antigens, including one, two, three, four, five, six, seven, eight, nine, ten, or more immunogenic domains of one, two, three, four or more HBV proteins. In some embodiments, the antigen is a fusion protein. In one aspect of the invention, fusion protein can include two or more proteins. In one aspect, the fusion protein can include two or more immunogenic domains and/or two or more epitopes of one or more proteins. An immunotherapeutic composition containing such antigens may provide antigen-specific immunization in a broad range of patients. For example, an antigen or fusion protein encompassed by the invention can include at least a portion of, or the full-length of, any one or more HBV proteins selected from: HBV surface protein (also called surface antigen or envelope protein or HBsAg), including the large (L), middle (M) and/or small (S) forms of surface protein and/or the pre-S1 and/or pre-S2 domains thereof; HBV precore protein; HBV core protein (also called core antigen or HBcAg); HBV e-antigen (also called HBeAg); HBV polymerase (including one or both domains of the polymerase, called the RT domain and the TP domain); HBV X antigen (also called X, X antigen, or HBx); and/or any one or more immunogenic domains of any one or more of these HBV proteins. In one embodiment, an antigen useful in an immunotherapeutic composition of the invention is from a single HBV protein (full-length, near full-length, or portion thereof comprising at least, one, two, three, four or more immunogenic domains of a full-length protein). In one embodiment of the invention, an immunotherapeutic composition includes one, two, three, four, five or more individual yeast vehicles, each expressing or containing a different HBV antigen(s).

Combinations of HBV antigens useful in the present invention include, but are not limited to (in any order within the fusion protein):

(1) surface protein (L, M and/or S and/or any one or combination of functional and/or immunological domains thereof, including, but not limited to pre-S1 and/or pre-S2 and/or the hepatocyte receptor domain of pre-S1) in combination with any one or more of: (a) precore/core/e (precore, core, e-antigen, and/or any one or combination of functional and/or immunological domains thereof); (b) polymerase (full-length, RT domain, TP domain and/ or any one or combination of functional and/or immunological domains thereof); and/or (c) X antigen (or any one or combination of functional and/or immunological domains thereof);

(2) precore/core/e (precore, core, e-antigen, and/or any one or combination of functional and/or immunological domains thereof) in combination with any one or more of: (a) surface protein (L, M and/or S and/or any one or combination of functional and/or immunological domains thereof, including, but not limited to pre-S1 and/or pre-S2 and/or the hepatocyte receptor domain of pre-S1); (b) polymerase (full-length, RT domain, TP domain and/or any one or combination of functional and/or immunological domains thereof); and/or (c) X antigen (or any one or combination of functional and/or immunological domains thereof);

(3) polymerase (full-length, RT domain, TP domain and/or any one or combination of functional and/or immunological domains thereof) in combination with any one or more of: (a) surface protein (L, M and/or S and/or any one or combination of functional and/or immunological domains thereof, including, but not limited to pre-S1 and/or pre-S2 and/or the hepatocyte receptor domain of pre-S1); (b) precore/core/e (precore, core, e-antigen, and/or any one or combination of functional and/or immunological domains thereof); and/or (c) X antigen (or any one or combination of functional and/or immunological domains thereof); or (4) X antigen (or any one or combination of functional and/or immunological domains thereof) in combination with any one or more of: (a) surface protein (L, M and/or S and/or any one or combination of functional and/or immunological domains thereof, including, but not limited to pre-S1 and/or pre-S2 and/or the hepatocyte receptor domain of pre-S1); (b) polymerase (full-length, RT domain, TP domain and/or any one or combination of functional and/or immunological domains thereof); and/or (c) precore/core/e (precore, core, e-antigen, and/or any one or combination of functional and/or immunological domains thereof).

Recombinant nucleic acid molecules and the proteins encoded thereby, including fusion proteins, as one embodiment of the invention, may be used in yeast-based immunotherapy compositions, or for any other suitable purpose for HBV antigen(s), including in an in vitro assay, for the production of antibodies, or in another immunotherapy composition, including another vaccine, that is not based on the yeast-based immunotherapy described herein. Expression of the proteins by yeast is one preferred embodiment, although other expression systems may be used to produce the proteins for applications other than a yeast-based immunotherapy composition.

According to the present invention, the general use herein of the term "antigen" refers: to any portion of a protein (peptide, partial protein, full-length protein), wherein the protein is naturally occurring or synthetically derived, to a cellular composition (whole cell, cell lysate or disrupted cells), to an organism (whole organism, lysate or disrupted cells) or to a carbohydrate, or other molecule, or a portion thereof. An antigen may elicit an antigen-specific immune response (e.g., a humoral and/or a cell-mediated immune response) against the same or similar antigens that are encountered by an element of the immune system (e.g., T cells, antibodies).

An antigen can be as small as a single epitope, a single immunogenic domain or larger, and can include multiple epitopes or immunogenic domains. As such, the size of an antigen can be as small as about 8-12 amino acids (i.e., a peptide) and as large as: a full length protein, a multimer, a fusion protein, a chimeric protein, a whole cell, a whole microorganism, or any portions thereof (e.g., lysates of whole cells or extracts of microorganisms). In addition, antigens can include carbohydrates, which can be loaded into a yeast vehicle or into a composition of the invention. It will be appreciated that in some embodiments (e.g., when the antigen is expressed by the yeast vehicle from a recombinant nucleic acid molecule), the antigen is a protein, fusion protein, chimeric protein, or fragment thereof, rather than an entire cell or microorganism.

When the antigen is to be expressed in yeast, an antigen is of a minimum size capable of being expressed recombinantly in yeast, and is typically at least or greater than 25 amino acids in length, or at least or greater than 26, at least or greater than 27, at least or greater than 28, at least or greater than 29, at least or greater than 30, at least or greater than 31, at least or greater than 32, at least or greater than 33, at least or greater than 34, at least or greater than 35, at least or greater than 36, at least or greater than 37, at least or greater than 38, at least or greater than 39, at least or greater than 40, at least or greater than 41, at least or greater than 42, at least or greater than 43, at least or greater than 44, at least or greater than 45, at least or greater than 46, at least or greater than 47, at least or greater than 48, at least or greater than 49, or at least or greater than 50 amino acids in length, or is at least 25-50 amino acids in length, at least 30-50 amino acids in length, or at least 35-50 amino acids in length, or at least 40-50 amino acids in length, or at least 45-50 amino acids in length. Smaller proteins may be expressed, and considerably larger proteins (e.g., hundreds of amino acids in length or even a few thousand amino acids in length) may be expressed. In one aspect, a full-length protein, or a structural or functional domain thereof, or an immunogenic domain thereof, that is lacking one or more amino acids from the N- and/or the C-terminus may be expressed (e.g., lacking between about 1 and about 20 amino acids from the N- and/or the C-terminus). Fusion proteins and chimeric proteins are also antigens that may be expressed in the invention. A "target antigen" is an antigen that is specifically targeted by an immunotherapeutic composition of the invention (i.e., an antigen against which elicitation of an immune response is desired). An "HBV antigen" is an antigen derived, designed, or produced from one or more HBV proteins such that targeting the antigen also targets the hepatitis B virus.

When referring to stimulation of an immune response, the term "immunogen" is a subset of the term "antigen", and therefore, in some instances, can be used interchangeably with the term "antigen". An immunogen, as used herein, describes an antigen which elicits a humoral and/or cell-mediated immune response (i.e., is immunogenic), such that administration of the immunogen to an individual mounts an antigen-specific immune response against the same or similar antigens that are encountered by the immune system of the individual. In one embodiment, an immunogen elicits a cell-mediated immune response, including a $CD4^+$ T cell response (e.g., TH1, TH2 and/or TH17) and/or a $CD8^+$ T cell response (e.g., a CTL response).

An "immunogenic domain" of a given antigen can be any portion, fragment or epitope of an antigen (e.g., a peptide fragment or subunit or an antibody epitope or other conformational epitope) that contains at least one epitope that acts as an immunogen when administered to an animal. Therefore, an immunogenic domain is larger than a single amino acid and is at least of a size sufficient to contain at least one epitope that can act as an immunogen. For example, a single protein can contain multiple different immunogenic domains. Immunogenic domains need not be linear sequences within a protein, such as in the case of a humoral immune response, where conformational domains are contemplated.

A "functional domain" of a given protein is a portion or functional unit of the protein that includes sequence or structure that is directly or indirectly responsible for at least one biological or chemical function associated with, ascribed to, or performed by the protein. For example, a functional domain can include an active site for enzymatic activity, a ligand binding site, a receptor binding site, a binding site for a molecule or moiety such as calcium, a phosphorylation site, or a transactivation domain. Examples of HBV functional domains include, but are not limited to, the viral hepatocyte receptor domain in pre-S1, or the reverse transcriptase domain or RNase H domain of polymerase.

A "structural domain" of a given protein is a portion of the protein or an element in the protein's overall structure that has an identifiable structure (e.g., it may be a primary or tertiary structure belonging to and indicative of several proteins within a class or family of proteins), is self-stabilizing and/or may fold independently of the rest of the protein. A structural domain is frequently associated with or features prominently in the biological function of the protein to which it belongs.

An epitope is defined herein as a single immunogenic site within a given antigen that is sufficient to elicit an immune response when provided to the immune system in the context of appropriate costimulatory signals and/or activated cells of the immune system. In other words, an epitope is the part of an antigen that is actually recognized by components of the immune system, and may also be referred to as an antigenic determinant. Those of skill in the art will recognize that T cell epitopes are different in size and composition from B cell or antibody epitopes, and that epitopes presented through the Class I MHC pathway differ in size and structural attributes from epitopes presented through the Class II MHC pathway. For example, T cell epitopes presented by Class I MHC molecules are typically between 8 and 11 amino acids in length, whereas epitopes presented by Class II MHC molecules are less restricted in length and may be from 8 amino acids up to 25 amino acids or longer. In addition, T cell epitopes have predicted structural characteristics depending on the specific MHC molecules bound by the epitope. Multiple different T cell epitopes have been identified in various HBV strains and for many human HLA types, several of which are identified in Table 5. In addition, epitopes for certain murine MHC haplotypes have been newly discovered herein and are also presented in Table 5 or in the Examples. Epitopes can be linear sequence epitopes or conformational epitopes (conserved binding regions). Most antibodies recognize conformational epitopes.

One exemplary embodiment of the invention relates to a fusion protein comprising an HBV antigen that is a multiprotein HBV antigen, and in this example, a fusion comprised of HBV large (L) surface antigen, including all of the hydrophobic transmembrane domains, and core antigen (HBcAg), described in detail below. Surface antigen and core are abundantly expressed in infected cells, are required for viral replication, and contain multiple $CD4^+$ and $CD8^+$ T cell epitopes. In addition, these antigens, particularly surface antigen, contain known mutation sites that can be induced by anti-viral therapy; these regions can therefore be modified, as needed, to provide additional immunotherapy compositions to target the "escape" mutations. An additional advantage of targeting these proteins, and particularly both proteins in a single immunotherapeutic composition, is the high degree of conservation at the amino acid level among different HBV genotypes. Both the core and surface (L) proteins are highly conserved between HBV genotypes A and C or between A and H, for example (see Table 4), which are genotypes prevalent in the Americas and Asia (Table 2). The core protein displays a 95% amino acid identity between genotypes A and C and between genotypes A and H. The large (L) surface protein is also highly conserved among the different HBV genotypes; a 90% amino acid identity exists between genotypes A and C, and 82% amino acid identity exists between genotypes A and H.

TABLE 4

| Comparison | Core | Surface (L) | X | Polymerase |
|---|---|---|---|---|
| HBV Genotype A vs. HBV Genotype C | 95 | 90 | 89 | 90 |
| HBV Genotype A vs. HBV Genotype H | 95 | 82 | 79 | 82 |

Therefore, one immunotherapeutic composition designed using one HBV genotype can be expected to induce an effective immune response against a highly similar HBV genotype, either through direct targeting of conserved epitopes or through epitope spreading as a result of initially targeting epitopes that are conserved between genotypes. Alternatively, because of the ease of producing the yeast-based immunotherapy compositions of the invention, it is straightforward to modify a sequence to encode a protein, domain, or epitope from a different genotype, or to include in the same construct different T cell epitopes or entire domains and/or proteins from two or more different HBV genotypes, in order to increase the wide applicability of the immunotherapy. Examples of such HBV antigens are described in detail and exemplified below. While one immunotherapeutic composition of the present invention was designed to target two HBV antigens, surface and core protein, in a single product, this approach can readily be expanded to incorporate the protein sequences of other essential, conserved, and immunogenic HBV viral proteins to result in even broader cellular immune responses. Such additional fusion proteins and immunotherapeutic compositions are described and exemplified herein.

In one embodiment of the invention, the HBV antigen(s) for use in a composition or method of the invention are selected from HBV antigens that have been designed to optimize or enhance their usefulness as clinical products, including in the context of a yeast-based immunotherapeutic composition. Such HBV antigens have been designed to produce an HBV yeast-based immunotherapeutic product that achieves one or more of the following goals: (1) compliance with the guidelines of the Recombinant DNA Advisory Committee (RAC) of the National Institutes of Health (NIH), wherein no more than two thirds (⅔) of the genome of an infectious agent may be used in a recombinant therapeutic or vaccine; (2) inclusion of a maximized number of known T cell epitopes associated with immune responses to acute/self-limiting HBV infections and/or chronic HBV infections (with prioritization in one aspect based on the acute/self-limiting epitope repertoire, as discussed below); (3) maximizing or prioritizing the inclusion of immunogenic domains, and more particularly T cell epitopes ($CD4^+$ and/or $CD8^+$ epitopes, and dominant and/or subdominant epitopes), that are the most conserved among HBV genotypes and/or sub-genotypes, or that can be readily modified to a consensus sequence or included in two or more forms to cover the most important sequence differences among target genotypes; and/or (4) minimizing the number of non-natural junctions within the sequence of the HBV antigen in the product.

Accordingly, the invention includes, in some embodiments, modification of HBV antigens from their naturally occurring or wild-type sequences in a given strain to meet one or more of criteria described above, as well as to include design elements and/or antigen design criteria described elsewhere herein. Such criteria and antigen design guidance is applicable to yeast-based immunotherapeutics comprising HBV antigens that are individual HBV proteins or domains, as well as HBV antigens that include combinations of HBV proteins or domains and particularly, multi-protein antigens/fusion proteins (e.g., HBV antigens from two or more different HBV proteins and/or domains thereof, such as combinations of antigens from HBV surface protein, polymerase, core, e-antigen, and/or X antigen). It will be appreciated that as the complexity of the HBV antigen increases, the utilization of more of these criteria are implemented in the construction of the antigen.

Therefore, in one embodiment of the invention, an HBV antigen useful in the present invention as a protein or fusion protein to be expressed by a yeast includes HBV sequences encoded by nucleotide sequences representing less than two thirds (⅔) of the HBV genome (i.e., the antigens are encoded by nucleic acid sequences that in total make up less than two thirds (⅔) of the HBV genome or meet the requirements of RAC for recombinant therapeutics and prophylactics). In one aspect, this embodiment can be achieved by selecting HBV antigens for expression in a yeast-based immunotherapeutic that meet the RAC requirements in their full-length or near-full-length form (e.g., X antigen is small and when used alone would meet the RAC requirements). In another aspect, this embodiment is achieved by modifying the structure of the protein(s) and/or domain(s) to be included in the HBV antigen, such as by deletion of sequence to truncate proteins or remove internal sequences from proteins, by including only selected functional, structural or immunogenic domains of a protein, or by choosing to eliminate the inclusion of a particular protein in the antigen construct altogether. In addition, HBV yeast-based immunotherapeutics may, in one embodiment, be produced as individual antigen constructs, and then used in combination in a manner that does not contravene any restrictions related to the viral genome.

In another embodiment of the invention, as discussed above, the inclusion of T cell epitopes in an HBV antigen construct (protein or fusion protein) is maximized, for example, if the HBV antigen included in the immunotherapeutic has been modified to meet another design consideration, such as the RAC requirement discussed above. In this embodiment, HBV antigens useful in a yeast-based immunotherapeutic are modified with the goal of maximizing the number of immunogenic domains, and in one aspect, the number of T cell epitopes, that are retained in the HBV antigen. In one aspect, the inclusion of T cell epitopes in an HBV antigen is prioritized as follows:

Epitopes identified in immune responses to both acute/self-limiting HBV infections and chronic HBV infections>Epitopes identified in immune responses to acute/self-limiting HBV infections>Epitopes identified in immune responses to chronic HBV infections.

In this embodiment, without being bound by theory, the inventors believe that immune responses from individuals who had acute or self-limiting HBV infections may be more productive in eliminating the viral infection than the immune responses from individuals who have chronic HBV infections. Therefore, the inclusion of T cell epitopes that appear to be associated with clearance of virus in these acute or self-limiting infections (whether dominant or sub-dominant) is prioritized as being more likely to elicit a beneficial immune response in an immunized individual. In addition, and again without being bound by theory, the inventors believe that the generation of an immune response against one or more HBV target antigens using yeast-based immunotherapy will result in an immune response in the immunized individual against not only the epitopes included in the yeast-based immunotherapeutic, but also against other HBV epitopes present in the individual. This phenomenon, referred to as "epitope spreading" allows for the design of HBV antigens that are focused on epitopes that appear to be most relevant to therapeutic benefit, and the mechanism of action of a yeast-based immunotherapeutic product then allows the immune system to expand the immune response to cover additional target epitopes, thereby enhancing a therapeutically productive or beneficial immune response against HBV.

Accordingly, an HBV antigen in one embodiment comprises one or more CTL epitopes (e.g., epitopes that are recognized by a T cell receptor of a cytotoxic T lymphocyte (CTL), when presented in the context of an appropriate Class I MHC molecule). In one aspect, the HBV antigen comprises one or more CD4$^+$ T cell epitopes (e.g., epitopes that are recognized by a T cell receptor of a CD4$^+$ T cell, in the context of an appropriate Class II MHC molecule). In one aspect, the HBV antigen comprises one or more CTL epitopes and one or more CD4$^+$ T cell epitopes. In one aspect, an HBV antigen useful in an immunotherapeutic composition of the invention comprises one or more of the exemplary HBV CTL epitopes described in Table 5. One of skill in the art will readily be able to identify the position of the corresponding sequence for each epitope in Table 5 in a given HBV sequence of any genotype, sub-genotype, or strain/isolate, given the guidance provided below, even though some amino acids may differ from those in Table 5. Examples of such differences are illustrated in Table 5. The invention is not limited to antigens comprising these epitopes as others will be known in the art and are contemplated for use in the invention. In one embodiment, the epitope can be modified to correspond to the sequence of the epitope within a given genotype, sub-genotype or strain/isolate of HBV, since there may be one or more amino acid differences at these epitopes among genotypes, sub-genotypes or stain/isolates.

TABLE 5

| Epitope | Sequence Identifier | HBV Antigen | HLA Preference |
|---|---|---|---|
| FLLTRILTI[1,2,3] | SEQ ID NO: 42 | Surface (e.g. positions 20-28 of S; e.g. corresponding to positions 194-202 of SEQ ID NO: 11, positions 201-209 of SEQ ID NO: 34, or positions 51-59 of SEQ ID NO: 36) | A*0201 |

TABLE 5-continued

| Epitope | Sequence Identifier | HBV Antigen | HLA Preference |
|---|---|---|---|
| GLSPTVWLSV[5] | SEQ ID NO: 43 | Surface (e.g. positions 185-194 of S; e.g. corresponding to positions 359-368 of SEQ ID NO: 11, positions 366-375 of SEQ ID NO: 34, or positions 216-225** of SEQ ID NO: 36) | A*0201 |
| FLPSDFFPSI[2,3,4] | SEQ ID NO: 44 | Core (e.g. positions 47-56 of Precore; e.g. corresponding to positions 47-56 of SEQ ID NO: 9, positions 424-433 of SEQ ID NO: 34, or positions 621-630 of SEQ ID NO: 36) | A*0201 |
| FLLSLGIHL[1] | SEQ ID NO: 45 | Polymerase (e.g. positions 575-583 of Pol; e.g. corresponding to positions 573-581 of SEQ ID NO: 10, or positions 486-494 of SEQ ID NO: 36) | A*0201 |
| WLSLLVPFV[1,3,5] | SEQ ID NO: 46 | Surface (e.g. positions 172-180 of S; e.g. corresponding to positions 346-354 of SEQ ID NO: 11, positions 353-361† of SEQ ID NO: 34, or positions 203-211 of SEQ ID NO: 36) | A*0201 |
| KYTSFPWLL | SEQ ID NO: 47 | Polymerase (e.g. positions 756-764 of Pol; e.g. corresponding to positions 756-764 of SEQ ID NO: 10) | A*2402 |
| YVNVNMGLK[4] | SEQ ID NO: 48 | Core (e.g. positions 117-125 of Precore; e.g. corresponding to positions 117-125 of SEQ ID NO: 9, positions 494-502 of SEQ ID NO: 34, or positions 691-699 of SEQ ID NO: 36) | A*1101 |
| EYLVSFGVW | SEQ ID NO: 49 | Core (e.g. positions 146-154 of Precore; e.g. corresponding to positions 146-154 of SEQ ID NO: 9, positions 523-531 of SEQ ID NO: 34, or positions 720-728 of SEQ ID NO: 36) | A*2402 |
| GLSRYVARL[3] | SEQ ID NO: 50 | Polymerase (e.g. positions 455-463 of Pol; e.g. corresponding to positions 453-461† of SEQ ID NO: 10, or positions 366-374 of SEQ ID NO: 36) | A*0201 |
| CLFKDWEEL[5] | SEQ ID NO: 51 | X (e.g. positions 115-123 of X; e.g. corresponding to positions 115-123§ of SEQ ID NO: 12, or positions 900-908§ of SEQ ID NO: 36) | A*02 |
| PLGFFPDH[5] | SEQ ID NO: 52 | Surface (e.g. positions 21-28 of Pre-S1; e.g. corresponding to positions 21-28 of SEQ ID NO: 11, positions 28-35 of SEQ ID NO: 34;, or positions 6-13 of SEQ ID NO: 36) | A*11 |
| IPIPSSWAF[5] | SEQ ID NO: 53 | Surface (e.g. positions 150-158 of S; e.g. corresponding to positions 324-332 of SEQ ID NO: 11, positions 331-339 of SEQ ID NO: 34, or positions 181-189 of SEQ ID NO: 36) | B*07 |
| LPSDFFPSV[5] | SEQ ID NO: 54 | Core (e.g. positions 48-56 of Precore; e.g. corresponding to positions 48-56∥ of SEQ ID NO: 9, positions 425-433∥ of | B*51 |

TABLE 5-continued

| Epitope | Sequence Identifier | HBV Antigen | HLA Preference |
|---|---|---|---|
| | | SEQ ID NO: 34, or positions 619-630[||] of SEQ ID NO: 36) | |
| MQWNSTALHQALQDP[5] | SEQ ID NO: 55 | Surface (e.g. positions 1-15 of pre-S2; e.g. ***corresponding to positions 120-134 of SEQ ID NO: 3) | A*3 |
| LLDPRVRGL[5] | SEQ ID NO: 56 | Surface (e.g. positions 12-20 of pre-S2; e.g. ***corresponding to positions 131-139 of SEQ ID NO: 3) | A*2 |
| SILSKTGDPV[5] | SEQ ID NO: 57 | Surface (e.g. positions 44-53 of a pre-S2; e.g. ***corresponding to positions 163-172 of SEQ ID NO: 3) | A*2 |
| VLQAGFFLL[5] | SEQ ID NO: 58 | Surface (e.g. positions 14-22 of S; e.g. ***corresponding to positions 188-196 of SEQ ID NO: 3) | A*2 |
| FLLTRILTI[5] | SEQ ID NO: 59 | Surface (e.g. positions 20-28 of S; e.g. ***corresponding to positions 194-202 of SEQ ID NO: 3) | A*2 |
| FLGGTPVCL[5] | SEQ ID NO: 60 | Surface (e.g. positions 41-49 of S; e.g. ***corresponding to positions 215-223 of SEQ ID NO: 3) | A*2 |
| LLCLIFLLV[5] | SEQ ID NO: 61 | Surface (e.g. positions 88-96 of S; e.g. ***corresponding to positions 262-270 of SEQ ID NO: 3) | A*2 |
| LVLLDYQGML[5] | SEQ ID NO: 62 | Surface (e.g. positions 95-104 of S; e.g. ***corresponding to positions 269-278 of SEQ ID NO: 3) | A*2 |
| LLDYQGMLPV[5] | SEQ ID NO: 63 | Surface (e.g. positions 97-106 of S; e.g. ***corresponding to positions 271-280 of SEQ ID NO: 3) | A*2 |
| SIVSPFIPLL[5] | SEQ ID NO: 64 | Surface (e.g. positions 207-216 of S; e.g. ***corresponding to positions 381-390 of SEQ ID NO: 3) | A*2 |
| ILSPFLPLL[5] | SEQ ID NO: 65 | Surface (e.g. positions 208-216 of S; e.g. ***corresponding to positions 382-390 of SEQ ID NO: 3) | A*2 |
| TPARVTGGVF[5] | SEQ ID NO: 66 | Polymerase (e.g. positions 367-376 of Pol; e.g. ***corresponding to positions 367-376 of SEQ ID NO: 2) | B*7 |
| LVVDFSQFSR[5] | SEQ ID NO: 67 | Polymerase (e.g. positions 390-399 of Pol; e.g. ***corresponding to positions 390-399 of SEQ ID NO: 2) | A*3 |
| SAICSVVRR[5] | SEQ ID NO: 68 | Polymerase (e.g. positions 533-541 of Pol; e.g. ***corresponding to positions 533-541 of SEQ ID NO: 2) | A*3 |
| YMDDVVLGA[5] | SEQ ID NO: 69 | Polymerase (e.g. positions 551-559 of Pol; e.g. ***corresponding to positions 551-559 of SEQ ID NO: 2) | A*2 |

TABLE 5-continued

| Epitope | Sequence Identifier | HBV Antigen | HLA Preference |
|---|---|---|---|
| ALMPLYACI[5] | SEQ ID NO: 70 | Polymerase (e.g. positions 655-663 of Pol; e.g. ***corresponding to positions 655-663 of SEQ ID NO: 2) | A*2 |
| QAFTFSPTYK[5] | SEQ ID NO: 71 | Polymerase (e.g. positions 667-676 of Pol; e.g. ***corresponding to positions 667-676 of SEQ ID NO: 2) | A*3 |
| ATVELLSFLP SDFFPSV[5] | SEQ ID NO: 72 | Core (e.g. positions 40-56 of Precore; e.g. ***corresponding to positions 40-56 of SEQ ID NO: 1) | A*2 |
| LPSDFFPSV[5] | SEQ ID NO: 73 | Core (e.g. positions 48-56 of Precore; e.g. ***corresponding to positions 48-56 of SEQ ID NO: 1) | B*51 |
| CLTFGRETV[5] | SEQ ID NO: 74 | Core (e.g. positions 136-144 of Precore; e.g. ***corresponding to positions 136-144 of SEQ ID NO: 1) | A*2 |
| VLEYLVSFGV[5] | SEQ ID NO: 75 | Core (e.g. positions 144-153 of Precore; e.g. ***corresponding to positions 144-153 of SEQ ID NO: 1) | A*2 |
| ILSTLPETTV[5] | SEQ ID NO: 76 | Core (e.g. positions 168-177 of Precore; e.g. ***corresponding to positions 168-177 of SEQ ID NO: 1) | A*2 |
| STLPETTVVRR[5] | SEQ ID NO: 77 | Core (e.g. positions 170-180 of Precore; e.g. ***corresponding to positions 170-180 of SEQ ID NO: 1) | A*3 |
| HLSLRGLFV[5] | SEQ ID NO: 78 | X (e.g. positions 52-60 of X; e.g. ***corresponding to positions 52-60 of SEQ ID NO: 4) | A*2 |
| VLHKRTLGL[5] | SEQ ID NO: 79 | X (e.g. positions 92-100 of X; e.g. ***corresponding to positions 92-100 of SEQ ID NO: 4) | A*2 |
| GLSAMSTTDL[5] | SEQ ID NO: 80 | X (e.g. positions 99-108 of X; e.g. ***corresponding to positions 99-108 of SEQ ID NO: 4) | A*2 |
| VLGGCRHKL[5] | SEQ ID NO: 81 | X (e.g. positions 133-141 of X; e.g. ***corresponding to positions of 133-141 SEQ ID NO: 4) | A*2 |
| NVSIWTHK[5] | SEQ ID NO: 82 | Polymerase (e.g. positions 49-57 of Pol; e.g. ***corresponding to positions 49-57 of SEQ ID NO: 2) | A*3 |
| KVGNFTGLY[5] | SEQ ID NO: 83 | Polymerase (e.g. positions 57-65 of Pol; e.g. ***corresponding to positions 57-65 of SEQ ID NO: 2) | A*3 |
| GLYSSTVPV[5] | SEQ ID NO: 84 | Polymerase (e.g. positions 63-71 of Pol; e.g. ***corresponding to positions 63-71 of SEQ ID NO: 2) | A*2 |

TABLE 5-continued

| Epitope | Sequence Identifier | HBV Antigen | HLA Preference |
|---|---|---|---|
| TLWKAGILYK[5] | SEQ ID NO: 85 | Polymerase (e.g. positions 152-161 of Pol; e.g. ***corresponding to positions of SEQ ID NO: 2) | A*3 |
| KYTSFPWLL[5] | SEQ ID NO: 86 | Polymerase (e.g. positions 756-764 of Pol; e.g. ***corresponding to positions 758-766 of SEQ ID NO: 2) | A*24 |
| ILRGTSFVYV[5] | SEQ ID NO: 87 | Polymerase (e.g. positions 773-782 of Pol; e.g. ***corresponding to positions 773-782 of SEQ ID NO: 2) | A*2 |
| SLYADSPSV[5] | SEQ ID NO: 88 | Polymerase (e.g. positions 816-824 of Pol; e.g. ***corresponding to positions 816-824 of SEQ ID NO: 2) | A*2 |
| KLHLYSHPI[6] | SEQ ID NO: 135 | Polymerase (e.g., positions 502-510 of Pol; e.g., ***corresponding to positions 502-510 of SEQ ID NO: 2) | A*2 |
| LLVPFVQWFV[6,7] | SEQ ID NO: 136 | Surface (e.g., positions 349-358 of S; e.g., ***corresponding to positions 349-358 of SEQ ID NO: 3) | A*2 |
| HLYSHPIIL[8] | SEQ ID NO: 137 | Polymerase (e.g., positions 504-512 of Pol; e.g., ***corresponding to positions 504-512 of SEQ ID NO: 2) | A*2 |
| WSPQAQGIL[9] | SEQ ID NO: 138 | Surface (e.g., positions 77-84 of S; e.g., ***corresponding to positions 77-84 of SEQ ID NO: 3) | H-2D$^b$ |
| VLLDYQGM[10] | SEQ ID NO: 139 | Surface (e.g., positions 270-277 of S; e.g., ***corresponding to positions 270-277 of SEQ ID NO: 3) | H-2K$^b$ |
| ASVRFSWL[10] | SEQ ID NO: 140 | Surface (e.g., positions 340-347 of S; e.g., ***corresponding to positions 340-347 of SEQ ID NO: 3) | H-2K$^b$ |

**Substitution of an Ala for Val at position 9 of SEQ ID NO: 43; at position 225 in SEQ ID NO: 36.
†Substitution of Gln-Ala for Leu-Val at positions 5 and 6 of SEQ ID NO: 46; at positions 357 and 358 in SEQ ID NO: 34.
‡Substitution of Pro for Ser at position 3 of SEQ ID NO: 50; at position 455 in SEQ ID NO: 10.
§Substitution of Val for Leu at position 2 of SEQ ID NO: 51; at position 116 in SEQ ID NO: 12 and position 901 in SEQ ID NO: 36.
¶Substitution of Ile for Val at position 9 of SEQ ID NO: 54; at position 56 in SEQ ID NO: 9, position 433 of SEQ ID NO: 34, and position 630 of SEQ ID NO: 36.
***One or more amino acid differences between the epitope sequence and the actual sequence of the corresponding larger protein or domain may exist due to genotype, sub-genotype or strain differences, although position of the epitope within the larger protein or domain can readily be determined.
[1]Zhang et al., *Journal of Hepatology* 50:1163-1173 (2009)
[2]Lopes et al., *J. Clin. Invest.* 118:1835-1845 (2008)
[3]Boettler et al., *J Virol* 80(7):3532-3540 (2006)
[4]Peng et al., *Mol. Immunol.* 45:963-970 (2008)
[5]Desmond 2008; www.allelefrequencies.net or Desmond et al., *Antiviral Ther.* 13:16-175 (2008)
[6]Webster et al., 2004, *J. Virol.* 78(11)5707-5719
[7]Vitiello, 1997, *Eur. J. Immunol.* 27(3): 671-678
[8]Sette et al., 1994, *J. Immunol.* 153(12): 5586-5592
[9]Murine H-2D$^b$ epitope, not previously reported
[10]Murine H-2K$^b$ epitope, not previously reported In one embodiment of the invention, useful HBV antigens can include in one or more yeast-based immunotherapeutic compositions an antigen comprising one or more T cell epitopes that has been described as or determined to be a "dominant" epitope (i.e., a T cell epitope that contributes to the development of a T cell response against the whole protein, and/or that is among the relatively small number of T cell epitopes within the large group of possible epitopes that most likely or most readily elicit CD4$^+$ and CD8$^+$ T cell responses, also referred to as an "immunodominant epitope"). In another embodiment, HBV antigens useful in the invention can include in the same or a different or additional yeast-based compositions, an HBV antigen comprising one or more T cell epitopes that has been described as or determined to be a "subdominant" epitope (i.e., a T cell epitope that is immunogenic, but to a lesser extent than an immunodominant epitope; the immune response generated by a sub-dominant epitope may be suppressed or outcompeted by the immune response to an immunodominant epitope). For an example of this effect with CTL responses to HBV T cell epitopes in mice, see Schirmbeck R., et al. *J. immunology* 168: 6253-6262, 2010; or Sette et al. *J Immunology* 166:1389-1397, 2001. In one aspect of the invention, different compositions comprising immunodominant or sub-dominant epitopes could be administered at the same site in an individual, or in one embodiment, at different sites in an individual (i.e., the composition comprising dominant epitopes being administered to one site and the composition comprising sub-dominant epitopes being administered to a different site). In some cases, a sub-dominant epitope may elicit a more therapeutically beneficial immune response than a dominant epitope. Therefore, if administered to separate sites, it may decrease the chance that an immune response to a dominant epitope would suppress or outcompete an immune response to a sub-dominant epitope, thereby maximizing the immune response as a whole and maximizing the protective or therapeutic benefit in an individual. This approach of providing different antigens in different compositions administered to different sites in the individual can also be utilized even if all epitopes are dominant or sub-dominant. Immunodominant epitopes and sub-dominant epitopes have been recognized to play a role in HBV infection and immune responses (see, e.g., Sette et al., 2001, supra. and Schirmbeck et al., 2002, supra).

In one embodiment of the invention, an HBV antigen useful in a yeast-based immunotherapeutic maximizes the inclusion of immunogenic domains, and particularly, T cell epitopes, that are conserved among genotypes and/or sub-genotypes, and/or includes immunogenic domains from several different genotypes and/or sub-genotypes and/or includes immunogenic domains that can readily be modified to produce multiple yeast-based immunotherapeutic products that differ in some minor respects, but are tailored to treat different individuals or populations of individuals based on the HBV genotype(s) or sub-genotype(s) that infect such individuals or populations of individuals. For example, the HBV antigen can be produced based on a genotype or sub-genotype that is most prevalent among individuals or populations of individuals to be protected or treated, and the HBV antigen includes the most conserved immunogenic domains from those genotypes. Alternatively or in addition, immunogenic domains can be modified to correspond to a consensus sequence for that domain or epitope, or more than one version of the epitope can be included in the construct.

In any embodiment of the invention related to the design of an HBV antigen for a yeast-based immunotherapeutic composition, in one aspect, artificial junctions between segments of a fusion protein comprising HBV antigens is minimized (i.e., the inclusion of non-natural sequences is limited or minimized to the extent possible). Without being bound by theory, it is believed that natural evolution has resulted in: i) contiguous sequences in the virus that most likely to be expressed well in another cell, such as a yeast; and ii) an immunoproteasome in antigen presenting cells that can properly digest and present those sequences to the immune system. The yeast-based immunotherapeutic product of the invention allows the host immune system to process and present target antigens; accordingly, a fusion protein with many unnatural junctions may be less useful in a yeast-based immunotherapeutic as compared to one that retains more of the natural HBV protein sequences.

In any of the HBV antigens described herein, including any of the fusion proteins, the following additional embodiments can apply. First, the N-terminal expression sequence and the C-terminal tag included in some of the fusion proteins are optional, and if used, may be selected from several different sequences described elsewhere herein to improve expression, stability, and/or allow for identification and/or purification of the protein. Alternatively, one or both of the N- or C-terminal sequences are omitted altogether. In addition, many different promoters suitable for use in yeast are known in the art and are encompassed for use to express HBV antigens according to the present invention. Furthermore, short intervening linker sequences (e.g., 1, 2, 3, 4, or 5, or larger, amino acid peptides) may be introduced between portions of the fusion protein for a variety of reasons, including the introduction of restriction enzyme sites to facilitate cloning and future manipulation of the constructs. Finally, as discussed in detail elsewhere herein, the sequences described herein are exemplary, and may be modified as described in detail elsewhere herein to substitute, add, or delete sequences in order to accommodate preferences for HBV genotype, HBV subgenotype, HBV strain or isolate, or consensus sequences and inclusion of preferred T cell epitopes, including dominant and/or sub-dominant T cell epitopes. A description of several different exemplary HBV antigens useful in the invention is provided below.

In any of the embodiments of the invention described herein, including any embodiment related to an immunotherapeutic composition, HBV antigen, fusion protein or use of such composition, HBV antigen or fusion protein, in one aspect, an amino acid of an HBV surface antigen useful as an HBV antigen or in a fusion protein or an immunotherapeutic composition of the invention can include, but is not limited to, SEQ ID NO:3, SEQ ID NO:7, SEQ ID NO:11, positions 21-47 of SEQ ID NO:11, positions 176-400 of SEQ ID NO:11, SEQ ID NO:15, SEQ ID NO:19, SEQ ID NO:23, SEQ ID NO:27, SEQ ID NO:31, positions 9-407 of SEQ ID NO:34, positions 6-257 of SEQ ID NO:36, positions 6-257 of SEQ ID NO:41, positions 92-343 of SEQ ID NO:92, positions 90-488 of SEQ ID NO:93, SEQ ID NO:97, positions 90-338 of SEQ ID NO:101, positions 7-254 of SEQ ID NO:102, positions 1-249 of SEQ ID NO:107, positions 1-249 of SEQ ID NO:108, positions 1-249 of SEQ ID NO:109, positions 1-249 of SEQ ID NO:110, positions 1-399 of SEQ ID NO:112, positions 1-399 of SEQ ID NO:114, or positions 1-399 of SEQ ID NO:116, positions 1-399 of SEQ ID NO:118, positions 1-399 of SEQ ID NO:120, positions 1-399 of SEQ ID NO:122, positions 1-399 of SEQ ID NO:124, positions 1-399 of SEQ ID NO:126, positions 231-629 of SEQ ID NO:128, positions 63-461 of SEQ ID NO:130, positions 289-687 of SEQ ID NO:132, positions 289-687 of SEQ ID NO:134, or a corresponding sequence from a different HBV strain.

In any of the embodiments of the invention described herein, including any embodiment related to an immunotherapeutic composition, HBV antigen, fusion protein or use of such composition, HBV antigen or fusion protein, in one aspect, an amino acid of an HBV polymerase antigen useful as an HBV antigen or in a fusion protein or an immunotherapeutic composition of the invention can include, but is not limited to, positions 383-602 of SEQ ID NO:2, positions 381-600 of SEQ ID NO:6, positions 381-600 of SEQ ID NO:10, positions 453 to 680 of SEQ ID NO:10, positions 370-589 of SEQ ID NO:14, positions 380-599 of SEQ ID NO:18, positions 381-600 of SEQ ID NO:22, positions 380-599 of SEQ ID NO:26, positions 381-600 of SEQ ID NO:30, positions 260 to 604 of SEQ ID NO:36, positions 7-351 of SEQ ID NO:38, positions 7-351 of SEQ ID NO:40, 260 to 604 of SEQ ID NO:41, positions 346 to 690 of SEQ ID NO:92, positions 90-434 of SEQ ID NO:94, SEQ ID NO:98, positions 339 to 566 of SEQ ID NO:101, positions 255 to 482 of SEQ ID NO:102, positions 250-477 of SEQ ID NO:107, positions 250-477 of SEQ ID NO:108, positions 250-477 of SEQ ID NO:109, positions 250-477 of SEQ ID NO:110, positions 582 to 809 of SEQ ID NO:120, positions 582 to 809 of SEQ ID NO:124, positions 642 to 869 of SEQ ID NO:126, positions 1 to 228 of SEQ ID NO:128, positions 1 to 228 of SEQ ID NO:132, positions 61 to 288 of SEQ ID NO:134, or a corresponding sequence from a different HBV strain.

In any of the embodiments of the invention described herein, including any embodiment related to an immunotherapeutic composition, HBV antigen, fusion protein or use of such composition, HBV antigen or fusion protein, in one aspect, an amino acid of an HBV core antigen useful as an HBV antigen or in a fusion protein or an immunotherapeutic composition of the invention can include, but is not limited to, positions 31-212 of SEQ ID NO:1, positions 31-212 of SEQ ID NO:5, positions 31-212 of SEQ ID NO:9, positions 37 to 188 of SEQ ID NO:9, positions 31-212 of SEQ ID NO:13, positions 31-212 of SEQ ID NO:17, positions 31-212 of SEQ ID NO:21, positions 14-194 of SEQ ID NO:25, positions 31-212 of SEQ ID NO:29, positions 408-589 of SEQ ID NO:34, positions 605 to 786 of SEQ ID NO:36, positions 352-533 of SEQ ID NO:38, positions 160-341 of SEQ ID NO:39, positions 605-786 of SEQ ID NO:41, positions 691-872 of SEQ ID NO:92, positions 90-271 of SEQ ID NO:95, SEQ ID NO:99, positions 567 to 718 of SEQ ID NO:101, positions 483 to 634 of SEQ ID NO:102, positions 2-183 of SEQ ID NO:105, positions 184-395 of SEQ ID NO:105, positions 396-578 of SEQ ID NO:105, positions 579-761 of SEQ ID NO:105, positions 2-183 of SEQ ID NO:106, 338-520 of SEQ ID NO:106, positions 478-629 of SEQ ID NO:107, positions 478-629 of SEQ ID NO:108, positions 478-629 of SEQ ID NO:109, positions 478-629 of SEQ ID NO:110, positions 400-581 of SEQ ID NO:112, positions 400-581 of SEQ ID NO:114, positions 400-581 of SEQ ID NO:116, positions 400-581 of SEQ ID NO:118, positions 400 to 581 of SEQ ID NO:120, positions 400 to 581 of SEQ ID NO:122, positions 400 to 581 of SEQ ID NO:124, positions 400 to 581 of SEQ ID NO:126, positions 630 to 811 of SEQ ID NO:128, positions 462 to 643 of SEQ ID NO:130, positions 688 to 869 of SEQ ID NO:132, positions 688 to 869 of SEQ ID NO:134, or a corresponding sequence from a different HBV strain.

In any of the embodiments of the invention described herein, including any embodiment related to an immunotherapeutic composition, HBV antigen, fusion protein or use of such composition, HBV antigen or fusion protein, in one aspect, an amino acid of an HBV X antigen useful as an HBV antigen or in a fusion protein or an immunotherapeutic composition of the invention can include, but is not limited to, SEQ ID NO:4, SEQ ID NO:8, SEQ ID NO:12, positions 2 to 154 of SEQ ID NO:12, SEQ ID NO:16, SEQ ID NO:20, SEQ ID NO:24, SEQ ID NO:28, SEQ ID NO:32, positions 52-68 followed by positions 84-126 of SEQ ID NO:4, positions 52-68 followed by positions 84-126 of SEQ ID NO:8, positions 52-68 followed by positions 84-126 of SEQ ID NO:12, positions 52-68 followed by positions 84-126 of SEQ ID NO:16, positions 52-68 followed by positions 84-126 of SEQ ID NO:20, positions 52-68 followed by positions 84-126 of SEQ ID NO:24, positions 52-68 followed by positions 84-126 of SEQ ID NO:28, positions 52-68 followed by positions 84-126 of SEQ ID NO:32, positions 787 to 939 of SEQ ID NO:36, positions 7-159 of SEQ ID NO:39, positions 873-1025 of SEQ ID NO:92, positions 90-242 of SEQ ID NO:96, SEQ ID NO:100, positions 719-778 of SEQ ID NO:101, positions 635-694 of SEQ ID NO:102, positions 184-337 of SEQ ID NO:106, positions 521-674 of SEQ ID NO:106, positions 630-689 of SEQ ID NO:107, positions 630-689 of SEQ ID NO:108, positions 630-689 of SEQ ID NO:109, positions 630-689 of SEQ ID NO:110, positions 582-641 of SEQ ID NO:122, positions 810-869 of SEQ ID NO:124, positions 582-641 of SEQ ID NO:126, positions 1-60 of SEQ ID NO:130, positions 229 to 288 of SEQ ID NO:132, positions 1 to 60 of SEQ ID NO:134, or a corresponding sequence from a different HBV strain.

HBV Antigens Comprising Surface Antigen and Core Protein.

In one embodiment of the invention, the HBV antigen(s) for use in a composition or method of the invention is a fusion protein comprising HBV antigens, wherein the HBV antigens comprise or consist of HBV large (L) surface antigen or at least one immunogenic domain thereof and HBV core protein (HBcAg) or at least one immunogenic domain thereof. In one aspect, the HBV large (L) surface antigen and/or the HBV core protein is full-length or near full-length. According to any embodiment of the present invention, reference to a "full-length" protein (or a full-length functional domain or full-length immunological domain) includes the full-length amino acid sequence of the protein or functional domain or immunological domain, as described herein or as otherwise known or described in a publicly available sequence. A protein or domain that is "near full-length", which is also a type of homologue of a protein, differs from a full-length protein or domain, by the addition or deletion or omission of 1, 2, 3, 4, 5, 6, 7, 8, 9, or 10 amino acids from the N- and/or C-terminus of such a full-length protein or full-length domain. General reference to a protein or domain can include both full-length and near full-length proteins, as well as other homologues thereof.

In one aspect, the HBV large (L) surface antigen or the HBV core protein comprises at least 80%, 85%, 90%, 91%, 92%, 93%, 94%, 95%, 96%, 97%, 98%, or 99% of the linear sequence of a full-length HBV large (L) surface antigen or HBV core protein, respectively, or of the linear sequence of a portion of HBV large surface antigen that comprises the hepatocyte receptor binding portion of pre-S1 and all or a portion of HBV small (S) surface antigen, of the linear amino acid sequences represented by SEQ ID NO:97 (optimized HBV surface antigen, described below), SEQ ID NO:99 (optimized core protein, described below), or a corresponding sequence from another HBV strain, as applicable. A variety of other sequences for suitable HBV surface antigens and HBV core antigens useful in the invention are described herein. In one aspect, the HBV large (L) surface antigen or the HBV core protein is at least 80%, 85%, 90%, 91%, 92%, 93%, 94%, 95%, 96%, 97%, 98%, or 99% identical to a full-length HBV large (L) surface antigen or HBV core protein, respectively, or to another HBV surface antigen or HBV core antigen described herein, including the amino acid sequence represented by SEQ ID NO:97 (optimized HBV surface antigen, described below), SEQ ID NO:99 (optimized core protein, described below), or a corresponding sequence from another HBV strain, as applicable.

Figure 2:
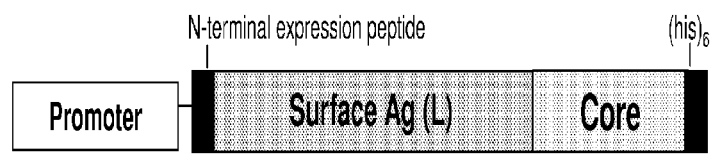
FIG. 2 is a schematic drawing showing the basic structure of a recombinant nucleic acid molecule encoding an HBV surface antigen/core fusion protein useful in a yeast-based immunotherapeutic composition of the invention.

Such a fusion protein is schematically represented in FIG. 2. One example of a composition comprising such a fusion protein is described in Example 1. In this embodiment, yeast (e.g., *Saccharomyces cerevisiae*) were engineered to express various HBV surface-core fusion proteins as shown in FIG. 2 under the control of the copper-inducible promoter, CUP1, or the TEF2 promoter. In each case, the HBV fusion protein was a single polypeptide with the following sequence elements fused in frame from N- to C-terminus, represented by SEQ ID NO:34: (1) an N-terminal peptide to impart resistance to proteasomal degradation and stabilize expression (e.g., positions 1 to 6 of SEQ ID NO:34); 2) a two amino acid spacer to introduce a SpeI restriction enzyme site; 3) the amino acid sequence of a near full-length (minus position 1) HBV genotype C large (L) surface antigen (e.g., positions 9 to 407 of SEQ ID NO:34 or positions 2-400 of SEQ ID NO:11 (which differs from SEQ ID NO:34 at positions 350-351 of SEQ ID NO:11, where a Leu-Val sequence in SEQ ID NO:11 is replaced with a Gln-Ala sequence at positions 357-358 of SEQ ID NO:34)); 4) the amino acid sequence of an HBV core antigen (e.g., positions 31-212 of SEQ ID NO:9 or positions 408 to 589 of SEQ ID NO:34); and 5) a hexahistidine tag (e.g., positions 590-595 of SEQ ID NO:34). Positions 28-54 of SEQ ID NO:34 comprise the hepatocyte receptor portion of large (L) surface protein. SEQ ID NO:34 contains multiple epitopes or domains that are believed to enhance the immunogenicity of the fusion protein. For example, positions 209-220, positions 389-397, positions 360-367, and positions 499-506, with respect to SEQ ID NO:34, comprise known MHC Class I binding and/or CTL epitopes. Positions 305-328 of SEQ ID NO:34 comprise an antibody epitope. A nucleic acid sequence encoding the fusion protein of SEQ ID NO:34 (codon optimized for yeast expression) is represented herein by SEQ ID NO:33. A yeast-based immunotherapy composition expressing this fusion protein is also referred to herein as GI-13002.

The amino acid segments used in any of the fusion proteins described herein can be modified by the use of additional amino acids flanking either end of any domain; the descriptions provided herein are exemplary. For example, a fusion protein according to this embodiment can include 1) the amino acid sequence of a near full-length (minus position 1) HBV genotype C large (L) surface antigen (e.g., positions 2-400 of SEQ ID NO:11 or positions 9 to 407 of SEQ ID NO:34); and 2) the amino acid sequence of an HBV core antigen (e.g., positions 31-212 of SEQ ID NO:9 or positions 408 to 589 of SEQ ID NO:34), and utilize no N- or C-terminal sequences, or utilize different N- or C-terminal sequences and/or linkers or no linkers between HBV sequences. In one embodiment, instead of the N-terminal peptide represented by positions 1-6 of SEQ ID NO:34, an N-terminal peptide represented by SEQ ID NO:89 or SEQ ID NO:90 is utilized, followed by the remainder of the fusion protein, including or not including the hexahistidine C-terminal tag. The fusion protein may also include one, two, three, four, five, six, or more linker (spacer) amino acids between HBV proteins or domains. The same alternate embodiments apply to any fusion protein or HBV antigen construct used in the invention as described herein.

The HBV sequences used to design this fusion protein and many of the others described and/or exemplified herein are based on isolates of a particular HBV genotype (e.g., genotype A, B, C, or D). However, it is an embodiment of the invention to add to or substitute into any portion of an HBV antigen described herein that is based on or derived from one particular genotype, sub-genotype, or strain, a corresponding sequence, or even a single or small amino acid substitution, insertion or deletion that occurs in a corresponding sequence, from any other HBV genotype(s), sub-genotype(s), or strain(s). In one embodiment, an HBV antigen can be produced by substituting an entire sequence(s) of an HBV antigen described herein with the corresponding sequence(s) from one or more different HBV genotypes, sub-genotypes or strain/isolates. Adding to or substituting a sequence from one HBV genotype or sub-genotype for another, for example, allows for the customization of the immunotherapeutic composition for a particular individual or population of individuals (e.g., a population of individuals within a given country or region of a country, in order to target the HBV genotype(s) that is most prevalent in that country or region of the country). Similarly, it is also an embodiment of the invention to use all or a portion of a consensus sequence derived from, determined from, or published for, a given HBV strain, genotype or subtype to make changes in the sequence of a given HBV antigen to more closely or exactly correspond to the consensus sequence. According to the present invention and as generally understood in the art, a "consensus sequence" is typically a sequence based on the most common nucleotide or amino acid at a particular position of a given sequence after multiple sequences are aligned.

As a particular example of the above-mentioned types of modifications, an HBV antigen can be modified to change a T cell epitope in a given sequence from one isolate to correspond more closely or exactly with a T cell epitope from a different isolate, or to correspond more closely or exactly with a consensus sequence for the T cell epitope. Such T cell epitopes can include dominant epitopes and/or sub-dominant epitopes. Indeed, according to the invention, HBV antigens can be designed that incorporate consensus sequences from a variety of HBV genotypes and/or subtypes, or mixtures of sequences from different HBV genotypes and/or subtypes. Alignments of major HBV proteins across exemplary sequences from each of the major known genotypes can be readily generated using publicly available software, which will inform the generation of consensus sequences, for example. Furthermore, consensus sequences for many HBV proteins have been published. Since there is a high degree of conservation at the amino acid level among different HBV genotypes, sub-genotypes and strains, it is straightforward to use the corresponding portions of HBV proteins from genotypes, sub-genotypes or strains other than those exemplified herein to create HBV antigens having a similar or the same overall structure as those described herein. Examples of such modifications are illustrated and exemplified herein.

By way of example, there can be minor differences among sequences of the same protein even within the same serotype and genotype (i.e., due to strain or isolate variations), although such differences in sequence identity will typically be less than 20% across the full length of the sequences being compared (i.e., the sequences will be at least 80% identical), and more typically, the sequences will be at least 85% identical, 90% identical, 91% identical, 92% identical, 93% identical, 94% identical, 95% identical, 96% identical, 97% identical, 98% identical, 99% identical, or 100% identical, over the full length of the compared sequences. For example, in the fusion protein described above (SEQ ID NO:34), the sequence for the large (L) surface antigen used in the fusion (positions 9-407 of SEQ ID NO:34) is from an HBV genotype C isolate, and is about 99% identical to positions 2-400 of SEQ ID NO:11, which is also from large (L) surface antigen from an HBV genotype C isolate (i.e., there are two different amino acids, at positions 350-351 of SEQ ID NO:11 (Gln-Ala) as compared to positions 357-358 of SEQ ID NO:34 (Leu-Val). However, either sequence is suitable for use in a fusion protein described herein, as are sequences from other HBV strains. Accordingly, in one embodiment, the sequences utilized in any of the HBV antigens described herein, including any of the fusion proteins described herein, can include the corresponding sequences from one or more different HBV genotypes, sub-genotypes, or strains.

The above-described utilization of consensus sequences and individual HBV genotypes has been applied to various HBV antigens described herein. For example, consensus sequence design has been applied to the fusion protein described above with reference to SEQ ID NO:34, which contains HBV surface proteins and HBV core proteins. Example 7 describes additional fusion proteins that are similar in design to the fusion protein represented by SEQ ID NO:34, but that are based on a consensus sequence for HBV genotypes A, B, C and D, respectively. A fusion protein comprising HBV surface and core proteins that is based on a consensus sequence for HBV genotype A, which is also schematically illustrated in FIG. 2, is a single polypeptide with the following sequence elements fused in frame from N- to C-terminus, represented by SEQ ID NO:112 (optional sequences that are not HBV sequences are not included in the base sequence of SEQ ID NO:112, but may be added to this sequence as in the construct described in Example 7): (1) optionally, an N-terminal peptide that is a synthetic N-terminal peptide designed to impart resistance to proteasomal degradation and stabilize expression represented by SEQ ID NO:37, which may be substituted by an N-terminal peptide represented by SEQ ID NO:89, SEQ ID NO:90, or another N-terminal peptide suitable for use with a yeast-based immunotherapeutic as described herein; (2) optionally, a linker peptide of from one to three or more amino acids linker sequences of one, two, three or more amino acids, such as the two amino acid linker of Thr-Ser; (3) the amino acid sequence of a near full-length (minus position 1) a consensus sequence for HBV genotype A large (L) surface antigen represented by positions 1 to 399 of SEQ ID NO:112; (4) the amino acid sequence of a consensus sequence for HBV genotype A core antigen represented by positions 400 to 581 of SEQ ID NO:112; and (5) optionally, a hexahistidine tag. A nucleic acid sequence encoding the fusion protein of SEQ ID NO:112 (codon optimized for yeast expression) is represented herein by SEQ ID NO:111. A yeast-based immunotherapy composition expressing this fusion protein is also referred to herein as GI-13006.

Example 7 also describes a fusion protein that is similar in design to the fusion protein represented by SEQ ID NO:34, but that is based on a consensus sequence for HBV genotype B. This fusion protein, which is also schematically illustrated in FIG. 2, is a single polypeptide with the following sequence elements fused in frame from N- to C-terminus, represented by SEQ ID NO:114 (optional sequences that are not HBV sequences are not included in the base sequence of SEQ ID NO:114, but may be added to this sequence as in the construct described in Example 7): (1) optionally, an N-terminal peptide that is a synthetic N-terminal peptide designed to impart resistance to proteasomal degradation and stabilize expression represented by SEQ ID NO:37, which may be substituted by an N-terminal peptide represented by SEQ ID NO:89, SEQ ID NO:90, or another N-terminal peptide suitable for use with a yeast-based immunotherapeutic as described herein; (2) optionally, a linker peptide of from one to three or more amino acids linker sequences of one, two, three or more amino acids, such as the two amino acid linker of Thr-Ser; (3) the amino acid sequence of a near full-length (minus position 1) a consensus sequence for HBV genotype B large (L) surface antigen represented by positions 1 to 399 of SEQ ID NO:114; (4) the amino acid sequence of a consensus sequence for HBV genotype B core antigen represented by positions 400 to 581 of SEQ ID NO:114; and (5) optionally, a hexahistidine tag. A nucleic acid sequence encoding the fusion protein of SEQ ID NO:114 (codon optimized for yeast expression) is represented herein by SEQ ID NO:113. A yeast-based immunotherapy composition expressing this fusion protein is also referred to herein as GI-13007.

Example 7 describes a fusion protein that is similar in design to the fusion protein represented by SEQ ID NO:34, but that is based on a consensus sequence for HBV genotype C. This fusion protein, which is also schematically illustrated in FIG. 2, is a single polypeptide with the following sequence elements fused in frame from N- to C-terminus, represented by SEQ ID NO:116 (optional sequences that are not HBV sequences are not included in the base sequence of SEQ ID NO:116, but may be added to this sequence as in the construct described in Example 7): (1) optionally, an N-terminal peptide that is a synthetic N-terminal peptide designed to impart resistance to proteasomal degradation and stabilize expression represented by SEQ ID NO:37, which may be substituted by an N-terminal peptide represented by SEQ ID NO:89, SEQ ID NO:90, or another N-terminal peptide suitable for use with a yeast-based immunotherapeutic as described herein; (2) optionally, a linker peptide of from one to three or more amino acids linker sequences of one, two, three or more amino acids, such as the two amino acid linker of Thr-Ser; (3) the amino acid sequence of a near full-length (minus position 1) a consensus sequence for HBV genotype C large (L) surface antigen represented by positions 1 to 399 of SEQ ID NO:116; (4) the amino acid sequence of a consensus sequence for HBV genotype C core antigen represented by positions 400 to 581 of SEQ ID NO:116; and (5) optionally, a hexahistidine tag. A nucleic acid sequence encoding the fusion protein of SEQ ID NO:116 (codon optimized for yeast expression) is represented herein by SEQ ID NO:115. A yeast-based immunotherapy composition expressing this fusion protein is also referred to herein as GI-13008.

Example 7 describes a fusion protein that is similar in design to the fusion protein represented by SEQ ID NO:34, but that is based on a consensus sequence for HBV genotype D. This fusion protein, which is also schematically illustrated in FIG. 2, is a single polypeptide with the following sequence elements fused in frame from N- to C-terminus, represented by SEQ ID NO:118 (optional sequences that are not HBV sequences are not included in the base sequence of SEQ ID NO:118, but may be added to this sequence as in the construct described in Example 7): (1) optionally, an N-terminal peptide that is a synthetic N-terminal peptide designed to impart resistance to proteasomal degradation and stabilize expression represented by SEQ ID NO:37, which may be substituted by an N-terminal peptide represented by SEQ ID NO:89, SEQ ID NO:90, or another N-terminal peptide suitable for use with a yeast-based immunotherapeutic as described herein; (2) optionally, a linker peptide of from one to three or more amino acids linker sequences of one, two, three or more amino acids, such as the two amino acid linker of Thr-Ser; (3) the amino acid sequence of a near full-length (minus position 1) a consensus sequence for HBV genotype D large (L) surface antigen represented by positions 1 to 399 of SEQ ID NO:118; (4) the amino acid sequence of a consensus sequence for HBV genotype D core antigen represented by positions 400 to 581 of SEQ ID NO:118; and (5) optionally, a hexahistidine tag. The amino acid sequence of a complete fusion protein described in Example 7 comprising SEQ ID NO:118 and including the N- and C-terminal peptides and linkers is represented herein by SEQ ID NO:151. A nucleic acid sequence encoding the fusion protein of SEQ ID NO:118 or SEQ ID NO:151 (codon optimized for yeast expression) is represented herein by SEQ ID NO:117. A yeast-based immunotherapy composition expressing this fusion protein is also referred to herein as GI-13009.

HBV Antigens Comprising Surface Antigen, Core Protein, Polymerase and X Antigen. In one embodiment of the invention, the HBV antigen(s) for use in a composition or method of the invention is a fusion protein comprising HBV antigens, wherein the HBV antigens comprise or consist of: the HBV surface antigen (large (L), medium (M) or small (S)) or at least one structural, functional or immunogenic domain thereof), HBV polymerase or at least one structural, functional or immunogenic domain thereof, the HBV core protein (HBcAg) or HBV e-antigen (HBeAg) or at least one structural, functional or immunogenic domain thereof, and the HBV X antigen (HBx) or at least one structural, functional or immunogenic domain thereof. In one aspect, any one or more of the HBV surface antigen, HBV polymerase, HBV core protein, HBV e-antigen, HBV X antigen, or domain thereof, is full-length or near full-length. In one aspect, any one or more of the HBV surface antigen, HBV polymerase, HBV core protein, HBV e-antigen, HBV X antigen, or domain thereof comprises at least 80%, 85%, 90%, 91%, 92%, 93%, 94%, 95%, 96%, 97%, 98%, or 99% of the linear sequence of a full-length HBV surface antigen, HBV polymerase, HBV core protein, HBV e-antigen, HBV X antigen, or domain thereof, respectively, or of the linear amino acid sequences represented by SEQ ID NO:97 (optimized HBV surface antigen, described below), SEQ ID NO:98 (optimized HBV polymerase, described below), SEQ ID NO:99 (optimized core protein, described below), SEQ ID NO:100 (optimized X antigen, described below), or a corresponding sequence from another HBV strain, as applicable. In one aspect, any one or more of the HBV surface antigen, HBV polymerase, HBV core protein, HBV e-antigen, HBV X antigen, or domain thereof is at least 80%, 85%, 90%, 91%, 92%, 93%, 94%, 95%, 96%, 97%, 98%, or 99% identical to a full-length HBV surface antigen, HBV polymerase, HBV core protein, HBV e-antigen, HBV X antigen, or domain thereof, respectively, or to the amino acid sequences represented by SEQ ID NO:97 (optimized HBV surface antigen, described below), SEQ ID NO:98 (optimized HBV polymerase, described below), SEQ ID NO:99 (optimized core protein, described below), or SEQ ID NO:100 (optimized X antigen, described below), or a corresponding sequence from another HBV strain, as applicable. A variety of suitable and exemplary sequences for HBV surface antigens, HBV polymerase antigens, HBV core antigens, and HBV X antigens are described herein.

In one embodiment of the invention, the HBV antigen(s) for use in a composition or method of the invention is a fusion protein comprising HBV antigens, wherein the HBV antigens comprise or consist of: the hepatocyte receptor portion of Pre-S1 of the HBV large (L) surface antigen or at least one immunogenic domain thereof, an HBV small (S) surface antigen (HBsAg) or at least one immunogenic domain thereof, the reverse transcriptase (RT) domain of HBV polymerase or at least one immunogenic domain thereof, the HBV core protein (HBcAg) or at least one immunogenic domain thereof, and the HBV X antigen (HBx) or at least one immunogenic domain thereof. In one aspect, any one or more of the hepatocyte receptor portion of Pre-S1 of the HBV large (L) surface antigen, the HBV small (S) surface antigen, the RT domain of HBV polymerase, the HBV core protein, X antigen, or domain thereof, is full-length or near full-length. In one aspect, any one or more of the hepatocyte receptor portion of Pre-S1 of the HBV large (L) surface antigen, the HBV small (S) surface antigen, the RT domain of HBV polymerase, the HBV core protein, X antigen, or domain thereof, comprises at least 80%, 85%, 90%, 91%, 92%, 93%, 94%, 95%, 96%, 97%, 98%, or 99% of the linear sequence of a full-length Pre-S1 of the HBV large (L) surface antigen, the HBV small (S) surface antigen, the RT domain of HBV polymerase, the HBV core protein, X antigen, or domain thereof, respectively. In one aspect, any one or more of the hepatocyte receptor portion of Pre-S1 of the HBV large (L) surface antigen, the HBV small (S) surface antigen, the RT domain of HBV polymerase, the HBV core protein, X antigen, or domain thereof is at least 80%, 85%, 90%, 91%, 92%, 93%, 94%, 95%, 96%, 97%, 98%, or 99% identical to a full-length hepatocyte receptor portion of Pre-S1 of the HBV large (L) surface antigen, the HBV small (S) surface antigen, the RT domain of HBV polymerase, the HBV core protein, X antigen, or domain thereof, respectively.

Figure 3:
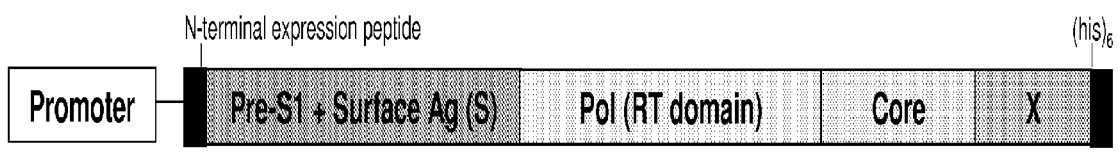
FIG. 3 is a schematic drawing showing the basic structure of a recombinant nucleic acid molecule encoding an HBV surface antigen/polymerase/core/X fusion protein useful in a yeast-based immunotherapeutic composition of the invention.

Such a fusion protein is schematically represented in FIG. 3. An example of a composition comprising this fusion protein is described in Example 2. In this embodiment, yeast (e.g., *Saccharomyces cerevisiae*) were engineered to express various HBV fusion proteins as schematically shown in FIG. 3 under the control of the copper-inducible promoter, CUP1, or the TEF2 promoter. In one case, the fusion protein is a single polypeptide with the following sequence elements fused in frame from N- to C-terminus, represented by SEQ ID NO:36: (1) an N-terminal peptide to impart resistance to proteasomal degradation and stabilize expression (e.g., positions 1 to 5 of SEQ ID NO:36); 2) the amino acid sequence of an HBV genotype C hepatocyte receptor domain of the pre-S1 portion of HBV large (L) surface protein (unique to L) (e.g., positions 21-47 of SEQ ID NO:11 or positions 6 to 32 of SEQ ID NO:36); 3) the amino acid sequence of a full-length HBV genotype C small (S) surface antigen (e.g., positions 176 to 400 of SEQ ID NO:11 or positions 33 to 257 of SEQ ID NO:36); 4) a two amino acid spacer/linker to facilitate cloning and manipulation of the sequences (e.g., positions 258 and 259 of SEQ ID NO:36); 5) the amino acid sequence of a portion of the HBV genotype C polymerase including the reverse transcriptase domain (e.g., positions 247 to 691 of SEQ ID NO:10 or positions 260 to 604 of SEQ ID NO:36); 6) an HBV genotype C core protein (e.g., positions 31-212 of SEQ ID NO:9 or positions 605 to 786 of SEQ ID NO:36); 7) the amino acid sequence of an HBV genotype C X antigen (e.g., positions 2 to 154 of SEQ ID NO:12 or positions 787 to 939 of SEQ ID NO:36); and 8) a hexahistidine tag (e.g., positions 940 to 945 of SEQ ID NO:36). A nucleic acid sequence encoding the fusion protein of SEQ ID NO:36 (codon optimized for yeast expression) is represented herein by SEQ ID NO:35. A yeast-based immunotherapy composition expressing this fusion protein is referred to herein as GI-13005.

In one alternate example of this embodiment, a fusion protein according to the embodiment described above or that below can include 1) the amino acid sequence of an HBV genotype C hepatocyte receptor domain of the pre-S1 portion of HBV large (L) surface protein (unique to L) (e.g., positions 21-47 of SEQ ID NO:11 or positions 6 to 32 of SEQ ID NO:36); 2) the amino acid sequence of a full-length HBV genotype C small (S) surface antigen (e.g., positions 176 to 400 of SEQ ID NO:11 or positions 33 to 257 of SEQ ID NO:36); 3) the amino acid sequence of a portion of the HBV genotype C polymerase including the reverse transcriptase domain (e.g., positions 247 to 691 of SEQ ID NO:10 or positions 260 to 604 of SEQ ID NO:36); 4) an HBV genotype C core protein (e.g., positions 31-212 of SEQ ID NO:9 or positions 605 to 786 of SEQ ID NO:36); and 5) the amino acid sequence of an HBV genotype C X antigen (e.g., positions 2 to 154 of SEQ ID NO:12 or positions 787 to 939 of SEQ ID NO:36), and utilize no N- or C-terminal sequences, or utilize different N- or C-terminal sequences, and/or use linkers or no linkers between HBV sequences.

In one embodiment, instead of the N-terminal peptide represented by positions 1-5 of SEQ ID NO:36, an N-terminal peptide represented by SEQ ID NO:89 or SEQ ID NO:90 is utilized (or a homologue thereof), followed by the remainder of the fusion protein as described. Example 2 describes such a fusion protein, which is also illustrated by the schematic depiction of the construct in FIG. 3. In this embodiment, yeast (e.g., *Saccharomyces cerevisiae*) were again engineered to express various HBV fusion proteins as schematically shown in FIG. 3 under the control of the copper-inducible promoter, CUP1, or the TEF2 promoter. In this second case, the fusion protein is a single polypeptide with the following sequence elements fused in frame from N- to C-terminus, represented by SEQ ID NO:92: (1) an N-terminal peptide to impart resistance to proteasomal degradation and stabilize or enhance expression (SEQ ID NO:89, positions 1 to 89 of SEQ ID NO:92); 2) a two amino acid spacer/linker (Thr-Ser) to facilitate cloning and manipulation of the sequences (positions 90 to 91 of SEQ ID NO:92); 3) the amino acid sequence of an HBV genotype C hepatocyte receptor domain of the pre-S1 portion of HBV large (L) surface protein (unique to L) (e.g., positions 21-47 of SEQ ID NO:11 or positions 92 to 118 of SEQ ID NO:92); 4) the amino acid sequence of a full-length HBV genotype C small (S) surface antigen (e.g., positions 176 to 400 of SEQ ID NO:11 or positions 119 to 343 of SEQ ID NO:92); 5) a two amino acid spacer/linker (Leu-Glu) to facilitate cloning and manipulation of the sequences (e.g., positions 344 to 345 of SEQ ID NO:92); 6) the amino acid sequence of a portion of the HBV genotype C polymerase including the reverse transcriptase domain (e.g., positions 247 to 691 of SEQ ID NO:10 or positions 346 to 690 of SEQ ID NO:92); 7) an HBV genotype C core protein (e.g., positions 31-212 of SEQ ID NO:9 or positions 691 to 872 of SEQ ID NO:92); 8) the amino acid sequence of an HBV genotype C X antigen (e.g., positions 2 to 154 of SEQ ID NO:12 or positions 873 to 1025 of SEQ ID NO:92); and 9) a hexahistidine tag (e.g., positions 1026 to 1031 of SEQ ID NO:92). A nucleic acid sequence encoding the fusion protein of SEQ ID NO:92 (codon-optimized for expression in yeast) is represented herein by SEQ ID NO:91. A yeast-based immunotherapy composition expressing this fusion protein is referred to herein as GI-13004.

SEQ ID NO:36 and SEQ ID NO:92 contain multiple epitopes or domains that are believed to enhance the immunogenicity of the fusion protein, including several described above for SEQ ID NO:34. In addition, the reverse transcriptase domain used in this fusion protein contains several amino acid positions that are known to become mutated as a drug-resistance response to treatment with various anti-viral drugs, and therefore, any one or more of these may be mutated in this fusion protein in order to provide a therapeutic or prophylactic immunotherapeutic that targets specific drug resistance (escape) mutations. These amino acid positions are, with respect to SEQ ID NO:36, at amino acid position: 432 (Val, known to mutate to a Leu after lamivudine therapy); position 439 (Leu, known to mutate to a Met after lamivudine therapy); position 453 (Ala, known to mutate to a Thr after tenofovir therapy); position 463 (Met, known to mutate to an Ile or Val after lamivudine therapy); and position 495 (Asn, known to mutate to Thr after adefovir therapy). These amino acid positions are, with respect to SEQ ID NO:92, at amino acid position: 518 (Val, known to mutate to a Leu after lamivudine therapy); position 525 (Leu, known to mutate to a Met after lamivudine therapy); position 539 (Ala, known to mutate to a Thr after tenofovir therapy); position 549 (Met, known to mutate to an Ile or Val after lamivudine therapy); and position 581 (Asn, known to mutate to Thr after adefovir therapy). Additional drug resistance mutations that are identified or that have been identified can be added, as desired, to create additional immunotherapeutics targeting such mutations, using the guidance provided herein.

In one embodiment of the invention, the valine at position 901 in SEQ ID NO:36 or the valine at position 987 of SEQ ID NO:92 (or the valine at position 116 of SEQ ID NO:12 or in any X antigen or domain thereof containing this corresponding position) is substituted with a leucine, to create the T cell epitope identified as SEQ ID NO:51 (see Table 5).

As discussed above, the invention includes the modification of HBV antigens from their naturally occurring or wild-type sequences for inclusion in a yeast-based immunotherapeutic that improve the clinical utility or meet required criteria for therapeutics or prophylactics related to infectious agents. By way of example, the following discussion and Examples 5-8 describe the design and construction of yeast-based immunotherapeutics that takes into consideration one or more criteria of RAC requirements, maximization of immunogenic domains associated with the most beneficial immune responses, maximization of conserved T cell epitopes, utilization of consensus sequences for a particular HBV genotype, and/or minimization of artificial junctions within the HBV antigen. For example, the following yeast-based immunotherapeutic composition exemplifies an HBV fusion protein meeting the requirements of the goals specified above, and comprising portions of each of the HBV major proteins: HBV surface antigen, polymerase, core and X antigen. To design this fusion protein, individual HBV antigens within the fusion were optimized or modified to reduce the size of the segments in the protein (e.g., to ensure that the protein represented less than ⅔ of the HBV genome), as well as to maximize the inclusion of T cell epitopes that have been associated with an immune response in acute/self-limiting HBV infection and/or chronic HBV infection, to maximize conserved epitopes, and to minimize non-natural sequences. One of skill in the art using this guidance can produce alternate optimized HBV proteins for use in an HBV antigen of the invention.

As described in more detail in Example 5, to construct an HBV surface antigen segment, a full-length large (L) surface antigen protein from HBV genotype C was reduced in size by truncation of the N- and C-terminal sequences, while maximizing the inclusion of known MHC T cell epitopes, using the prioritization for inclusion of T cell epitopes associated with acute/self-limiting infections. The resulting surface antigen segment is represented by SEQ ID NO:97.

To construct the segment of the fusion protein comprising HBV polymerase (see Example 5), substantial portions of a full-length polymerase from HBV genotype C were eliminated by focusing on inclusion of the active site domain (from the RT domain), which is the most conserved region of the protein among HBV genotypes and isolates, and which includes several sites where drug resistance mutations have been known to occur. The HBV polymerase segment was designed to maximize known T cell epitopes, using the prioritization strategy discussed above, and to modify one of the T cell epitopes to correspond exactly to a known T cell epitope that differed by a single amino acid. The resulting HBV polymerase antigen segment is represented by SEQ ID NO:98.

To construct the segment of the fusion protein comprising HBV Core antigen (see Example 5), a full-length Core protein from HBV genotype C was modified to reduce the size of the protein while maximizing the number of T cell epitopes by inclusion and by modification of sequence to created perfect matches to certain known T cell epitopes. In addition, sequence was removed that contained exceptionally positively charged C-terminus which may be toxic to yeast by competitive interference with natural yeast RNA binding proteins which often are arginine rich (positively charged). The resulting HBV Core antigen segment is represented by SEQ ID NO:99.

To construct the segment of the fusion protein comprising HBV X antigen (see Example 5), a full-length X antigen from HBV genotype C was truncated to reduce the size of the protein, while maximizing the retention of most of the known T cell epitopes. Single amino acid changes were also introduced to correspond to the published T cell epitope sequences, and sequence flanking the T cell epitopes at the ends of the segment was retained to facilitate efficient processing and presentation of the correct epitopes by an antigen presenting cell. The resulting HBV X antigen segment is represented by SEQ ID NO:100.

Finally, as described in Example 5, a complete fusion protein was constructed by linking the four HBV segments described above to form a single protein optimized for clinical use. Two different exemplary fusion proteins were created, each with a different N-terminal peptide added to enhance and/or stabilize expression of the fusion protein in yeast. As described previously herein with respect to all of the other proteins used in a yeast-based immunotherapeutic compositions described herein, the N-terminal peptide can be replaced with a different synthetic or natural N-terminal peptide or with a homologue thereof, or the N-terminal peptide can be omitted altogether and a methionine included at position one. In addition, linker sequences of one, two, three or more amino acids may be added between segments of the fusion protein, if desired. For example, a two amino acid linker sequence such as Thr-Ser may be inserted between the N-terminal peptide and the first HBV antigen in the fusion protein, and/or between two HBV antigens in the fusion protein. Also, while these constructs were designed using HBV proteins from genotype C as the backbone, any other HBV genotype, sub-genotype, or HBV proteins from different strains or isolates can be used to design the protein segments. In one aspect, consensus sequences from a given HBV genotype can be used to design or form the protein segments, as described in additional fusion proteins below. Finally, if one or more segments are excluded from the fusion protein as described herein, then the sequence from the remaining segments can be expanded in length, if desired, to include additional T cell epitopes and/or flanking regions of the remaining proteins.

Example 5 describes an HBV fusion protein, which is also illustrated by the schematic depiction of the construct in FIG. 3, that is a single polypeptide with the following sequence elements fused in frame from N- to C-terminus, represented by SEQ ID NO:101: (1) an N-terminal peptide that is an alpha factor prepro sequence, to impart resistance to proteasomal degradation and stabilize expression represented by SEQ ID NO:89 (positions 1-89 of SEQ ID NO:101); (2) an optimized portion of an HBV large (L) surface antigen represented by SEQ ID NO:97 (positions 90 to 338 of SEQ ID NO:101, e.g., corresponding to positions 120 to 368 of SEQ ID NO:11 plus optimization of epitopes); (3) an optimized portion of the reverse transcriptase (RT) domain of HBV polymerase represented by SEQ ID NO:98 (positions 339 to 566 of SEQ ID NO:101, e.g., corresponding to positions 453 to 680 of SEQ ID NO:10 plus optimization of epitopes); (4) an optimized portion of HBV Core protein represented by SEQ ID NO:99 (positions 567 to 718 of SEQ ID NO:101 e.g., corresponding to positions 37 to 188 of SEQ ID NO:9 plus optimization of epitopes); (5) an optimized portion of HBV X antigen represented by SEQ ID NO:100 (positions 719 to 778 of SEQ ID NO:101, e.g., corresponding to positions 52 to 127 of SEQ ID NO:12 plus optimization of epitopes); and (6) a hexahistidine tag (e.g., positions 779 to 784 of SEQ ID NO:101). In one embodiment, the linker sequence of threonine (Thr or T)-serine (Ser or S) is used between the N-terminal peptide of SEQ ID NO:89 and the first HBV protein (optimized portion of HBV large surface antigen), thereby extending the total length of SEQ ID NO:101 by two amino acids.

Example 5 also describes a fusion protein, which is also illustrated by the schematic depiction of the construct in FIG. 3, that is a single polypeptide with the following sequence elements fused in frame from N- to C-terminus, represented by SEQ ID NO:102: (1) an N-terminal peptide that is a synthetic N-terminal peptide designed to impart resistance to proteasomal degradation and stabilize expression represented by SEQ ID NO:37 (positions 1-6 of SEQ ID NO:102); (2) an optimized portion of an HBV large (L) surface antigen represented by positions 2 to 248 of SEQ ID NO:97 (positions 7 to 254 of SEQ ID NO:102, e.g., corresponding to positions 120 to 368 of SEQ ID NO:11 plus optimization of epitopes); (3) an optimized portion of the reverse transcriptase (RT) domain of HBV polymerase represented by SEQ ID NO:98 (positions 255 to 482 of SEQ ID NO:102, e.g., corresponding to positions 453 to 680 of SEQ ID NO:10 plus optimization of epitopes); (4) an optimized portion of HBV Core protein represented by SEQ ID NO:99 (positions 483 to 634 of SEQ ID NO:102, e.g., corresponding to positions 37 to 188 of SEQ ID NO:9 plus optimization of epitopes); (5) an optimized portion of HBV X antigen represented by SEQ ID NO:100 (positions 635 to 694 of SEQ ID NO:102, e.g., corresponding to positions 52 to 127 of SEQ ID NO:12 plus optimization of epitopes); and (6) a hexahistidine tag (e.g., positions 695 to 700 of SEQ ID NO:102). In one embodiment, the linker sequence of threonine (Thr or T)-serine (Ser or S) is used between the N-terminal peptide of SEQ ID NO:37 and the first HBV protein (optimized portion of HBV large surface antigen), thereby extending the total length of SEQ ID NO:102 by two amino acids. In one embodiment, an optimized portion of an HBV large (L) surface antigen used in the fusion protein described above is represented by positions 1 to 248 of SEQ ID NO:97 (thereby extending the total length of SEQ ID NO:102 by one amino acid). In one embodiment both the T-S linker and positions 1-248 of SEQ ID NO:97 are used in SEQ ID NO:102.

As discussed above, the invention includes the modification of HBV antigens from their naturally occurring or wild-type sequences for inclusion in a yeast-based immunotherapeutic that improve the clinical utility or meet required criteria for therapeutics or prophylactics related to infectious agents, utilizing consensus sequences from a given HBV genotype to design or form the protein segments. By way of example, additional HBV antigens for use in a yeast-based immunotherapeutic of the invention were designed to illustrate this type of modification. As in the design of the HBV fusion proteins represented described above, to produce these additional fusion proteins, individual HBV antigens within the fusion were optimized or modified to reduce the size of the segments in the protein (e.g., to ensure that the protein represented less than ⅔ of the HBV genome), as well as to maximize the inclusion of T cell epitopes that have been associated with an immune response in acute/self-limiting HBV infection and/or chronic HBV infection, to maximize conserved epitopes, to minimize non-natural sequences, and also to utilize consensus sequences for each of genotype A-D that were built from multiple sources of HBV sequences (e.g., Yu and Yuan et al, 2010, for S, Core and X, where consensus sequences were generated from 322 HBV sequences, or for Pol (RT), from the Stanford University HIV Drug Resistance Database, HBVseq and HBV Site Release Notes). In designing the following four exemplary fusion proteins comprising HBV antigens, the consensus sequence for the given HBV genotype was used unless using the consensus sequence altered one of the known acute self-limiting T cells epitopes or one of the known polymerase escape mutation sites, in which case, these positions followed the published sequence for these epitopes or mutation sites. Additional antigens could be constructed based solely on consensus sequences or using other published epitopes as they become known.

Example 7 describes a fusion protein that is similar in design to the fusion protein represented by SEQ ID NO:101 or SEQ ID NO:102 (illustrated schematically by FIG. 3), but that is based on a consensus sequence for HBV genotype A. This fusion protein is a single polypeptide with the following sequence elements fused in frame from N- to C-terminus, represented by SEQ ID NO:107 (optional sequences that are not HBV sequences are not included in the base sequence of SEQ ID NO:107, but may be added to this sequence as in the construct described in Example 7): (1) optionally, an N-terminal peptide that is a synthetic N-terminal peptide designed to impart resistance to proteasomal degradation and stabilize expression represented by SEQ ID NO:37, which may be substituted by an N-terminal peptide represented by SEQ ID NO:89, SEQ ID NO:90, or another N-terminal peptide suitable for use with a yeast-based immunotherapeutic as described herein; (2) optionally, a linker peptide of from one to three or more amino acids linker sequences of one, two, three or more amino acids, such as the two amino acid linker of Thr-Ser; (3) an optimized portion of an HBV large (L) surface antigen represented by positions 1 to 249 of SEQ ID NO:107, which is a consensus sequence for HBV genotype A utilizing the design strategy discussed above; (4) an optimized portion of the reverse transcriptase (RT) domain of HBV polymerase represented by positions 250 to 477 of SEQ ID NO:107, which is a consensus sequence for HBV genotype A utilizing the design strategy discussed above; (5) an optimized portion of HBV Core protein represented by positions 478 to 629 of SEQ ID NO:107, which is a consensus sequence for HBV genotype A utilizing the design strategy discussed above; (6) an optimized portion of HBV X antigen represented by positions 630 to 689 of SEQ ID NO:107, which is a consensus sequence for HBV genotype A utilizing the design strategy discussed above; and (7) optionally, a hexahistidine tag. A yeast-based immunotherapy composition expressing this fusion protein is also referred to herein as GI-13010.

Example 7 also describes a fusion protein that is similar in design to the fusion protein represented by SEQ ID NO:101 or SEQ ID NO:102 (illustrated schematically by FIG. 3), but that is based on a consensus sequence for HBV genotype B. This fusion protein is a single polypeptide with the following sequence elements fused in frame from N- to C-terminus, represented by SEQ ID NO:108 (optional sequences that are not HBV sequences are not included in the base sequence of SEQ ID NO:108, but may be added to this sequence as in the construct described in Example 7): (1) optionally, an N-terminal peptide that is a synthetic N-terminal peptide designed to impart resistance to proteasomal degradation and stabilize expression represented by SEQ ID NO:37, which may be substituted by an N-terminal peptide represented by SEQ ID NO:89, SEQ ID NO:90, or another N-terminal peptide suitable for use with a yeast-based immunotherapeutic as described herein; (2) optionally, a linker peptide of from one to three or more amino acids linker sequences of one, two, three or more amino acids, such as the two amino acid linker of Thr-Ser; (3) an optimized portion of an HBV large (L) surface antigen represented by positions 1 to 249 of SEQ ID NO:108, which is a consensus sequence for HBV genotype B utilizing the design strategy discussed above; (4) an optimized portion of the reverse transcriptase (RT) domain of HBV polymerase represented by positions 250 to 477 of SEQ ID NO:108, which is a consensus sequence for HBV genotype B utilizing the design strategy discussed above; (5) an optimized portion of HBV Core protein represented by positions 478 to 629 of SEQ ID NO:108, which is a consensus sequence for HBV genotype B utilizing the design strategy discussed above; (6) an optimized portion of HBV X antigen represented by positions 630 to 689 of SEQ ID NO:108, which is a consensus sequence for HBV genotype B utilizing the design strategy discussed above; and (7) optionally, a hexahistidine tag. A yeast-based immunotherapy composition expressing this fusion protein is also referred to herein as GI-13011.

Example 7 also describes a fusion protein that is similar in design to the fusion protein represented by SEQ ID NO:101 or SEQ ID NO:102 (illustrated schematically by FIG. 3), but that is based on a consensus sequence for HBV genotype C. This fusion protein is a single polypeptide with the following sequence elements fused in frame from N- to C-terminus, represented by SEQ ID NO:109 (optional sequences that are not HBV sequences are not included in the base sequence of SEQ ID NO:109, but may be added to this sequence as in the construct described in Example 7): (1) optionally, an N-terminal peptide that is a synthetic N-terminal peptide designed to impart resistance to proteasomal degradation and stabilize expression represented by SEQ ID NO:37, which may be substituted by an N-terminal peptide represented by SEQ ID NO:89, SEQ ID NO:90, or another N-terminal peptide suitable for use with a yeast-based immunotherapeutic as described herein; (2) optionally, a linker peptide of from one to three or more amino acids linker sequences of one, two, three or more amino acids, such as the two amino acid linker of Thr-Ser; (3) an optimized portion of an HBV large (L) surface antigen represented by positions 1 to 249 of SEQ ID NO:109, which is a consensus sequence for HBV genotype C utilizing the design strategy discussed above; (4) an optimized portion of the reverse transcriptase (RT) domain of HBV polymerase represented by positions 250 to 477 of SEQ ID NO:109, which is a consensus sequence for HBV genotype C utilizing the design strategy discussed above; (5) an optimized portion of HBV Core protein represented by positions 478 to 629 of SEQ ID NO:109, which is a consensus sequence for HBV genotype C utilizing the design strategy discussed above; (6) an optimized portion of HBV X antigen represented by positions 630 to 689 of SEQ ID NO:109, which is a consensus sequence for HBV genotype C utilizing the design strategy discussed above; and (7) optionally, a hexahistidine tag. A yeast-based immunotherapy composition expressing this fusion protein is also referred to herein as GI-13012.

Example 7 also describes a fusion protein that is similar in design to the fusion protein represented by SEQ ID NO:101 or SEQ ID NO:102 (illustrated schematically by FIG. 3), but that is based on a consensus sequence for HBV genotype D. This fusion protein is a single polypeptide with the following sequence elements fused in frame from N- to C-terminus, represented by SEQ ID NO:110 (optional sequences that are not HBV sequences are not included in the base sequence of SEQ ID NO:110, but may be added to this sequence as in the construct described in Example 7): (1) optionally, an N-terminal peptide that is a synthetic N-terminal peptide designed to impart resistance to proteasomal degradation and stabilize expression represented by SEQ ID NO:37, which may be substituted by an N-terminal peptide represented by SEQ ID NO:89, SEQ ID NO:90, or another N-terminal peptide suitable for use with a yeast-based immunotherapeutic as described herein; (2) optionally, a linker peptide of from one to three or more amino acids linker sequences of one, two, three or more amino acids, such as the two amino acid linker of Thr-Ser; (3) an optimized portion of an HBV large (L) surface antigen represented by positions 1 to 249 of SEQ ID NO:110, which is a consensus sequence for HBV genotype D utilizing the design strategy discussed above; (4) an optimized portion of the reverse transcriptase (RT) domain of HBV polymerase represented by positions 250 to 477 of SEQ ID NO:110, which is a consensus sequence for HBV genotype D utilizing the design strategy discussed above; (5) an optimized portion of HBV Core protein represented by positions 478 to 629 of SEQ ID NO:110, which is a consensus sequence for HBV genotype D utilizing the design strategy discussed above; (6) an optimized portion of HBV X antigen represented by positions 630 to 689 of SEQ ID NO:110, which is a consensus sequence for HBV genotype D utilizing the design strategy discussed above; and (7) optionally, a hexahistidine tag. A yeast-based immunotherapy composition expressing this fusion protein which comprises an N-terminal sequence represented by SEQ ID NO:37 is referred to herein as GI-13013. A yeast-based immunotherapy composition expressing this fusion protein which comprises an N-terminal sequence represented by SEQ ID NO:89 is referred to herein as GI-13014.

As discussed above, it is one embodiment of the invention to change the order of HBV protein segments within a fusion protein described herein. Accordingly, although the constructs utilizing four HBV proteins as described above are provided in the order of a surface antigen fused to a polymerase antigen fused to a Core antigen fused to an X antigen, the invention is not limited to this particular order of proteins within the construct, and indeed, other arrangements of fusion segments may be used and in some aspects, may improve the resulting immunotherapeutic compositions. For example, rearrangement of segments within a fusion protein may improve or modify expression of the HBV antigen in yeast, or may improve or modify the immunogenicity or other functional attribute of the HBV antigen. In one aspect of this embodiment, the invention contemplates beginning with one HBV antigen that expresses well in yeast and/or provides positive functional data (e.g., is immunogenic), and adding additional HBV proteins or domains to that HBV antigen in order to expand the potential antigens or epitopes that are contained within the HBV antigen. Example 8 provides an example of additional arrangements of the four HBV proteins described above.

Example 8 describes a fusion protein that contains sequences from HBV surface antigen, core protein, polymerase and X antigen, where the sequences were derived from segments of the fusion proteins represented by SEQ ID NO:110 and SEQ ID NO:118, and where the fusion protein utilizes a different order of fusion segments as compared to SEQ ID NO:110. This antigen is based on a consensus sequence for HBV genotype D; however, it would be straightforward to produce a fusion protein having a similar overall structure using the corresponding fusion segments from the fusion proteins represented by SEQ ID NO:107 or SEQ ID NO:112 (genotype A), SEQ ID NO:108 or SEQ ID NO:114 (genotype B), SEQ ID NO:109 or SEQ ID NO:116 (genotype C), or using the corresponding sequences from a different HBV genotype, sub-genotype, consensus sequence or strain. In this example, yeast (e.g., *Saccharomyces cerevisiae*) were engineered to express this fusion protein under the control of the copper-inducible promoter, CUP1, and the resulting yeast-HBV immunotherapy composition can be referred to herein as GI-13017, schematically illustrated in FIG. 10. The fusion protein represented by SEQ ID NO:124 comprises, in order, surface antigen, core, polymerase and X antigen sequences, as a single polypeptide with the following sequence elements fused in frame from N- to C-terminus, represented by SEQ ID NO:124 (optional sequences that are not HBV sequences are not included in the base sequence of SEQ ID NO:124, but may be added to this sequence as in the construct described in Example 8): (1) optionally, an N-terminal peptide that is a synthetic N-terminal peptide designed to impart resistance to proteasomal degradation and stabilize expression represented by SEQ ID NO:37 (in the construct described in Example 8), which may be substituted by an N-terminal peptide represented by SEQ ID NO:89, SEQ ID NO:90, or another N-terminal peptide suitable for use with a yeast-based immunotherapeutic as described herein; (2) optionally, a linker peptide of from one to three or more amino acids, such as the two amino acid linker of Thr-Ser (in the construct described in Example 8); (3) the amino acid sequence of a near full-length (minus position 1) consensus sequence for HBV genotype D large (L) surface antigen represented by positions 1 to 399 of SEQ ID NO:124 (corresponding to positions 1 to 399 of SEQ ID NO:118); 4) the amino acid sequence of a consensus sequence for HBV genotype D core antigen represented by positions 400 to 581 of SEQ ID NO:124 (corresponding to positions 400 to 581 of SEQ ID NO:118); (5) an optimized portion of the reverse transcriptase (RT) domain of HBV polymerase using a consensus sequence for HBV genotype D, represented by positions 582 to 809 of SEQ ID NO:124 (corresponding to positions to 250 to 477 of SEQ ID NO:110); (6) an optimized portion of HBV X antigen using a consensus sequence for HBV genotype D, represented by positions 810 to 869 of SEQ ID NO:124 (corresponding to positions 630 to 689 of SEQ ID NO:110); and (7) optionally, a hexahistidine tag (in the construct described in Example 8). SEQ ID NO:124 contains multiple T cell epitopes (human and murine), which can be found in Table 5. A nucleic acid sequence encoding the fusion protein of SEQ ID NO:124 (codon-optimized for expression in yeast) is represented herein by SEQ ID NO:123.

Example 8 also describes another fusion protein that contains sequences from HBV surface antigen, core protein, X antigen, and polymerase, where the sequences were derived from segments of the fusion proteins represented by SEQ ID NO:110 and SEQ ID NO:118, but where the fusion protein utilizes a different order of fusion segments as compared to SEQ ID NO:110. This antigen is also based on a consensus sequence for HBV genotype D; however, it would be straightforward to produce a fusion protein having a similar overall structure using the corresponding fusion segments from the fusion proteins represented by SEQ ID NO:107 or SEQ ID NO:112 (genotype A), SEQ ID NO:108 or SEQ ID NO:114 (genotype B), SEQ ID NO:109 or SEQ ID NO:116 (genotype C), or using the corresponding sequences from a different HBV genotype, sub-genotype, consensus sequence or strain. In this example, yeast (e.g., *Saccharomyces cerevisiae*) were engineered to express this fusion protein under the control of the copper-inducible promoter, CUP1, and the resulting yeast-HBV immunotherapy composition can be referred to herein as GI-13018, schematically illustrated in FIG. 11. The fusion protein represented by SEQ ID NO:126 comprises, in order, surface antigen, core, X antigen, and polymerase sequences, as a single polypeptide with the following sequence elements fused in frame from N- to C-terminus, represented by SEQ ID NO:126 (optional sequences that are not HBV sequences are not included in the base sequence of SEQ ID NO:126, but may be added to this sequence as in the construct described in Example 8): (1) optionally, an N-terminal peptide that is a synthetic N-terminal peptide designed to impart resistance to proteasomal degradation and stabilize expression represented by SEQ ID NO:37 (in the construct described in Example 8), which may be substituted by an N-terminal peptide represented by SEQ ID NO:89, SEQ ID NO:90, or another N-terminal peptide suitable for use with a yeast-based immunotherapeutic as described herein; (2) optionally, a linker peptide of from one to three or more amino acids, such as the two amino acid linker of Thr-Ser (in the construct described in Example 8); (3) the amino acid sequence of a near full-length (minus position 1) consensus sequence for HBV genotype D large (L) surface antigen represented by positions 1 to 399 of SEQ ID NO:126 (corresponding to positions 1 to 399 of SEQ ID NO:118); 4) the amino acid sequence of a consensus sequence for HBV genotype D core antigen represented by positions 400 to 581 of SEQ ID NO:126 (corresponding to positions 400 to 581 of SEQ ID NO:118); (5) an optimized portion of HBV X antigen using a consensus sequence for HBV genotype D, represented by positions 582 to 641 of SEQ ID NO:126 (corresponding to positions 630 to 689 of SEQ ID NO:110); (5) an optimized portion of the reverse transcriptase (RT) domain of HBV polymerase using a consensus sequence for HBV genotype D, represented by positions 642 to 869 of SEQ ID NO:126 (corresponding to positions to 250 to 477 of SEQ ID NO:110); and (7) optionally, a hexahistidine tag (in the construct described in Example 8). SEQ ID NO:126 contains multiple T cell epitopes (human and murine), which can be found in Table 5. A nucleic acid sequence encoding the fusion protein of SEQ ID NO:126 (codon-optimized for expression in yeast) is represented herein by SEQ ID NO:125.

Example 8 describes another fusion protein that contains sequences from HBV polymerase, X antigen, surface antigen, core protein, where the sequences were derived from segments of the fusion proteins represented by SEQ ID NO:110 and SEQ ID NO:118, but where the fusion protein utilizes a different order of fusion segments as compared to SEQ ID NO:110. This antigen is based on a consensus sequence for HBV genotype D; however, it would be straightforward to produce a fusion protein having a similar overall structure using the corresponding fusion segments from the fusion proteins represented by SEQ ID NO:107 or SEQ ID NO:112 (genotype A), SEQ ID NO:108 or SEQ ID NO:114 (genotype B), SEQ ID NO:109 or SEQ ID NO:116 (genotype C), or using the corresponding sequences from a different HBV genotype, sub-genotype, consensus sequence or strain. In this example, yeast (e.g., *Saccharomyces cerevisiae*) were engineered to express this fusion protein under the control of the copper-inducible promoter, CUP1, and the resulting yeast-HBV immunotherapy composition can be referred to herein as GI-13021, schematically illustrated in FIG. 14. The fusion protein represented by SEQ ID NO:132 comprises, in order, polymerase, X antigen, surface antigen, and core, as a single polypeptide with the following sequence elements fused in frame from N- to C-terminus, represented by SEQ ID NO:132 (optional sequences that are not HBV sequences are not included in the base sequence of SEQ ID NO:132, but may be added to this sequence as in the construct described in Example 8): (1) optionally, an N-terminal peptide that is a synthetic N-terminal peptide designed to impart resistance to proteasomal degradation and stabilize expression represented by SEQ ID NO:37 (in the construct described in Example 8), which may be substituted by an N-terminal peptide represented by SEQ ID NO:89, SEQ ID NO:90, or another N-terminal peptide suitable for use with a yeast-based immunotherapeutic as described herein; (2) optionally, a linker peptide of from one to three or more amino acids, such as the two amino acid linker of Thr-Ser (in the construct described in Example 8); (3) an optimized portion of the reverse transcriptase (RT) domain of HBV polymerase using a consensus sequence for HBV genotype D, represented by positions 1 to 228 of SEQ ID NO:132 (corresponding to positions to 250 to 477 of SEQ ID NO:110); (4) an optimized portion of HBV X antigen using a consensus sequence for HBV genotype D, represented by positions 229 to 288 of SEQ ID NO:132 (corresponding to positions 630 to 689 of SEQ ID NO:110); (5) the amino acid sequence of a near full-length (minus position 1) consensus sequence for HBV genotype D large (L) surface antigen represented by positions 289 to 687 of SEQ ID NO:132 (corresponding to positions 1 to 399 of SEQ ID NO:118); (6) the amino acid sequence of a consensus sequence for HBV genotype D core antigen represented by positions 688 to 869 of SEQ ID NO:132 (corresponding to positions 400 to 581 of SEQ ID NO:118); and (7) optionally, a hexahistidine tag (in the construct described in Example 8). SEQ ID NO:132 contains multiple T cell epitopes (human and murine), which can be found in Table 5. A nucleic acid sequence encoding the fusion protein of SEQ ID NO:132 (codon-optimized for expression in yeast) is represented herein by SEQ ID NO:131.

Example 8 also describes a fusion protein that contains sequences from HBV X antigen, polymerase, surface antigen, and core protein, where the sequences were derived from segments of the fusion proteins represented by SEQ ID NO:110 and SEQ ID NO:118, but where the fusion protein utilizes a different order of fusion segments as compared to SEQ ID NO:110. This antigen is based on a consensus sequence for HBV genotype D; however, it would be straightforward to produce a fusion protein having a similar overall structure using the corresponding fusion segments from the fusion proteins represented by SEQ ID NO:107 or SEQ ID NO:112 (genotype A), SEQ ID NO:108 or SEQ ID NO:114 (genotype B), SEQ ID NO:109 or SEQ ID NO:116 (genotype C), or using the corresponding sequences from a different HBV genotype, sub-genotype, consensus sequence or strain. In this example, yeast (e.g., *Saccharomyces cerevisiae*) were engineered to express this fusion protein under the control of the copper-inducible promoter, CUP1, and the resulting yeast-HBV immunotherapy composition can be referred to herein as GI-13022, schematically illustrated in FIG. 15. The fusion protein represented by SEQ ID NO:134 comprises, in order, X antigen, polymerase, surface antigen, and core protein, as a single polypeptide with the following sequence elements fused in frame from N- to C-terminus, represented by SEQ ID NO:134 (optional sequences that are not HBV sequences are not included in the base sequence of SEQ ID NO:134, but may be added to this sequence as in the construct described in Example 8): (1) optionally, an N-terminal peptide that is a synthetic N-terminal peptide designed to impart resistance to proteasomal degradation and stabilize expression represented by SEQ ID NO:37 (in the construct described in Example 8), which may be substituted by an N-terminal peptide represented by SEQ ID NO:89, SEQ ID NO:90, or another N-terminal peptide suitable for use with a yeast-based immunotherapeutic as described herein; (2) optionally, a linker peptide of from one to three or more amino acids, such as the two amino acid linker of Thr-Ser (in the construct described in Example 8); (3) an optimized portion of HBV X antigen using a consensus sequence for HBV genotype D, represented by positions 1 to 60 of SEQ ID NO:134 (corresponding to positions 630 to 689 of SEQ ID NO:110); (4) an optimized portion of the reverse transcriptase (RT) domain of HBV polymerase using a consensus sequence for HBV genotype D, represented by positions 61 to 288 of SEQ ID NO:134 (corresponding to positions to 250 to 477 of SEQ ID NO:110); (5) the amino acid sequence of a near full-length (minus position 1) consensus sequence for HBV genotype D large (L) surface antigen represented by positions 289 to 687 of SEQ ID NO:134 (corresponding to positions 1 to 399 of SEQ ID NO:118); (6) the amino acid sequence of a consensus sequence for HBV genotype D core antigen represented by positions 688 to 869 of SEQ ID NO:134 (corresponding to positions 400 to 581 of SEQ ID NO:118); and (7) optionally, a hexahistidine tag (in the construct described in Example 8). SEQ ID NO:134 contains multiple T cell epitopes (human and murine), which can be found in Table 5. A nucleic acid sequence encoding the fusion protein of SEQ ID NO:134 (codon-optimized for expression in yeast) is represented herein by SEQ ID NO:133.

HBV Antigens Comprising Surface Antigen, Core Protein and X Antigen. In one embodiment of the invention, the HBV antigen(s) for use in a composition or method of the invention is a fusion protein comprising HBV antigens, wherein the HBV antigens comprise or consist of: the HBV surface antigen (large (L), medium (M) or small (S)) or at least one structural, functional or immunogenic domain thereof), the HBV core protein (HBcAg) or HBV e-antigen (HBeAg) or at least one structural, functional or immunogenic domain thereof, and the HBV X antigen (HBx) or at least one structural, functional or immunogenic domain thereof. In one aspect, any one or more of the HBV surface antigen, HBV core protein, HBV e-antigen, HBV X antigen, or domain thereof, is full-length or near full-length. In one aspect, any one or more of the HBV surface antigen, HBV core protein, HBV e-antigen, HBV X antigen, or domain thereof comprises at least 80%, 85%, 90%, 91%, 92%, 93%, 94%, 95%, 96%, 97%, 98%, or 99% of the linear sequence of a full-length HBV surface antigen, HBV core protein, HBV e-antigen, HBV X antigen, or domain thereof, respectively, or of the amino acid sequences represented by SEQ ID NO:97 (optimized HBV surface antigen), SEQ ID NO:99 (optimized core protein), SEQ ID NO:100 (optimized X antigen), or a corresponding sequence from another HBV strain, as applicable. In one aspect, any one or more of the HBV surface antigen, HBV core protein, HBV e-antigen, HBV X antigen, or domain thereof is at least 80%, 85%, 90%, 91%, 92%, 93%, 94%, 95%, 96%, 97%, 98%, or 99% identical to a full-length HBV surface antigen, HBV core protein, HBV e-antigen, HBV X antigen, or domain thereof, respectively, or to the amino acid sequences represented by SEQ ID NO:97 (optimized HBV surface antigen), SEQ ID NO:99 (optimized core protein), SEQ ID NO:100 (optimized X antigen), or a corresponding sequence from another HBV strain, as applicable. A variety of suitable and exemplary sequences for additional HBV surface antigens, HBV core antigens, and HBV X antigens useful in this construct are described herein.

Example 8 describes a fusion protein that contains sequences from HBV surface antigen, core protein, and X antigen, where the sequences were derived from segments of the fusion proteins represented by SEQ ID NO:110 and SEQ ID NO:118. This antigen is based on a consensus sequence for HBV genotype D; however, it would be straightforward to produce a fusion protein having a similar overall structure using the corresponding fusion segments from the fusion proteins represented by SEQ ID NO:107 or SEQ ID NO:112 (genotype A), SEQ ID NO:108 or SEQ ID NO:114 (genotype B), SEQ ID NO:109 or SEQ ID NO:116 (genotype C), or using the corresponding sequences from a different HBV genotype, sub-genotype, consensus sequence or strain. In this example, yeast (e.g., *Saccharomyces cerevisiae*) were engineered to express this fusion protein under the control of the copper-inducible promoter, CUP1, and the resulting yeast-HBV immunotherapy composition can be referred to herein as GI-13016, schematically illustrated in FIG. 9. The fusion protein represented by SEQ ID NO:122 comprises, in order, surface antigen, core, and X antigen sequences, as a single polypeptide with the following sequence elements fused in frame from N- to C-terminus, represented by SEQ ID NO:122 (optional sequences that are not HBV sequences are not included in the base sequence of SEQ ID NO:122, but may be added to this sequence as in the construct described in Example 8): (1) optionally, an N-terminal peptide that is a synthetic N-terminal peptide designed to impart resistance to proteasomal degradation and stabilize expression represented by SEQ ID NO:37 (in the construct described in Example 8), which may be substituted by an N-terminal peptide represented by SEQ ID NO:89, SEQ ID NO:90, or another N-terminal peptide suitable for use with a yeast-based immunotherapeutic as described herein; (2) optionally, a linker peptide of from one to three or more amino acids, such as the two amino acid linker of Thr-Ser (in the construct described in Example 8); (3) the amino acid sequence of a near full-length (minus position 1) consensus sequence for HBV genotype D large (L) surface antigen represented by positions 1 to 399 of SEQ ID NO:122 (corresponding to positions 1 to 399 of SEQ ID NO:118); 4) the amino acid sequence of a consensus sequence for HBV genotype D core antigen represented by positions 400 to 581 of SEQ ID NO:122 (corresponding to positions 400 to 581 of SEQ ID NO:118); (5) an optimized portion of HBV X antigen using a consensus sequence for HBV genotype D, represented by positions 582 to 641 of SEQ ID NO:122 (corresponding to positions 630 to 689 of SEQ ID NO:110); and (6) optionally, a hexahistidine tag (in the construct described in Example 8). SEQ ID NO:122 contains multiple T cell epitopes (human and murine), which can be found in Table 5. A nucleic acid sequence encoding the fusion protein of SEQ ID NO:122 (codon-optimized for expression in yeast) is represented herein by SEQ ID NO:121.

Example 8 also describes a fusion protein that contains sequences from HBV surface antigen, core protein, and X antigen, where, as in the fusion protein comprising SEQ ID NO:122, the sequences were derived from segments of the fusion proteins represented by SEQ ID NO:110 and SEQ ID NO:118. This fusion protein differs from the fusion protein comprising SEQ ID NO:122, however, in the arrangement of the fusion segments within the fusion protein. This antigen is based on a consensus sequence for HBV genotype D; however, it would be straightforward to produce a fusion protein having a similar overall structure using the corresponding fusion segments from the fusion proteins represented by SEQ ID NO:107 or SEQ ID NO:112 (genotype A), SEQ ID NO:108 or SEQ ID NO:114 (genotype B), SEQ ID NO:109 or SEQ ID NO:116 (genotype C), or using the corresponding sequences from a different HBV genotype, sub-genotype, consensus sequence or strain. In this example, yeast (e.g., *Saccharomyces cerevisiae*) were engineered to express this fusion protein under the control of the copper-inducible promoter, CUP1, and the resulting yeast-HBV immunotherapy composition can be referred to herein as GI-13020, schematically illustrated in FIG. 13. The fusion protein represented by SEQ ID NO:130 comprises, in order, X antigen, surface antigen, and core antigen sequences, as a single polypeptide with the following sequence elements fused in frame from N- to C-terminus, represented by SEQ ID NO:130 (optional sequences that are not HBV sequences are not included in the base sequence of SEQ ID NO:130, with the exception of the Leu-Glu linker between the X antigen segment and the surface antigen segment in the construct exemplified here, but may be added to this sequence as in the construct described in Example 8): (1) optionally, an N-terminal peptide that is a synthetic N-terminal peptide designed to impart resistance to proteasomal degradation and stabilize expression represented by SEQ ID NO:37 (in the construct described in Example 8), which may be substituted by an N-terminal peptide represented by SEQ ID NO:89, SEQ ID NO:90, or another N-terminal peptide suitable for use with a yeast-based immunotherapeutic as described herein; (2) optionally, a linker peptide of from one to three or more amino acids, such as the two amino acid linker of Thr-Ser (in the construct described in Example 8); (3) an optimized portion of HBV X antigen using a consensus sequence for HBV genotype D, represented by positions 1 to 60 of SEQ ID NO:130 (corresponding to positions 630 to 689 of SEQ ID NO:110); (4) optionally, a linker peptide of from one to three or more amino acids, such as the two amino acid linker of Leu-Glu (in the construct described in Example 8), represented by positions 61 to 62 of SEQ ID NO:130; (5) the amino acid sequence of a near full-length (minus position 1) consensus sequence for HBV genotype D large (L) surface antigen represented by positions 63 to 461 of SEQ ID NO:130 (corresponding to positions 1 to 399 of SEQ ID NO:118); (6) the amino acid sequence of a consensus sequence for HBV genotype D core antigen represented by positions 462 to 643 of SEQ ID NO:130 (corresponding to positions 400 to 581 of SEQ ID NO:118); and (7) optionally, a hexahistidine tag (in the construct described in Example 8). SEQ ID NO:130 contains multiple T cell epitopes (human and murine), which can be found in Table 5. The amino acid sequence of the complete fusion protein described in Example 8 comprising SEQ ID NO:130 and including the N- and C-terminal peptides and all linkers is represented herein by SEQ ID NO:150. A nucleic acid sequence encoding the fusion protein of SEQ ID NO:130 or SEQ ID NO:150 (codon-optimized for expression in yeast) is represented herein by SEQ ID NO:129.

HBV Antigens Comprising Surface Antigen, Core Protein and Polymerase. In one embodiment of the invention, the HBV antigen(s) for use in a composition or method of the invention is a fusion protein comprising HBV antigens, wherein the HBV antigens comprise or consist of: the HBV surface antigen (large (L), medium (M) or small (S)) or at least one structural, functional or immunogenic domain thereof), the HBV core protein (HBcAg) or HBV e-antigen (HBeAg) or at least one structural, functional or immunogenic domain thereof, and the HBV polymerase or at least one structural, functional or immunogenic domain thereof (e.g., the reverse transcriptase (RT) domain). In one aspect, any one or more of the HBV surface antigen, HBV core protein, HBV e-antigen, HBV polymerase, or domain thereof, is full-length or near full-length. In one aspect, any one or more of the HBV surface antigen, HBV core protein, HBV e-antigen, HBV polymerase, or domain thereof comprises at least 80%, 85%, 90%, 91%, 92%, 93%, 94%, 95%, 96%, 97%, 98%, or 99% of the linear sequence of a full-length HBV surface antigen, HBV core protein, HBV e-antigen, HBV polymerase, or domain thereof, respectively, or of the amino acid sequences represented by SEQ ID NO:97 (optimized HBV surface antigen), SEQ ID NO:99 (optimized core protein), SEQ ID NO:98 (optimized polymerase), or a corresponding sequence from another HBV strain, as applicable. In one aspect, any one or more of the HBV surface antigen, HBV core protein, HBV e-antigen, HBV polymerase, or domain thereof is at least 80%, 85%, 90%, 91%, 92%, 93%, 94%, 95%, 96%, 97%, 98%, or 99% identical to a full-length HBV surface antigen, HBV core protein, HBV e-antigen, HBV polymerase, or domain thereof, respectively, or to the amino acid sequences represented by SEQ ID NO:97 (optimized HBV surface antigen), SEQ ID NO:99 (optimized core protein), SEQ ID NO:98 (optimized polymerase), or a corresponding sequence from another HBV strain, as applicable. A variety of suitable and exemplary sequences for HBV surface antigens, HBV polymerase antigens, and HBV core antigens are described herein.

Figure 7:
FIG. 7 is a schematic drawing showing the basic structure of a recombinant nucleic acid molecule encoding an HBV surface antigen/polymerase/core fusion protein useful in a yeast-based immunotherapeutic composition of the invention.

One example of such a fusion protein is schematically represented in FIG. 7. An example of a composition comprising this fusion protein is described in Example 3. In this embodiment, yeast (e.g., *Saccharomyces cerevisiae*) are engineered to express various HBV surface-polymerase-core fusion proteins under the control of the copper-inducible promoter, CUP1, or the TEF2 promoter. In each case, the fusion protein is a single polypeptide with the following sequence elements fused in frame from N- to C-terminus, represented by SEQ ID NO:41: (1) an N-terminal peptide to impart resistance to proteasomal degradation and stabilize expression (e.g., positions 1 to 5 of SEQ ID NO:41); 2) an amino acid sequence of the amino HBV hepatocyte receptor domain of the pre-S1 portion of HBV large (L) surface protein (unique to L) (e.g., positions 21-47 of SEQ ID NO:11 or positions 6 to 32 of SEQ ID NO:41); 3) the amino acid sequence of an HBV small (S) surface protein (e.g., positions 176 to 400 of SEQ ID NO:11 or positions 33 to 257 of SEQ ID NO:41); 4) a two amino acid spacer/linker to facilitate cloning and manipulation of the sequences (e.g., positions 258 and 259 of SEQ ID NO:41); 5) the amino acid sequence of an HBV polymerase comprising the reverse transcriptase domain (e.g., positions 247 to 691 of SEQ ID NO:10 or positions 260 to 604 of SEQ ID NO:41); 6) the amino acid sequence of an HBV core protein (e.g., positions 31-212 of SEQ ID NO:9 or positions 605 to 786 of SEQ ID NO:41); and 7) a hexahistidine tag (e.g., positions 787 to 792 of SEQ ID NO:41). The sequence also contains epitopes or domains that are believed to enhance the immunogenicity of the fusion protein. In addition, in one embodiment, the sequence of this construct can be modified to introduce one or more or all of the following anti-viral resistance mutations: rtM204I, rtL180M, rtM204V, rtV173L, rtN236T, rtA194T (positions given with respect to the full-length amino acid sequence for HBV polymerase). In one embodiment, six different immunotherapy compositions are created, each one containing one of these mutations. In other embodiments, all or some of the mutations are included in a single fusion protein. In one embodiment, this construct also contains one or more anti-viral resistance mutations in the surface antigen. The amino acid segments used in any of the fusion proteins described herein can be modified by the use of additional amino acids flanking either end of any domain; the examples provided herein are exemplary. For example, a fusion protein according to this embodiment can include 1) an amino acid sequence of the amino HBV hepatocyte receptor domain of the pre-S1 portion of HBV large (L) surface protein (unique to L) (e.g., positions 21-47 of SEQ ID NO:11 or positions 6 to 32 of SEQ ID NO:41); 2) the amino acid sequence of an HBV small (S) surface protein (e.g., positions 176 to 400 of SEQ ID NO:11 or positions 33 to 257 of SEQ ID NO:41); 3) the amino acid sequence of an HBV polymerase comprising the reverse transcriptase domain (e.g., positions 247 to 691 of SEQ ID NO:10 or positions 260 to 604 of SEQ ID NO:41); and 4) the amino acid sequence of an HBV core protein (e.g., positions 31-212 of SEQ ID NO:9 or positions 605 to 786 of SEQ ID NO:41), and utilize no N- or C-terminal sequences, or utilize different N- or C-terminal sequences, and/or use linkers or no linkers between HBV sequences. In one embodiment, instead of the N-terminal peptide represented by positions 1-5 of SEQ ID NO:41, an N-terminal peptide represented by SEQ ID NO:89 or SEQ ID NO:90 is utilized, followed by the remainder of the fusion protein as described.

Another example of such a fusion protein is described in Example 8. Example 8 exemplifies a fusion protein that contains sequences from HBV surface antigen, core protein, and polymerase where the sequences were derived from segments of the fusion proteins represented by SEQ ID NO:110 and SEQ ID NO:118. This antigen is based on a consensus sequence for HBV genotype D; however, it would be straightforward to produce a fusion protein having a similar overall structure using the corresponding fusion segments from the fusion proteins represented by SEQ ID NO:107 or SEQ ID NO:112 (genotype A), SEQ ID NO:108 or SEQ ID NO:114 (genotype B), SEQ ID NO:109 or SEQ ID NO:116 (genotype C), or using the corresponding sequences from a different HBV genotype, sub-genotype, consensus sequence or strain. In this example, yeast (e.g., *Saccharomyces cerevisiae*) were engineered to express this fusion protein under the control of the copper-inducible promoter, CUP1, and the resulting yeast-HBV immunotherapy composition can be referred to herein as GI-13015, schematically illustrated in FIG. 8. The fusion protein represented by SEQ ID NO:120 comprises, in order, surface antigen, core protein, and polymerase sequences, as a single polypeptide with the following sequence elements fused in frame from N- to C-terminus, represented by SEQ ID NO:120 (optional sequences that are not HBV sequences are not included in the base sequence of SEQ ID NO:120, but may be added to this sequence as in the construct described in Example 8): (1) optionally, an N-terminal peptide that is a synthetic N-terminal peptide designed to impart resistance to proteasomal degradation and stabilize expression represented by SEQ ID NO:37 (in the construct described in Example 8), which may be substituted by an N-terminal peptide represented by SEQ ID NO:89, SEQ ID NO:90, or another N-terminal peptide suitable for use with a yeast-based immunotherapeutic as described herein; (2) optionally, a linker peptide of from one to three or more amino acids, such as the two amino acid linker of Thr-Ser (in the construct described in Example 8); (3) the amino acid sequence of a near full-length (minus position 1) consensus sequence for HBV genotype D large (L) surface antigen represented by positions 1 to 399 of SEQ ID NO:120 (corresponding to positions 1 to 399 of SEQ ID NO:118); (4) the amino acid sequence of a consensus sequence for HBV genotype D core antigen represented by positions 400 to 581 of SEQ ID NO:120 (corresponding to positions 400 to 581 of SEQ ID NO:118); (5) an optimized portion of the reverse transcriptase (RT) domain of HBV polymerase using a consensus sequence for HBV genotype D, represented by positions 582 to 809 of SEQ ID NO:120 (corresponding to positions to 250 to 477 of SEQ ID NO:110); and (6) optionally, a hexahistidine tag (in the construct described in Example 8). SEQ ID NO:120 contains multiple T cell epitopes (human and murine), which can be found in Table 5. A nucleic acid sequence encoding the fusion protein of SEQ ID NO:120 (codon-optimized for expression in yeast) is represented herein by SEQ ID NO:119.

Yet another example of such a fusion protein is described in Example 8. Example 8 exemplifies a fusion protein that contains sequences from HBV polymerase, surface antigen, and core protein, where the sequences were derived from segments of the fusion proteins represented by SEQ ID NO:110 and SEQ ID NO:118. This fusion protein differs from the fusion protein comprising SEQ ID NO:120 in the arrangement of the fusion segments within the fusion protein. This antigen is based on a consensus sequence for HBV genotype D; however, it would be straightforward to produce a fusion protein having a similar overall structure using the corresponding fusion segments from the fusion proteins represented by SEQ ID NO:107 or SEQ ID NO:112 (genotype A), SEQ ID NO:108 or SEQ ID NO:114 (genotype B), SEQ ID NO:109 or SEQ ID NO:116 (genotype C), or using the corresponding sequences from a different HBV genotype, sub-genotype, consensus sequence or strain. In this example, yeast (e.g., *Saccharomyces cerevisiae*) were engineered to express this fusion protein under the control of the copper-inducible promoter, CUP1, and the resulting yeast-HBV immunotherapy composition can be referred to herein as GI-13019, schematically illustrated in FIG. 12. The fusion protein represented by SEQ ID NO:128 comprises, in order, polymerase, surface antigen, and core sequences, as a single polypeptide with the following sequence elements fused in frame from N- to C-terminus, represented by SEQ ID NO:128 (optional sequences that are not HBV sequences are not included in the base sequence of SEQ ID NO:128, with the exception of the Leu-Glu linker between the polymerase segment and the surface antigen segment in the construct exemplified here, but may be added to this sequence as in the construct described in Example 8): (1) optionally, an N-terminal peptide that is a synthetic N-terminal peptide designed to impart resistance to proteasomal degradation and stabilize expression represented by SEQ ID NO:37 (in the construct described in Example 8), which may be substituted by an N-terminal peptide represented by SEQ ID NO:89, SEQ ID NO:90, or another N-terminal peptide suitable for use with a yeast-based immunotherapeutic as described herein; (2) optionally, a linker peptide of from one to three or more amino acids, such as the two amino acid linker of Thr-Ser (in the construct described in Example 8); (3) an optimized portion of the reverse transcriptase (RT) domain of HBV polymerase using a consensus sequence for HBV genotype D, represented by positions 1 to 228 of SEQ ID NO:128 (corresponding to positions to 250 to 477 of SEQ ID NO:110); (4) optionally, a linker peptide of from one to three or more amino acids, such as the two amino acid linker of Leu-Glu (in the construct described in Example 8), represented by positions 229 to 230 of SEQ ID NO:128; (5) the amino acid sequence of a near full-length (minus position 1) consensus sequence for HBV genotype D large (L) surface antigen represented by positions 231 to 629 of SEQ ID NO:128 (corresponding to positions 1 to 399 of SEQ ID NO:118); (6) the amino acid sequence of a consensus sequence for HBV genotype D core antigen represented by positions 630 to 811 of SEQ ID NO:128 (corresponding to positions 400 to 581 of SEQ ID NO:118); and (7) optionally, a hexahistidine tag (in the construct described in Example 8). SEQ ID NO:128 contains multiple T cell epitopes (human and murine), which can be found in Table 5. A nucleic acid sequence encoding the fusion protein of SEQ ID NO:128 (codon-optimized for expression in yeast) is represented herein by SEQ ID NO:127.

HBV Antigens Comprising Polymerase and Core Protein. In one embodiment of the invention, the HBV antigen(s) for use in a composition or method of the invention is a fusion protein comprising HBV antigens, wherein the HBV antigens comprise or consist of HBV polymerase (the RT domain) or at least one immunogenic domain thereof and an HBV core protein (HBcAg) or at least one immunogenic domain thereof. In one aspect, one or both of the RT domain of HBV polymerase or the HBV core protein is full-length or near full-length. In one aspect, one or both of the RT domain of HBV polymerase or the HBV core protein or a domain thereof comprises at least 80%, 85%, 90%, 91%, 92%, 93%, 94%, 95%, 96%, 97%, 98%, or 99% of the linear sequence of a full-length the RT domain of HBV polymerase or the HBV core protein or a domain thereof, respectively, or to the amino acid sequences represented by SEQ ID NO:98 (optimized HBV polymerase), SEQ ID NO:99 (optimized core protein), or a corresponding sequence from another HBV strain, as applicable. In one aspect, one or both of the RT domain of HBV polymerase or the HBV core protein or a domain thereof is at least 80%, 85%, 90%, 91%, 92%, 93%, 94%, 95%, 96%, 97%, 98%, or 99% identical to a full-length RT domain of HBV polymerase or the HBV core protein or a domain thereof, respectively, or to the amino acid sequences represented by SEQ ID NO:98 (optimized HBV polymerase), SEQ ID NO:99 (optimized core protein), or a corresponding sequence from another HBV strain, as applicable. A variety of suitable and exemplary sequences for HBV polymerase antigens and HBV core antigens are described herein.

Figure 4:
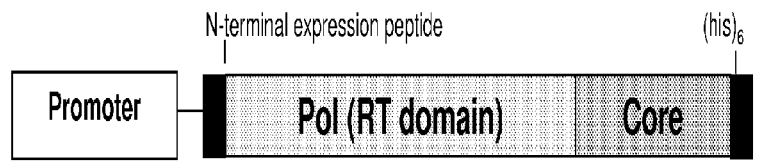
FIG. 4 is a schematic drawing showing the basic structure of a recombinant nucleic acid molecule encoding an HBV polymerase/core fusion protein useful in a yeast-based immunotherapeutic composition of the invention.

One example of this antigen is schematically represented in FIG. 4. One example of a composition comprising this fusion protein is described in Example 3. In this embodiment, yeast (e.g., *Saccharomyces cerevisiae*) are engineered to express various HBV polymerase-core fusion proteins as shown schematically in FIG. 4 under the control of the copper-inducible promoter, CUP1, or the TEF2 promoter. In each case, the fusion protein is a single polypeptide with the following sequence elements fused in frame from N- to C-terminus, represented by SEQ ID NO:38: (1) an N-terminal peptide to impart resistance to proteasomal degradation and stabilize expression (e.g., SEQ ID NO:37 or positions 1 to 6 of SEQ ID NO:38); 2) the amino acid sequence of a portion of the HBV genotype C polymerase including the reverse transcriptase domain (e.g., positions 347 to 691 of SEQ ID NO:10 or positions 7 to 351 of SEQ ID NO:38); 3) an HBV genotype C core protein (e.g., positions 31 to 212 of SEQ ID NO:9 or positions 352 to 533 of SEQ ID NO:38); and 4) a hexahistidine tag (e.g., positions 534 to 539 of SEQ ID NO:38). The sequence also contains epitopes or domains that are believed to enhance the immunogenicity of the fusion protein. The amino acid segments used in any of the fusion proteins described herein can be modified by the use of additional amino acids flanking either end of any domain; the examples provided herein are exemplary. For example, a fusion protein according to this embodiment can include 1) the amino acid sequence of a portion of the HBV genotype C polymerase including the reverse transcriptase domain (e.g., positions 347 to 691 of SEQ ID NO:10 or positions 7 to 351 of SEQ ID NO:38); and 2) an HBV genotype C core protein (e.g., positions 31 to 212 of SEQ ID NO:9 or positions 352 to 533 of SEQ ID NO:38), and utilize no N- or C-terminal sequences, or utilize different N- or C-terminal sequences, and/or use linkers or no linkers between HBV sequences. In one embodiment, instead of the N-terminal peptide represented by SEQ ID NO:37, an N-terminal peptide represented by SEQ ID NO:89 or SEQ ID NO:90 is utilized, followed by the remainder of the fusion protein.

HBV Antigens Comprising X Antigen and Core Protein. In one embodiment of the invention, the HBV antigen(s) for use in a composition or method of the invention is a fusion protein comprising HBV antigens, wherein the HBV antigens comprise or consist of HBV X antigen or at least one immunogenic domain thereof and HBV core protein (HBcAg) or at least one immunogenic domain thereof. In one aspect, one or both of the HBV X antigen or the HBV core protein is full-length or near full-length. In one aspect, one or both of the HBV X antigen or the HBV core protein or a domain thereof comprises at least 80%, 85%, 90%, 91%, 92%, 93%, 94%, 95%, 96%, 97%, 98%, or 99% of the linear sequence of a full-length HBV X antigen or HBV core protein or domain thereof, respectively, or to the amino acid sequences represented by SEQ ID NO:99 (optimized core protein), SEQ ID NO:100 (optimized X antigen), or a corresponding sequence from another HBV strain, as applicable. In one aspect, one or both of the HBV X antigen or the HBV core protein or a domain thereof is at least 80%, 85%, 90%, 91%, 92%, 93%, 94%, 95%, 96%, 97%, 98%, or 99% identical to a full-length HBV X antigen or HBV core protein or domain thereof, respectively, or to the amino acid sequences represented by SEQ ID NO:99 (optimized core protein), SEQ ID NO:100 (optimized X antigen), or a corresponding sequence from another HBV strain, as applicable. A variety of suitable and exemplary sequences for HBV core antigens and HBV X antigens are described herein.

Figure 5:
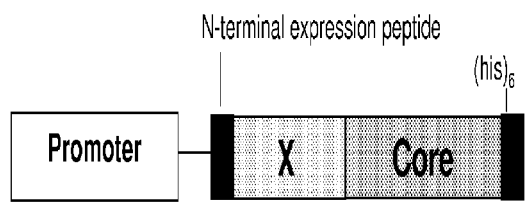
FIG. 5 is a schematic drawing showing the basic structure of a recombinant nucleic acid molecule encoding an HBV X/core fusion protein useful in a yeast-based immunotherapeutic composition of the invention.

This fusion protein is schematically represented in FIG. 5. An example of a composition comprising this fusion protein is described in Example 3. In this embodiment, yeast (e.g., *Saccharomyces cerevisiae*) are engineered to express various HBV X-core fusion proteins as shown schematically in FIG. 5 under the control of the copper-inducible promoter, CUP1, or the TEF2 promoter. In each case, the fusion protein is a single polypeptide with the following sequence elements fused in frame from N- to C-terminus, represented by SEQ ID NO:39 (1) an N-terminal peptide to impart resistance to proteasomal degradation and stabilize expression (e.g. SEQ ID NO:37 or positions 1 to 6 of SEQ ID NO:39); 2) the amino acid sequence of a near full-length (minus position 1) HBV genotype C X antigen (e.g., positions 2 to 154 of SEQ ID NO:12 or positions 7 to 159 of SEQ ID NO:39); 3) an HBV genotype C core protein (e.g., positions 31 to 212 of SEQ ID NO:9 or positions 160 to 341 of SEQ ID NO:39); and 4) a hexahistidine tag (e.g., positions 342 to 347 of SEQ ID NO:39). The sequence also contains epitopes or domains that are believed to enhance the immunogenicity of the fusion protein. The amino acid segments used in any of the fusion proteins described herein can be modified by the use of additional amino acids flanking either end of any domain; the examples provided herein are exemplary. For example, a fusion protein according to this embodiment can include 1) the amino acid sequence of a near full-length (minus position 1) HBV genotype C X antigen (e.g., positions 2 to 154 of SEQ ID NO:12 or positions 7 to 159 of SEQ ID NO:39); and 2) an HBV genotype C core protein (e.g., positions 31 to 212 of SEQ ID NO:9 or positions 160 to 341 of SEQ ID NO:39), and utilize no N- or C-terminal sequences, or utilize different N- or C-terminal sequences, and/or use linkers or no linkers between HBV sequences. In one embodiment, instead of the N-terminal peptide represented by SEQ ID NO:37, an N-terminal peptide represented by SEQ ID NO:89 or SEQ ID NO:90 is utilized, followed by the remainder of the fusion protein as described.

HBV Antigens Comprising Single HBV Proteins. In one embodiment of the invention, an HBV antigen is comprised of a single HBV protein (e.g., one HBV protein selected from surface, core, e-antigen, polymerase, or X antigen) or one or more domains (structural, functional, and/or immunological) from a single HBV protein. This embodiment of the invention is particularly useful for creating a yeast-based immunotherapeutic composition that can be used, for example, in combination with one or more other yeast-based immunotherapeutic compositions for the treatment or prophylaxis of HBV, or in sequence with one or more other yeast-based immunotherapeutic compositions for the treatment or prophylaxis of HBV, or to follow a prophylactic approach with a therapeutic approach if the patient becomes infected. For example, the yeast-based immunotherapeutic composition including an HBV surface antigen of this embodiment can be combined with a second yeast-based immunotherapeutic composition including a different HBV protein/antigen, such as an HBV X antigen (described below), and further, with additional "single HBV protein" yeast-based immunotherapeutics, as desired (e.g., a yeast-based immunotherapeutic composition including an HBV Precore, Core or e-antigen and/or a yeast-based immunotherapeutic composition including an HBV polymerase antigen or domain thereof). These "single HBV protein yeast immunotherapeutics" can be used in combination or sequence with each other and/or in combination or sequence with other multi-HBV protein yeast-based immunotherapeutics, such as those described in the Examples or elsewhere herein. Alternatively, or in addition, a "single HBV protein yeast immunotherapeutic" such as this HBV surface antigen yeast-based immunotherapeutic can be produced using the HBV sequence for any given genotype or sub-genotype, and additional HBV surface antigen yeast-based immunotherapeutics can be produced using the HBV sequences for any one or more additional genotype or sub-genotype. This strategy effectively creates a "spice rack" of different HBV antigens and genotypes and/or sub-genotypes to each of which is provided in the context of a yeast-based immunotherapeutic of the invention, or in a strategy that includes at least one yeast-based immunotherapeutic of the invention. Accordingly, any combination of one, two, three, four, five, six, seven, eight, nine, ten or more of these yeast-based immunotherapeutics can be selected for use to treat a particular patient or population of patients who are infected with HBV, illustrating the flexibility of the present invention to be customized or tailored to meet the needs of a particular patient, population of patients, demographic, or other patient grouping.

In one embodiment of the invention, the HBV antigen(s) for use in a composition or method of the invention is an HBV antigen comprising or consisting of: (a) an HBV surface antigen protein and/or one or more domains (structural, functional or immunogenic) thereof, which can include the hepatocyte receptor portion of Pre-S1 of the HBV large (L) surface antigen, the HBV large (L) surface antigen, the HBV middle (M) surface antigen, the HBV small (S) surface antigen (HBsAg), or any domain or combination thereof; (b) an HBV polymerase antigen, which can include one or more domains (structural, functional, or immunogenic) of HBV polymerase, such as the reverse transcriptase (RT) domain (a functional domain) of HBV polymerase; (c) an HBV precore antigen, an HBV core antigen and/or HBV e-antigen, or one or more domains thereof (structural, functional or immunogenic), which can include one or more domains or portions of HBV Precore containing sequences from both HBV core and HBV e-antigen, or one or the other of these proteins; or (d) an HBV X antigen, which can include one or more domains (structural, functional or immunogenic) of HBV X antigen. In one aspect, any one or more of these proteins or domains is full-length or near full-length. In one aspect, one or more of these proteins or domains comprise or consist of 1, 2, 3, 4, 5, 6, 7, 8, 9, or 10 or more immunogenic domains. In one aspect, any one or more of these proteins or domains comprises at least 80%, 85%, 90%, 91%, 92%, 93%, 94%, 95%, 96%, 97%, 98%, or 99% of the linear sequence of the corresponding full-length sequence or a domain thereof. In one aspect, any one or more of these proteins or domains is at least 80%, 85%, 90%, 91%, 92%, 93%, 94%, 95%, 96%, 97%, 98%, or 99% identical to the corresponding full-length sequence or a domain thereof. A variety of suitable and exemplary sequences for HBV surface antigens, HBV polymerase antigens, HBV core antigens, and HBV X antigens are described herein.

An example of a composition comprising a surface antigen protein is described in Example 5. In this embodiment, yeast (e.g., *Saccharomyces cerevisiae*) are engineered to express HBV surface proteins under the control of a suitable promoter, such as the copper-inducible promoter, CUP1, or the TEF2 promoter. The protein is a single polypeptide comprising HBV near-full-length HBV large (L) surface antigen (to accommodate the presence of an N-terminal sequence selected to enhance or stabilize expression of the antigen), represented by SEQ ID NO:93: (1) an N-terminal peptide of SEQ ID NO:89 (positions 1-89 of SEQ ID NO:93); 2) the amino acid sequence of a near full-length (minus position 1) HBV genotype C large (L) surface antigen (e.g., positions 2-400 of SEQ ID NO:11 or positions 90 to 488 of SEQ ID NO:93); and 3) a hexahistidine tag (e.g., positions 489 to 494 of SEQ ID NO:93). Alternatively, the N-terminal peptide can be replaced with SEQ ID NO:37 or a homologue thereof or another N-terminal peptide described herein. In one embodiment, this construct also contains one or more anti-viral resistance mutations in the surface antigen. While this example utilizes large (L) surface antigen as an HBV antigen that may maximize the exposure of immunogenic epitopes generated by the immune system, small portions of surface antigen, including any domains or combinations of domains of surface antigen, can be produced using the guidance provided herein. In addition, while the exemplary immunotherapeutic is shown using a genotype C sequence, sequences from other genotypes, sub-genotypes, and/or strains or isolates of HBV can be used instead.

Figure 6:
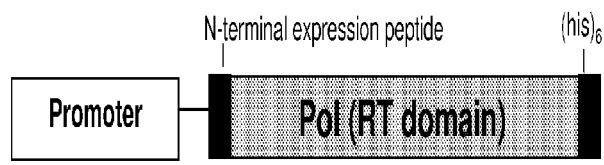
FIG. 6 is a schematic drawing showing the basic structure of a recombinant nucleic acid molecule encoding an HBV polymerase fusion protein useful in a yeast-based immunotherapeutic composition of the invention.

An example of a composition comprising an HBV polymerase antigen is described in Example 3 and also in Example 5. The HBV antigen described in Example 5 is schematically represented in FIG. 6. In this embodiment, yeast (e.g., *Saccharomyces cerevisiae*) are engineered to express various HBV polymerase proteins under the control of the copper-inducible promoter, CUP1, or the TEF2 promoter. In each case, the fusion protein is a single polypeptide with the following sequence elements fused in frame from N- to C-terminus, represented by SEQ ID NO:40 (1) an N-terminal peptide to impart resistance to proteasomal degradation and stabilize expression (SEQ ID NO:37, or positions 1 to 6 of SEQ ID NO:40; 2) the amino acid sequence of a portion of the HBV genotype C polymerase including the reverse transcriptase domain (e.g., positions 347 to 691 of SEQ ID NO:10 or positions 7 to 351 of SEQ ID NO:40); and 3) a hexahistidine tag (e.g., positions 352 to 357 of SEQ ID NO:40). The sequence also contains epitopes or domains that are believed to enhance the immunogenicity of the fusion protein. In addition, in one embodiment, the sequence of this construct can be modified to introduce one or more or all of the following anti-viral resistance mutations: rtM204I, rtL180M, rtM204V, rtV173L, rtN236T, rtA194T (positions given with respect to the full-length amino acid sequence for HBV polymerase). In one embodiment, six different immunotherapy compositions are created, each one containing one of these mutations. In other embodiments, all or some of the mutations are included in a single fusion protein. The amino acid segments used in any of the fusion proteins described herein can be modified by the use of additional amino acids flanking either end of any domain; the examples provided herein are exemplary. For example, a fusion protein according to this embodiment can include the amino acid sequence of a portion of the HBV genotype C polymerase including the reverse transcriptase domain (e.g., positions 347 to 691 of SEQ ID NO:10 or positions 7 to 351 of SEQ ID NO:40), and utilize no N- or C-terminal sequences, or utilize different N- or C-terminal sequences, and/or use linkers or no linkers between HBV sequences. In one embodiment, instead of the N-terminal peptide represented by SEQ ID NO:37, an N-terminal peptide represented by SEQ ID NO:89 or SEQ ID NO:90 is utilized, followed by the remainder of the fusion protein as described.

In the embodiment shown in Example 5, yeast (e.g., *Saccharomyces cerevisiae*) are engineered to express HBV polymerase proteins under the control of a suitable promoter, such as the copper-inducible promoter, CUP1, or the TEF2 promoter. The protein is a single polypeptide comprising HBV reverse transcriptase (RT) domain of polymerase (Pol), represented by SEQ ID NO:94: (1) an N-terminal peptide of SEQ ID NO:89 (positions 1-89 of SEQ ID NO:94); 2) the amino acid sequence of a portion of the HBV genotype C polymerase including the reverse transcriptase domain (e.g., positions 347 to 691 of SEQ ID NO:10 or positions 90 to 434 of SEQ ID NO:94); and 3) a hexahistidine tag (e.g., positions 435 to 440 of SEQ ID NO:94). The sequence also contains epitopes or domains that are believed to enhance the immunogenicity of the fusion protein. In addition, in one embodiment, the sequence of this construct can be modified to introduce one or more or all of the following anti-viral resistance mutations: rtM204I, rtL180M, rtM204V, rtV173L, rtN236T, rtA194T (positions given with respect to the full-length amino acid sequence for HBV polymerase). Alternatively, the N-terminal peptide can be replaced with SEQ ID NO:37 or a homologue thereof or another N-terminal peptide described herein.

An example of a composition comprising an HBV Precore, Core or e-antigen is described in Example 5. Yeast (e.g., *Saccharomyces cerevisiae*) are engineered to express HBV Core proteins under the control of a suitable promoter, such as the copper-inducible promoter, CUP1, or the TEF2 promoter. The protein is a single polypeptide comprising near full-length HBV Core protein, represented by SEQ ID NO:95: (1) an N-terminal peptide of SEQ ID NO:89 (positions 1-89 of SEQ ID NO:95); 2) the amino acid sequence of a portion of the HBV genotype C Core protein (e.g., positions 31 to 212 of SEQ ID NO:9 or positions 90 to 271 of SEQ ID NO:95); and 3) a hexahistidine tag (e.g., positions 272 to 277 of SEQ ID NO:95). The sequence also contains epitopes or domains that are believed to enhance the immunogenicity of the fusion protein. Alternatively, the N-terminal peptide can be replaced with SEQ ID NO:37 or a homologue thereof or another N-terminal peptide described herein.

An example of a yeast-based immunotherapeutic composition comprising an HBV X antigen is described in Example 5. Yeast (e.g., *Saccharomyces cerevisiae*) are engineered to express HBV X antigens under the control of a suitable promoter, such as the copper-inducible promoter, CUP1, or the TEF2 promoter. The protein is a single polypeptide comprising near full-length HBV X antigen, represented by SEQ ID NO:96: (1) an N-terminal peptide of SEQ ID NO:89 (positions 1-89 of SEQ ID NO:96); 2) the amino acid sequence of a portion of the HBV genotype C X antigen (e.g., positions 2 to 154 of SEQ ID NO:12 or positions 90 to 242 of SEQ ID NO:96); and 3) a hexahistidine tag (e.g., positions 243 to 248 of SEQ ID NO:96). The sequence contains epitopes or domains that are believed to enhance the immunogenicity of the fusion protein. Alternatively, the N-terminal peptide can be replaced with SEQ ID NO:37 or a homologue thereof or another N-terminal peptide described herein.

HBV Antigens Comprising HBV Proteins from Two or More Genotypes. Another embodiment of the invention relates to HBV antigens for use in an immunotherapeutic composition of the invention that maximizes the targeting of HBV genotypes and/or sub-genotypes in order to provide compositions with the potential to treat a large number of individuals or populations of individuals using one composition. Such compositions are generally more efficient to produce (i.e., have a production advantage by including multiple antigens and/or a consensus approach to targeting genotypes) and are more efficient to utilize in a wide variety of clinical settings (e.g., one composition may serve many different types of patient populations in many different geographical settings). As discussed above, to produce such HBV antigens, conserved antigens and/or conserved domains (among HBV genotypes) can be selected, and the antigens can be designed to maximize the inclusion of conserved immunological domains.

In one aspect of this embodiment, an HBV antigen is provided that includes in a single yeast-based immunotherapeutic a single HBV protein or domain thereof (e.g., surface, polymerase, core/e or X) that is repeated two, three, four, five or more times within the antigen construct, each time using a sequence from a different HBV genotype or subgenotype. In this aspect, multiple dominant or prevalent genotypes can be targeted in one yeast-based immunotherapeutic, increasing clinical and manufacturing efficacy. These antigens can be modified, if desired, to maximize the inclusion of consensus sequences, including consensus T cell epitopes within the antigens, which may otherwise contain subtle differences due to sub-genotype, strain or isolate differences.

Accordingly, in one embodiment of the invention, the HBV antigen(s) for use in a composition or method of the invention is an HBV antigen comprising or consisting of two or more repeated HBV antigens of the same protein or domain, but of different HBV genotypes (e.g., two or more HBV Core or e-antigens, which can include one or more domains (structural, functional or immunogenic) of HBV Core or e-antigen, wherein the antigens include the same or similar antigen from each of HBV genotype C and HBV genotype D, to form a Core-Core fusion where each Core protein is a different genotype). In one aspect, the HBV protein used in such constructs is full-length or near full-length protein or domain. In one aspect, the HBV antigen comprises or consists of 1, 2, 3, 4, 5, 6, 7, 8, 9, or 10 or more immunogenic domains. In one aspect, any one or more of these proteins or domains comprises at least 80%, 85%, 90%, 91%, 92%, 93%, 94%, 95%, 96%, 97%, 98%, or 99% of the linear sequence of the corresponding full-length sequence. In one aspect, any one or more of these proteins or domains is at least 80%, 85%, 90%, 91%, 92%, 93%, 94%, 95%, 96%, 97%, 98%, or 99% identical to the sequence of the corresponding full-length sequence.

Such an antigen is exemplified in Example 6. In this embodiment, yeast (e.g., *Saccharomyces cerevisiae*) are engineered to express an HBV fusion protein under the control of a suitable promoter, such as the copper-inducible promoter, CUP1, or the TEF2 promoter. The protein is a single polypeptide comprising four Core antigens, each one from a different genotype (HBV genotypes A, B, C and D), represented by SEQ ID NO:105: 1) an N-terminal methionine at position 1 of SEQ ID NO:105; 2) the amino acid sequence of a near full-length Core protein from HBV genotype A (e.g., positions 31 to 212 of SEQ ID NO:1 or positions 2 to 183 of SEQ ID NO:105); 3) the amino acid sequence of a near full-length Core protein from HBV genotype B (e.g., positions 30 to 212 of SEQ ID NO:5 or positions 184 to 395 of SEQ ID NO: 105); 4) the amino acid sequence of a near full-length Core protein from HBV genotype C (e.g., positions 30 to 212 of SEQ ID NO:9 or positions 396 to 578 of SEQ ID NO: 105); 5) the amino acid sequence of a near full-length Core protein from HBV genotype D (e.g., positions 30 to 212 of SEQ ID NO:13 or positions 579 to 761 of SEQ ID NO: 105); and 5) a hexahistidine tag (e.g., positions 762 to 767 of SEQ ID NO: 105). The sequence also contains epitopes or domains that are believed to enhance the immunogenicity of the fusion protein. The N-terminal methionine at position 1 can be substituted with SEQ ID NO:37 or a homologue thereof, or with an alpha prepro sequence of SEQ ID NO:89 or SEQ ID NO:90, or a homologue thereof, or any other suitable N-terminal sequence if desired. In addition, linker sequences can be inserted between HBV proteins to facilitate cloning and manipulation of the construct, if desired. This is an exemplary construct, as any other combination of HBV genotypes and/or sub-genotypes can be substituted into this design as desired to construct a single antigen yeast-based HBV immunotherapeutic product with broad clinical applicability and efficient design for manufacturing. The amino acid sequence of SEQ ID NO:105 also contains several known T cell epitopes, and certain epitopes have been modified to correspond to the published sequence for the given epitope (see Table 5).

In another aspect of this embodiment, more than one protein or domain from a single HBV genotype is included in an HBV antigen useful in the invention, which may be selected to maximize the most conserved protein sequences encoded by the HBV genome or to maximize the inclusion of therapeutically or prophylactically useful immunogenic domains within the antigen. These antigens are then repeated within the same fusion protein, but using the same or similar sequences from a different HBV genotype or subgenotype. In this aspect, multiple dominant or prevalent genotypes can also be targeted in one yeast-based immunotherapeutic, again increasing clinical and manufacturing efficacy. These antigens can also be modified, if desired, to maximize the inclusion of consensus T cell epitopes within the antigens, which may otherwise contain subtle differences due to sub-genotype, strain or isolate differences.

Accordingly, in one embodiment of the invention, the HBV antigen(s) for use in a composition or method of the invention is an HBV antigen comprising or consisting of at least two different HBV proteins or domains thereof, each of which is repeated two or more times, but wherein the repeated sequences are from different HBV genotypes (e.g., two or more HBV Core and two or more X antigens, or domains thereof, wherein the antigens include the same or similar antigen from each of HBV genotype C and HBV genotype D, to form a Core-X-Core-X fusion (or any other order of segments within the fusion) where each Core protein is a different genotype and each X antigen is a different genotype). In one aspect, the HBV protein used in such constructs is full-length or near full-length protein or domain. In one aspect, the HBV antigen comprises or consists of 1, 2, 3, 4, 5, 6, 7, 8, 9, or 10 or more immunogenic domains. In one aspect, any one or more of these proteins or domains comprises at least 80%, 85%, 90%, 91%, 92%, 93%, 94%, 95%, 96%, 97%, 98%, or 99% of the linear sequence of the corresponding full-length sequence. In one aspect, any one or more of these proteins or domains is at least 80%, 85%, 90%, 91%, 92%, 93%, 94%, 95%, 96%, 97%, 98%, or 99% to the sequence of the corresponding full-length sequence.

Such an antigen is exemplified in Example 6. In this embodiment, yeast (e.g., *Saccharomyces cerevisiae*) are engineered to express an HBV fusion protein under the control of a suitable promoter, such as the copper-inducible promoter, CUP1, or the TEF2 promoter. The protein is a single polypeptide comprising two Core antigens and two X antigens, each one of the pair from a different genotype (HBV genotypes A and C), represented by SEQ ID NO:106: 1) an N-terminal methionine at position 1 of SEQ ID NO:106; 2) the amino acid sequence of a near full-length Core protein from HBV genotype A (e.g., positions 31 to 212 of SEQ ID NO:1 or positions 2 to 183 of SEQ ID NO:106); 3) the amino acid sequence of a full-length X antigen from HBV genotype A (e.g., positions SEQ ID NO:4 or positions 184 to 337 of SEQ ID NO:106); 4) the amino acid sequence of a near full-length Core protein from HBV genotype C (e.g., positions 30 to 212 of SEQ ID NO:9 or positions 338 to 520 of SEQ ID NO:106); 5) the amino acid sequence of a full-length X antigen from HBV genotype C (e.g., SEQ ID NO:8 or positions 521 to 674 of SEQ ID NO:106); and 5) a hexahistidine tag (e.g., positions 675 to 680 of SEQ ID NO:106). The sequence also contains epitopes or domains that are believed to enhance the immunogenicity of the fusion protein. The N-terminal methionine at position 1 can be substituted with SEQ ID NO:37 or a homologue thereof, or with an alpha prepro sequence of SEQ ID NO:89 or SEQ ID NO:90, or a homologue thereof. The amino acid sequence of SEQ ID NO:106 also contains several known T cell epitopes, and certain epitopes have been modified to correspond to the published sequence for the given epitope (see Table 5).

Additional Embodiments Regarding HBV Antigens. In some aspects of the invention, amino acid insertions, deletions, and/or substitutions can be made for one, two, three, four, five, six, seven, eight, nine, ten, or more amino acids of a wild-type or reference HBV protein, provided that the resulting HBV protein, when used as an antigen in a yeast-HBV immunotherapeutic composition of the invention, elicits an immune response against the target or wild-type or reference HBV protein, which may include an enhanced immune response, a diminished immune response, or a substantially similar immune response. For example, the invention includes the use of HBV agonist antigens, which may include one or more T cell epitopes that have been mutated to enhance the T cell response against the HBV agonist, such as by improving the avidity or affinity of the epitope for an MHC molecule or for the T cell receptor that recognizes the epitope in the context of MHC presentation. HBV protein agonists may therefore improve the potency or efficiency of a T cell response against native HBV proteins that infect a host.

Referring to any of the above-described HBV antigens, including the fusion proteins that have amino acid sequences including or represented by SEQ ID NO:34, SEQ ID NO:36, SEQ ID NO:38, SEQ ID NO:39, SEQ ID NO:40, SEQ ID NO:41, SEQ ID NO:92, SEQ ID NO:101, SEQ ID NO:102, SEQ ID NO:107, SEQ ID NO:108, SEQ ID NO:109, SEQ ID NO:110, SEQ ID NO:112, SEQ ID NO:114, SEQ ID NO:116, SEQ ID NO:118, SEQ ID NO:120, SEQ ID NO:122, SEQ ID NO:124, SEQ ID NO:126, SEQ ID NO:128, SEQ ID NO:130, SEQ ID NO:132, SEQ ID NO:134, SEQ ID NO:150 or SEQ ID NO:151, it is an aspect of the invention to use one or more of the HBV antigens from individual HBV proteins within the fusion protein (e.g., from HBV surface antigen, HBV polymerase, HBV core/e-antigen, and/or HBV X antigen) to construct "single protein" antigens (e.g., antigens from only one of these HBV proteins), or to construct fusion proteins using only two or three of the HBV protein segments, if applicable to the given reference fusion protein. It is also an aspect of the invention to change the order of HBV protein segments within the fusion protein. As another alternate design, HBV genotypes and/or consensus sequences can be combined, where two, three, four or more genotypes and/or consensus sequences are used to construct the fusion protein.

The invention also includes homologues of any of the above-described fusion proteins, as well as the use of homologues, variants, or mutants of the individual HBV proteins or portions thereof (including any functional and/or immunogenic domains) that are part of such fusion proteins or otherwise described herein. In one aspect, the invention includes the use of fusion proteins or individual (single) HBV proteins or HBV antigens, having amino acid sequences that are at least 85%, 86%, 87%, 88%, 89%, 90%, 91%, 92%, 93%, 94%, 95%, 96%, 97%, 98%, or 99% identical to the amino acid sequence of any one of the fusion proteins or individual HBV proteins or HBV antigens, respectively, described herein, including any of the HBV proteins, HBV antigens and fusion proteins referenced by a specific sequence identifier herein, over the full length of the fusion protein, or with respect to a defined segment in the fusion protein or a defined protein or domain thereof (immunogenic domain or functional domain (i.e., a domain with at least one biological activity)) that forms part of the fusion protein. Many CTL epitopes (epitopes that are recognized by cytotoxic T lymphocytes from patients infected with HBV) and escape mutations (mutations that arise in an HBV protein due to selective pressure from an anti-viral drug) are known in the art, and this information can also be used to make substitutions or create variants or homologues of the HBV antigens described herein in order to provide a specific sequence in the HBV antigen of the invention.

Yeast-Based Immunotherapy Compositions. In various embodiments of the invention, the invention includes the use of at least one "yeast-based immunotherapeutic composition" (which phrase may be used interchangeably with "yeast-based immunotherapy product", "yeast-based immunotherapy composition", "yeast-based composition", "yeast-based immunotherapeutic", "yeast-based vaccine", or derivatives of these phrases). An "immunotherapeutic composition" is a composition that elicits an immune response sufficient to achieve at least one therapeutic benefit in a subject. As used herein, yeast-based immunotherapeutic composition refers to a composition that includes a yeast vehicle component and that elicits an immune response sufficient to achieve at least one therapeutic benefit in a subject. More particularly, a yeast-based immunotherapeutic composition is a composition that includes a yeast vehicle component and can elicit or induce an immune response, such as a cellular immune response, including without limitation a T cell-mediated cellular immune response. In one aspect, a yeast-based immunotherapeutic composition useful in the invention is capable of inducing a CD8$^+$ and/or a CD4$^+$ T cell-mediated immune response and in one aspect, a CD8$^+$ and a CD4$^+$ T cell-mediated immune response. Optionally, a yeast-based immunotherapeutic composition is capable of eliciting a humoral immune response. A yeast-based immunotherapeutic composition useful in the present invention can, for example, elicit an immune response in an individual such that the individual is protected from HBV infection and/or is treated for HBV infection or for symptoms resulting from HBV infection.

Yeast-based immunotherapy compositions of the invention may be either "prophylactic" or "therapeutic". When provided prophylactically, the compositions of the present invention are provided in advance of any symptom of HBV infection. Such a composition could be administered at birth, in early childhood, or to adults. The prophylactic administration of the immunotherapy compositions serves to prevent subsequent HBV infection, to resolve an infection more quickly or more completely if HBV infection subsequently ensues, and/or to ameliorate the symptoms of HBV infection if infection subsequently ensues. When provided therapeutically, the immunotherapy compositions are provided at or after the onset of HBV infection, with the goal of ameliorating at least one symptom of the infection and preferably, with a goal of eliminating the infection, providing a long lasting remission of infection, and/or providing long term immunity against subsequent infections or reactivations of the virus. In one aspect, a goal of treatment is loss of detectable HBV viral load or reduction of HBV viral load (e.g., below detectable levels by PCR or <2000 IU/ml). In one aspect, a goal of treatment is sustained viral clearance for at least 6 months after the completion of therapy. In one aspect, a goal of treatment is the loss of detectable serum HBeAg and/or HBsAg proteins. In one aspect, a goal of treatment is the development of antibodies against the hepatitis B surface antigen (anti-HBs) and/or antibodies against HBeAg. In one aspect, the goal of treatment is seroconversion, which may be defined by: (a) 10 or more sample ratio units (SRU) as determined by radioimmunoassay; (b) a positive result as determined by enzyme immunoassay; or (c) detection of an antibody concentration of ≥10 mIU/ml (10 SRU is comparable to 10 mIU/mL of antibody). In one aspect, a goal of treatment is normalization of serum alanine aminotransferase (ALT) levels, improvement in liver inflammation and/or improvement in liver fibrosis.

Typically, a yeast-based immunotherapy composition includes a yeast vehicle and at least one antigen or immunogenic domain thereof expressed by, attached to, or mixed with the yeast vehicle, wherein the antigen is heterologous to the yeast, and wherein the antigen comprises one or more HBV antigens or immunogenic domains thereof. In some embodiments, the antigen or immunogenic domain thereof is provided as a fusion protein. Several HBV fusion proteins suitable for use in the compositions and methods of the invention have been described above. In one aspect of the invention, fusion protein can include two or more antigens. In one aspect, the fusion protein can include two or more immunogenic domains of one or more antigens, or two or more epitopes of one or more antigens.

In any of the yeast-based immunotherapy compositions used in the present invention, the following aspects related to the yeast vehicle are included in the invention. According to the present invention, a yeast vehicle is any yeast cell (e.g., a whole or intact cell) or a derivative thereof (see below) that can be used in conjunction with one or more antigens, immunogenic domains thereof or epitopes thereof in a therapeutic composition of the invention, or in one aspect, the yeast vehicle can be used alone or as an adjuvant. The yeast vehicle can therefore include, but is not limited to, a live intact (whole) yeast microorganism (i.e., a yeast cell having all its components including a cell wall), a killed (dead) or inactivated intact yeast microorganism, or derivatives of intact/whole yeast including: a yeast spheroplast (i.e., a yeast cell lacking a cell wall), a yeast cytoplast (i.e., a yeast cell lacking a cell wall and nucleus), a yeast ghost (i.e., a yeast cell lacking a cell wall, nucleus and cytoplasm), a subcellular yeast membrane extract or fraction thereof (also referred to as a yeast membrane particle and previously as a subcellular yeast particle), any other yeast particle, or a yeast cell wall preparation.

Yeast spheroplasts are typically produced by enzymatic digestion of the yeast cell wall. Such a method is described, for example, in Franzusoff et al., 1991, *Meth. Enzymol.* 194, 662-674., incorporated herein by reference in its entirety.

Yeast cytoplasts are typically produced by enucleation of yeast cells. Such a method is described, for example, in Coon, 1978, *Natl. Cancer Inst. Monogr.* 48, 45-55 incorporated herein by reference in its entirety.

Yeast ghosts are typically produced by resealing a permeabilized or lysed cell and can, but need not, contain at least some of the organelles of that cell. Such a method is described, for example, in Franzusoff et al., 1983, *J. Biol. Chem.* 258, 3608-3614 and Bussey et al., 1979, *Biochim. Biophys. Acta* 553, 185-196, each of which is incorporated herein by reference in its entirety.

A yeast membrane particle (subcellular yeast membrane extract or fraction thereof) refers to a yeast membrane that lacks a natural nucleus or cytoplasm. The particle can be of any size, including sizes ranging from the size of a natural yeast membrane to microparticles produced by sonication or other membrane disruption methods known to those skilled in the art, followed by resealing. A method for producing subcellular yeast membrane extracts is described, for example, in Franzusoff et al., 1991, *Meth. Enzymol.* 194, 662-674. One may also use fractions of yeast membrane particles that contain yeast membrane portions and, when the antigen or other protein was expressed recombinantly by the yeast prior to preparation of the yeast membrane particles, the antigen or other protein of interest. Antigens or other proteins of interest can be carried inside the membrane, on either surface of the membrane, or combinations thereof (i.e., the protein can be both inside and outside the membrane and/or spanning the membrane of the yeast membrane particle). In one embodiment, a yeast membrane particle is a recombinant yeast membrane particle that can be an intact, disrupted, or disrupted and resealed yeast membrane that includes at least one desired antigen or other protein of interest on the surface of the membrane or at least partially embedded within the membrane.

An example of a yeast cell wall preparation is a preparation of isolated yeast cell walls carrying an antigen on its surface or at least partially embedded within the cell wall such that the yeast cell wall preparation, when administered to an animal, stimulates a desired immune response against a disease target.

Any yeast strain can be used to produce a yeast vehicle of the present invention. Yeast are unicellular microorganisms that belong to one of three classes: Ascomycetes, Basidiomycetes and Fungi Imperfecti. One consideration for the selection of a type of yeast for use as an immune modulator is the pathogenicity of the yeast. In one embodiment, the yeast is a non-pathogenic strain such as *Saccharomyces cerevisiae*. The selection of a non-pathogenic yeast strain minimizes any adverse effects to the individual to whom the yeast vehicle is administered. However, pathogenic yeast may be used if the pathogenicity of the yeast can be negated by any means known to one of skill in the art (e.g., mutant strains).

Genera of yeast strains that may be used in the invention include but are not limited to *Saccharomyces, Candida, Cryptococcus, Hansenula, Kluyveromyces, Pichia, Rhodotorula, Schizosaccharomyces* and *Yarrowia*. In one aspect, yeast genera are selected from *Saccharomyces, Candida, Hansenula, Pichia* or *Schizosaccharomyces*, and in one aspect, yeast genera are selected from *Saccharomyces, Hansenula*, and *Pichia*, and in one aspect, *Saccharomyces* is used. Species of yeast strains that may be used in the invention include but are not limited to *Saccharomyces cerevisiae, Saccharomyces carlsbergensis, Candida albicans, Candida kefr, Candida tropicalis, Cryptococcus laurentii, Cryptococcus neoformans, Hansenula anomala, Hansenula polymorpha, Kluyveromyces fragilis, Kluyveromyces lactis, Kluyveromyces marxianus* var. *lactis, Pichia pastoris, Rhodotorula rubra, Schizosaccharomyces pombe*, and *Yarrowia lipolytica*. It is to be appreciated that a number of these species include a variety of subspecies, types, subtypes, etc. that are intended to be included within the aforementioned species. In one aspect, yeast species used in the invention include *S. cerevisiae, C. albicans, H. polymorpha, P. pastoris* and *S. pombe*. *S. cerevisiae* is useful as it is relatively easy to manipulate and being "Generally Recognized As Safe" or "GRAS" for use as food additives (GRAS, FDA proposed Rule 62FR18938, Apr. 17, 1997). One embodiment of the present invention is a yeast strain that is capable of replicating plasmids to a particularly high copy number, such as a *S. cerevisiae* cir° strain. The *S. cerevisiae* strain is one such strain that is capable of supporting expression vectors that allow one or more target antigen(s) and/or antigen fusion protein(s) and/or other proteins to be expressed at high levels. In addition, any mutant yeast strains can be used in the present invention, including those that exhibit reduced post-translational modifications of expressed target antigens or other proteins, such as mutations in the enzymes that extend N-linked glycosylation.

In most embodiments of the invention, the yeast-based immunotherapy composition includes at least one antigen, immunogenic domain thereof, or epitope thereof The antigens contemplated for use in this invention include any HBV antigen or immunogenic domain thereof, including mutants, variants and agonists of HBV proteins or domains thereof, against which it is desired to elicit an immune response for the purpose of prophylactically or therapeutically immunizing a host against HBV infection. HBV antigens that are useful in various embodiments of the invention have been described in detail above.

Optionally, proteins, including fusion proteins, which are used as a component of the yeast-based immunotherapeutic composition of the invention are produced using constructs that are particularly useful for improving or enhancing the expression, or the stability of expression, of recombinant antigens in yeast. Typically, the desired antigenic protein(s) or peptide(s) are fused at their amino-terminal end to: (a) a specific synthetic peptide that stabilizes the expression of the fusion protein in the yeast vehicle or prevents posttranslational modification of the expressed fusion protein (such peptides are described in detail, for example, in U.S. Patent Publication No. 2004-0156858 A1, published Aug. 12, 2004, incorporated herein by reference in its entirety); (b) at least a portion of an endogenous yeast protein, including but not limited to alpha factor, wherein either fusion partner provides improved stability of expression of the protein in the yeast and/or a prevents post-translational modification of the proteins by the yeast cells (such proteins are also described in detail, for example, in U.S. Patent Publication No. 2004-0156858 A1, supra); and/or (c) at least a portion of a yeast protein that causes the fusion protein to be expressed on the surface of the yeast (e.g., an Aga protein, described in more detail herein). In addition, the present invention optionally includes the use of peptides that are fused to the C-terminus of the antigen-encoding construct, particularly for use in the selection and identification of the protein. Such peptides include, but are not limited to, any synthetic or natural peptide, such as a peptide tag (e.g., hexahistidine) or any other short epitope tag. Peptides attached to the C-terminus of an antigen according to the invention can be used with or without the addition of the N-terminal peptides discussed above.

In one embodiment, a synthetic peptide useful in a fusion protein is linked to the N-terminus of the antigen, the peptide consisting of at least two amino acid residues that are heterologous to the antigen, wherein the peptide stabilizes the expression of the fusion protein in the yeast vehicle or prevents posttranslational modification of the expressed fusion protein. The synthetic peptide and N-terminal portion of the antigen together form a fusion protein that has the following requirements: (1) the amino acid residue at position one of the fusion protein is a methionine (i.e., the first amino acid in the synthetic peptide is a methionine); (2) the amino acid residue at position two of the fusion protein is not a glycine or a proline (i.e., the second amino acid in the synthetic peptide is not a glycine or a proline); (3) none of the amino acid residues at positions 2-6 of the fusion protein is a methionine (i.e., the amino acids at positions 2-6, whether part of the synthetic peptide or the protein, if the synthetic peptide is shorter than 6 amino acids, do not include a methionine); and (4) none of the amino acids at positions 2-6 of the fusion protein is a lysine or an arginine (i.e., the amino acids at positions 2-6, whether part of the synthetic peptide or the protein, if the synthetic peptide is shorter than 5 amino acids, do not include a lysine or an arginine). The synthetic peptide can be as short as two amino acids, but in one aspect, is 2-6 amino acids (including 3, 4, 5 amino acids), and can be longer than 6 amino acids, in whole integers, up to about 200 amino acids, 300 amino acids, 400 amino acids, 500 amino acids, or more.

In one embodiment, a fusion protein comprises an amino acid sequence of M-X2-X3-X4-X5-X6, wherein M is methionine; wherein X2 is any amino acid except glycine, proline, lysine or arginine; wherein X3 is any amino acid except methionine, lysine or arginine; wherein X4 is any amino acid except methionine, lysine or arginine; wherein X5 is any amino acid except methionine, lysine or arginine; and wherein X6 is any amino acid except methionine, lysine or arginine. In one embodiment, the X6 residue is a proline. An exemplary synthetic sequence that enhances the stability of expression of an antigen in a yeast cell and/or prevents post-translational modification of the protein in the yeast includes the sequence M-A-D-E-A-P (SEQ ID NO:37). Another exemplary synthetic sequence with the same properties is M-V. In addition to the enhanced stability of the expression product, these fusion partners do not appear to negatively impact the immune response against the immunizing antigen in the construct. In addition, the synthetic fusion peptides can be designed to provide an epitope that can be recognized by a selection agent, such as an antibody.

In one embodiment, the HBV antigen is linked at the N-terminus to a yeast protein, such as an alpha factor prepro sequence (also referred to as the alpha factor signal leader sequence, the amino acid sequence of which is exemplified herein by SEQ ID NO:89 or SEQ ID NO:90. Other sequences for yeast alpha factor prepro sequence are known in the art and are encompassed for use in the present invention.

In one aspect of the invention, the yeast vehicle is manipulated such that the antigen is expressed or provided by delivery or translocation of an expressed protein product, partially or wholly, on the surface of the yeast vehicle (extracellular expression). One method for accomplishing this aspect of the invention is to use a spacer arm for positioning one or more protein(s) on the surface of the yeast vehicle. For example, one can use a spacer arm to create a fusion protein of the antigen(s) or other protein of interest with a protein that targets the antigen(s) or other protein of interest to the yeast cell wall. For example, one such protein that can be used to target other proteins is a yeast protein (e.g., cell wall protein 2 (cwp2), Aga2, Pir4 or Flo1 protein) that enables the antigen(s) or other protein to be targeted to the yeast cell wall such that the antigen or other protein is located on the surface of the yeast. Proteins other than yeast proteins may be used for the spacer arm; however, for any spacer arm protein, it is most desirable to have the immunogenic response be directed against the target antigen rather than the spacer arm protein.

As such, if other proteins are used for the spacer arm, then the spacer arm protein that is used should not generate such a large immune response to the spacer arm protein itself such that the immune response to the target antigen(s) is overwhelmed. One of skill in the art should aim for a small immune response to the spacer arm protein relative to the immune response for the target antigen(s). Spacer arms can be constructed to have cleavage sites (e.g., protease cleavage sites) that allow the antigen to be readily removed or processed away from the yeast, if desired. Any known method of determining the magnitude of immune responses can be used (e.g., antibody production, lytic assays, etc.) and are readily known to one of skill in the art.

Another method for positioning the target antigen(s) or other proteins to be exposed on the yeast surface is to use signal sequences such as glycosylphosphatidyl inositol (GPI) to anchor the target to the yeast cell wall. Alternatively, positioning can be accomplished by appending signal sequences that target the antigen(s) or other proteins of interest into the secretory pathway via translocation into the endoplasmic reticulum (ER) such that the antigen binds to a protein which is bound to the cell wall (e.g., cwp).

In one aspect, the spacer arm protein is a yeast protein. The yeast protein can consist of between about two and about 800 amino acids of a yeast protein. In one embodiment, the yeast protein is about 10 to 700 amino acids. In another embodiment, the yeast protein is about 40 to 600 amino acids. Other embodiments of the invention include the yeast protein being at least 250 amino acids, at least 300 amino acids, at least 350 amino acids, at least 400 amino acids, at least 450 amino acids, at least 500 amino acids, at least 550 amino acids, at least 600 amino acids, or at least 650 amino acids. In one embodiment, the yeast protein is at least 450 amino acids in length. Another consideration for optimizing antigen surface expression, if that is desired, is whether the antigen and spacer arm combination should be expressed as a monomer or as dimer or as a trimer, or even more units connected together. This use of monomers, dimers, trimers, etc. allows for appropriate spacing or folding of the antigen such that some part, if not all, of the antigen is displayed on the surface of the yeast vehicle in a manner that makes it more immunogenic.

Use of yeast proteins can stabilize the expression of fusion proteins in the yeast vehicle, prevents posttranslational modification of the expressed fusion protein, and/or targets the fusion protein to a particular compartment in the yeast (e.g., to be expressed on the yeast cell surface). For delivery into the yeast secretory pathway, exemplary yeast proteins to use include, but are not limited to: Aga (including, but not limited to, Aga1 and/or Aga2); SUC2 (yeast invertase); alpha factor signal leader sequence; CPY; Cwp2p for its localization and retention in the cell wall; BUD genes for localization at the yeast cell bud during the initial phase of daughter cell formation; Flo1p; Pir2p; and Pir4p.

Other sequences can be used to target, retain and/or stabilize the protein to other parts of the yeast vehicle, for example, in the cytosol or the mitochondria or the endoplasmic reticulum or the nucleus. Examples of suitable yeast protein that can be used for any of the embodiments above include, but are not limited to, TK, AF, SEC7; phosphoenolpyruvate carboxykinase PCK1, phosphoglycerokinase PGK and triose phosphate isomerase TPI gene products for their repressible expression in glucose and cytosolic localization; the heat shock proteins SSA1, SSA3, SSA4, SSC1, whose expression is induced and whose proteins are more thermostable upon exposure of cells to heat treatment; the mitochondrial protein CYC1 for import into mitochondria; ACT1.

Methods of producing yeast vehicles and expressing, combining and/or associating yeast vehicles with antigens and/or other proteins and/or agents of interest to produce yeast-based immunotherapy compositions are contemplated by the invention.

According to the present invention, the term "yeast vehicle-antigen complex" or "yeast-antigen complex" is used generically to describe any association of a yeast vehicle with an antigen, and can be used interchangeably with "yeast-based immunotherapy composition" when such composition is used to elicit an immune response as described above. Such association includes expression of the antigen by the yeast (a recombinant yeast), introduction of an antigen into a yeast, physical attachment of the antigen to the yeast, and mixing of the yeast and antigen together, such as in a buffer or other solution or formulation. These types of complexes are described in detail below.

In one embodiment, a yeast cell used to prepare the yeast vehicle is transfected with a heterologous nucleic acid molecule encoding a protein (e.g., the antigen) such that the protein is expressed by the yeast cell. Such a yeast is also referred to herein as a recombinant yeast or a recombinant yeast vehicle. The yeast cell can then be loaded into the dendritic cell as an intact cell, or the yeast cell can be killed, or it can be derivatized such as by formation of yeast spheroplasts, cytoplasts, ghosts, or subcellular particles, any of which is followed by loading of the derivative into the dendritic cell. Yeast spheroplasts can also be directly transfected with a recombinant nucleic acid molecule (e.g., the spheroplast is produced from a whole yeast, and then transfected) in order to produce a recombinant spheroplast that expresses an antigen or other protein.

In general, the yeast vehicle and antigen(s) and/or other agents can be associated by any technique described herein. In one aspect, the yeast vehicle was loaded intracellularly with the antigen(s) and/or agent(s). In another aspect, the antigen(s) and/or agent(s) was covalently or non-covalently attached to the yeast vehicle. In yet another aspect, the yeast vehicle and the antigen(s) and/or agent(s) were associated by mixing. In another aspect, and in one embodiment, the antigen(s) and/or agent(s) is expressed recombinantly by the yeast vehicle or by the yeast cell or yeast spheroplast from which the yeast vehicle was derived.

A number of antigens and/or other proteins to be produced by a yeast vehicle of the present invention is any number of antigens and/or other proteins that can be reasonably produced by a yeast vehicle, and typically ranges from at least one to at least about 6 or more, including from about 2 to about 6 heterologous antigens and or other proteins.

Expression of an antigen or other protein in a yeast vehicle of the present invention is accomplished using techniques known to those skilled in the art. Briefly, a nucleic acid molecule encoding at least one desired antigen or other protein is inserted into an expression vector in such a manner that the nucleic acid molecule is operatively linked to a transcription control sequence in order to be capable of effecting either constitutive or regulated expression of the nucleic acid molecule when transformed into a host yeast cell. Nucleic acid molecules encoding one or more antigens and/or other proteins can be on one or more expression vectors operatively linked to one or more expression control sequences. Particularly important expression control sequences are those which control transcription initiation, such as promoter and upstream activation sequences. Any suitable yeast promoter can be used in the present invention and a variety of such promoters are known to those skilled in the art. Promoters for expression in *Saccharomyces cerevisiae* include, but are not limited to, promoters of genes encoding the following yeast proteins: alcohol dehydrogenase I (ADH1) or II (ADH2), CUP1, phosphoglycerate kinase (PGK), triose phosphate isomerase (TPI), translational elongation factor EF-1 alpha (TEF2), glyceraldehyde-3-phosphate dehydrogenase (GAPDH; also referred to as TDH3, for triose phosphate dehydrogenase), galactokinase (GAL1), galactose-1-phosphate uridyl-transferase (GAL7), UDP-galactose epimerase (GAL10), cytochrome c1 (CYC1), Sec7 protein (SEC7) and acid phosphatase (PHO5), including hybrid promoters such as ADH2/GAPDH and CYC1/GAL10 promoters, and including the ADH2/GAPDH promoter, which is induced when glucose concentrations in the cell are low (e.g., about 0.1 to about 0.2 percent), as well as the CUP1 promoter and the TEF2 promoter. Likewise, a number of upstream activation sequences (UASs), also referred to as enhancers, are known. Upstream activation sequences for expression in *Saccharomyces cerevisiae* include, but are not limited to, the UASs of genes encoding the following proteins: PCK1, TPI, TDH3, CYC1, ADH1, ADH2, SUC2, GAL1, GAL7 and GAL10, as well as other UASs activated by the GAL4 gene product, with the ADH2 UAS being used in one aspect. Since the ADH2 UAS is activated by the ADR1 gene product, it may be preferable to overexpress the ADR1 gene when a heterologous gene is operatively linked to the ADH2 UAS. Transcription termination sequences for expression in *Saccharomyces cerevisiae* include the termination sequences of the α-factor, GAPDH, and CYC1 genes.

Transcription control sequences to express genes in methyltrophic yeast include the transcription control regions of the genes encoding alcohol oxidase and formate dehydrogenase.

Transfection of a nucleic acid molecule into a yeast cell according to the present invention can be accomplished by any method by which a nucleic acid molecule can be introduced into the cell and includes, but is not limited to, diffusion, active transport, bath sonication, electroporation, microinjection, lipofection, adsorption, and protoplast fusion. Transfected nucleic acid molecules can be integrated into a yeast chromosome or maintained on extrachromosomal vectors using techniques known to those skilled in the art. Examples of yeast vehicles carrying such nucleic acid molecules are disclosed in detail herein. As discussed above, yeast cytoplast, yeast ghost, and yeast membrane particles or cell wall preparations can also be produced recombinantly by transfecting intact yeast microorganisms or yeast spheroplasts with desired nucleic acid molecules, producing the antigen therein, and then further manipulating the microorganisms or spheroplasts using techniques known to those skilled in the art to produce cytoplast, ghost or subcellular yeast membrane extract or fractions thereof containing desired antigens or other proteins.

Effective conditions for the production of recombinant yeast vehicles and expression of the antigen and/or other protein by the yeast vehicle include an effective medium in which a yeast strain can be cultured. An effective medium is typically an aqueous medium comprising assimilable carbohydrate, nitrogen and phosphate sources, as well as appropriate salts, minerals, metals and other nutrients, such as vitamins and growth factors. The medium may comprise complex nutrients or may be a defined minimal medium. Yeast strains of the present invention can be cultured in a variety of containers, including, but not limited to, bioreactors, Erlenmeyer flasks, test tubes, microtiter dishes, and Petri plates. Culturing is carried out at a temperature, pH and oxygen content appropriate for the yeast strain. Such culturing conditions are well within the expertise of one of ordinary skill in the art (see, for example, Guthrie et al. (eds.), 1991, Methods in Enzymology, vol. 194, Academic Press, San Diego).

In some embodiments of the invention, yeast are grown under neutral pH conditions. As used herein, the general use of the term "neutral pH" refers to a pH range between about pH 5.5 and about pH 8, and in one aspect, between about pH 6 and about 8. One of skill the art will appreciate that minor fluctuations (e.g., tenths or hundredths) can occur when measuring with a pH meter. As such, the use of neutral pH to grow yeast cells means that the yeast cells are grown in neutral pH for the majority of the time that they are in culture. In one embodiment, yeast are grown in a medium maintained at a pH level of at least 5.5 (i.e., the pH of the culture medium is not allowed to drop below pH 5.5). In another aspect, yeast are grown at a pH level maintained at about 6, 6.5, 7, 7.5 or 8. The use of a neutral pH in culturing yeast promotes several biological effects that are desirable characteristics for using the yeast as vehicles for immunomodulation. For example, culturing the yeast in neutral pH allows for good growth of the yeast without negative effect on the cell generation time (e.g., slowing of doubling time). The yeast can continue to grow to high densities without losing their cell wall pliability. The use of a neutral pH allows for the production of yeast with pliable cell walls and/or yeast that are more sensitive to cell wall digesting enzymes (e.g., glucanase) at all harvest densities. This trait is desirable because yeast with flexible cell walls can induce different or improved immune responses as compared to yeast grown under more acidic conditions, e.g., by promoting the secretion of cytokines by antigen presenting cells that have phagocytosed the yeast (e.g., TH1-type cytokines including, but not limited to, IFN-γ, interleukin-12 (IL-12), and IL-2, as well as proinflammatory cytokines such as IL-6). In addition, greater accessibility to the antigens located in the cell wall is afforded by such culture methods. In another aspect, the use of neutral pH for some antigens allows for release of the di-sulfide bonded antigen by treatment with dithiothreitol (DTT) that is not possible when such an antigen-expressing yeast is cultured in media at lower pH (e.g., pH 5).

In one embodiment, control of the amount of yeast glycosylation is used to control the expression of antigens by the yeast, particularly on the surface. The amount of yeast glycosylation can affect the immunogenicity and antigenicity of the antigen expressed on the surface, since sugar moieties tend to be bulky. As such, the existence of sugar moieties on the surface of yeast and its impact on the three-dimensional space around the target antigen(s) should be considered in the modulation of yeast according to the invention. Any method can be used to reduce the amount of glycosylation of the yeast (or increase it, if desired). For example, one could use a yeast mutant strain that has been selected to have low glycosylation (e.g., mnn1, och1 and mnn9 mutants), or one could eliminate by mutation the glycosylation acceptor sequences on the target antigen. Alternatively, one could use a yeast with abbreviated glycosylation patterns, e.g., *Pichia*. One can also treat the yeast using methods that reduce or alter the glycosylation.

In one embodiment of the present invention, as an alternative to expression of an antigen or other protein recombinantly in the yeast vehicle, a yeast vehicle is loaded intracellularly with the protein or peptide, or with carbohydrates or other molecules that serve as an antigen and/or are useful as immunomodulatory agents or biological response modifiers according to the invention. Subsequently, the yeast vehicle, which now contains the antigen and/or other proteins intracellularly, can be administered to an individual or loaded into a carrier such as a dendritic cell. Peptides and proteins can be inserted directly into yeast vehicles of the present invention by techniques known to those skilled in the art, such as by diffusion, active transport, liposome fusion, electroporation, phagocytosis, freeze-thaw cycles and bath sonication. Yeast vehicles that can be directly loaded with peptides, proteins, carbohydrates, or other molecules include intact yeast, as well as spheroplasts, ghosts or cytoplasts, which can be loaded with antigens and other agents after production. Alternatively, intact yeast can be loaded with the antigen and/or agent, and then spheroplasts, ghosts, cytoplasts, or subcellular particles can be prepared therefrom. Any number of antigens and/or other agents can be loaded into a yeast vehicle in this embodiment, from at least 1, 2, 3, 4 or any whole integer up to hundreds or thousands of antigens and/or other agents, such as would be provided by the loading of a microorganism or portions thereof, for example.

In another embodiment of the present invention, an antigen and/or other agent is physically attached to the yeast vehicle. Physical attachment of the antigen and/or other agent to the yeast vehicle can be accomplished by any method suitable in the art, including covalent and non-covalent association methods which include, but are not limited to, chemically crosslinking the antigen and/or other agent to the outer surface of the yeast vehicle or biologically linking the antigen and/or other agent to the outer surface of the yeast vehicle, such as by using an antibody or other binding partner. Chemical cross-linking can be achieved, for example, by methods including glutaraldehyde linkage, photoaffinity labeling, treatment with carbodiimides, treatment with chemicals capable of linking di-sulfide bonds, and treatment with other cross-linking chemicals standard in the art. Alternatively, a chemical can be contacted with the yeast vehicle that alters the charge of the lipid bilayer of yeast membrane or the composition of the cell wall so that the outer surface of the yeast is more likely to fuse or bind to antigens and/or other agent having particular charge characteristics. Targeting agents such as antibodies, binding peptides, soluble receptors, and other ligands may also be incorporated into an antigen as a fusion protein or otherwise associated with an antigen for binding of the antigen to the yeast vehicle.

When the antigen or other protein is expressed on or physically attached to the surface of the yeast, spacer arms may, in one aspect, be carefully selected to optimize antigen or other protein expression or content on the surface. The size of the spacer arm(s) can affect how much of the antigen or other protein is exposed for binding on the surface of the yeast. Thus, depending on which antigen(s) or other protein(s) are being used, one of skill in the art will select a spacer arm that effectuates appropriate spacing for the antigen or other protein on the yeast surface. In one embodiment, the spacer arm is a yeast protein of at least 450 amino acids. Spacer arms have been discussed in detail above.

In yet another embodiment, the yeast vehicle and the antigen or other protein are associated with each other by a more passive, non-specific or non-covalent binding mechanism, such as by gently mixing the yeast vehicle and the antigen or other protein together in a buffer or other suitable formulation (e.g., admixture).

In one embodiment of the invention, the yeast vehicle and the antigen or other protein are both loaded intracellularly into a carrier such as a dendritic cell or macrophage to form the therapeutic composition or vaccine of the present invention. Alternatively, an antigen or other protein can be loaded into a dendritic cell in the absence of the yeast vehicle.

In one embodiment, intact yeast (with or without expression of heterologous antigens or other proteins) can be ground up or processed in a manner to produce yeast cell wall preparations, yeast membrane particles or yeast fragments (i.e., not intact) and the yeast fragments can, in some embodiments, be provided with or administered with other compositions that include antigens (e.g., DNA vaccines, protein subunit vaccines, killed or inactivated pathogens) to enhance immune responses. For example, enzymatic treatment, chemical treatment or physical force (e.g., mechanical shearing or sonication) can be used to break up the yeast into parts that are used as an adjuvant.

In one embodiment of the invention, yeast vehicles useful in the invention include yeast vehicles that have been killed or inactivated. Killing or inactivating of yeast can be accomplished by any of a variety of suitable methods known in the art. For example, heat inactivation of yeast is a standard way of inactivating yeast, and one of skill in the art can monitor the structural changes of the target antigen, if desired, by standard methods known in the art. Alternatively, other methods of inactivating the yeast can be used, such as chemical, electrical, radioactive or UV methods. See, for example, the methodology disclosed in standard yeast culturing textbooks such as *Methods of Enzymology*, Vol. 194, Cold Spring Harbor Publishing (1990). Any of the inactivation strategies used should take the secondary, tertiary or quaternary structure of the target antigen into consideration and preserve such structure as to optimize its immunogenicity.

Yeast vehicles can be formulated into yeast-based immunotherapy compositions or products of the present invention, including preparations to be administered to a subject directly or first loaded into a carrier such as a dendritic cell, using a number of techniques known to those skilled in the art. For example, yeast vehicles can be dried by lyophilization. Formulations comprising yeast vehicles can also be prepared by packing yeast in a cake or a tablet, such as is done for yeast used in baking or brewing operations. In addition, yeast vehicles can be mixed with a pharmaceutically acceptable excipient, such as an isotonic buffer that is tolerated by a host or host cell. Examples of such excipients include water, saline, Ringer's solution, dextrose solution, Hank's solution, and other aqueous physiologically balanced salt solutions. Nonaqueous vehicles, such as fixed oils, sesame oil, ethyl oleate, or triglycerides may also be used. Other useful formulations include suspensions containing viscosity-enhancing agents, such as sodium carboxymethylcellulose, sorbitol, glycerol or dextran. Excipients can also contain minor amounts of additives, such as substances that enhance isotonicity and chemical stability. Examples of buffers include phosphate buffer, bicarbonate buffer and Tris buffer, while examples of preservatives include thimerosal, m- or o-cresol, formalin and benzyl alcohol. Standard formulations can either be liquid injectables or solids which can be taken up in a suitable liquid as a suspension or solution for injection. Thus, in a non-liquid formulation, the excipient can comprise, for example, dextrose, human serum albumin, and/or preservatives to which sterile water or saline can be added prior to administration.

In one embodiment of the present invention, a composition can include additional agents, which may also be referred to as biological response modifier compounds, or the ability to produce such agents/modifiers. For example, a yeast vehicle can be transfected with or loaded with at least one antigen and at least one agent/biological response modifier compound, or a composition of the invention can be administered in conjunction with at least one agent/biological response modifier. Biological response modifiers include adjuvants and other compounds that can modulate immune responses, which may be referred to as immunomodulatory compounds, as well as compounds that modify the biological activity of another compound or agent, such as a yeast-based immunotherapeutic, such biological activity not being limited to immune system effects. Certain immunomodulatory compounds can stimulate a protective immune response whereas others can suppress a harmful immune response, and whether an immunomodulatory is useful in combination with a given yeast-based immunotherapeutic may depend, at least in part, on the disease state or condition to be treated or prevented, and/or on the individual who is to be treated. Certain biological response modifiers preferentially enhance a cell-mediated immune response whereas others preferentially enhance a humoral immune response (i.e., can stimulate an immune response in which there is an increased level of cell-mediated compared to humoral immunity, or vice versa.). Certain biological response modifiers have one or more properties in common with the biological properties of yeast-based immunotherapeutics or enhance or complement the biological properties of yeast-based immunotherapeutics. There are a number of techniques known to those skilled in the art to measure stimulation or suppression of immune responses, as well as to differentiate cell-mediated immune responses from humoral immune responses, and to differentiate one type of cell-mediated response from another (e.g., a TH17 response versus a TH1 response).

Agents/biological response modifiers useful in the invention may include, but are not limited to, cytokines, chemokines, hormones, lipidic derivatives, peptides, proteins, polysaccharides, small molecule drugs, antibodies and antigen binding fragments thereof (including, but not limited to, anti-cytokine antibodies, anti-cytokine receptor antibodies, anti-chemokine antibodies), vitamins, polynucleotides, nucleic acid binding moieties, aptamers, and growth modulators. Some suitable agents include, but are not limited to, IL-1 or agonists of IL-1 or of IL-1R, anti-IL-1 or other IL-1 antagonists; IL-6 or agonists of IL-6 or of IL-6R, anti-IL-6 or other IL-6 antagonists; IL-12 or agonists of IL-12 or of IL-12R, anti-IL-12 or other IL-12 antagonists; IL-17 or agonists of IL-17 or of IL-17R, anti-IL-17 or other IL-17 antagonists; IL-21 or agonists of IL-21 or of IL-21R, anti-IL-21 or other IL-21 antagonists; IL-22 or agonists of IL-22 or of IL-22R, anti-IL-22 or other IL-22 antagonists; IL-23 or agonists of IL-23 or of IL-23R, anti-IL-23 or other IL-23 antagonists; IL-25 or agonists of IL-25 or of IL-25R, anti-IL-25 or other IL-25 antagonists; IL-27 or agonists of IL-27 or of IL-27R, anti-IL-27 or other IL-27 antagonists; type I interferon (including IFN-α) or agonists or antagonists of type I interferon or a receptor thereof; type II interferon (including IFN-γ) or agonists or antagonists of type II interferon or a receptor thereof; anti-CD40 antibody, CD40L, anti-CTLA-4 antibody (e.g., to release anergic T cells); T cell co-stimulators (e.g., anti-CD137, anti-CD28, anti-CD40); alemtuzumab (e.g., CamPath®), denileukin diftitox (e.g., ONTAK®); anti-CD4; anti-CD25; anti-PD-1, anti-PD-L1, anti-PD-L2; agents that block FOXP3 (e.g., to abrogate the activity/kill CD4$^+$/CD25$^+$ T regulatory cells); Flt3 ligand, imiquimod (Aldara™), granulocyte-macrophage colony stimulating factor (GM-CSF); granulocyte-colony stimulating factor (G-CSF), sargramostim (Leukine®); hormones including without limitation prolactin and growth hormone; Toll-like receptor (TLR) agonists, including but not limited to TLR-2 agonists, TLR-4 agonists, TLR-7 agonists, and TLR-9 agonists; TLR antagonists, including but not limited to TLR-2 antagonists, TLR-4 antagonists, TLR-7 antagonists, and TLR-9 antagonists; anti-inflammatory agents and immunomodulators, including but not limited to, COX-2 inhibitors (e.g., Celecoxib, NSAIDS), glucocorticoids, statins, and thalidomide and analogues thereof including IMiD™s (which are structural and functional analogues of thalidomide (e.g., REV- LIMID® (lenalidomide), ACTIMID® (pomalidomide)); proinflammatory agents, such as fungal or bacterial components or any proinflammatory cytokine or chemokine; immunotherapeutic vaccines including, but not limited to, virus-based vaccines, bacteria-based vaccines, or antibody-based vaccines; and any other immunomodulators, immunopotentiators, anti-inflammatory agents, and/or pro-inflammatory agents. Any combination of such agents is contemplated by the invention, and any of such agents combined with or administered in a protocol with (e.g., concurrently, sequentially, or in other formats with) a yeast-based immunotherapeutic is a composition encompassed by the invention. Such agents are well known in the art. These agents may be used alone or in combination with other agents described herein.

Agents can include agonists and antagonists of a given protein or peptide or domain thereof. As used herein, an "agonist" is any compound or agent, including without limitation small molecules, proteins, peptides, antibodies, nucleic acid binding agents, etc., that binds to a receptor or ligand and produces or triggers a response, which may include agents that mimic the action of a naturally occurring substance that binds to the receptor or ligand. An "antagonist" is any compound or agent, including without limitation small molecules, proteins, peptides, antibodies, nucleic acid binding agents, etc., that blocks or inhibits or reduces the action of an agonist.

Compositions of the invention can further include or can be administered with (concurrently, sequentially, or intermittently with) any other compounds or compositions that are useful for preventing or treating HBV infection or any compounds that treat or ameliorate any symptom of HBV infection. A variety of agents are known to be useful for preventing and/or treating or ameliorating HBV infection. Such agents include, but are not limited to, anti-viral compounds, including, but not limited to, nucleotide analogue reverse transcriptase inhibitor (nRTIs). In one aspect of the invention, suitable anti-viral compounds include, but are not limited to: tenofovir (VIREAD®), lamivudine (EPIVIR®), adefovir (HEPSERA®), telbivudine (TYZEKA®), entecavir (BARACLUDE®), and combinations thereof, and/or interferons, such as interferon-α2a or pegylated interferon-α2a (PEGASYS®) or interferon-λ. These agents are typically administered for long periods of time (e.g., daily or weekly for up to one to five years or longer). In addition, compositions of the invention can be used together with other immunotherapeutic compositions, including prophylactic and/or therapeutic immunotherapy. For example, prophylactic vaccines for HBV have been commercially available since the early 1980's. These commercial vaccines are non-infectious, subunit viral vaccines providing purified recombinant hepatitis B virus surface antigen (HBsAg), and can be administered beginning at birth. While no therapeutic immunotherapeutic compositions have been approved in the U.S. for the treatment of HBV, such compositions can include HBV protein or epitope subunit vaccines, HBV viral vector vaccines, cytokines, and/or other immunomodulatory agents (e.g., TLR agonists, immunomodulatory drugs).

The invention also includes a kit comprising any of the compositions described herein, or any of the individual components of the compositions described herein.

Methods for Administration or Use of Compositions of the Invention

Compositions of the invention, which can include any one or more (e.g., combinations of two, three, four, five, or more) yeast-based immunotherapeutic compositions described herein, HBV antigens including HBV proteins and fusion proteins, and/or recombinant nucleic acid molecules encoding such HBV proteins or fusion proteins described above, and other compositions comprising such yeast-based compositions, antigens, proteins, fusion proteins, or recombinant molecules described herein, can be used in a variety of in vivo and in vitro methods, including, but not limited to, to treat and/or prevent HBV infection and its sequelae, in diagnostic assays for HBV, or to produce antibodies against HBV.

One embodiment of the invention relates to a method to treat chronic hepatitis B virus (HBV) infection, and/or to prevent, ameliorate or treat at least one symptom of chronic HBV infection, in an individual or population of individuals. The method includes the step of administering to an individual or a population of individuals who are chronically infected with HBV one or more immunotherapeutic compositions of the invention. In one aspect, the composition is an immunotherapeutic composition comprising one or more HBV antigens as described herein, which can include a yeast-based immunotherapeutic composition. In one aspect, the composition includes a protein or fusion protein comprising HBV antigens as described herein, and/or recombinant nucleic acid molecule encoding such protein or fusion protein. In one embodiment, the individual or population of individuals has chronic HBV infection. In one aspect, the individual or population of individuals is additionally treated with at least one other therapeutic compound useful for the treatment of HBV infection. Such therapeutic compounds include, but are not limited to, direct-acting antiviral drugs (e.g., those described above or elsewhere herein) and/or interferons and/or other immunotherapeutic or immunomodulatory agents. In one aspect, such therapeutic compounds include host-targeted therapeutics (e.g., cyclophilin inhibitors which can interfere with viral replication, or re-entry inhibitors that can interfere with the viral life cycle (re-infection)).

"Standard Of Care" or "SOC" generally refers to the current approved standard of care for the treatment of a specific disease. In chronic HBV infection, SOC may be one of several different approved therapeutic protocols, and include, but may not be limited to, interferon therapy and/or anti-viral therapy. Currently approved anti-viral drugs for the treatment of HBV infection include tenofovir(VIREAD®), lamivudine (EPIVIR®), adefovir (HEPSERA®), telbivudine (TYZEKA®) and entecavir (BARACLUDE®). The anti-viral drugs prescribed most often for chronic HBV infection currently are tenofovir and entecavir. Interferon useful for the treatment of chronic HBV infection includes a type I interferon such as interferon-α, including, but not limited to interferon-α2 or pegylated interferon-α2 (e.g., PEGASYS®). In one embodiment, the interferon is a type III interferon, including without limitation, interferon-λ1, interferon-λ2, and/or interferon-λ3. The immunotherapeutic composition of the invention can be administered prior to, concurrently with, intermittently with, and/or after one or more anti-viral(s) and/or interferon and/or other immunotherapeutic or immunomodulatory agents. The other therapeutic compounds may also be administered prior to or after treatment with the immunotherapeutic compositions of the invention.

HBV infection is typically diagnosed in an individual by detection of HBsAg (hepatitis B virus surface antigen) and/or HBeAg (e-antigen) in the blood of the infected individual. The detection of HBeAg in the serum reflects active viral replication, and clinical outcome of infection can be correlated with e-antigen status, although long-term remission (or cure) is better predicted using HBsAg seroconversion when using current therapies (see below). Detection of IgM core antibody may also be used to detect acute HBV infection during the first 6-12 months of infection. Persistence of HBsAg in the blood for more than 6 months typically identifies chronic HBV infection. In addition, chronic HBV infection can be diagnosed by identifying HBV DNA (>2000 IU/ml), which can be combined with detection or identification of elevated serum alanine aminotransferase (ALT) and/or aspartate aminotrasferase (AST) levels (e.g., more than twice the upper limit of normal).

Recovery from the viral infection (complete response, or the endpoint for a treatment of HBV) is determined by HBeAg/HBsAg seroconversion, which is loss of HBeAg and HBsAg, respectively, and the development of antibodies against the hepatitis B surface antigen (anti-HBs) and/or antibodies against HBeAg. Clinical studies have defined seroconversion, or a protective antibody (anti-HBs) level as: (a) 10 or more sample ratio units (SRU) as determined by radioimmunoassay; (b) a positive result as determined by enzyme immunoassay; or (c) detection of an antibody concentration of ≥10 mIU/ml (10 SRU is comparable to 10 mIU/mL of antibody). Seroconversion can take years to develop in a chronically infected patient under current standard of care treatment (i.e., anti-viral drugs or interferon). Patients can also be monitored for loss or marked reduction of viral DNA (below detectable levels by PCR or <2000 IU/ml), normalization of serum alanine aminotransferase (ALT) levels, and improvement in liver inflammation and fibrosis. "ALT" is a well-validated measure of hepatic injury and serves as a surrogate for hepatic inflammation. In prior large hepatitis trials, reductions and/or normalization of ALT levels (ALT normalization) have been shown to correlate with improved liver function and reduced liver fibrosis as determined by serial biopsy.

Another embodiment of the invention relates to a method to immunize an individual or population of individuals against HBV in order to prevent HBV infection, prevent chronic HBV infection, and/or reduce the severity of HBV infection in the individual or population of individuals. The method includes the step of administering to an individual or population of individuals that is not infected with HBV (or believed not to be infected with HBV), a composition of the invention. In one aspect, the composition is an immunotherapeutic composition comprising one or more HBV antigens as described herein, including one or more yeast-based immunotherapeutic compositions. In one aspect, the composition includes a fusion protein comprising HBV antigens as described herein, or recombinant nucleic acid molecule encoding such fusion protein.

As used herein, the phrase "treat" HBV infection, or any permutation thereof (e.g., "treated for HBV infection", etc.) generally refers to applying or administering a composition of the invention once the infection (acute or chronic) has occurred, with the goal of reduction or elimination of detectable viral titer (e.g., reduction of viral DNA (below detectable levels by PCR or <2000 IU/ml)), reaching seroconversion (development of antibodies against HBsAg and/or HBeAg and concurrent loss or reduction of these proteins from the serum), reduction in at least one symptom resulting from the infection in the individual, delaying or preventing the onset and/or severity of symptoms and/or downstream sequelae caused by the infection, reduction of organ or physiological system damage (e.g., cirrhosis) resulting from the infection (e.g., reduction of abnormal ALT levels, reduction of liver inflammation, reduction of liver fibrosis), prevention and/or reduction in the frequency and incidence of hepatocellular carcinoma (HCC), improvement in organ or system function that was negatively impacted by the infection (normalization of serum ALT levels, improvement in liver inflammation, improvement in liver fibrosis), improvement of immune responses against the infection, improvement of long term memory immune responses against the infection, reduced reactivation of HBV virus, and/or improved general health of the individual or population of individuals.

In one aspect, a goal of treatment is sustained viral clearance for at least 6 months after the completion of therapy. In one aspect, a goal of treatment is the loss of detectable serum HBeAg and/or HBsAg proteins. In one aspect, a goal of treatment is the development of antibodies against the hepatitis B surface antigen (anti-HBs) and/or antibodies against HBeAg. In one aspect, the goal of treatment is seroconversion, which may be defined by: (a) 10 or more sample ratio units (SRU) as determined by radioimmunoassay; (b) a positive result as determined by enzyme immunoassay; or (c) detection of an antibody concentration of >10 mIU/ml (10 SRU is comparable to 10 mIU/mL of antibody).

To "prevent" HBV infection, or any permutation thereof (e.g., "prevention of HBV infection", etc.), generally refers to applying or administering a composition of the invention before an infection with HBV has occurred, with the goal of preventing infection by HBV, preventing chronic infection by HBV (i.e., enabling an individual to clear an acute HBV infection without further intervention), or, should the infection later occur, at least reducing the severity, and/or length of infection and/or the physiological damage caused by the chronic infection, including preventing or reducing the severity or incidence of at least one symptom resulting from the infection in the individual, and/or delaying or preventing the onset and/or severity of symptoms and/or downstream sequelae caused by the infection, in an individual or population of individuals. In one aspect, the present invention can be used to prevent chronic HBV infection, such as by enabling an individual who becomes acutely infected with HBV subsequent to administration of a composition of the invention to clear the infection and not become chronically infected.

The present invention includes the delivery (administration, immunization) of one or more immunotherapeutic compositions of the invention, including a yeast-based immunotherapy composition, to a subject. The administration process can be performed ex vivo or in vivo, but is typically performed in vivo. Ex vivo administration refers to performing part of the regulatory step outside of the patient, such as administering a composition of the present invention to a population of cells (dendritic cells) removed from a patient under conditions such that a yeast vehicle, antigen(s) and any other agents or compositions are loaded into the cell, and returning the cells to the patient. The therapeutic composition of the present invention can be returned to a patient, or administered to a patient, by any suitable mode of administration.

Administration of a composition can be systemic, mucosal and/or proximal to the location of the target site (e.g., near a site of infection). Suitable routes of administration will be apparent to those of skill in the art, depending on the type of condition to be prevented or treated, the antigen used, and/or the target cell population or tissue. Various acceptable methods of administration include, but are not limited to, intravenous administration, intraperitoneal administration, intramuscular administration, intranodal administration, intracoronary administration, intraarterial administration (e.g., into a carotid artery), subcutaneous administration, transdermal delivery, intratracheal administration, intraarticular administration, intraventricular administration, inhalation (e.g., aerosol), intracranial, intraspinal, intraocular, aural, intranasal, oral, pulmonary administration, impregnation of a catheter, and direct injection into a tissue. In one aspect, routes of administration include: intravenous, intraperitoneal, subcutaneous, intradermal, intranodal, intramuscular, transdermal, inhaled, intranasal, oral, intraocular, intraarticular, intracranial, and intraspinal. Parenteral delivery can include intradermal, intramuscular, intraperitoneal, intrapleural, intrapulmonary, intravenous, subcutaneous, atrial catheter and venal catheter routes. Aural delivery can include ear drops, intranasal delivery can include nose drops or intranasal injection, and intraocular delivery can include eye drops. Aerosol (inhalation) delivery can also be performed using methods standard in the art (see, for example, Stribling et al., *Proc. Natl. Acad. Sci. USA* 189:11277-11281, 1992). Other routes of administration that modulate mucosal immunity may be useful in the treatment of viral infections. Such routes include bronchial, intradermal, intramuscular, intranasal, other inhalatory, rectal, subcutaneous, topical, transdermal, vaginal and urethral routes. In one aspect, an immunotherapeutic composition of the invention is administered subcutaneously.

With respect to the yeast-based immunotherapy compositions of the invention, in general, a suitable single dose is a dose that is capable of effectively providing a yeast vehicle and an antigen (if included) to a given cell type, tissue, or region of the patient body in an amount effective to elicit an antigen-specific immune response against one or more HBV antigens or epitopes, when administered one or more times over a suitable time period. For example, in one embodiment, a single dose of a yeast vehicle of the present invention is from about $1 \times 10^5$ to about $5 \times 10^7$ yeast cell equivalents per kilogram body weight of the organism being administered the composition. In one aspect, a single dose of a yeast vehicle of the present invention is from about 0.1 Y.U. ($1 \times 10^6$ cells) to about 100 Y.U. ($1 \times 10^9$ cells) per dose (i.e., per organism), including any interim dose, in increments of $0.1 \times 10^6$ cells (i.e., $1.1 \times 10^6$, $1.2 \times 10^6$, $1.3 \times 10^6$ ... ). In one embodiment, doses include doses between 1 Y.U and 40 Y.U., doses between 1 Y.U. and 50 Y.U., doses between 1 Y.U. and 60 Y.U., doses between 1 Y.U. and 70 Y.U., or doses between 1 Y.U. and 80 Y.U., and in one aspect, between 10 Y.U. and 40 Y.U., 50 Y.U., 60 Y.U., 70 Y.U., or 80 Y.U. In one embodiment, the doses are administered at different sites on the individual but during the same dosing period. For example, a 40 Y.U. dose may be administered via by injecting 10 Y.U. doses to four different sites on the individual during one dosing period, or a 20 Y.U. dose may be administered by injecting 5 Y.U. doses to four different sites on the individual, or by injecting 10Y.U. doses to two different sites on the individual, during the same dosing period. The invention includes administration of an amount of the yeast-based immunotherapy composition (e.g., 1, 2, 3, 4, 5, 6, 7, 8, 9 10, 11, 12, 13, 14, 15, 16, 17, 18, 19, 20 Y.U. or more) at 1, 2, 3, 4, 5, 6, 7, 8, 9, 10, or more different sites on an individual to form a single dose.

"Boosters" or "boosts" of a therapeutic composition are administered, for example, when the immune response against the antigen has waned or as needed to provide an immune response or induce a memory response against a particular antigen or antigen(s). Boosters can be administered from about 1, 2, 3, 4, 5, 6, 7, or 8 weeks apart, to monthly, to bimonthly, to quarterly, to annually, to several years after the original administration. In one embodiment, an administration schedule is one in which from about $1 \times 10^5$ to about $5 \times 10^7$ yeast cell equivalents of a composition per kg body weight of the organism is administered at least 1, 2, 3, 4, 5, 6, 7, 8, 9, 10, or more times over a time period of from weeks, to months, to years. In one embodiment, the doses are administered weekly for 1, 2, 3, 4, 5, 6, 7, 8, 9, 10 or more doses, followed by monthly doses as needed to achieve the desired inhibition or elimination of the HBV virus. For example, the doses can be administered until the individual achieves seroconversion, until HBV DNA titers fall below 2000 IU/ml, and/or until ALT levels normalize. In one embodiment, the doses are administered in a 4-weekly protocol (every 4 weeks, or on day 1, week 4, week 8, week 12, etc., for between 2 and 10 doses or longer as determined by the clinician). Additional doses can be administered even after the individual achieves seroconversion, if desired, although such dosing may not be necessary.

With respect to administration of yeast-based immunotherapeutic compositions described herein, a single composition can be administered to an individual or population of individuals or combination of such compositions can be administered. For example, the invention provides several "single protein" compositions or compositions directed against a particular genotype, as well as multi-protein compositions and compositions that target multiple genotypes, or sub-genotypes. Accordingly, two or more compositions can be selected in a "spice rack" approach to most effectively prevent or treat HBV infection in a given individual or population of individuals.

In one aspect of the invention, one or more additional therapeutic agents are administered sequentially with the yeast-based immunotherapy composition. In another embodiment, one or more additional therapeutic agents are administered before the yeast-based immunotherapy composition is administered. In another embodiment, one or more additional therapeutic agents are administered after the yeast-based immunotherapy composition is administered. In one embodiment, one or more additional therapeutic agents are administered in alternating doses with the yeast-based immunotherapy composition, or in a protocol in which the yeast-based composition is administered at prescribed intervals in between or with one or more consecutive doses of the additional agents, or vice versa. In one embodiment, the yeast-based immunotherapy composition is administered in one or more doses over a period of time prior to commencing the administration of the additional agents. In other words, the yeast-based immunotherapeutic composition is administered as a monotherapy for a period of time, and then the agent administration is added, either concurrently with new doses of yeast-based immunotherapy, or in an alternating fashion with yeast-based immunotherapy. Alternatively, the agent may be administered for a period of time prior to beginning administration of the yeast-based immunotherapy composition. In one aspect, the yeast is engineered to express or carry the agent, or a different yeast is engineered or produced to express or carry the agent.

In one aspect of the invention, when a treatment course of interferon or anti-viral compound therapy begins, additional doses of the immunotherapeutic composition are administered over the same period of time, or for at least a portion of that time, and may continue to be administered once the course of interferon or anti-viral compound has ended. However, the dosing schedule for the immunotherapy over the entire period may be, and is expected to typically be, different than that for the interferon or the anti-viral compound. For example, the immunotherapeutic composition may be administered on the same days or at least 3-4 days after the last given (most recent) dose of interferon or anti-viral (or any suitable number of days after the last dose), and may be administered daily, weekly, biweekly, monthly, bimonthly, or every 3-6 months, or at longer intervals as determined by the physician. During an initial period of monotherapy administration of the immunotherapeutic composition, if utilized, the immunotherapeutic composition is preferably administered weekly for between 4 and 12 weeks, followed by monthly administration (regardless of when the additional interferon or anti-viral therapy is added into the protocol). In one aspect, the immunotherapeutic composition is administered weekly for four or five weeks, followed by monthly administration thereafter, until conclusion of the complete treatment protocol.

In aspects of the invention, an immunotherapeutic composition and other agents can be administered together (concurrently). As used herein, concurrent use does not necessarily mean that all doses of all compounds are administered on the same day at the same time. Rather, concurrent use means that each of the therapy components (e.g., immunotherapy and interferon therapy, or immunotherapy and anti-viral therapy) are started at approximately the same period (within hours, or up to 1-7 days of each other) and are administered over the same general period of time, noting that each component may have a different dosing schedule (e.g., interferon weekly, immunotherapy monthly, anti-viral daily or weekly). In addition, before or after the concurrent administration period, any one of the agents or immunotherapeutic compositions can be administered without the other agent(s).

It is contemplated by the present invention that the use of an immunotherapeutic composition of the invention with an anti-viral such as tenofovir or entecavir will enable a shorter time course for the use of the anti-viral drug. Similar results are expected when combining an immunotherapeutic of the invention with interferon. Dosing requirements for the anti-viral or interferon may also be reduced or modified as a result of combination with the immunotherapeutic of the invention to generally improve the tolerance of the patient for the drug. In addition, it is contemplated that the immunotherapeutic composition of the invention will enable seroconversion or sustained viral responses for patients in whom anti-viral therapy alone fails to achieve these endpoints. In other words, more patients will achieve seroconversion when an immunotherapeutic composition of the invention is combined with an anti-viral or interferon than will achieve seroconversion by using anti-virals or interferon alone. Under current SOC for HBV infection, anti-virals may be administered for 6 months to one year, two years, three years, four years, five years, or longer (e.g., indefinitely). By combining such therapy with an immunotherapeutic composition of the invention, the time for the administration of the anti-viral may be reduced by several months or years. It is contemplated that use of the immunotherapeutic compositions of the present invention, as a monotherapy or in combination with anti-viral and/or immunomodulatory approaches will be effective to achieve loss of HBsAg and/or HBeAg; HBeAg seroconversion, HBsAg seroconversion, or complete seroconversion; and in many individuals, sustained viral clearance for at least 6 months after the completion of therapy. In some patients, immunotherapy according to the present invention, when used as a monotherapy or in combination with anti-viral and/or immunomodulatory approaches, may achieve loss of HBsAg and/or HBeAg, but not achieve seroconversion (development of anti-HBs or anti-HBeAg). In this scenario, it is an embodiment of the invention to additionally use, alone or in combination with the yeast-based immunotherapy of the invention and/or anti-virals or other immunomodulatory agents, an agent such as the current prophylactic recombinant HBV subunit vaccine, in order to achieve complete response in the patient.

As used herein, the term "anti-viral" refers to any compound or drug, typically a small-molecule inhibitor or antibody, which targets one or more steps in the virus life cycle with direct anti-viral therapeutic effects. In one embodiment of the invention, the anti-viral compound or drug to be administered in the same therapeutic protocol with an immunotherapeutic composition of the invention is selected from tenofovir (VIREAD®), lamivudine (EPIVIR®), adefovir (HEPSERA®), telbivudine (TYZEKA®) and entecavir (BARACLUDE®), or any analog or derivative thereof, or any composition comprising or containing such compound, drug, analog or derivative.

Tenofovir (tenofovir disoproxil fumarate or TDF), or ({[(2R)-1-(6-amino-9H-purin-9-yl)propan-2-yl]oxy}methyl)phosphonic acid, is a nucleotide analogue reverse transcriptase inhibitor (nRTIs). For the treatment of HBV infection, tenofovir is typically administered to adults as a pill taken at a dose of 300 mg (tenofovir disproxil fumarate) once daily. Dosage for pediatric patients is based on body weight of the patient (8 mg per kg body weight, up to 300 mg once daily) and may be provided as tablet or oral powder.

Lamivudine, or 2',3'-dideoxy-3'-thiacytidine, commonly called 3TC, is a potent nucleoside analog reverse transcriptase inhibitor (nRTI). For the treatment of HBV infection, lamivudine is administered as a pill or oral solution taken at a dose of 100 mg once a day (1.4-2 mg/lb. twice a day for children 3 months to 12 years old).

Adefovir (adefovir dipivoxil), or 9-[2-[[bis[(pivaloyloxy)methoxy]-phosphinyl]-methoxy]ethyl]adenine, is an orally-administered nucleotide analog reverse transcriptase inhibitor (ntRTI). For the treatment of HBV infection, adefovir is administered as a pill taken at a dose of 10 mg once daily.

Telbivudine, or 1-(2-deoxy-β-L-erythro-pentofuranosyl)-5-methylpyrimidine-2,4(1H,3H)-dione, is a synthetic thymidine nucleoside analogue (the L-isomer of thymidine). For the treatment of HBV infection, telbivudine is administered as a pill or oral solution taken at a dose of 600 mg once daily.

Entecavir, or 2-Amino-9-[(1S,3R,4S)-4-hydroxy-3-(hydroxymethyl)-2-methylidenecyclopentyl]-6,9-dihydro-3H-purin-6-one, is a nucleoside analog (guanine analogue) that inhibits reverse transcription, DNA replication and transcription of the virus. For the treatment of HBV infection, entecavir is administered as a pill or oral solution taken at a dose of 0.5 mg once daily (1 mg daily for lamivudine-refractory or telbivudine resistance mutations).

In one embodiment of the invention, the interferon to be administered in a therapeutic protocol with an immunotherapeutic composition of the invention is an interferon, and in one aspect, interferon-α, and in one aspect, interferon-α2b (administered by subcutaneous injection 3 times per week); or pegylated interferon-α2a (e.g. PEGASYS®). As used herein, the term "interferon" refers to a cytokine that is typically produced by cells of the immune system and by a wide variety of cells in response to the presence of double-stranded RNA. Interferons assist the immune response by inhibiting viral replication within host cells, activating natural killer cells and macrophages, increasing antigen presentation to lymphocytes, and inducing the resistance of host cells to viral infection. Type I interferons include interferon-α. Type III interferons include interferon-λ. Interferons useful in the methods of the present invention include any type I or type III interferon, including interferon-α, interferon-α2, and in one aspect, longer lasting forms of interferon, including, but not limited to, pegylated interferons, interferon fusion proteins (interferon fused to albumin), and controlled-release formulations comprising interferon (e.g., interferon in microspheres or interferon with polyaminoacid nanoparticles). One interferon, PEGASYS®, pegylated interferon-α2a, is a covalent conjugate of recombinant interferon-α2a (approximate molecular weight [MW] 20,000 daltons) with a single branched bis-monomethoxy polyethylene glycol (PEG) chain (approximate MW 40,000 daltons). The PEG moiety is linked at a single site to the interferon-α moiety via a stable amide bond to lysine. Pegylated interferon-α2a has an approximate molecular weight of 60,000 daltons.

Interferon is typically administered by intramuscular or subcutaneous injection, and can be administered in a dose of between 3 and 10 million units, with 3 million units being preferred in one embodiment. Doses of interferon are administered on a regular schedule, which can vary from 1, 2, 3, 4, 5, or 6 times a week, to weekly, biweekly, every three weeks, or monthly. A typical dose of interferon that is currently available is provided weekly, and that is a preferred dosing schedule for interferon, according to the present invention. For the treatment of HBV, pegylated interferon-α2a is currently administered subcutaneously once a week at a dose of 180 mg (1.0 ml viral or 0.5 ml prefilled syringe), for a total of 48 weeks. The dose amount and timing can be varied according to the preferences and recommendations of the physician, as well as according to the recommendations for the particular interferon being used, and it is within the abilities of those of skill in the art to determine the proper dose. It is contemplated that by using interferon therapy together with an immunotherapeutic composition of the invention, the dose strength and/or number of doses of interferon (length of time on interferon and/or intervals between doses of interferon) can be reduced.

In the method of the present invention, compositions and therapeutic compositions can be administered to animal, including any vertebrate, and particularly to any member of the Vertebrate class, Mammalia, including, without limitation, primates, rodents, livestock and domestic pets. Livestock include mammals to be consumed or that produce useful products (e.g., sheep for wool production). Mammals to treat or protect include humans, dogs, cats, mice, rats, goats, sheep, cattle, horses and pigs.

An "individual" is a vertebrate, such as a mammal, including without limitation a human. Mammals include, but are not limited to, farm animals, sport animals, pets, primates, mice and rats. The term "individual" can be used interchangeably with the term "animal", "subject" or "patient".

General Techniques Useful in the Invention

The practice of the present invention will employ, unless otherwise indicated, conventional techniques of molecular biology (including recombinant techniques), microbiology, cell biology, biochemistry, nucleic acid chemistry, and immunology, which are well known to those skilled in the art. Such techniques are explained fully in the literature, such as, *Methods of Enzymology*, Vol. 194, Guthrie et al., eds., Cold Spring Harbor Laboratory Press (1990); *Biology and activities of yeasts*, Skinner, et al., eds., Academic Press (1980); *Methods in yeast genetics: a laboratory course manual*, Rose et al., Cold Spring Harbor Laboratory Press (1990); *The Yeast Saccharomyces: Cell Cycle and Cell Biology*, Pringle et al., eds., Cold Spring Harbor Laboratory Press (1997); *The Yeast Saccharomyces: Gene Expression*, Jones et al., eds., Cold Spring Harbor Laboratory Press (1993); *The Yeast Saccharomyces: Genome Dynamics, Protein Synthesis, and Energetics*, Broach et al., eds., Cold Spring Harbor Laboratory Press (1992); *Molecular Cloning: A Laboratory Manual*, second edition (Sambrook et al., 1989) and *Molecular Cloning: A Laboratory Manual*, third edition (Sambrook and Russel, 2001), (jointly referred to herein as "Sambrook"); Current Protocols in Molecular Biology (F. M. Ausubel et al., eds., 1987, including supplements through 2001); *PCR: The Polymerase Chain Reaction*, (Mullis et al., eds., 1994); Harlow and Lane (1988), *Antibodies, A Laboratory Manual*, Cold Spring Harbor Publications, New York; Harlow and Lane (1999) *Using Antibodies: A Laboratory Manual*, Cold Spring Harbor Laboratory Press, Cold Spring Harbor, N.Y. (jointly referred to herein as "Harlow and Lane"), Beaucage et al. eds., *Current Protocols in Nucleic Acid Chemistry*, John Wiley & Sons, Inc., New York, 2000); Casarett and Doull's *Toxicology The Basic Science of Poisons*, C. Klaassen, ed., 6th edition (2001), and *Vaccines*, S. Plotkin and W. Orenstein, eds., 3rd edition (1999).

General Definitions

A "TARMOGEN®" (GlobeImmune, Inc., Louisville, Colo.) generally refers to a yeast vehicle expressing one or more heterologous antigens extracellularly (on its surface), intracellularly (internally or cytosolically) or both extracellularly and intracellularly. TARMOGEN® products have been generally described (see, e.g., U.S. Pat. No. 5,830,463). Certain yeast-based immunotherapy compositions, and methods of making and generally using the same, are also described in detail, for example, in U.S. Pat. Nos. 5,830,463, 7,083,787, 7,736,642, Stubbs et al., *Nat. Med.* 7:625-629 (2001), Lu et al., *Cancer Research* 64:5084-5088 (2004), and in Bernstein et al., *Vaccine* 2008 Jan. 24; 26(4):509-21, each of which is incorporated herein by reference in its entirety.

As used herein, the term "analog" refers to a chemical compound that is structurally similar to another compound but differs slightly in composition (as in the replacement of one atom by an atom of a different element or in the presence of a particular functional group, or the replacement of one functional group by another functional group). Thus, an analog is a compound that is similar or comparable in function and appearance, but has a different structure or origin with respect to the reference compound.

The terms "substituted", "substituted derivative" and "derivative", when used to describe a compound, means that at least one hydrogen bound to the unsubstituted compound is replaced with a different atom or a chemical moiety.

Although a derivative has a similar physical structure to the parent compound, the derivative may have different chemical and/or biological properties than the parent compound. Such properties can include, but are not limited to, increased or decreased activity of the parent compound, new activity as compared to the parent compound, enhanced or decreased bioavailability, enhanced or decreased efficacy, enhanced or decreased stability in vitro and/or in vivo, and/or enhanced or decreased absorption properties.

In general, the term "biologically active" indicates that a compound (including a protein or peptide) has at least one detectable activity that has an effect on the metabolic or other processes of a cell or organism, as measured or observed in vivo (i.e., in a natural physiological environment) or in vitro (i.e., under laboratory conditions).

According to the present invention, the term "modulate" can be used interchangeably with "regulate" and refers generally to upregulation or downregulation of a particular activity. As used herein, the term "upregulate" can be used generally to describe any of: elicitation, initiation, increasing, augmenting, boosting, improving, enhancing, amplifying, promoting, or providing, with respect to a particular activity. Similarly, the term "downregulate" can be used generally to describe any of: decreasing, reducing, inhibiting, ameliorating, diminishing, lessening, blocking, or preventing, with respect to a particular activity.

In one embodiment of the present invention, any of the amino acid sequences described herein can be produced with from at least one, and up to about 20, additional heterologous amino acids flanking each of the C- and/or N-terminal ends of the specified amino acid sequence. The resulting protein or polypeptide can be referred to as "consisting essentially of" the specified amino acid sequence. According to the present invention, the heterologous amino acids are a sequence of amino acids that are not naturally found (i.e., not found in nature, in vivo) flanking the specified amino acid sequence, or that are not related to the function of the specified amino acid sequence, or that would not be encoded by the nucleotides that flank the naturally occurring nucleic acid sequence encoding the specified amino acid sequence as it occurs in the gene, if such nucleotides in the naturally occurring sequence were translated using standard codon usage for the organism from which the given amino acid sequence is derived. Similarly, the phrase "consisting essentially of", when used with reference to a nucleic acid sequence herein, refers to a nucleic acid sequence encoding a specified amino acid sequence that can be flanked by from at least one, and up to as many as about 60, additional heterologous nucleotides at each of the 5' and/or the 3' end of the nucleic acid sequence encoding the specified amino acid sequence. The heterologous nucleotides are not naturally found (i.e., not found in nature, in vivo) flanking the nucleic acid sequence encoding the specified amino acid sequence as it occurs in the natural gene or do not encode a protein that imparts any additional function to the protein or changes the function of the protein having the specified amino acid sequence.

According to the present invention, the phrase "selectively binds to" refers to the ability of an antibody, antigen-binding fragment or binding partner of the present invention to preferentially bind to specified proteins. More specifically, the phrase "selectively binds" refers to the specific binding of one protein to another (e.g., an antibody, fragment thereof, or binding partner to an antigen), wherein the level of binding, as measured by any standard assay (e.g., an immunoassay), is statistically significantly higher than the background control for the assay. For example, when performing an immunoassay, controls typically include a reaction well/tube that contain antibody or antigen binding fragment alone (i.e., in the absence of antigen), wherein an amount of reactivity (e.g., non-specific binding to the well) by the antibody or antigen-binding fragment thereof in the absence of the antigen is considered to be background. Binding can be measured using a variety of methods standard in the art including enzyme immunoassays (e.g., ELISA, immunoblot assays, etc.).

Reference to a protein or polypeptide used in the present invention includes full-length proteins, fusion proteins, or any fragment, domain, conformational epitope, or homologue of such proteins, including functional domains and immunological domains of proteins. More specifically, an isolated protein, according to the present invention, is a protein (including a polypeptide or peptide) that has been removed from its natural milieu (i.e., that has been subject to human manipulation) and can include purified proteins, partially purified proteins, recombinantly produced proteins, and synthetically produced proteins, for example. As such, "isolated" does not reflect the extent to which the protein has been purified. Preferably, an isolated protein of the present invention is produced recombinantly. According to the present invention, the terms "modification" and "mutation" can be used interchangeably, particularly with regard to the modifications/mutations to the amino acid sequence of proteins or portions thereof (or nucleic acid sequences) described herein.

As used herein, the term "homologue" is used to refer to a protein or peptide which differs from a naturally occurring protein or peptide (i.e., the "prototype" or "wild-type" protein) by minor modifications to the naturally occurring protein or peptide, but which maintains the basic protein and side chain structure of the naturally occurring form. Such changes include, but are not limited to: changes in one or a few amino acid side chains; changes one or a few amino acids, including deletions (e.g., a truncated version of the protein or peptide) insertions and/or substitutions; changes in stereochemistry of one or a few atoms; and/or minor derivatizations, including but not limited to: methylation, glycosylation, phosphorylation, acetylation, myristoylation, prenylation, palmitation, amidation and/or addition of glycosylphosphatidyl inositol. A homologue can have enhanced, decreased, or substantially similar properties as compared to the naturally occurring protein or peptide. A homologue can include an agonist of a protein or an antagonist of a protein. Homologues can be produced using techniques known in the art for the production of proteins including, but not limited to, direct modifications to the isolated, naturally occurring protein, direct protein synthesis, or modifications to the nucleic acid sequence encoding the protein using, for example, classic or recombinant DNA techniques to effect random or targeted mutagenesis.

A homologue of a given protein may comprise, consist essentially of, or consist of, an amino acid sequence that is at least about 45%, or at least about 50%, or at least about 55%, or at least about 60%, or at least about 65%, or at least about 70%, or at least about 75%, or at least about 80%, or at least about 85%, or at least about 90%, or at least about 91% identical, or at least about 92% identical, or at least about 93% identical, or at least about 94% identical, or at least about 95% identical, or at least about 96% identical, or at least about 97% identical, or at least about 98% identical, or at least about 99% identical (or any percent identity between 45% and 99%, in whole integer increments), to the amino acid sequence of the reference protein. In one embodiment, the homologue comprises, consists essentially of, or consists of, an amino acid sequence that is less than 100% identical, less than about 99% identical, less than about 98% identical, less than about 97% identical, less than about 96% identical, less than about 95% identical, and so on, in increments of 1%, to less than about 70% identical to the naturally occurring amino acid sequence of the reference protein.

A homologue may include proteins or domains of proteins that are "near full-length", which means that such a homologue differs from the full-length protein, functional domain or immunological domain (as such protein, functional domain or immunological domain is described herein or otherwise known or described in a publicly available sequence) by the addition of or deletion of 1, 2, 3, 4, 5, 6, 7, 8, 9, or 10 amino acids from the N- and/or the C-terminus of such full-length protein or full-length functional domain or full-length immunological domain.

As used herein, unless otherwise specified, reference to a percent (%) identity refers to an evaluation of homology which is performed using: (1) a BLAST 2.0 Basic BLAST homology search using blastp for amino acid searches and blastn for nucleic acid searches with standard default parameters, wherein the query sequence is filtered for low complexity regions by default (described in Altschul, S. F., Madden, T. L., Schääffer, A. A., Zhang, J., Zhang, Z., Miller, W. & Lipman, D. J. (1997) "Gapped BLAST and PSI-BLAST: a new generation of protein database search programs." Nucleic Acids Res. 25:3389-3402, incorporated herein by reference in its entirety); (2) a BLAST 2 alignment (using the parameters described below); (3) and/or PSI-BLAST with the standard default parameters (Position-Specific Iterated BLAST. It is noted that due to some differences in the standard parameters between BLAST 2.0 Basic BLAST and BLAST 2, two specific sequences might be recognized as having significant homology using the BLAST 2 program, whereas a search performed in BLAST 2.0 Basic BLAST using one of the sequences as the query sequence may not identify the second sequence in the top matches. In addition, PSI-BLAST provides an automated, easy-to-use version of a "profile" search, which is a sensitive way to look for sequence homologues.

The program first performs a gapped BLAST database search. The PSI-BLAST program uses the information from any significant alignments returned to construct a position-specific score matrix, which replaces the query sequence for the next round of database searching. Therefore, it is to be understood that percent identity can be determined by using any one of these programs.

Two specific sequences can be aligned to one another using BLAST 2 sequence as described in Tatusova and Madden, (1999), "Blast 2 sequences—a new tool for comparing protein and nucleotide sequences", FEMS Microbiol Lett. 174: 247-250, incorporated herein by reference in its entirety. BLAST 2 sequence alignment is performed in blastp or blastn using the BLAST 2.0 algorithm to perform a Gapped BLAST search (BLAST 2.0) between the two sequences allowing for the introduction of gaps (deletions and insertions) in the resulting alignment. For purposes of clarity herein, a BLAST 2 sequence alignment is performed using the standard default parameters as follows.

For blastn, using 0 BLOSUM62 matrix:
Reward for match=1
Penalty for mismatch=−2
Open gap (5) and extension gap (2) penalties
gap x_dropoff (50) expect (10) word size (11) filter (on)
For blastp, using 0 BLOSUM62 matrix:
Open gap (11) and extension gap (1) penalties
gap x_dropoff (50) expect (10) word size (3) filter (on).

An isolated nucleic acid molecule is a nucleic acid molecule that has been removed from its natural milieu (i.e., that has been subject to human manipulation), its natural milieu being the genome or chromosome in which the nucleic acid molecule is found in nature. As such, "isolated" does not necessarily reflect the extent to which the nucleic acid molecule has been purified, but indicates that the molecule does not include an entire genome or an entire chromosome in which the nucleic acid molecule is found in nature. An isolated nucleic acid molecule can include a gene. An isolated nucleic acid molecule that includes a gene is not a fragment of a chromosome that includes such gene, but rather includes the coding region and regulatory regions associated with the gene, but no additional genes that are naturally found on the same chromosome. An isolated nucleic acid molecule can also include a specified nucleic acid sequence flanked by (i.e., at the 5' and/or the 3' end of the sequence) additional nucleic acids that do not normally flank the specified nucleic acid sequence in nature (i.e., heterologous sequences). Isolated nucleic acid molecule can include DNA, RNA (e.g., mRNA), or derivatives of either DNA or RNA (e.g., cDNA). Although the phrase "nucleic acid molecule" primarily refers to the physical nucleic acid molecule and the phrase "nucleic acid sequence" primarily refers to the sequence of nucleotides on the nucleic acid molecule, the two phrases can be used interchangeably, especially with respect to a nucleic acid molecule, or a nucleic acid sequence, being capable of encoding a protein or domain of a protein.

A recombinant nucleic acid molecule is a molecule that can include at least one of any nucleic acid sequence encoding any one or more proteins described herein operatively linked to at least one of any transcription control sequence capable of effectively regulating expression of the nucleic acid molecule(s) in the cell to be transfected. Although the phrase "nucleic acid molecule" primarily refers to the physical nucleic acid molecule and the phrase "nucleic acid sequence" primarily refers to the sequence of nucleotides on the nucleic acid molecule, the two phrases can be used interchangeably, especially with respect to a nucleic acid molecule, or a nucleic acid sequence, being capable of encoding a protein. In addition, the phrase "recombinant molecule" primarily refers to a nucleic acid molecule operatively linked to a transcription control sequence, but can be used interchangeably with the phrase "nucleic acid molecule" which is administered to an animal.

A recombinant nucleic acid molecule includes a recombinant vector, which is any nucleic acid sequence, typically a heterologous sequence, which is operatively linked to the isolated nucleic acid molecule encoding a fusion protein of the present invention, which is capable of enabling recombinant production of the fusion protein, and which is capable of delivering the nucleic acid molecule into a host cell according to the present invention. Such a vector can contain nucleic acid sequences that are not naturally found adjacent to the isolated nucleic acid molecules to be inserted into the vector. The vector can be either RNA or DNA, either prokaryotic or eukaryotic, and preferably in the present invention, is a virus or a plasmid. Recombinant vectors can be used in the cloning, sequencing, and/or otherwise manipulating of nucleic acid molecules, and can be used in delivery of such molecules (e.g., as in a DNA composition or a viral vector-based composition). Recombinant vectors are preferably used in the expression of nucleic acid molecules, and can also be referred to as expression vectors. Preferred recombinant vectors are capable of being expressed in a transfected host cell.

In a recombinant molecule of the present invention, nucleic acid molecules are operatively linked to expression vectors containing regulatory sequences such as transcription control sequences, translation control sequences, origins of replication, and other regulatory sequences that are compatible with the host cell and that control the expression of nucleic acid molecules of the present invention. In particular, recombinant molecules of the present invention include nucleic acid molecules that are operatively linked to one or more expression control sequences. The phrase "operatively linked" refers to linking a nucleic acid molecule to an expression control sequence in a manner such that the molecule is expressed when transfected (i.e., transformed, transduced or transfected) into a host cell.

According to the present invention, the term "transfection" is used to refer to any method by which an exogenous nucleic acid molecule (i.e., a recombinant nucleic acid molecule) can be inserted into a cell. The term "transformation" can be used interchangeably with the term "transfection" when such term is used to refer to the introduction of nucleic acid molecules into microbial cells, such as algae, bacteria and yeast. In microbial systems, the term "transformation" is used to describe an inherited change due to the acquisition of exogenous nucleic acids by the microorganism and is essentially synonymous with the term "transfection." Therefore, transfection techniques include, but are not limited to, transformation, chemical treatment of cells, particle bombardment, electroporation, microinjection, lipofection, adsorption, infection and protoplast fusion.

The following experimental results are provided for purposes of illustration and are not intended to limit the scope of the invention.

EXAMPLES

Example 1

The following example describes the production of a yeast-based immunotherapeutic composition for the treatment or prevention of hepatitis B virus (HBV) infection.

In this experiment, yeast (e.g., *Saccharomyces cerevisiae*) were engineered to express various HBV surface-core fusion proteins, each having the basic structure shown in FIG. 2, under the control of the copper-inducible promoter, CUP1, or the TEF2 promoter. In each case, the HBV fusion protein was a single polypeptide of approximately 595 amino acids, with the following sequence elements fused in frame from N- to C-terminus, represented by SEQ ID NO:34 (1) an N-terminal peptide to impart resistance to proteasomal degradation and stabilize expression (positions 1 to 6 of SEQ ID NO:34); 2) a two amino acid spacer (Thr-Ser) to introduce a SpeI restriction enzyme site; 3) the amino acid sequence of a near full-length (minus position 1) HBV genotype C large (L) surface antigen (e.g., positions 9 to 407 of SEQ ID NO:34, corresponding to positions 2-400 of SEQ ID NO:11, which differs from SEQ ID NO:34 at positions 350-351 of SEQ ID NO:11, where a Leu-Val sequence in SEQ ID NO:11 is replaced with a Gln-Ala sequence at positions 357-358 of SEQ ID NO:34); 4) the amino acid sequence of an HBV core antigen (e.g., positions 408 to 589 of SEQ ID NO:34 or positions 31-212 of SEQ ID NO:9); and 5) a hexahistidine tag (positions 590-595 of SEQ ID NO:34). A nucleic acid sequence encoding the fusion protein of SEQ ID NO:34 (codon optimized for yeast expression) is represented herein by SEQ ID NO:33. Positions 28-54 of SEQ ID NO:34 comprise the hepatocyte receptor portion of large (L) surface protein. SEQ ID NO:34 contains multiple epitopes or domains that are believed to enhance the immunogenicity of the fusion protein. For example, at positions 209-220, positions 389-397, positions 360-367, and positions 499-506, with respect to SEQ ID NO:34, comprise known MHC Class I binding and/or CTL epitopes. Positions 305-328 of SEQ ID NO:34 comprise an antibody epitope. This fusion protein and corresponding yeast-based immunotherapeutic comprising this protein can be generally referred to herein as "Score", "MADEAP-Score", "M-Score", or "GI-13002".

Briefly, DNA encoding nearly full length large surface antigen (L) fused to full length core antigen was codon optimized for expression in yeast, and then digested with EcoRI and NotI and inserted behind the CUP1 promoter (pGI-100), or the TEF2 promoter (pTK57-1), in yeast 2 um expression vectors. The fusion protein encoded by these constructs is represented herein by SEQ ID NO:34 (encoded by nucleotide sequence SEQ ID NO:33) and has an expected approximate molecular weight of 66 kDa. The resulting plasmids were introduced into Saccharomyces cerevisiae W303α yeast by Lithium acetate/polyethylene glycol transfection, and primary transfectants were selected on solid minimal plates lacking uracil (UDM; uridine dropout medium). Colonies were re-streaked onto UDM or ULDM (uridine and leucine dropout medium) and allowed to grow for 3 days at 30° C. Liquid cultures lacking uridine (U2 medium: 20 g/L glucose; 6.7 g/L of yeast nitrogen base containing ammonium sulfate; 0.04 mg/mL each of histidine, leucine, tryptophan, and adenine) or lacking uridine and leucine (UL2 medium: 20 g/L glucose; 6.7 g/L of yeast nitrogen base containing ammonium sulfate; and 0.04 mg/mL each of his, tryptophan, and adenine) were inoculated from plates and starter cultures were grown for 20 h at 30° C., 250 rpm. pH buffered media containing 4.2 g/L of Bis-Tris (BT-U2; BT-UL2) was also inoculated to evaluate growth of the yeast under neutral pH conditions. Primary cultures were used to inoculate final cultures of the same formulation and growth was continued until a density or 1.1 to 4.0 YU/mL was reached.

For TEF2 strains (constitutive expression), cells were harvested, washed and heat killed at 56° C. for 1 h in PBS. Live cells were also processed for comparison. For CUP1 strains (inducible expression), expression was induced in the same medium with 0.5 mM copper sulfate for 5 h at 30° C., 250 rpm. Cells were harvested, washed and heat killed at 56° C. for 1 h in PBS. Live cells were also processed for comparison.

Figure 16:
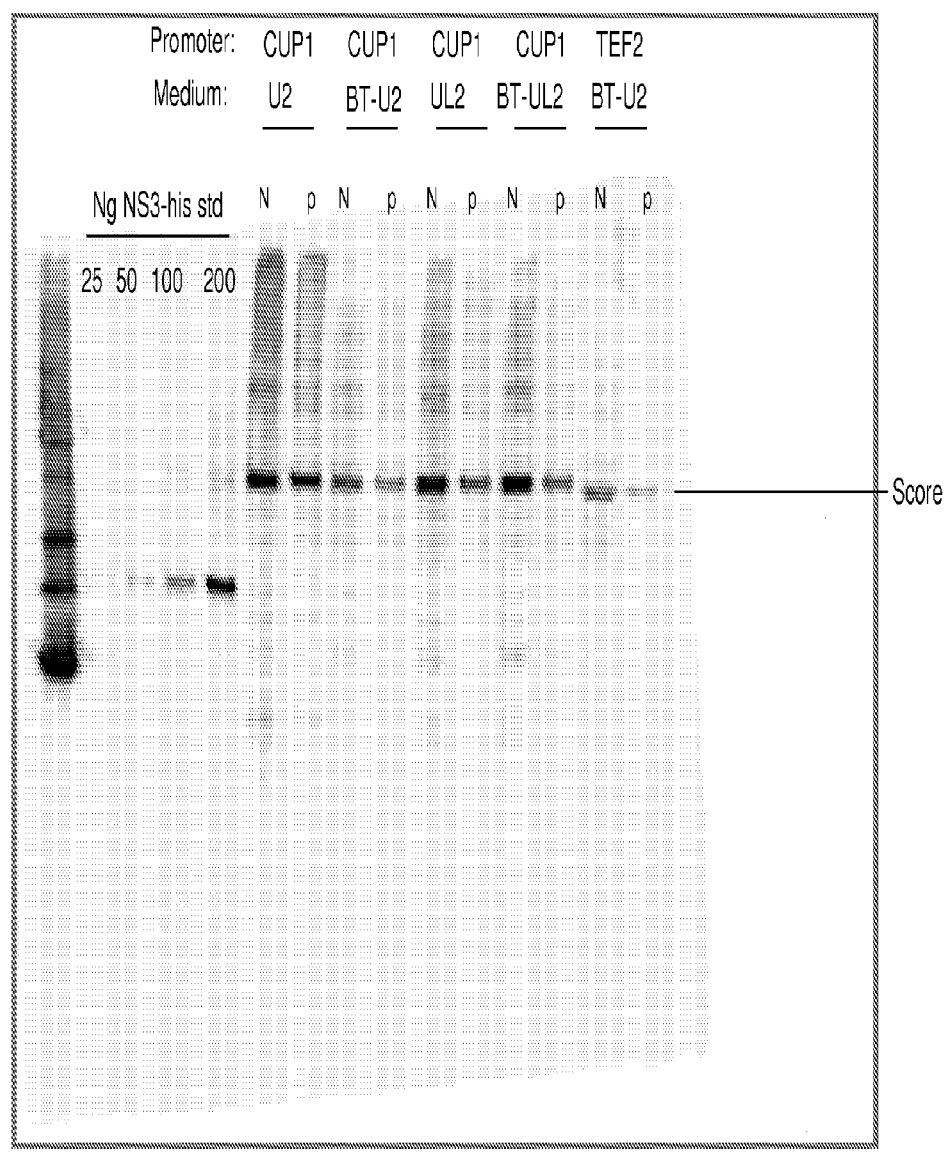
FIG. 16 is a digital image of a Western blot showing expression of several yeast-based immunotherapeutic compositions expressing an HBV Surface antigen/Core fusion protein (heat-killed, whole yeast).
Figure 17:
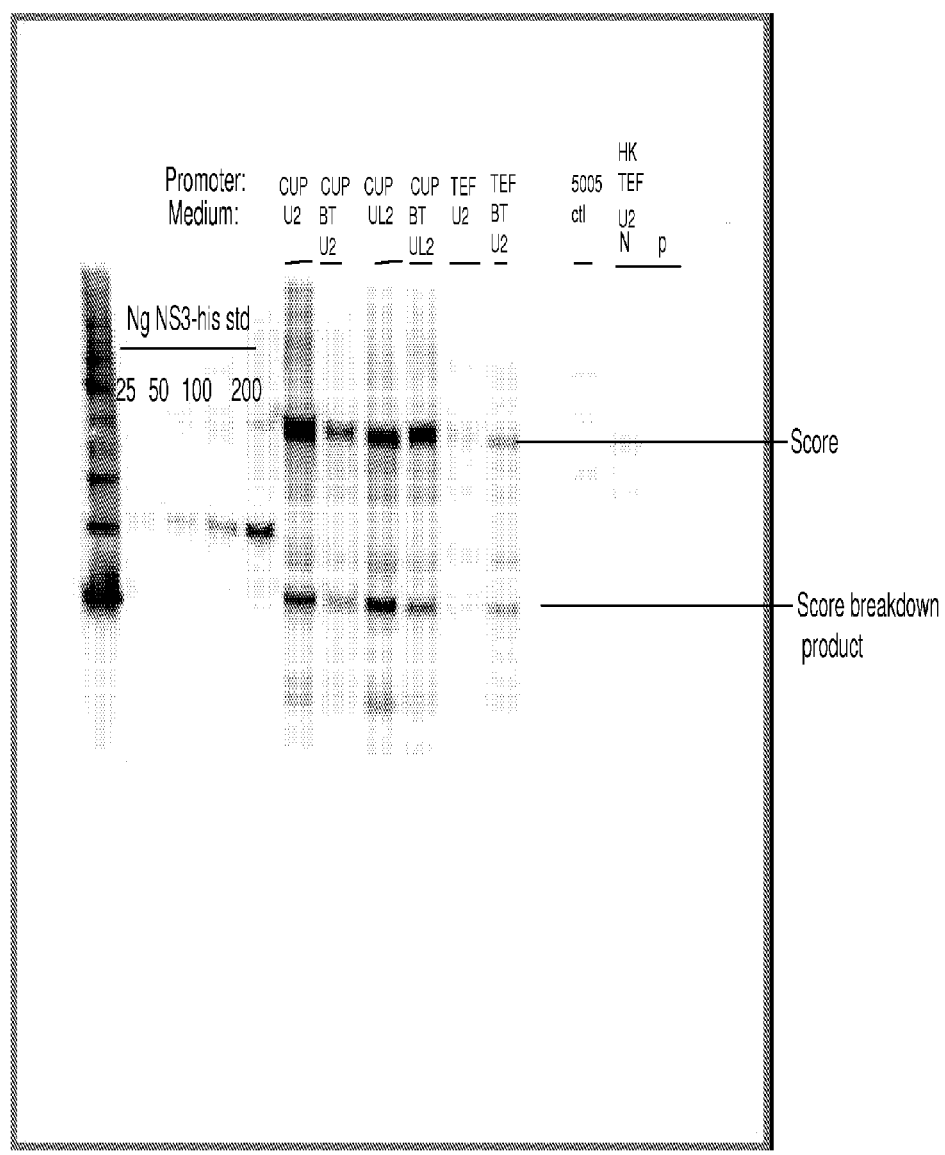
FIG. 17 is a digital image of a Western blot showing expression of several yeast-based immunotherapeutic compositions expressing an HBV Surface antigen/Core fusion protein (live, whole yeast).
Figure 18:
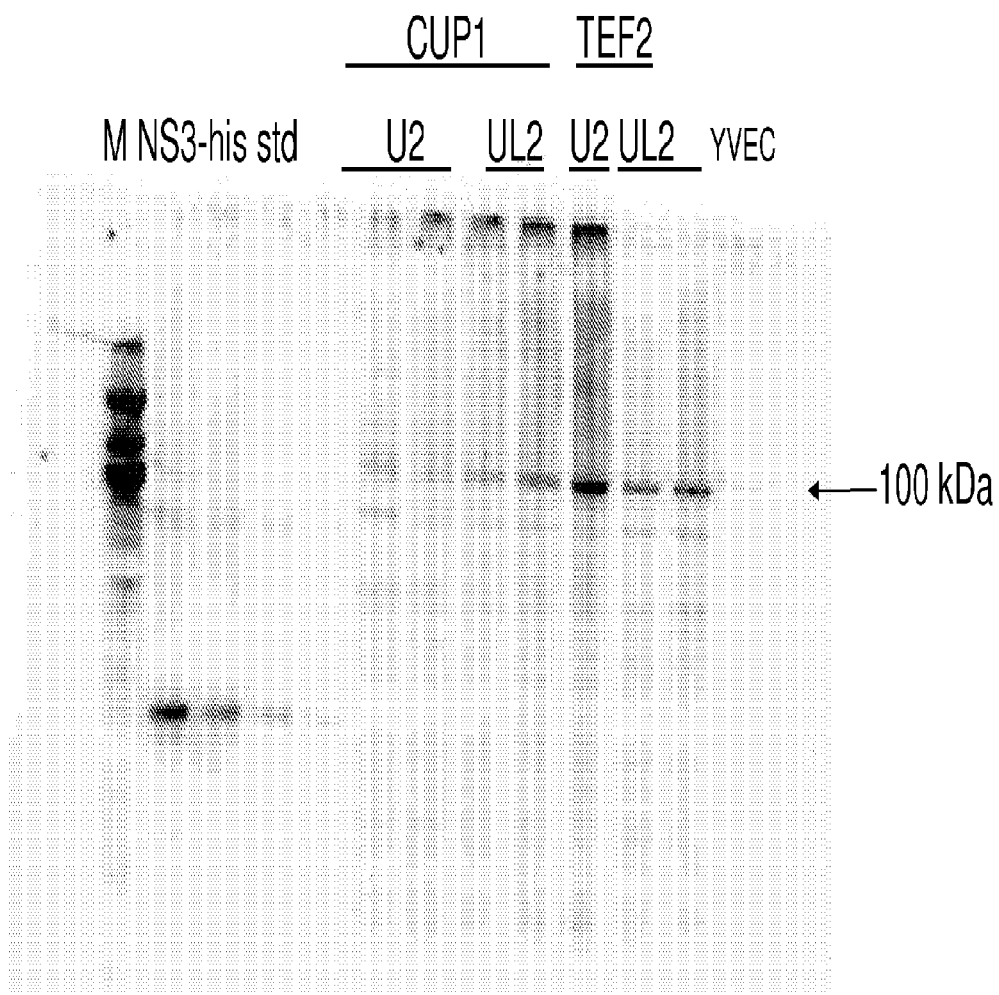
FIG. 18 is a digital image of a Western blot showing expression of several yeast-based immunotherapeutic compositions expressing an HBV surface antigen/polymerase/core/X fusion protein.
Figure 19:
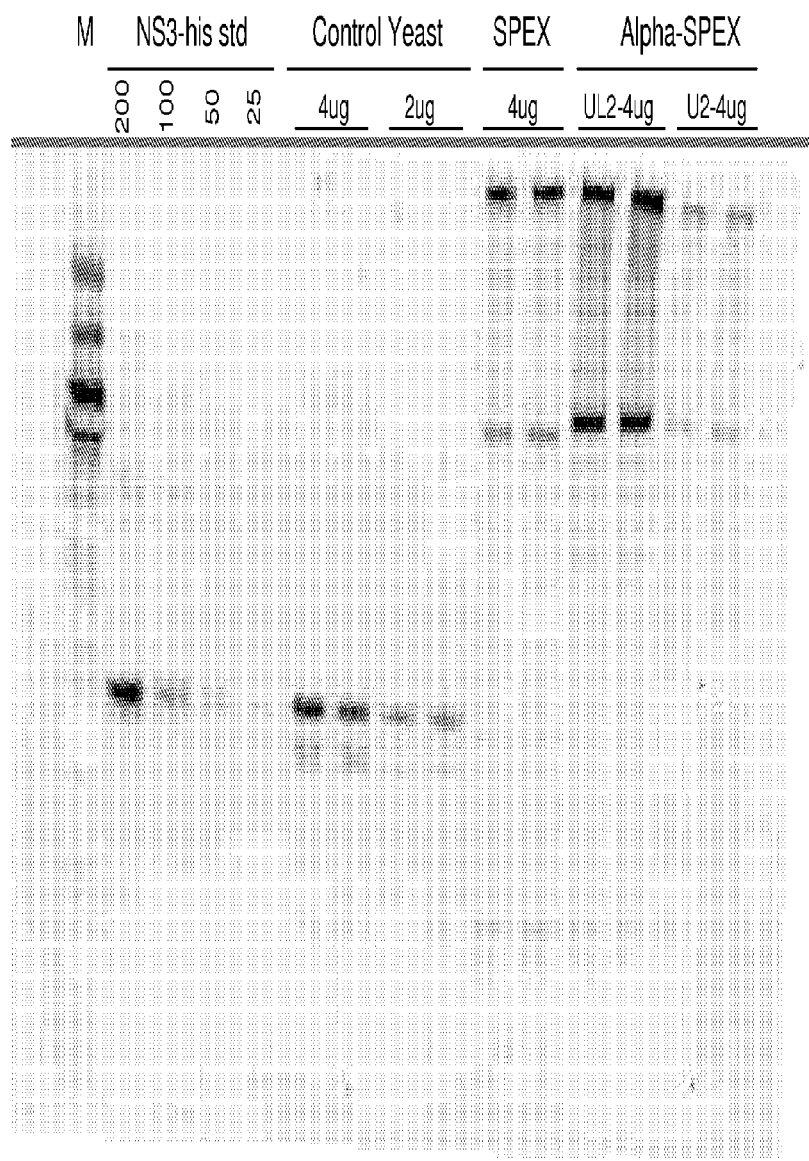
FIG. 19 is a digital image of a Western blot showing expression of several yeast-based immunotherapeutic compositions expressing an HBV surface antigen/polymerase/core/X fusion protein.

After heat kill of TEF2 and CUP1 cultures, cells were washed three times in PBS. Total protein expression was measured by a TCA precipitation/nitrocellulose binding assay and antigen expression was measured by western blot using an anti-his tag monoclonal antibody. The antigen was quantified by interpolation from a standard curve of recombinant, hexa-histidine tagged NS3 protein that was processed on the same western blot. Results are shown in FIG. 16 (heat-killed) and FIG. 17 (live yeast). These figures show that the yeast-based immunotherapy composition of the invention expresses the HBV surface-core fusion protein well using both promoters, and can be identified by Western blot in both heat-killed and live yeast cells. The calculated antigen expression by this yeast-based immunotherapeutic was ~5000 ng protein per Y.U. (Yeast Unit; One Yeast Unit (Y.U.) is $1\times10^7$ yeast cells or yeast cell equivalents) or 76 pmol protein per Y.U.

Example 2

The following example describes the production of another yeast-based immunotherapeutic composition for the treatment or prevention of hepatitis B virus (HBV) infection.

Yeast (e.g., *Saccharomyces cerevisiae*) were engineered to express various HBV fusion proteins, each having the structure schematically shown in FIG. 3, under the control of the copper-inducible promoter, CUP1, or the TEF2 promoter. In each case, the fusion protein was a single polypeptide of approximately 945 amino acids, with the following sequence elements fused in frame from N- to C-terminus, represented by SEQ ID NO:36: (1) an N-terminal peptide to impart resistance to proteasomal degradation and stabilize expression (positions 1 to 5 of SEQ ID NO:36); 2) the amino acid sequence of an HBV genotype C hepatocyte receptor domain of the pre-S1 portion of HBV large (L) surface protein (unique to L) (e.g., positions 21-47 of SEQ ID NO:11 or positions 6 to 32 of SEQ ID NO:36); 3) the amino acid sequence of a full-length HBV genotype C small (S) surface antigen (e.g., positions 176 to 400 of SEQ ID NO:11 or positions 33 to 257 of SEQ ID NO:36); 4) a two amino acid spacer/linker (Leu-Glu) to facilitate cloning and manipulation of the sequences (positions 258 and 259 of SEQ ID NO:36); 5) the amino acid sequence of a portion of the HBV genotype C polymerase including the reverse transcriptase domain (e.g., positions 247 to 691 of SEQ ID NO:10 or positions 260 to 604 of SEQ ID NO:36); 6) an HBV genotype C core protein (e.g., positions 31-212 of SEQ ID NO:9 or positions 605 to 786 of SEQ ID NO:36); 7) the amino acid sequence of an HBV genotype C X antigen (e.g., positions 2 to 154 of SEQ ID NO:12 or positions 787 to 939 of SEQ ID NO:36); and 8) a hexahistidine tag (positions 940 to 945 of SEQ ID NO:36). This fusion protein and corresponding yeast-based immunotherapeutic comprising this protein can be generally referred to herein as "MADEAP-Spex", "M-Spex", or "GI-13005".

A nucleic acid sequence encoding the fusion protein of SEQ ID NO:36 (codon optimized for yeast expression) is represented herein by SEQ ID NO:35. SEQ ID NO:36 has an expected approximate molecular weight of 106-107 kDa. SEQ ID NO:36 contains multiple epitopes or domains that are believed to enhance the immunogenicity of the fusion protein, including several described above for SEQ ID NO:34. In addition, the reverse transcriptase domain used in this fusion protein contains several amino acid positions that are known to become mutated as a drug-resistance response to treatment with anti-viral drugs, and therefore, may be mutated in this fusion protein in order to provide a therapeutic or prophylactic immunotherapeutic that targets specific drug resistance (escape) mutations. These amino acid positions are, with respect to SEQ ID NO:36, at amino acid position: 432 (Val, known to mutate to a Leu after lamivudine therapy); position 439 (Leu, known to mutate to a Met after lamivudine therapy); position 453 (Ala, known to mutate to a Thr after tenofovir therapy); position 463 (Met, known to mutate to an Ile or Val after lamivudine therapy); and position 495 (Asn, known to mutate to Thr after adefovir therapy).

To create a second yeast-based immunotherapeutic utilizing a different N-terminal peptide in the antigen, yeast (e.g., *Saccharomyces cerevisiae*) were engineered to express various HBV fusion proteins, also having the basic structure schematically shown in FIG. 3, under the control of the copper-inducible promoter, CUP1, or the TEF2 promoter. In this second case, an alpha factor prepro sequence (represented by SEQ ID NO:89) was used in place of the synthetic N-terminal peptide described above in the fusion represented by SEQ ID NO:36. Briefly, the new fusion protein was a single polypeptide with the following sequence elements fused in frame from N- to C-terminus, represented by SEQ ID NO:92: (1) an N-terminal peptide to impart resistance to proteasomal degradation and stabilize or enhance expression (SEQ ID NO:89, positions 1 to 89 of SEQ ID NO:92); 2) a two amino acid spacer/linker (Thr-Ser) to facilitate cloning and manipulation of the sequences (positions 90 to 91 of SEQ ID NO:92); 3) the amino acid sequence of an HBV genotype C hepatocyte receptor domain of the pre-S1 portion of HBV large (L) surface protein (unique to L) (e.g., positions 21-47 of SEQ ID NO:11 or positions 92 to 118 of SEQ ID NO:92); 4) the amino acid sequence of a full-length HBV genotype C small (S) surface antigen (e.g., positions 176 to 400 of SEQ ID NO:11 or positions 119 to 343 of SEQ ID NO:92); 5) a two amino acid spacer/linker (Leu-Glu) to facilitate cloning and manipulation of the sequences (e.g., positions 344 to 345 of SEQ ID NO:92); 6) the amino acid sequence of a portion of the HBV genotype C polymerase including the reverse transcriptase domain (e.g., positions 247 to 691 of SEQ ID NO:10 or positions 346 to 690 of SEQ ID NO:92); 7) an HBV genotype C core protein (e.g., positions 31-212 of SEQ ID NO:9 or positions 691 to 872 of SEQ ID NO:92); 8) the amino acid sequence of an HBV genotype C X antigen (e.g., positions 2 to 154 of SEQ ID NO:12 or positions 873 to 1025 of SEQ ID NO:92); and 9) a hexahistidine tag (e.g., positions 1026 to 1031 of SEQ ID NO:92). This fusion protein and corresponding yeast-based immunotherapeutic comprising this protein can be generally referred to herein as “alpha-Spex”, “a-Spex”, or GI-13004.

A nucleic acid sequence encoding the fusion protein of SEQ ID NO:92 (codon optimized for yeast expression) is represented herein by SEQ ID NO:91. SEQ ID NO:92 has an expected approximate molecular weight of 123 kDa. SEQ ID NO:92 contains multiple epitopes or domains that are believed to enhance the immunogenicity of the fusion protein, including several described above for SEQ ID NO:34 and SEQ ID NO:36. In addition, the reverse transcriptase domain used in this fusion protein contains several amino acid positions that are known to become mutated as a drug-resistance response to treatment with anti-viral drugs, and therefore, may be mutated in this fusion protein in order to provide a therapeutic or prophylactic immunotherapeutic that targets specific drug resistance (escape) mutations. These amino acid positions are, with respect to SEQ ID NO:92, at amino acid position: 518 (Val, known to mutate to a Leu after lamivudine therapy); position 525 (Leu, known to mutate to a Met after lamivudine therapy); position 539 (Ala, known to mutate to a Thr after tenofovir therapy); position 549 (Met, known to mutate to an Ile or Val after lamivudine therapy); and position 581 (Asn, known to mutate to Thr after adefovir therapy).

To create these immunotherapeutic compositions comprising the amino acid sequences represented by SEQ ID NO:36 and SEQ ID NO:92, DNA encoding the above-described conserved regions of surface antigen (hepatocyte receptor region of pre-S1 or large surface antigen, and full-length small surface antigen) and the reverse transcriptase region of polymerase were fused to full length core and full length X antigen. The DNA was codon-optimized for expression in yeast and then digested with EcoRI and NotI and inserted behind the CUP1 promoter (pGI-100) or the TEF2 promoter (pTK57-1) in yeast 2 um expression vectors. The resulting plasmids were introduced into *Saccharomyces cerevisiae* W303α yeast by Lithium acetate/polyethylene glycol transfection, and primary transfectants were selected on solid minimal plates lacking Uracil (UDM; uridine dropout medium). Colonies were re-streaked onto UDM or ULDM (uridine and leucine dropout medium) and allowed to grow for 3 days at 30° C.

Liquid cultures lacking uridine (U2) or lacking uridine and leucine (UL2) were inoculated from plates and starter cultures were grown for 20 h at 30° C., 250 rpm. pH buffered Media containing 4.2 g/L of Bis-Tris (BT-U2; BT-UL2) were also inoculated to evaluate growth of the yeast under neutral pH conditions (data not shown). Primary cultures were used to inoculate final cultures of the same formulation and growth was continued until a density or 1.1 to 4.0 YU/mL was reached. For TEF2 strains (constitutive expression), cells were harvested, washed and heat killed at 56° C. for 1 h in PBS. For CUP1 strains (inducible expression), expression was induced in the same medium with 0.5 mM copper sulfate for 5 h at 30° C., 250 rpm. Cells were harvested, washed and heat killed at 56° C. for 1 h in PBS. Live cells were also processed for comparison (data not shown).

After heat kill of TEF2 and CUP1 cultures, cells were washed three times in PBS. Total protein expression was measured by a TCA precipitation/nitrocellulose binding assay and antigen expression was measured by western blot using an anti-his tag monoclonal antibody. The antigen was quantified by interpolation from a standard curve of recombinant, hexa-histidine tagged NS3 protein that was processed on the same western blot.

For the yeast-based immunotherapeutic expressing the fusion protein represented by SEQ ID NO:36 (GI-13005), results are shown in FIG. 18. FIG. 18 shows that the yeast-based immunotherapy composition of the invention expresses the fusion protein well using both promoters, and can be identified by Western blot in heat-killed yeast cells (expression was also achieved in live yeast cells, data not shown). The calculated antigen expression by this yeast-based immunotherapeutic was ~1200 ng protein per Y.U. or 11 pmol protein per Y.U., for growth in UL2.

For the yeast-based immunotherapeutic expressing the fusion protein represented by SEQ ID NO:92 (GI-13004), results are shown in FIG. 19. FIG. 19 shows expression of this yeast-based immunotherapy composition under the control of the CUP1 promoter (identified in FIG. 19 as Alpha-SPEX) as compared to a yeast-based immunotherapeutic that expresses an unrelated antigen (Control Yeast) and to the yeast-based immunotherapeutic composition expressing an HBV fusion protein represented by SEQ ID NO:36 (SPEX). FIG. 19 shows that the yeast-based immunotherapeutics expresses the relevant fusion proteins well, and can be identified by Western blot in heat-killed yeast cells. The calculated antigen expression by this yeast-based immunotherapeutic (Alpha-SPEX) was ~5000 ng protein per Y.U. or 41 pmol protein per Y.U. for growth in UL2.

Example 3

The following example describes the production of additional yeast-based immunotherapeutic composition for the treatment or prevention of hepatitis B virus (HBV) infection.

In this experiment, yeast (e.g., *Saccharomyces cerevisiae*) are engineered to express various HBV polymerase-core fusion proteins, as shown schematically in FIG. 4, under the control of the copper-inducible promoter, CUP1, or the TEF2 promoter. In each case, the fusion protein is a single polypeptide of approximately 527 amino acids, with the following sequence elements fused in frame from N- to C-terminus, represented by SEQ ID NO:38: (1) an N-terminal peptide to impart resistance to proteasomal degradation and stabilize expression (SEQ ID NO:37; positions 1 to 6 of SEQ ID NO:38); 2) the amino acid sequence of a portion of the HBV genotype C polymerase including the reverse transcriptase domain (e.g., positions 347 to 691 of SEQ ID NO:10 or positions 7 to 351 of SEQ ID NO:38); 3) an HBV genotype C core protein (e.g., positions 31 to 212 of SEQ ID NO:9 or positions 352 to 533 of SEQ ID NO:38); and 4) a hexahistidine tag (e.g., positions 534 to 539 of SEQ ID NO:38). SEQ ID NO:38 has a predicted molecular weight of approximately 58 kDa. The sequence also contains epitopes or domains that are believed to enhance the immunogenicity of the fusion protein. In additional constructs, the N-terminal peptide of SEQ ID NO:37 is replaced with a different synthetic N-terminal peptide represented by a homologue of SEQ ID NO:37 that meets the same basic structural requirements of SEQ ID NO:37 as described in detail in the specification, or the N-terminal peptide of SEQ ID NO:37 is replaced with the N-terminal peptide of SEQ ID NO:89 or SEQ ID NO:90, and in another construct, the N-terminal peptide is omitted and a methionine is included at position one.

In another experiment, yeast (e.g., *Saccharomyces cerevisiae*) are engineered to express various HBV X-core fusion proteins as shown schematically in FIG. 5 under the control of the copper-inducible promoter, CUP1, or the TEF2 promoter. In each case, the fusion protein is a single polypeptide of approximately 337 amino acids with the following sequence elements fused in frame from N- to C-terminus, represented by SEQ ID NO:39 (1) an N-terminal peptide to impart resistance to proteasomal degradation and stabilize expression (SEQ ID NO:37; positions 1 to 6 of SEQ ID NO:39); 2) the amino acid sequence of a near full-length (minus position 1) HBV genotype C X antigen (e.g., positions 2 to 154 of SEQ ID NO:12 or positions 7 to 159 of SEQ ID NO:39); 3) an HBV genotype C core protein (e.g., positions 31 to 212 of SEQ ID NO:9 or positions 160 to 341 of SEQ ID NO:39); and 4) a hexahistidine tag (positions 342 to 347 of SEQ ID NO:39). SEQ ID NO:39 has a predicted approximate molecular weight of 37 kDa. The sequence also contains epitopes or domains that are believed to enhance the immunogenicity of the fusion protein. In additional constructs, the N-terminal peptide of SEQ ID NO:37 is replaced with a different synthetic N-terminal peptide represented by a homologue of SEQ ID NO:37 that meets the same basic structural requirements of SEQ ID NO:37 as described in detail in the specification, or the N-terminal peptide of SEQ ID NO:37 is replaced with the N-terminal peptide of SEQ ID NO:89 or SEQ ID NO:90, and in another construct, the N-terminal peptide is omitted and a methionine is included at position one.

In another experiment, yeast (e.g., *Saccharomyces cerevisiae*) are engineered to express various HBV polymerase proteins as shown schematically in FIG. 6 under the control of the copper-inducible promoter, CUP1, or the TEF2 promoter. In each case, the fusion protein is a single polypeptide with the following sequence elements fused in frame from N- to C-terminus, represented by SEQ ID NO:40 (1) an N-terminal peptide to impart resistance to proteasomal degradation and stabilize expression (SEQ ID NO:37, or positions 1 to 6 of SEQ ID NO:40); 2) the amino acid sequence of a portion of the HBV genotype C polymerase including the reverse transcriptase domain (e.g., positions 347 to 691 of SEQ ID NO:10 or positions 7 to 351 of SEQ ID NO:40); and 3) a hexahistidine tag (positions 352 to 357 of SEQ ID NO:40). The sequence also contains epitopes or domains that are believed to enhance the immunogenicity of the fusion protein. In addition, in one embodiment, the sequence of this construct can be modified to introduce one or more or all of the following anti-viral resistance mutations: rtM204I, rtL180M, rtM204V, rtV173L, rtN236T, rtA194T (positions given with respect to the full-length amino acid sequence for HBV polymerase). In one embodiment, six different immunotherapy compositions are created, each one containing one of these mutations. In other embodiments, all or some of the mutations are included in a single fusion protein. In additional constructs, the N-terminal peptide of SEQ ID NO:37 is replaced with a different synthetic N-terminal peptide represented by a homologue of SEQ ID NO:37 that meets the same basic structural requirements of SEQ ID NO:37 as described in detail in the specification, or the N-terminal peptide of SEQ ID NO:37 is replaced with the N-terminal peptide of SEQ ID NO:89 or SEQ ID NO:90, and in another construct, the N-terminal peptide is omitted and a methionine is included at position one.

In another experiment, yeast (e.g., *Saccharomyces cerevisiae*) are engineered to express various HBV polymerase-surface-core fusion proteins as shown schematically in FIG. 7 under the control of the copper-inducible promoter, CUP1, or the TEF2 promoter. In each case, the fusion protein is a single polypeptide with the following sequence elements fused in frame from N- to C-terminus, represented by SEQ ID NO:41: (1) an N-terminal peptide to impart resistance to proteasomal degradation and stabilize expression (e.g., positions 1 to 5 of SEQ ID NO:41); 2) an amino acid sequence of the amino HBV hepatocyte receptor domain of the pre-S1 portion of HBV large (L) surface protein (unique to L) (e.g., positions 21-47 of SEQ ID NO:11 or positions 6 to 32 of SEQ ID NO:41); 3) the amino acid sequence of an HBV small (S) surface protein (e.g., positions 176 to 400 of SEQ ID NO:11 or positions 33 to 257 of SEQ ID NO:41); 4) a two amino acid spacer/linker to facilitate cloning and manipulation of the sequences (e.g., positions 258 and 259 of SEQ ID NO:41); 5) the amino acid sequence of an HBV polymerase comprising the reverse transcriptase domain (e.g., positions 247 to 691 of SEQ ID NO:10 or positions 260 to 604 of SEQ ID NO:41); 6) the amino acid sequence of an HBV core protein (e.g., positions 31-212 of SEQ ID NO:9 or positions 605 to 786 of SEQ ID NO:41); and 7) a hexahistidine tag (e.g., positions 787 to 792 of SEQ ID NO:41). The sequence also contains epitopes or domains that are believed to enhance the immunogenicity of the fusion protein. In addition, in one embodiment, the sequence of this construct can be modified to introduce one or more or all of the following anti-viral resistance mutations: rtM204I, rtL180M, rtM204V, rtV173L, rtN236T, rtA194T (positions given with respect to the full-length amino acid sequence for HBV polymerase). In one embodiment, six different immunotherapy compositions are created, each one containing one of these mutations. In other embodiments, all or some of the mutations are included in a single fusion protein. In one embodiment, this construct also contains one or more anti-viral resistance mutations in the surface antigen. In additional constructs, the N-terminal peptide represented by positions 1 to 5 of SEQ ID NO:41 is replaced with a different synthetic N-terminal peptide represented by a homologue of positions 1 to 5 of SEQ ID NO:41 that meets the same basic structural requirements of positions 1 to 5 of SEQ ID NO:41 (or of SEQ ID NO:37) as described in detail in the specification, or the N-terminal peptide of positions 1 to 5 of SEQ ID NO:41 is replaced with the N-terminal peptide of SEQ ID NO:89 or SEQ ID NO:90, and in another construct, the N-terminal peptide is omitted and a methionine is included at position one.

To produce any of the above-described fusion proteins and yeast-based immunotherapy compositions expressing such proteins, briefly, DNA encoding the fusion protein is codon optimized for expression in yeast and then digested with EcoRI and NotI and inserted behind the CUP1 promoter (pGI-100) or the TEF2 promoter (pTK57-1) in yeast 2 um expression vectors. The resulting plasmids are introduced into *Saccharomyces cerevisiae* W303α yeast by Lithium acetate/polyethylene glycol transfection, and primary transfectants are selected on solid minimal plates lacking Uracil (UDM; uridine dropout medium). Colonies are re-streaked onto UDM or ULDM (uridine and leucine dropout medium) and allowed to grow for 3 days at 30° C.

Liquid cultures lacking uridine (U2) or lacking uridine and leucine (UL2) are inoculated from plates and starter cultures were grown for 20 h at 30° C., 250 rpm. pH buffered Media containing 4.2 g/L of Bis-Tris (BT-U2; BT-UL2) can also be inoculated to evaluate growth of the yeast under neutral pH conditions. Primary cultures are used to inoculate final cultures of the same formulation and growth is continued until a density or 1.1 to 4.0 YU/mL is reached. For TEF2 strains (constitutive expression), cells are harvested, washed and heat killed at 56° C. for 1 h in PBS. For CUP1 strains (inducible expression), expression is induced in the same medium with 0.5 mM copper sulfate for 5 h at 30° C., 250 rpm. Cells are harvested, washed and heat killed at 56° C. for 1 h in PBS. Live cells are also processed for comparison.

After heat kill of TEF2 and CUP1 cultures, cells are washed three times in PBS. Total protein expression is measured by a TCA precipitation/nitrocellulose binding assay and protein expression is measured by western blot using an anti-his tag monoclonal antibody. Fusion protein is quantified by interpolation from a standard curve of recombinant, hexahistidine tagged NS3 protein that was processed on the same western blot.

Example 4

The following example describes the production of additional yeast-based immunotherapeutic compositions for the treatment or prevention of hepatitis B virus (HBV) infection.

This example describes the production of four different yeast-based immunotherapeutic compositions, each one designed to express one HBV protein. These "single HBV protein yeast immunotherapeutics" can be used in combination or in sequence with each other and/or in combination or in sequence with other yeast-based immunotherapeutics, such as those described in any of Examples 1-3 and 5-8, including multi-HBV protein yeast-based immunotherapeutics described herein. In addition, a "single HBV protein yeast immunotherapeutic", such as those described in this example, can be produced using the HBV sequence for any given genotype or sub-genotype, and additional HBV surface antigen yeast-based immunotherapeutics can be produced using the HBV sequences for any one or more additional genotypes or sub-genotypes, in order to provide a "spice rack" of different HBV antigens and genotypes and/or subgenotypes, each of which is provided in the context of a yeast-based immunotherapeutic of the invention, or in an immunization/administration strategy that includes at least one yeast-based immunotherapeutic of the invention.

In this example, the following four yeast-based immunotherapeutic products are produced:

HBV Surface Antigen. *Saccharomyces cerevisiae* are engineered to express an HBV surface protein under the control of the copper-inducible promoter, CUP1, or the TEF2 promoter. In each case, the fusion protein is a single polypeptide with the following sequence elements fused in frame from N- to C-terminus, represented by SEQ ID NO:93: 1) an N-terminal peptide of SEQ ID NO:89 (positions 1-89 of SEQ ID NO:93); 2) the amino acid sequence of a near full-length (minus position 1) HBV genotype C large (L) surface antigen (e.g., positions 2-400 of SEQ ID NO:11 or positions 90 to 488 of SEQ ID NO:93); and 3) a hexahistidine tag (e.g., positions 489 to 494 of SEQ ID NO:93). Alternatively, the N-terminal peptide can be replaced with SEQ ID NO:37 or a homologue thereof or another N-terminal peptide described herein.

HBV Polymerase Antigen. *Saccharomyces cerevisiae* are engineered to express the following HBV Polymerase protein under the control of the copper-inducible promoter, CUP1, or the TEF2 promoter. In each case, the fusion protein is a single polypeptide with the following sequence elements fused in frame from N- to C-terminus, represented by SEQ ID NO:94: 1) an N-terminal peptide of SEQ ID NO:89 (positions 1-89 of SEQ ID NO:94); 2) the amino acid sequence of a portion of the HBV genotype C polymerase including the reverse transcriptase domain (e.g., positions 347 to 691 of SEQ ID NO:10 or positions 90 to 434 of SEQ ID NO:94); and 3) a hexahistidine tag (e.g., positions 435 to 440 of SEQ ID NO:94). Alternatively, the N-terminal peptide can be replaced with SEQ ID NO:37 or a homologue thereof or another N-terminal peptide described herein.

HBV Core Antigen. *Saccharomyces cerevisiae* are engineered to express the following HBV Core protein under the control of the copper-inducible promoter, CUP1, or the TEF2 promoter. In each case, the fusion protein is a single polypeptide with the following sequence elements fused in frame from N- to C-terminus, represented by SEQ ID NO:95: 1) an N-terminal peptide of SEQ ID NO:89 (positions 1-89 of SEQ ID NO:95); 2) the amino acid sequence of a portion of the HBV genotype C Core protein (e.g., positions 31 to 212 of SEQ ID NO:9 or positions 90 to 271 of SEQ ID NO:95); and 3) a hexahistidine tag (e.g., positions 272 to 277 of SEQ ID NO:95). Alternatively, the N-terminal peptide can be replaced with SEQ ID NO:37 or a homologue thereof or another N-terminal peptide described herein.

HBV X Antigen. *Saccharomyces cerevisiae* are engineered to express the following HBV X antigen under the control of the copper-inducible promoter, CUP1, or the TEF2 promoter. In each case, the fusion protein is a single polypeptide with the following sequence elements fused in frame from N- to C-terminus, represented by SEQ ID NO:96: 1) an N-terminal peptide of SEQ ID NO:89 (positions 1-89 of SEQ ID NO:96); 2) the amino acid sequence of a portion of the HBV genotype C X antigen (e.g., positions 2 to 154 of SEQ ID NO:12 or positions 90 to 242 of SEQ ID NO:96); and 3) a hexahistidine tag (e.g., positions 243 to 248 of SEQ ID NO:96). Alternatively, the N-terminal peptide can be replaced with SEQ ID NO:37 or a homologue thereof or another N-terminal peptide described herein.

To create these immunotherapeutic compositions, briefly, DNA encoding the fusion protein is codon optimized for expression in yeast and then digested with EcoRI and NotI and inserted behind the CUP1 promoter (pGI-100) or the TEF2 promoter (pTK57-1) in yeast 2 um expression vectors. The resulting plasmids are introduced into *Saccharomyces cerevisiae* W303α yeast by Lithium acetate/polyethylene glycol transfection, and primary transfectants are selected on solid minimal plates lacking uracil (UDM; uridine dropout medium). Colonies are re-streaked onto UDM or ULDM (uridine and leucine dropout medium) and allowed to grow for 3 days at 30° C.

Liquid cultures lacking uridine (U2) or lacking uridine and leucine (UL2) are inoculated from plates and starter cultures were grown for 20 h at 30° C., 250 rpm. pH buffered Media containing 4.2 g/L of Bis-Tris (BT-U2; BT-UL2) may also be inoculated to evaluate growth of the yeast under neutral pH conditions. Primary cultures are used to inoculate final cultures of the same formulation and growth is continued until a density or 1.1 to 4.0 YU/mL is reached. For TEF2 strains (constitutive expression), cells are harvested, washed and heat killed at 56° C. for 1 h in PBS. For CUP1 strains (inducible expression), expression is induced in the same medium with 0.5 mM copper sulfate for 5 h at 30° C., 250 rpm. Cells are harvested, washed and heat killed at 56° C. for 1 h in PBS. Live cells are also processed for comparison.

After heat kill of TEF2 and CUP1 cultures, cells are washed three times in PBS. Total protein expression is measured by a TCA precipitation/nitrocellulose binding assay and protein expression is measured by western blot using an anti-his tag monoclonal antibody. Fusion protein is quantified by interpolation from a standard curve of recombinant, hexa-histidine tagged NS3 protein that was processed on the same western blot.

Example 5

The following example describes the production of several different yeast-based immunotherapeutic compositions for the treatment or prevention of hepatitis B virus (HBV) infection.

This example describes the production of yeast-based immunotherapeutics expressing proteins that have been designed to achieve one or more of the following goals: (1) produce a multi-antigen HBV construct that comprises less than about 690 amino acids (corresponding to less than two thirds of the HBV genome), in order to produce a yeast-based immunotherapeutic clinical product that is compliant with the guidelines of the Recombinant DNA Advisory Committee (RAC), if necessary; (2) produce a multi-antigen HBV construct containing a maximized number of known T cell epitopes associated with immune responses to acute/self-limiting HBV infections and/or chronic HBV infections; (3) produce a multi-antigen HBV construct containing T cell epitopes that are most conserved among genotypes; and/or (4) produce a multi-antigen HBV construct modified to correspond more closely to one or more consensus sequences, consensus epitopes, and/or epitope(s) from particular genotypes. The modifications demonstrated in this example can be applied individually or together to any other yeast-based immunotherapeutic described or contemplated herein.

In one experiment, a yeast-based immunotherapeutic composition that comprises a yeast expressing a fusion protein meeting the requirements of the goals specified above, and comprising portions of each of the HBV major proteins: HBV surface antigen, polymerase, core and X antigen, was designed. To design this fusion protein, individual HBV antigens within the fusion were reduced in size (as compared to full-length), and the fusion segments were individually modified to maximize the inclusion of known T cell epitopes corresponding to those identified in Table 5. Inclusion of T cell epitopes in this fusion protein was prioritized as follows:

Epitopes identified in immune responses to both acute/self-limiting HBV infections and chronic HBV infections>Epitopes identified in immune responses to acute/self-limiting HBV infections>Epitopes identified in immune responses to chronic HBV infections Artificial junctions were also minimized in the design of each segment of this fusion protein because, without being bound by theory, it is believed that natural evolution has resulted in: i) contiguous sequences in the virus that express well; and ii) an immunoproteasome in antigen presenting cells that can properly digest and present those sequences to the immune system. Accordingly, a fusion protein with many unnatural junctions may be less useful in a yeast-based immunotherapeutic as compared to one that retains more of the natural HBV protein sequences.

To construct a segment comprising HBV surface antigen for use in a fusion protein, a full-length large (L) surface antigen protein from HBV genotype C was reduced in size by truncation of the N- and C-terminal sequences (positions 1 to 119 and positions 369 to 400 of large antigen were removed, as compared to a full-length L surface antigen protein, such as that represented by SEQ ID NO:11). The remaining portion was selected, in part, to maximize the inclusion of known MHC Class I T cell epitopes corresponding to those identified in Table 5, using the prioritization for inclusion of T cell epitopes described above. The resulting surface antigen segment is represented by SEQ ID NO:97.

To construct the segment comprising HBV polymerase for use in a fusion protein, substantial portions of a full-length polymerase from HBV genotype C, which is a very large protein of about 842 amino acids, were eliminated by focusing on inclusion of the active site domain (from the RT domain), which is the most conserved region of the protein among HBV genotypes and isolates. The RT domain also includes several sites where drug resistance mutations have been known to occur; thus, this portion of the construct can be further modified in other versions, as needed, to target escape mutations of targeted therapy. In fusion proteins including fewer HBV proteins, the size of the polymerase segment can be expanded, if desired. The selected portion of the HBV polymerase was included to maximize known T cell epitopes, using the prioritization strategy discussed above. Sequence of full-length polymerase that was therefore eliminated included sequence outside of the RT domain, and sequences within the RT domain that contained no known T cell epitopes, or that included two epitopes identified in less than 17% or 5%, respectively, of genotype A patients where these epitopes were identified (see Desmond et al., 2008 and Table 5). All but one of the remaining T cell epitopes in the HBV polymerase genotype C segment were perfect matches to the published epitopes from the genotype A analysis, and the one epitope with a single amino acid mismatch was modified to correspond to the published epitope. The resulting HBV polymerase antigen segment is represented by SEQ ID NO:98.

To construct the segment comprising HBV core antigen for use in a fusion protein, a full-length Core protein (e.g., similar to positions 31-212 of SEQ ID NO:9) from HBV genotype C was modified as follows: i) a single amino acid within a T cell epitope of the genotype C-derived protein was modified to create a perfect match to a known T cell epitope described in Table 5; ii) seven amino acids of the N-terminus, which did not contain a T cell epitope, were removed, preserving some flanking amino acids N-terminal to the first known T cell epitope in the protein; and iii) the 24 C terminal amino acids of Core were removed, which does not delete known epitopes, but which does remove an exceptionally positively charged C-terminus. A positively charged C-terminus is a good candidate for removal from an antigen to be expressed in yeast, as such sequences may, in some constructs, be toxic to yeast by competitive interference with natural yeast RNA binding proteins which often are arginine rich (positively charged). Accordingly, removal of this portion of Core is acceptable. The resulting HBV Core antigen segment is represented by SEQ ID NO:99.

To construct a segment comprising HBV X antigen for use in a fusion protein, a full-length X antigen from HBV genotype C (e.g., similar to SEQ ID NO:12) was truncated at the N- and C-terminus to produce a segment of X antigen that includes most of the known T cell epitopes from Table 5, which are clustered in the X antigen. Two of the epitopes were modified by single amino acid changes to correspond to the published T cell epitope sequences, and sequence flanking the T cell epitopes at the ends of the segment was retained to facilitate efficient processing and presentation of the correct epitopes by an antigen presenting cell. The resulting HBV X antigen segment is represented by SEQ ID NO:100.

To construct a complete fusion protein containing all four HBV protein segments, the four HBV segments described above were linked (surface-pol-core-X) to form a single protein that optimizes the inclusion of T cell epitopes spanning all proteins encoded by the HBV genome, and that is expected to meet criteria for viral proteins for anticipated clinical use.

Two different fusion proteins were ultimately created, each with a different N-terminal peptide added to enhance and/or stabilize expression of the fusion protein in yeast. In addition, a hexahistidine peptide was included at the C-terminus to aid with the identification of the protein. As for all of the other proteins used in the yeast-based immunotherapeutic compositions described herein, in additional constructs, the N-terminal peptide of SEQ ID NO:37 or SEQ ID NO:89 utilized in this example can be replaced with a different synthetic N-terminal peptide (e.g., a homologue of SEQ ID NO:37 that meets the same basic structural requirements of SEQ ID NO:37 as described in detail in the specification), or with a homologue of the N-terminal peptide of SEQ ID NO:89 or SEQ ID NO:90, and in another construct, the N-terminal peptide is omitted and a methionine is included at position one. In addition, linker sequences of one, two, three or more amino acids may be added between segments of the fusion protein, if desired. Also, while these constructs were designed using HBV proteins from genotype C as the backbone, any other HBV genotype, sub-genotype, or HBV proteins from different strains or isolates can be used to design these protein segments, as exemplified in Example 7. Finally, if one or more segments are excluded from the fusion protein as described herein, then the sequence from the remaining segments can be expanded to include additional T cell epitopes and flanking regions of the proteins (e.g., see Example 8).

To produce yeast-based immunotherapeutic compositions comprising a fusion protein constructed of the HBV segments described above, yeast (e.g., *Saccharomyces cerevisiae*) are engineered to express various HBV surface-polymerase-core-X fusion proteins, optimized as discussed above, under the control of the copper-inducible promoter, CUP1, or the TEF2 promoter.

In one construct, the fusion protein is a single polypeptide with the following sequence elements fused in frame from N- to C-terminus, represented by SEQ ID NO:101: (1) an N-terminal peptide that is an alpha factor prepro sequence, to impart resistance to proteasomal degradation and stabilize expression represented by SEQ ID NO:89 (positions 1-89 of SEQ ID NO:101); (2) an optimized portion of an HBV large (L) surface antigen represented by SEQ ID NO:97 (positions 90 to 338 of SEQ ID NO:101); (3) an optimized portion of the reverse transcriptase (RT) domain of HBV polymerase represented by SEQ ID NO:98 (positions 339 to 566 of SEQ ID NO:101); (4) an optimized portion of HBV Core protein represented by SEQ ID NO:99 (positions 567 to 718 of SEQ ID NO:101); (5) an optimized portion of HBV X antigen represented by SEQ ID NO:100 (positions 719 to 778 of SEQ ID NO:101); and (6) a hexahistidine tag (e.g., positions 779 to 784 of SEQ ID NO:101).

In a second construct, the fusion protein is a single polypeptide with the following sequence elements fused in frame from N- to C-terminus, represented by SEQ ID NO:102: (1) an N-terminal peptide that is a synthetic N-terminal peptide designed to impart resistance to proteasomal degradation and stabilize expression represented by SEQ ID NO:37 (positions 1-6 of SEQ ID NO:102); (2) an optimized portion of an HBV large (L) surface antigen represented by positions 2 to 248 of SEQ ID NO:97 (positions 7 to 254 of SEQ ID NO:102); (3) an optimized portion of the reverse transcriptase (RT) domain of HBV polymerase represented by SEQ ID NO:98 (positions 255 to 482 of SEQ ID NO:102); (4) an optimized portion of HBV Core protein represented by SEQ ID NO:99 (positions 483 to 634 of SEQ ID NO:102); (5) an optimized portion of HBV X antigen represented by SEQ ID NO:100 (positions 635 to 694 of SEQ ID NO:102); and (6) a hexahistidine tag (e.g., positions 695 to 700 of SEQ ID NO:102).

Yeast-based immunotherapy compositions expressing these fusion proteins are produced using the same protocol described in detail in Example 1-4.

Example 6

The following example describes the production of additional yeast-based HBV immunotherapeutic compositions that maximize the targeting of HBV genotypes and/or sub-genotypes in conjunction with conserved antigen and/or epitope inclusion within a single composition, in order to provide single compositions with the potential to treat a large number of individuals or populations of individuals.

To prepare a construct comprising multiple different genotypes within the same yeast-based immunotherapeutic, yeast (e.g., *Saccharomyces cerevisiae*) are engineered to express an HBV fusion protein under the control of a suitable promoter, such as the copper-inducible promoter, CUP1, or the TEF2 promoter. The protein is a single polypeptide comprising four Core antigens, each one from a different genotype (HBV genotypes A, B, C and D), represented by SEQ ID NO:105: 1) an N-terminal methionine at position 1 of SEQ ID NO:105; 2) the amino acid sequence of a near full-length Core protein from HBV genotype A (e.g., positions 31 to 212 of SEQ ID NO:1 or positions 2 to 183 of SEQ ID NO: 105); 3) the amino acid sequence of a near full-length Core protein from HBV genotype B (e.g., positions 30 to 212 of SEQ ID NO:5 or positions 184 to 395 of SEQ ID NO: 105); 4) the amino acid sequence of a near full-length Core protein from HBV genotype C (e.g., positions 30 to 212 of SEQ ID NO:9 or positions 396 to 578 of SEQ ID NO: 105); 5) the amino acid sequence of a near full-length Core protein from HBV genotype D (e.g., positions 30 to 212 of SEQ ID NO:13 or positions 579 to 761 of SEQ ID NO: 105); and 5) a hexahistidine tag (e.g., positions 762 to 767 of SEQ ID NO: 105). The sequence also contains epitopes or domains that are believed to enhance the immunogenicity of the fusion protein. The N-terminal methionine at position 1 can be substituted with SEQ ID NO:37 or a homologue thereof, or with an alpha prepro sequence of SEQ ID NO:89 or SEQ ID NO:90, or a homologue thereof, or any other suitable N-terminal sequence if desired. In addition, linker sequences can be inserted between HBV proteins to facilitate cloning and manipulation of the construct, if desired. This is an exemplary construct, as any other combination of HBV genotypes and/or subgenotypes can be substituted into this design as desired to construct a single antigen yeast-based HBV immunotherapeutic product with broad clinical applicability and efficient design for manufacturing. The amino acid sequence of SEQ ID NO:105 also contains several known T cell epitopes, and certain epitopes have been modified to correspond to the published sequence for the given epitope, which can be identified by comparison of the sequence to the epitopes shown in Table 5, for example.

To prepare a construct comprising more than one HBV antigen and more than one genotype within the same yeast-based immunotherapeutic, yeast (e.g., *Saccharomyces cerevisiae*) are engineered to express an HBV fusion protein under the control of a suitable promoter, such as the copper-inducible promoter, CUP1, or the TEF2 promoter. The protein is a single polypeptide comprising two Core antigens and two X antigens, each one of the pair from a different genotype (HBV genotypes A and C), represented by SEQ ID NO:106: 1) an N-terminal methionine at position 1 of SEQ ID NO:106; 2) the amino acid sequence of a near full-length Core protein from HBV genotype A (e.g., positions 31 to 212 of SEQ ID NO:1 or positions 2 to 183 of SEQ ID NO:106); 3) the amino acid sequence of a full-length X antigen from HBV genotype A (e.g., positions SEQ ID NO:4 or positions 184 to 337 of SEQ ID NO:106); 4) the amino acid sequence of a near full-length Core protein from HBV genotype C (e.g., positions 30 to 212 of SEQ ID NO:9 or positions 338 to 520 of SEQ ID NO:106); 5) the amino acid sequence of a full-length X antigen from HBV genotype C (e.g., SEQ ID NO:8 or positions 521 to 674 of SEQ ID NO:106); and 5) a hexahistidine tag (e.g., positions 675 to 680 of SEQ ID NO:106). The sequence also contains epitopes or domains that are believed to enhance the immunogenicity of the fusion protein. The N-terminal methionine at position 1 can be substituted with SEQ ID NO:37 or a homologue thereof, or with an alpha prepro sequence of SEQ ID NO:89 or SEQ ID NO:90, or a homologue thereof. The amino acid sequence of SEQ ID NO:106 also contains several known T cell epitopes, and certain epitopes have been modified to correspond to the published sequence for the given epitope, which can be identified by comparison of the sequence to the epitopes shown in Table 5, for example.

Yeast-based immunotherapy compositions expressing these fusion proteins are produced using the same protocol described in detail in Example 1-4.

Example 7

The following example describes the production of additional yeast-based HBV immunotherapeutic compositions that utilize consensus sequences for HBV genotypes, further maximizing the targeting of HBV genotypes and/or subgenotypes in conjunction with conserved antigen and/or epitope inclusion, in order to provide compositions with the potential to treat a large number of individuals or populations of individuals using one composition.

To design several constructs that include HBV segments from each of surface protein, core, polymerase, and X antigen, the fusion protein structure described in Example 5 for SEQ ID NO:101 and SEQ ID NO:102 (and therefore the subparts of these fusion proteins represented by SEQ ID NO:97 (Surface antigen), SEQ ID NO:98 (Polymerase), SEQ ID NO:99 (Core antigen), and SEQ ID NO:100 (X antigen)) was used as a template. With reference to consensus sequences for each of HBV genotype A, B, C and D that were built from multiple sources of HBV sequences (e.g., Yu and Yuan et al, 2010, for S, Core and X, where consensus sequences were generated from 322 HBV sequences, or for Pol (RT), from the Stanford University HIV Drug Resistance Database, HBVseq and HBV Site Release Notes), sequences in the template structure were replaced with consensus sequences corresponding to the same positions, unless using the consensus sequence altered one of the known acute self-limiting T cells epitopes or one of the known polymerase escape mutation sites, in which case, these positions followed the published sequence for these epitopes or mutation sites. Additional antigens could be constructed based solely on consensus sequences or using other published epitopes as they become known.

A first construct based on a consensus sequence for HBV genotype A was designed as follows. Using SEQ ID NO:97, SEQ ID NO:98, SEQ ID NO:99 and SEQ ID NO:100, which were designed to reduce the size of the fusion segments (as compared to full-length), to maximize the inclusion of known T cell epitopes corresponding to those identified in Table 5 (priority as discussed above), and to minimize artificial junctions, new fusion segments were created based on a consensus sequence for HBV genotype A. The new surface antigen segment is represented by positions 1-249 of SEQ ID NO:107. The new polymerase (RT) segment is represented by positions 250-477 of SEQ ID NO:107. The new Core segment is represented by positions 478-629 of SEQ ID NO:107. The new X antigen segment is represented by positions 630-689 of SEQ ID NO:107. This complete fusion protein is a single polypeptide with the following sequence elements fused in frame from N- to C-terminus, wherein the HBV sequences are represented by SEQ ID NO:107 (non-HBV sequences denoted as "optional" were not included in the base sequence of SEQ ID NO:107, but were actually added to the fusion protein described in this example): (1) an optional N-terminal peptide that is a synthetic N-terminal peptide designed to impart resistance to proteasomal degradation and stabilize expression represented by SEQ ID NO:37; (2) an optional linker peptide of Thr-Ser; (3) an optimized portion of an HBV large (L) surface antigen represented by positions 1 to 249 of SEQ ID NO:107, which is a consensus sequence for HBV genotype A utilizing the design strategy discussed above; (4) an optimized portion of the reverse transcriptase (RT) domain of HBV polymerase represented by positions 250 to 477 of SEQ ID NO:107, which is a consensus sequence for HBV genotype A utilizing the design strategy discussed above; (5) an optimized portion of HBV Core protein represented by positions 478 to 629 of SEQ ID NO:107, which is a consensus sequence for HBV genotype A utilizing the design strategy discussed above; (6) an optimized portion of HBV X antigen represented by positions 630 to 689 of SEQ ID NO:107, which is a consensus sequence for HBV genotype A utilizing the design strategy discussed above; and (7) an optional hexahistidine tag (six histidine residues following position 689 of SEQ ID NO:107). A yeast-based immunotherapy composition expressing this complete fusion protein is also referred to herein as GI-13010. The fusion protein and corresponding yeast-based immunotherapeutic can also be referred to herein as "SPEXv2-A" or "Spex-A".

A second construct based on a consensus sequence for HBV genotype B was designed as follows. Using SEQ ID NO:97, SEQ ID NO:98, SEQ ID NO:99 and SEQ ID NO:100, which were designed to reduce the size of the fusion segments (as compared to full-length), to maximize the inclusion of known T cell epitopes corresponding to those identified in Table 5 (priority as discussed above), and to minimize artificial junctions, new fusion segments were created based on a consensus sequence for HBV genotype B. The new surface antigen segment is represented by positions 1-249 of SEQ ID NO:108. The new polymerase (RT) segment is represented by positions 250-477 of SEQ ID NO:108. The new Core segment is represented by positions 478-629 of SEQ ID NO:108. The new X antigen segment is represented by positions 630-689 of SEQ ID NO:108. This fusion protein is a single polypeptide with the following sequence elements fused in frame from N- to C-terminus, represented by SEQ ID NO:108 (non-HBV sequences denoted as "optional" were not included in the base sequence of SEQ ID NO:108, but were actually added to the fusion protein described in this example): (1) an optional N-terminal peptide that is a synthetic N-terminal peptide designed to impart resistance to proteasomal degradation and stabilize expression represented by SEQ ID NO:37; (2) an optional linker peptide of Thr-Ser; (3) an optimized portion of an HBV large (L) surface antigen represented by positions 1 to 249 of SEQ ID NO:108, which is a consensus sequence for HBV genotype B utilizing the design strategy discussed above; (4) an optimized portion of the reverse transcriptase (RT) domain of HBV polymerase represented by positions 250 to 477 of SEQ ID NO:108, which is a consensus sequence for HBV genotype B utilizing the design strategy discussed above; (5) an optimized portion of HBV Core protein represented by positions 478 to 629 of SEQ ID NO:108, which is a consensus sequence for HBV genotype B utilizing the design strategy discussed above; (6) an optimized portion of HBV X antigen represented by positions 630 to 689 of SEQ ID NO:108, which is a consensus sequence for HBV genotype B utilizing the design strategy discussed above; and (7) an optional hexahistidine tag. A yeast-based immunotherapy composition expressing this complete fusion protein is also referred to herein as GI-13011. The fusion protein and corresponding yeast-based immunotherapeutic can also be referred to herein as "SPEXv2-B" or "Spex-B".

A third construct based on a consensus sequence for HBV genotype C was designed as follows. Using SEQ ID NO:97, SEQ ID NO:98, SEQ ID NO:99 and SEQ ID NO:100, which were designed to reduce the size of the fusion segments (as compared to full-length), to maximize the inclusion of known T cell epitopes corresponding to those identified in Table 5 (priority as discussed above), and to minimize artificial junctions, new fusion segments were created based on a consensus sequence for HBV genotype C. The new surface antigen segment is represented by positions 1-249 of SEQ ID NO:109. The new polymerase (RT) segment is represented by positions 250-477 of SEQ ID NO:109. The new Core segment is represented by positions 478-629 of SEQ ID NO:109. The new X antigen segment is represented by positions 630-689 of SEQ ID NO:109. This fusion protein is a single polypeptide with the following sequence elements fused in frame from N- to C-terminus, represented by SEQ ID NO:109 (non-HBV sequences denoted as "optional" were not included in the base sequence of SEQ ID NO:109, but were actually added to the fusion protein described in this example): (1) an optional N-terminal peptide that is a synthetic N-terminal peptide designed to impart resistance to proteasomal degradation and stabilize expression represented by SEQ ID NO:37; (2) an optional linker peptide of Thr-Ser; (3) an optimized portion of an HBV large (L) surface antigen represented by positions 1 to 249 of SEQ ID NO:109, which is a consensus sequence for HBV genotype C utilizing the design strategy discussed above; (4) an optimized portion of the reverse transcriptase (RT) domain of HBV polymerase represented by positions 250 to 477 of SEQ ID NO:109, which is a consensus sequence for HBV genotype C utilizing the design strategy discussed above; (5) an optimized portion of HBV Core protein represented by positions 478 to 629 of SEQ ID NO:109, which is a consensus sequence for HBV genotype C utilizing the design strategy discussed above; (6) an optimized portion of HBV X antigen represented by positions 630 to 689 of SEQ ID NO:109, which is a consensus sequence for HBV genotype C utilizing the design strategy discussed above; and (7) an optional hexahistidine tag. A yeast-based immunotherapy composition expressing this complete fusion protein is also referred to herein as GI-13012. The fusion protein and corresponding yeast-based immunotherapeutic can also be referred to herein as "SPEXv2-C" or "Spex-C".

A fourth construct based on a consensus sequence for HBV genotype D was designed as follows. Using SEQ ID NO:97, SEQ ID NO:98, SEQ ID NO:99 and SEQ ID NO:100, which were designed to reduce the size of the fusion segments (as compared to full-length), to maximize the inclusion of known T cell epitopes corresponding to those identified in Table 5 (priority as discussed above), and to minimize artificial junctions, new fusion segments were created based on a consensus sequence for HBV genotype D. The new surface antigen segment is represented by positions 1-249 of SEQ ID NO:110. The new polymerase (RT) segment is represented by positions 250-477 of SEQ ID NO:110. The new Core segment is represented by positions 478-629 of SEQ ID NO:110. The new X antigen segment is represented by positions 630-689 of SEQ ID NO:110. This fusion protein is a single polypeptide with the following sequence elements fused in frame from N- to C-terminus, represented by SEQ ID NO:110 (non-HBV sequences denoted as "optional" were not included in the base sequence of SEQ ID NO:110, but were actually added to the fusion protein described in this example): (1) an optional N-terminal peptide that is a synthetic N-terminal peptide designed to impart resistance to proteasomal degradation and stabilize expression represented by SEQ ID NO:37; (2) an optional linker peptide of Thr-Ser; (3) an optimized portion of an HBV large (L) surface antigen represented by positions 1 to 249 of SEQ ID NO: 110, which is a consensus sequence for HBV genotype D utilizing the design strategy discussed above; (4) an optimized portion of the reverse transcriptase (RT) domain of HBV polymerase represented by positions 250 to 477 of SEQ ID NO: 110, which is a consensus sequence for HBV genotype D utilizing the design strategy discussed above; (5) an optimized portion of HBV Core protein represented by positions 478 to 629 of SEQ ID NO: 110, which is a consensus sequence for HBV genotype D utilizing the design strategy discussed above; (6) an optimized portion of HBV X antigen represented by positions 630 to 689 of SEQ ID NO: 110, which is a consensus sequence for HBV genotype D utilizing the design strategy discussed above; and (7) an optional hexahistidine tag. A yeast-based immunotherapy composition expressing this complete fusion protein is also referred to herein as GI-13013. A yeast-based immunotherapy composition expressing a similar fusion protein (containing SEQ ID NO:110), except that the N-terminal peptide of SEQ ID NO:37 is substituted with the alpha factor sequence of SEQ ID NO:89, is referred to herein as GI-13014. The fusion protein and corresponding yeast-based immunotherapeutic can also be referred to herein as "SPEXv2-D", "Spex-D", or "M-SPEXv2-D" (for GI-13013) or "a-SPEXv2-D" for (GI-13014).

Additional HBV fusion proteins for use in a yeast-based immunotherapeutic were designed using the application of consensus sequences for four HBV genotypes to demonstrate how alterations similar to those made in the fusion proteins described above (SEQ ID NOs:107-110) can be made in a different HBV fusion protein, such as that described by SEQ ID NO:34, which contains HBV Surface proteins and HBV Core proteins. To design these additional HBV antigens and corresponding yeast-based immunotherapy compositions, the fusion protein structure described above for SEQ ID NO:34 (and therefore the subparts of these fusion proteins (Surface antigen and Core) was used as a template. As above for the constructs described above, consensus sequences for each of HBV genotype A, B, C and D were built from multiple sources of HBV sequences (e.g., Yu and Yuan et al, 2010, for S and Core), and sequences in the template structure were replaced with consensus sequences corresponding to the same positions, unless using the consensus sequence altered one of the known acute self-limiting T cells epitopes or one of the known polymerase escape mutation sites, in which case, these positions followed the published sequence for these epitopes or mutation sites.

A first construct based on a consensus sequence for HBV genotype A was designed as follows. Using SEQ ID NO:34 as a template, a new fusion protein was created based on a consensus sequence for HBV genotype A, represented here by SEQ ID NO:112. This fusion protein is a single polypeptide with the following sequence elements fused in frame from N- to C-terminus, represented by SEQ ID NO:112 (non-HBV sequences denoted as "optional" are not included in the base sequence of SEQ ID NO:112, but were actually added to the fusion protein described in this example): (1) an optional N-terminal peptide that is a synthetic N-terminal peptide designed to impart resistance to proteasomal degradation and stabilize expression represented by SEQ ID NO:37; (2) an optional linker peptide of Thr-Ser; (3) a consensus sequence for HBV genotype A large (L) surface antigen represented by positions 1 to 399 of SEQ ID NO:112; 4) the amino acid sequence of a consensus sequence for HBV genotype A core antigen represented by positions 400 to 581 of SEQ ID NO:112; and (5) an optional hexahistidine tag. A nucleic acid sequence encoding the fusion protein comprising SEQ ID NO:112 (codon optimized for yeast expression) is represented herein by SEQ ID NO:111. A yeast-based immunotherapy composition expressing this fusion protein is also referred to herein as GI-13006. The fusion protein and corresponding yeast-based immunotherapeutic can also be referred to herein as "Score-A".

A second construct based on a consensus sequence for HBV genotype B was designed as follows. Using SEQ ID NO:34 as a template, a new fusion protein was created based on a consensus sequence for HBV genotype B, represented here by SEQ ID NO:114. This fusion protein is a single polypeptide with the following sequence elements fused in frame from N- to C-terminus, represented by SEQ ID NO:114 (non-HBV sequences denoted as "optional" are not included in the base sequence of SEQ ID NO:114, but were actually added to the fusion protein described in this example): (1) an optional N-terminal peptide that is a synthetic N-terminal peptide designed to impart resistance to proteasomal degradation and stabilize expression represented by SEQ ID NO:37; (2) an optional linker peptide of Thr-Ser; (3) a consensus sequence for HBV genotype B large (L) surface antigen represented by positions 1 to 399 of SEQ ID NO:114; 4) the amino acid sequence of a consensus sequence for HBV genotype B core antigen represented by positions 400 to 581 of SEQ ID NO:114; and (5) an optional hexahistidine tag. A nucleic acid sequence encoding the fusion protein comprising SEQ ID NO:114 (codon optimized for yeast expression) is represented herein by SEQ ID NO:113. A yeast-based immunotherapy composition expressing this fusion protein is also referred to herein as GI-13007. The fusion protein and corresponding yeast-based immunotherapeutic can also be referred to herein as "Score-B".

A third construct based on a consensus sequence for HBV genotype C was designed as follows. Using SEQ ID NO:34 as a template, a new fusion protein was created based on a consensus sequence for HBV genotype C, represented here by SEQ ID NO:116. This fusion protein is a single polypeptide with the following sequence elements fused in frame from N- to C-terminus, represented by SEQ ID NO:116 (non-HBV sequences denoted as "optional" are not included in the base sequence of SEQ ID NO:116, but were actually added to the fusion protein described in this example): (1) an optional N-terminal peptide that is a synthetic N-terminal peptide designed to impart resistance to proteasomal degradation and stabilize expression represented by SEQ ID NO:37; (2) an optional linker peptide of Thr-Ser; (3) a consensus sequence for HBV genotype C large (L) surface antigen represented by positions 1 to 399 of SEQ ID NO:116; 4) the amino acid sequence of a consensus sequence for HBV genotype C core antigen represented by positions 400 to 581 of SEQ ID NO:116; and (5) an optional hexahistidine tag. A nucleic acid sequence encoding the fusion protein comprising SEQ ID NO:116 (codon optimized for yeast expression) is represented herein by SEQ ID NO:115. A yeast-based immunotherapy composition expressing this fusion protein is also referred to herein as GI-13008. The fusion protein and corresponding yeast-based immunotherapeutic can also be referred to herein as "Score-C".

A fourth construct based on a consensus sequence for HBV genotype D was designed as follows. Using SEQ ID NO:34 as a template, a new fusion protein was created based on a consensus sequence for HBV genotype D, represented here by SEQ ID NO:118. This fusion protein is a single polypeptide with the following sequence elements fused in frame from N- to C-terminus, represented by SEQ ID NO:118 (non-HBV sequences denoted as "optional" are not included in the base sequence of SEQ ID NO:118, but were actually added to the fusion protein described in this example): (1) an optional N-terminal peptide that is a synthetic N-terminal peptide designed to impart resistance to proteasomal degradation and stabilize expression represented by SEQ ID NO:37; (2) an optional linker peptide of Thr-Ser; (3) a consensus sequence for HBV genotype D large (L) surface antigen represented by positions 1 to 399 of SEQ ID NO:118; 4) the amino acid sequence of a consensus sequence for HBV genotype D core antigen represented by positions 400 to 581 of SEQ ID NO:118; and (5) an optional hexahistidine tag. The amino acid sequence of the complete fusion protein comprising SEQ ID NO:118 and the N- and C-terminal peptides and linker peptide is represented herein by SEQ ID NO:151. A nucleic acid sequence encoding the fusion protein comprising SEQ ID NO:118 or SEQ ID NO:151 (codon optimized for yeast expression) is represented herein by SEQ ID NO:117. A yeast-based immunotherapy composition expressing this fusion protein is also referred to herein as GI-13009. The fusion proteins and corresponding yeast-based immunotherapeutic can also be referred to herein as "Score-D".

The yeast-based immunotherapy compositions of GI-13010 (comprising SEQ ID NO:107), GI-13011 (comprising SEQ ID NO:108), GI-13012 (comprising SEQ ID NO:109), GI-13013 (comprising SEQ ID NO:110), GI-13006 (comprising SEQ ID NO:112), GI-13007 (comprising SEQ ID NO:114), GI-13008 (comprising SEQ ID NO:116) and GI-13009 (comprising SEQ ID NO:118) were produced as described for other compositions above. Briefly, DNA encoding the fusion protein was codon optimized for expression in yeast and then inserted behind the CUP1 promoter (pGI-100) in yeast 2 um expression vectors. The resulting plasmids were introduced into Saccharomyces cerevisiae W303α yeast by Lithium acetate/polyethylene glycol transfection. Yeast transformants of each plasmid were isolated on solid minimal plates lacking uracil (UDM; uridine dropout medium). Colonies were re-streaked onto ULDM (uridine and leucine dropout medium) and allowed to grow for 3 days at 30° C. Liquid starter cultures lacking uridine and leucine (UL2; formulation provided in Example 1) were inoculated from plates and starter cultures were grown for 18 h at 30° C., 250 rpm. Primary cultures were used to inoculate final cultures of UL2 and growth continued until a density of 2 YU/mL was reached. Cultures were induced with 0.5 mM copper sulfate for 3 h and then cells were washed in PBS, heat-killed at 56° C. for 1 h, and washed three times in PBS. Total protein content was measured by a TCA precipitation/nitrocellulose binding assay and HBV antigen expression was measured by western blot using an anti-his tag monoclonal antibody.

Figure 20:
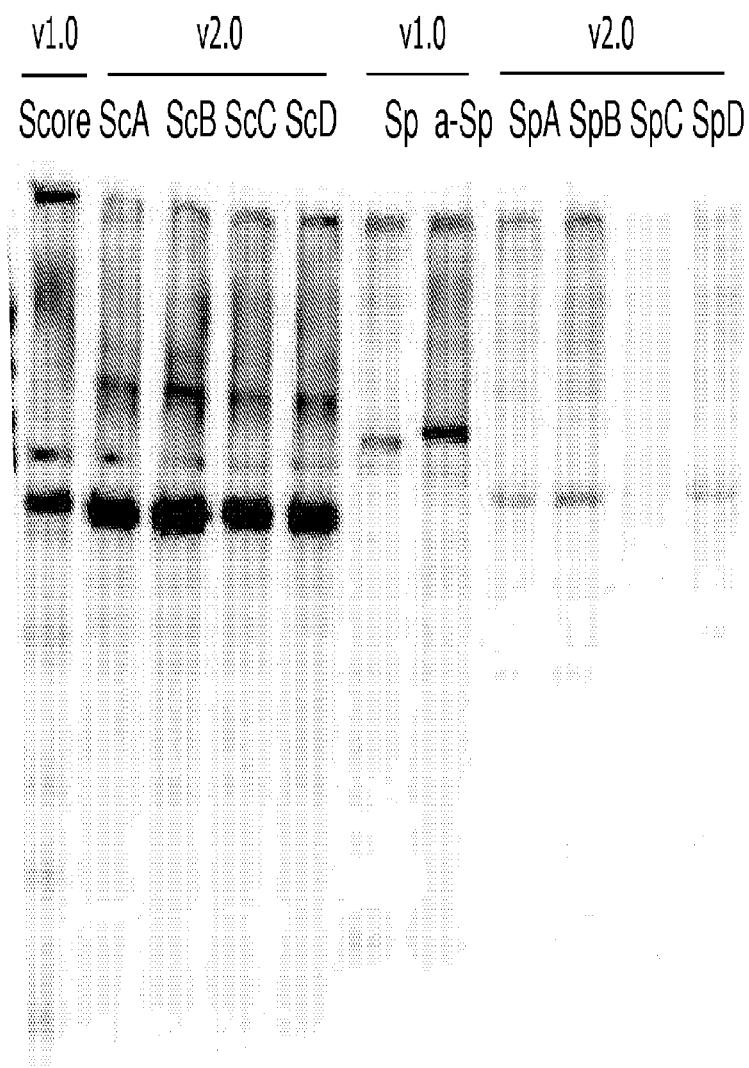
FIG. 20 is a digital image of a Western blot showing expression of several yeast-based immunotherapeutic compositions expressing HBV antigens comprising surface-core fusion proteins (Sc) or surface-polymerase-core-X fusion proteins (Sp).

The results are shown in FIG. 20. The lanes in the blot shown in FIG. 20 contain protein from the following yeast-based immunotherapeutics: Lane 1 (v1.0; Score)=GI-13002 (expressing SEQ ID NO:34); Lane 2 (v2.0; ScA)=GI-13006 (expressing SEQ ID NO:112); Lane 3 (v2.0; ScB)=GI-13007 (expressing SEQ ID NO:114); Lane 4 (v2.0; ScC)=GI-13008 (expressing SEQ ID NO:116); Lane 5 (v2.0; ScD)=GI-13009 (expressing SEQ ID NO:118); Lane 6 (v1.0; Sp)=GI-13005 (expressing SEQ ID NO:36); Lane 7 (v1.0; a-Sp)=GI-13004 (expressing SEQ ID NO:92); Lane 8 (v2.0; SpA)=GI-13010 (expressing SEQ ID NO:107); Lane 9 (v2.0; SpB)=GI-13011 (expressing SEQ ID NO:108); Lane 10 (v2.0; SpC)=GI-13012 (expressing SEQ ID NO:109); Lane 11 (v2.0; SpD)=GI-13013 (expressing SEQ ID NO:110).

The results show that each of the HBV antigens comprising the combination of surface antigen and core ("Score" antigens), i.e., GI-13002 (Score), GI-13006 (ScA; Score-A), GI-13007 (ScB; Score-B), GI-13008 (ScC; Score-C), and GI-13009 (ScD; Score-D) expressed robustly in yeast. Typical Score v2.0 expression levels in these and similar experiments were in the range of approximately 90 to 140 pmol/YU (i.e., 5940 ng/YU to 9240 ng/YU). Expression levels of the HBV antigens comprising all four HBV proteins (surface, polymerase, core and X, or "Spex") was variable. Specifically, expression of the antigens from GI-13010 (SpA; Spex-A), GI-13011 (SpB; Spex-B), GI-13012 (SpC; Spex-D) and GI-13013 (SpD; Spex-D) was substantially lower than expression of the "Score" antigens, as well as the antigens from GI-13005 (Sp; Spex) and GI-13004 (a-Sp; a-Spex). Expression of the antigen in GI-13012 (SpC; Spex-C) was barely detectable. Taken together, these results indicate that as a group, HBV antigens comprising surface antigen and core express very well in yeast, whereas HBV antigens comprising all of surface antigen, polymerase, core and X have variable expression in yeast, and generally express less well than the "Score" antigens.

Example 8

The following example describes the production of additional yeast-based HBV immunotherapeutic compositions that utilize consensus sequences for HBV genotypes, and additionally demonstrate the use of alternate configurations/arrangements of HBV protein segments within a fusion protein in order to modify or improve the expression of an HBV antigen in yeast and/or improve or modify the immunogenicity or other functional attribute of the HBV antigen.

In this example, new fusion proteins were designed that append X antigen and/or polymerase antigens to the N- or C-terminus of the combination of surface antigen fused to core. These constructs were designed in part based on the rationale that because the fusion proteins arranged in the configuration generally referred to herein as "Score" (e.g., SEQ ID NO:34, SEQ ID NO:112, SEQ ID NO:114, SEQ ID NO:116 and SEQ ID NO:118) express very well in yeast, it may be advantageous to utilize this base configuration (i.e., surface antigen fused to core protein) to produce HBV antigens comprising additional HBV protein components. Such strategies may improve expression of multi-protein antigens and/or improve or modify the functionality of such antigens in the context of immunotherapy. For example, without being bound by theory, the inventors proposed that the expression of an HBV antigen using three or all four HBV proteins could be improved by constructing the fusion protein using surface-core (in order) as a base, and then appending the other antigens to this construct.

Accordingly, to exemplify this embodiment of the invention, eight new fusion proteins were designed and constructed, and yeast-based immunotherapy products expressing these proteins were produced. In each case, the fusion protein used a surface-core fusion protein as a base that was derived from segments of the fusion protein represented by SEQ ID NO:118, which is a surface-core fusion protein described in Example 7 utilizing a consensus sequence for HBV genotype D and optimized to maximize the use of conserved immunological epitopes. All possible arrangements of a polymerase segment and/or an X antigen segment were appended to this base configuration, utilizing segments derived from the fusion protein represented by SEQ ID NO:110, which is a multi-protein HBV fusion protein described in Example 7 that was constructed to reduce the size of the protein segments, maximize the use of conserved immunological epitopes, and utilize a consensus sequence for HBV genotype D. While these eight resulting antigens are based on a consensus sequence for HBV genotype D, it would be straightforward to produce a fusion protein having a similar overall structure using the corresponding fusion segments from the fusion proteins represented by SEQ ID NO:107 and/or SEQ ID NO:112 (genotype A), SEQ ID NO:108 and/or SEQ ID NO:114 (genotype B), SEQ ID NO:109 and/or SEQ ID NO:116 (genotype C), or using the corresponding sequences from a different HBV genotype, sub-genotype, consensus sequence or strain.

Figure 8:
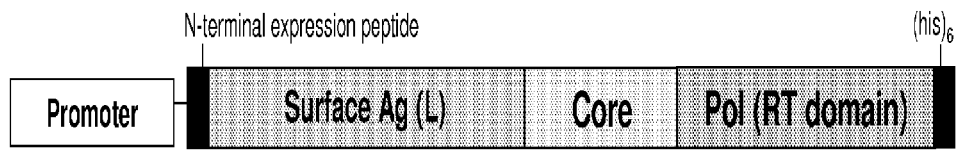
FIG. 8 is a schematic drawing showing the basic structure of a recombinant nucleic acid molecule encoding an HBV surface antigen/core/polymerase fusion protein useful in a yeast-based immunotherapeutic composition of the invention.

To produce the first composition, yeast (e.g., Saccharomyces cerevisiae) were engineered to express a new HBV fusion protein, schematically illustrated in FIG. 8, under the control of the copper-inducible promoter, CUP1. The resulting yeast-HBV immunotherapy composition can be referred to herein as GI-13015. This fusion protein, also referred to herein as "Score-Pol" and represented by SEQ ID NO:120, comprises, in order, surface antigen, core protein, and polymerase sequences, as a single polypeptide with the following sequence elements fused in frame from N- to C-terminus (non-HBV sequences denoted as "optional" were not included in the base sequence of SEQ ID NO:120, but were actually added to the fusion protein described in this example): (1) an optional N-terminal peptide that is a synthetic N-terminal peptide designed to impart resistance to proteasomal degradation and stabilize expression represented by SEQ ID NO:37; (2) an optional linker peptide of Thr-Ser; (3) the amino acid sequence of a near full-length (minus position 1) consensus sequence for HBV genotype D large (L) surface antigen represented by positions 1 to 399 of SEQ ID NO:120 (corresponding to positions 1 to 399 of SEQ ID NO:118); (4) the amino acid sequence of a consensus sequence for HBV genotype D core antigen represented by positions 400 to 581 of SEQ ID NO:120 (corresponding to positions 400 to 581 of SEQ ID NO:118); (5) an optimized portion of the reverse transcriptase (RT) domain of HBV polymerase using a consensus sequence for HBV genotype D, represented by positions 582 to 809 of SEQ ID NO:120 (corresponding to positions to 250 to 477 of SEQ ID NO:110); and (6) an optional hexahistidine tag. SEQ ID NO:120 contains multiple T cell epitopes (human and murine), which can be found in Table 5. A nucleic acid sequence encoding the fusion protein of SEQ ID NO:120 (codon-optimized for expression in yeast) is represented herein by SEQ ID NO:119.

Figure 9:
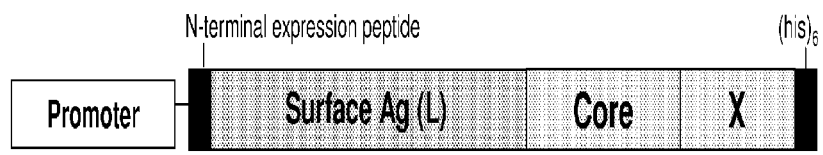
FIG. 9 is a schematic drawing showing the basic structure of a recombinant nucleic acid molecule encoding an HBV surface antigen/core/X fusion protein useful in a yeast-based immunotherapeutic composition of the invention.

To produce the second composition, yeast (e.g., *Saccharomyces cerevisiae*) were engineered to express a new HBV fusion protein, schematically illustrated in FIG. 9, under the control of the copper-inducible promoter, CUP1. The resulting yeast-HBV immunotherapy composition can be referred to herein as GI-13016. This fusion protein, also referred to herein as "Score-X" and represented by SEQ ID NO:122, comprises, in order, surface antigen, core, and X antigen sequences, as a single polypeptide with the following sequence elements fused in frame from N- to C-terminus (non-HBV sequences denoted as "optional" were not included in the base sequence of SEQ ID NO:122, but were actually added to the fusion protein described in this example): (1) an optional N-terminal peptide that is a synthetic N-terminal peptide designed to impart resistance to proteasomal degradation and stabilize expression represented by SEQ ID NO:37; (2) an optional linker peptide of Thr-Ser; (3) the amino acid sequence of a near full-length (minus position 1) consensus sequence for HBV genotype D large (L) surface antigen represented by positions 1 to 399 of SEQ ID NO:122 (corresponding to positions 1 to 399 of SEQ ID NO:118); 4) the amino acid sequence of a consensus sequence for HBV genotype D core antigen represented by positions 400 to 581 of SEQ ID NO:122 (corresponding to positions 400 to 581 of SEQ ID NO:118); (5) an optimized portion of HBV X antigen using a consensus sequence for HBV genotype D, represented by positions 582 to 641 of SEQ ID NO:122 (corresponding to positions 630 to 689 of SEQ ID NO:110); and (6) an optional hexahistidine tag. SEQ ID NO:122 contains multiple T cell epitopes (human and murine), which can be found in Table 5. A nucleic acid sequence encoding the fusion protein comprising SEQ ID NO:122 (codon-optimized for expression in yeast) is represented herein by SEQ ID NO:121.

Figure 10:
FIG. 10 is a schematic drawing showing the basic structure of a recombinant nucleic acid molecule encoding an HBV surface antigen/core/polymerase/X fusion protein useful in a yeast-based immunotherapeutic composition of the invention.

To produce the third composition, yeast (e.g., *Saccharomyces cerevisiae*) were engineered to express a new HBV fusion protein, schematically illustrated in FIG. 10, under the control of the copper-inducible promoter, CUP1. The resulting yeast-HBV immunotherapy composition can be referred to herein as GI-13017. This fusion protein, also referred to herein as "Score-Pol-X" and represented by SEQ ID NO:124 comprises, in order, surface antigen, core, polymerase and X antigen sequences, as a single polypeptide with the following sequence elements fused in frame from N- to C-terminus (non-HBV sequences denoted as "optional" were not included in the base sequence of SEQ ID NO:124, but were actually added to the fusion protein described in this example): (1) an optional N-terminal peptide that is a synthetic N-terminal peptide designed to impart resistance to proteasomal degradation and stabilize expression represented by SEQ ID NO:37; (2) an optional linker peptide of Thr-Ser; (3) the amino acid sequence of a near full-length (minus position 1) consensus sequence for HBV genotype D large (L) surface antigen represented by positions 1 to 399 of SEQ ID NO:124 (corresponding to positions 1 to 399 of SEQ ID NO:118); 4) the amino acid sequence of a consensus sequence for HBV genotype D core antigen represented by positions 400 to 581 of SEQ ID NO:124 (corresponding to positions 400 to 581 of SEQ ID NO:118); (5) an optimized portion of the reverse transcriptase (RT) domain of HBV polymerase using a consensus sequence for HBV genotype D, represented by positions 582 to 809 of SEQ ID NO:124 (corresponding to positions to 250 to 477 of SEQ ID NO:110); (6) an optimized portion of HBV X antigen using a consensus sequence for HBV genotype D, represented by positions 810 to 869 of SEQ ID NO:124 (corresponding to positions 630 to 689 of SEQ ID NO:110); and (7) an optional hexahistidine tag. SEQ ID NO:124 contains multiple T cell epitopes (human and murine), which can be found in Table 5. A nucleic acid sequence encoding the fusion protein comprising SEQ ID NO:124 (codon-optimized for expression in yeast) is represented herein by SEQ ID NO:123.

Figure 11:
FIG. 11 is a schematic drawing showing the basic structure of a recombinant nucleic acid molecule encoding an HBV surface antigen/core/X/polymerase fusion protein useful in a yeast-based immunotherapeutic composition of the invention.

To produce the fourth composition, yeast (e.g., *Saccharomyces cerevisiae*) were engineered to express a new HBV fusion protein, schematically illustrated in FIG. 11, under the control of the copper-inducible promoter, CUP1. The resulting yeast-HBV immunotherapy composition can be referred to herein as GI-13018. This fusion protein, also referred to herein as "Score-X-Pol" and represented by SEQ ID NO:126 comprises, in order, surface antigen, core, X antigen, and polymerase sequences, as a single polypeptide with the following sequence elements fused in frame from N- to C-terminus (non-HBV sequences denoted as "optional" were not included in the base sequence of SEQ ID NO:126, but were actually added to the fusion protein described in this example): (1) an optional N-terminal peptide that is a synthetic N-terminal peptide designed to impart resistance to proteasomal degradation and stabilize expression represented by SEQ ID NO:37; (2) an optional linker peptide of Thr-Ser; (3) the amino acid sequence of a near full-length (minus position 1) consensus sequence for HBV genotype D large (L) surface antigen represented by positions 1 to 399 of SEQ ID NO:126 (corresponding to positions 1 to 399 of SEQ ID NO:118); 4) the amino acid sequence of a consensus sequence for HBV genotype D core antigen represented by positions 400 to 581 of SEQ ID NO:126 (corresponding to positions 400 to 581 of SEQ ID NO:118); (5) an optimized portion of HBV X antigen using a consensus sequence for HBV genotype D, represented by positions 582 to 641 of SEQ ID NO:126 (corresponding to positions 630 to 689 of SEQ ID NO:110); (5) an optimized portion of the reverse transcriptase (RT) domain of HBV polymerase using a consensus sequence for HBV genotype D, represented by positions 642 to 869 of SEQ ID NO:126 (corresponding to positions to 250 to 477 of SEQ ID NO:110); and (7) an optional hexahistidine tag. SEQ ID NO:126 contains multiple T cell epitopes (human and murine), which can be found in Table 5. A nucleic acid sequence encoding the fusion protein comprising SEQ ID NO:126 (codon-optimized for expression in yeast) is represented herein by SEQ ID NO:125.

Figure 12:
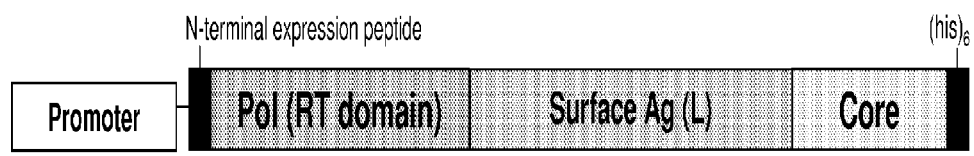
FIG. 12 is a schematic drawing showing the basic structure of a recombinant nucleic acid molecule encoding an HBV polymerase/surface antigen/core fusion protein useful in a yeast-based immunotherapeutic composition of the invention.

To produce the fifth composition, yeast (e.g., *Saccharomyces cerevisiae*) were engineered to express a new HBV fusion protein, schematically illustrated in FIG. 12, under the control of the copper-inducible promoter, CUP1. The resulting yeast-HBV immunotherapy composition can be referred to herein as GI-13019. This fusion protein, also referred to herein as "Pol-Score" and represented by SEQ ID NO:128 comprises, in order, polymerase, surface antigen, and core sequences, as a single polypeptide with the following sequence elements fused in frame from N- to C-terminus (non-HBV sequences denoted as "optional" were not included in the base sequence of SEQ ID NO:128, with the exception of the Leu-Glu linker between the polymerase segment and the surface antigen segment in the construct exemplified here, but were actually added to the fusion protein described in this example): (1) an optional N-terminal peptide that is a synthetic N-terminal peptide designed to impart resistance to proteasomal degradation and stabilize expression represented by SEQ ID NO:37; (2) an optional linker peptide of Thr-Ser; (3) an optimized portion of the reverse transcriptase (RT) domain of HBV polymerase using a consensus sequence for HBV genotype D, represented by positions 1 to 228 of SEQ ID NO:120 (corresponding to positions to 250 to 477 of SEQ ID NO:110); (4) a linker peptide (optional) of Leu-Glu, represented by positions 229 to 230 of SEQ ID NO:128; (5) the amino acid sequence of a near full-length (minus position 1) consensus sequence for HBV genotype D large (L) surface antigen represented by positions 231 to 629 of SEQ ID NO:128 (corresponding to positions 1 to 399 of SEQ ID NO:118); (6) the amino acid sequence of a consensus sequence for HBV genotype D core antigen represented by positions 630 to 811 of SEQ ID NO:128 (corresponding to positions 400 to 581 of SEQ ID NO:118); and (7) an optional hexahistidine tag. SEQ ID NO:128 contains multiple T cell epitopes (human and murine), which can be found in Table 5. A nucleic acid sequence encoding the fusion protein comprising SEQ ID NO:128 (codon-optimized for expression in yeast) is represented herein by SEQ ID NO:127.

Figure 13:
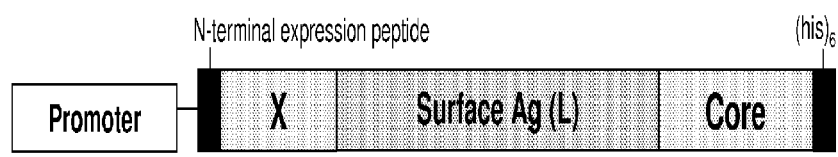
FIG. 13 is a schematic drawing showing the basic structure of a recombinant nucleic acid molecule encoding an HBV X/surface antigen/core fusion protein useful in a yeast-based immunotherapeutic composition of the invention.

To produce the sixth composition, yeast (e.g., *Saccharomyces cerevisiae*) were engineered to express a new HBV fusion protein, schematically illustrated in FIG. 13, under the control of the copper-inducible promoter, CUP1. The resulting yeast-HBV immunotherapy composition can be referred to herein as GI-13020. This fusion protein, also referred to herein as "X-Score" and represented by SEQ ID NO:130 comprises, in order, X antigen, surface antigen, and core sequences, as a single polypeptide with the following sequence elements fused in frame from N- to C-terminus, (non-HBV sequences denoted as "optional" were not included in the base sequence of SEQ ID NO:130, with the exception of the Leu-Glu linker between the X segment and the surface antigen segment in the construct exemplified here, but were actually added to the fusion protein described in this example): (1) an optional N-terminal peptide that is a synthetic N-terminal peptide designed to impart resistance to proteasomal degradation and stabilize expression represented by SEQ ID NO:37; (2) an optional linker peptide of Thr-Ser; (3) an optimized portion of HBV X antigen using a consensus sequence for HBV genotype D, represented by positions 1 to 60 of SEQ ID NO:130 (corresponding to positions 630 to 689 of SEQ ID NO:110); (4) a linker peptide (optional) of Leu-Glu, represented by positions 61 to 62 of SEQ ID NO:130; (5) the amino acid sequence of a near full-length (minus position 1) consensus sequence for HBV genotype D large (L) surface antigen represented by positions 63 to 461 of SEQ ID NO:130 (corresponding to positions 1 to 399 of SEQ ID NO:118); (6) the amino acid sequence of a consensus sequence for HBV genotype D core antigen represented by positions 462 to 643 of SEQ ID NO:130 (corresponding to positions 400 to 581 of SEQ ID NO:118); and (7) an optional hexahistidine tag. SEQ ID NO:130 contains multiple T cell epitopes (human and murine), which can be found in Table 5. The amino acid sequence of the complete fusion protein comprising SEQ ID NO:130 and the N- and C-terminal peptides and linkers is represented herein by SEQ ID NO:150. A nucleic acid sequence encoding the fusion protein comprising SEQ ID NO:130 or SEQ ID NO:150 (codon-optimized for expression in yeast) is represented herein by SEQ ID NO:129.

Figure 14:
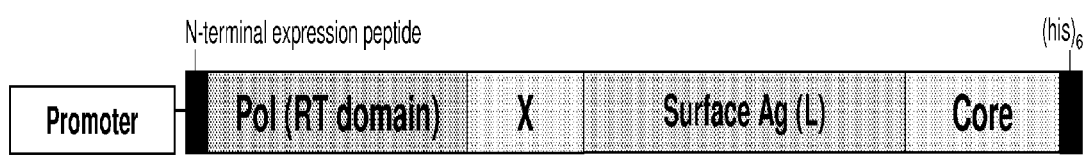
FIG. 14 is a schematic drawing showing the basic structure of a recombinant nucleic acid molecule encoding an HBV polymerase/X/surface antigen/core fusion protein useful in a yeast-based immunotherapeutic composition of the invention.

To produce the seventh composition, yeast (e.g., *Saccharomyces cerevisiae*) were engineered to express a new HBV fusion protein, schematically illustrated in FIG. 14, under the control of the copper-inducible promoter, CUP1. The resulting yeast-HBV immunotherapy composition can be referred to herein as GI-13021. This fusion protein, also referred to herein as "Pol-X-Score" and represented by SEQ ID NO:132 comprises, in order, polymerase, X antigen, surface antigen, and core, as a single polypeptide with the following sequence elements fused in frame from N- to C-terminus (non-HBV sequences denoted as "optional" were not included in the base sequence of SEQ ID NO:132, but were actually added to the fusion protein described in this example): (1) an optional N-terminal peptide that is a synthetic N-terminal peptide designed to impart resistance to proteasomal degradation and stabilize expression represented by SEQ ID NO:37; (2) an optional linker peptide of Thr-Ser; (3) an optimized portion of the reverse transcriptase (RT) domain of HBV polymerase using a consensus sequence for HBV genotype D, represented by positions 1 to 228 of SEQ ID NO:132 (corresponding to positions to 250 to 477 of SEQ ID NO:110); (4) an optimized portion of HBV X antigen using a consensus sequence for HBV genotype D, represented by positions 229 to 288 of SEQ ID NO:132 (corresponding to positions 630 to 689 of SEQ ID NO:110); (5) the amino acid sequence of a near full-length (minus position 1) consensus sequence for HBV genotype D large (L) surface antigen represented by positions 289 to 687 of SEQ ID NO:132 (corresponding to positions 1 to 399 of SEQ ID NO:118); (6) the amino acid sequence of a consensus sequence for HBV genotype D core antigen represented by positions 688 to 869 of SEQ ID NO:132 (corresponding to positions 400 to 581 of SEQ ID NO:118); and (7) an optional hexahistidine tag. SEQ ID NO:132 contains multiple T cell epitopes (human and murine), which can be found in Table 5. A nucleic acid sequence encoding the fusion protein comprising SEQ ID NO:132 (codon-optimized for expression in yeast) is represented herein by SEQ ID NO:131.

Figure 15:
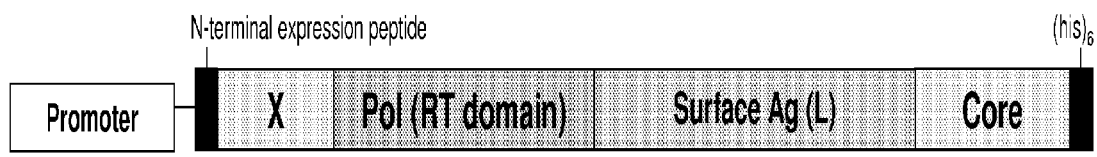
FIG. 15 is a schematic drawing showing the basic structure of a recombinant nucleic acid molecule encoding an HBV X/polymerase/surface antigen/core fusion protein useful in a yeast-based immunotherapeutic composition of the invention.

To produce the eighth composition, yeast (e.g., *Saccharomyces cerevisiae*) were engineered to express a new HBV fusion protein, schematically illustrated in FIG. 15, under the control of the copper-inducible promoter, CUP1. The resulting yeast-HBV immunotherapy composition can be referred to herein as GI-13022. This fusion protein, also referred to herein as "X-Pol-Score" and represented by SEQ ID NO:134 comprises, in order, X antigen, polymerase, surface antigen, and core protein, as a single polypeptide with the following sequence elements fused in frame from N- to C-terminus (non-HBV sequences denoted as "optional" were not included in the base sequence of SEQ ID NO:134, but were actually added to the fusion protein described in this example): (1) an optional N-terminal peptide that is a synthetic N-terminal peptide designed to impart resistance to proteasomal degradation and stabilize expression represented by SEQ ID NO:37; (2) an optional linker peptide of Thr-Ser; (3) an optimized portion of HBV X antigen using a consensus sequence for HBV genotype D, represented by positions 1 to 60 of SEQ ID NO:134 (corresponding to positions 630 to 689 of SEQ ID NO:110); (4) an optimized portion of the reverse transcriptase (RT) domain of HBV polymerase using a consensus sequence for HBV genotype D, represented by positions 61 to 288 of SEQ ID NO:134 (corresponding to positions to 250 to 477 of SEQ ID NO:110); (5) the amino acid sequence of a near full-length (minus position 1) consensus sequence for HBV genotype D large (L) surface antigen represented by positions 289 to 687 of SEQ ID NO:134 (corresponding to positions 1 to 399 of SEQ ID NO:118); (6) the amino acid sequence of a consensus sequence for HBV genotype D core antigen represented by positions 688 to 869 of SEQ ID NO:134 (corresponding to positions 400 to 581 of SEQ ID NO:118); and (7) an optional hexahistidine tag. SEQ ID NO:134 contains multiple T cell epitopes (human and murine), which can be found in Table 5. A nucleic acid sequence encoding the fusion protein comprising SEQ ID NO:134 (codon-optimized for expression in yeast) is represented herein by SEQ ID NO:133.

To produce each of the yeast-based immunotherapy compositions described above, yeast transformants of each plasmid were isolated on solid minimal plates lacking uracil (UDM; uridine dropout medium). Colonies were re-streaked onto ULDM and UDM plates and allowed to grow for 3 days at 30° C. Liquid starter cultures lacking uridine and leucine (UL2) or lacking uridine (U2) were inoculated from plates and starter cultures were grown for 18 h at 30° C., 250 rpm. Primary cultures were used to inoculate intermediate cultures of U2 or UL2 and growth was continued until a density of approximately 2 YU/mL was reached. Intermediate cultures were used to inoculate final cultures to a density of 0.05 YU/mL and these were incubated until the cell density reached 1-3 YU/mL. Final cultures were then induced with 0.5 mM copper sulfate for 3 h and cells were washed in PBS, heat killed at 56° C. for 1 h, and washed three times in PBS. Total protein content was measured with a TCA precipitation/nitrocellulose binding assay and HBV antigen expression was measured by Western blot using an anti-his tag monoclonal antibody. Lysates from two yeast immunotherapeutic compositions described in Example 7 as GI-13008 (SEQ ID NO:116; "Score-C") or GI-13009 (SEQ ID NO:118; "Score-D") were used as a basis of comparison to a yeast expressing the base surface-core antigen product.

Figure 21:
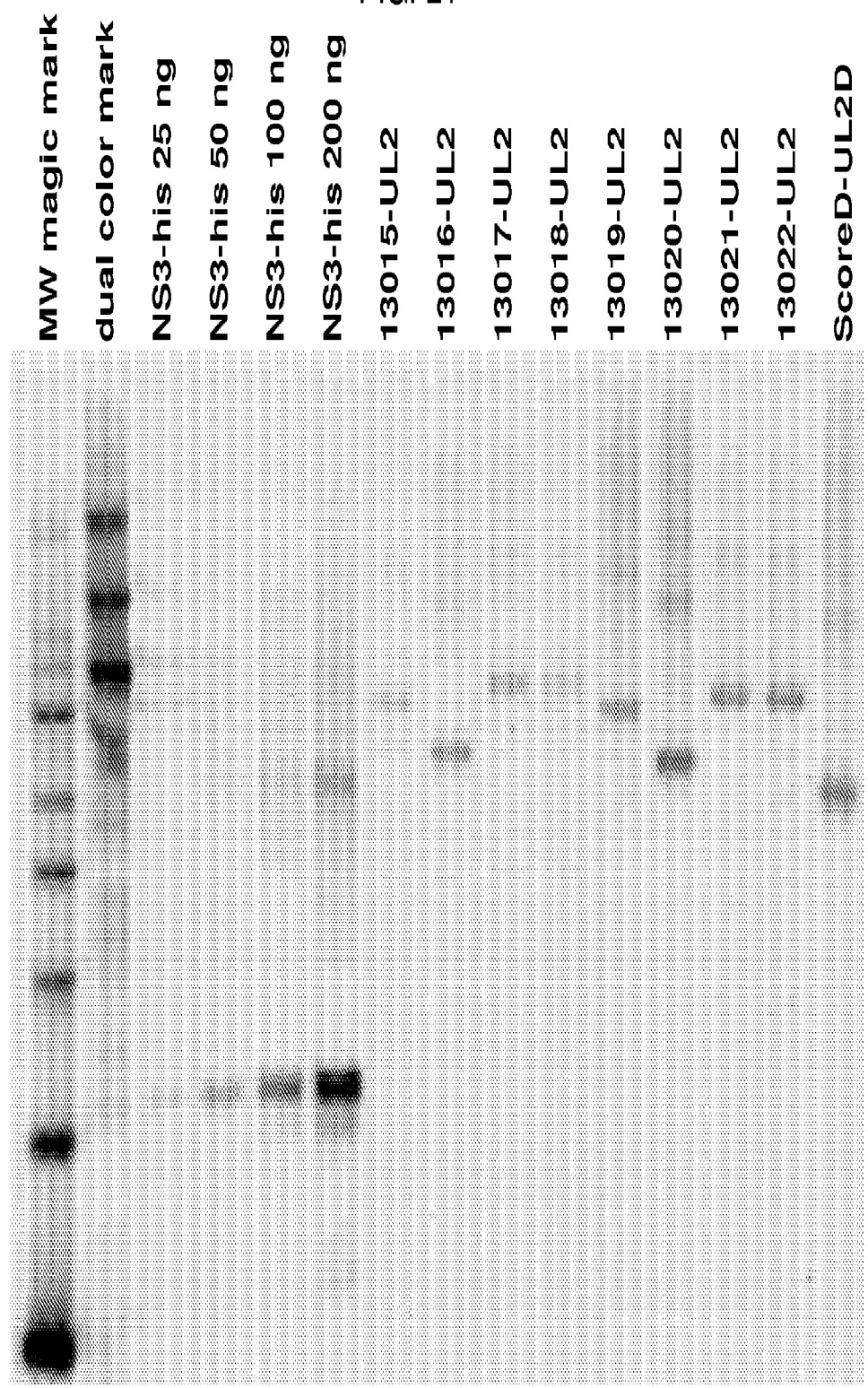
FIG. 21 is a digital image of a Western blot showing expression of HBV antigens from several yeast-based HBV immunotherapeutic compositions cultured in UL2 medium.

FIG. 21 is a blot showing the expression of all eight constructs in yeast cultured in UL2 medium (1 μg of protein loaded) as compared to expression of the construct in the yeast immunotherapeutic described in Example 7 as GI-13009 (SEQ ID NO:118; "Score-D"). Referring to FIG. 21, lanes 1 and 2 contain molecular weight markers, and lanes 4-6 contain recombinant hexahistidine tagged NS3 protein that was processed on the same blot in order to quantify antigen by interpolation from a standard curve generated from these lanes. Lanes 7-14 contain lysates from each yeast-based immunotherapeutic denoted by number (e.g., GI-13015) grown in UL2 medium, and lane 15 contains the lysate from the GI-13009 comparison. Additional western blots from yeast cultured in U2 medium, as well as additional blots evaluating different amounts of protein loading on the gel are not shown here, but overall, the results indicated that all eight antigens were expressed to detectable levels in at least one growth medium.

Figure 22:
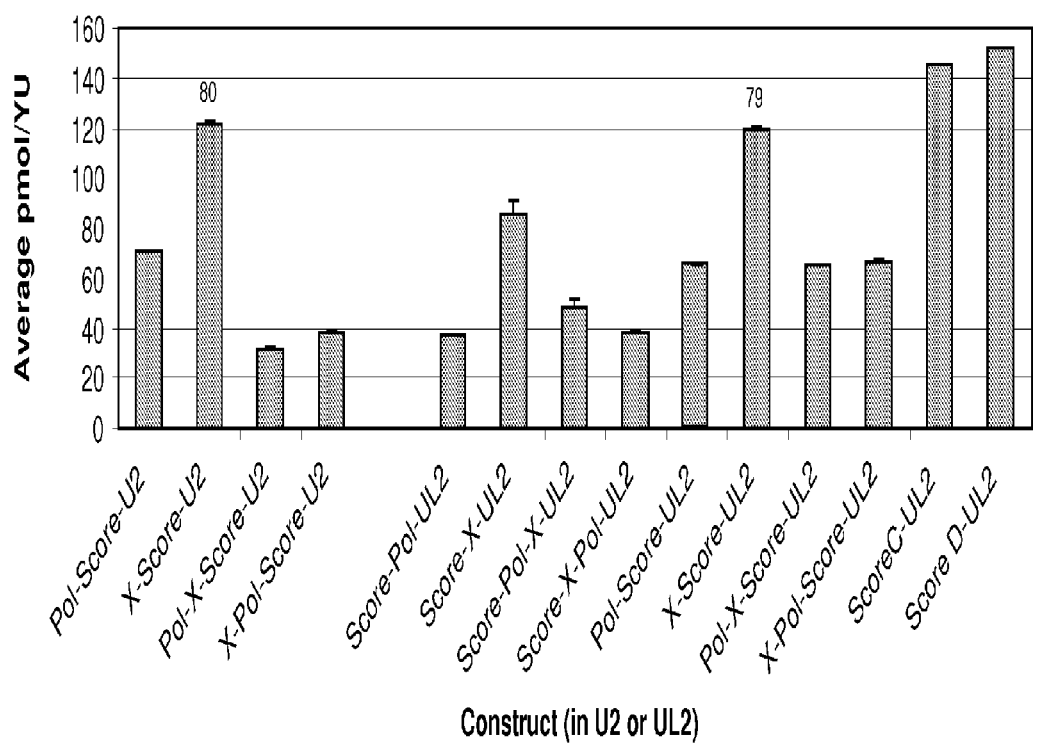
FIG. 22 is a bar graph showing the average expression of HBV antigens from several yeast-based HBV immunotherapeutic compositions cultured in UL2 medium or U2 medium (error bars are Standard Deviation).

The overall expression results are summarized in FIG. 22 as a bar graph for those cultures that had detectable expression of target antigen in U2 or UL2 medium as compared to expression of antigens in GI-13008 (Score-C) and GI-13009 (Score-D). Referring to FIG. 22, the HBV antigens are denoted below each bar using the reference to antigen arrangement in the fusion protein as described for each construct above, along with the medium used to culture the corresponding yeast that expressed the antigen (i.e., "Pol-Score-U2" refers to the HBV antigen that is a polymerase-surface-core fusion protein, represented by SEQ ID NO:128 and expressed by GI-13019 in U2 medium). The results indicated that expression of the antigen denoted "X-Score" (expressed by GI-13020; SEQ ID NO:130) was particularly robust, at ~122 pmol/YU, which was approximately 79-80% of the expression level obtained for Score-C (GI-13008) or Score-D (GI-13009) on a molar basis (either medium). Expression of the antigens expressed by GI-13015 (Score-Pol; SEQ ID NO:120), GI-13016 (Score-X; SEQ ID NO:122), GI-13017 (Score-Pol-X; SEQ ID NO:124) and GI-13018 (Score-X-Pol; SEQ ID NO:126) in U2 medium was below the level of quantification in this experiment, although each of these antigens were expressed when the same yeast-based immunotherapeutic was grown in UL2 medium (see FIG. 22). In general, antigen configurations containing the polymerase reverse transcriptase (RT) domain accumulated to lower levels than those containing only S-core with or without the addition of X antigen. Taking the data shown in this and prior Examples as a whole, the antigen configurations of surface-core ("Score" or "SCORE"; all similar constructs) and X-surface-core ("X-Score" or "X-SCORE"; GI-13020) were the highest expressing antigen configurations among all yeast-based HBV immunotherapeutics tested.

Example 9

The following example describes preclinical experiments in mice to demonstrate the safety, immunogenicity, and in vivo efficacy of yeast-based HBV immunotherapy compositions of the invention.

To evaluate the yeast-based HBV immunotherapy compositions in preclinical studies, a variety of in vitro and in vivo assays that detect induction of antigen-specific lymphocytes by yeast-based HBV immunotherapy compositions of the invention were employed, including lymphocyte proliferation, cell-mediated cytotoxicity, cytokine secretion, and protection from tumor challenge (e.g., killing of tumors engineered to express HBV proteins in vivo).

To support these studies, yeast-based HBV immunotherapy compositions described in Examples 1 and 2 were used initially, with additional studies performed using yeast-based HBV immunotherapy compositions described in 7 and 8 or elsewhere herein. However, these studies can be readily applied to any yeast-based HBV immunotherapy composition of the invention, and the results provided herein can be extrapolated to other HBV compositions comprising the same antigen base or similar antigen constructs. The results of these initial experiments are described below.

As a general protocol that can be adapted for any yeast-based HBV immunotherapy composition, mice (e.g., female BALB/c and/or C57BL/6 mice) are injected with a suitable amount of a yeast-based HBV immunotherapy composition, e.g., 4-5 YU (administered subcutaneously in 2-2.5 YU injections at 2 different injection sites). Optionally, an injection of anti-CD40 antibody is administered the day following the yeast compositions. Mice are immunized weekly or biweekly, for 1, 2, or 3 doses, and a final booster dose is optionally administered 3-4 weeks after the last weekly or biweekly dose. Mice are sacrificed 7-9 days after the final injection. Spleen cell suspensions, and/or lymph node suspensions, pooled from each group, are prepared and subjected to in vitro stimulation (IVS) conditions utilizing HBV-specific stimuli in the form of HBV peptides and/or HBV antigens, which may include yeast expressing HBV antigens. Control cultures are stimulated with non-HBV peptides, which can include an ovalbumin peptide, or a non-relevant viral peptide (e.g., a peptide from HIV). Standard assays are employed to evaluate immune responses induced by administration of yeast-based HBV immunotherapy compositions and include lymphocyte proliferation as assessed by $^3$H-thymidine incorporation, cell-mediated cytotoxicity assays (CTL assays) employing $^{51}$Cr-labeled target cells (or other targets labeled for overnight CTL), quantification of cytokine secretion by cytokine assay or ELISPOT (e.g., IFN-γ, IL-12, TNF-α, IL-6, and/or IL-2, etc.), and protection from tumor challenge (e.g., in vivo challenge with tumor cells recombinantly engineered to express HBV antigens).

Yeast-based HBV immunotherapy compositions are expected to be immunogenic as demonstrated by their ability to elicit HBV antigen-specific T cell responses as measured by the assays described above.

In initial experiments, two of the yeast-based HBV immunotherapy products described in Examples 1 and 2 were tested in lymphocyte proliferation assays (LPA) to determine whether immunization with these products elicits antigen-specific CD4$^+$ T cell proliferation. More specifically, the yeast-based immunotherapy product (GI-13002) expressing a fusion protein represented by SEQ ID NO:34 under the control of the CUP1 promoter, also known as "SCORE" and more specifically described in Example 1 above, and the yeast-based immunotherapy product (GI-13004) expressing a fusion protein represented by SEQ ID NO:92 under the control of the CUP1 promoter and also known as "a-SPEX" and more specifically described in Example 2, were each used to immunize mice and evaluate CD4$^+$ T cells specific for the surface and/or Core antigens that are targeted in both products using lymphocyte proliferation assays (LPAs).

Female BALB/c mice were immunized three times weekly with 5 YU of "SCORE" or a-SPEX subcutaneously at 2 different sites on the mouse (2.5 YU/flank). Control mice were vaccinated with empty vector yeast (denoted "YVEC") or nothing (denoted "Naïve"). One week after the third immunization, mice were humanely sacrificed and spleens and periaortal and inguinal draining lymph nodes (LNs) were removed and processed to single cell suspensions. LN cells from the two types of nodes were pooled and stimulated in vitro (IVS) with a mixture of recombinant core and surface antigen ("S/Core mix") or a class II restricted mimetope peptide (GYHGSSLY, SEQ ID NO:103, denoted "Class II SAg mimetope peptide"), previously reported to elicit proliferation of T cells from SAg-immunized BALB/c mice (Rajadhyaksha et al (1995). PNAS 92: 1575-1579).

Spleen cells were subjected to CD4$^+$ T cell enrichment by Magnetic Activated Cell Sorting (MACS) and incubated with the same antigens as described for LN. After 4 days incubation, IVS cultures were pulsed with tritiated ($^3$H) thymidine for 18 h, and cellular DNA was harvested on glass fiber microfilters. The level of incorporated $^3$H-thymidine was measured by scintillation counting. Replicate LN cultures from SCORE-immunized mice were assayed in parallel. Interferon gamma (IFN-γ) production by ELISpot was used as an additional means to assess T cell activation.

Figure 23:
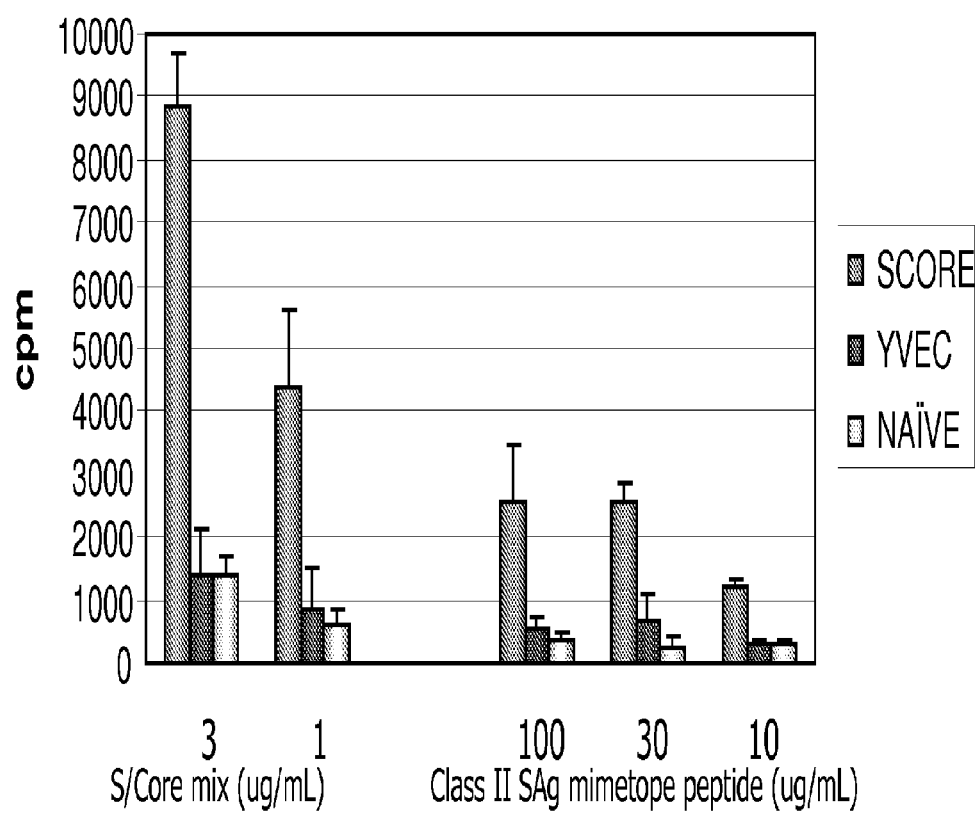
FIG. 23 is a graph showing the proliferation of splenic CD4$^+$ T cells from mice immunized with a yeast-based immunotherapeutic product expressing an HBV Surface-Core antigen (SCORE) to an S/Core antigen mix or to a MHC Class II SAg mimetope peptide (error bars are Standard Deviation).
Figure 24:
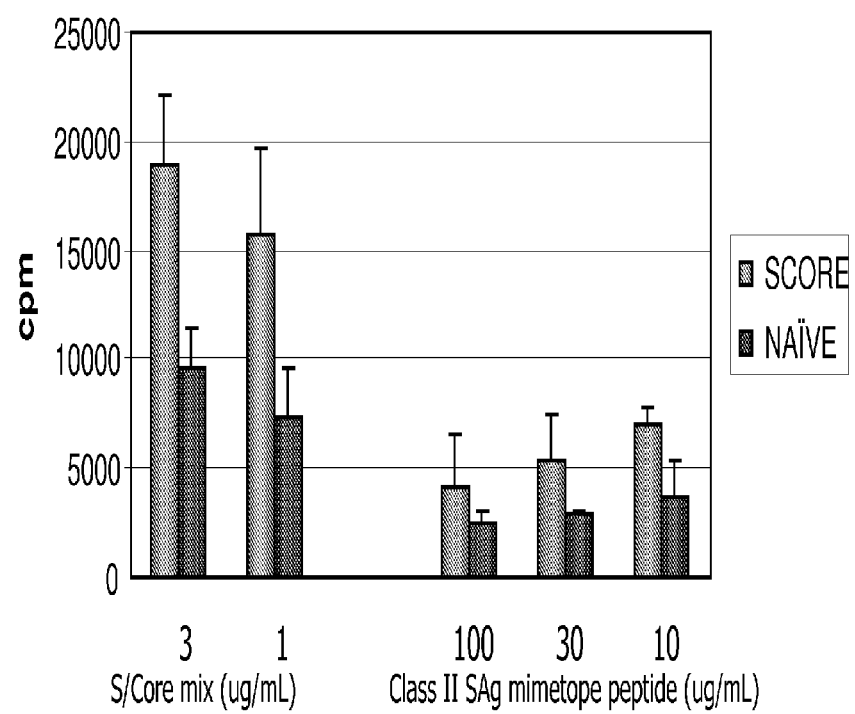
FIG. 24 is a graph showing the proliferation of lymph node T cells from mice immunized with a yeast-based immunotherapeutic product expressing an HBV Surface-Core antigen (SCORE) to an S/Core antigen mix or to a MHC Class II SAg mimetope peptide (error bars are Standard Deviation).
Figure 26:
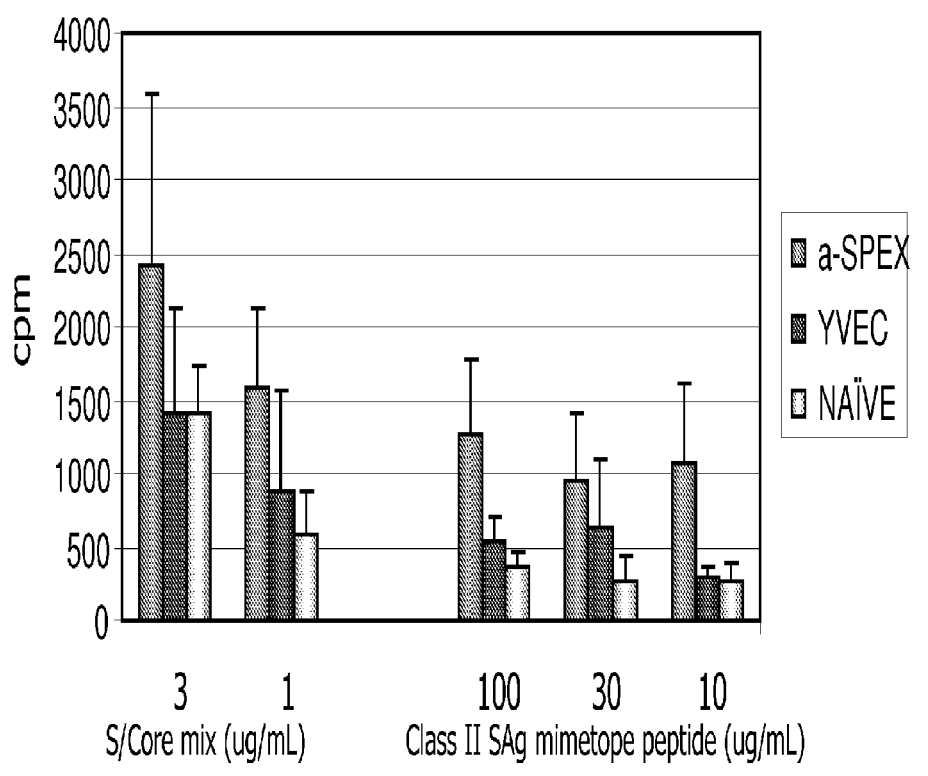

As shown in FIG. 23, FIG. 24 and FIG. 26, CD4$^+$ T cells from SCORE- or a-SPEX-immunized mice proliferated in response to the recombinant S- and Core antigen mixture. Splenic T cells from SCORE-immunized mice (FIG. 23) showed >5 fold higher level of proliferation than T cells from YVEC-immunized (empty vector control) or Naïve mice, indicating that the effect is specific for the Surface-Core fusion protein (i.e., antigen-specific T cell response). T cells from SCORE-immunized mice incubated with the HBV mimetope peptide also proliferated to higher levels than peptide-pulsed YVEC or Naïve controls, providing further evidence of the antigen-specificity of the yeast-based immunotherapeutic product response. These effects are also dependent upon the amount of antigen added to IVS, with optimal activity occurring at 3 μg/ml (recombinant antigen) or 30 μg/mL (peptide).

As shown in FIG. 24, LN cells from SCORE-immunized mice also proliferated in response to IVS with these same antigens, although the difference in proliferation between SCORE vs. Naive or YVEC-immunized animals was smaller than for isolated splenic CD4$^+$ T cells.

Figure 25:
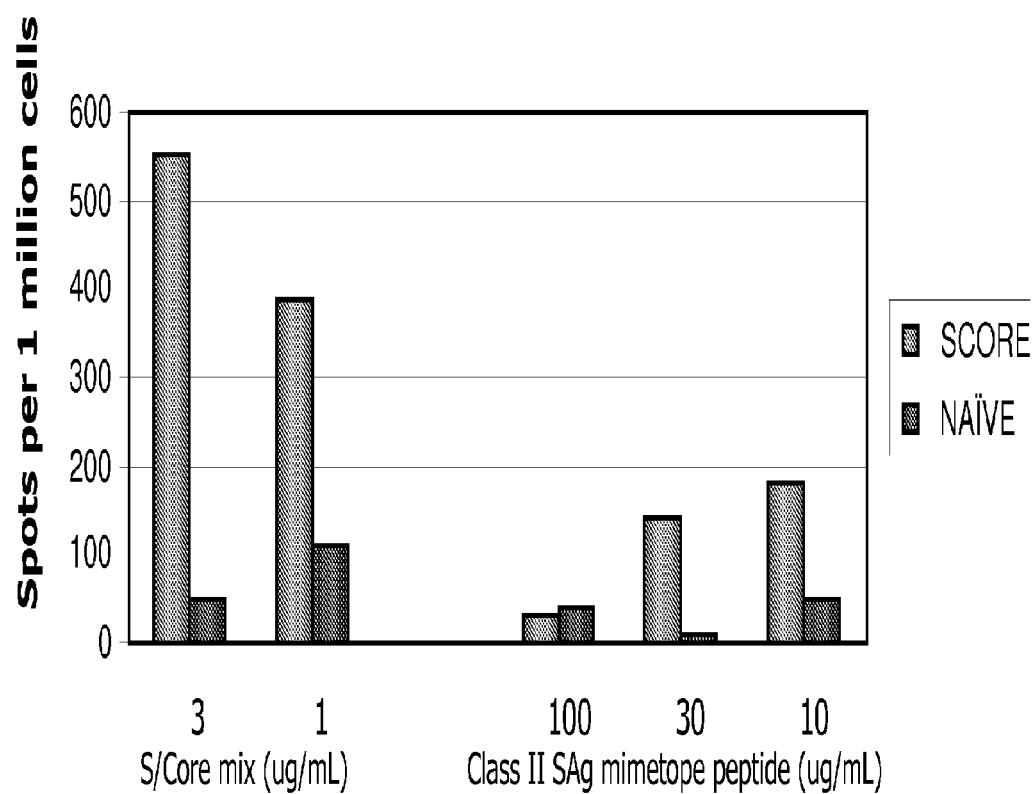
FIG. 25 is a graph showing the interferon-γ (IFN-γ) ELISpot response of lymph node T cells from mice immunized with a yeast-based immunotherapeutic product expressing an HBV Surface-Core antigen (SCORE) to an S/Core antigen mix or to a MHC Class II SAg mimetope peptide.

The ELISpot data (FIG. 25) indicate that LN preparations from SCORE-immunized mice re-stimulated with S+C mix contain >10-fold more IFN-γ secreting cells than LNs from Naive animals. IVS with HBV peptide (SEQ ID NO:103) also elicited an IFN-γ response. Specifically, the SCORE LN preps contained >3.5-fold more IFN-γ-producing cells than Naive LN preps (FIG. 25). These data collectively show that SCORE (yeast-based immunotherapy expressing the fusion protein comprising surface antigen and core) elicits HBV antigen-specific T cell responses in both spleen and LN, and that these responses can be amplified by IVS with purified antigens in a dose-dependent fashion.

Similar analyses with a-SPEX (FIG. 26) showed that this yeast-based HBV immunotherapeutic product also elicits T cell proliferative responses. a-SPEX elicited about a 30% increase as compared to YVEC in IVS performed with the recombinant antigen mixture. Overall, the responses observed with a-SPEX were lower than those observed with SCORE. The difference in magnitude of the response may reflect the fact that antigen expression in a-SPEX is less than half that of SCORE on a molar basis. Alternatively, without being bound by theory, these results may indicate that the configuration of the antigens expressed by the yeast influence expression level, processing efficiency through the endosome/proteasome, or other parameters of the immune response. The proliferation of T cells from a-SPEX mice using the 100 μg/mL peptide was at least 2-fold greater than the proliferation in YVEC vaccinated mice (FIG. 26, right three columns).

Example 10

The following example describes the immunological evaluation of two yeast-based HBV immunotherapeutics of the invention using cytokine profiles.

One way to characterize the cellular immune response elicited as a result of immunization with yeast-based HBV immunotherapeutics of the invention is to evaluate the cytokine profiles produced upon ex vivo stimulation of spleen preparations from the immunized animals.

In these experiments, female C57Bl/6 mice were immunized with GI-13002 ("SCORE", a yeast-based immunotherapeutic expressing the HBV surface-core fusion protein represented by SEQ ID NO:34, Example 1) and GI-13005 ("M-SPEX", a yeast-based immunotherapeutic expressing the HBV surface-pol-core-X fusion protein represented by SEQ ID NO:36 under the control of the CUP1 promoter, Example 2), YVEC (empty vector control yeast), or nothing (Naïve) as follows: 2 YU of yeast-based immunotherapeutic or control yeast were injected subcutaneously at 2 different sites on the animal on days 0, 7, & 28. Anti-CD40 antibody was administered by intraperitoneal (IP) injection on day 1 to provide additional activation of dendritic cells (DCs) beyond the level of activation provided by yeast-based therapeutic.

The anti-CD40 antibody treatment is optional, but the use of the antibody can boost the level of antigen-specific CD8+ T cells when attempting to detect these cells by direct pentamer staining (such data not shown in this experiment). Nine days after the last immunization, spleens were removed and processed into single cell suspensions. The cells were put into in vitro stimulation (IVS) cultures for 48 h with a mixture of 2 HBV peptides pools (denoted "P" in FIG. 27 and FIG. 28 and "HBVP" in FIGS. 29A and 29B), or with mitomycin C-treated naive syngeneic splenocytes pulsed with the 2 peptides (denoted "PPS" in FIG. 27 and FIG. 28 and "HPPS" in FIGS. 29A and 29B). The peptides are H-2K$^b$-restricted and have following sequences: ILSPFLPLL (SEQ ID NO:65, see Table 5) and MGLKFRQL (SEQ ID NO:104). The cultures were subjected to replicate Luminex analysis of IL1β, IL-12, and IFN-γ.

These cytokines were evaluated because they are associated with the types of immune responses that are believed to be associated with a productive or effective immune response against HBV. IL-1β is a pro-inflammatory cytokine produced by antigen presenting cells, and is a cytokine known to be induced by immunization with yeast-based immunotherapy compositions. IL-12 is also produced by antigen presenting cells and promotes CD8+ cytotoxic T lymphocyte (CTL) activity. IFN-γ is produced by CD8+ cytotoxic T lymphocytes in the development of the adaptive immune response and also promoted Th1 CD4+ T cell differentiation.

Figure 27:
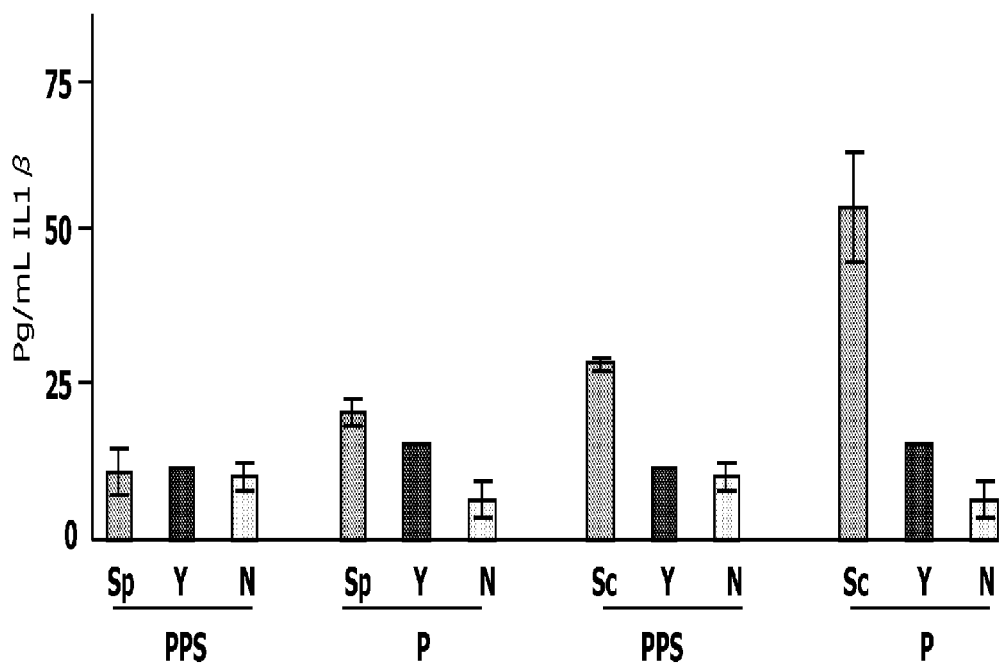
FIG. 27 is a graph showing IL-1β production in splenocytes from mice immunized with: (a) a yeast-based immunotherapeutic product expressing an HBV Surface-Pol-E/Core-X antigen (denoted Sp), left columns; or (b) a yeast-based immunotherapeutic product expressing an HBV Surface-Core antigen (denoted Sc) (error bars are Standard Deviation).
Figure 28:
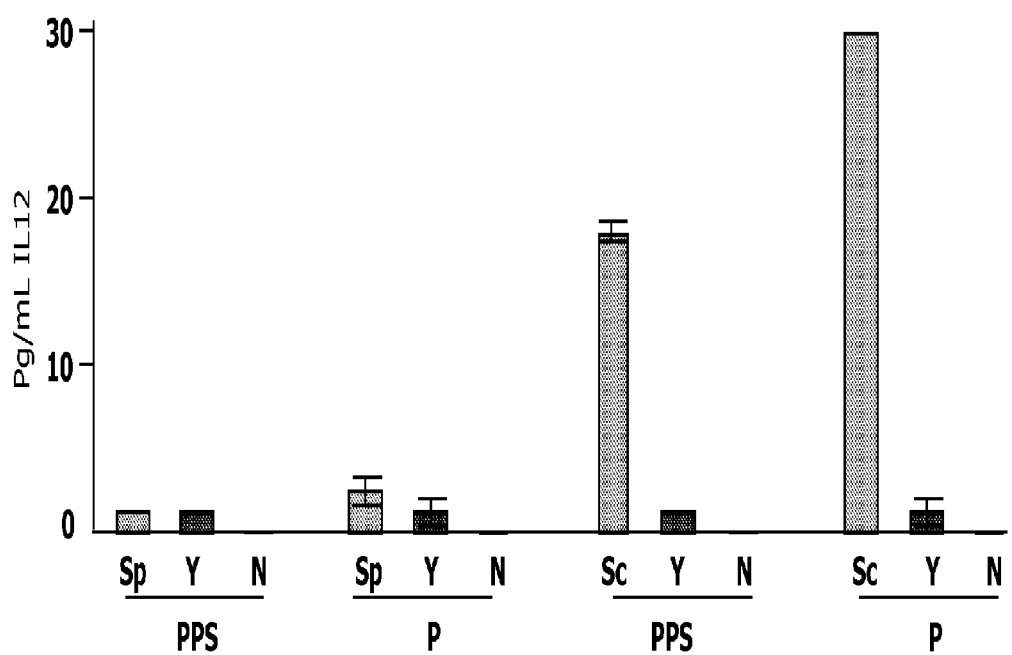
FIG. 28 is a graph showing IL-12p70 production in splenocytes from mice immunized with: (a) a yeast-based immunotherapeutic product expressing an HBV Surface-Pol-Core-X antigen (denoted Sp), left columns; or (b) a yeast-based immunotherapeutic product expressing an HBV Surface-Core antigen (denoted Sc) (error bars are Standard Deviation).
Figure 29A:
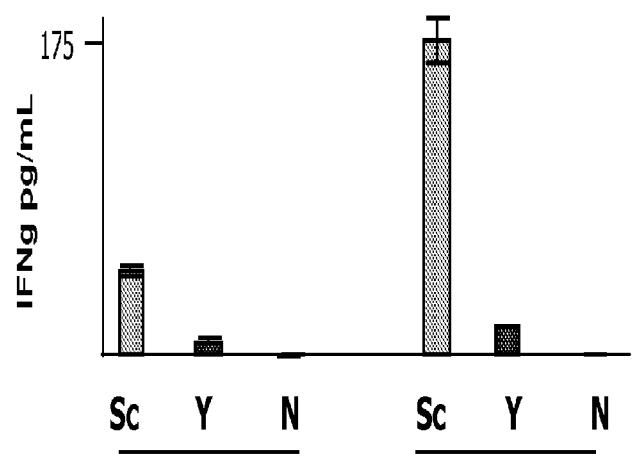
Figure 29B:
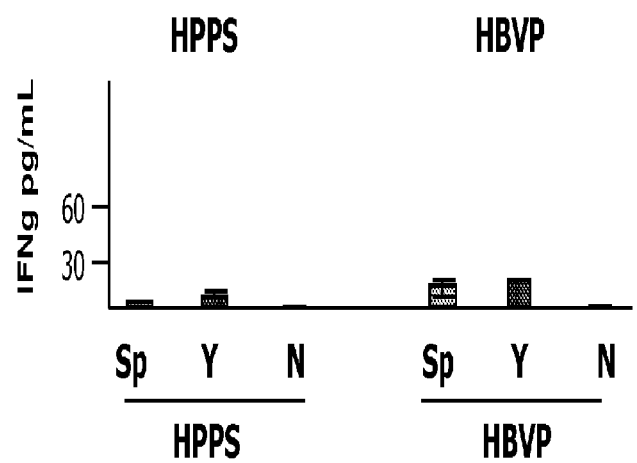

The results, shown in FIG. 27 (IL-1β, FIG. 28 (IL-12), FIG. 29A (IFN-γ; SCORE-immunized), and FIG. 29B (IFN-γ; M-SPEX-immunized) show that all three cytokines are produced by splenocytes from Score-immunized mice (denoted "Sc" in FIG. 27, FIG. 28 and FIG. 29A) in response to direct IVS with peptide pool alone, and that the response is greater for SCORE-immunized than for YVEC (denoted "Y" in FIG. 27, FIG. 28 and FIGS. 29A and 29B) or Naive (denoted "N" in FIG. 27, FIG. 28 and FIGS. 29A and 29B) mice, demonstrating that immunization with SCORE elicits an antigen-specific immune response resulting in production of these three cytokines IVS with peptide-pulsed syngeneic splenocytes also elicited an antigen specific response although of lower magnitude. Splenocytes from M-SPEX-vaccinated mice (denoted "Sp" in FIG. 27, FIG. 28 and FIG. 29B) produced an overall lower level of the cytokines than those from SCORE-vaccinated mice. Nevertheless, the amount of IL12p70 produced in response to M-SPEX is higher than the amount produced by YVEC or Naïve, indicating an antigen-specific immune response induced by this yeast-based immunotherapeutic composition. It is expected that a-SPEX (GI-13004; Example 2), which expressed higher levels of antigen and induced a CD4+ proliferative response in the assays described in Example 9, will elicit higher levels of cytokine production.

Additional cytokine assays were performed using female BALB/c mice immunized with one of the same two yeast-based immunotherapeutic products. In these experiments, female BALB/c mice were immunized with SCORE (GI-13002; denoted "Sc" in FIGS. 30A-30D), M-SPEX (GI-13005; denoted "Sp" in FIGS. 30A-30D), YVEC (denoted "Y" in FIGS. 30A-30D), or nothing (Naïve, denoted "N" in FIGS. 30A-30D) as follows: 2 YU of yeast product were administered at 2 sites on days 0, 11, 39, 46, 60, and 67. As in the experiment above, anti-CD40 antibody was administered i.p. Nine days after the last immunization (day 76) spleens were removed, processed into single cell suspensions, and subjected to IVS for 48 h with a mixture of recombinant HBV Surface and Core proteins (denoted "HBV Sag+Core Ag" in FIGS. 30A-30D). Supernatants were collected and evaluated by Luminex for production of IL1β, IL-6, IL-13, and IL12p70. IL-6 is a pro-inflammatory cytokine produced by antigen presenting cells and T cells and is believed to be an important cytokine in the mechanism of action of yeast-based immunotherapeutic products. IL-13 is also a pro-inflammatory cytokine produced by T cells and is closely related to IL-4 and promotion of a Th2 CD4+immune response.

Figure 30A:
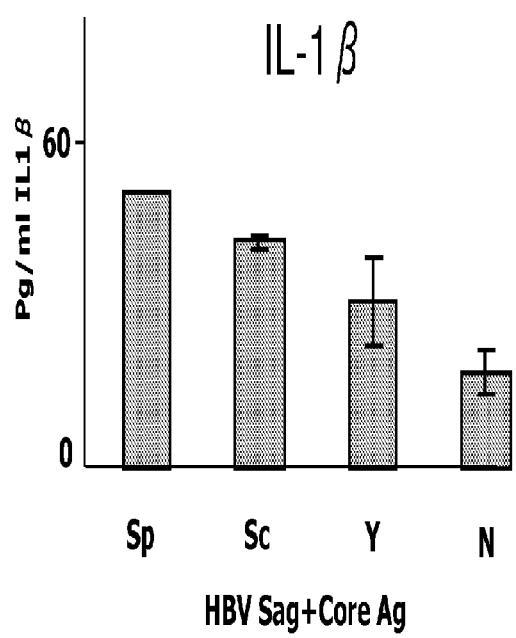
FIGS. 30A-D are graphs showing IL-1β (FIG. 30A), IL-6 (FIG. 30B), IL-13 (FIG. 30C), and IL-12p70 (FIG. 30D) production in splenocytes from mice immunized with: (a) a yeast-based immunotherapeutic product expressing an HBV Surface-Pol-Core-X antigen (denoted Sp), left columns; or (b) a yeast-based immunotherapeutic product expressing an HBV Surface-Core antigen (denoted Sc).
Figure 30B:
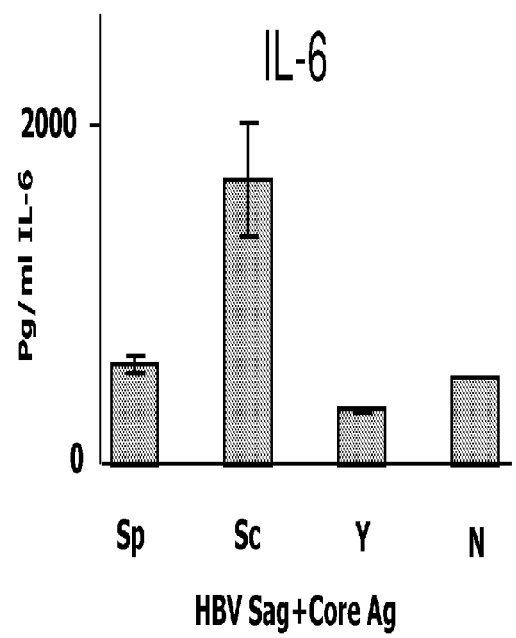
Figure 30C:
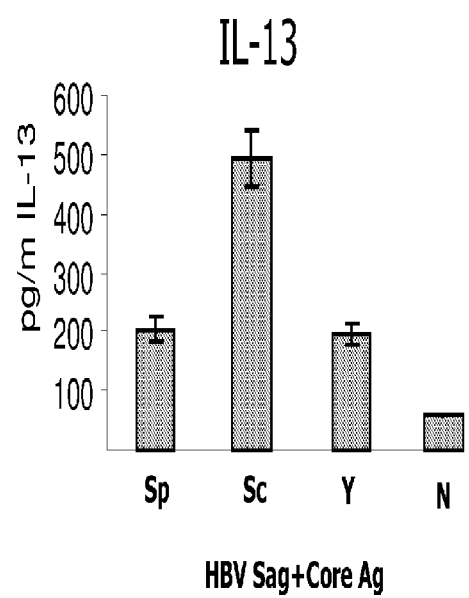
Figure 30D:
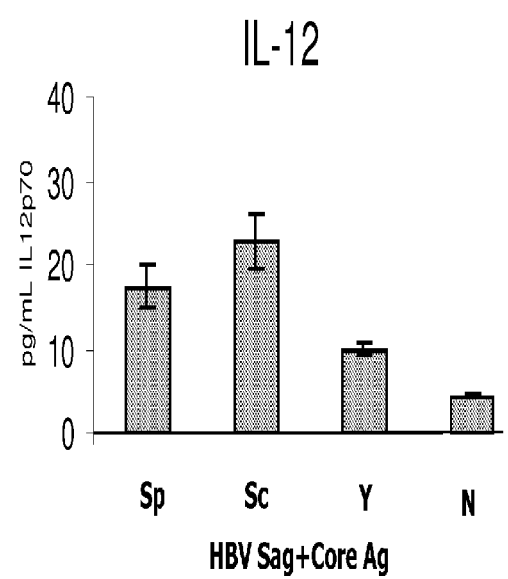

The results, shown in FIG. 30A (IL-1β, FIG. 30B (IL-6), FIG. 30C (IL-13) and FIG. 30D (IL-12) show that splenocytes from SCORE-immunized mice produced IL-1β, IL-6, IL12p70, and IL-13 in response to the surface and core antigen mix and that the magnitude of the response was higher than for splenocytes from YVEC-immunized or Naive mice. This antigen specificity is consistent with results obtained for LPA in BALB/c mice (see Example 9) and for cytokine release assays in C57Bl/6 mice (see above).

Splenocytes from M-SPEX immunized mice produced antigen-specific signals for IL-1β (FIG. 30A) but not for the other cytokines As with the findings in C57Bl/6, this apparent difference in potency between SCORE and M-SPEX may be explained by the lower antigen content of the latter. It is expected that a-SPEX (expressing a fusion protein represented by SEQ ID NO:92, described in Example 2), which expresses higher levels of antigen, will induce improved antigen-specific cytokine production, and in addition, IVS assays featuring the additional antigens expressed by this product or others that incorporate other HBV antigens (HBV X and Polymerase antigens) are expected to reveal additional immunogenicity.

Example 11

The following example describes immunogenicity testing in vivo of a yeast-based immunotherapeutic composition for HBV.

In this experiment, the yeast-based immunotherapy product (GI-13002) expressing a fusion protein represented by SEQ ID NO:34 under the control of the CUP1 promoter, also known as "SCORE" and more specifically described in Example 1 was used in an adoptive transfer method in which T cells from SCORE-immunized mice were transferred to recipient Severe Combined Immune Deficient (SCID) mice prior to tumor implantation in the SCID mice.

Briefly, female C57BL/6 mice (age 4-6 weeks) were subcutaneously immunized with GI-13002 (SCORE), YVEC (yeast containing empty vector), or nothing (naive) at 2 sites (2.5 YU flank, 2.5 YU scruff) on days 0, 7 and 14. One cohort of SCORE-immunized mice was additionally injected intraperitoneally (i.p.) with 50 µg of anti-CD40 antibody one day after each immunization. On day 24, mice were sacrificed and total splenocytes were prepared and counted. Twenty-five million splenocytes in 200 µL PBS were injected i.p. into naive recipient 4-6 week old female SCID mice. Twenty four hours post-transfer, the recipients were challenged subcutaneously (s.c.) in the ribcage area with 300,000 SCORE-antigen expressing EL4 tumor cells (denoted "EL-4-Score"), or tumor cells expressing irrelevant ovalbumin antigen. Tumor growth was monitored by digital caliper measurement at 1 to 2 day intervals starting at day 10 post tumor challenge.

Figure 31:
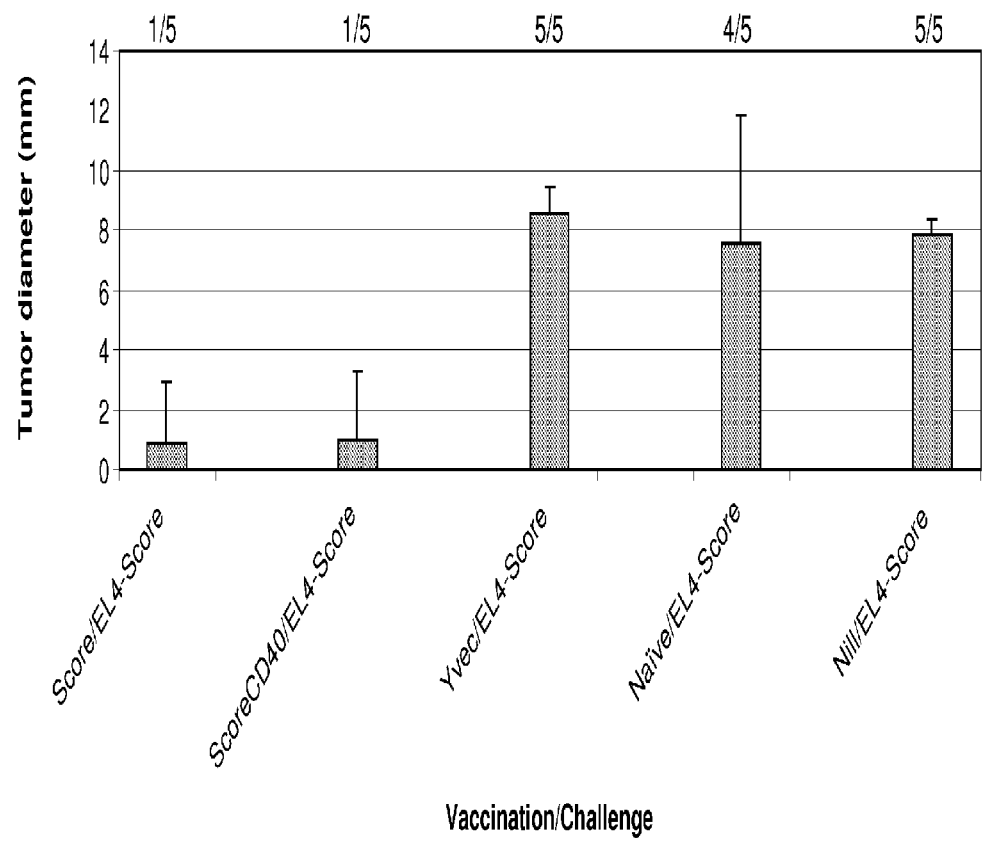
FIG. 31 is a bar graph showing that mice immunized with GI-13002 or GI-13002+anti-CD40 antibody, but not YVEC, elicited comparable protection from challenge with EL4 tumors expressing the target HBV antigen (error bars are Standard Deviation).

The results at 10 days post tumor challenge, shown in FIG. 31, demonstrated that splenocytes from mice immunized with GI-13002 (SCORE) or GI-13002+anti-CD40 antibody, but not from YVEC or naive mice, elicited comparable protection from challenge with EL4 tumors expressing the SCORE antigen (FIG. 31, first and second bars from left). The number of mice with tumors 10 days post challenge are indicated above each bar in FIG. 31. T cells from GI-13002-immunized mice had no effect on the growth of EL4 tumors expressing an unrelated antigen (not shown). Splenocytes from YVEC-immunized mice (FIG. 31, middle bar) did not affect tumor growth, as the size and number of tumors in this group were comparable to those of mice receiving no splenocytes (FIG. 31, far right bar) or those mice receiving splenocytes from naïve mice (FIG. 31, second bar from right). These results indicate that immunization with a yeast-based immunotherapeutic composition expressing a surface antigen-core fusion protein generates an antigen-specific immune response that protects SCID mice from tumor challenge. Co-administration of the dendritic cell (DC)-activating anti-CD40 antibody did not influence the extent of protection.

Example 12

The following example describes the immunogenicity testing of two yeast-based immunotherapy compositions for HBV using interferon-γ (IFN-γ) ELISpot assays.

This experiment was designed to evaluate two optimized yeast-based immunotherapy compositions described in Example 7 for the ability to induce HBV antigen-specific T cells in mice immunized with these compositions. The experiment also tested whether novel HBV peptide sequences designed with computational algorithms and sequences obtained from the published literature can be used to re-stimulate T cell responses that were generated by these immunotherapy compositions.

In this experiment, the yeast-based immunotherapy composition described in Example 7 as GI-13008 ("Score-C", comprising SEQ ID NO:116) and the yeast-based immunotherapy composition described in Example 7 as GI-13013 ("Spex-D", comprising SEQ ID NO:110) were evaluated for immunogenicity. Peptide sequences used in this experiment are shown in Table 7. The sequences denoted ZGP-5 and ZGP-7 are from the published literature whereas the remaining peptides were identified computationally with BIMAS or SYFPEITHI predictive algorithms. The prefixes "Db" or "Kb" refer to the haplotype of C57BL/6 mice: H-2D$^b$ and H2-K$^b$, respectively.

TABLE 7

| Peptide name | Amino acid sequence | Sequence Identifier | MHC Class | HBV Antigen |
|---|---|---|---|---|
| Db9-84 | WSPQAQGIL | SEQ ID NO: 138 | I | Sag |
| Db9-94 | TVPANPPPA | SEQ ID NO: 141 | I | Sag |
| Db9-283 | GMLPVCPLL | SEQ ID NO: 142 | I | Sag |
| Db9-499 | MGLKIRQLL | SEQ ID NO: 143 | I | Core |
| Kb8-249 | ICPGYRWM | SEQ ID NO: 144 | I | Sag |
| Kb8-262 | IIFLFILL | SEQ ID NO: 145 | I | Sag |
| Kb8-277 | VLLDYQGM | SEQ ID NO: 139 | I | Sag |
| Kb8-347 | ASVRFSWL | SEQ ID NO: 140 | I | Sag |
| Kb8-360 | FVQWFVGL | SEQ ID NO: 146 | I | Sag |
| Kb8-396 | LLPIFFCL | SEQ ID NO: 147 | I | Sag |

TABLE 7-continued

| Peptide name | Amino acid sequence | Sequence Identifier | MHC Class | HBV Antigen |
|---|---|---|---|---|
| ZGP-5 | VSFGVWIRTPPAYRPPNAPIL | SEQ ID NO: 148 | II | Core |
| ZGP-7 | ILSPFLPL | SEQ ID NO: 149 | I | Sag |

Female C57BL/6 mice (age 4-6 weeks) were subcutaneously immunized with GI-13008 (Score-C), GI-13013 (Spex-D), YVEC (empty vector yeast control), or nothing (naive) at 2 sites (2.5 YU flank, 2.5 YU scruff) on days 0, 7 and 14. On day 20, mice were sacrificed and total splenocytes were prepared, depleted of red blood cells, counted, and incubated at 200,000 cells/well for four days in complete RPMI containing 5% fetal calf serum plus the peptide stimulants listed in Table 7 (10 μM for D$^b$ and K$^b$ peptides; 30 μg/mL for ZGP peptides) or a mixture of recombinant HBV SAg and Core antigen (3 μg/mL total). Concanavalin A was added as a positive control stimulant.

Figure 32:
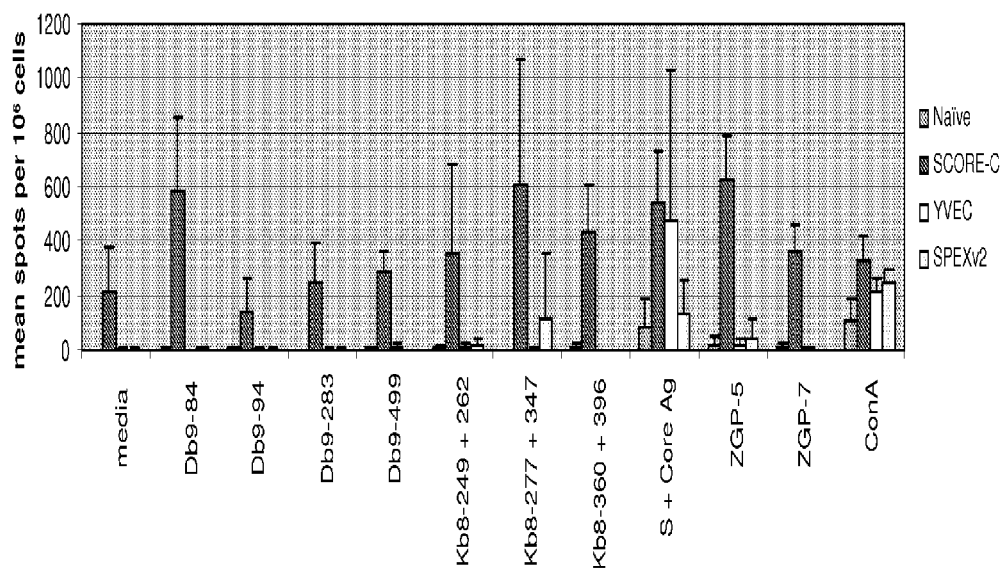
FIG. 32 is a bar graph showing the results of an IFN-γ ELISpot assay comparing T cell responses of mice immunized with GI-13008 (SCORE-C) and GI-13013 (SPEXv2) as compared to YVEC using a variety of HBV peptides and antigens (error bars are Standard Deviation).

The results (FIG. 32) show that immunization of C57BL/6 mice with GI-13008 (Score-C) elicits IFNγ ELISpot responses directed against HBV surface (S) and core antigens with particular specificity for the following peptides: Db9-84, Kb8-277 and/or Kb8-347, ZGP-5, and ZGP-7. These peptides elicited IFNγ responses greater than those from wells containing medium alone, or from wells containing splenocytes from GI-13013 (Spex-D)-immunized, YVEC-immunized, or Naive mice. Recombinant S+Core antigen mixture also elicited an IFNγ response, although the YVEC control cells in that particular stimulant group produced background signal which precluded the evaluation of an antigen-specific contribution for the S+Core antigen mix. These data indicate that GI-13008 (Score-C), which expresses a surface-core fusion protein, elicits HBV-antigen specific immune responses that can be re-stimulated with selected peptides ex vivo, and that these responses are more readily detectable than those elicited by GI-13013 (Spex-D).

Example 13

The following example describes an experiment in which a yeast-based immunotherapy composition for HBV was tested for the ability to stimulate IFNγ production from peripheral blood mononuclear cells (PBMCs) from a subject vaccinated with a commercial HBV prophylactic vaccine.

In this experiment, the yeast-based immunotherapy product known as GI-13002 ("Score", comprising SEQ ID NO:34, Example 1) was tested for its ability to stimulate IFNγ production from PBMCs isolated from a subject who was vaccinated with commercial HBV prophylactic vaccine (ENGERIX-B®, GlaxoSmithKline), which is a prophylactic vaccine containing a recombinant purified hepatitis B virus surface antigen (HBsAg) adsorbed on an aluminum-based adjuvant.

Briefly, blood was collected and PBMCs were isolated from a healthy HBV-naive human subject expressing the HLA-A*0201 allele. The PBMCs were frozen for later analysis. The subject was then vaccinated with ENGERIX-B® (injection 1), blood was collected at days 12 and 29 post-injection, and PBMCs were isolated and frozen. The subject was vaccinated a second time with ENGERIX-B® (injection 2, "boost") and blood was collected on days 10, 21, and 32 post-boost. PBMCs were isolated and frozen for each time point.

After the series of PBMC samples was acquired and frozen, the cells from all time points were thawed, washed, and incubated with the empty vector yeast control (YVEC) or with GI-13002 at a 5:1 yeast:PBMC ratio for 3 days in a 37° C./5% $CO_2$ incubator. The cells were then transferred to an IFNγ ELISpot plate, incubated for 18 h, and processed to develop ELISpots according to standardized procedures.

Figure 33:
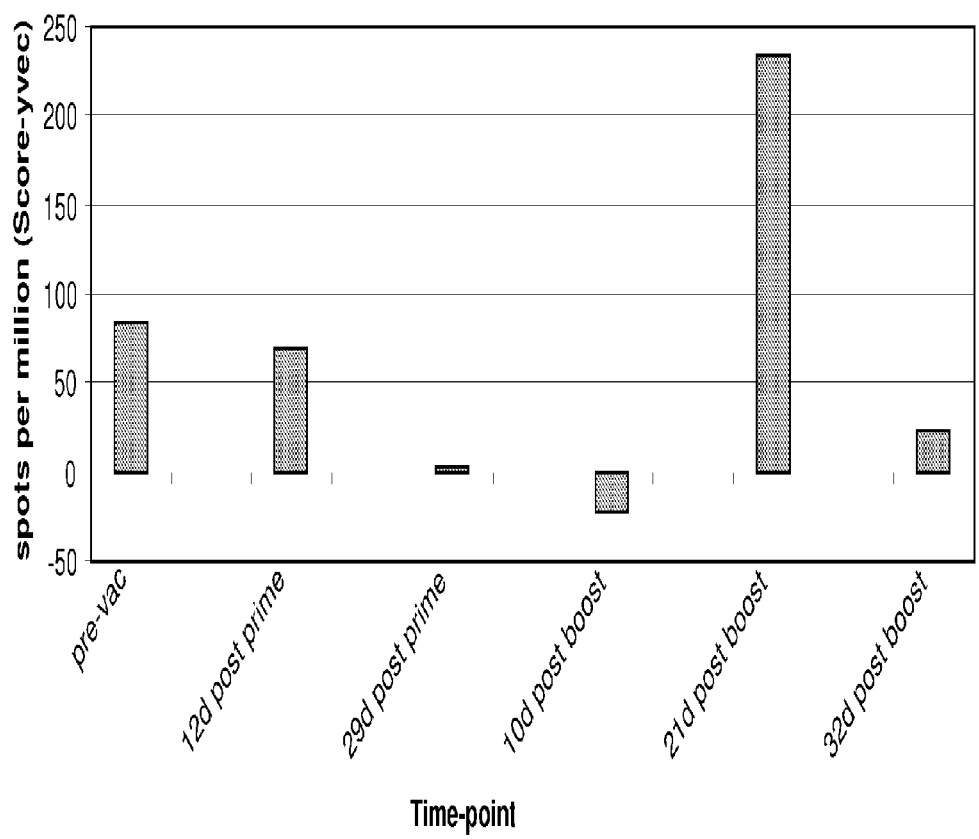
FIG. 33 is a bar graph showing IFN-γ ELISpot responses to stimulation with GI-13002 from a human subject pre- and post-immunization, and post-boost, with a prophylactic HBV vaccine.

As shown in FIG. 33 (columns denote time periods pre- and post-priming immunization or post-boost), a substantial ELISpot response was observed for GI-13002-treated PBMCs that was higher than that of YVEC-treated PBMCs at the day 21 post-boost time-point (GI-13002 ELISpots minus YVEC ELISpots ~230 spots per one million PBMCs). The level of YVEC-subtracted Score ELISpots was above the number observed for other time-points and 2.8 fold above the signal obtained for the pre-vaccination sample. The only substantial structural difference between the yeast-based compositions of GI-13002 and YVEC is the presence of the surface-core fusion protein (the HBV antigen) within the vector carried by GI-13002 (i.e., YVEC has an "empty" vector). Therefore, the result indicates that GI-13002 elicited antigen-specific stimulation of T cells in the PBMCs of the subject. Because the ENGERIX-B® vaccine contains recombinant surface antigen, but not core antigen, and because the subject was negative for HBV virus (had not been infected with HBV), this result also indicates that the IFNγ production observed was derived from HBsAg-specific (surface antigen-specific), rather than core antigen-specific, T cells.

Example 14

The following example describes the evaluation of yeast-based immunotherapy compositions for HBV in vivo in murine immunization models.

In this experiment, the yeast-based immunotherapy product known as GI-13009 ("SCORE-D", comprising SEQ ID NO:118, Example 7), and the yeast-based immunotherapy product known as GI-13020 ("X-SCORE", comprising SEQ ID NO:130, Example 8) were administered to C57BL/6 mice, BALB/c mice and HLA-A2 transgenic mice (B6.Cg-Tg (HLA-A/H2-D)2Enge/J; The Jackson Laboratory, provided under a license from the University of Virginia Patent Foundation). The HLA-A2 transgenic mice used in these experiments express an interspecies hybrid class I MHC gene, AAD, which contains the alpha-1 and alpha-2 domains of the human HLA-A2.1 gene and the alpha-3 transmembrane and cytoplasmic domains of the mouse H-$2D^d$ gene, under the direction of the human HLA-A2.1 promoter. The chimeric HLA-A2.1/H2-$D^d$ MHC Class I molecule mediates efficient positive selection of mouse T cells to provide a more complete T cell repertoire capable of recognizing peptides presented by HLA-A2.1 Class I molecules. The peptide epitopes presented and recognized by mouse T cells in the context of the HLA-A2.1/H2-$D^d$ class I molecule are the same as those presented in HLA-A2.1$^+$humans. Accordingly, this transgenic strain enables the modeling of human T cell immune responses to HLA-A2 presented antigens.

The goal of these experiments was to evaluate the breadth and magnitude of HBV antigen-specific immune responses that are generated by immunization with the yeast-based HBV immunotherapeutics in mice with varied MHC alleles, including one expressing a human MHC(HLA) molecule. Immunogenicity testing was done post-immunization by ex vivo stimulation of spleen or lymph node cells with relevant HBV antigens, followed by assessment of T cell responses by: IFN-γ/IL-2 dual color ELISpot, lymphocyte proliferation assay (LPA), Luminex multi-cytokine analysis, and/or intracellular cytokine staining (ICCS). ICCS was used to determine the contribution of $CD4^+$ and $CD8^+$ T cells to the antigen-specific production of IFN-γ and TNF-α.

In each of the experiments described below, mice were vaccinated subcutaneously with yeast-based HBV immunotherapeutics or yeast-based control (described below) according to the same regimen: injection at 2 sites (flank, scruff) with 2.5 YU of the yeast composition per site, once per week for 3 weeks. Controls included YVEC (control yeast containing an empty vector, i.e., no antigen), OVAX2010 (a control yeast immunotherapy composition that expresses the non-HBV antigen, ovalbumin), and the combination of YVEC with soluble recombinant antigens (ovalbumin or HBV antigens) and anti-CD40 antibody. The specific experiments and treatment cohorts are shown in Tables 8 and 9 below. Mice were euthanized 8 days (HLA-A2 transgenic, Experiment 1) or 14 days (C57BL/6 and BALB/c, Experiment 2) after the third immunization, and spleen and inguinal lymph nodes were dissected and incubated with various antigenic stimuli (HBV class I and class II MHC-restricted peptides, recombinant proteins, and HBV-antigen expressing tumor cell lines) for 5 days, as indicated below. For Luminex analysis, culture supernatants were harvested and evaluated for the production of 10 different cytokines (Th1 and Th2 type) at 48 h after antigen addition. For ELISpot assays, cells were incubated on IFN-γ antibody-coated plates for the last 24 h of the 5 day in vitro stimulation (IVS), followed by standardized spot detection and counting. For LPAs, cells were pulsed with $^3$H-thymidine for the last 18 h of the 5 day IVS, and the amount of isotope incorporated into newly synthesized DNA was then measured by scintillation counting. For ICCS, after a full 7 day stimulation, were subjected to Ficoll gradient centrifugation to eliminate dead cells, and 1 million viable cells per well (96 well U-bottom plates) were then incubated for 5 hours with the same antigenic stimuli at a range of concentrations (titration), and then permeablized, and subjected to staining with fluorochrome coupled-antibodies recognizing intracellular IFN-γ and TNF-a plus cell surface markers CD4 and CD8. The percentage of $CD4^+$ or $CD8^+$ T cells expressing the cytokines was determined by flow cytometry.

Table 8 describes the experimental cohorts and protocol for Experiment 1. In this experiment, HLA-A2 cohorts of mice were immunized using the protocol described above, and the mice were euthanized for immune analysis 8 days after the third immunization. Group A ("YVEC") received the yeast YVEC control according to the immunization schedule described above; Group B ("SCORE-D (GI-13009-UL2)") received GI-13009 grown in UL2 medium (see Example 7) according to the immunization schedule described above; and Group C ("X-SCORE (GI-13020-U2)") received GI-13020 grown in U2 medium (see Example 8) according to the immunization schedule described above.

TABLE 8

| Group | HLA-A2 Mice (#, treatment) |
| --- | --- |
| A | 3, YVEC |
| B | 3, SCORE-D/GI-13009-UL2 |
| C | 3, X-SCORE/GI-13020-U2 |

Figure 34:
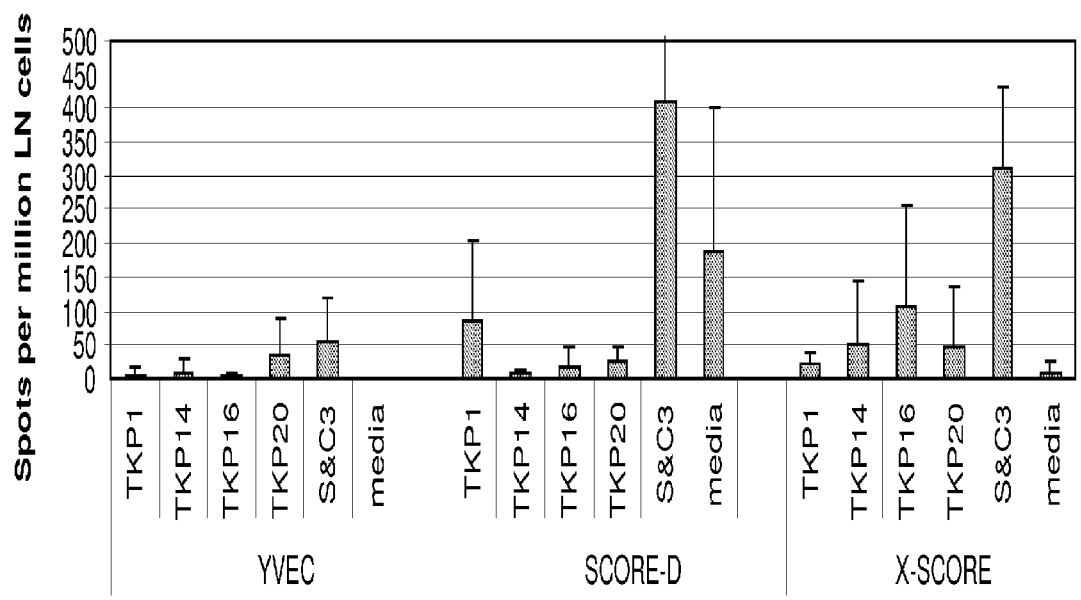
FIG. 34 is a bar graph showing HBV antigen-specific IFN-γ ELISpot responses from lymph node cells isolated from HLA-A2 transgenic mice immunized with GI-13009 (SCORE-D) or GI-13020 (X-SCORE) as compared to mice immunized with a yeast control (YVEC) (error bars are Standard Deviation).

IFN-γ ELISpot assay results from the lymph node cells harvested from mice in Experiment 1 are shown in FIG. 34. This figure shows the results of restimulation of lymph node cells from the immunized mice with various HBV peptides as compared to a medium control (note that the peptide denoted "TKO20" is a peptide from X antigen (X52-60) that is contained within the immunotherapeutic X-SCORE, but is not present in SCORE-D). The results indicated that lymph node cells from both SCORE-D (GI-13009)-immunized and X-SCORE (GI-13020)-immunized mice possess T cells that produce IFN-γ in response to in vitro stimulation with a mixture of 3 μg/ml each of recombinant HBV surface and core antigens (FIG. 34; denoted "S&C3"). This ELISpot response was greater than that observed for YVEC-immunized mice (yeast controls) treated with the same stimulant, indicating that the HBV surface and/or core antigens within the yeast-based immunotherapeutic compositions (SCORE-D and X-SCORE) are required for the induction of the IFN-γ response. Furthermore, the results indicate that the restimulation using HBV antigen in the IVS results in efficient IFN-γ production, since wells containing medium alone showed a much lower ELISpot response.

FIG. 34 also shows that a selected HLA-A2-restricted epitope from HBV core (TKP16; Core:115-124 VLEYLVSFGV; SEQ ID NO:75) known in the field to be important in patients with acute HBV exposure and clearance, elicits a response in X-SCORE-immunized mice that is greater than that observed for media only wells. Further refinement of the peptide concentration and incubation times for the ELISpot assay is expected to increase the magnitude and reduce the variability in the observed response for these antigens.

Figure 35:
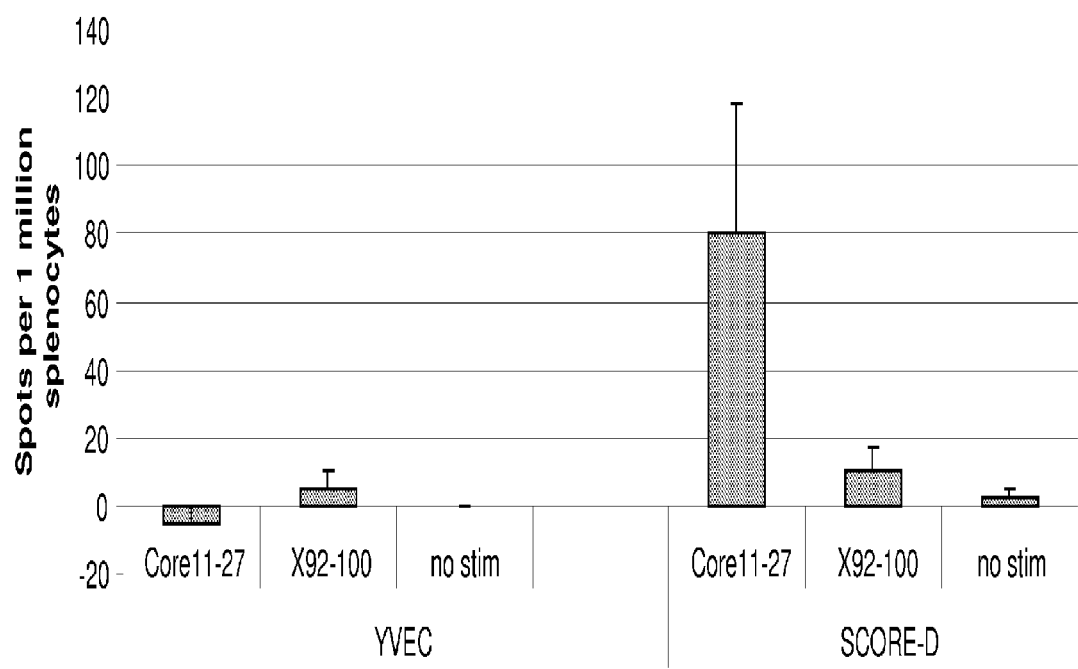
FIG. 35 is a bar graph showing HBV antigen-specific IFN-γ ELISpot responses from spleen cells isolated from HLA-A2 transgenic mice immunized with GI-13009 (SCORE-D) as compared to mice immunized with a yeast control (YVEC) (error bars are Standard Error).

FIG. 35 shows the IFN-γ ELISpot assay results from the spleen cells harvested from SCORE-D-immunized mice in Experiment 1. The HBV core peptide denoted "Core11-27" (ATVELLSFLPSDFFPSV (SEQ ID NO:72)) is contained within the antigen expressed by SCORE-D, whereas the HBV X peptide denoted "X92-100" is not contained within the antigen expressed by SCORE-D and is therefore a control peptide in this experiment. As shown in FIG. 35, spleen cells from the SCORE-D immunized HLA-A2 transgenic mice produced an IFN-γ ELISpot response upon in vitro stimulation with the known HLA-A2 restricted HBV core epitope, denoted "Core 11-27". This response was greater than that observed from spleen cells that were stimulated in vitro with an irrelevant peptide (denoted "X92-100"), medium alone, or for any IVS treatment wells for splenocytes from YVEC-immunized mice.

Therefore, the initial results from Experiment 1 show that both SCORE-D and X—SCORE elicit HBV antigen-specific T cell responses in HLA-A2 transgenic mice immunized with these yeast-based immunotherapy compositions.

Table 9 describes the experimental cohorts and protocol for Experiment 2. In this experiment, C57BL/6 and BALB/c cohorts of mice were immunized using the protocol described above, and the mice were euthanized for immune analysis two weeks after the third immunization. Group A ("Naïve") received no treatment; Group B ("YVEC") received the yeast YVEC control according to the immunization schedule described above; Group C ("X-SCORE (GI-13020-U2)") received GI-13020 grown in U2 medium (see Example 8) according to the immunization schedule described above; Group D ("SCORE-D (GI-13009-UL2)") received GI-13009 grown in UL2 medium (see Example 7) according to the immunization schedule described above; and Group E ("OVAX2010") received the yeast control expressing ovalbumin according to the immunization schedule described above.

TABLE 9

| Group | C57BL/6 Mice (#, treatment) | BALB/c Mice (#, treatment) |
|---|---|---|
| A | 8, Naïve | 8, Naive |
| B | 8, YVEC | 8, YVEC |
| C | 8, X-SCORE (GI-13020-U2) | 8, X-SCORE (GI-13020-U2) |
| D | 8, SCORE-D (GI-13009-UL2) | 8, SCORE-D (GI-13009-UL2) |
| E | 8, OVAX2010 | 7, OVAX2010 |

Figure 36:
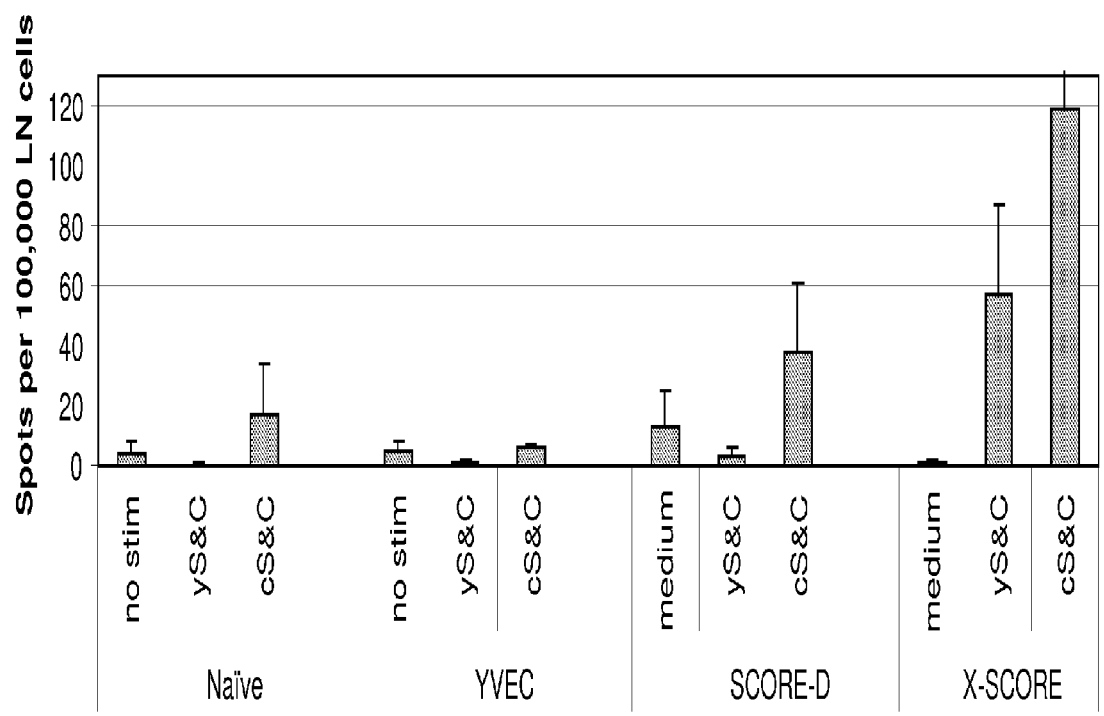
FIG. 36 is a bar graph showing HBV antigen-specific IFN-γ ELISpot responses from lymph node cells isolated from C57BL/6 mice immunized with GI-13009 (SCORE-D) or GI-13020 (X-SCORE) as compared to mice immunized with a yeast control (YVEC) or Naïve mice (error bars are Standard Deviation).

FIG. 36 shows the results of the ELISpot assays for lymph node cells isolated from C57BL/6 mice immunized as indicated in Experiment 2 (Table 9). These results demonstrated that both X-SCORE and SCORE-D elicited IFN-γ responses in wild type C57BL/6 mice. Lymph node cells from X-SCORE-immunized mice stimulated in vitro with purified, *Pichia pastoris*-expressed surface and core antigens (denoted yS&C; IVS with 1:1 mix of *Pichia*-expressed surface and core antigens, 3 μg/mL each) produced a meaningful IFN-γ immune response. The same lymph node cell preparations from both X-SCORE- and SCORE-D-immunized mice, when stimulated with *E. coli*-expressed surface and core antigens (denoted cS&C; IVS with 1:1 mix of *E. coli* expressed surface and core antigens, 3 μg/mL each), produced higher overall ELISpot responses than those observed for the *Pichia*-expressed recombinant antigens. The column labeled "no stim" in FIG. 36 denotes IVS conditions where cRPMI medium alone was provided (no antigen). In general, immunization with X-SCORE elicited a greater effect than SCORE-D, and both HBV yeast-based immunotherapy compositions elicited a greater response than that observed for YVEC-immunized (yeast control) or Naive mice. These data indicate that both SCORE-D and X-SCORE produce HBV-antigen specific immune responses that are detectable in ex vivo lymph node cell preparations from C57BL/6 mice.

Figure 37:
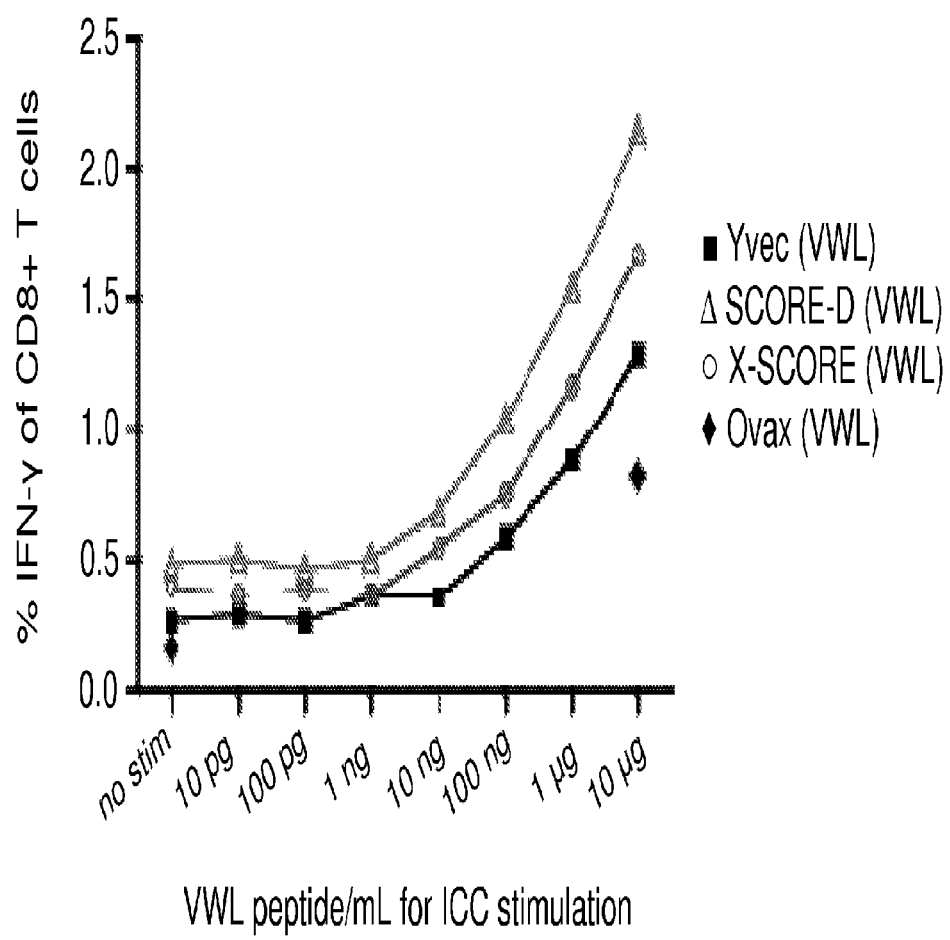
FIG. 37 is a line graph showing HBV antigen-specific CD8$^+$ T cell responses to an MHC Class I-restricted HBV peptide in C57BL/6 mice immunized with GI-13009 (SCORE-D) or GI-13020 (X-SCORE) as compared to mice immunized with a yeast control (YVEC) or a yeast-based immunotherapeutic expressing ovalbumin (OVAX).

FIG. 37 shows the intracellular cytokine staining (ICCS) assay results for C57BL/6 mice conducted in Experiment 2 (Table 9). The results showed that immunization of C57BL/6 mice with either X-SCORE or SCORE-D elicits IFN-γ-producing CD8$^+$ T cells that are specific for the MHC Class I, H-2K$^b$-restricted peptide from surface antigen, denoted "VWL" (VWLSVIWM; SEQ ID NO:152). This effect was dependent upon the concentration of peptide added to cells during the 5 hour incubation of the ICCS procedure; greater concentrations of peptide resulted in an increasing difference in the level of IFN-γ producing CD8$^+$ T cells for HBV yeast-based immunotherapeutics (SCORE-D and X-SCORE) versus irrelevant the yeast controls (Ovax and Yvec), with maximal separation occurring at 10 μg/mL of peptide.

Figure 38:
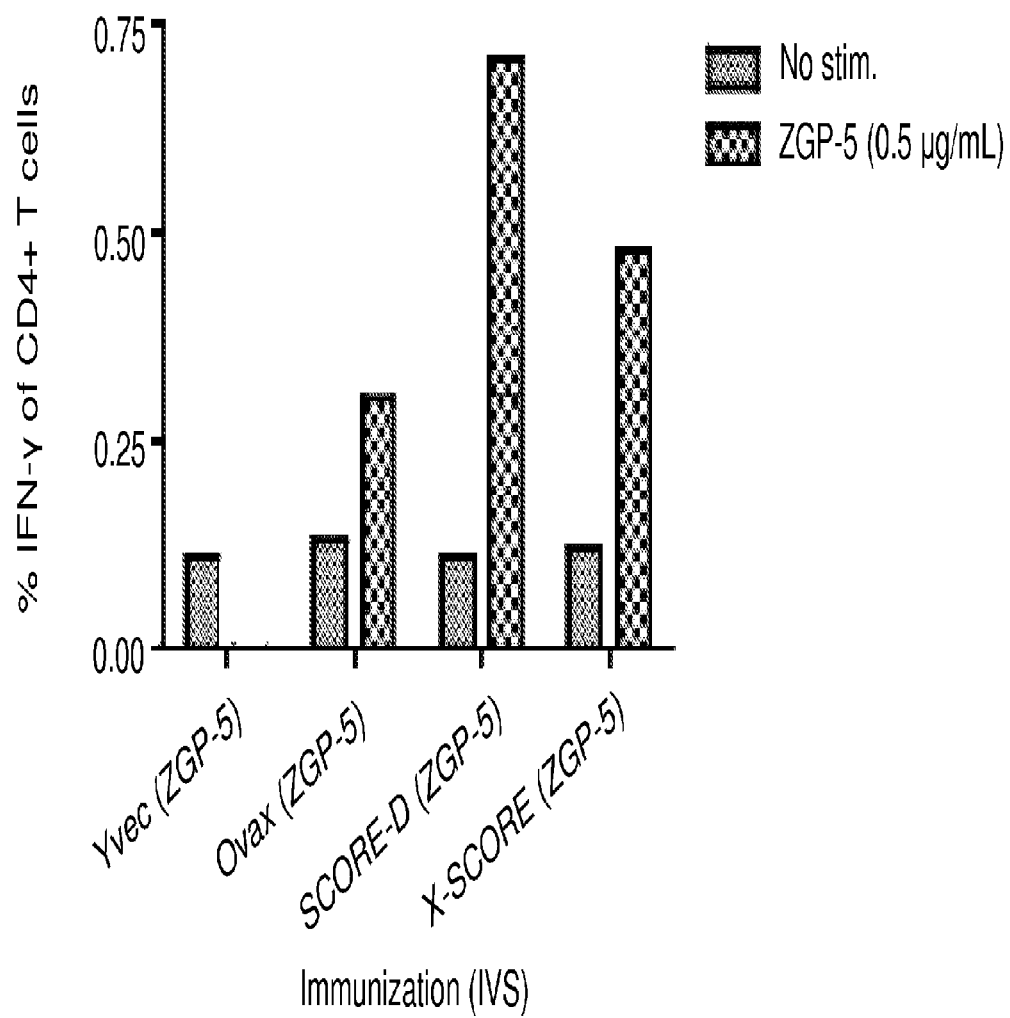
FIG. 38 is a bar graph showing HBV antigen-specific CD4$^+$ T cell responses to an MHC Class II-restricted HBV peptide in C57BL/6 mice immunized with GI-13009 (SCORE-D) or GI-13020 (X-SCORE) as compared to mice immunized with a yeast control (YVEC) or a yeast-based immunotherapeutic expressing ovalbumin (OVAX).

The ICCS assays of Experiment 2 also showed that immunization of C57BL/6 mice with X-SCORE and SCORE-D elicited IFN-γ-producing CD4$^+$ T cells specific for the MHC Class II-restricted HBV peptide from core protein denoted "ZGP-5" (VSFGVWIRTPPAYRPPNAPIL; SEQ ID NO:148), with 0.5 μg/mL of peptide added during the 5 hour incubation period of the ICCS procedure (FIG. 38).

Taken together with the ELISpot results described above, these data indicate that both SCORE-D and X-SCORE yeast-based immunotherapeutic compositions elicit HBV antigen-specific, effector CD4$^+$ and CD8$^+$ T cells that are detected by ex vivo stimulation of lymph node and spleen cells with recombinant HBV antigens and HBV peptides. The T cell responses occur in both wild type C57BL/6 mice (H2-Kb) and in HLA-A2 transgenic mice, indicating the potential of these vaccines to elicit immune responses in the context of diverse major histocompatibility types.

Based on the results described in this Example above for HLA-A2 mice and C57BL/6 mice, as well as the results of the experiments described in Examples 9, 10, 11 and 12, it is expected that results with BALB/c mice immunized with either SCORE-D or X—SCORE will also demonstrate that the yeast-based HBV immunotherapeutic compositions elicit HBV antigen-specific, effector CD4$^+$ and CD8$^+$ T cells in these mice. Indeed, initial results from the BALB/c cohorts were positive for CD8$^+$ T cell responses (data not shown). It is further expected that lymphocyte proliferation assays and Luminex cytokine release analyses will show that both SCORE-D and X-SCORE induce immune responses specifically targeted to the HBV antigen sequences present in the yeast immunotherapeutics, and that these responses will be observed in all three mouse strains (HLA-A2 transgenic, C57BL/6 and BALB/c).

Example 15

The following example describes an experiment in which yeast-based immunotherapy compositions for HBV are evaluated for the ability to stimulate IFNγ production from PBMCs isolated from donors of varied HBV antigen exposure.

In this experiment, the yeast-based immunotherapy product known as GI-13009 ("Score-D", comprising SEQ ID NO:118, Example 7), and the yeast-based immunotherapy product known as GI-13020 ("X-Score", comprising SEQ ID NO:130, Example 8) are tested for their ability to stimulate IFNγ production from PBMCs isolated from donors of varied HBV antigen exposure. In this experiment, one group of donors has previously been vaccinated with ENGERIX-B® (GlaxoSmithKline) or with RECOMBIVAX HB® (Merck & Co., Inc.), one group of donors is naïve to HBV antigen ("normal"), and one group of donors is a chronic HBV patient (a subject chronically infected with HBV). ENGERIX-B® is a prophylactic recombinant subunit vaccine containing a recombinant purified hepatitis B virus surface antigen (HBsAg) produced in yeast cells, purified and then adsorbed on an aluminum-based adjuvant. RECOMBIVAX HB® is a prophylactic recombinant subunit vaccine derived from HBV surface antigen (HBsAg) produced in yeast cells and purified to contain less than 1% yeast protein. All donors express the HLA-A*0201 allele.

The donor PBMCs are incubated in 6-well flat-bottomed tissue culture plates (10$^7$ PBMCs per well) for 3 h in a 5% CO$_2$ incubator in complete RPMI medium containing 10% fetal bovine serum. Non-adherent cells are removed and discarded and the adherent cells are treated with recombinant human interleukin-4 (IL-4) and recombinant human granulocyte macrophage colony-stimulating factor (GM-CSF) (20 and 50 ng/mL, respectively) for 5 days to generate immature dendritic cells (iDCs). The iDCs are then incubated with ant-CD40 antibody (1 μg/ml), YVEC (yeast control comprising an empty vector), or the yeast-based products GI-13020 or GI-13009, for 48 h in a 5% CO$_2$ incubator at 37° C., to generate mature DCs. For anti-CD40 antibody-treated DCs, cells are additionally pulsed with HLA-A*0201-restricted HBV peptides using standard methods. All DC groups are PBS-washed and then removed from plates with a cell harvester in PBS. Cells are irradiated (30 Gy) and used to stimulate the autologous donor PBMCs at a DC:PBMCs ratio of 1:10. Stimulation is conducted for 7 days (round 1) of which the last 4 days are conducted in medium containing recombinant human IL-2. The stimulated PBMCs are then subjected to Ficoll gradient centrifugation, and the isolated viable cells subjected to a second round of IVS with yeast-pulsed or peptide-pulsed DCs prepared as described above. The stimulated PBMCs are then incubated with HBV peptide(s) or controls in the presence of 20 U/mL rhIL-2 in 96 well plates coated with antibody specific for IFN-γ, and ELISpot detection is conducted using standard manufacturer procedures. It is expected that PBMCs stimulated with autologous SCORE-D- or X-SCORE-fed DCs, or with HBV peptide-pulsed DCs, will respond to exogenous HBV peptides to a greater degree than PBMCs stimulated with YVEC-fed or unpulsed DCs, and that this effect will be more pronounced for HBV ENGERIX® or RECOMBIVAX HB® vaccine recipients than for donors who are naive to HBV antigen exposure.

Example 16

The following example describes preclinical experiments using human PBMCs to demonstrate the immunogenicity of yeast-based HBV immunotherapy compositions of the invention in humans.

Specifically, these experiments are designed to determine whether HBV surface antigen-specific and/or HBV core antigen-specific CD8$^+$ T cells can be detected in the peripheral blood mononuclear cells (PBMCs) of HBV carriers following 2 rounds of in vitro stimulation (IVS) with yeast-based HBV immunotherapy compositions containing HBV surface antigen and HBV core.

PBMCs are obtained from human donors confirmed to be positive for HBV (based on serum HBsAg status). Total DNA is isolated from 0.5 mL whole blood and typed for HLA in order to identify the correct HBV pentamer for testing (see table below).

TABLE 10

| HLA type | Pentamer Peptide Sequence | Antigen |
|---|---|---|
| A*0201 | FLLTRILTI (SEQ ID NO: 42) | Surface |
| A*0201 | GLSPTVWLSV (SEQ ID NO: 43) | Surface |
| A*0201 | FLPSDFFPSI (SEQ ID NO: 44) | Core |
| A*1101 | YVNVNMGLK (SEQ ID NO: 48) | Core |
| A*2402 | EYLVSFGVW (SEQ ID NO: 49) | Core |

Dendritic cells (DCs) are prepared from the PBMCs isolated from the donors described above by culturing PBMCs for 5 days in the presence of GM-CSF and IL-4. The DCs are subsequently incubated with yeast-based HBV immunotherapy compositions (e.g., those described in any of Examples 1-8 or elsewhere herein) or control yeast (e.g., "YVEC", which is Saccharomyces cerevisiae yeast that is transformed with an empty vector, or vector that does not contain an antigen-encoding insert), at a ratio of 1:1 (yeast:DCs). Control DC cultures also include DCs incubated with HBV peptides, control peptides (non-HBV peptides), or nothing.

After 48-hours in co-culture, the DCs are used as antigen presenting cells (APCs) for stimulation of autologous T cells (i.e., T cells from the donors). Each cycle of stimulation, designated as IVS (in vitro stimulation), consists of 3 days culture in the absence of IL-2, followed by 4 additional days in the presence of recombinant IL-2 (20 U/ml). At the end of IVS 2, T cells are stained with a control tetramer or pentamer or a tetramer or pentamer specific for an HBV peptide epitope identified above. The percentage of CD8+ T cells that stain positive with the tetramer or pentamer is quantified by flow cytometry.

It is expected that stimulation of donor T cells from HBV-positive donors with a yeast-HBV immunotherapeutic of the invention increases the percentage of tetramer/pentamer-positive CD8+ T cells in at least some or a majority of the donors, as compared to controls, indicating that human T cells from HBV-infected individuals have the capacity to recognize HBV proteins carried by the yeast-based immunotherapy as immunogens.

Additional experiments similar to those above are run using donor PBMCs from normal (non-HBV infected) individuals. It is expected that stimulation of donor T cells from normal donors with a yeast-HBV immunotherapeutic of the invention increases the percentage of tetramer/pentamer-positive CD8+ T cells in at least some or a majority of the donors, as compared to controls, indicating that human T cells from non-infected individuals also have the capacity to recognize HBV proteins carried by the yeast-based immunotherapy as immunogens.

In an additional experiment, HBV-specific T cells from three of the donors from the experiments described above are expanded in vitro using DCs incubated with HBV yeast-based immunotherapeutics (e.g., those described in any of Examples 1-8 or elsewhere herein) for 2 cycles of IVS (as described above). A third IVS is carried out with DCs matured in presence of CD40L and pulsed with the HBV peptide(s). At day 5, CD8+ T cells are isolated and used in an overnight cytotoxic T lymphocyte (CTL) assay against tumor cell targets expressing HBV antigens, at various effector:target (ET) ratios. The percentage of CD8+ T cells that stain positive with a control tetramer/pentamer versus an HBV-specific tetramer/pentamer is measured.

It is expected that T cells from some or all of the donors will be capable of generating CD8+ CTLs that can kill targets expressing HBV antigens. These data will demonstrate that yeast-HBV immunotherapeutic compositions can generate HBV-specific CTLs that are capable of killing an HBV antigen-expressing tumor cell.

Example 17

The following example describes a phase 1 clinical trial in healthy volunteers.

A 12-week, open-label dose escalation phase 1 clinical study is performed using a yeast-based HBV immunotherapy composition described herein as GI-13009 ("SCORE-D", comprising SEQ ID NO:118, Example 7), or alternatively, the yeast-based HBV immunotherapy composition described herein as GI-13020 ("X-SCORE", comprising SEQ ID NO:130, Example 8) is used. Other yeast-based HBV immunotherapy compositions described herein (e.g., any of those described in Examples 1-8) can be utilized in a similar phase 1 clinical trial. The yeast-based HBV immunotherapy product for the phase 1 clinical trial is selected from pre-clinical studies (e.g., those described in any one of Examples 9-17) on the basis of considerations including strongest net immune response profile (e.g., amplitude of response for T cell epitopes that are most predictive of positive outcome, and/or breadth of immune response across the range of epitopes).

Subjects are immune active and healthy volunteers with no prior or current indication or record of HBV infection.

Approximately 48 subjects (6 arms, 8 subjects per arm) meeting these criteria are administered the yeast-based HBV immunotherapy composition in a sequential dose cohort escalation protocol utilizing one of two different dosing protocols as follows:

Protocol A: Prime-Boost Dosing (4 Weekly Doses Starting at Day 1, Followed by 2 Monthly Doses at Week 4 & Week 8)

Arm 1A: 20 Y.U. (administered in 10 Y.U. doses to 2 different sites);

Arm 2A: 40 Y.U. (administered in 10 Y.U. doses to 4 different sites);

Arm 3A: 80 Y.U. (administered in 20 Y.U. doses to 4 different sites)

4-Weely Dosing (Three Total Doses Administered at Day 1, Week 4 and Week 8)

Arm 1B: 20 Y.U. (administered in 10 Y.U. doses to 2 different sites);

Arm 2B: 40 Y.U. (administered in 10 Y.U. doses to 4 different sites);

Arm 3B: 80 Y.U. (administered in 20 Y.U. doses to 4 different sites)

All doses are administered subcutaneously and the dose is divided among two or four sites on the body (every visit) as indicated above. Safety and immunogenicity (e.g., antigen-specific T cell responses measured by ELISpot and T cell proliferation) are assessed. Specifically, an ELISpot-based algorithm is developed for categorical responders. ELISpot assays measuring regulatory T cells (Treg) are also assessed and CD4+ T cell proliferation in response to HBV antigens is assessed and correlated with the development of anti-*Saccharomyces cerevisiae* antibodies (ASCA).

It is expected that the yeast-based HBV immunotherapeutic will be well-tolerated and show immunogenicity as measured by one or more of ELISpot assay, lymphocyte proliferation assay (LPA), ex vivo T cell stimulation by HBV antigens, and/or ASCA.

Example 18

The following example describes a phase 1b/2a clinical trial in subjects chronically infected with hepatitis B virus.

Due to a tendency of HBV infected patients to experience destabilizing exacerbations of hepatitis as part of the natural history of the disease, yeast-based HBV immunotherapy is initiated after some period of partial or complete virologic control using anti-viral-based therapy, with a primary efficacy goal of improving seroconversion rates. In this first consolidation approach, yeast-based HBV immunotherapy is used in patients after they achieve HBV DNA negativity by PCR to determine whether seroconversion rates can be improved in combination with continued anti-viral therapy.

An open-label dose escalation phase 1b/2a clinical trial is run using a yeast-based HBV immunotherapy composition described herein as GI-13009 ("SCORE-D", comprising SEQ ID NO:118, Example 7), or alternatively, the yeast-based HBV immunotherapy composition described herein as GI-13020 ("X-SCORE", comprising SEQ ID NO:130, Example 8) is used. Other yeast-based HBV immunotherapy compositions described herein (e.g., any of those described in Examples 1-8) can be utilized in a similar phase 1 clinical trial. Subjects are immune active and chronically infected with hepatitis B virus (HBV) that is well controlled by anti-viral therapy (i.e., tenofovir disoproxil fumarate, or TDF (VIREAD®)) as measured by HBV DNA levels. Subjects are negative for HBV DNA (below detectable levels by PCR or <2000 IU/ml), but to qualify for this study, subjects must be HBeAg positive and have no evidence of cirrhosis or decompensation.

In stage one of this study, approximately 40 subjects (~5 subjects per arm) meeting these criteria are administered the yeast-based HBV immunotherapy composition in a sequential dose cohort escalation protocol utilizing dose ranges from 0.05 Y.U. to 80 Y.U. (e.g., 0.05 Y.U., 10 Y.U., 20 Y.U., and 40-80 Y.U.). In one protocol, 5 weekly doses will be administered subcutaneously (weekly dosing for 4 weeks), followed by 2-4 monthly doses also administered subcutaneously, with continued anti-viral therapy during treatment with the yeast-based HBV immunotherapy (prime-boost protocol). In a second protocol, a 4-weekly dosing protocol is followed, where subjects receive a total of three doses administered on day 1, week 4 and week 8, using the same escalating dose strategy as set forth above. Optionally, in one study, a single patient cohort (5-6 patients) will receive subcutaneous injections of placebo (PBS) on the same schedule as the immunotherapy plus continued anti-viral therapy. Conservative stopping rules are in place for ALT flares and signs of decompression.

In the second stage of this trial, subjects (n=60) are randomized 30 per arm to continue on anti-viral (TDF) alone or anti-viral plus the yeast-based HBV immunotherapeutic protocol (dose 1 and dose 2) for up to 48 weeks.

Safety, HBV antigen kinetics, HBeAg and HBsAg seroconversion, and immunogenicity (e.g., antigen-specific T cell responses measured by ELISpot) are assessed. In addition, dose-dependent biochemical (ALT) and viral load is monitored. Specifically, measurement of serum HBsAg decline during treatment between the 3-treatment arms at weeks 12, 24, 48 is measured, and HBsAg-loss/seroconversion is measured at week 48.

An increase in rates of HBsAg loss and/or seroconversion to >20% at 48 weeks in subjects receiving the yeast-based immunotherapy and TDF, as compared to subjects receiving TDF alone, is considered a clinically meaningful advancement. The yeast-based HBV immunotherapy composition is expected to provide a therapeutic benefit to chronically infected HBV patients. The immunotherapy is expected to be safe and well-tolerated at all doses delivered. Patients receiving at least the highest dose of yeast-based HBV immunotherapy are expected to show treatment-emergent, HBV-specific T cell responses as determined by ELISPOT, and patients with prior baseline HBV-specific T cell responses are expected to show improved HBV-specific T cell responses while on treatment. Patients receiving yeast-based HBV immunotherapy are expected to show improvement in seroconversion rates as compared to the anti-viral group and/or as compared to the placebo controlled group, if utilized. Improvements in ALT normalization are expected in patients receiving yeast-based HBV immunotherapy.

In an alternate trial, HBeAg negative patients meeting the other criteria (immune active, chronically HBV infected, well-controlled on anti-virals, with no signs of decompensation) are treated in a similar dose escalation trial as described above (or at the maximum tolerated dose or best dose identified in the trial described above). Patients are monitored for safety, immunogenicity, and HBsAg seroconversion.

Example 19

The following example describes a phase 1b/2a clinical trial in subjects chronically infected with hepatitis B virus.

An open-label dose escalation phase 1b/2a clinical trial is run using a yeast-based HBV immunotherapy composition described herein as GI-13009 ("SCORE-D", comprising SEQ ID NO:118, Example 7), or alternatively, the yeast-based HBV immunotherapy composition described herein as GI-13020 ("X-SCORE", comprising SEQ ID NO:130, Example 8) is used. Other yeast-based HBV immunotherapy compositions described herein (e.g., any of those described in Examples 1-8) can be utilized in a similar phase 1b/2a clinical trial. Subjects are immune active and chronically infected with hepatitis B virus (HBV) that has been controlled by anti-viral therapy (e.g. tenofovir (VIREAD®)) for at least 3 months. Subjects are not required to have completely cleared the virus to enroll in the study, i.e., patients may be positive or negative for HBV DNA (negativity determined as below detectable levels by PCR or <2000 IU/ml); however, to qualify for this study, subjects have no evidence of cirrhosis or decompensation. Patients may be HBeAg-positive, although HBeAg-negative patients can be included in the study.

30-40 subjects (6-10 patients per cohort) meeting these criteria are administered the yeast-based HBV immunotherapy composition in a sequential dose cohort escalation protocol utilizing dose ranges from 0.05 Y.U. to 40 Y.U. (e.g., 0.05 Y.U., 0.5 Y.U., 4 Y.U., 40Y.U.), or utilizing dose ranges from 0.05 Y.U. to 80 Y.U. (e.g., 0.05 Y.U., 10 Y.U., 20 Y.U., 40/80 Y.U.). In one protocol, 5 weekly doses will be administered subcutaneously (weekly dosing for 4 weeks), followed by 2-4 monthly doses also administered subcutaneously, with continued anti-viral therapy during treatment with the yeast-based HBV immunotherapy (prime-boost protocol). In a second protocol, a 4-weekly dosing protocol is followed, where subjects receive a total of three doses administered on day 1, week 4 and week 8, using the same escalating dose strategy as set forth above. In one study, a single patient cohort (5-6 patients) will receive subcutaneous injections of placebo (PBS) on the same schedule as the immunotherapy plus continued anti-viral therapy. Conservative stopping rules are in place for ALT flares and signs of decompression.

Safety, HBeAg and HBsAg seroconversion, viral control (e.g., development of viral negativity or trend toward viral negativity), and immunogenicity (e.g., antigen-specific T cell responses measured by ELISpot) are assessed. In addition, dose-dependent biochemical (ALT) and viral load is monitored.

>1 log 10 reduction in HB-SAg by 24 weeks or >1 log 10 reduction in HB-eAg by 12 weeks are considered to be endpoints for phase 2a. For HBV seroconversion, an SAg seroconversion of 10% by 24 weeks, and 15% by 48 weeks, and/or an eAg seroconversion rate of 25% by 24 weeks or 50% by 48 weeks are success criteria.

The yeast-based HBV immunotherapy composition is expected to provide a therapeutic benefit to chronically infected HBV patients. The immunotherapy is expected to be safe and well-tolerated at all doses delivered. Patients receiving at least the highest dose of yeast-based HBV immunotherapy are expected to show treatment-emergent, HBV-specific T cell responses as determined by ELISPOT and patients with prior baseline HBV-specific T cell responses show improved HBV-specific T cell responses while on treatment. Patients receiving yeast-based HBV immunotherapy will show improvement in seroconversion rates as compared to available comparative data for the given anti-viral and/or as compared to the placebo controlled group. Patients receiving yeast-based HBV immunotherapy will show improvement in viral loss (e.g., viral negativity as measured by PCR). Improvements in ALT normalization are expected in patients receiving yeast-based HBV immunotherapy.

Example 20

The following example describes a phase 2 clinical trial in subjects chronically infected with hepatitis B virus.

A randomized phase 2 clinical trial in patients chronically infected with HBV treats treatment-naive, HBeAg-positive (and possibly HBeAg-negative) subjects with ALT>2×ULN and viral loads >1 million copies. The subjects (~60 subjects per arm adjusted based on phase 1 study signal) must have at least 6 months of prior anti-viral therapy, and have viral negativity for 2 consecutive visits at least one month apart. Subjects are randomized into two arms. Arm 1 patients receive 24-48 weeks of yeast-based HBV immunotherapy (e.g., yeast-based HBV immunotherapy composition described herein as GI-13009 ("SCORE-D", comprising SEQ ID NO:118, Example 7), or alternatively, the yeast-based HBV immunotherapy composition described herein as GI-13020 ("X-SCORE", comprising SEQ ID NO:130, Example 8). All patients receiving immunotherapy continue anti-viral therapy (e.g., tenofovir (VIREAD®)). Arm 2 patients receive a placebo (PBS control injection) with continued anti-viral therapy. The primary endpoint is seroconversion and viral negativity. Additional yeast-based HBV immunotherapy compositions described herein (e.g., any of those described in Examples 1-8) can also be utilized in a phase 2 trial with similar design.

Patients who achieve seroconversion receive 6-12 month consolidation therapy on either yeast-immunotherapy and antivirals (Arm 1) or antivirals alone (Arm 2), followed by a 6 month treatment holiday. The number of patients remaining in remission after completion of the 6 month holiday represent the secondary endpoint of the study. Additional endpoints include safety, immunogenicity and ALT normalization, as discussed in the Examples describing human clinical trials above.

The yeast-based HBV immunotherapy composition is expected to provide a therapeutic benefit to chronically infected HBV patients. The immunotherapy is expected to be safe and well-tolerated. Patients receiving yeast-based HBV immunotherapy are expected to show treatment-emergent, HBV-specific T cell responses as determined by ELISPOT and patients with prior baseline HBV-specific T cell responses show improved HBV-specific T cell responses while on treatment. Patients receiving yeast-based HBV immunotherapy are expected to show an improvement in seroconversion rates as compared to the placebo controlled group. Patients receiving yeast-based HBV immunotherapy are expected to show an improvement in viral loss (e.g., viral negativity as measured by PCR). Improvements in ALT normalization are expected in patients receiving yeast-based HBV immunotherapy.

While various embodiments of the present invention have been described in detail, it is apparent that modifications and adaptations of those embodiments will occur to those skilled in the art. It is to be expressly understood, however, that such modifications and adaptations are within the scope of the present invention, as set forth in the following claims.

What is claimed is:

1. A method of treating hepatitis B virus (HBV) infection or at least one symptom resulting from HBV infection in a subject, comprising administering to the subject that has been infected with HBV an immunotherapeutic composition comprising:
   a) a yeast vehicle comprising a fusion protein;
   b) the fusion protein comprising HBV antigens, wherein the HBV antigens consist of:
      i) an HBV X antigen having an amino acid sequence that is at least 90% identical to positions 1-60 of SEQ ID NO:130;
      ii) an HBV surface antigen having an amino acid sequence that is at least 90% identical to positions 63-461 of SEQ ID NO:130; and
      iii) an HBV core antigen having an amino acid sequence that is at least 90% identical to positions 462-643 of SEQ ID NO:130.

2. The method of claim 1, wherein the subject is administered the immunotherapeutic composition in a dose from 0.1 Y.U. to 100 Y.U.

3. The method of claim 1, wherein the subject is administered the immunotherapeutic composition in a dose from about 2 Y.U. to about 80 Y.U.

4. The method of claim 1, wherein the subject is administered the immunotherapeutic composition in a dose of 2 Y.U., 10 Y.U., 40 Y.U. or 80 Y.U.

5. The method of claim 1, wherein the immunotherapeutic composition is administered weekly.

6. The method of claim 1, wherein the immunotherapeutic composition is administered bi-weekly.

7. The method of claim 1, wherein the immunotherapeutic composition is administered tri-weekly.

8. The method of claim 1, wherein the immunotherapeutic composition is administered monthly.

9. The method of claim 1, wherein the immunotherapeutic composition is administered at more than one site on the subject.

10. The method of claim 1, wherein the amino acid sequence of the HBV X antigen is at least 95% identical to positions 1-60 of SEQ ID NO:130.

11. The method of claim 1, wherein the amino acid sequence of the HBV X antigen consists of positions 1-60 of SEQ ID NO:130.

12. The method of claim 1, wherein the amino acid sequence of the HBV surface antigen is at least 95% identical to positions 63-461 of SEQ ID NO:130.

13. The method of claim 1, wherein the amino acid sequence of the HBV surface antigen consists of positions 63-461 of SEQ ID NO:130.

14. The method of claim 1, wherein the amino acid sequence of the HBV core antigen is at least 95% identical to positions 462-643 of SEQ ID NO:130.

15. The method of claim 1, wherein the amino acid sequence of the HBV core antigen consists of positions 462-643 of SEQ ID NO:130.

16. The method of claim 1, wherein the HBV antigens consist of:
   i) an HBV X antigen having an amino acid sequence that is at least 95% identical to positions 1-60 of SEQ ID NO:130;
   ii) an HBV surface antigen having an amino acid sequence that is at least 95% identical to positions 63-461 of SEQ ID NO:130; and
   iii) an HBV core antigen having an amino acid sequence that is at least 95% identical to positions 462-643 of SEQ ID NO:130.

17. The method of claim 1, wherein the HBV antigens consist of the amino acid sequence that is at least 90% identical to SEQ ID NO:130.

18. The method of claim 1, wherein the HBV antigens consist of the amino acid sequence that is at least 95% identical to SEQ ID NO:130.

19. The method of claim 1, wherein the HBV antigens consist of the amino acid sequence of SEQ ID NO:130.

20. The method of claim 1, wherein the fusion protein comprises the amino acid sequence of SEQ ID NO:130.

21. The method of claim 1, wherein the fusion protein comprises the amino acid sequence of SEQ ID NO:150.

22. The method of claim 1, wherein the fusion protein consists of the amino acid sequence of SEQ ID NO:150.

23. The method of claim 1, wherein the HBV antigens are arranged in the following order, from N- to C-terminus, in the fusion protein: HBV X antigen, HBV surface antigen, HBV core antigen.

24. The method of claim 1, wherein the yeast vehicle is a whole yeast.

25. The method of claim 24, wherein the whole yeast is heat-inactivated.

26. The method of claim 24, wherein the whole yeast has been lyophilized.

27. The method of claim 24, wherein the whole yeast is from *Saccharomyces cerevisiae*.

28. The method of claim 1, wherein the yeast vehicle is from *Saccharomyces cerevisiae*.

29. A method of treating hepatitis B virus (HBV) infection in a subject, comprising administering to the subject an immunotherapeutic composition comprising:
   a) a yeast comprising a fusion protein;
   b) the fusion protein comprising an amino acid sequence that is at least 90% identical to SEQ ID NO:130.

30. The method of claim 29, wherein the fusion protein comprises an amino acid sequence that is at least 95% identical to SEQ ID NO 130.

31. The method of claim 29, wherein the fusion protein comprises an amino acid sequence that is at least 90% identical to SEQ ID NO:150.

32. The method of claim 29, wherein the fusion protein comprises an amino acid sequence that is at least 95% identical to SEQ ID NO:150.

33. The method of claim 29, wherein the subject is administered the immunotherapeutic composition in a dose of 2 Y.U., 10 Y.U., 40 Y.U. or 80 Y.U.

34. The method of claim 29, wherein the immunotherapeutic composition is administered monthly.

35. The method of claim 29, wherein the immunotherapeutic composition is administered at more than one site on the subject.

36. The method of claim 29, wherein the yeast is a whole heat-inactivated yeast from *Saccharomyces cerevisiae*.

37. A method of treating chronic hepatitis B virus (HBV) infection in a subject comprising administering to the subject an immunotherapeutic composition comprising:
   a) a whole, heat-inactivated yeast from *Saccharomyces cerevisiae* comprising a fusion protein;
   b) the fusion protein expressed by the yeast, and comprising SEQ ID NO:130.

38. The method of claim 37, wherein the fusion protein comprises SEQ ID NO:150.

* * * * *